US008234129B2

(12) United States Patent
Michon et al.

(10) Patent No.: US 8,234,129 B2
(45) Date of Patent: Jul. 31, 2012

(54) SYSTEMS AND METHODS FOR OBTAINING, STORING, PROCESSING AND UTILIZING IMMUNOLOGIC AND OTHER INFORMATION OF INDIVIDUALS AND POPULATIONS

(75) Inventors: Francis Michon, Bethesda, MD (US); Samuel L. Moore, Sykesville, MD (US); Peter C. Fusco, Silver Spring, MD (US); Samuel J. Wohlstadter, Madison, VA (US); Charles Quentin Davis, Frederick, MD (US); Aaron Haleva, Oakhurst, NJ (US)

(73) Assignee: Wellstat Vaccines, LLC, Gaithersburg, MD (US)

( * ) Notice: Subject to any disclaimer, the term of this patent is extended or adjusted under 35 U.S.C. 154(b) by 0 days.

(21) Appl. No.: 11/796,727

(22) Filed: Apr. 27, 2007

(65) Prior Publication Data

US 2008/0091471 A1    Apr. 17, 2008

Related U.S. Application Data

(63) Continuation-in-part of application No. 11/255,161, filed on Oct. 18, 2005.

(60) Provisional application No. 60/796,266, filed on Apr. 27, 2006.

(51) Int. Cl.
*A61B 5/00* (2006.01)
(52) U.S. Cl. ............ 705/3; 705/2; 705/4; 600/368; 600/300; 719/316
(58) Field of Classification Search ............ 707/104.1; 435/7.24, 69.3; 600/300, 368; 705/3, 4; 719/316; 424/185.1
See application file for complete search history.

(56) References Cited

U.S. PATENT DOCUMENTS 5,658,744 A * 8/1997 Ochoa et al. ............ 435/7.24
(Continued)

FOREIGN PATENT DOCUMENTS
WO    03057011 A2    7/2003

OTHER PUBLICATIONS

"The influence of provider behavior, parental characteristics, and a public policy initiative on the immunization status of children followed by private pediatricians: a study from pediatric research in office settings" by J. Taylor, P.M. Darden, E. Slora, C. Hasemeier, L. Asmussen and R. Wasserman, published by Pediatrics, vol. 99, No. 2, Feb. 1997.*

(Continued)

*Primary Examiner* — Dilek B Cobanoglu
(74) *Attorney, Agent, or Firm* — Lewis J. Kreisler

(57) ABSTRACT

A system and method for assessing immunological status of individuals and populations is presented. The method includes establishing a database containing a plurality of records, each record containing information representative of the immune status of an individual, including (1) bioassay results, and (2) individual specific information such as, medical history, clinical observations and historical, demographic, lifestyle, and familial/genetic information. By processing the information trends and/or patterns are obtained correlating various variables in the records across an individual, population or sub-population. The identified trends and/or patterns can, for example, be used in health care related decision making. In exemplary embodiments such processing can include generating a set of correlations and for each correlation generating a set of explanatory or relevant hypotheses. Then, for example, each hypothesis can be automatically refuted or supported, to the extent possible. The identified correlations, their associated hypotheses and the results of such automated vetting can then be reported to a user.

10 Claims, 112 Drawing Sheets

U.S. PATENT DOCUMENTS

| | | | |
|---|---|---|---|
| 5,660,176 A | | 8/1997 | Iliff |
| 5,692,220 A * | | 11/1997 | Diamond et al. ............. 600/368 |
| 5,732,397 A | | 3/1998 | DeTore et al. |
| 5,839,438 A * | | 11/1998 | Graettinger et al. .......... 600/300 |
| 5,860,917 A * | | 1/1999 | Comanor et al. ............. 600/300 |
| 5,960,443 A * | | 9/1999 | Young et al. ................ 707/104.1 |
| 6,266,645 B1 * | | 7/2001 | Simpson ............................ 705/3 |
| 6,287,254 B1 | | 9/2001 | Dodds |
| 2002/0059030 A1 | | 5/2002 | Otworth et al. |
| 2002/0095585 A1 | | 7/2002 | Scott |
| 2002/0188480 A1 * | | 12/2002 | Liebeskind et al. .............. 705/4 |
| 2003/0065535 A1 | | 4/2003 | Karlov et al. |
| 2003/0208382 A1 * | | 11/2003 | Westfall ............................ 705/3 |
| 2004/0003132 A1 * | | 1/2004 | Stanley et al. ................. 709/316 |
| 2004/0015337 A1 | | 1/2004 | Thomas et al. |
| 2004/0122705 A1 | | 6/2004 | Sabol et al. |
| 2004/0267568 A1 | | 12/2004 | Chandler et al. |
| 2005/0071204 A1 * | | 3/2005 | Parankirinathan ................ 705/4 |
| 2006/0002949 A1 * | | 1/2006 | Glenn et al. ............... 424/185.1 |
| 2006/0030006 A1 * | | 2/2006 | Druilhe ........................ 435/69.3 |
| 2006/0074719 A1 | | 4/2006 | Horner |
| 2006/0218010 A1 | | 9/2006 | Michon et al. |

OTHER PUBLICATIONS

"Health-Based Risk Assessment: Risk adjusted payments and beyond"; Kathryn E. Martin, Deborah L. Rogal and Sharon B. Arnold; Jan. 2004.*

Miller; Combining Tabular, Rule-Based, and Procedural Knowledge in Computer-Based Guidelines for Childhood Immunization; Center for Medical Informatics, Yale University, Dec. 1996.*

Taylor, J.A., et al.; "The Influence of Provider Behavior, Parental Characteristics, and a Public Policy Initiative on the Immunization Status of Children Followed by Private Pediatricians: A Study From Pediatric Research in Office Settings"; Pediatrics; vol. 99:2; pp. 209-215 (1997).

Pending (as of Oct. 18, 2005) Claims from U.S. Appl. No. 11/255,161.

Pending (as of Nov. 10, 2008) Claims from U.S. Appl. No. 12/291,529.

* cited by examiner

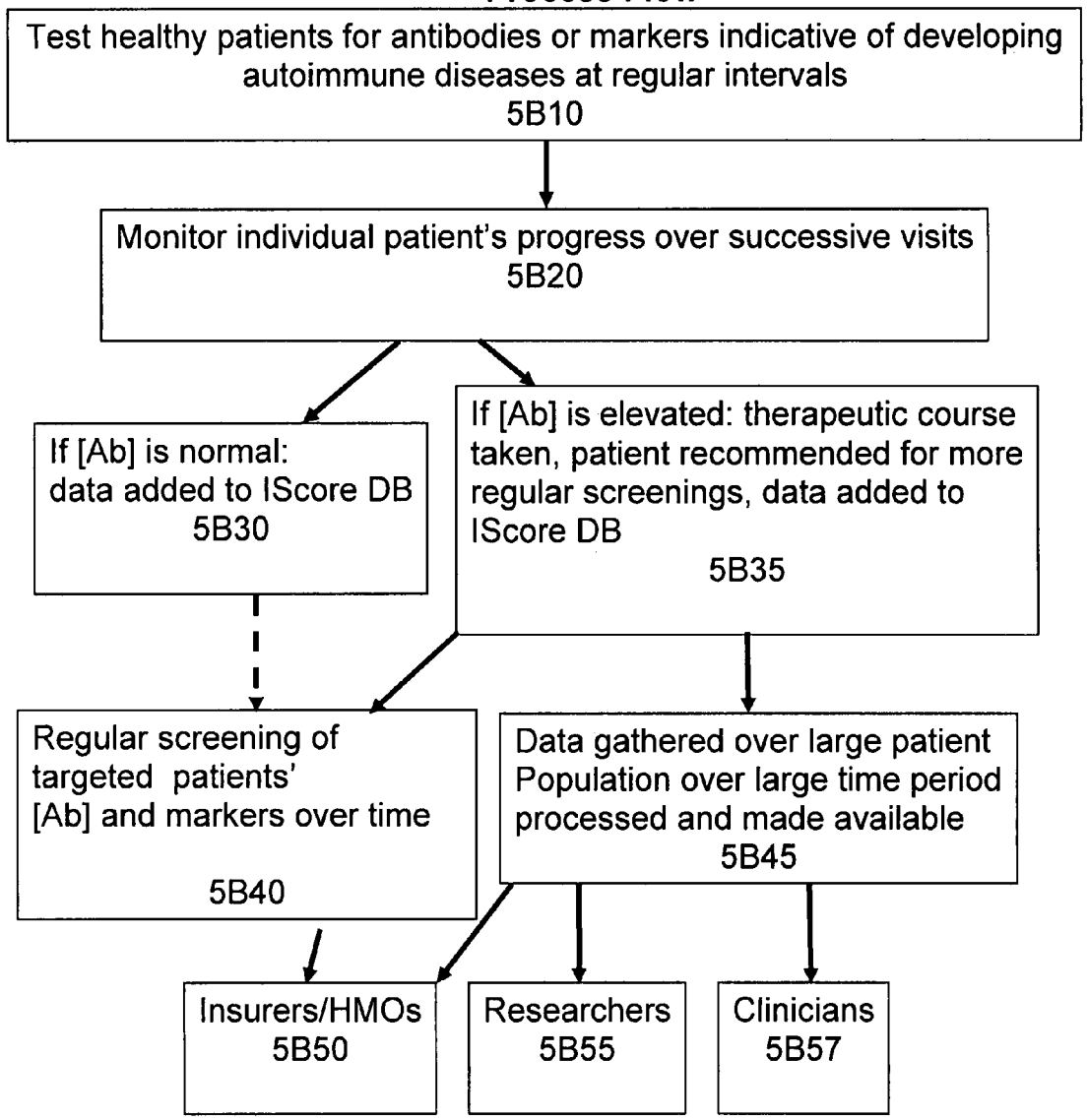
Fig. 5B – ImmunoScore Exemplary Autoimmune Process Flow

FIG. 1. CMV seroprevalence by age group in Australia. T bars represent 95% CIs.

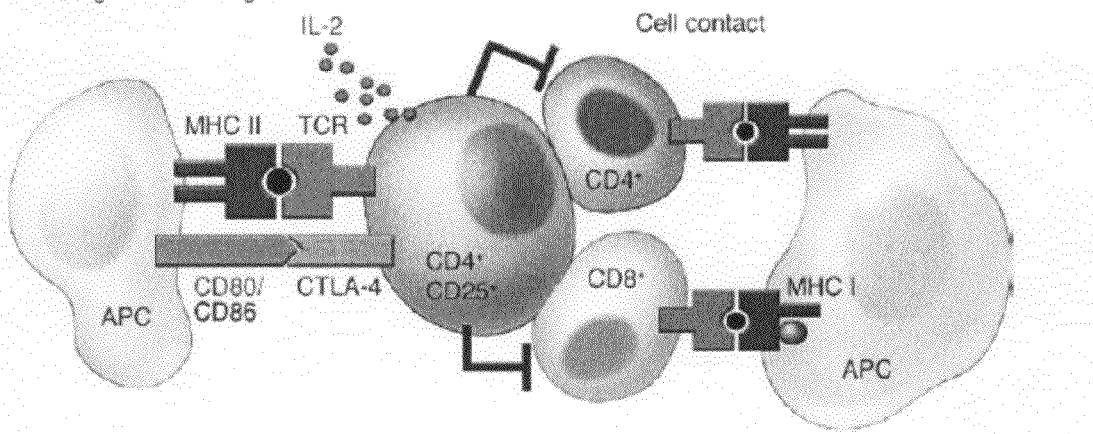
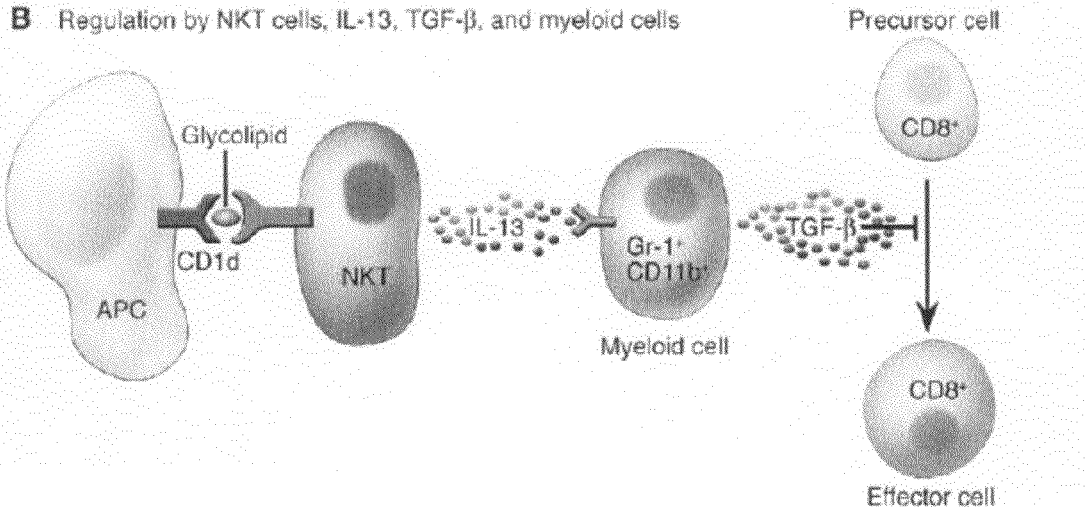
Fig. 5D

| | |
|---|---|
| IMMUNOSCORE | ANTIBODYHBS |
| GAMP | ANTIBODYDIPHTHERIA |
| GAMPACTIVITY | ANTIBODYTETANUS |
| GCMP | ANTIBODYPT1 |
| GCMPACTIVITY | ANTIBODYPRN1 |
| GWMP | ANTIBODYFHA1 |
| GWMPACTIVITY | ANTIBODYFIMBRIAE |
| GYMP | ANTIBODYPRP |
| GYMPACTIVITY | ANTIBODYPOLIO1 |
| GBMP | ANTIBODYPOLIO2 |
| GBMPACTIVITY | ANTIBODYPOLIO3 |
| C5 | ANTIBODYMEASLES |
| C6 | ANTIBODYRUBELLA |
| C7 | ANTIBODYVARICELLA |
| C8 | ANTIBODYPNEUMOCOCCALSEROTYPES |
| C9 | ANTIBODYIGG |
| PROPERDIN | ANTIBODYIGA |
| MBL | ANTIBODYIGM |
| FCYRLLA | ANTIBODYHSVIGG |
| IL_1 | ANTIBODYHSV1 |
| IL_1R | ANTIBODYHSV2 |
| IL_6 | ANTIBODYGONORRHOEAE |
| IL_10 | ANTIBODYPALLIDUM |
| | TCELLPALLIDUM |
| | ANTIBODYHIV |
| | TCELLHIV |
| | ANTIBODYGBS1 |
| | ANTIBODYGBS2 |
| | ANTIBODYGBS3 |
| | ANTIBODYTH1CYTOKINE |
| | ANTIBODYTH2CYTOKINE |

Figure 6: Assay Results in Example Database

| |
|---|
| Vaccinate patient with vaccine X |
| Do not vaccinate the patient with vaccine X |
| Retest patient immediately |
| Retest patient in X days |
| Monitor patient for symptom X |
| Administer additional test X; rerun analysis in light of new test results |
| Make an entry into patient's medical history of X |
| Treat patient for condition X |

Figure 7: Diagnostic Module Recommendation Types

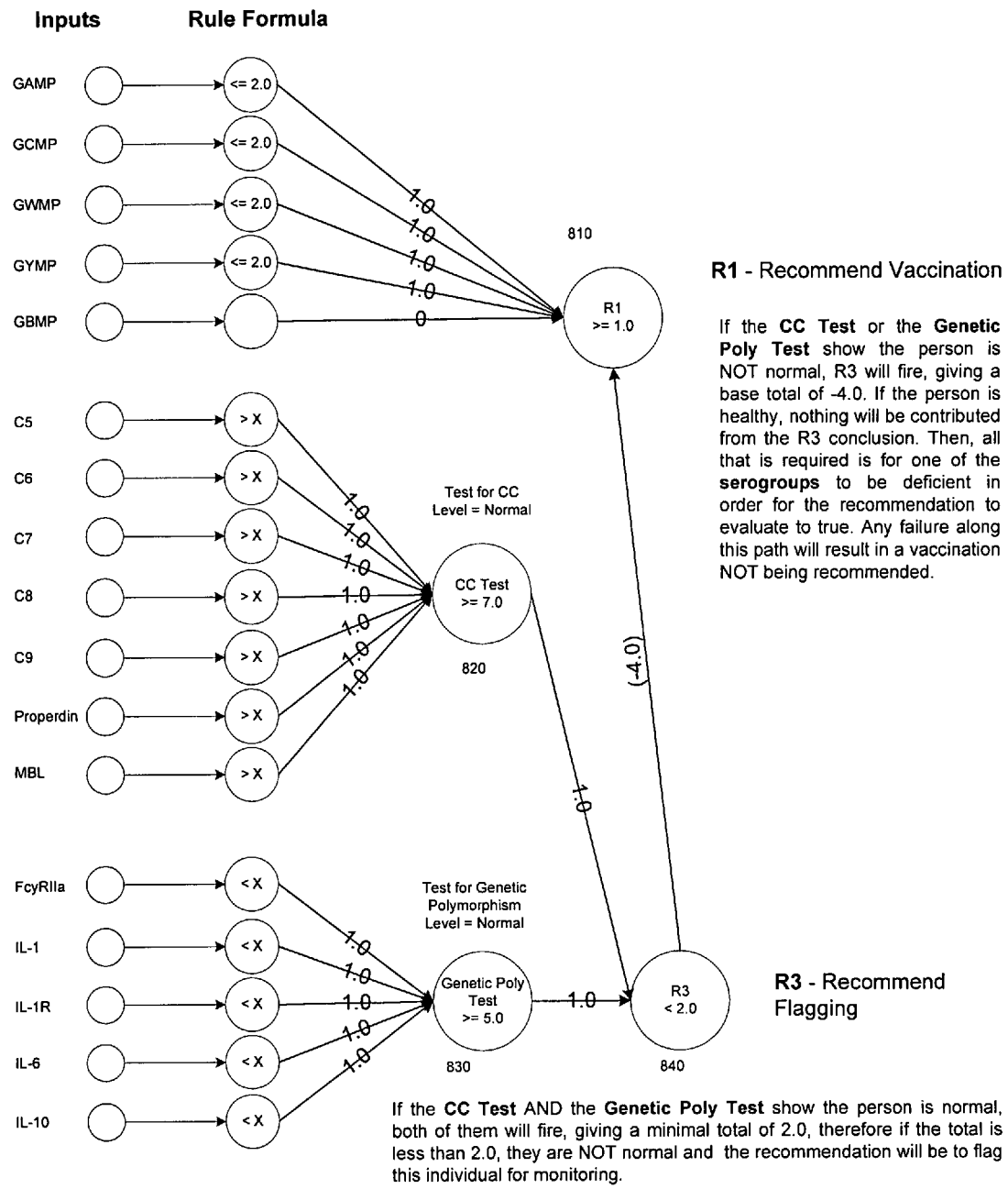
Fig. 8: Example Perceptron Network

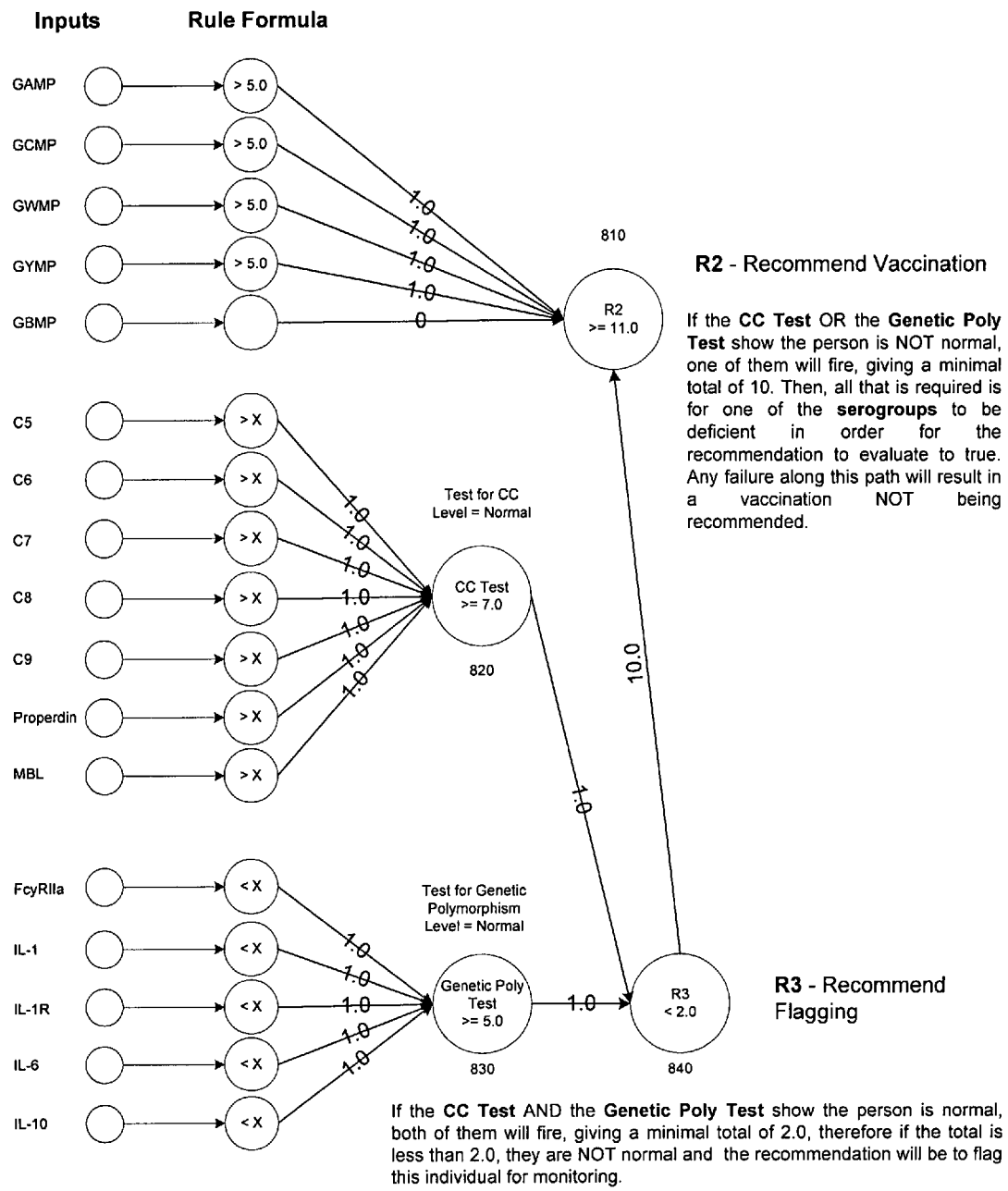
Fig. 8A: Example Perceptron Network

Figure 9: XML Representation of Perceptron Network

```xml
<?xml version="1.0" ?>
<TestRule>
<Name>SerumIgGVPS</Name>
<InputNeurons>
  <InputNeuron id="ruleR1_1" field="serumIgGLevelA" operator="lessThan"
     value="2.0" />
  <InputNeuron id="ruleR1_2" field="serumIgGLevelC" operator="lessThan"
     value="2.0" />
  <InputNeuron id="ruleR1_3" field="serumIgGLevelW" operator="lessThan"
     value="2.0" />
  <InputNeuron id="ruleR1_4" field="serumIgGLevelY" operator="lessThan"
     value="2.0" />
  <InputNeuron id="ruleR2_1" field="serumIgGLevelA" operator="lessThan"
     value="5.0" />
  <InputNeuron id="ruleR2_2" field="serumIgGLevelC" operator="lessThan"
     value="5.0" />
  <InputNeuron id="ruleR2_3" field="serumIgGLevelW" operator="lessThan"
     value="5.0" />
  <InputNeuron id="ruleR2_4" field="serumIgGLevelY" operator="lessThan"
     value="5.0" />
  <InputNeuron id="ruleCC_1" field="C5" operator="greaterThan" value="1.0" />
  <InputNeuron id="ruleCC_2" field="C6" operator="greaterThan" value="1.0" />
  <InputNeuron id="ruleCC_3" field="C7" operator="greaterThan" value="1.0" />
  <InputNeuron id="ruleCC_4" field="C8" operator="greaterThan" value="1.0" />
  <InputNeuron id="ruleCC_5" field="C9" operator="greaterThan" value="1.0" />
  <InputNeuron id="ruleCC_6" field="Properdin" operator="greaterThan" value="1.0"
     />
  <InputNeuron id="ruleCC_7" field="MBL" operator="greaterThan" value="1.0" />
  <InputNeuron id="ruleGP_1" field="FcyRIIa" operator="greaterThan" value="1.0" />
  <InputNeuron id="ruleGP_2" field="IL1" operator="greaterThan" value="1.0" />
  <InputNeuron id="ruleGP_3" field="IL1R" operator="greaterThan" value="1.0" />
  <InputNeuron id="ruleGP_4" field="IL6" operator="greaterThan" value="1.0" />
  <InputNeuron id="ruleGP_5" field="IL10" operator="greaterThan" value="1.0" />
</InputNeurons>
<InputDefinitions>
<IntputDefinition>
  <Name>serumIgGLevelA</Name>
  <Units>ug/mL</Units>
  <Definition>The Serum IgG Levels for vaccine-preventable serogroups A of
     Neisseria meningitidis</Definition>
</IntputDefinition>
<IntputDefinition>
  <Name>serumIgGLevelC</Name>
  <Units>ug/mL</Units>
  <Definition>The Serum IgG Levels for vaccine-preventable serogroups C of
     Neisseria meningitidis</Definition>
</IntputDefinition>
```

Figure 9: XML Representation of Perceptron Network
(Continued #1)

```xml
- <IntputDefinition>
  <Name>serumIgGLevelW</Name>
  <Units>ug/mL</Units>
  <Definition>The Serum IgG Levels for vaccine-preventable serogroups W-135 of
     Neisseria meningitidis</Definition>
     </IntputDefinition>
- <IntputDefinition>
  <Name>serumIgGLevelY</Name>
  <Units>ug/mL</Units>
  <Definition>The Serum IgG Levels for vaccine-preventable serogroups Y of
     Neisseria meningitidis</Definition>
     </IntputDefinition>
- <IntputDefinition>
  <Name>C5</Name>
  <Units>ug/mL</Units>
  <Definition>Serum level of the complement component C5</Definition>
     </IntputDefinition>
- <IntputDefinition>
  <Name>C6</Name>
  <Units>ug/mL</Units>
  <Definition>Serum level of the complement component C6</Definition>
     </IntputDefinition>
- <IntputDefinition>
  <Name>C7</Name>
  <Units>ug/mL</Units>
  <Definition>Serum level of the complement component C7</Definition>
     </IntputDefinition>
- <IntputDefinition>
  <Name>C8</Name>
  <Units>ug/mL</Units>
  <Definition>Serum level of the complement component C8</Definition>
     </IntputDefinition>
- <IntputDefinition>
  <Name>C9</Name>
  <Units>ug/mL</Units>
  <Definition>Serum level of the complement component C9</Definition>
     </IntputDefinition>
- <IntputDefinition>
  <Name>Properdin</Name>
  <Units>ug/mL</Units>
  <Definition>Serum level of the complement component Properdin</Definition>
     </IntputDefinition>
- <IntputDefinition>
  <Name>MBL</Name>
  <Units>ug/mL</Units>
```

Figure 9: XML Representation of Perceptron Network
(Continued #2)

```
    <Definition>Serum level of the complement component Mannose-binding lectin
       (MBL)</Definition>
       </IntputDefinition>
-   <IntputDefinition>
    <Name>FcyRIIa</Name>
    <Units>ug/mL</Units>
    <Definition>Measurement of genetic polymorphism for FcyRIIa
       receptor</Definition>
       </IntputDefinition>
-   <IntputDefinition>
    <Name>IL1</Name>
    <Units>ug/mL</Units>
    <Definition>Measurement of genetic polymorphism for IL-1 receptor</Definition>
       </IntputDefinition>
-   <IntputDefinition>
    <Name>IL1R</Name>
    <Units>ug/mL</Units>
    <Definition>Measurement of genetic polymorphism for IL-1R receptor</Definition>
       </IntputDefinition>
-   <IntputDefinition>
    <Name>IL6</Name>
    <Units>ug/mL</Units>
    <Definition>Measurement of genetic polymorphism for IL-6 receptor</Definition>
       </IntputDefinition>
-   <IntputDefinition>
    <Name>IL10</Name>
    <Units>ug/mL</Units>
    <Definition>Measurement of genetic polymorphism for IL-10 receptor</Definition>
       </IntputDefinition>
       </InputDefinitions>
-   <HiddenNeurons>
-   <NeuronDefinition id="CCTest" operator="greaterOrEqual" value="7.0"
       function="SUM">
    <Definition>Measurement of the serum levels of complement
       components.</Definition>
    <Result>Patient is deficient in the Complement Components</Result>
-   <OutputDefinitionRules>
    <OutputDefinitionRule formulaid="ruleCC_1" weight="1.0" />
    <OutputDefinitionRule formulaid="ruleCC_2" weight="1.0" />
    <OutputDefinitionRule formulaid="ruleCC_3" weight="1.0" />
    <OutputDefinitionRule formulaid="ruleCC_4" weight="1.0" />
    <OutputDefinitionRule formulaid="ruleCC_5" weight="1.0" />
    <OutputDefinitionRule formulaid="ruleCC_6" weight="1.0" />
    <OutputDefinitionRule formulaid="ruleCC_7" weight="1.0" />
       </OutputDefinitionRules>
       </NeuronDefinition>
```

**Figure 9: XML Representation of Perceptron Network
(Continued #3)**

```
<NeuronDefinition id="GeneticPolyTest" operator="greaterOrEqual" value="5.0"
    function="SUM">
  <Definition>Measurement of genetic polymorphisms.</Definition>
  <Result>Patient has Genetic Polymorphisms present.</Result>
  <OutputDefinitionRules>
    <OutputDefinitionRule formulaid="ruleGP_1" weight="1.0" />
    <OutputDefinitionRule formulaid="ruleGP_2" weight="1.0" />
    <OutputDefinitionRule formulaid="ruleGP_3" weight="1.0" />
    <OutputDefinitionRule formulaid="ruleGP_4" weight="1.0" />
    <OutputDefinitionRule formulaid="ruleGP_5" weight="1.0" />
  </OutputDefinitionRules>
</NeuronDefinition>
<NeuronDefinition id="R3" operator="lessThan" value="2.0" function="SUM">
  <Definition>If the CC Test AND the Genetic Poly Test show the person is normal,
    both of them will fire, giving us a minimal total of 2.0, therefore if the total is
    less than 2.0, they are NOT normal and the recommendation will be to flag this
    individual for monitoring.</Definition>
  <Result>Flag patient for monitoring</Result>
  <OutputDefinitionRules>
    <OutputDefinitionRule formulaid="CCTest" weight="1.0" />
    <OutputDefinitionRule formulaid="GeneticPolyTest" weight="1.0" />
  </OutputDefinitionRules>
</NeuronDefinition>
</HiddenNeurons>
<OutputNeurons>
<NeuronDefinition id="R1" operator="greaterOrEqual" value="1.0" function="SUM">
  <Definition>If the CC Test or the Genetic Poly Test show the person is NOT normal,
    R3 will fire, giving us a base total of -4.0. If the person is healthy, nothing will
    be contributed from the R3 conclusion. Then, all that is required is for one of
    the serogroups to be deficient in order for the recommendation to evaluate to
    true. Any failure along this path will result in a vaccination NOT being
    recommended.</Definition>
  <Result>Vaccination Recommended</Result>
  <OutputDefinitionRules>
    <OutputDefinitionRule formulaid="ruleR1_1" weight="1.0" />
    <OutputDefinitionRule formulaid="ruleR1_2" weight="1.0" />
    <OutputDefinitionRule formulaid="ruleR1_3" weight="1.0" />
    <OutputDefinitionRule formulaid="ruleR1_4" weight="1.0" />
    <OutputDefinitionRule formulaid="R3" weight="-4.0" />
  </OutputDefinitionRules>
</NeuronDefinition>
<NeuronDefinition id="R2" operator="greaterOrEqual" value="11.0" function="SUM">
```

Figure 9: XML Representation of Perceptron Network
(Continued #4)

<Definition>If the CC Test OR the Genetic Poly Test show the person is NOT normal,
one of them will fire, giving us a minimal total of 10. Then, all that is required
is for one of the serogroups to be deficient in order for the recommendation to
evaluate to true. Any failure along this path will result in a vaccination NOT
being recommended.</Definition>
<Result>Vaccination Recommended</Result>
- <OutputDefinitionRules>
  <OutputDefinitionRule formulaid="ruleR2_1" weight="1.0" />
  <OutputDefinitionRule formulaid="ruleR2_2" weight="1.0" />
  <OutputDefinitionRule formulaid="ruleR2_3" weight="1.0" />
  <OutputDefinitionRule formulaid="ruleR2_4" weight="1.0" />
  <OutputDefinitionRule formulaid="R3" weight="10.0" />
    </OutputDefinitionRules>
    </NeuronDefinition>
    </OutputNeurons>
    </TestRule>

| | |
|---|---|
| ~ | not |
| C(x) | cost of x |
| $CD_X$ | contracting disease X |
| D | death |
| IS | immune status |
| P( x \| y and z) | the probability of x occurring given y and z |
| T(x) | treating x |
| $V_X$ | vaccinate against disease X (more broadly, intervene against disease X) |

Figure 10: Symbology for Diagnostic Goals

Figure 11: Diagnostic Goals

1.1 Conventional Approaches

1.1.1 Vaccinate/intervene against disease X if will reduce occurrence disease X not taking into account patient's IS if
$$P(CD_X | V_X) < P(CD_X | \sim V_X)$$
then $V_X$.

1.1.2 Vaccinate/intervene against disease X if will reduce health care costs directly related to disease X, not taking into account patient's IS if
$$P(CD_X | V_X) * C(T_X | CD_X \text{ and } V_X) + C(V_X) < P(CD_X | \sim V_X) * C(T_X | CD_X \text{ and } \sim V_X)$$
then $V_X$.

1.2 Optimize welfare of the patient

1.2.1 Vaccinate/intervene against disease X if will reduce occurrence disease X if
$$P(CD_X | V_X \text{ and } IS) < P(CD_X | \sim V_X \text{ and } IS)$$
then $V_X$.

1.2.2 Vaccinate/intervene against disease X if will reduce occurrence of any disease if
$$P(CD | V_X \text{ and } IS) < P(CD | \sim V_X \text{ and } IS)$$
then $V_X$.

1.3 Optimize health care costs

1.3.1 Vaccinate/intervene against disease X if will reduce health care costs directly related to disease X if
$$P(CD_X | V_X \text{ and } IS) * C(T_X | CD_X \text{ and } V_X \text{ and } IS) + C(V_X) < P(CD_X | \sim V_X \text{ and } IS) * C(T_X | CD_X \text{ and } \sim V_X \text{ and } IS)$$
then $V_X$.

1.3.2 Vaccinate/intervene against disease X if will reduce overall disease-related health care costs if
$$\sum_{i = alldiseases, includingX} [ P(CD_i | V_X \text{ and } IS) * C(T_i | CD_i \text{ and } V_X \text{ and } IS)] + C(V_X) <$$
$$\sum_{i = alldiseases, includingX} [ P(CDi | \sim V_X \text{ and } IS) * C(Ti | CD_i \text{ and } \sim V_X \text{ and } IS)$$
then $V_X$.

Figure 11: Diagnostic Goals (Continued)

1.4    Optimize life-insurance costs

1.4.1    Vaccinate/intervene against disease X if will increase life-expectancy if $P(CD_X \mid V_X \text{ and } IS) * P(D \mid CD_X \text{ and } V_X \text{ and } IS) +$
$P(\sim CD_X \mid V_X \text{ and } IS) * P(D \mid \sim CD_X \text{ and } V_X \text{ and } IS)$
$<$
$P(CD_X \mid \sim V_X \text{ and } IS) * P(D \mid CD_X \text{ and } \sim V_X \text{ and } IS) +$
$P(\sim CD_X \mid \sim V_X \text{ and } IS) * P(D \mid \sim CD_X \text{ and } \sim V_X \text{ and } IS)$ then $V_X$.

Figure 12: Example Database Schema, Patient Info

```
create table Patient_Info (
    PT_ID   NUMBER(9)
        CONSTRAINT ptid_nn NOT NULL ,
    PT_FT_NM   VARCHAR2(100),
    PT_LT_NM   VARCHAR2(100),
    PT_BIRTH_DT DATE
        CONSTRAINT birthdate_nn NOT NULL,
    PT_GENDER CHAR(1)
        CONSTRAINT gender_nn NOT NULL ,
    PT_ADDRESS1   VARCHAR2(200) ,
    PT_ADDRESS2   VARCHAR2(200) ,
    PT_CITY   VARCHAR2(50) ,
    PT_ZIP_CODE   NUMBER(5),
    PT_STATE   CHAR(2) ,
    PT_COUNTRY   VARCHAR2(200) ,
    PT_RES_TEL   NUMBER(9) ,
    PT_IS_LATINO   NUMBER(1) ,
    PT_IS_WHITE   NUMBER(1) ,
    PT_IS_BLACK   NUMBER(1) ,
    PT_IS_AFRCN_AMRCN   NUMBER(1) ,
    PT_IS_ASIAN   NUMBER(1) ,
    PT_IS_NTV_HAWAI   NUMBER(1) ,
    PT_IS_PAC_ISLNDR   NUMBER(1) ,
    PT_IS_AMRN_INDN   NUMBER(1) ,
    PT_IS_NTV_ALSK   NUMBER(1)
)

TABLESPACE IMMUNOPRINT_PROD;

create table VISIT_INFO (
    VT_ID NUMBER(10)
        CONSTRAINT vtid_nn NOT NULL ,
    PT_ID   NUMBER(9),
    VT_DT      DATE
        CONSTRAINT vtDate_nn NOT NULL ,
    PT_AGE_AT_VISIT      NUMBER(5,2),
    PT_IS_PREG         NUMBER(1) ,
    PT_LAST_GESTATION    DATE ,
    PT_TOBACCO_USE      NUMBER(1) ,
    PT_TOBACCO_FREQ        NUMBER(10) ,
    PAYMENT_SRC       NUMBER(10) ,
    VT_ADVERSE_REASON  NUMBER(10) ,
    VT_REASON1         VARCHAR2(200) ,
    VT_REASON2         VARCHAR2(200) ,
```

Figure 12: Example Database Schema, Patient Info (Continued #1)

```
VT_REASON3              VARCHAR2(200),
VT_MAJOR_REASON         NUMBER(10),
PT_HEIGHT       NUMBER(5,2),
PT_WEIGHT       NUMBER(5,2),
PT_TEMPERATURE          NUMBER(5,2),
PT_S_BLD_PRESSURE       NUMBER(5,2),
PT_D_BLD_PRESS          NUMBER(5,2),
VT_DURATION             FLOAT(3),
VT_DISP_FOLLOW_UP_REQ   NUMBER(1),
VT_DISP_RETURN_IF_NEEDED NUMBER(1),
VT_DISP_REFER_OTHR_PHY          NUMBER(1),
VT_DISP_RETURN_AT_SPEC_TIME     NUMBER(1),
VT_DISP_TEL_FOLLOW_UP           NUMBER(1),
VT_DISP_REFER_EMERGENCY         NUMBER(1),
VT_DISP_ADMIT_TO_HOSPITAL       NUMBER(1),
VT_DISP_OTHER           NUMBER(1),
VT_DISP_OTHER_DETAIL    VARCHAR2(300),
PT_PRIMARY_PHY          NUMBER(1),
PT_IS_REFERAL           NUMBER(1),
PT_IS_ESTABLISHED       NUMBER(1),
PT_NUM_PREV_VISITS      NUMBER(3),
PT_PRIMARY_DIAG         VARCHAR2(300),
PT_DIAG2        VARCHAR2(300),
PT_DIAG3        VARCHAR2(300),
PT_PRE_AIDS             NUMBER(1),
PT_PRE_ANAPHYLAXSIS     NUMBER(1),
PT_PRE_ANEMIA           NUMBER(1),
PT_PRE_ARTHRITIS        NUMBER(1),
PT_PRE_ARTIFICIAL_HEART_VALS    NUMBER(1),
PT_PRE_ARTIFICIAL_JOINT NUMBER(1),
PT_PRE_ASTHMA           NUMBER(1),
PT_PRE_ALLERGIES        NUMBER(1),
PT_PRE_ALLERGIES_DET VARCHAR2(200),
PT_PRE_BACK_PROBLEM     NUMBER(1),
PT_PRE_BLD_DIS          NUMBER(1),
PT_PRE_CANCER           NUMBER(1),
PT_PRE_CANCER_DET       NUMBER(1),
PT_PRE_CHEMO            NUMBER(1),
PT_PRE_CIRCULATRY_PROB  NUMBER(1),
PT_PRE_CHF      NUMBER(1),
PT_PRE_CHRONIC_RENAL_FAIL       NUMBER(1),
PT_PRE_COLD             NUMBER(1),
PT_PRE_COPD             NUMBER(1),
PT_PRE_CORTISONE        NUMBER(1),
```

Figure 12: Example Database Schema, Patient Info (Continued #2)

```
PT_PRE_CON_HEART_LESIONS        NUMBER(1),
PT_PRE_COUGH_PRESISTENT         NUMBER(1),
PT_PRE_COUGH_UP_BLD             NUMBER(1),
PT_PRE_DEPRESSION               NUMBER(1),
PT_PRE_DIABETES                 NUMBER(1),
PT_PRE_DRASTIC_WGT_LOSS         NUMBER(1),
PT_PRE_DRUG_DEP                 NUMBER(1),
PT_PRE_EPILEPSY                 NUMBER(1),
PT_PRE_EXCESSIVE_BLEEDING       NUMBER(1),
PT_PRE_FAINTING                 NUMBER(1),
PT_PRE_FOOD_ALLERGIES           NUMBER(1),
PT_PRE_FEN_PHEN_USED            NUMBER(1),
PT_PRE_REDUX_USED               NUMBER(1),
PT_PRE_HEART_PROB_DET           VARCHAR2(300),
PT_PRE_HEMOPHILIA               NUMBER(1),
PT_PRE_HERPES                   NUMBER(1),
PT_PRE_HEP                      NUMBER(1),
PT_PRE_HEP_TYP1                 VARCHAR2(4),
PT_PRE_HEP_TYP2                 VARCHAR2(4),
PT_PRE_HYPERLIPIDEMIA           NUMBER(1),
PT_PRE_HYPERTENSION             NUMBER(1),
PT_PRE_INCEST                   NUMBER(1),
PT_PRE_CHILD_ABUSE              NUMBER(1),
PT_PRE_JAUNDICE                 NUMBER(1),
PT_PRE_HIV_POS                  NUMBER(1),
PT_PRE_KIDNEY_DIS_MAL           NUMBER(1),
PT_PRE_LATEX_ALLERGY            NUMBER(1),
PT_PRE_LIVER_DIS                NUMBER(1),
PT_PRE_MITRAL_VALVE_PROLAPSE    NUMBER(1),
PT_PRE_NERV_PROB                NUMBER(1),
PT_PRE_OBESITY                  NUMBER(1),
PT_PRE_OSTEOPOROSIS             NUMBER(1),
PT_PRE_PACEMAKER                NUMBER(1),
PT_PRE_PERSIST_DIARRHEA         NUMBER(1),
PT_PRE_PSYCHIATIC_CARE          NUMBER(1),
PT_PRE_RAPID_WGT_LOSS           NUMBER(1),
PT_PRE_RADIATION_TREAT          NUMBER(1),
PT_PRE_RADIATION_DET            VARCHAR2(200),
PT_PRE_REPLACE_SURG             NUMBER(1),
PT_PRE_REPLACE_SURG_DET         VARCHAR2(200),
PT_PRE_RESPIRATORY_DIS          NUMBER(1),
PT_PRE_SKIN_RASH                NUMBER(1),
PT_PRE_SP_DIET                  NUMBER(1),
```

Figure 13: Example Database Schema, Visit Info

```
PT_PRE_SP_DIET_DESC         VARCHAR2(200),
PT_PRE_SPINA_BIFIDA         NUMBER(1),
PT_PRE_STRESS               NUMBER(1),
PT_PRE_STROKE               NUMBER(1),
PT_PRE_SURGICAL_IMPLANTS         NUMBER(1),
PT_PRE_SURGICAL_IMPLANTS_DET     VARCHAR2(200),
PT_PRE_SWELLING_FEET_ANKLES      NUMBER(1),
PT_PRE_THYROID_DIS          NUMBER(1),
PT_PRE_TONSILLITIS          NUMBER(1),
PT_PRE_TUBERCULOSIS         NUMBER(1),
PT_PRE_ULCER                NUMBER(1),
PT_PRE_COLITIS              NUMBER(1),
PT_PRE_VENERIAL_DIS         NUMBER(1),
PT_PRE_CONDITION_DET        VARCHAR2(400),
PT_PRE_DIS_MANG_ENROLL           NUMBER(1),
DIGNOSTIC_SRV_PERF          NUMBER(1),
BREAST_EXAM                 NUMBER(1),
PELVIC_EXAM                 NUMBER(1),
RECTAL_EXAM                 NUMBER(1),
SKIN_EXAM         NUMBER(1),
DEPRESSION_SCREEN           NUMBER(1),
BONE_MATERIAL_DENSITY            NUMBER(1),
MAMMOGRAPHY                 NUMBER(1),
   MRI       NUMBER(1),
   CT        NUMBER(1),
   PET       NUMBER(1),
   ULTRASOUND              NUMBER(1)
) TABLESPACE IMMUNOPRINT_PROD;
```

Figure 14: Example Database Schema, Test Results

```
create table VISIT_TEST_RESULTS (
    VT_ID NUMBER(10)
            CONSTRAINT tvtid_nn NOT NULL ,
    PT_ID  NUMBER(9)
            CONSTRAINT tptid_nn NOT NULL ,
    IMMUNOSCORE          Number(10,4),
    GAMP         Number(10,4),
    GAMPActivity         Number(10,4),
    GCMP         Number(10,4),
    GCMPActivity  Number(10,4),
    GWMP                 Number(10,4),
    GWMPActivity         Number(10,4),
    GYMP         Number(10,4),
    GYMPActivity         Number(10,4),
    GBMP         Number(10,4),
    GBMPActivity         Number(10,4),
    C5           Number(10,4),
    C6           Number(10,4),
    C7           Number(10,4),
    C8           Number(10,4),
    C9           Number(10,4),
    PROPERDIN Number(10,4),
    MBL          Number(10,4),
    FCYRLLA              Number(10,4),
    IL_1         Number(10,4),
    IL_1R        Number(10,4),
    IL_6         Number(10,4),
    IL_10        Number(10,4),
    antibodyHBs          Number(10,4),
    antibodyDiphtheria   Number(10,4),
    antibodyTetanus              Number(10,4),
    antibodyPT1          Number(10,4),
    antibodyPRN1         Number(10,4),
    antibodyFHA1                 Number(10,4),
    antibodyFimbriae     Number(10,4),
    antibodyPRP          Number(10,4),
    antibodyPolio1               Number(10,4),
    antibodyPolio2               Number(10,4),
    antibodyPolio3               Number(10,4),
    antibodyMeasles              Number(10,4),
    antibodyRubella              Number(10,4),
    antibodyVaricella    Number(10,4),
    antibodyPneumococcalSerotypes       Number(10,4),
```

Figure 14: Example Database Schema, Test Results (Continued)

```
antibodyIgG         Number(10,4),
antibodyIgA         Number(10,4),
antibodyIgM         Number(10,4),
antibodyHSVIgG      Number(10,4),
antibodyHSV1        Number(10,4),
antibodyHSV2        Number(10,4),
antibodyGonorrhoeae Number(10,4),
antibodyPallidum    Number(10,4),
tCellPallidum       Number(10,4),
antibodyHIV         Number(10,4),
tCellHIV            Number(10,4),
antibodyGBS1        Number(10,4),
antibodyGBS2        Number(10,4),
antibodyGBS3        Number(10,4),
antibodyTh1Cytokine Number(10,4),
antibodyTh2Cytokine Number(10,4)
TABLESPACE IMMUNOPRINT_PROD;
```

Figure 15: Patient Age Intervals

| Pt Age At Visit (Age in years) |
|---|
| 0.17 |
| 0.5 |
| 1 |
| 2 |
| 5 |
| 12 |
| 16 |
| 21 |

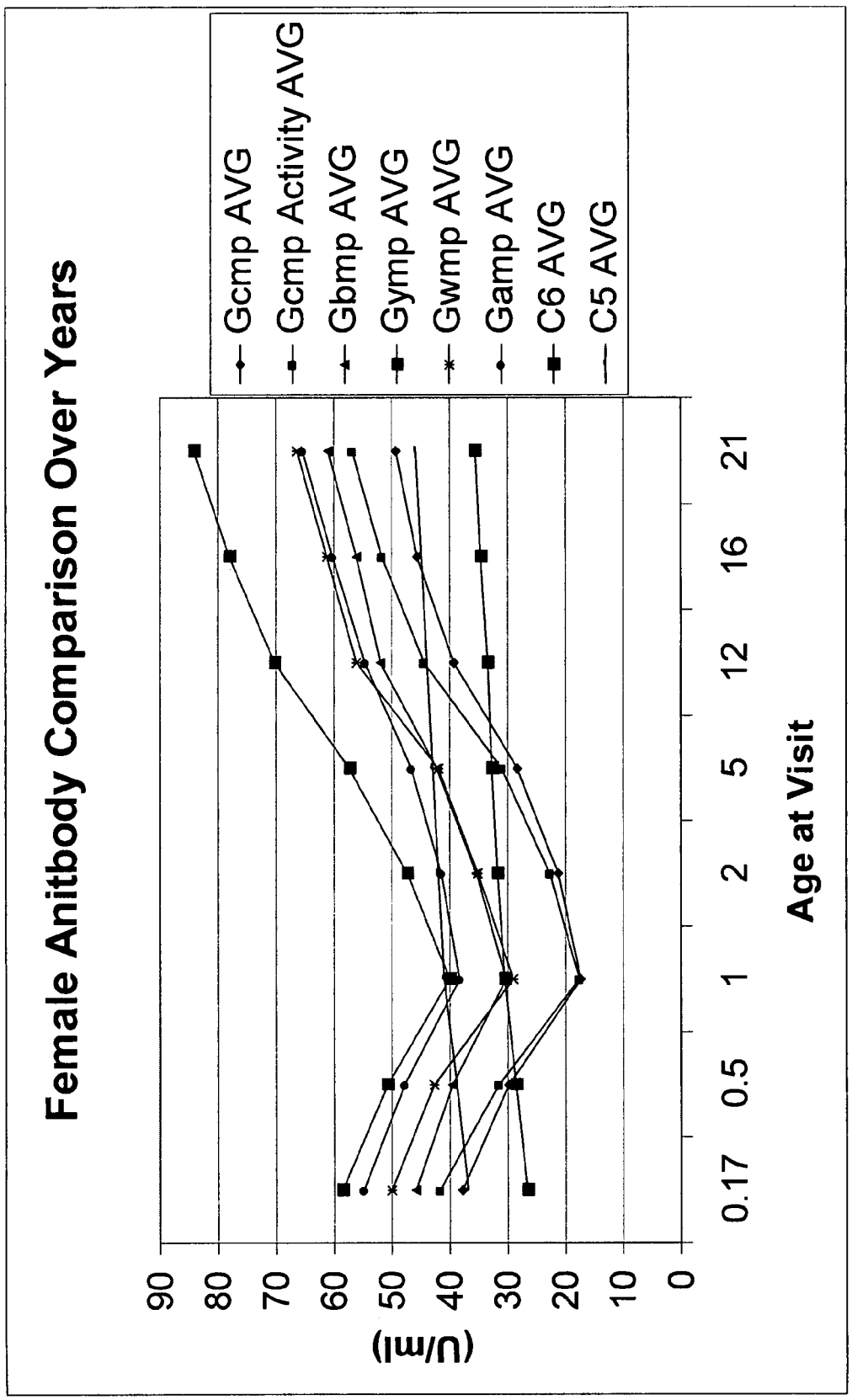
Figure 16: Example of Levels of Various Antibodies in Female Simulated Population

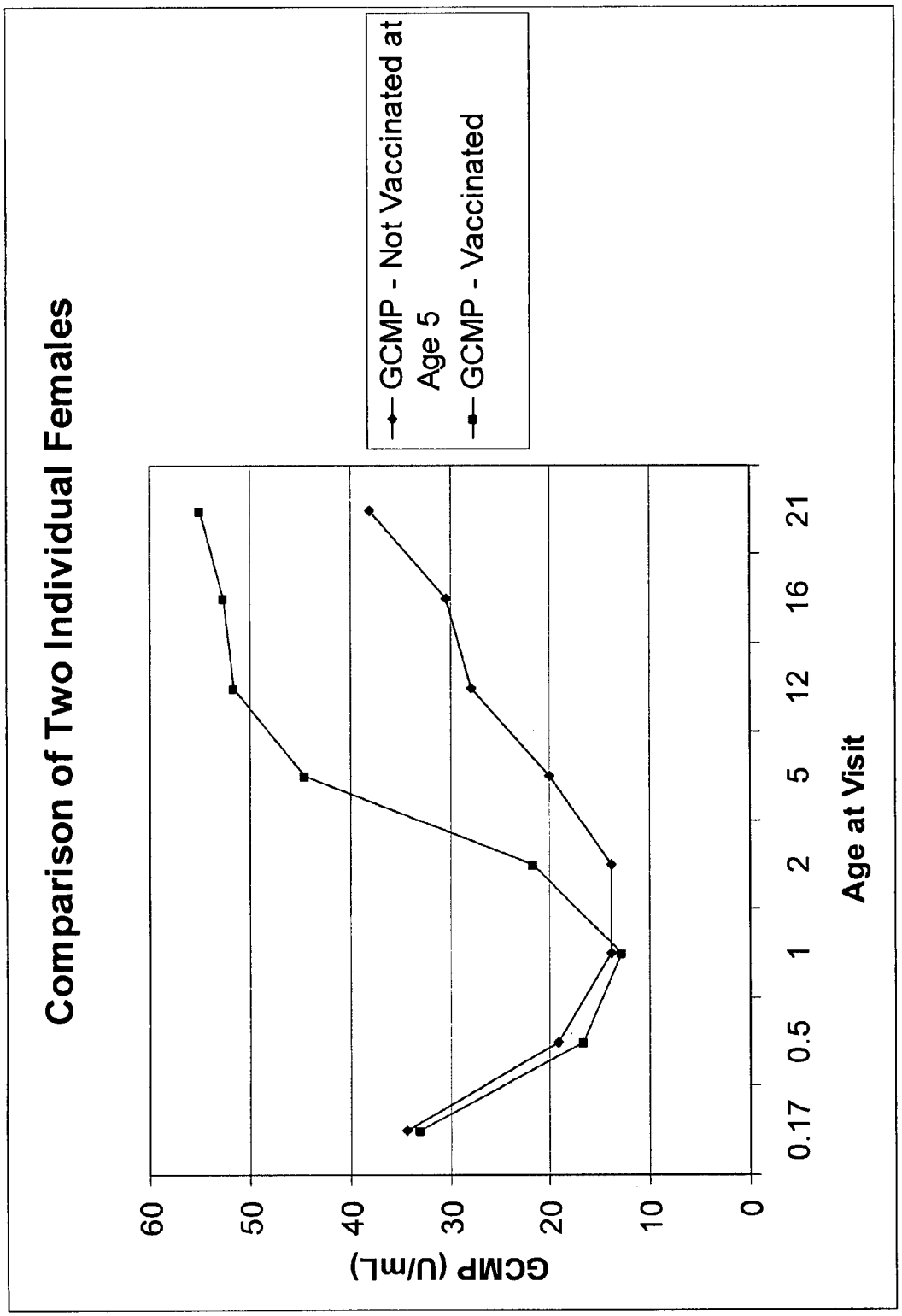
Figure 17: Example of Comparison between Vaccinated and Non-Vaccinated Individuals

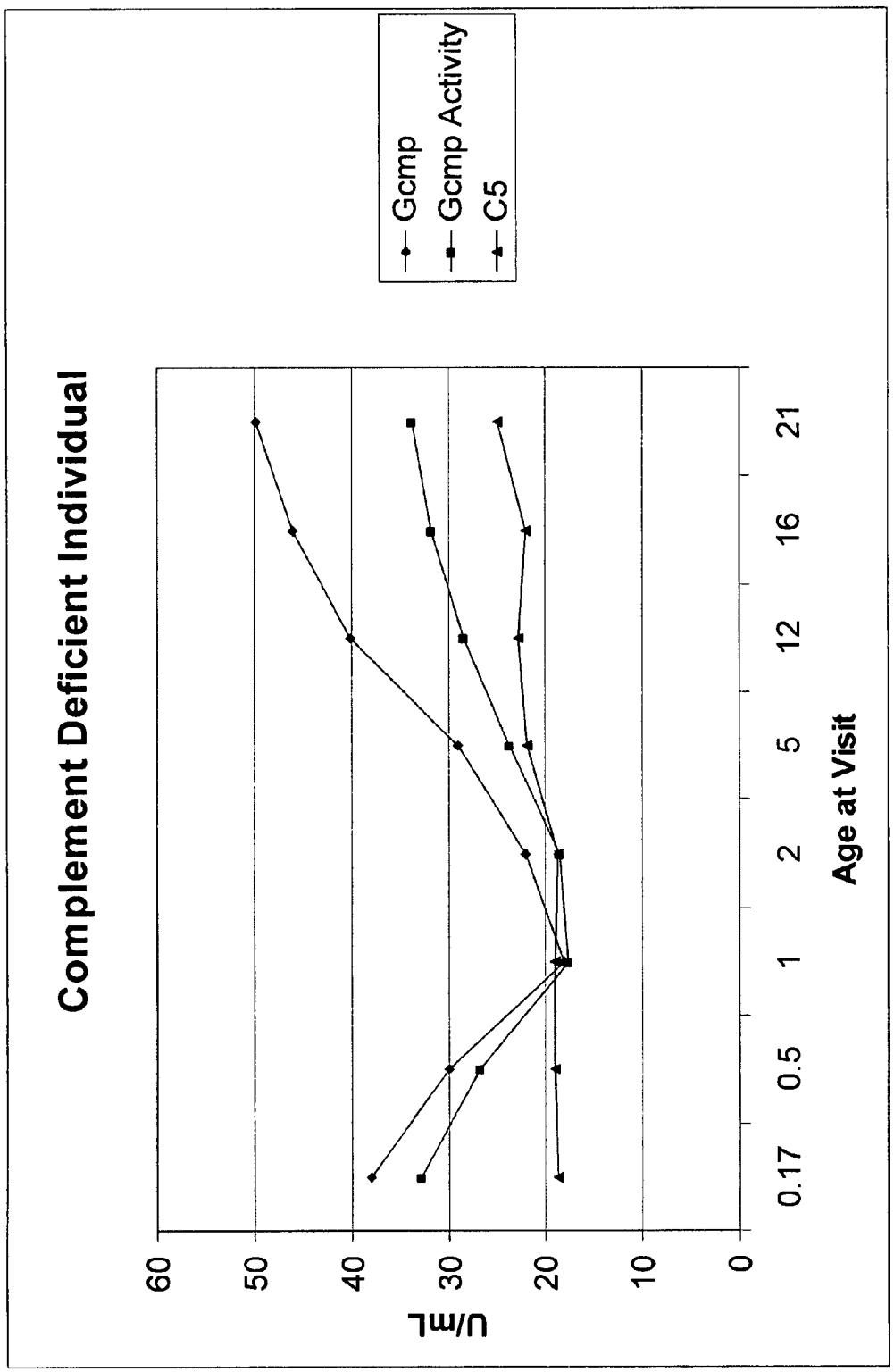
Figure 18: Antibody Levels in a Complement-Deficient Individual

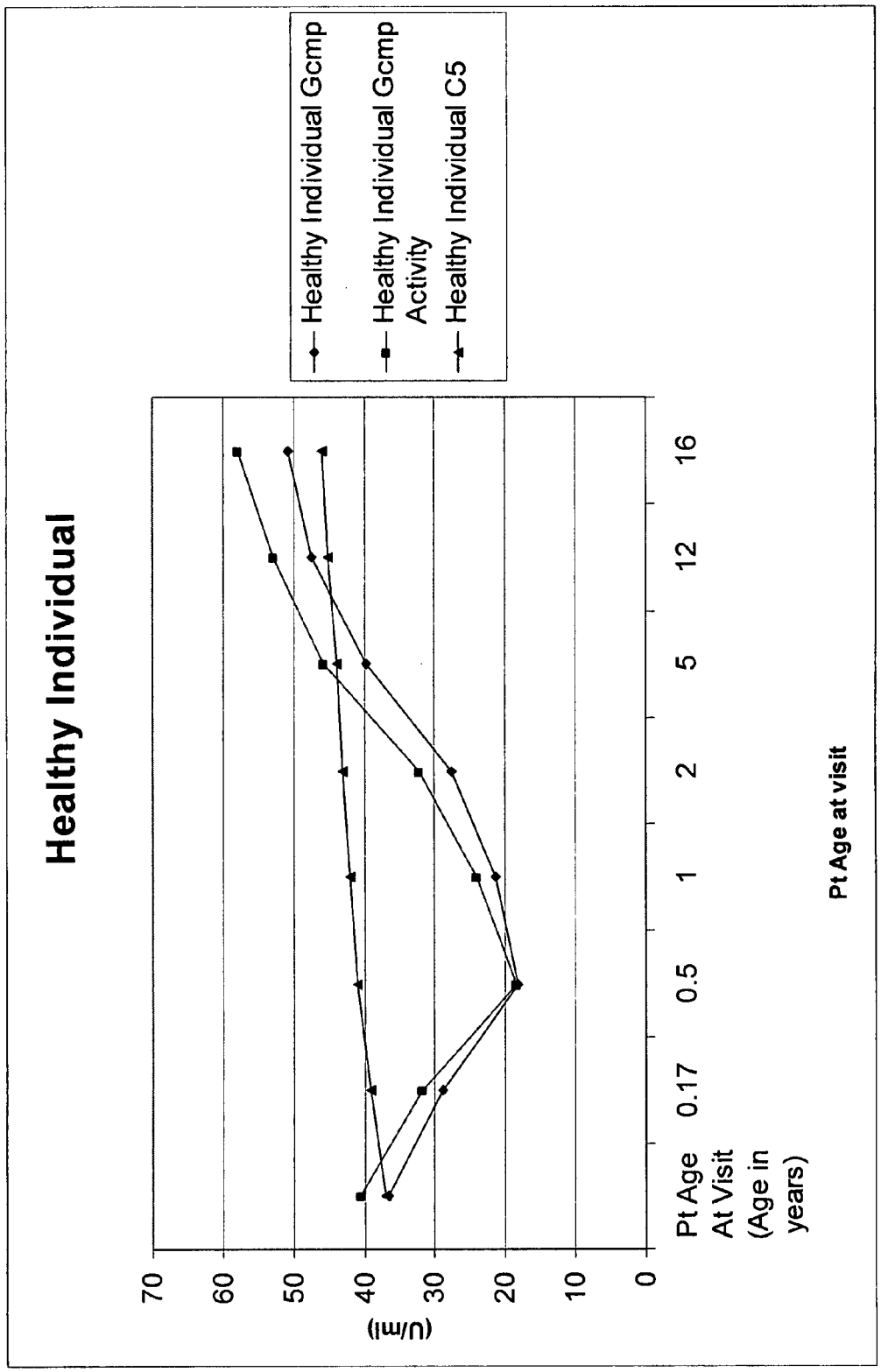
Figure 19: Antibody Levels in an Individual With No Complement Deficiency

```
SELECT * FROM PATIENT_INFO
WHERE PT_LT_NM LIKE "SMITH" AND
PT_GENDER = 0;
```

Figure 19A: Example SQL Query

| Pt Age At Visit (Age in years) | Activity Vs Gcmp | Gamp Vs Gcmp | Gbmp Vs Gcmp | Gwmp Vs Gcmp | Gymp Vs Gcmp | C5 Vs Gcmp | C6 Vs Gcmp |
|---|---|---|---|---|---|---|---|
| 0.17 | | | | | | | |
| 0.5 | 0.99277579 | 0.630974777 | 0.848328143 | 0.771686375 | 0.829087982 | 0.6619765 | 0.0634558 |
| 1 | 0.75627538 | 0.760620792 | 0.782187342 | 0.779572654 | 0.784921088 | 0.7689116 | 0.0005239 |
| 2 | 0.75314684 | 0.807785412 | 0.809991603 | 0.75287188 | 0.706625551 | 0.5747302 | 0.0946182 |
| 5 | 0.66128901 | 0.769878799 | 0.763862956 | 0.730078492 | 0.618853492 | 0.3573768 | 0.1401185 |
| 12 | 0.67390454 | 0.787933834 | 0.817882396 | 0.711657244 | 0.641775362 | 0.0380292 | 0.1086897 |
| 16 | 0.7418404 | 0.823973559 | 0.802267384 | 0.755366227 | 0.761504743 | 0.0301347 | 0.0305234 |
| 21 | 0.78471377 | 0.862998692 | 0.912548481 | 0.791712354 | 0.826684706 | 0.1550324 | 0.0034005 |

Figure 19B: Correlation Among Antibody Levels in Female Population

All

| Field | All Regions | SS Africa | North Africa | Latin America | SE Asia | East Europe | Asia |
|---|---|---|---|---|---|---|---|
| Rubella Antibody Level | 0.01696 | 0.01725 | 0.02820 | 0.02087 | 0.01259 | 0.04209 | -0.00071 |
| Hep A Optical Density | 0.00289 | -0.01292 | -0.00383 | 0.00548 | 0.00428 | 0.01470 | 0.01250 |
| Measles Dade | 0.05962 | 0.02176 | 0.02851 | 0.04458 | 0.01731 | 0.05282 | 0.05664 |
| Measles Zeus | -0.00011 | -0.00678 | 0.00019 | 0.00005 | -0.04094 | -0.01052 | -0.00276 |
| Measles Ratios (Zeus) | -0.01871 | 0.00109 | 0.00262 | 0.00396 | -0.02531 | 0.01040 | 0.01574 |
| Measles Titre (Dade) | 0.00311 | 0.01208 | 0.03572 | 0.03274 | 0.00604 | 0.04483 | 0.02312 |
| Mumps Optical Density (Dade) | 0.04576 | 0.01728 | 0.02362 | 0.04142 | 0.01191 | 0.01783 | 0.02968 |
| Mumps Titration Dilution | -0.01614 | 0.01365 | 0.01055 | 0.00607 | -0.00101 | 0.00922 | -0.00684 |
| Varicella Titration Dilution | 0.58748 | 0.20802 | 0.20782 | 0.38211 | 0.34543 | 0.19549 | 0.44194 |

Males

| Field | All Regions | SS Africa | North Africa | Latin America | SE Asia | East Europe | Asia |
|---|---|---|---|---|---|---|---|
| Rubella Antibody Level | 0.00934 | 0.00894 | 0.04803 | -0.00329 | 0.09510 | 0.08321 | -0.00672 |
| Hep A Optical Density | 0.03123 | -0.00313 | -0.04762 | 0.03915 | 0.02641 | 0.07062 | 0.13102 |
| Measles Dade | 0.06740 | 0.09839 | -0.00457 | 0.05990 | 0.02038 | 0.08383 | 0.07644 |
| Measles Zeus | -0.00961 | 0.00902 | -0.02355 | 0.00266 | -0.02102 | 0.05920 | -0.03069 |
| Measles Ratios (Zeus) | -0.02176 | 0.01126 | -0.03130 | -0.02775 | -0.03309 | 0.03816 | -0.08083 |
| Measles Titre (Dade) | -0.01926 | -0.03419 | 0.06316 | 0.00003 | -0.04670 | 0.04905 | -0.03836 |
| Mumps Optical Density (Dade) | 0.08632 | 0.10904 | 0.05878 | 0.03885 | 0.00055 | 0.01187 | 0.08915 |
| Mumps Titration Dilution | -0.06019 | -0.05772 | 0.06635 | -0.03401 | -0.03514 | -0.01228 | -0.06619 |
| Varicella Titration Dilution | 0.66187 | 0.65630 | 0.32436 | 0.46052 | 0.70381 | 0.34140 | 0.72795 |

Females

| Field | All Regions | SS Africa | North Africa | Latin America | SE Asia | East Europe | Asia |
|---|---|---|---|---|---|---|---|
| Rubella Antibody Level | 0.01442 | 0.04756 | 0.02948 | 0.04313 | 0.02369 | 0.00416 | -0.08200 |
| Hep A Optical Density | 0.02049 | 0.00261 | 0.04691 | 0.01933 | 0.04588 | 0.01965 | -0.00638 |
| Measles Dade | 0.05086 | 0.03566 | 0.05466 | 0.00542 | 0.07098 | 0.05822 | 0.08963 |
| Measles Zeus | -0.00056 | -0.00007 | -0.00366 | -0.00014 | -0.01859 | -0.04096 | -0.02937 |
| Measles Ratios (Zeus) | -0.03599 | -0.01193 | 0.00604 | -0.04593 | -0.03991 | -0.00520 | -0.03539 |
| Measles Titre (Dade) | 0.01452 | 0.02839 | 0.09569 | 0.04440 | -0.01764 | 0.04325 | 0.00504 |
| Mumps Optical Density (Dade) | 0.10631 | 0.03880 | 0.05131 | 0.10664 | 0.01757 | 0.01200 | 0.05186 |
| Mumps Titration Dilution | -0.06906 | 0.00698 | -0.02306 | -0.00748 | 0.00162 | 0.01922 | 0.04560 |
| Varicella Titration Dilution | 0.70476 | 0.38696 | 0.51598 | 0.70693 | 0.42507 | 0.42465 | 0.68231 |

Fig. 20
Correlations of Various DB Variables With Varicella OD

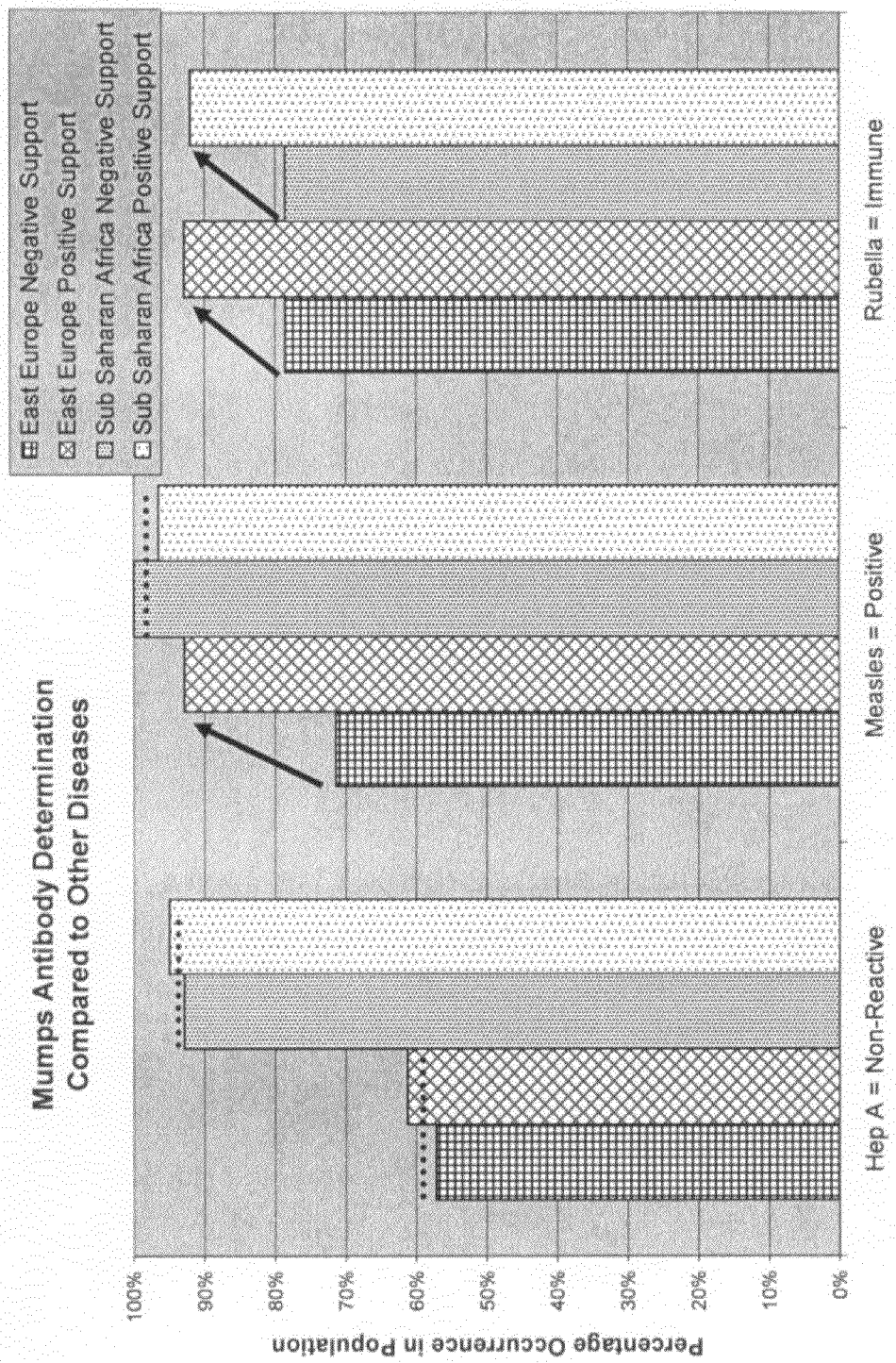

Figs. 20G1 (3 tables)

Overall CMV correlation

| Field | All Regions | SS Africa | Latin America | SE Asia | East Europe | South Asia |
|---|---|---|---|---|---|---|
| Diphtheria IU | 0.06204 | 0.10449 | -0.09148 | -0.18938 | -0.13492 | -0.00316 |
| Diphtheria OD | -0.07111 | -0.09896 | 0.05128 | -0.29001 | -0.12947 | 0.00146 |
| Hep A | -0.12213 | -0.02422 | -0.15587 | 0.04140 | -0.10287 | 0.00909 |
| Hep B Core Antibody OD | 0.00586 | -0.05385 | -0.03272 | -0.11704 | 0.13585 | 0.00206 |
| Hep B e Antibody Ratio | 0.03304 | 0.06827 | 0.03741 | 0.01687 | -0.00750 | 0.00257 |
| Hep B e Antigen Ratio | -0.19936 | 0.07626 | 0.03741 | -0.21239 | -0.03802 | 0.00257 |
| Hep B e Surface Antibody OD | -0.00325 | 0.00089 | -0.00247 | -0.12866 | 0.09006 | 0.00073 |
| Hep B e Surface Antigen OD | -0.03144 | -0.18986 | 0.03823 | -0.16545 | -0.07491 | 0.00253 |
| Hep C Antibody OD | 0.00495 | 0.02174 | 0.10211 | 0.00317 | 0.00652 | -0.00145 |
| Measles OD (Dade Behring) | 0.17864 | -0.01226 | 0.19262 | 0.22281 | 0.13331 | 0.00295 |
| Measles OD (Zeus) | 0.07232 | 0.07635 | -0.09413 | 0.11893 | -0.00308 | 0.01283 |
| Measles Ration (Zeus) | 0.07194 | -0.06741 | 0.12509 | 0.12624 | -0.01158 | -0.02105 |
| Measles Titre (Dade Behring) | -0.17866 | 0.00730 | 0.01042 | 0.12894 | 0.01403 | -0.00102 |
| Mumps OD (Dade Behring) | 0.16097 | 0.23983 | 0.25732 | 0.02840 | 0.12708 | 0.00923 |
| Mumps Titre (Dade Behring) | -0.06321 | -0.05410 | -0.28924 | -0.14047 | 0.18477 | -0.01486 |
| Rubella Antibody IU | 0.05919 | 0.03829 | 0.16911 | 0.12973 | -0.11395 | 0.00245 |
| Tetanus IU | 0.01262 | -0.21588 | 0.14538 | -0.20496 | 0.24935 | 0.00430 |
| Tetanus OD | -0.02347 | 0.03881 | -0.11208 | 0.08103 | 0.20311 | -0.00295 |
| Varicella OD (Dade Behring) | 0.12002 | 0.22144 | 0.20910 | 0.08154 | 0.02806 | -0.00024 |
| Varicella Titre (Dade Behring) | -0.14047 | -0.01540 | -0.53989 | 0.00325 | -0.15981 | -0.00017 |

Fig. 20G1(a)

Male CMV correlation

| Field | All Regions | SS Africa | Latin America | SE Asia | East Europe | South Asia |
|---|---|---|---|---|---|---|
| Diphtheria IU | 0.02906 | 0.17924 | -0.11410 | 0.02620 | 0.04988 | -0.00541 |
| Diphtheria OD | 0.06772 | 0.10382 | -0.17861 | -0.05509 | 0.16817 | 0.00678 |
| Hep A | -0.18047 | -0.06131 | -0.15461 | -0.07196 | 0.08356 | 0.17128 |
| Hep B Core Antibody OD | 0.02261 | 0.13834 | 0.00385 | -0.10567 | 0.14086 | 0.00983 |
| Hep B e Antibody Ratio | 0.29491 | -0.13476 | 0.10816 | 0.21147 | 0.00000 | 0.00000 |
| Hep B e Antigen Ratio | 0.13834 | 0.11882 | 0.10816 | 0.07390 | 0.00000 | 0.00000 |
| Hep B e Surface Antibody OD | 0.00145 | 0.11679 | -0.11530 | -0.03051 | -0.12289 | -0.00095 |
| Hep B e Surface Antigen OD | -0.31524 | 0.00825 | 0.10817 | -0.13486 | 0.00007 | 0.00735 |
| Hep C Antibody OD | 0.01603 | -0.03577 | 0.31195 | -0.07468 | 0.14488 | -0.00428 |
| Measles OD (Dade Behring) | 0.26703 | 0.01208 | 0.18602 | 0.12403 | 0.18079 | -0.01491 |
| Measles OD (Zeus) | 0.15716 | -0.03273 | 0.14405 | -0.04802 | -0.06837 | 0.03105 |
| Measles Ration (Zeus) | -0.26186 | -0.15489 | -0.04757 | -0.03479 | 0.08315 | -0.29836 |
| Measles Titre (Dade Behring) | -0.16172 | 0.00186 | 0.05042 | 0.09964 | 0.08136 | 0.01985 |
| Mumps OD (Dade Behring) | 0.12068 | 0.26562 | -0.02806 | -0.03802 | -0.03296 | 0.04378 |
| Mumps Titre (Dade Behring) | -0.19629 | -0.02223 | -0.15811 | -0.13448 | -0.24760 | -0.10340 |
| Rubella Antibody IU | 0.05636 | -0.07312 | 0.37438 | 0.19762 | -0.38694 | 0.00403 |
| Tetanus IU | 0.01990 | -0.07942 | 0.01139 | 0.00638 | 0.03102 | 0.00389 |
| Tetanus OD | -0.13006 | -0.12992 | 0.00851 | -0.09768 | 0.29323 | -0.00802 |
| Varicella OD (Dade Behring) | 0.16154 | 0.35122 | 0.01538 | 0.06709 | 0.01039 | 0.01751 |
| Varicella Titre (Dade Behring) | -0.05466 | 0.05537 | -0.05841 | 0.20709 | -0.14953 | -0.02540 |

Female CMV correlation

| Field | All Regions | SS Africa | Latin America | SE Asia | East Europe | South Asia |
|---|---|---|---|---|---|---|
| Diphtheria IU | -0.01927 | -0.02802 | -0.03632 | -0.22799 | -0.19753 | -0.07972 |
| Diphtheria OD | -0.10361 | -0.05515 | 0.08559 | -0.28254 | -0.21964 | -0.04970 |
| Hep A | -0.09124 | -0.03799 | -0.07101 | -0.00655 | -0.15721 | 0.00270 |
| Hep B Core Antibody OD | -0.01619 | -0.13328 | -0.01215 | 0.01694 | 0.13912 | 0.09476 |
| Hep B e Antibody Ratio | -0.13054 | -0.00060 | 0.00000 | -0.09236 | -0.04423 | 0.04483 |
| Hep B e Antigen Ratio | -0.14065 | -0.04431 | 0.00000 | -0.12263 | -0.06602 | 0.04483 |
| Hep B e Surface Antibody OD | 0.00550 | -0.00621 | 0.01014 | -0.01461 | 0.17660 | 0.12429 |
| Hep B e Surface Antigen OD | 0.03234 | 0.00295 | 0.00092 | -0.07911 | 0.06099 | 0.04455 |
| Hep C Antibody OD | -0.05002 | -0.02311 | -0.08615 | -0.01943 | -0.25055 | 0.08390 |
| Measles OD (Dade Behring) | 0.14521 | -0.01250 | 0.13860 | 0.23976 | 0.06459 | 0.07813 |
| Measles OD (Zeus) | 0.07052 | 0.08213 | -0.05278 | 0.19630 | 0.09404 | -0.05483 |
| Measles Ration (Zeus) | 0.08024 | -0.01039 | 0.06806 | 0.07083 | -0.04506 | 0.00159 |
| Measles Titre (Dade Behring) | -0.08155 | 0.09647 | -0.03716 | 0.07114 | 0.06712 | -0.04388 |
| Mumps OD (Dade Behring) | 0.18499 | 0.15122 | 0.15483 | -0.10822 | 0.11605 | 0.09558 |
| Mumps Titre (Dade Behring) | -0.05000 | -0.00329 | -0.10505 | -0.12886 | 0.17188 | 0.03786 |
| Rubella Antibody IU | 0.09883 | 0.01915 | 0.08088 | 0.00996 | -0.02508 | 0.09023 |
| Tetanus IU | -0.00963 | 0.01915 | 0.06354 | -0.21386 | 0.13183 | 0.07122 |
| Tetanus OD | 0.00905 | -0.07171 | -0.06639 | 0.08111 | 0.03791 | -0.01818 |
| Varicella OD (Dade Behring) | 0.07723 | 0.10620 | 0.10278 | 0.12192 | -0.01955 | -0.03307 |
| Varicella Titre (Dade Behring) | -0.06276 | 0.07725 | -0.29395 | -0.18099 | -0.03024 | 0.07746 |

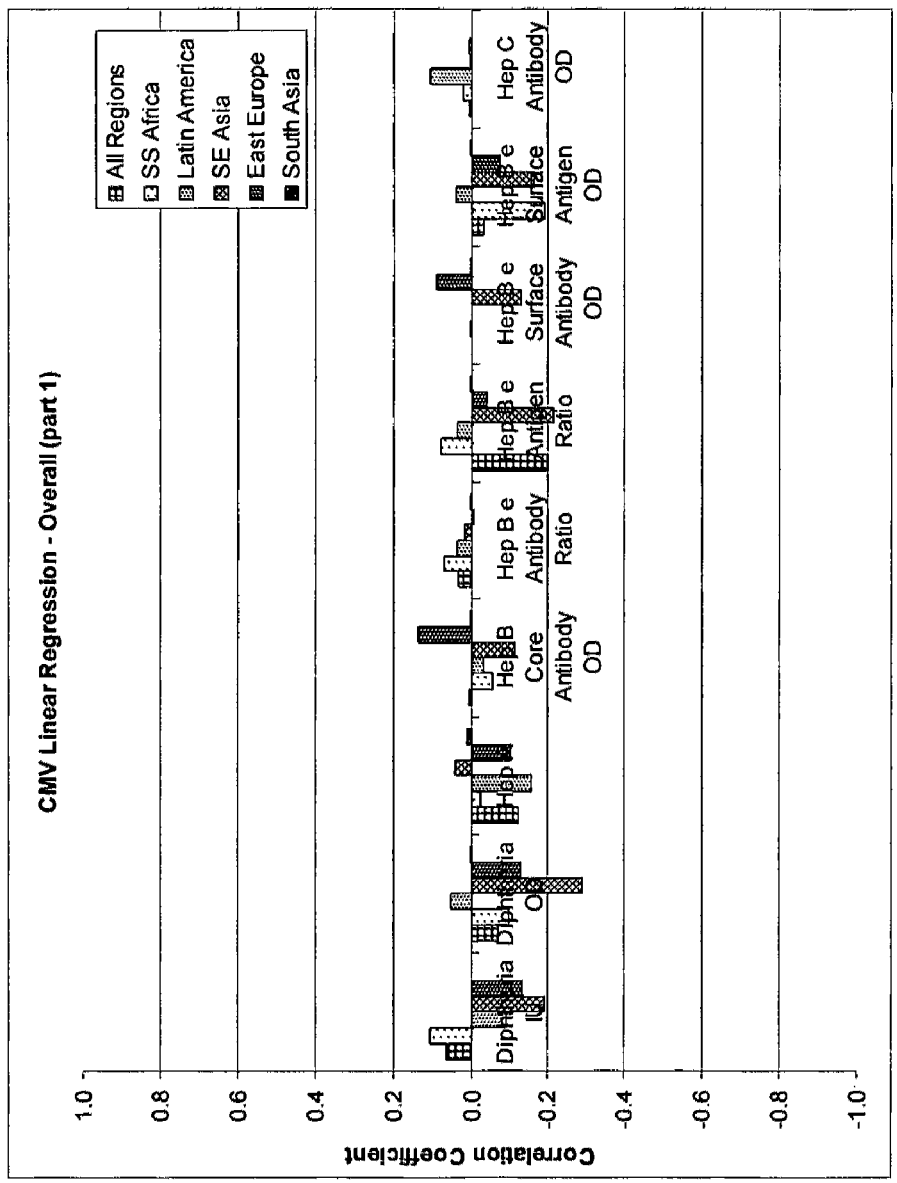
Fig. 20G2

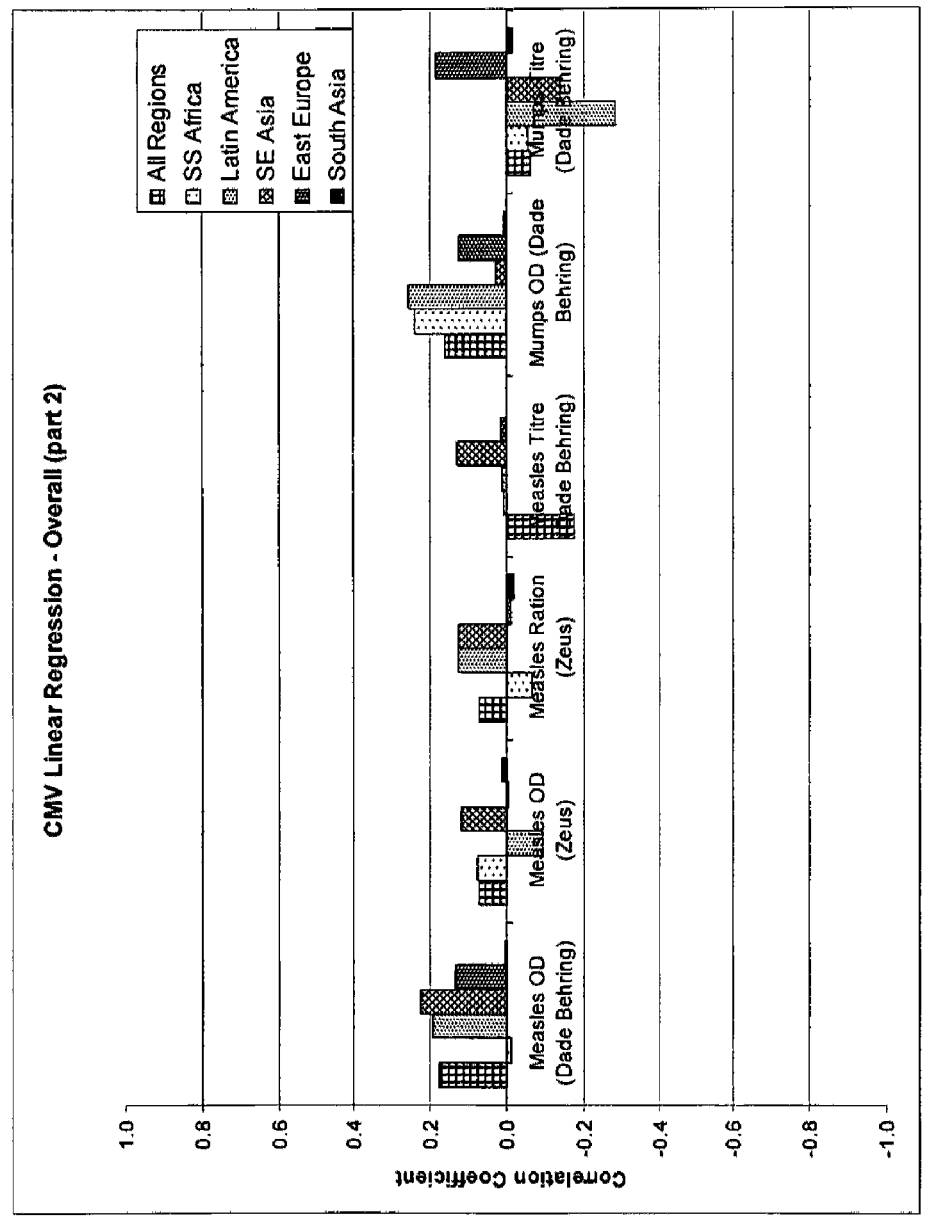
Fig. 20G3

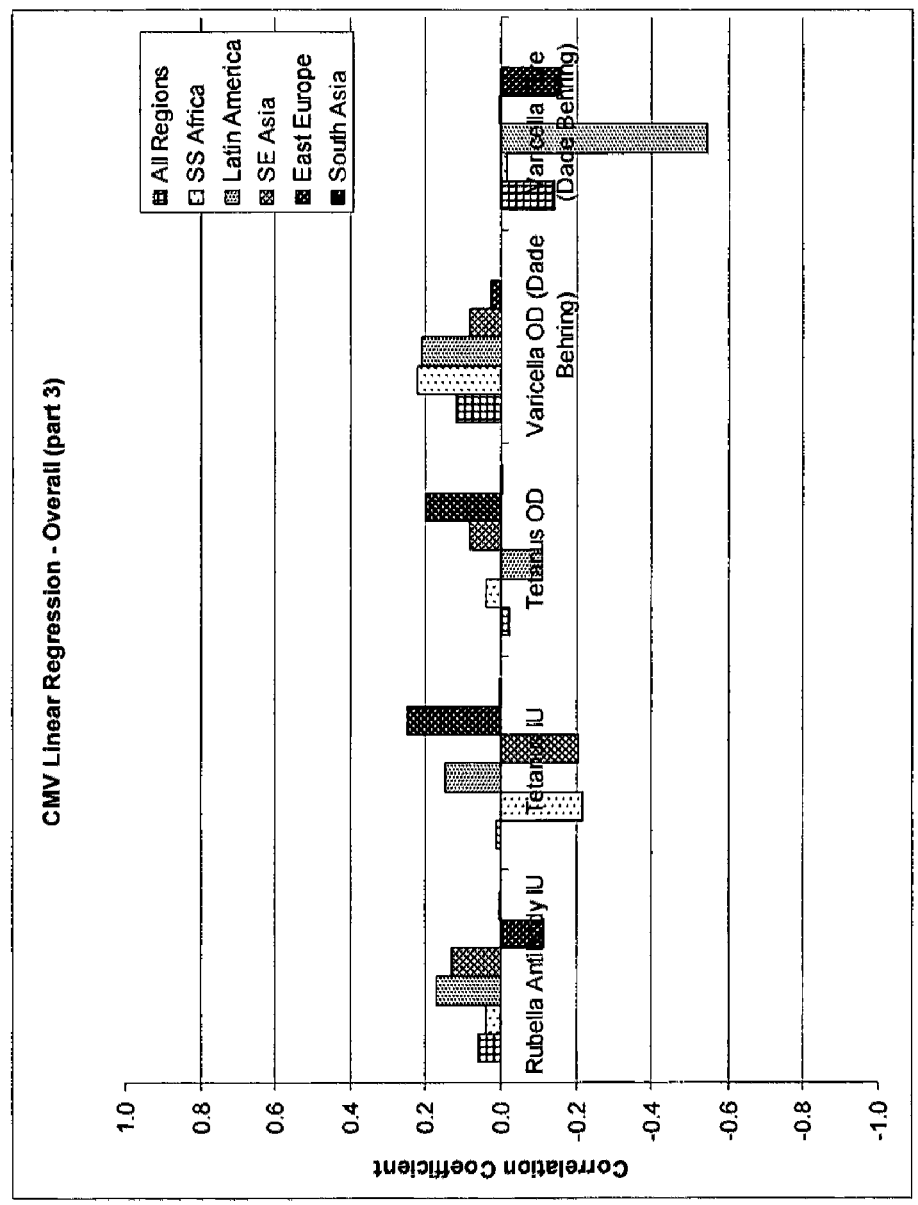
Fig. 20G4

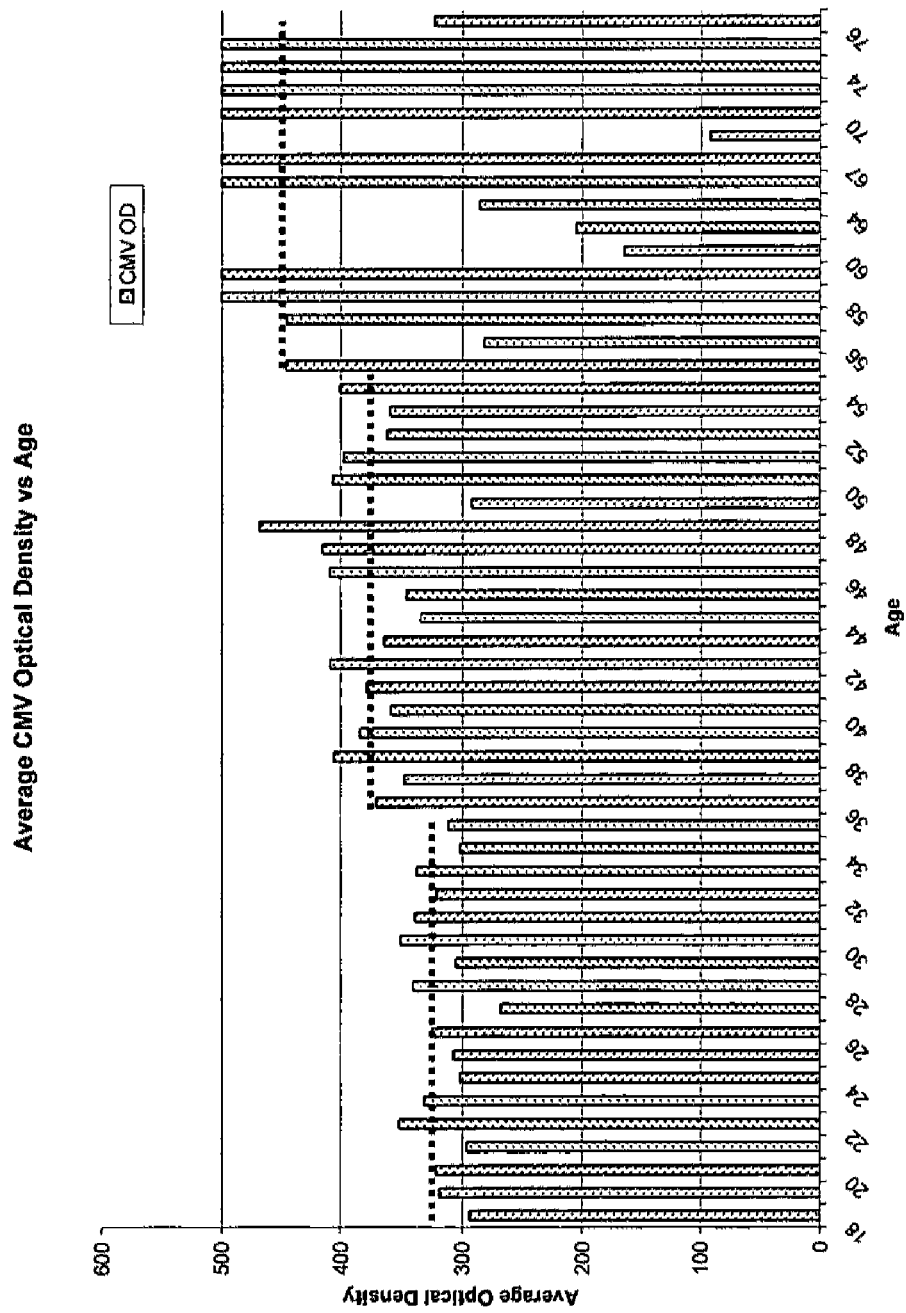
Fig. 20G5

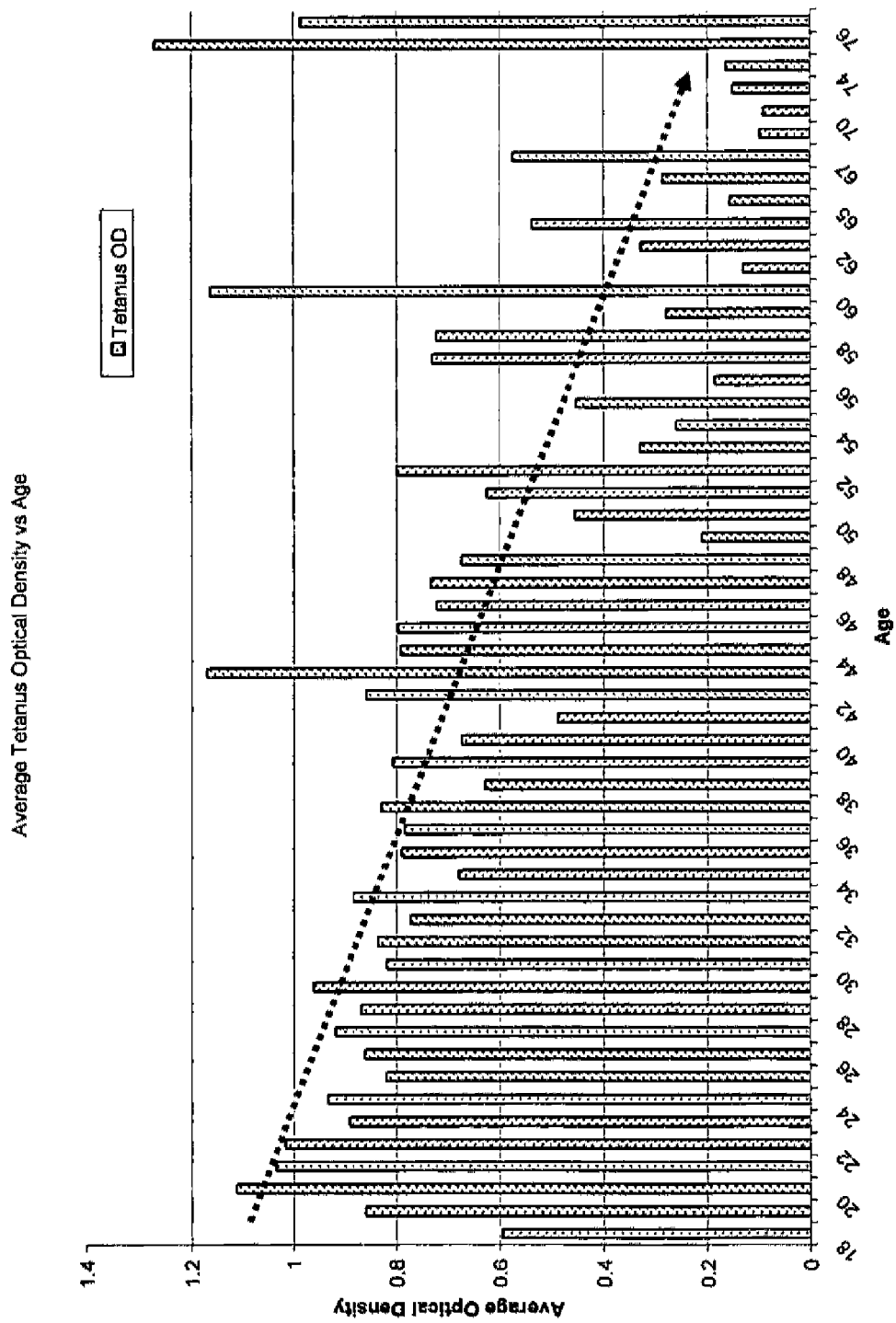
Fig. 20G6

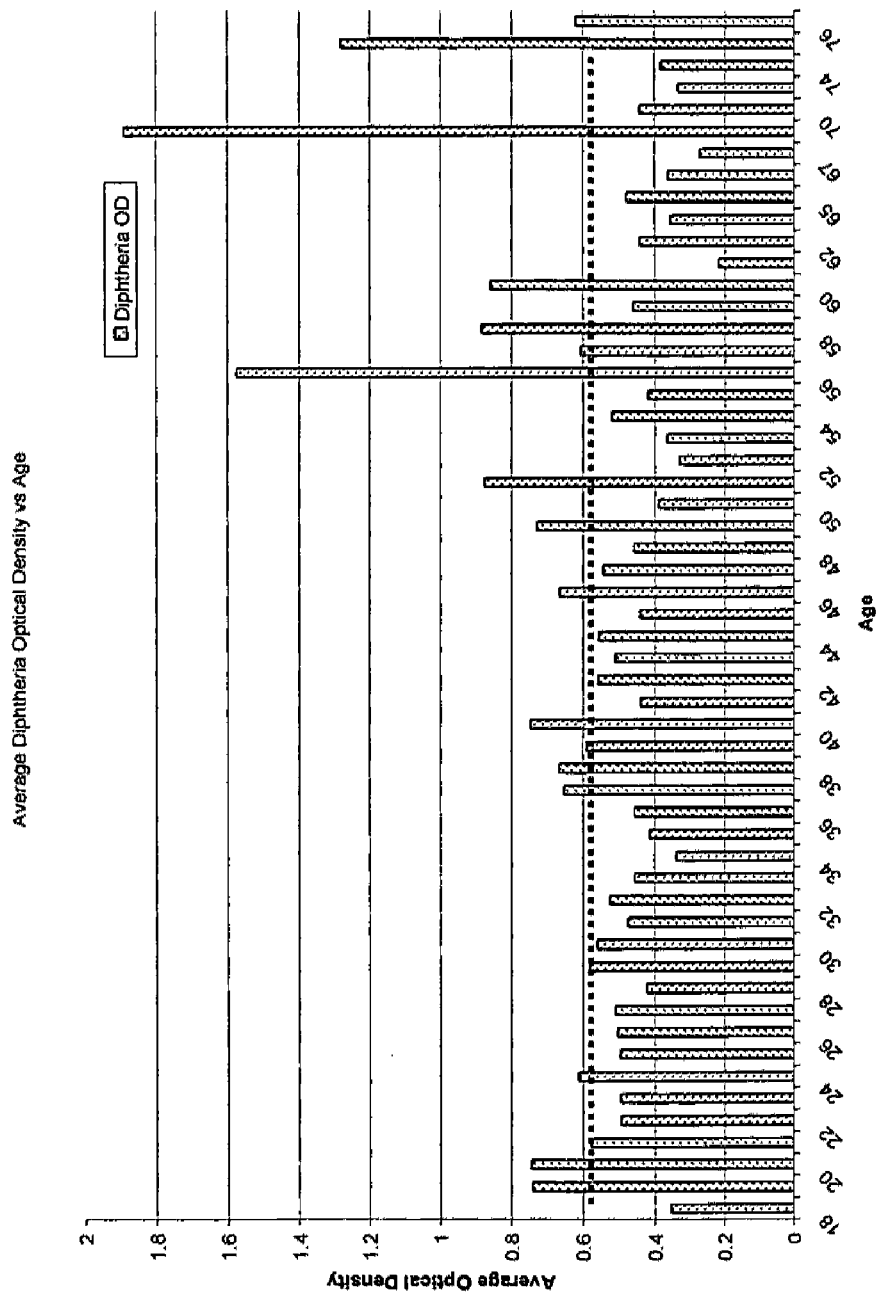
Fig. 20G7

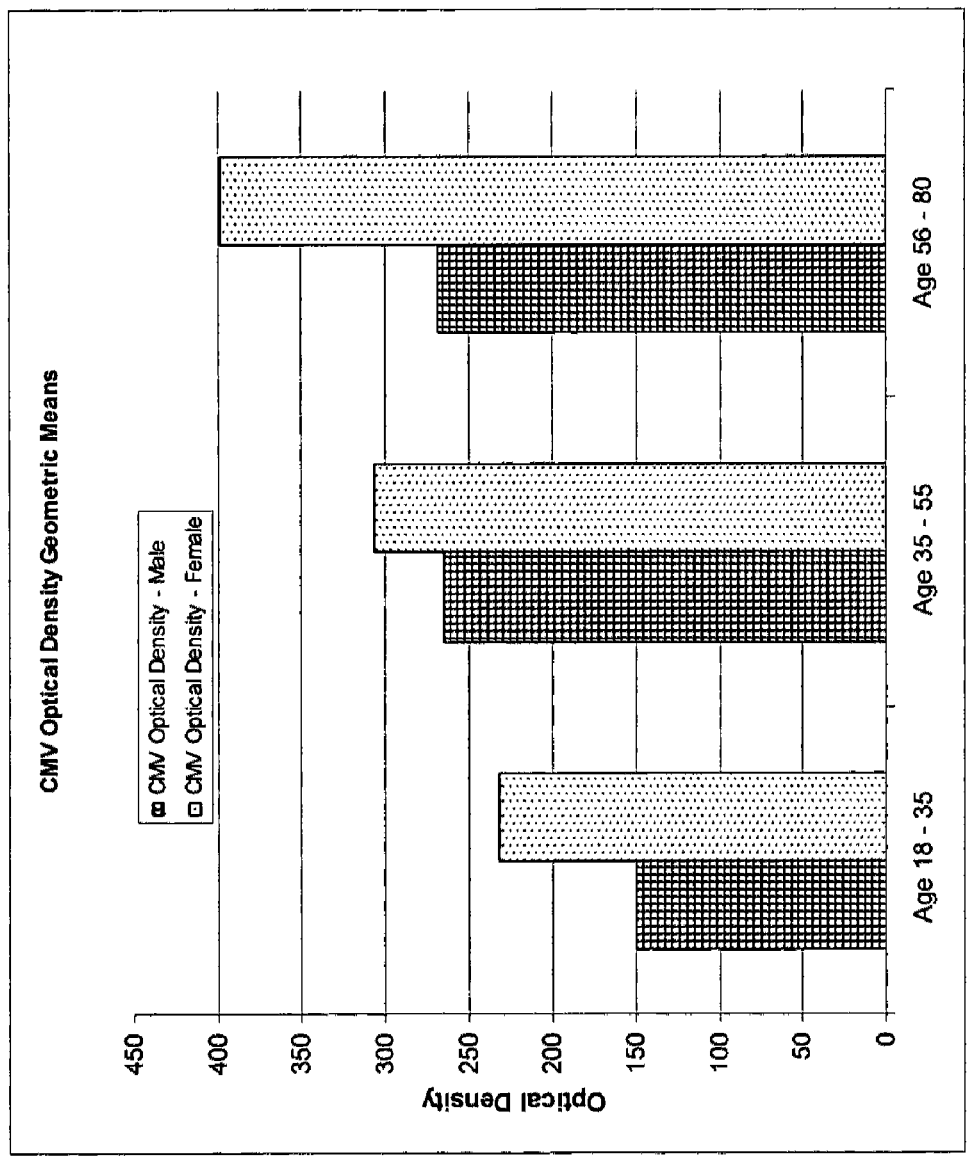
Fig. 20G8

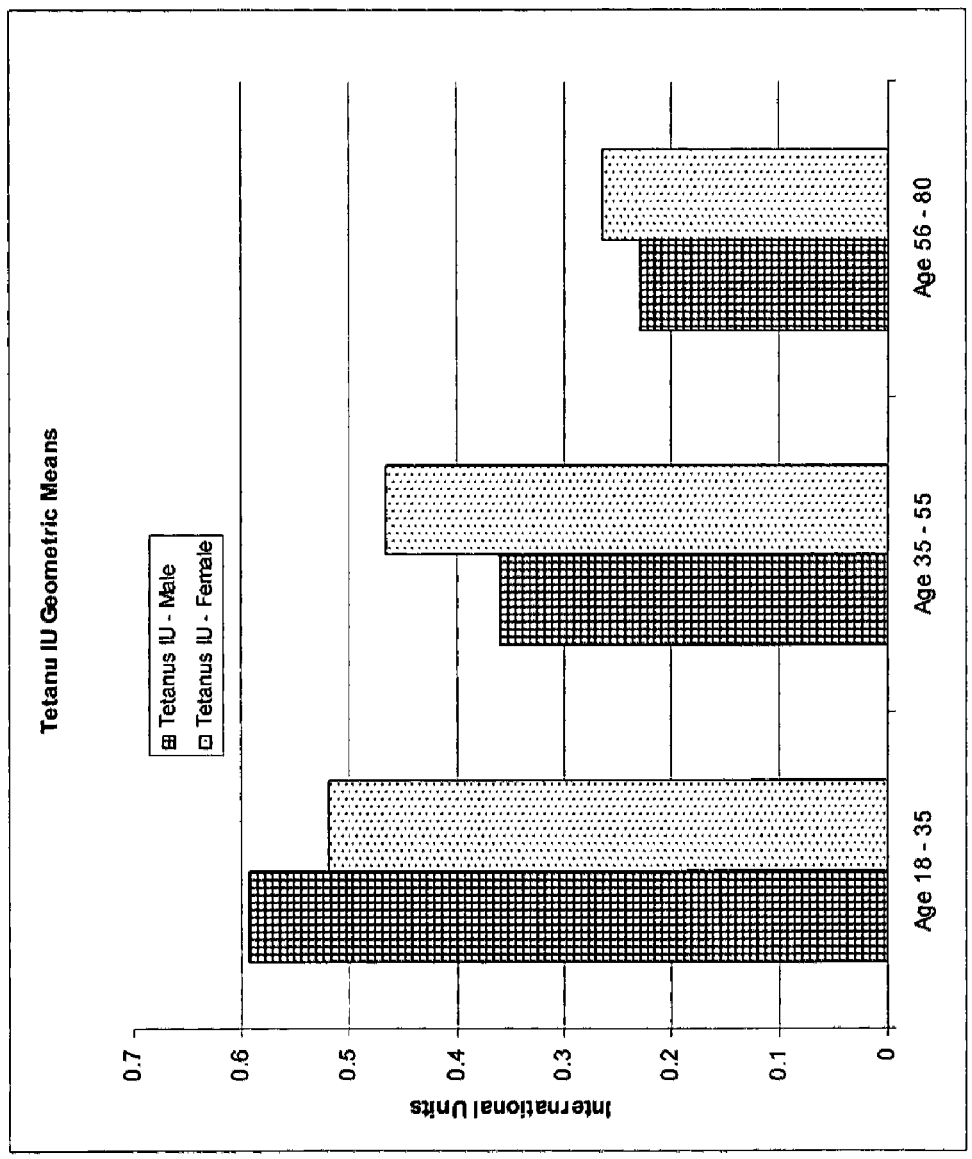
Fig. 20G9

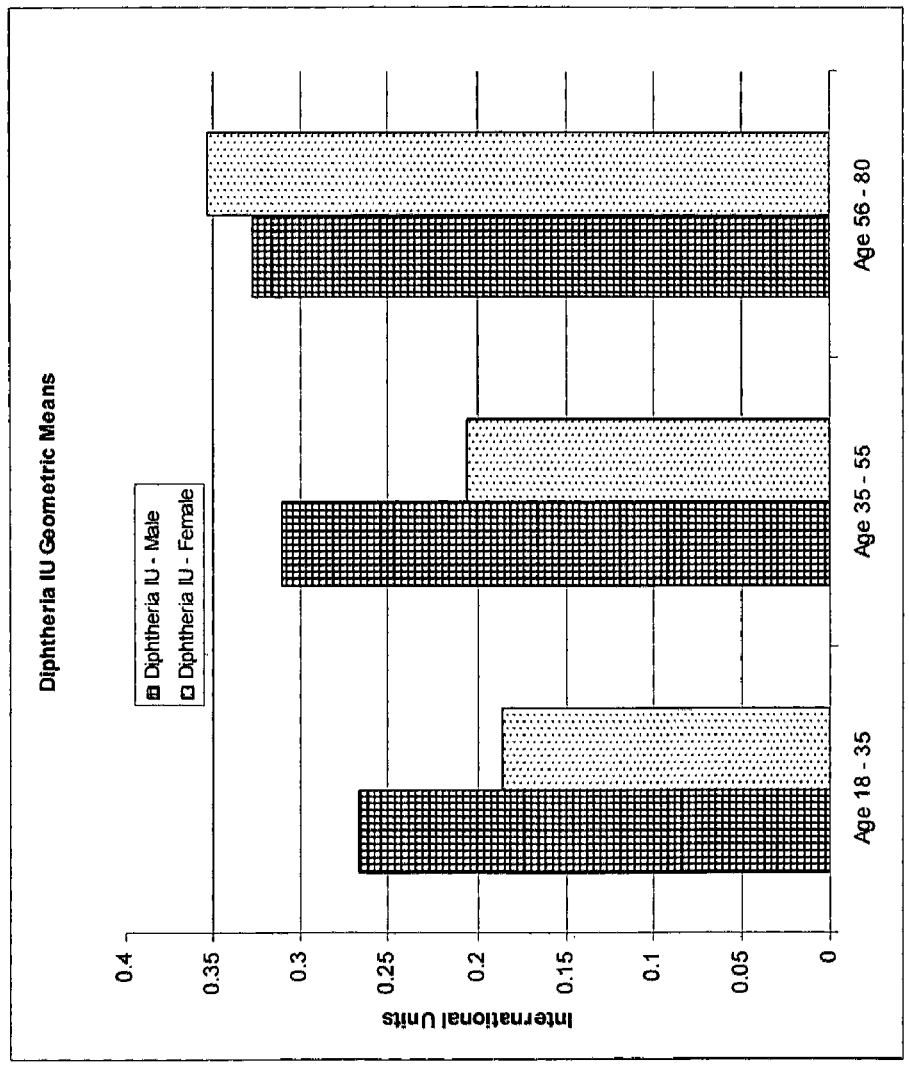
Fig. 20G10

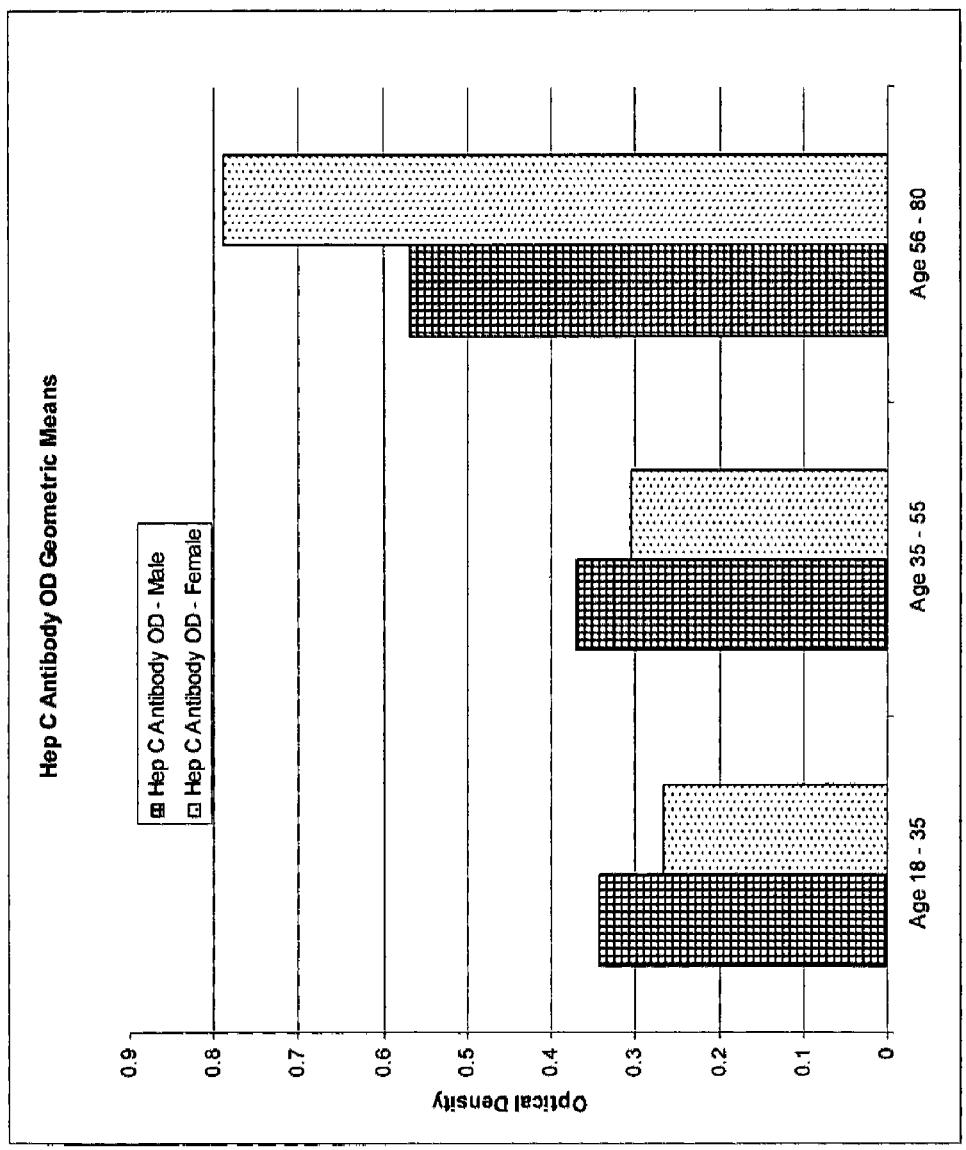
Fig. 20G11

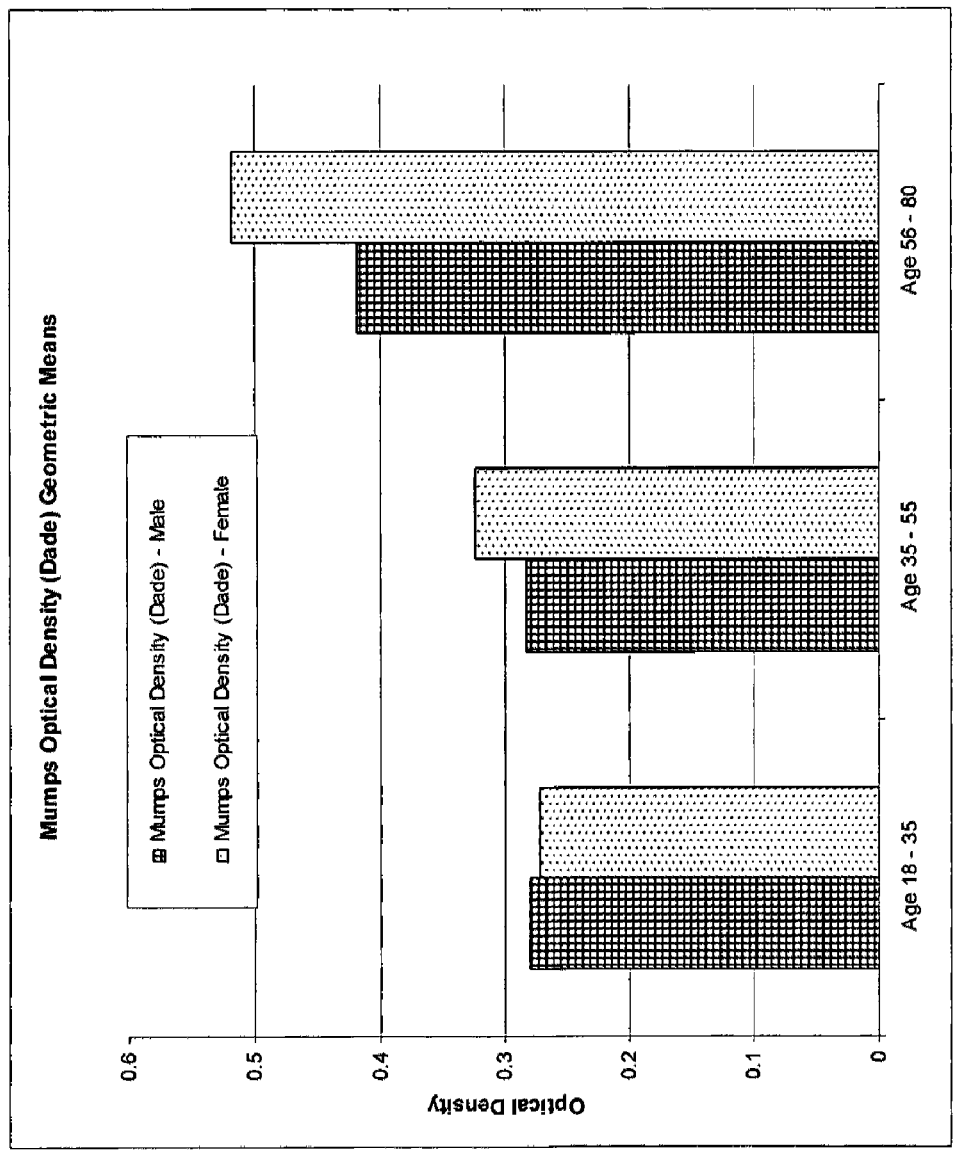
Fig. 20G12

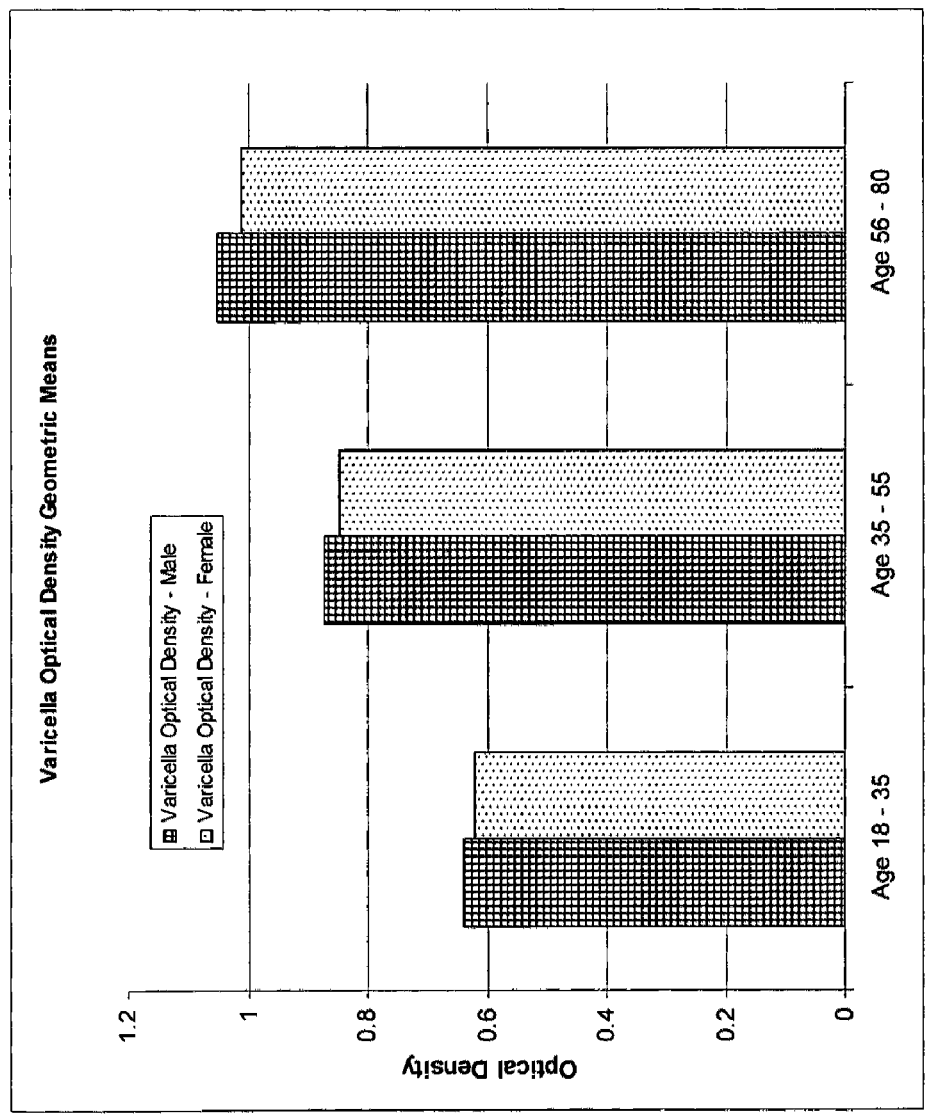
Fig. 20G13

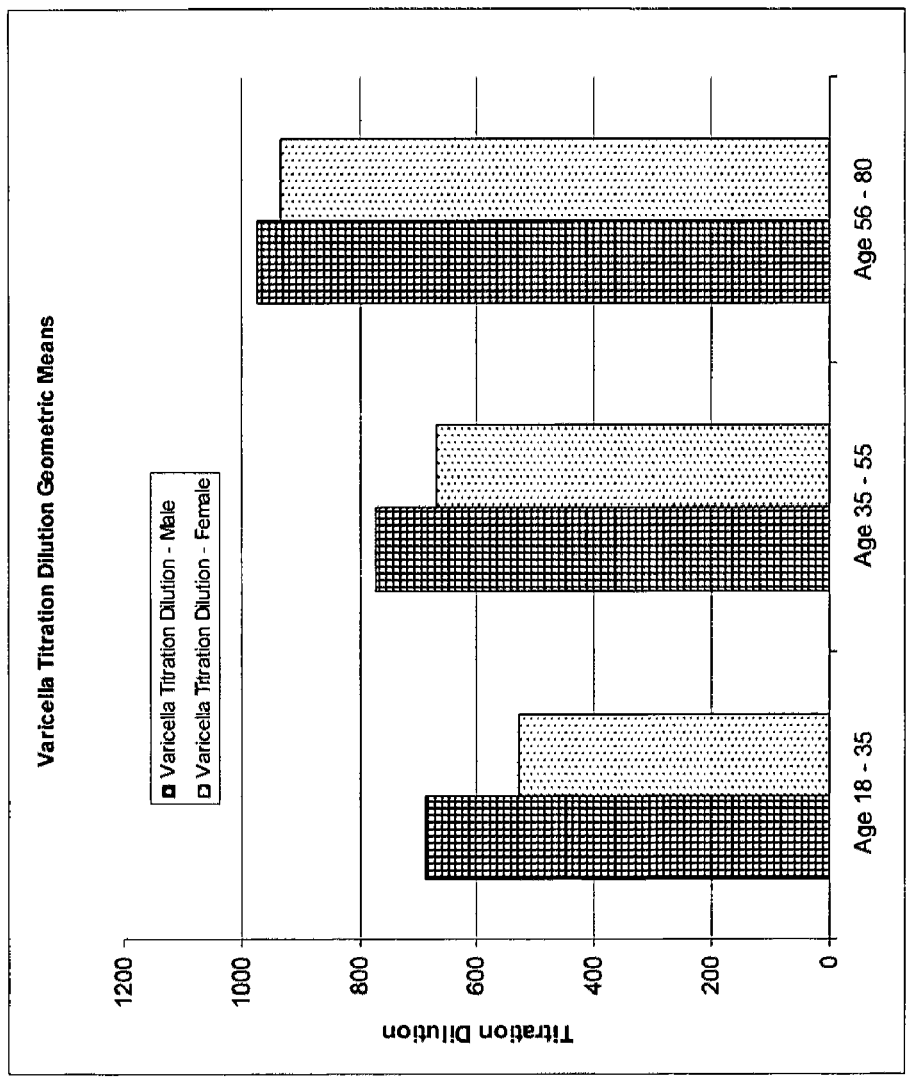
Fig. 20G14

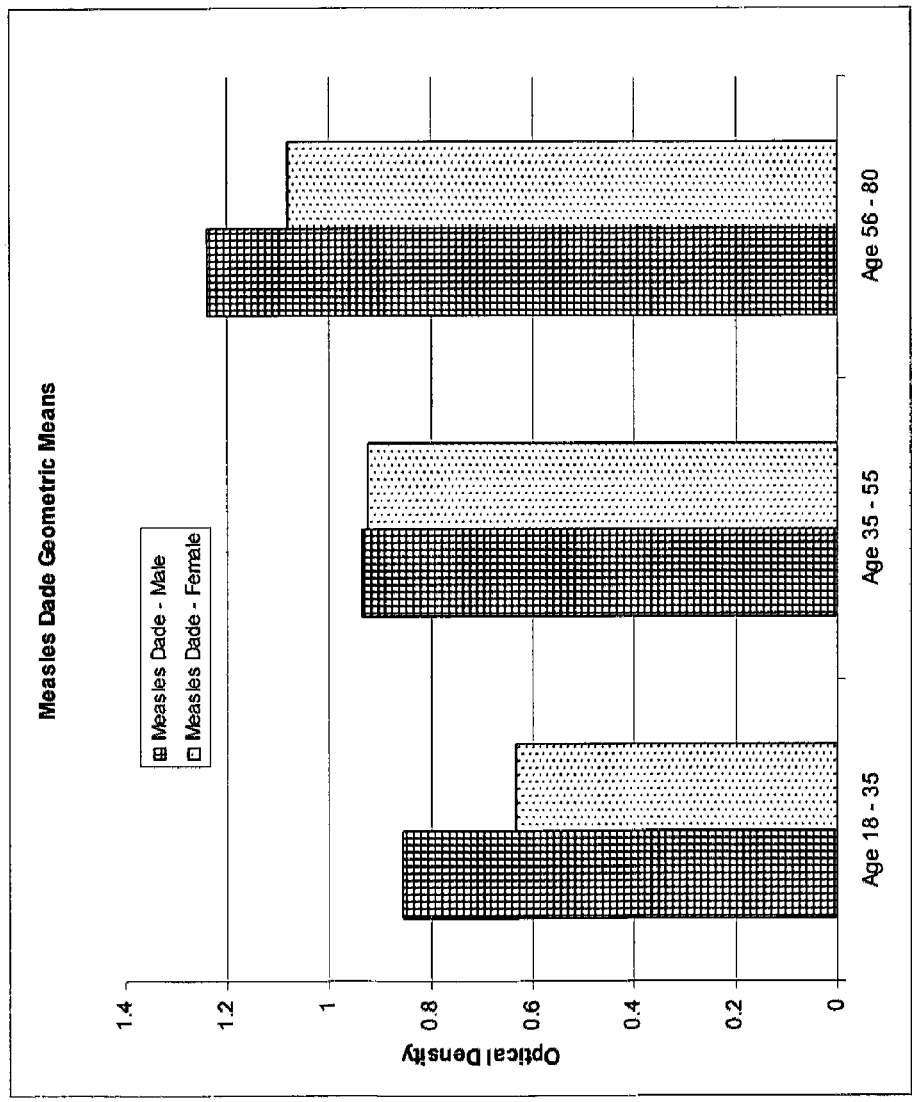
Fig. 20G15

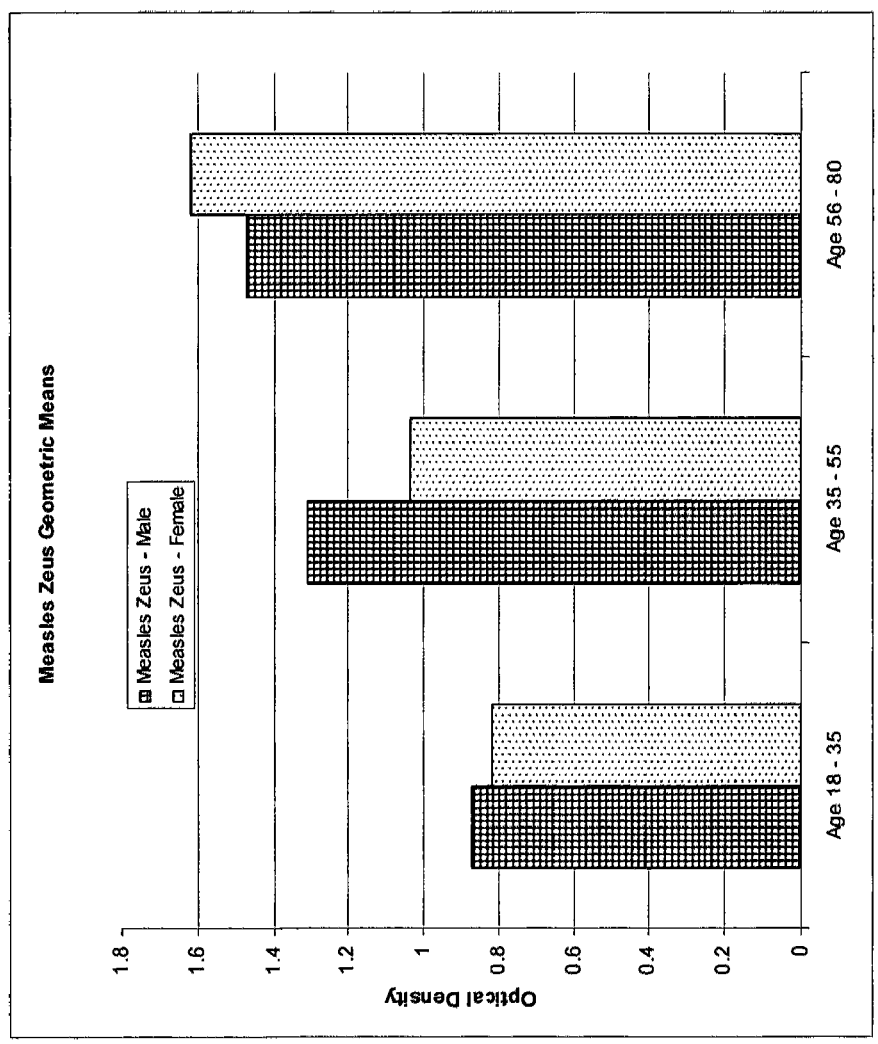
Fig. 20G16

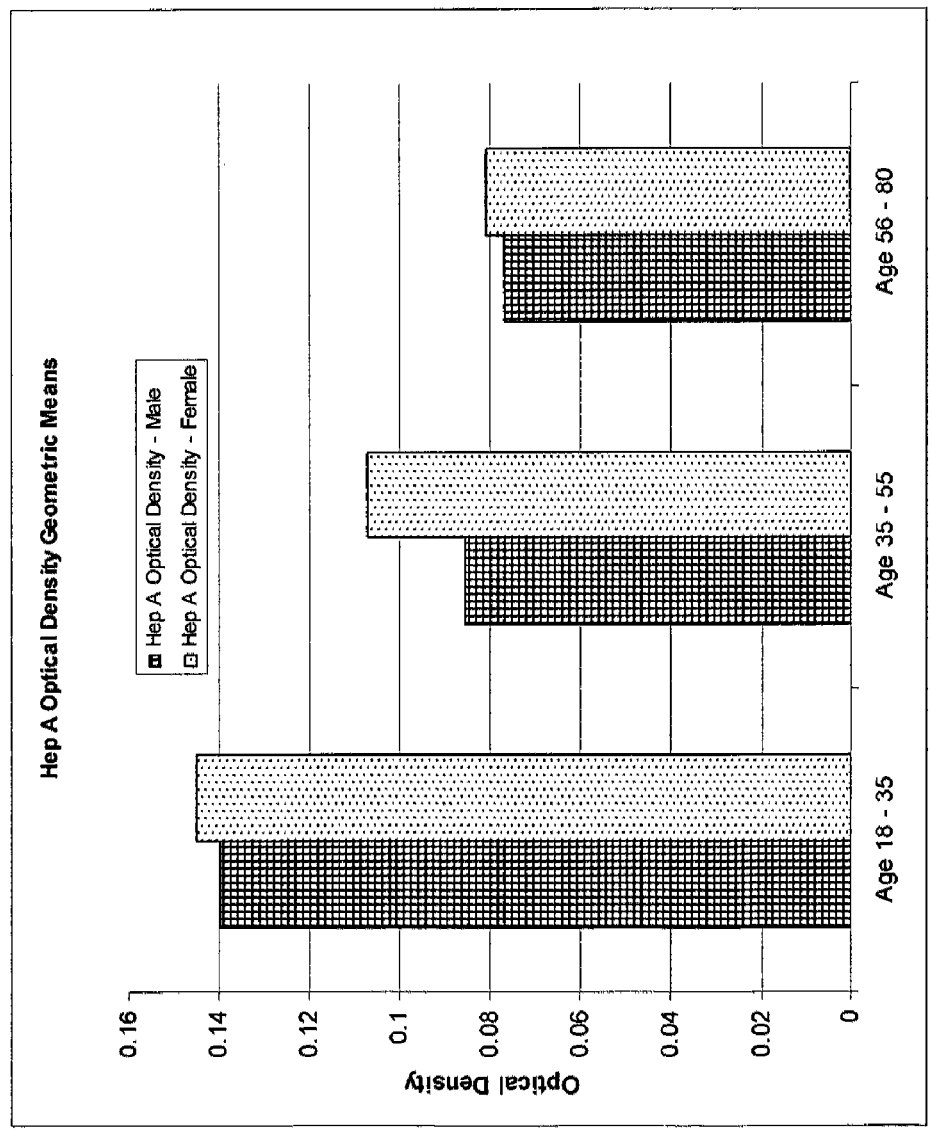
Fig. 20G17

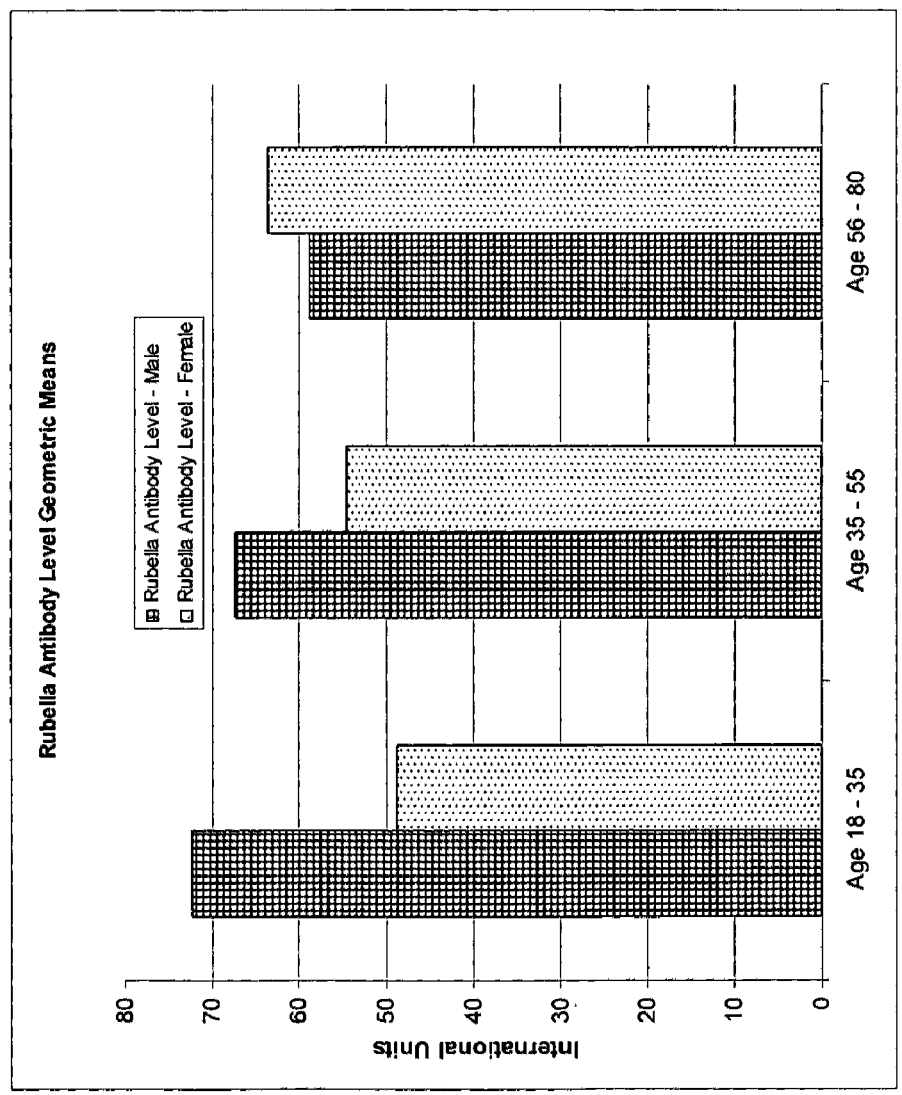
Fig. 20G18

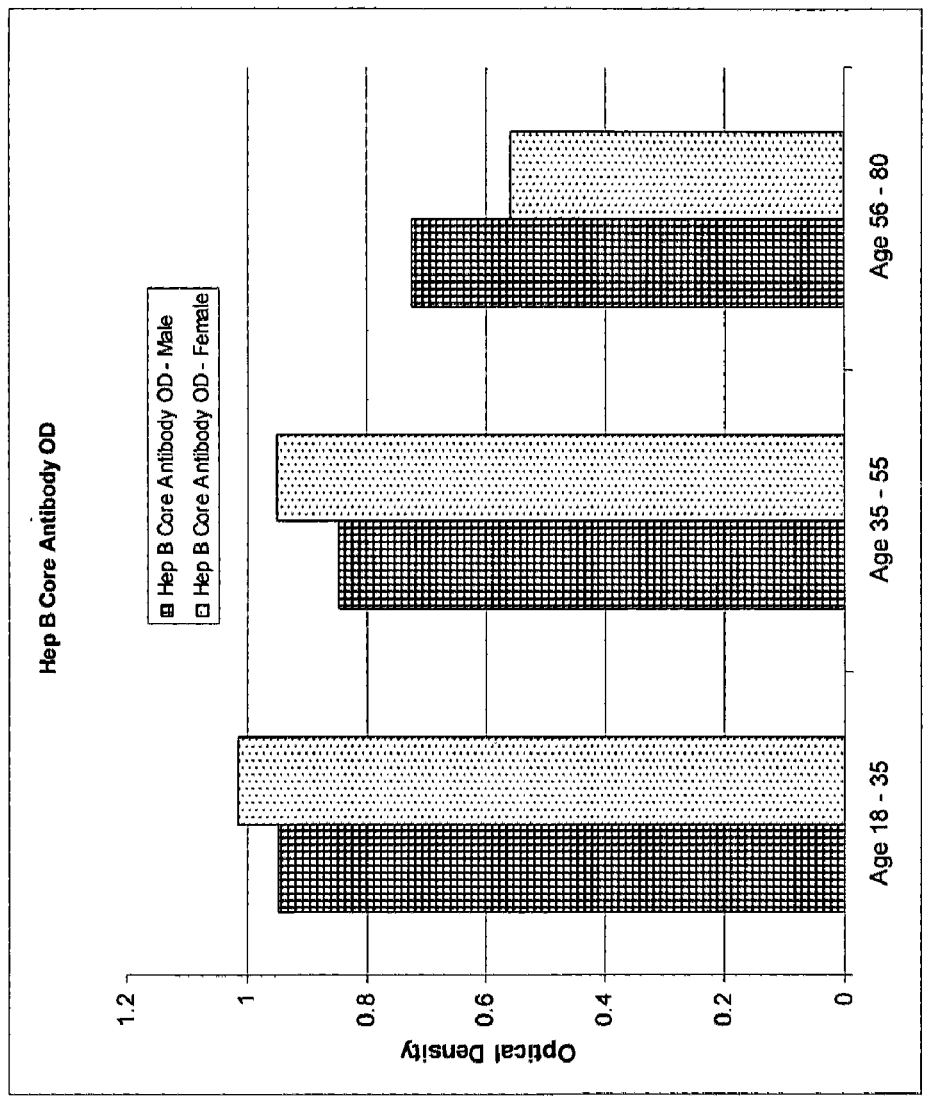
Fig. 20G19

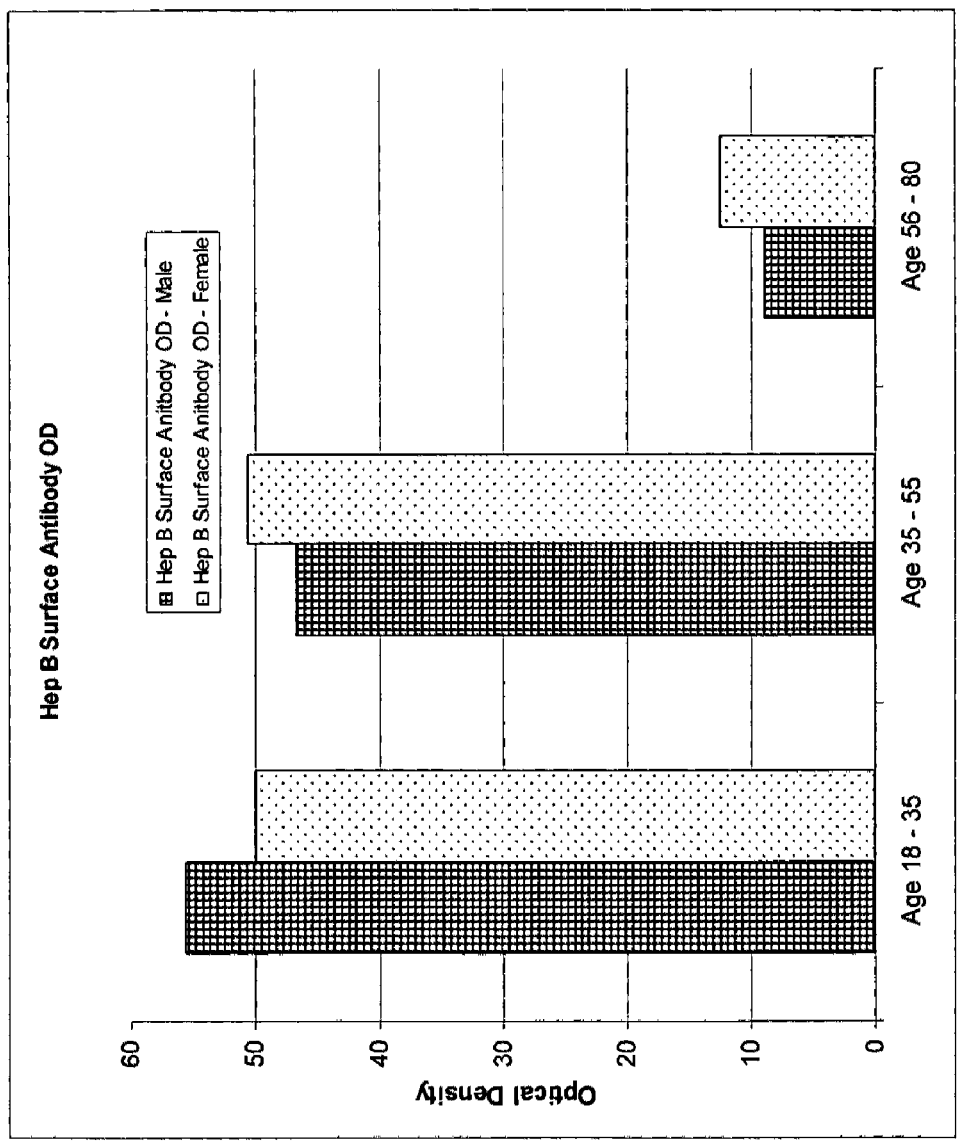
Fig. 20G20

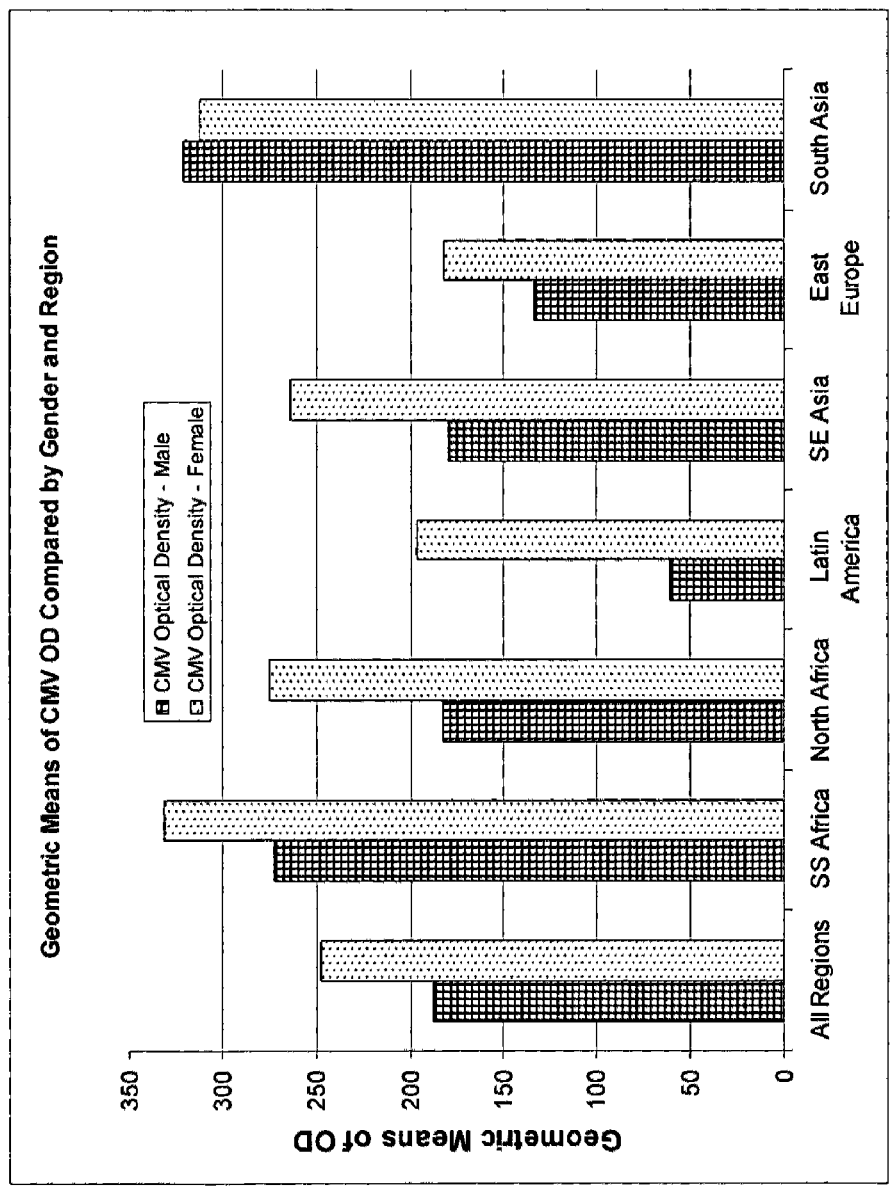
Fig. 20G21

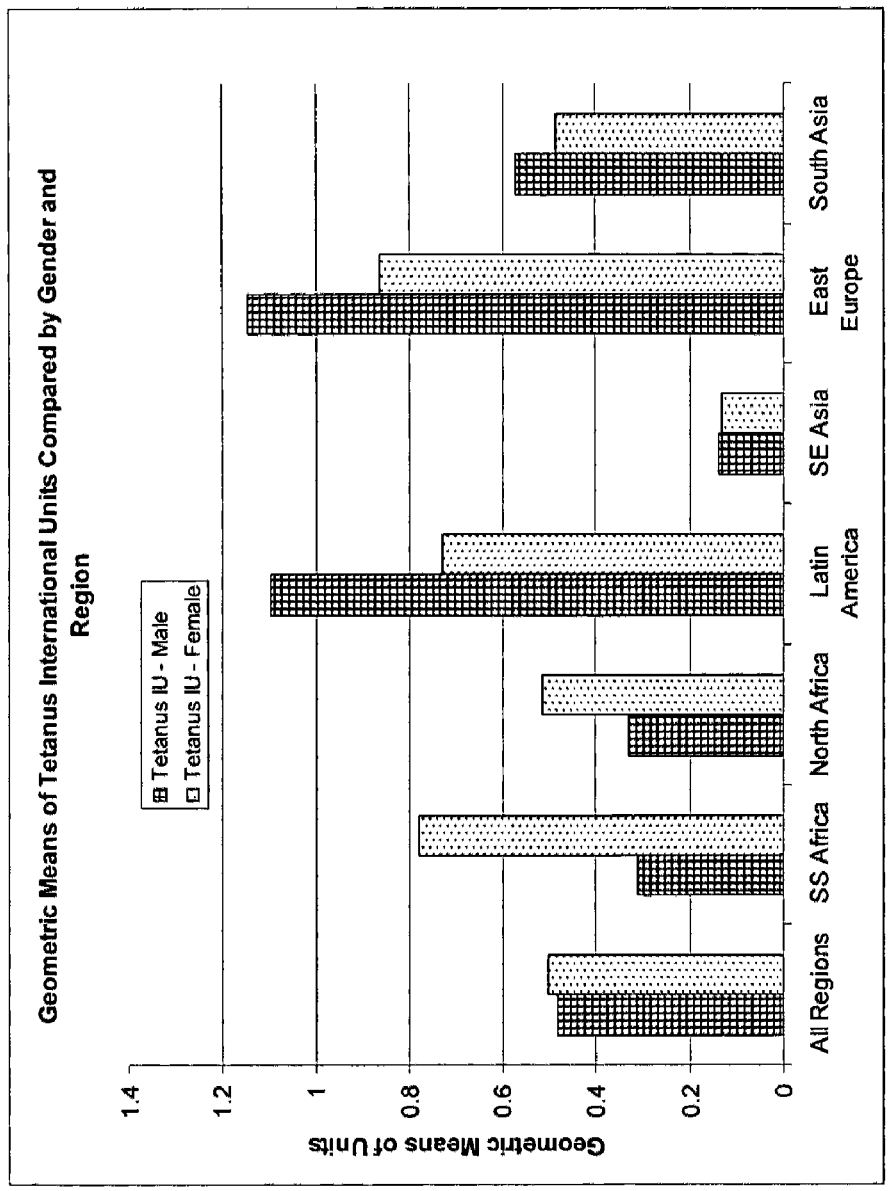
Fig. 20G22

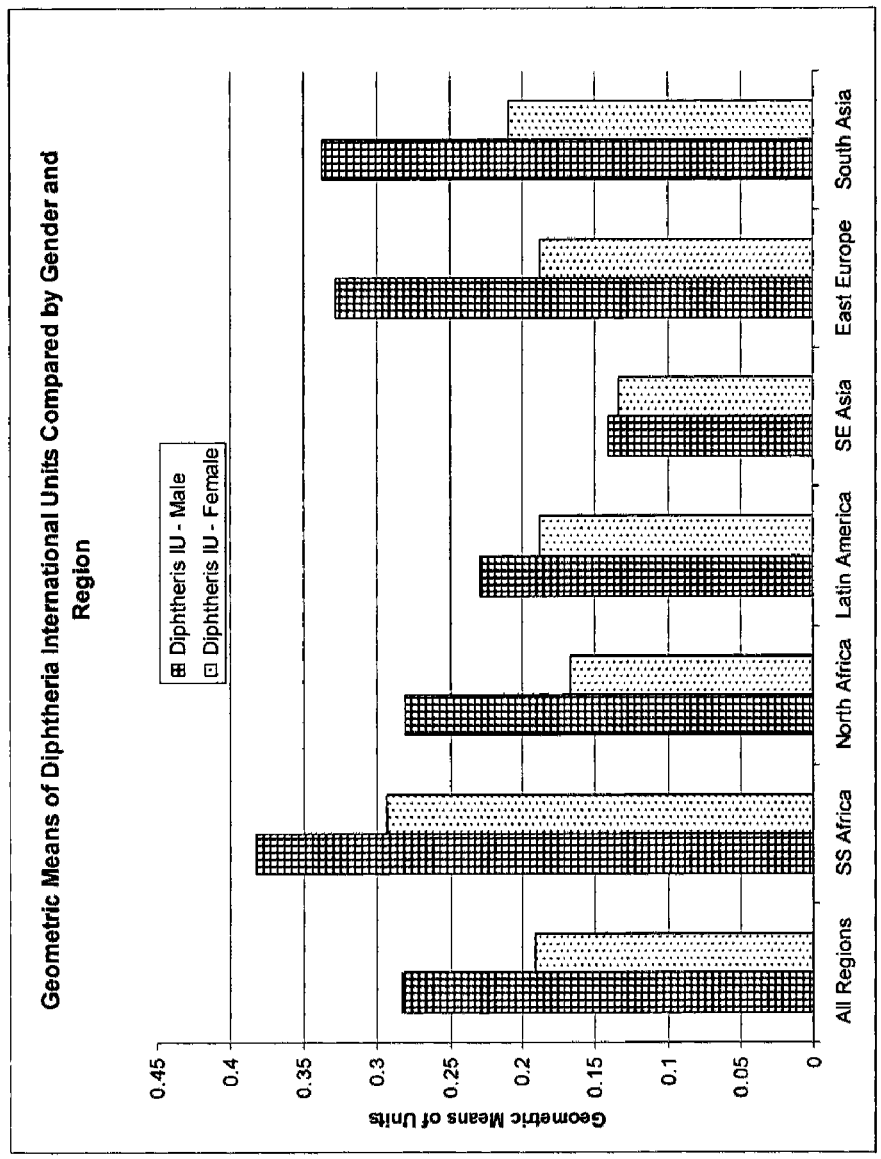
Fig. 20G23

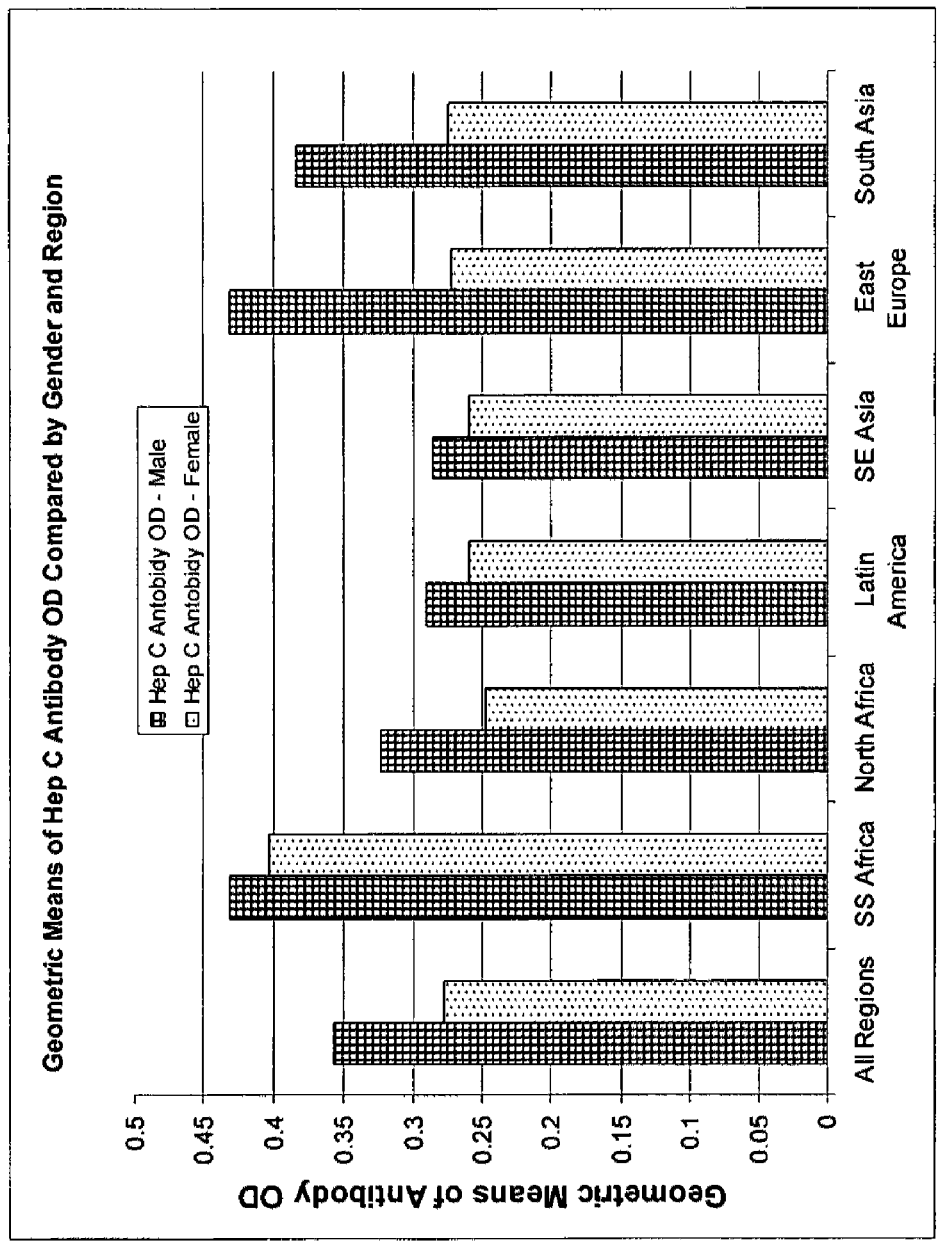
Fig. 20G24

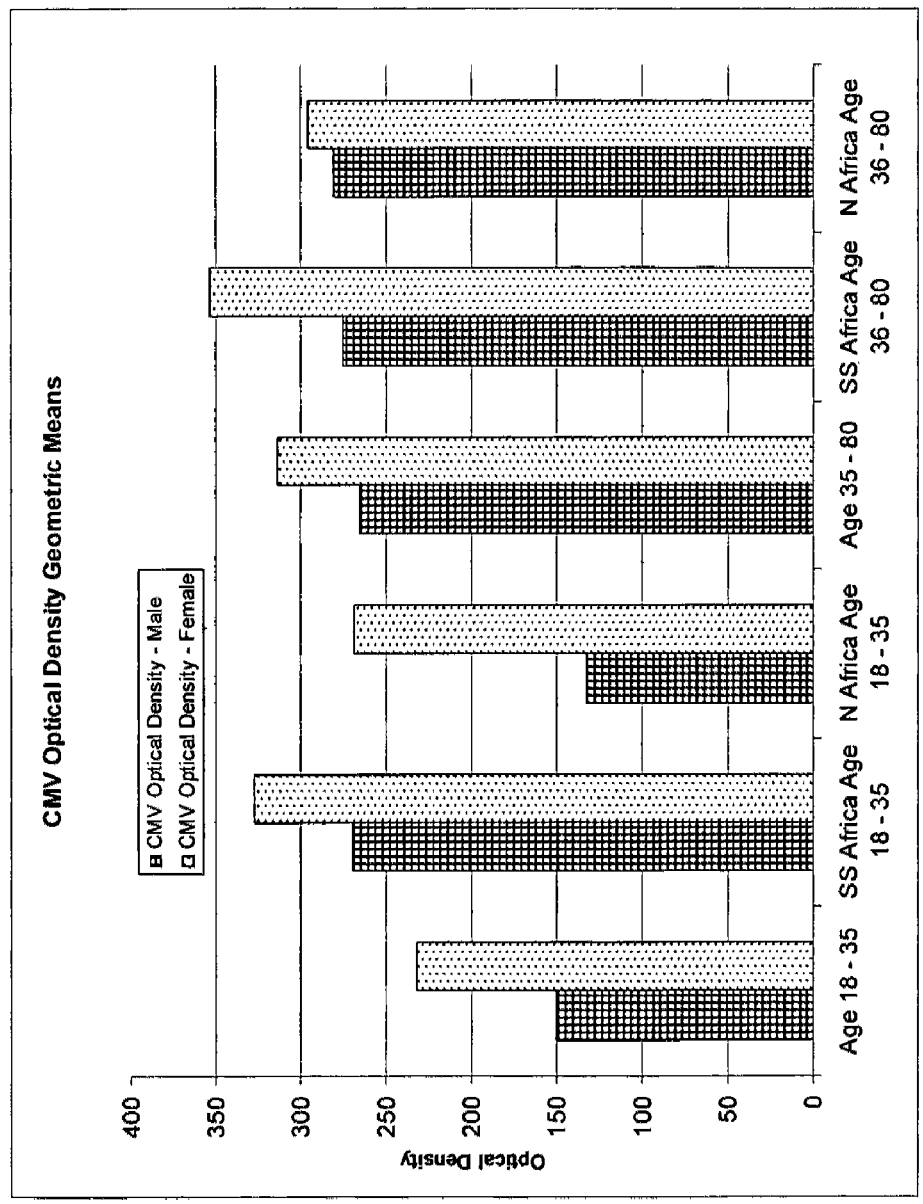
Fig. 20G25

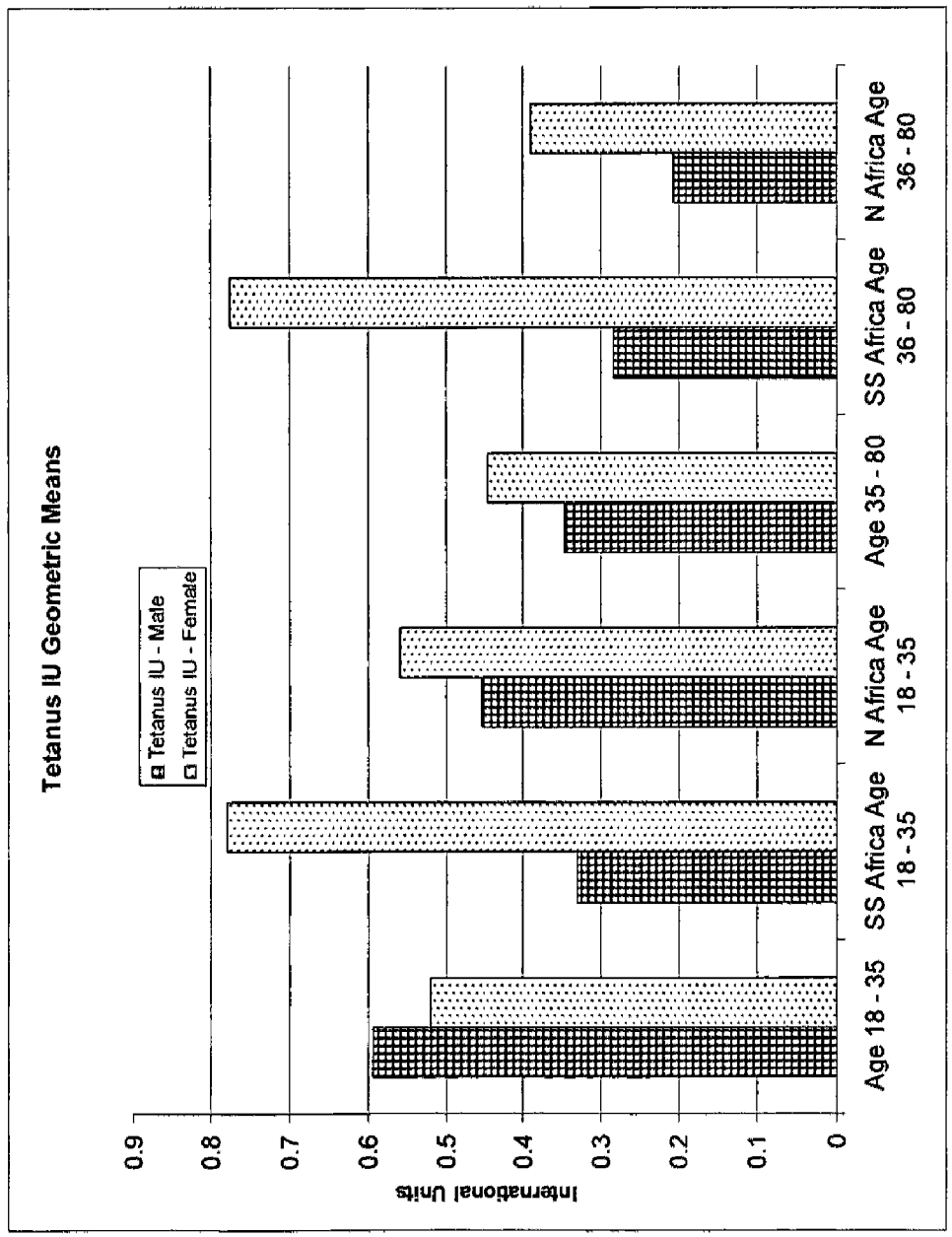
Fig. 20G26

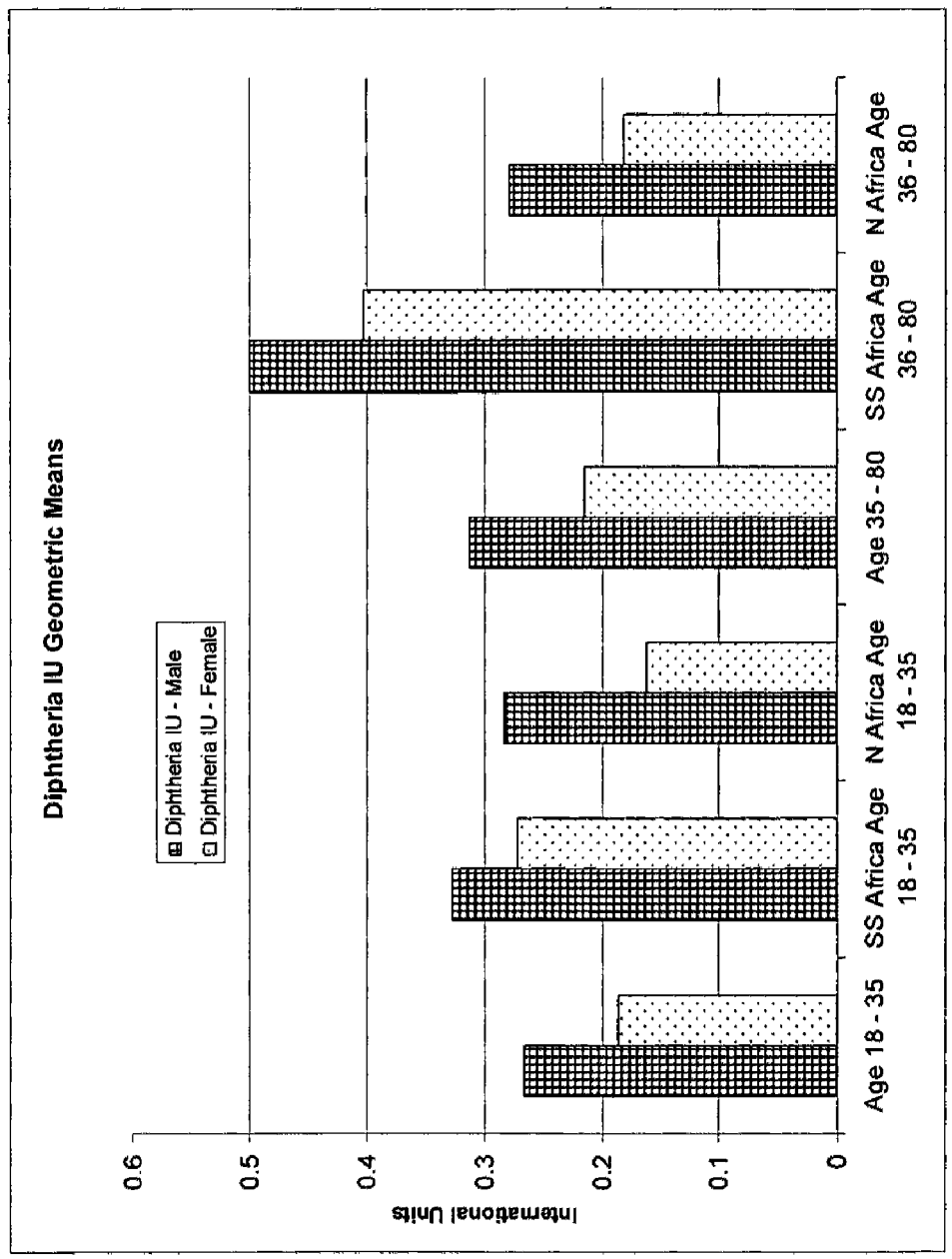
Fig. 20G27

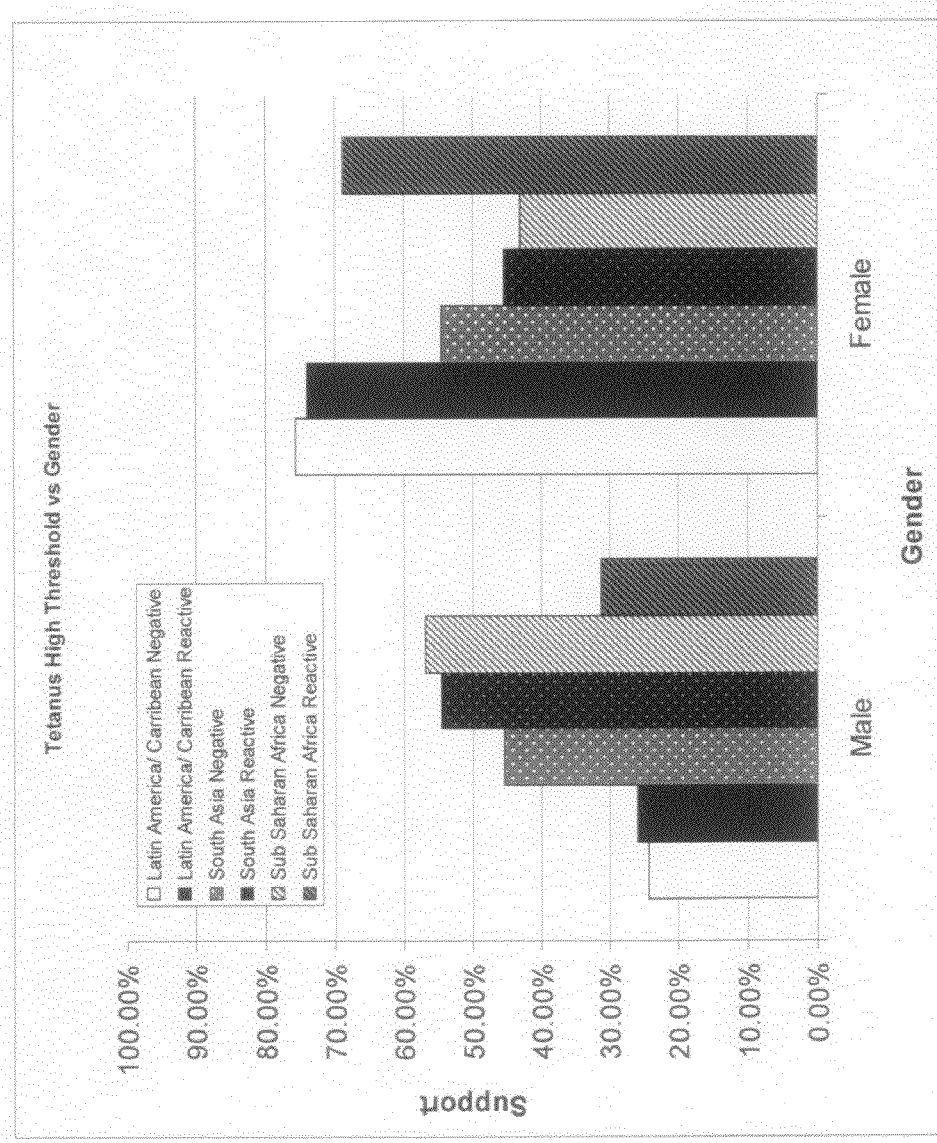
Fig. 20G28

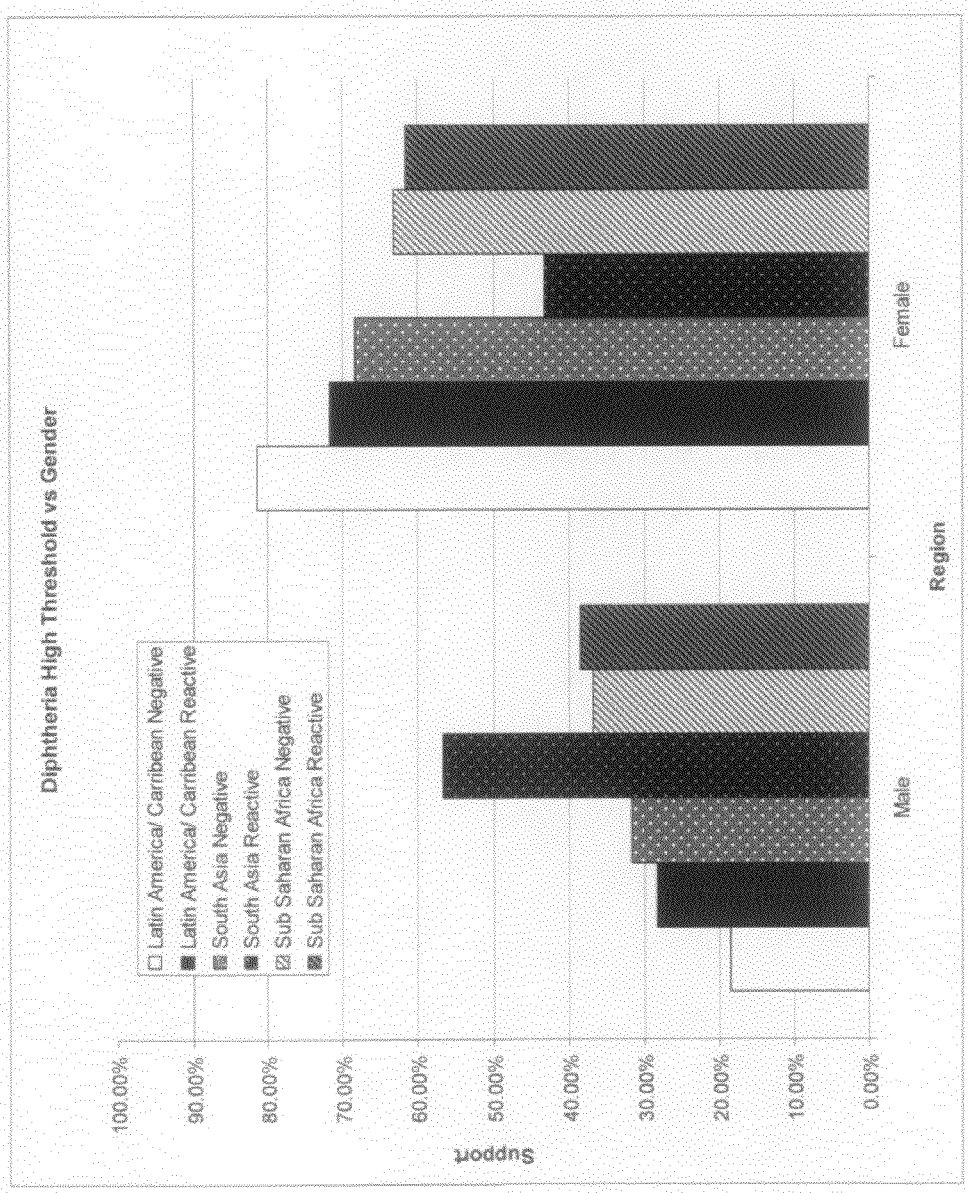
Fig. 20G29

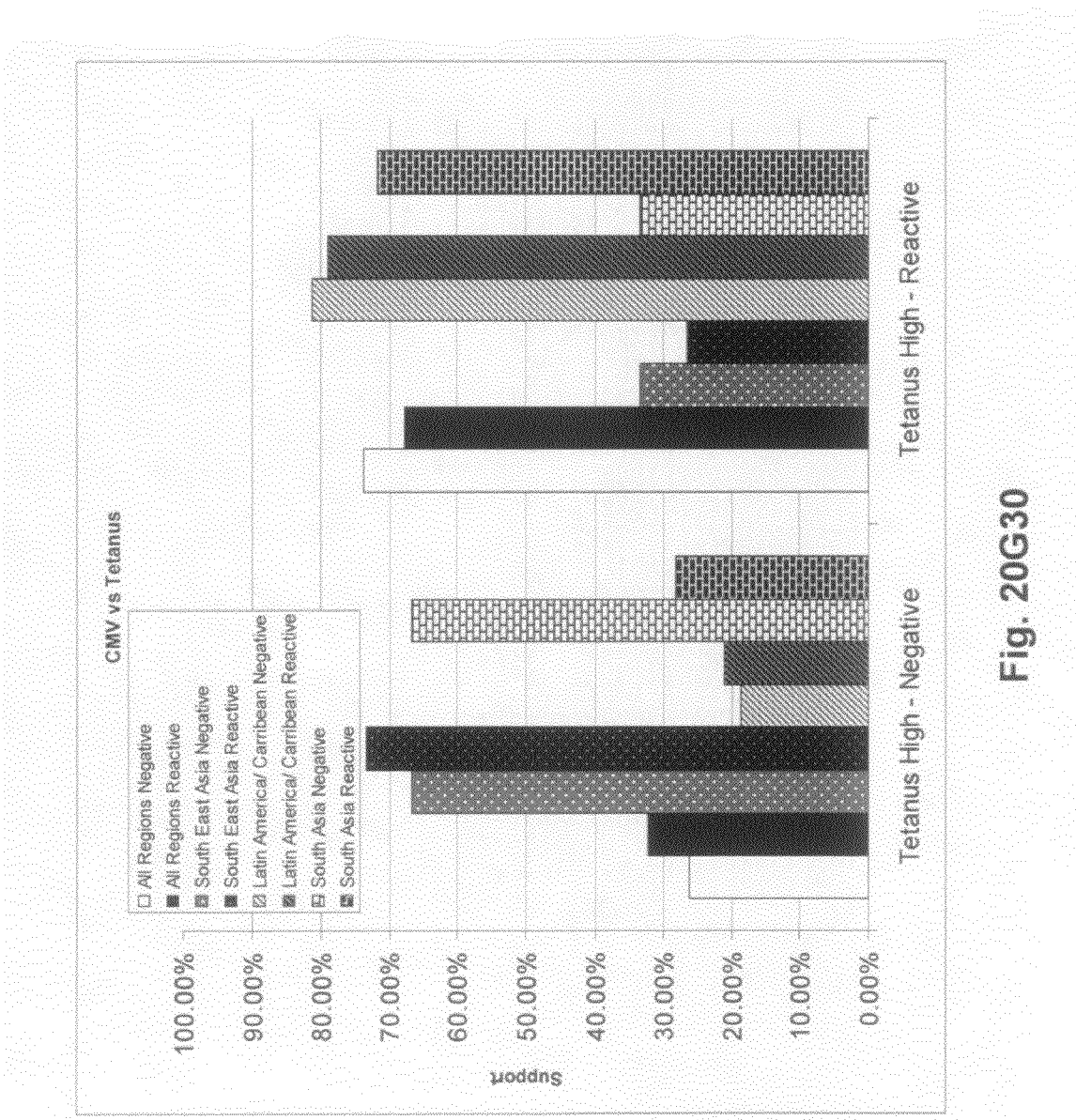
Fig. 20G30

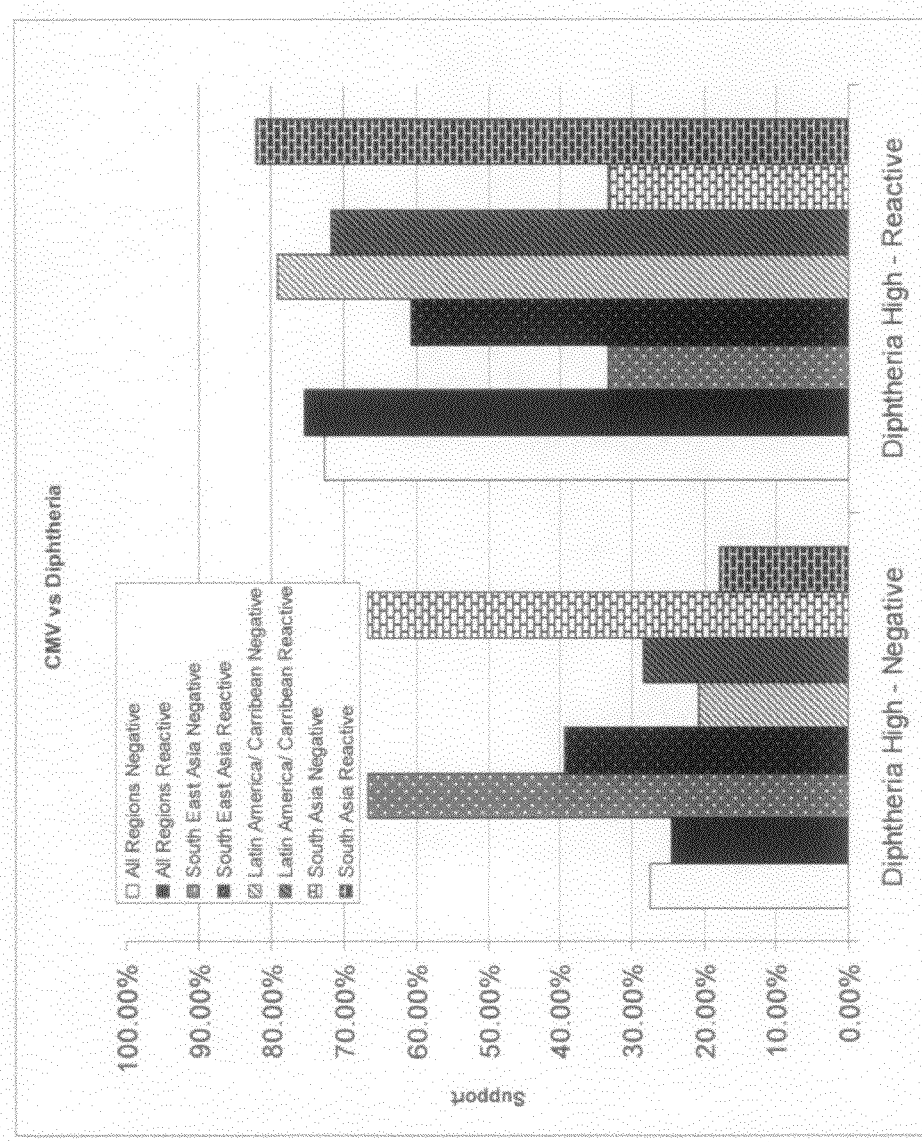
Fig. 20G31

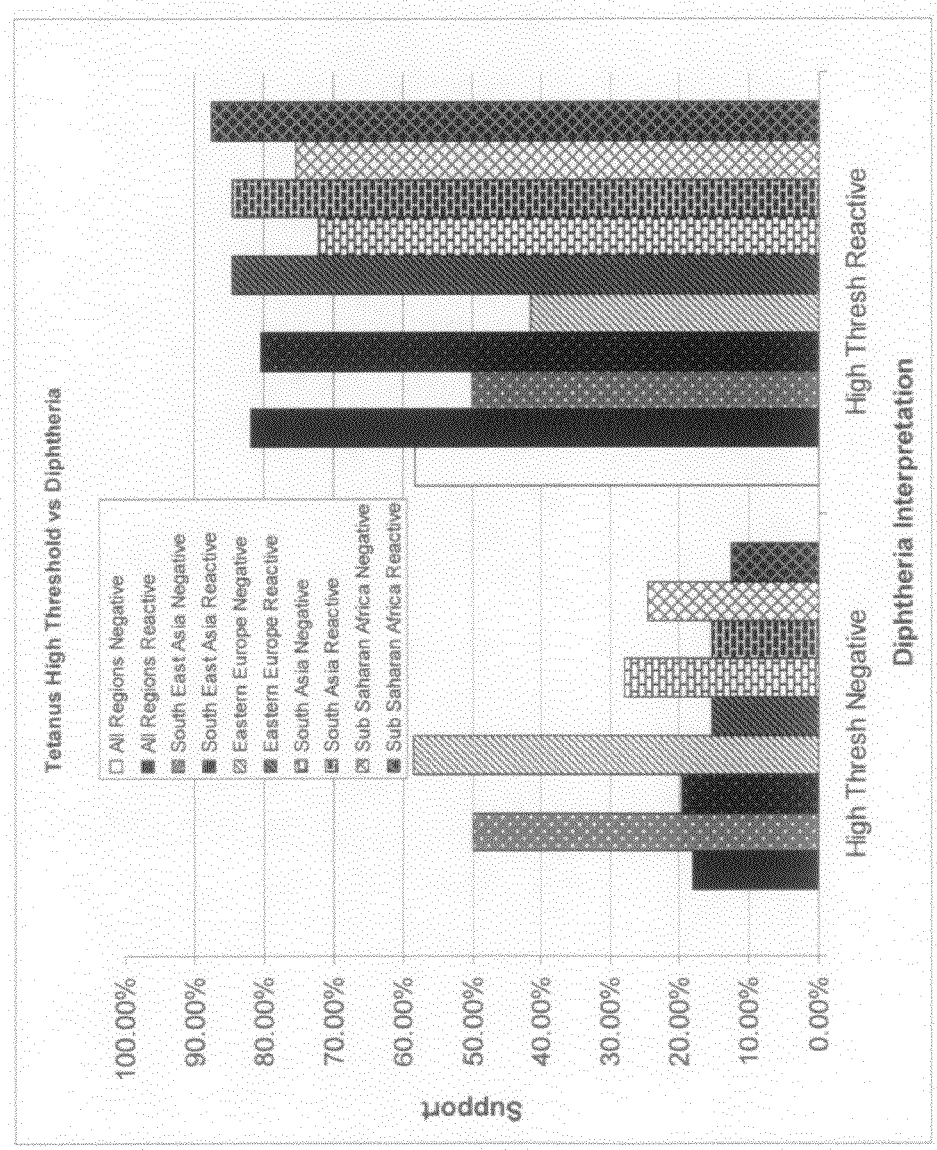
Fig. 20G32

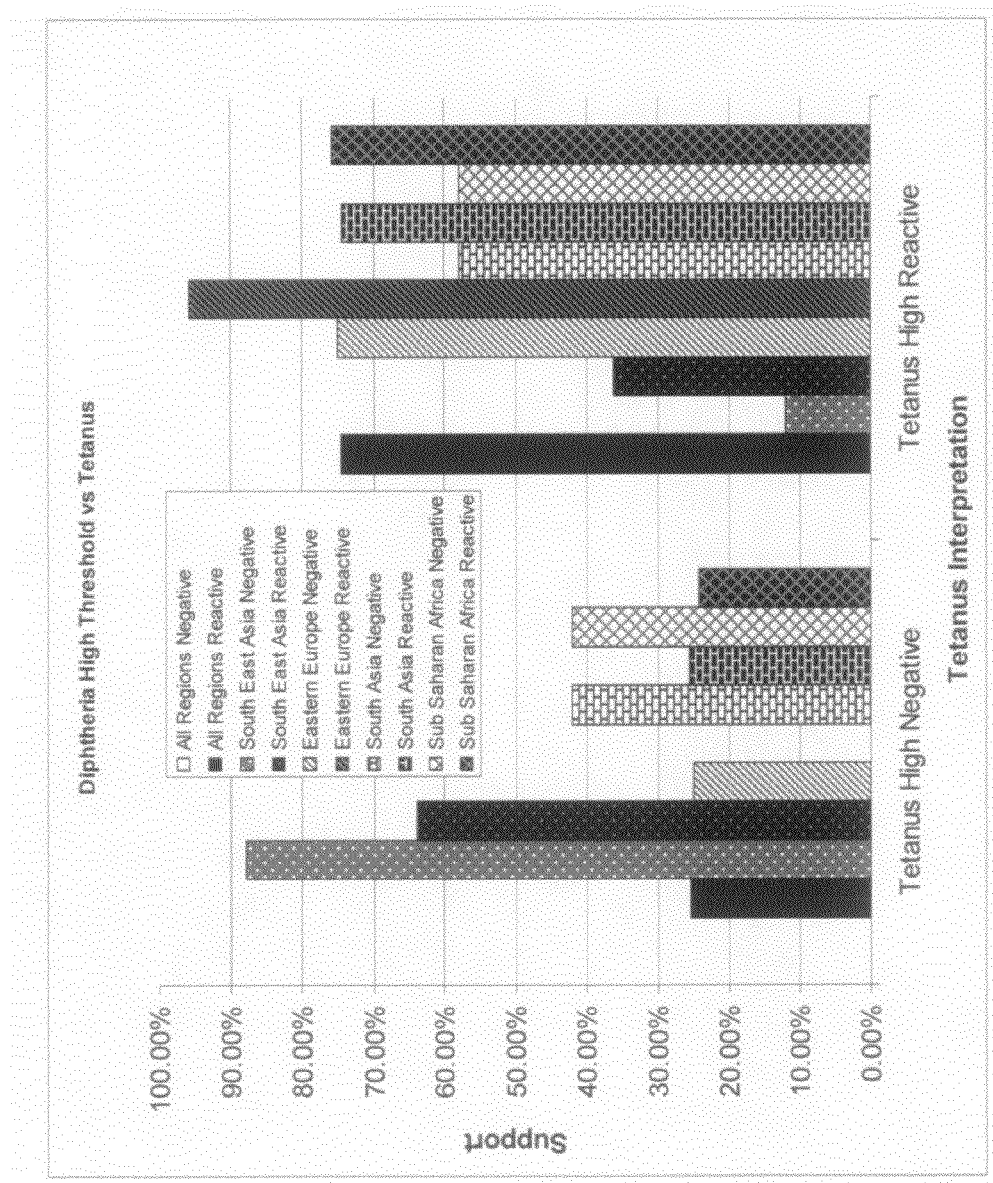
Fig. 20G33

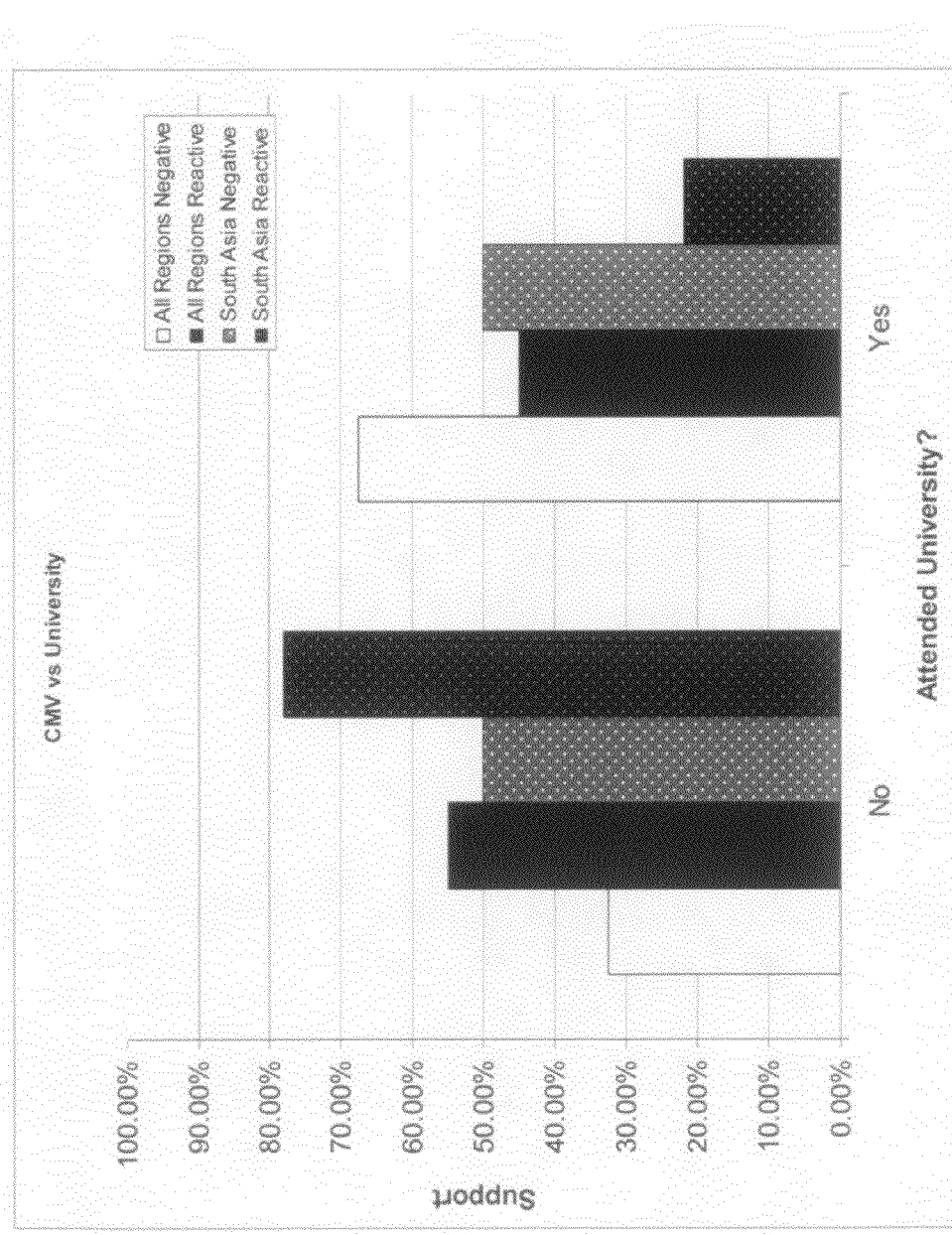
Fig. 20G34

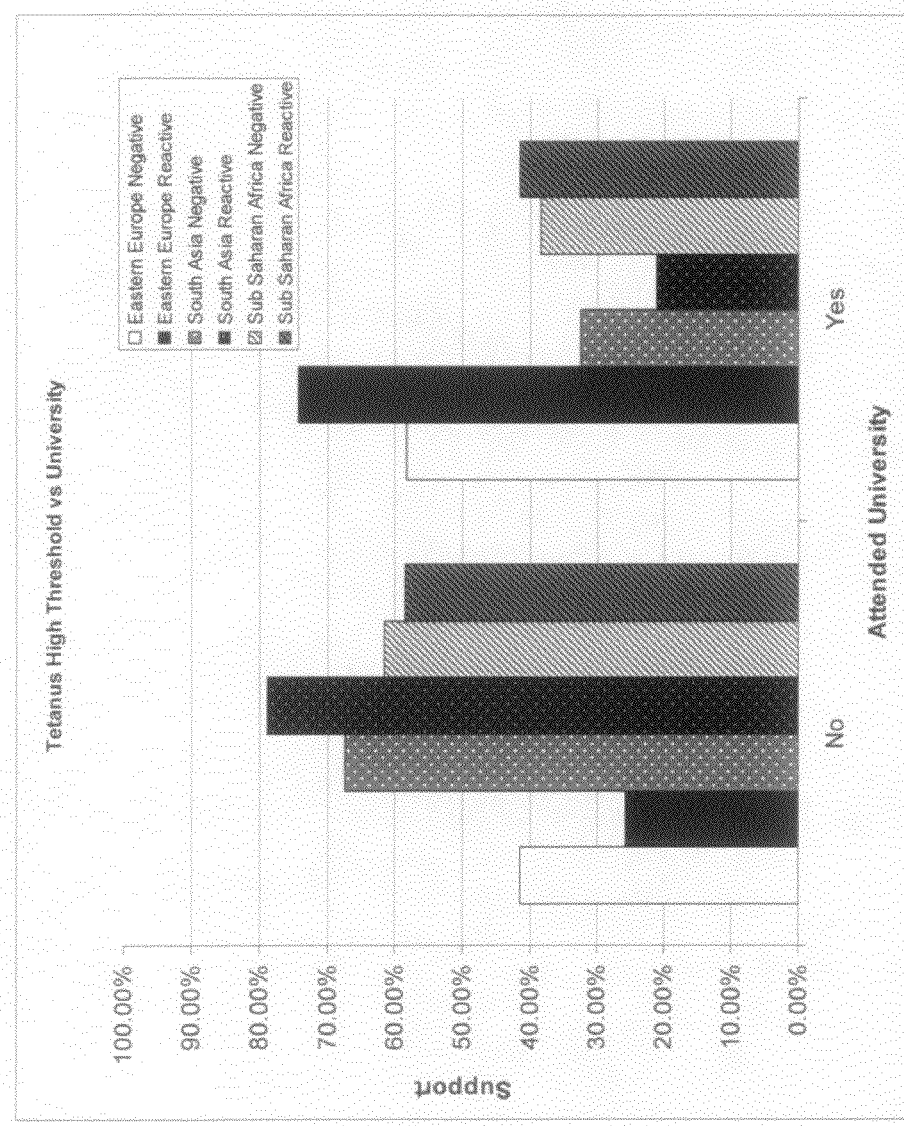
Fig. 20G35

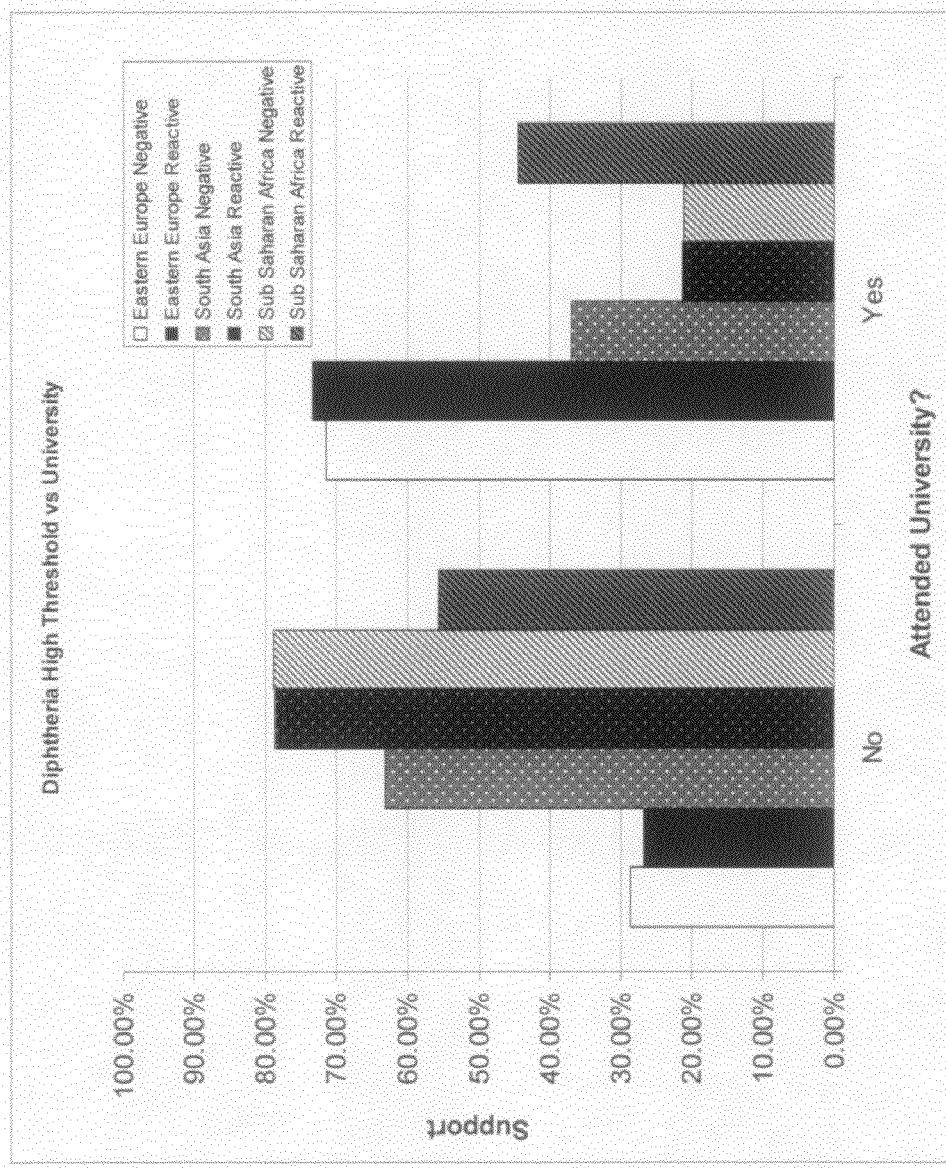
Fig. 20G36

Fig. 20G37(a)

| Data - numbers | | Tetanus Low | | Tetanus High | | Diphtheria Low | | Diphtheria High | |
|---|---|---|---|---|---|---|---|---|---|
| Region | Gender | Negative | Reactive | Negative | Reactive | Negative | Reactive | Negative | Reactive |
| Sub Saharan Africa | M |  | 92 | 37 | 55 |  | 92 | 14 | 78 |
|  | F | 1 | 148 | 28 | 121 |  | 148 | 24 | 125 |
| South Asia | M |  | 156 | 39 | 117 | 1 | 156 | 18 | 138 |
|  | F | 2 | 142 | 47 | 97 |  | 142 | 39 | 105 |
| North Africa | M |  | 43 | 20 | 23 |  | 43 | 9 | 34 |
|  | F |  | 113 | 34 | 79 | 2 | 113 | 42 | 71 |
| Latin America / Carribean | M |  | 83 | 17 | 66 |  | 83 | 17 | 66 |
|  | F | 1 | 241 | 53 | 189 |  | 241 | 75 | 167 |
| East Europe | M |  | 46 | 3 | 43 | 1 | 46 | 6 | 40 |
|  | F |  | 102 | 9 | 93 |  | 102 | 22 | 80 |
| South East Asia | M |  | 62 | 46 | 16 |  | 62 | 20 | 42 |
|  | F |  | 154 | 114 | 40 |  | 154 | 71 | 83 |
| Grand Total |  | 4 | 1382 | 447 | 939 | 4 | 1382 | 357 | 1029 |

Fig. 20G37(b)

| Percentages | | Tetanus Low | | Tetanus High | | Diphtheria Low | | Diphtheria High | |
|---|---|---|---|---|---|---|---|---|---|
| Region | Gender | Negative | Reactive | Negative | Reactive | Negative | Reactive | Negative | Reactive |
| Sub Saharan Africa | M | 0.00% | 100.00% | 40.22% | 59.78% | 0.00% | 100.00% | 15.22% | 84.78% |
|  | F | 0.67% | 99.33% | 18.79% | 81.21% | 0.67% | 99.33% | 16.11% | 83.89% |
| South Asia | M | 0.00% | 100.00% | 25.00% | 75.00% | 0.00% | 100.00% | 11.54% | 88.46% |
|  | F | 1.39% | 98.61% | 32.64% | 67.36% | 1.39% | 98.61% | 27.08% | 72.92% |
| North Africa | M | 0.00% | 100.00% | 46.51% | 53.49% | 0.00% | 100.00% | 20.93% | 79.07% |
|  | F | 0.00% | 100.00% | 30.09% | 69.91% | 0.00% | 100.00% | 37.17% | 62.83% |
| Latin America / Carribean | M | 0.00% | 100.00% | 20.48% | 79.52% | 0.00% | 100.00% | 20.48% | 79.52% |
|  | F | 0.41% | 99.59% | 21.90% | 78.10% | 0.41% | 99.59% | 30.99% | 69.01% |
| East Europe | M | 0.00% | 100.00% | 6.52% | 93.48% | 0.00% | 100.00% | 13.04% | 86.96% |
|  | F | 0.00% | 100.00% | 8.82% | 91.18% | 0.00% | 100.00% | 21.57% | 78.43% |
| South East Asia | M | 0.00% | 100.00% | 74.19% | 25.81% | 0.00% | 100.00% | 32.26% | 67.74% |
|  | F | 0.00% | 100.00% | 74.03% | 25.97% | 0.00% | 100.00% | 46.10% | 53.90% |
| Grand Total |  | 0.29% | 99.71% | 32.25% | 67.75% | 0.29% | 99.71% | 25.76% | 74.24% |

| Data - numbers | | CMV | | | | CMV (Alternative) | | | Hep A | |
|---|---|---|---|---|---|---|---|---|---|---|
| Region | Gender | Unknown | Negative | Reactive | Unknown | Negative | Reactive | Nonreactive | Reactive |
| Sub Saharan Africa | M | 15 | | 77 | 15 | 35 | 42 | 3 | 89 |
| | F | 42 | | 107 | 41 | 38 | 70 | 8 | 141 |
| South Asia | M | 11 | 3 | 142 | 11 | 49 | 96 | 2 | 154 |
| | F | 10 | 3 | 131 | 10 | 44 | 90 | 6 | 138 |
| North Africa | M | 5 | 4 | 34 | 5 | 14 | 24 | 4 | 39 |
| | F | 20 | 6 | 87 | 20 | 37 | 56 | 4 | 108 |
| Latin America / Carribean | M | 3 | 21 | 59 | 3 | 58 | 22 | 20 | 63 |
| | F | 18 | 22 | 202 | 18 | 103 | 121 | 37 | 205 |
| East Europe | M | 3 | 5 | 38 | 3 | 26 | 17 | 14 | 32 |
| | F | 3 | 7 | 92 | 3 | 54 | 45 | 39 | 63 |
| South East Asia | M | 7 | 4 | 51 | 7 | 29 | 26 | 16 | 46 |
| | F | 19 | 5 | 130 | 19 | 74 | 61 | 43 | 111 |
| Grand Total | | 156 | 80 | 1150 | 155 | 561 | 670 | 196 | 1189 |

Fig. 20G37(c)

| Percentages | | CMV | | | | CMV (Alternative) | | | Hep A | |
|---|---|---|---|---|---|---|---|---|---|---|
| Region | Gender | Unknown | Negative | Reactive | Unknown | Negative | Reactive | Nonreactive | Reactive |
| Sub Saharan Africa | M | 16.30% | 0.00% | 83.70% | 16.30% | 38.04% | 45.65% | 3.26% | 96.74% |
| | F | 28.19% | 0.00% | 71.81% | 27.52% | 25.50% | 46.98% | 5.37% | 94.63% |
| South Asia | M | 7.05% | 1.92% | 91.03% | 7.05% | 31.41% | 61.54% | 1.28% | 98.72% |
| | F | 6.94% | 2.08% | 90.97% | 6.94% | 30.56% | 62.50% | 4.17% | 95.83% |
| North Africa | M | 11.63% | 9.30% | 79.07% | 11.63% | 32.56% | 55.81% | 9.30% | 90.70% |
| | F | 17.70% | 5.31% | 76.99% | 17.70% | 32.74% | 49.56% | 3.57% | 96.43% |
| Latin America / Carribean | M | 3.61% | 25.30% | 71.08% | 3.61% | 69.88% | 26.51% | 24.10% | 75.90% |
| | F | 7.44% | 9.09% | 83.47% | 7.44% | 42.56% | 50.00% | 15.29% | 84.71% |
| East Europe | M | 6.52% | 10.87% | 82.61% | 6.52% | 56.52% | 36.96% | 30.43% | 69.57% |
| | F | 2.94% | 6.86% | 90.20% | 2.94% | 52.94% | 44.12% | 38.24% | 61.76% |
| South East Asia | M | 11.29% | 6.45% | 82.26% | 11.29% | 46.77% | 41.94% | 25.81% | 74.19% |
| | F | 12.34% | 3.25% | 84.42% | 12.34% | 48.05% | 39.61% | 27.92% | 72.08% |
| Grand Total | | 11.26% | 5.77% | 82.97% | 11.18% | 40.48% | 48.34% | 14.15% | 85.85% |

| Data - numbers | | Varicella | | | Rubella | | | Measles | | |
|---|---|---|---|---|---|---|---|---|---|---|
| Region | Gender | Equivocal | Negative | Positive | Equivocal | Negative | Positive | Equivocal | Negative | Positive |
| Sub Saharan Africa | M | 1 | 6 | 85 | | 84 | 8 | | 1 | 91 |
| | F | 3 | 4 | 142 | 4 | 142 | 7 | | 2 | 143 |
| South Asia | M | 2 | 12 | 142 | | 144 | 12 | | 1 | 155 |
| | F | 2 | 19 | 123 | 1 | 125 | 19 | | 1 | 142 |
| North Africa | M | | 3 | 40 | | 39 | 4 | | | 43 |
| | F | | 3 | 109 | | 102 | 11 | | 6 | 106 |
| Latin America / Carribean | M | | 5 | 78 | 3 | 75 | 8 | 3 | 2 | 78 |
| | F | 3 | 17 | 222 | 10 | 210 | 32 | 10 | 24 | 208 |
| East Europe | M | 2 | 3 | 41 | | 45 | 1 | 3 | 4 | 42 |
| | F | 1 | 4 | 97 | 3 | 91 | 11 | 3 | 10 | 89 |
| South East Asia | M | | 4 | 58 | 4 | 57 | 5 | 4 | 1 | 57 |
| | F | 5 | 6 | 143 | 2 | 107 | 47 | 2 | 14 | 138 |
| Grand Total | | 19 | 86 | 1280 | 27 | 1221 | 165 | 27 | 66 | 1292 |

Fig. 20G37(f)

| Percentages | | Varicella | | | Rubella | | | Measles | | |
|---|---|---|---|---|---|---|---|---|---|---|
| Region | Gender | Equivocal | Negative | Positive | Equivocal | Negative | Positive | Equivocal | Negative | Positive |
| Sub Saharan Africa | M | 1.09% | 6.52% | 92.39% | 0.00% | 91.30% | 8.70% | 0.00% | 1.09% | 98.91% |
| | F | 2.01% | 2.68% | 95.30% | 2.68% | 95.30% | 4.70% | 2.68% | 1.34% | 95.97% |
| South Asia | M | 1.28% | 7.69% | 91.03% | 0.00% | 92.31% | 7.69% | 0.00% | 0.64% | 99.36% |
| | F | 1.39% | 13.19% | 85.42% | 0.69% | 86.81% | 13.19% | 0.69% | 0.69% | 98.61% |
| North Africa | M | 0.00% | 6.98% | 93.02% | 0.00% | 90.70% | 9.30% | 0.00% | 0.00% | 100.00% |
| | F | 0.00% | 2.68% | 97.32% | 0.00% | 90.27% | 9.73% | 0.00% | 5.36% | 94.64% |
| Latin America / Carribean | M | 0.00% | 6.02% | 93.98% | 3.61% | 90.36% | 9.64% | 3.61% | 2.41% | 93.98% |
| | F | 1.24% | 7.02% | 91.74% | 4.13% | 86.78% | 13.22% | 4.13% | 9.92% | 85.95% |
| East Europe | M | 4.35% | 6.52% | 89.13% | 0.00% | 97.83% | 2.17% | 0.00% | 8.70% | 91.30% |
| | F | 0.98% | 3.92% | 95.10% | 2.94% | 89.22% | 10.78% | 2.94% | 9.80% | 87.25% |
| South East Asia | M | 0.00% | 6.45% | 93.55% | 6.45% | 91.94% | 8.06% | 6.45% | 1.61% | 91.94% |
| | F | 3.25% | 3.90% | 92.86% | 1.30% | 69.48% | 30.52% | 1.30% | 9.09% | 89.61% |
| Grand Total | | 1.37% | 6.21% | 92.42% | 1.95% | 88.10% | 11.90% | 1.95% | 4.77% | 93.29% |

Fig. 20G37(g)

| Data - numbers | | Hep B e Antigen | | | Hep C Antibody | | | |
|---|---|---|---|---|---|---|---|---|
| Region | Gender | Unknown | Nonreactive | Reactive | Unknown | Grayzone | Nonreactive | Reactive |
| Sub Saharan Africa | M | 85 | 7 | | 15 | | 70 | 7 |
| | F | 144 | 4 | 1 | 42 | | 99 | 8 |
| South Asia | M | 156 | | | 11 | | 138 | 7 |
| | F | 143 | 1 | | 11 | | 132 | 1 |
| North Africa | M | 40 | 3 | | 5 | | 37 | 1 |
| | F | 110 | 3 | | 20 | 1 | 92 | |
| Latin America / Carribean | M | 82 | 1 | | 3 | | 78 | 2 |
| | F | 241 | 1 | | 18 | 2 | 220 | 2 |
| East Europe | M | 43 | 3 | | 3 | | 40 | 3 |
| | F | 96 | 5 | 1 | 3 | 1 | 97 | 1 |
| South East Asia | M | 56 | 6 | | 7 | 1 | 54 | |
| | F | 147 | 6 | 1 | 19 | | 133 | 2 |
| Grand Total | | 1343 | 40 | 3 | 157 | 5 | 1190 | 34 |

Fig. 20G37(h)

| Percentages | | Hep B e Antigen | | | Hep C Antibody | | | |
|---|---|---|---|---|---|---|---|---|
| Region | Gender | Unknown | Nonreactive | Reactive | Unknown | Grayzone | Nonreactive | Reactive |
| Sub Saharan Africa | M | 92.39% | 7.61% | 0.00% | 16.30% | 0.00% | 76.09% | 7.61% |
| | F | 96.64% | 2.68% | 0.67% | 28.19% | 0.00% | 66.44% | 5.37% |
| South Asia | M | 100.00% | 0.00% | 0.00% | 7.05% | 0.00% | 88.46% | 4.49% |
| | F | 99.31% | 0.69% | 0.00% | 7.64% | 0.00% | 91.67% | 0.69% |
| North Africa | M | 93.02% | 6.98% | 0.00% | 11.63% | 0.00% | 86.05% | 2.33% |
| | F | 97.35% | 2.65% | 0.00% | 17.70% | 0.88% | 81.42% | 0.00% |
| Latin America / Carribean | M | 98.80% | 1.20% | 0.00% | 3.61% | 0.00% | 93.98% | 2.41% |
| | F | 99.59% | 0.41% | 0.00% | 7.44% | 0.83% | 90.91% | 0.83% |
| East Europe | M | 93.48% | 6.52% | 0.00% | 6.52% | 0.00% | 86.96% | 6.52% |
| | F | 94.12% | 4.90% | 0.98% | 2.94% | 0.98% | 95.10% | 0.98% |
| South East Asia | M | 90.32% | 9.68% | 0.00% | 11.29% | 1.61% | 87.10% | 0.00% |
| | F | 95.45% | 3.90% | 0.65% | 12.34% | 0.00% | 86.36% | 1.30% |
| Grand Total | | 96.90% | 2.89% | 0.22% | 11.33% | 0.36% | 85.86% | 2.45% |

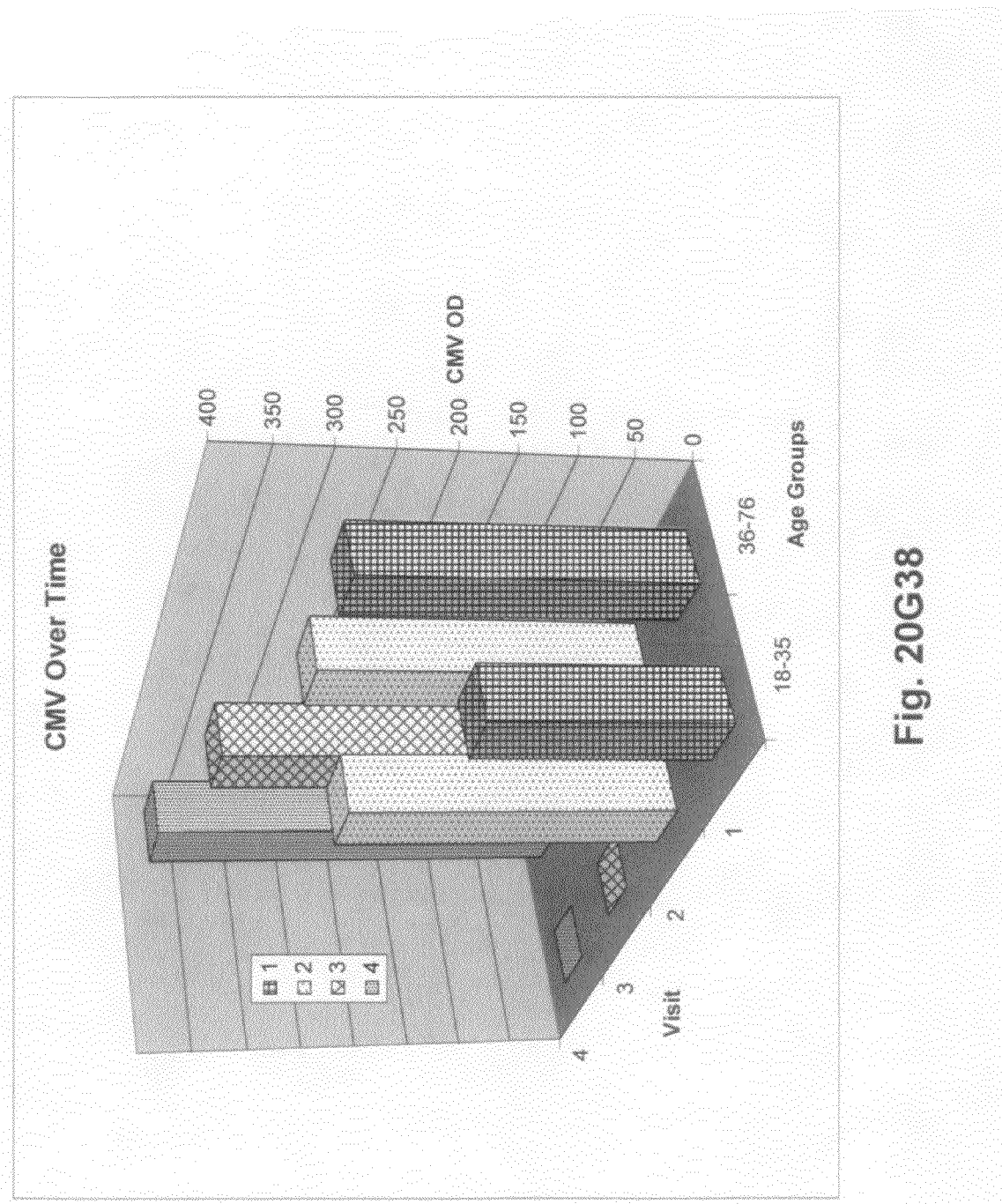
Fig. 20G38

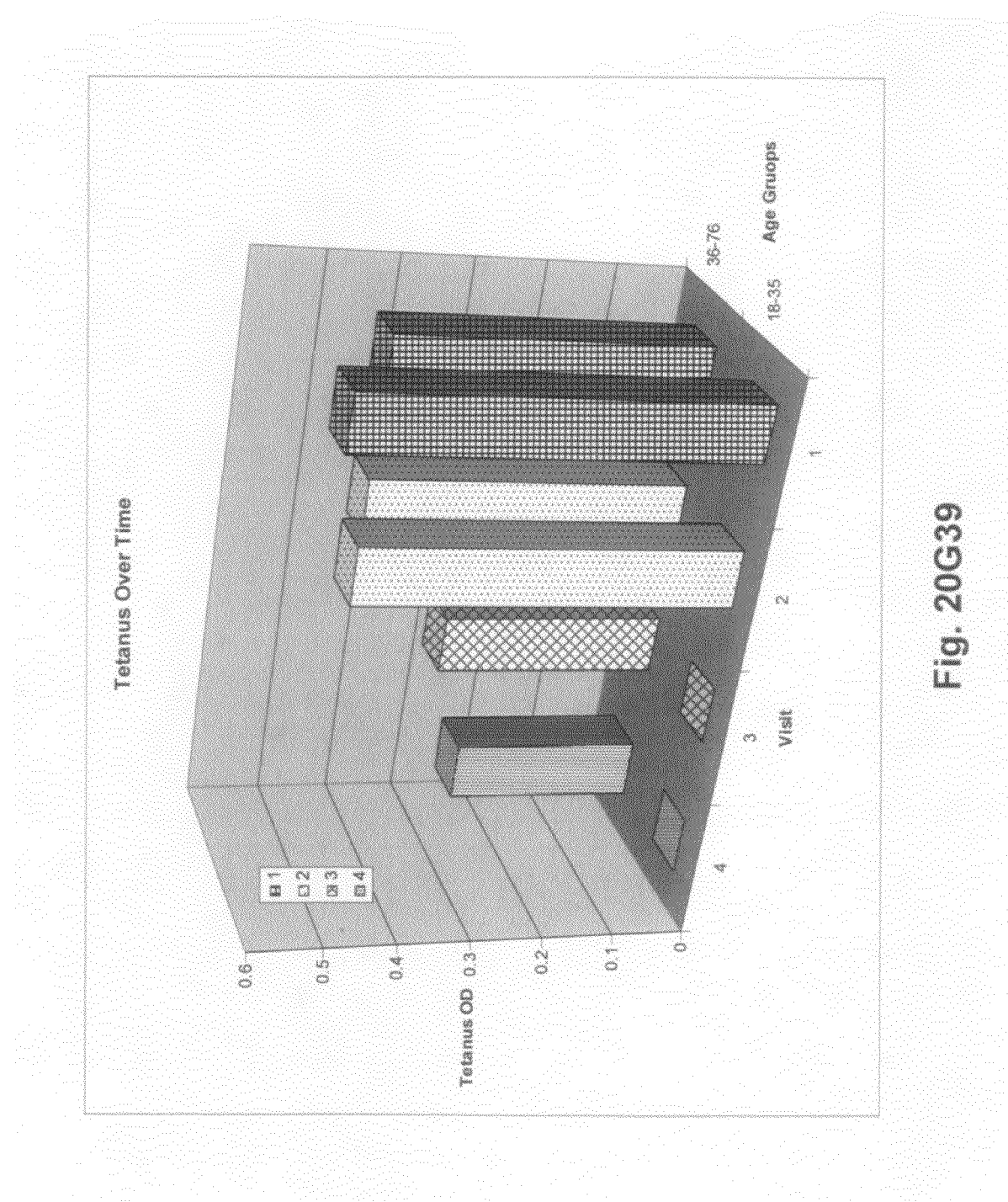
Fig. 20G39

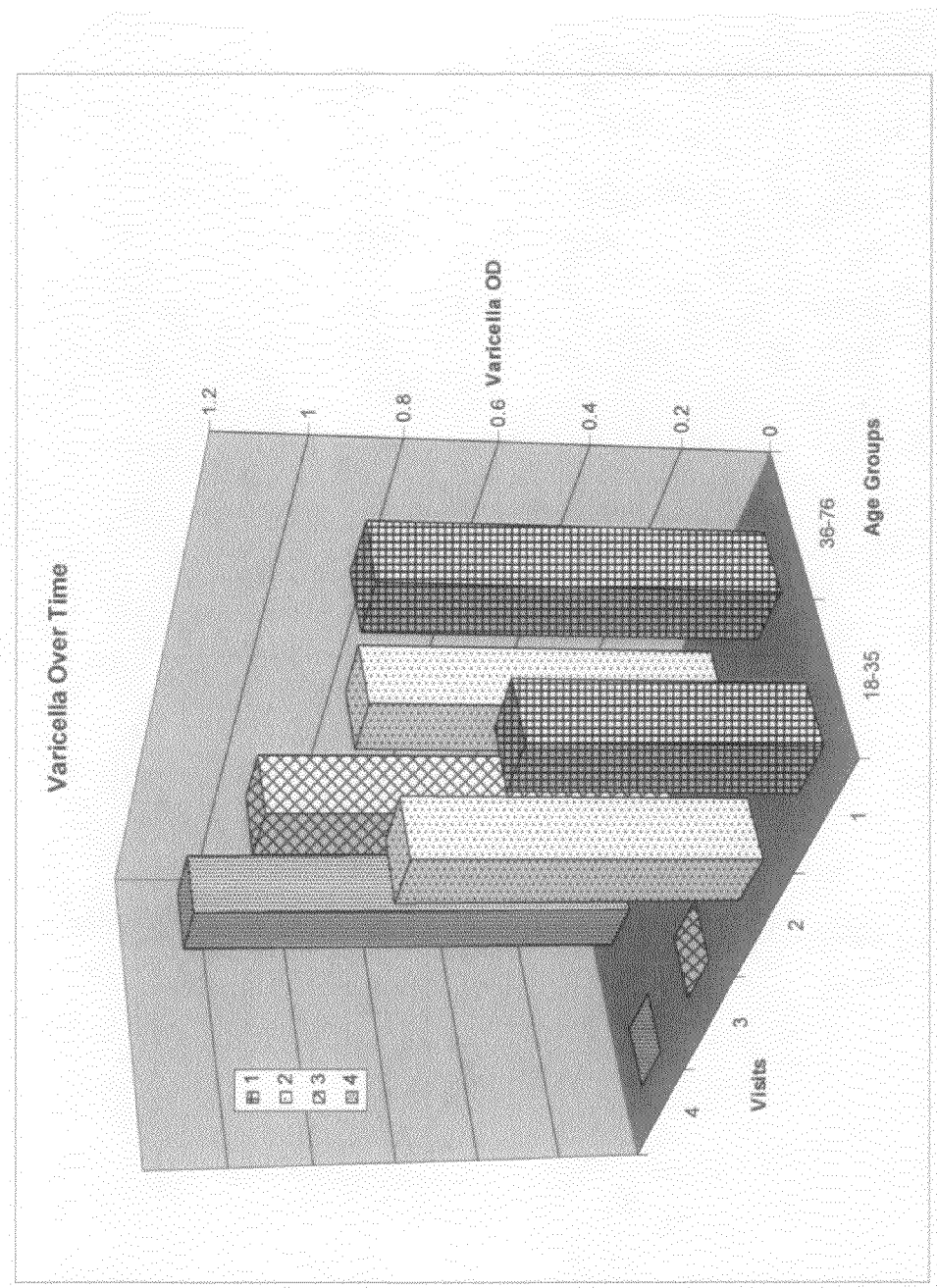
Fig. 20G40

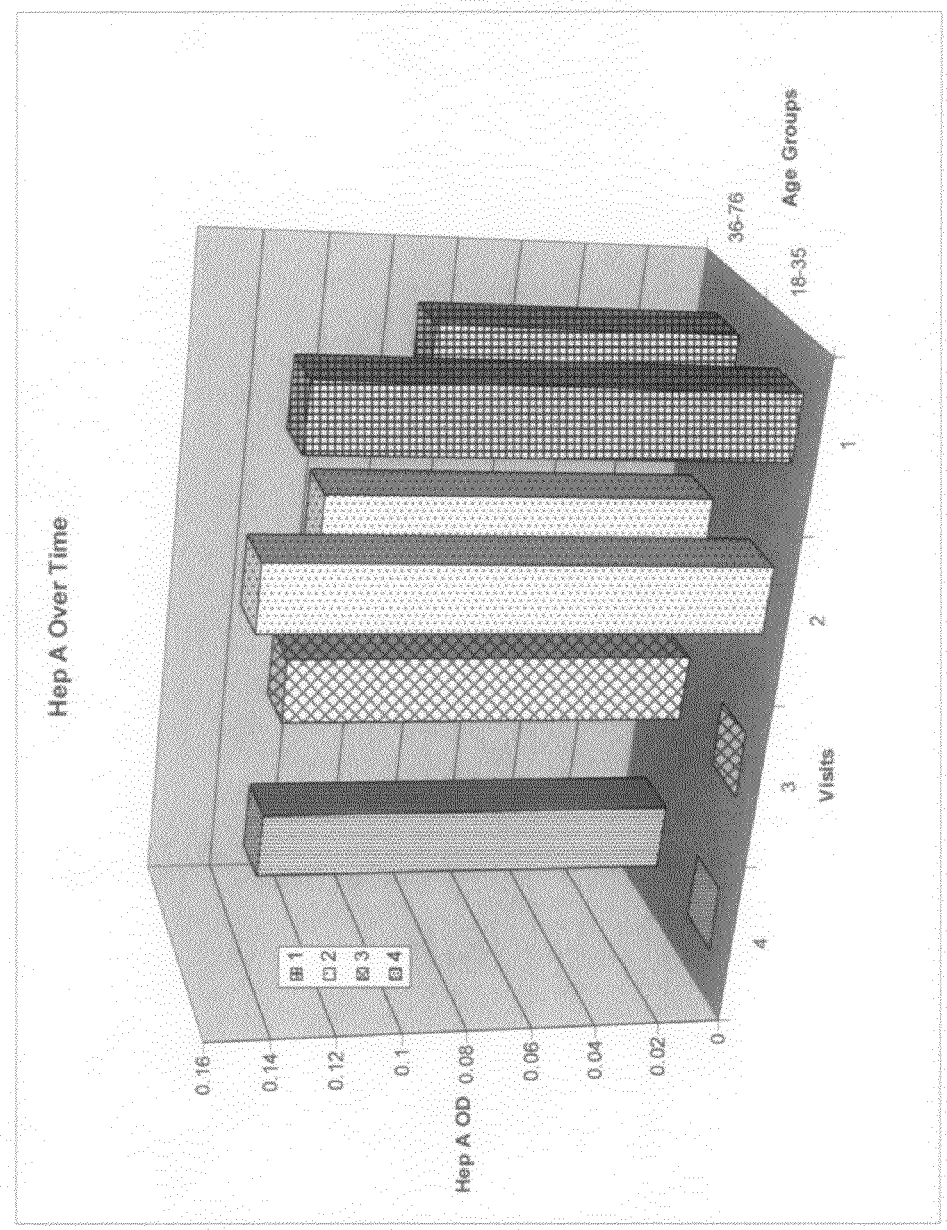
Fig. 20G41

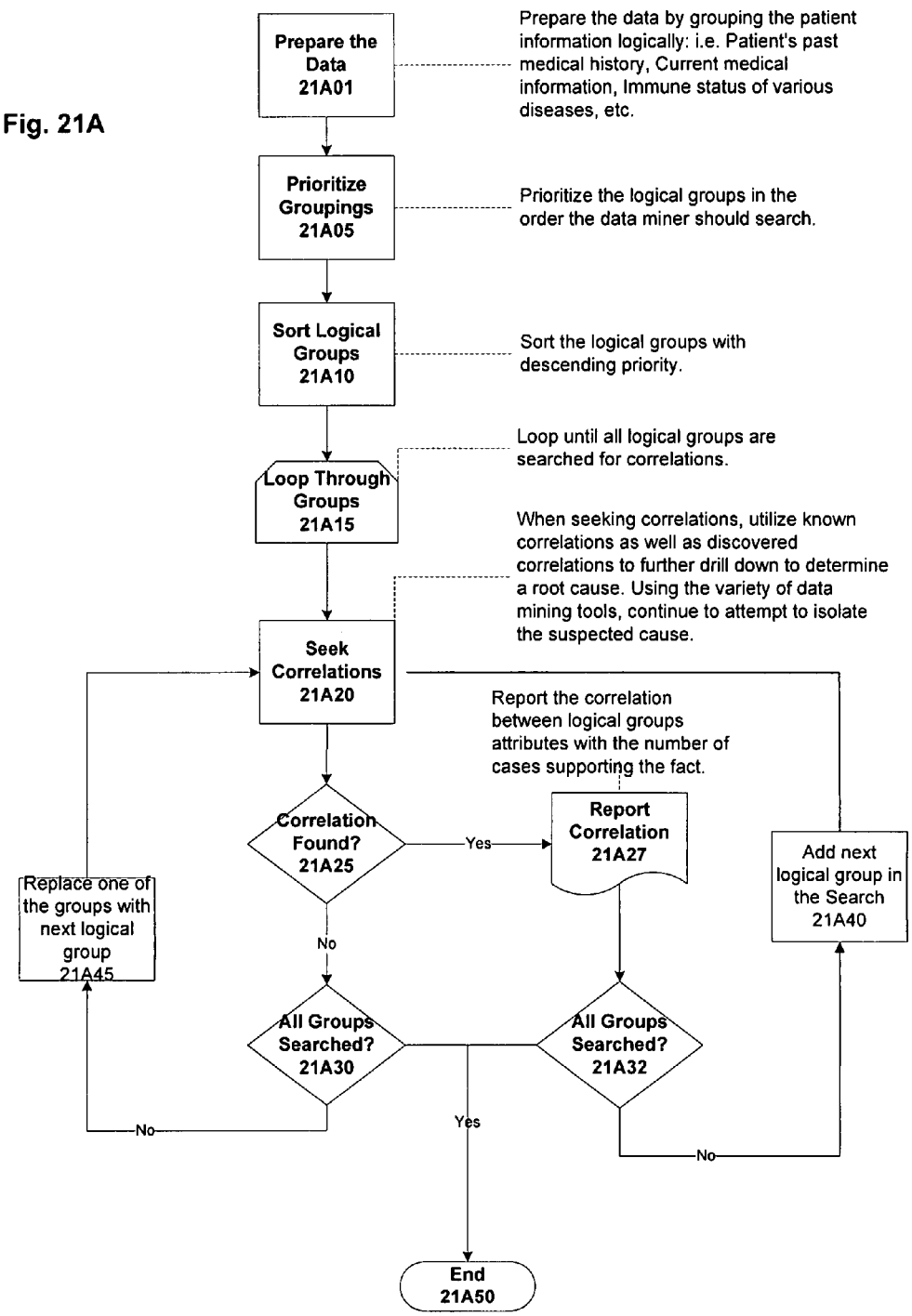

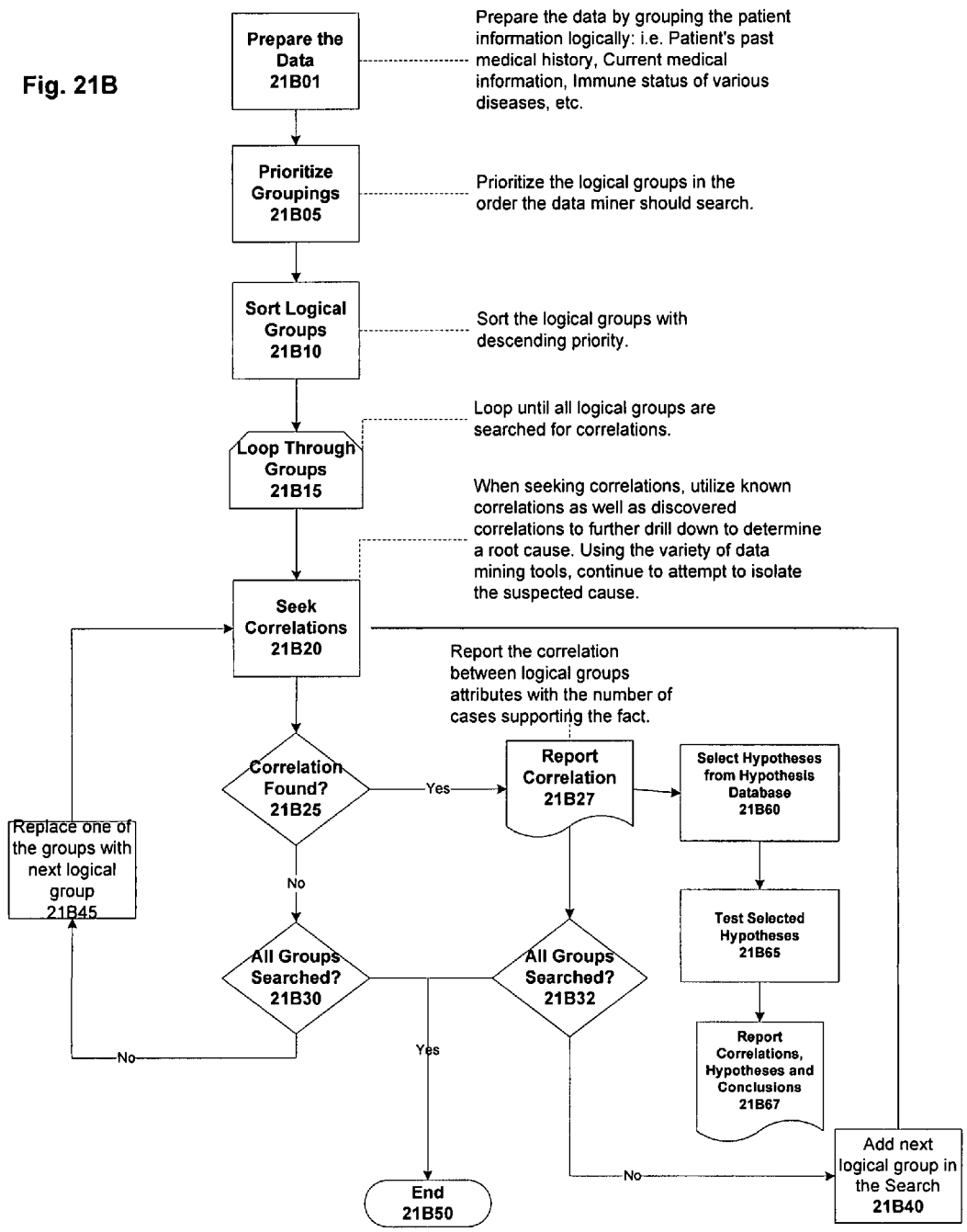

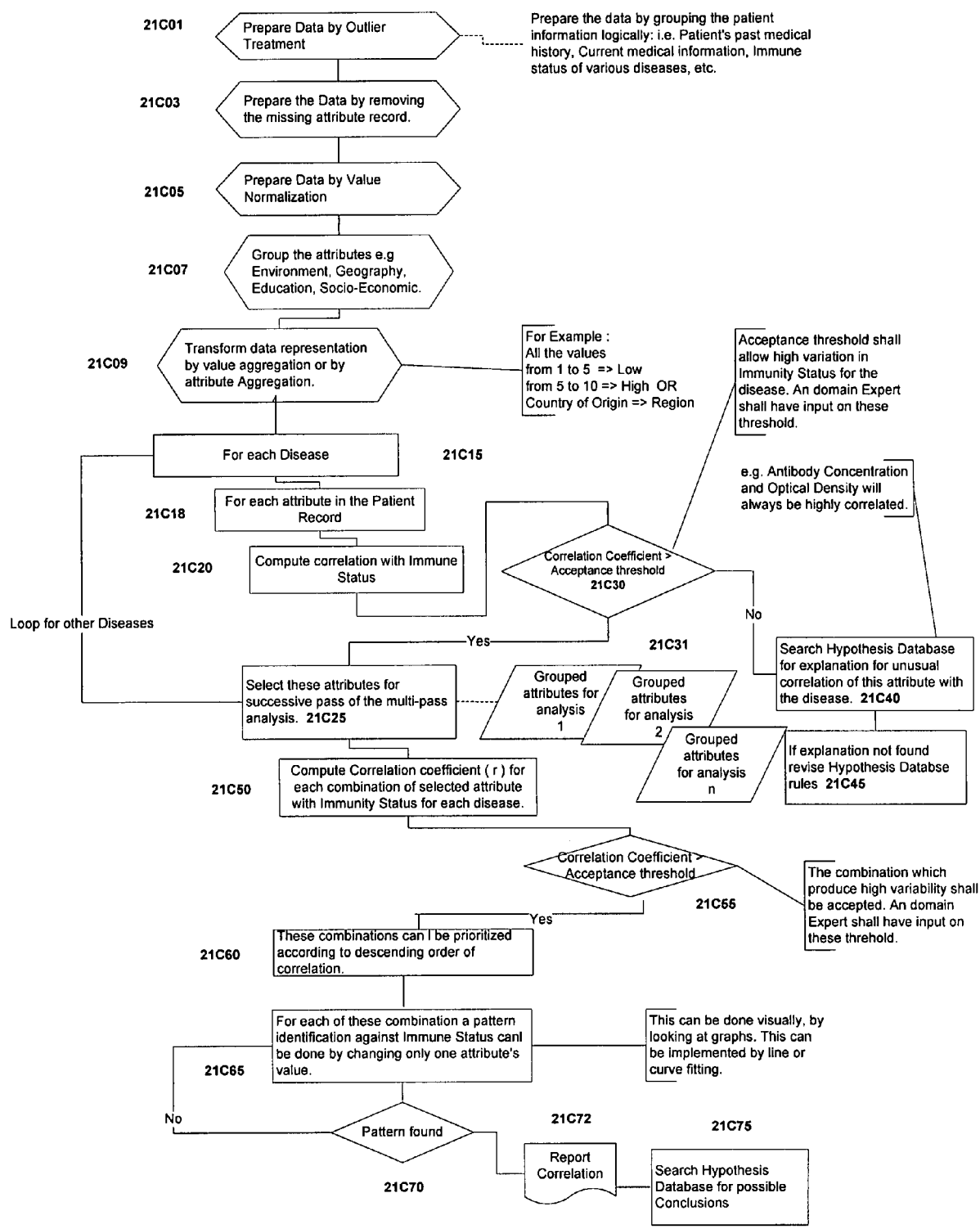
Fig. 21C Automated Pattern Detection Process Flow

SYSTEMS AND METHODS FOR OBTAINING, STORING, PROCESSING AND UTILIZING IMMUNOLOGIC AND OTHER INFORMATION OF INDIVIDUALS AND POPULATIONS

CROSS-REFERENCE TO RELATED APPLICATIONS

This application is a continuation-in-part of, and hereby fully incorporates herein by reference, U.S. Utility patent application Ser. No. 11/255,161, filed on Oct. 18, 2005 ("the Immunologic Informatics Patent"), which was published on Sep. 28, 2006 as United States Patent Application Publication No. 2006/0218010 A1. Additionally, this application claims the benefit of U.S. Provisional Patent Application Ser. No. 60/796,266, filed on Apr. 27, 2006.

TECHNICAL FIELD

The present invention relates to individualized health care, immunology and medical informatics, and more particularly to systems and methods for acquiring, storing, processing and utilizing immunologic and other information of individuals and populations in various applications.

BACKGROUND OF THE INVENTION

Personalized medicine is considered by many to be the wave of the future. A personalized medicine approach seeks to identify whether a given individual needs a given treatment or intervention prior to administering it, rather than relying on "standards" representing an average person in a group or population.

This approach is based on the well known fact that some individuals in a demographic population have naturally low or naturally high values which are not best measured against a statistical mean for the demographic population, but against that individual's own measured history.

For example, vaccines are a immunologic prophylactic whose frequency and dose is determined at the population level. Vaccines are approved for routine human use by regulatory agencies from different countries where the vaccines are to be applied, such as, for example, the U.S. the Food and Drug Administration (FDA). After approval, population-wide recommendations for use are made by various medical agencies, such as the Advisory Committee on Immunization Practices (ACIP), whose members represent experts in the vaccine field. The ACIP is a U.S. committee, to assist and advise the Secretary of Health and Human Services, as well as the Centers for Disease Control and Prevention (CDC), on how to best implement vaccination strategies to prevent disease. Written recommendations are developed with immunization schedules that are published and updated as needed for both pediatric and adult populations. From these recommendations, certain vaccines are mandated for school entry and government-sponsored programs.

Although such mandated schedules are the norm, the need for them varies across populations. They represent an a priori approach that does not take into account individual specifics. Immunity to disease wanes over time, but may be maintained at low levels or recalled, through immunologic memory, upon subsequent exposure to the corresponding infectious agent or cross-reactive antigens in the environment. For inactivated or subunit-based T cell-dependent vaccines, however, protective immunity may not last beyond 10 years.

For example, the protective responses to diphtheria, tetanus, and pertussis vaccines (DTaP, Td) have been shown to be absent after about 10 years, which is why Td (tetanus and diphtheria) boosters are recommended every 10 years. For T cell-independent vaccines, such as pneumococcal and meningococcal polysaccharides, there is no immunologic memory, and immunity may be gone in only 3 to 5 years. The result of these facts is that vaccinating everyone according to a standard protocol can often result in either under-vaccinating or over-vaccinating in various individual cases.

Result of Over-Vaccinating: Type III Hypersensitivity Reactions

Thus, while generalizations about the timing for boosters, whether at 3 or 5 or 10 years, represents one approach to the problem of maintaining long-term immunity, other problems can arise if the duration of immunity does not follow the expected pattern. For example, it is well known that Tetanus boosters for adults (such as, for example, those administered in emergency rooms to prevent tetanus after someone steps on a rusty nail), often lead to local adverse reactions at the injection site, particularly if the last booster was not too many years earlier. Because it may be difficult to determine when the last immunization was received for tetanus, health care providers tend to err on the side of caution by boosting.

While this general booster approach may readily prevent tetanus, the possibility of high levels of circulating antibodies may lead to an Arthus reaction, which is a local type III hypersensitivity reaction due to the development of immune complexes composed of IgG antibodies and the vaccine antigen. The immune complexes activate complement which binds to complement receptors on the mast cells to cause the release of granules and increased vascular permeability. This can ultimately lead to tissue damage. In an extreme case, a more generalized or systemic reaction can occur, where immune complexes are deposited in the kidneys and joints, leading to arthritis and glomerulonephritis. Subsequent cellular immune responses and tissue damage with respect to the glomerulus can lead to permanent loss of kidney function. The CDC has recently noted that certain vaccines produce increased rates of local or systemic reactions in certain recipients when administered too frequently, and that such reactions are thought to result from the formation of antigen-antibody complexes (Centers for Disease Control and Prevention, *General Recommendations on immunization: Recommendations of the Advisory Committee on Immunization Practices and the American Academy of Family Physicians*. MMWR 2002; 51(No. RR-2):1-36).

A solution for the prevention of such a type III hypersensitivity problem resulting from over-vaccination would be to assess a person's immune status with respect to the offending antigen, and make an existential determination of when to optimally administer the vaccine booster. For example, concerning vaccinations for internationally adopted children of unknown immune status, the CDC states: "If avoiding unnecessary injections is desired, judicious use of serologic testing might be helpful in determining which immunizations are needed." Regarding DTaP vaccinations specifically, the CDC also states: "If a revaccination approach is adopted and a severe local reaction occurs, serologic testing for specific IgG antibody to tetanus and diphtheria toxins can be measured before administering additional doses." (see pages 20 and 21 of the CDC 2002 reference cited above.) In this way, serologic testing could be used to determine whether an antibody level is low enough to warrant further boosting of the immune system for a specific antigen, minimizing the risk of adverse reactions from over-vaccinations.

Result of Under-Vaccinating: Increased Susceptibility to Infection

Certain individuals may be genetically predisposed to infections as a result of a compromised immune system. For example, there are people that have been identified to be at greater risk of meningococcal disease due to late-stage complement deficiency, since complement usually mediates antibody-dependent killing of meningococci. Others have been shown to be susceptible to a variety of diseases (e.g., leprosy, salmonellosis, *Pseudomonas aeruginosa* infections, *Yersinia* infections, *Listeria monocytogenes* infections, streptococcal diseases, tuberculosis, Lyme disease, *Chlamydia trachomatis* infections, *Helicobacter pylori* infections, HIV disease, and various other viral infections) that appear to be correlated to a different HLA haplotype. Still others have been shown to have increased susceptibility to certain diseases (e.g., *Haemophilus influenzae* type B meningitis in Eskimos, Apaches, and Navajos) because their immune systems respond with a less effective antibody repertoire based on variable-region gene haplotypes. A solution to this susceptibility problem would be to screen people for the appropriate biologic or genetic markers and vaccinate accordingly. Vaccinations would help to enhance the compromised immune systems with higher levels of specific antibodies that could enable other immune mechanisms (e.g., opsonophagocytosis instead of complement-mediated lysis), overcome low antibody avidity with greater antibody numbers, or alter the relative balance of antibody repertoires. In addition, continuous serologic testing (e.g., annually) of the immune status would allow for optimum timing of vaccinations to counter the relentless waning of immunity over time while still avoiding the potential problems of over immunizing.

Determination of the immune status of individuals to, for example, vaccine-preventable diseases requires an assay system that can detect antibodies that may be present at very low levels, especially when natural or vaccine exposure may have been many years previously. In addition, such an assay system could be used more generally to assess an individual's immune competence at different stages of that individual's life, as well as to also measure the vaccine status of individuals with varying special needs and requirements (e.g., military personnel or travelers).

What is thus needed in the art is a system and method for measuring and processing immunologic information of individuals and populations through various points in time of their lives so as to better track each individual's immune status and make appropriate diagnostic, prophylactic and therapeutic recommendations.

What is further needed in the art is a supporting structure to conveniently store the results of such screenings for easy access and processing, for data mining purposes as well as for use in a variety of commercial, research and governmental applications where a knowledge of the immunological indicia of customers, subjects and citizens can create efficiencies and optimizations, as well as allow for the exploitation of commercial opportunities and improve the quality of life.

SUMMARY OF THE INVENTION

A system and method for assessing the immunological status of one or more individuals in a patient population is presented. The method includes establishing a database comprising a plurality of records of information each representative of the immune status of an individual in the population, each of said records including (1) current information from one or more assays for the presence of a biochemical, and (2) individual specific information comprising one or more of said individual's medical history, said individual's doctors' observations and historical, demographic, lifestyle, and familial information relating to said individual. The method further includes processing the information in said database to find trends or patterns relating to the immune status of individuals in said patient population; and using the said trends or patterns as part of a health care related decision making process. In exemplary embodiments of the present invention, processing the information in the database includes generating a list of correlations between variables or fields in the database, and for each correlation in the list generating a set of hypotheses that may explain said correlation. In exemplary embodiments of the present invention, as to each hypothesis in the set, automatically refuting, supporting or stating that there is insufficient data to analyze said hypothesis by further processing of the database; and reporting the correlations, their associated hypotheses and the refutation, support, or determination of insufficient data to refute or support, to a user.

BRIEF DESCRIPTION OF THE DRAWINGS

Section I Figures

FIG. 5B depicts exemplary process flow for autoimmune disease screening and follow-up according to an exemplary embodiment of the present invention;

FIG. 5D illustrates mechanisms of downregulation or attenuation of immune response;

Section II Figures

FIG. 6 depicts exemplary assay results in an exemplary database according to the present invention;

FIG. 7 depicts exemplary diagnostic module recommendation types according to an exemplary embodiment of the present invention;

FIG. 8 illustrates an exemplary perceptron network which implements a rule for a normal individual using as inputs the results of an exemplary menigicoccal diagnostic panel;

FIG. 8A illustrates the exemplary perceptron network of FIG. 8 implementing a similar rule for an abnormal individual;

FIG. 9 depicts an XML representation of the exemplary perceptron networks of FIGS. 8 and 8A;

FIG. 10 depicts an exemplary symbology for diagnostic goals which can be used to articulate diagnostic goals in an exemplary embodiment of the present invention;

FIG. 11 illustrates exemplary diagnostic goals using the symbology of FIG. 10;

FIG. 12 illustrates an exemplary database schema for patient information according to an exemplary embodiment of the present invention;

FIG. 13 illustrates an exemplary database schema for visit information according to an exemplary embodiment of the present invention;

FIG. 14 illustrates an exemplary database schema for test results according to an exemplary embodiment of the present invention;

FIG. 15 depicts exemplary patient age intervals used in an exemplary database according to an exemplary embodiment of the present invention;

FIG. 16 is a plot of an exemplary female antibody comparison over a number of years according to an exemplary embodiment of the present invention.

Figure 1:
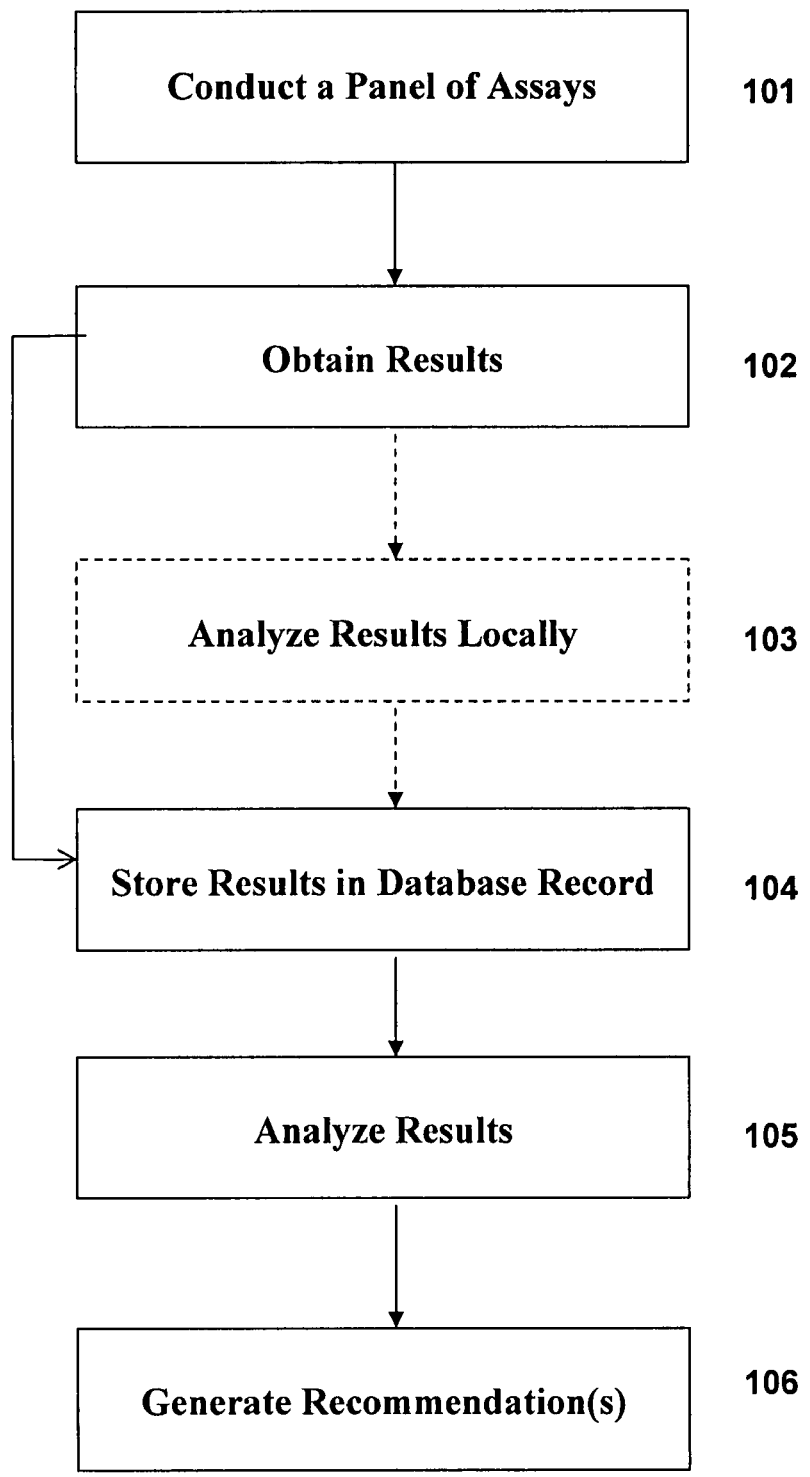
FIG. 1 depicts a generalized exemplary process flow according to exemplary embodiments of the present invention.
Figure 20A:
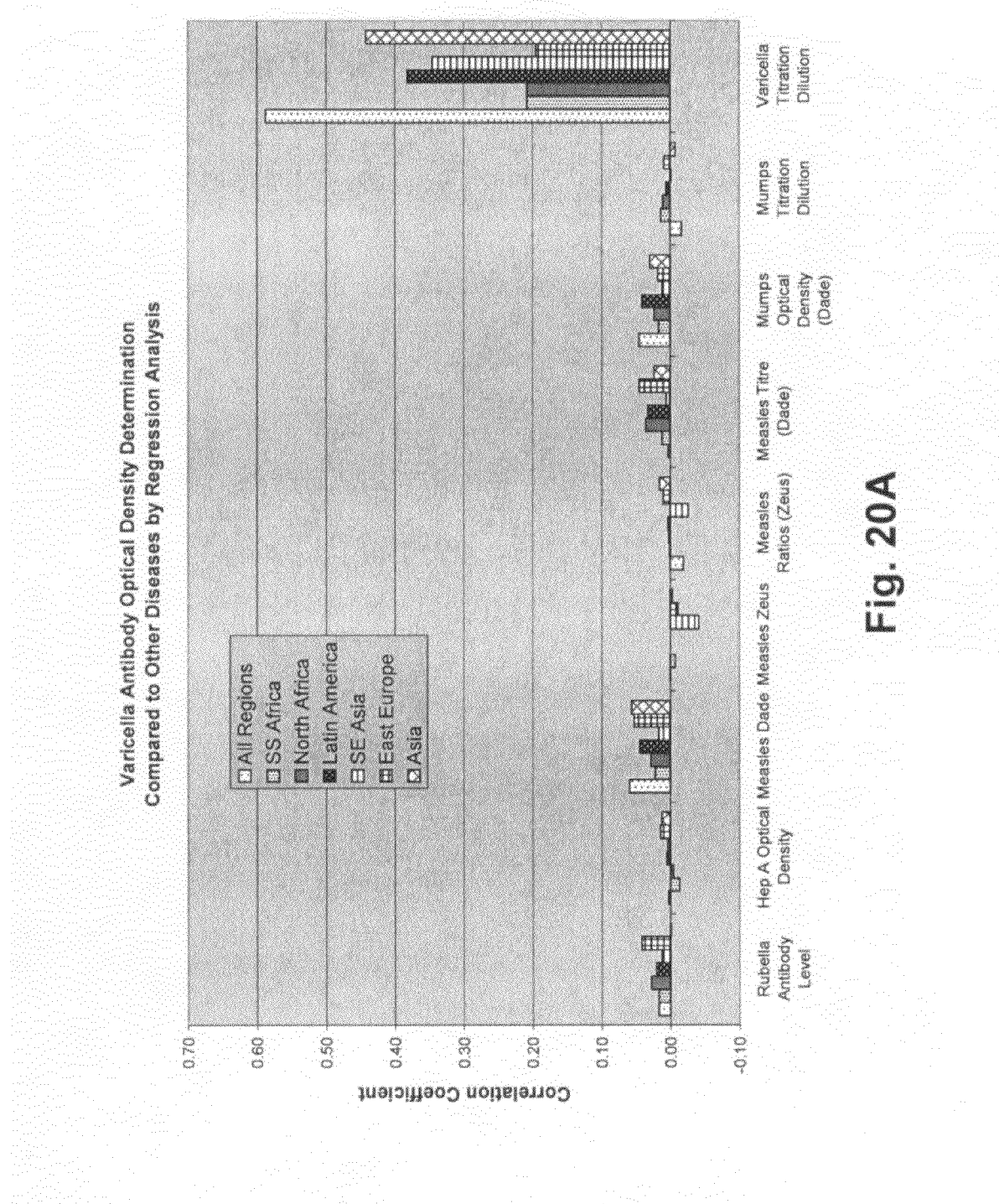
Figure 20B:
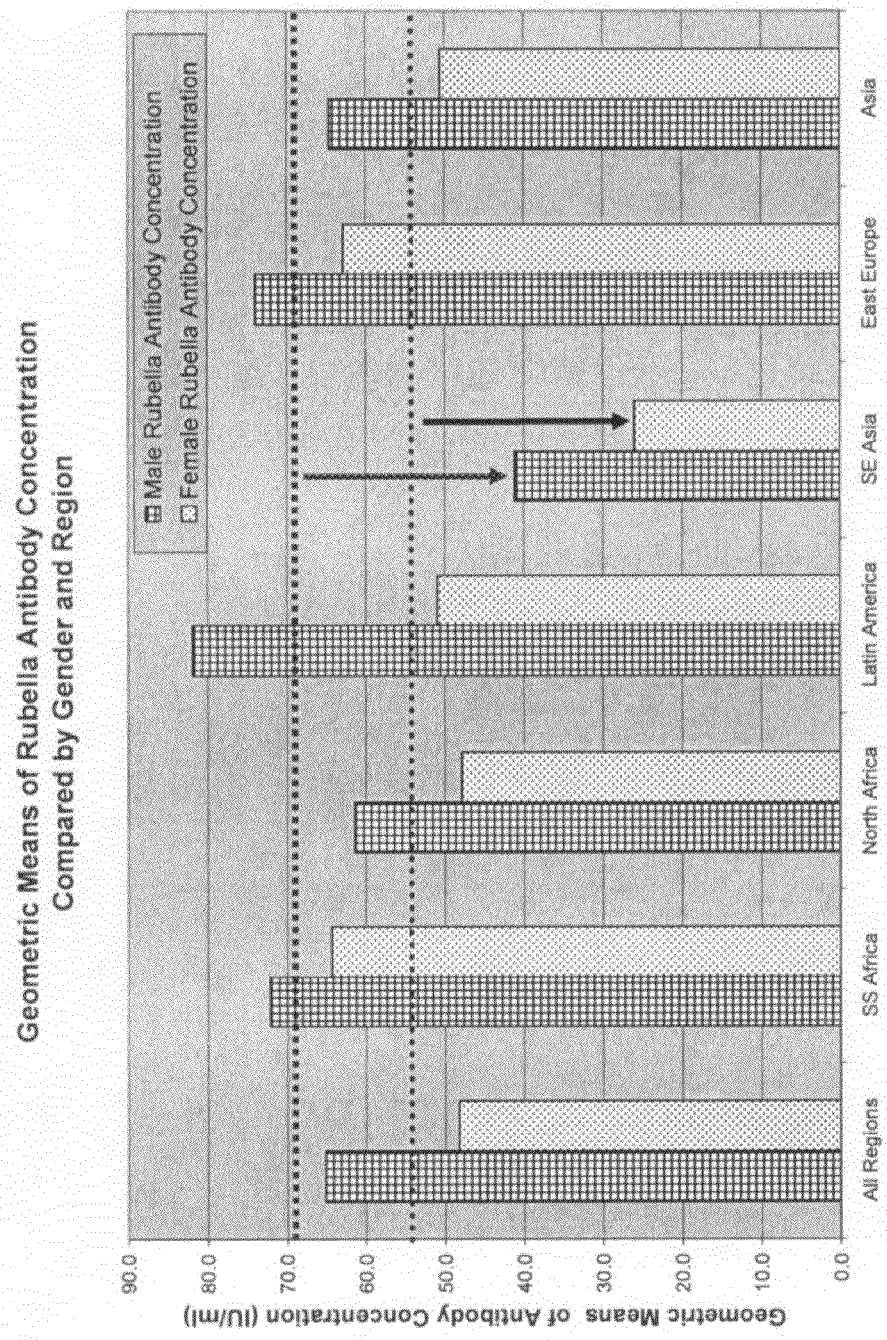
Figure 20C:
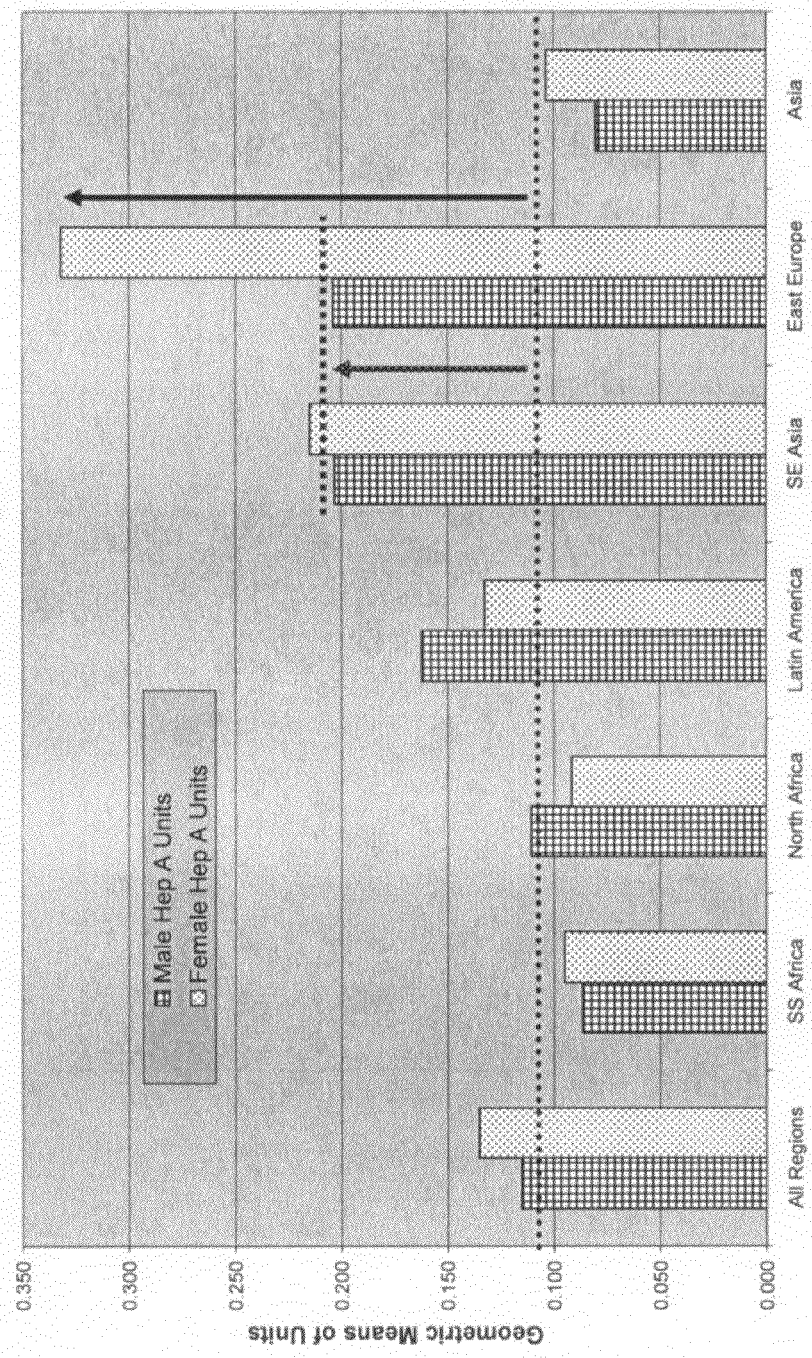
Figure 20D:
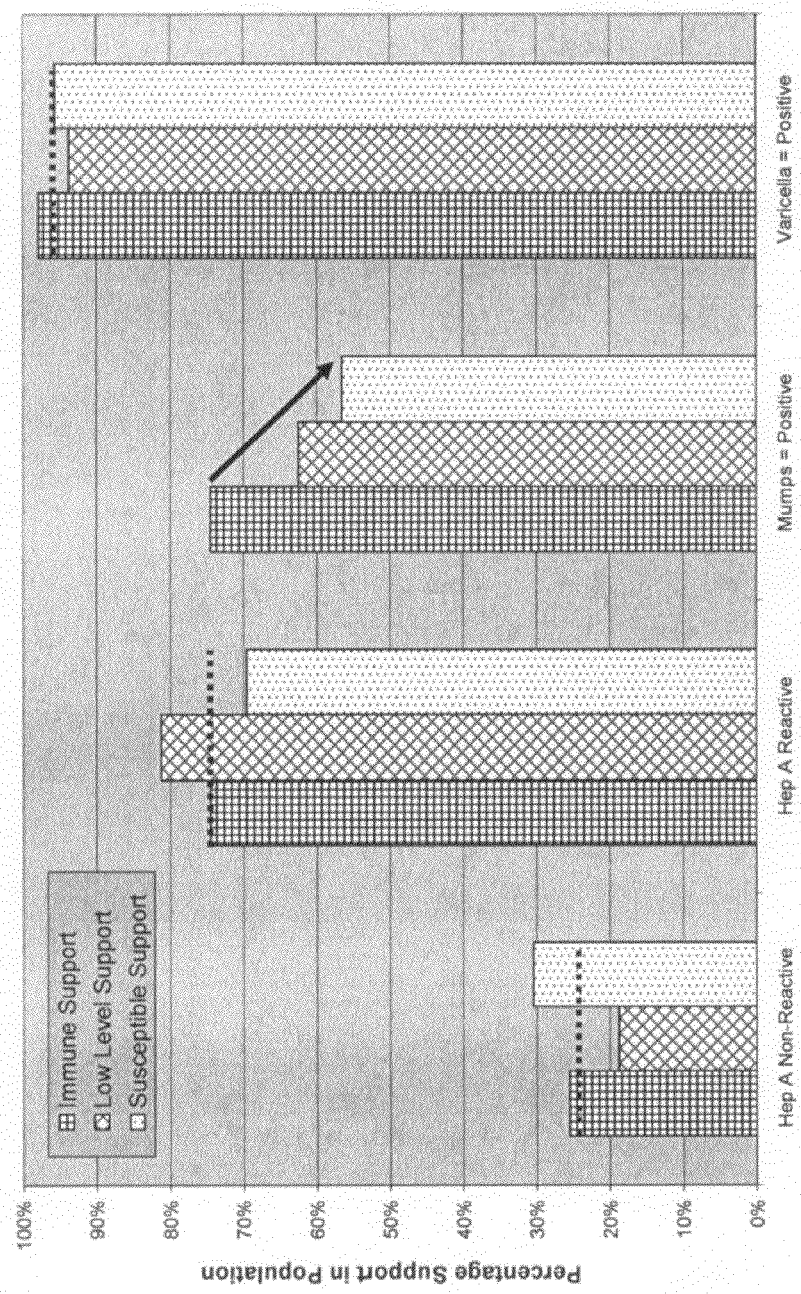
Figure 20F:
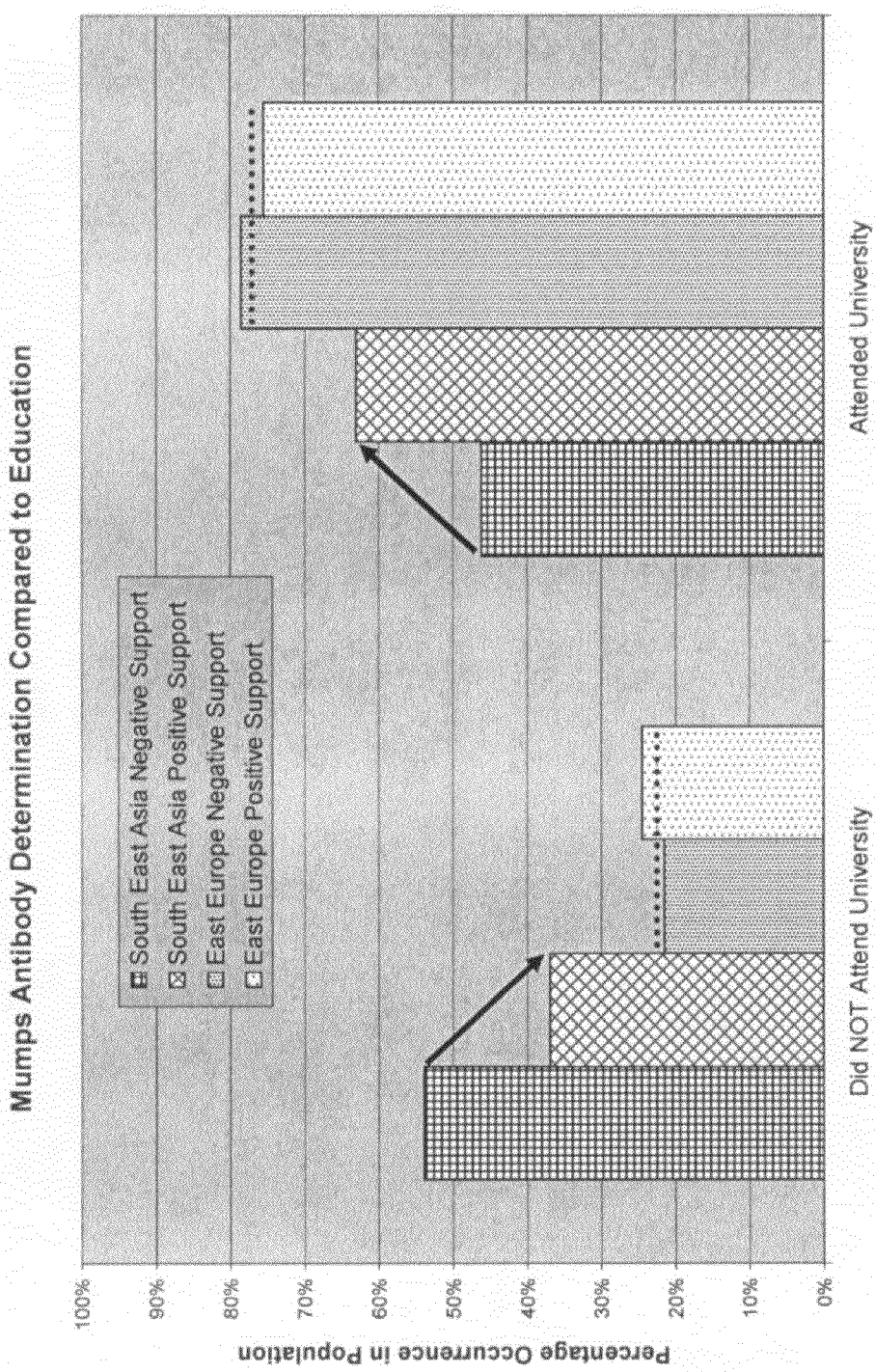

FIG. 17 is a plot of an exemplary comparison of two individual females, one vaccinated and one not vaccinated, according to an exemplary embodiment of the present invention;

FIG. 18 is a plot of exemplary antibody levels in a compliment-deficient individual according to an exemplary embodiment of the present invention;

FIG. 19 is a plot of exemplary antibody levels in a healthy individual according to an exemplary embodiment of the present invention;

FIG. 19A is an example SQL query according to an exemplary embodiment of the present invention; and FIG. 19B is a table illustrating the correlation among antibody levels in an exemplary female population according to an exemplary embodiment of the present invention;

FIGS. 20 through 20F illustrate exemplary data mining results obtained from operating on an exemplary database according to an exemplary embodiment of the present invention;

FIGS. 20G1 through 20G41 illustrate additional exemplary data mining results obtained from operating on an expanded version of an exemplary database according to an exemplary embodiment of the present invention;

FIG. 21A illustrates an exemplary pattern detection process flow according to an exemplary embodiment of the present invention;

FIG. 21B illustrates an exemplary pattern detection process flow with hypothesis generation according to an exemplary embodiment of the present invention;

FIG. 21C illustrates an exemplary automatic pattern detection process flow according to an exemplary embodiment of the present invention;

Section III Figures

Figure 22:
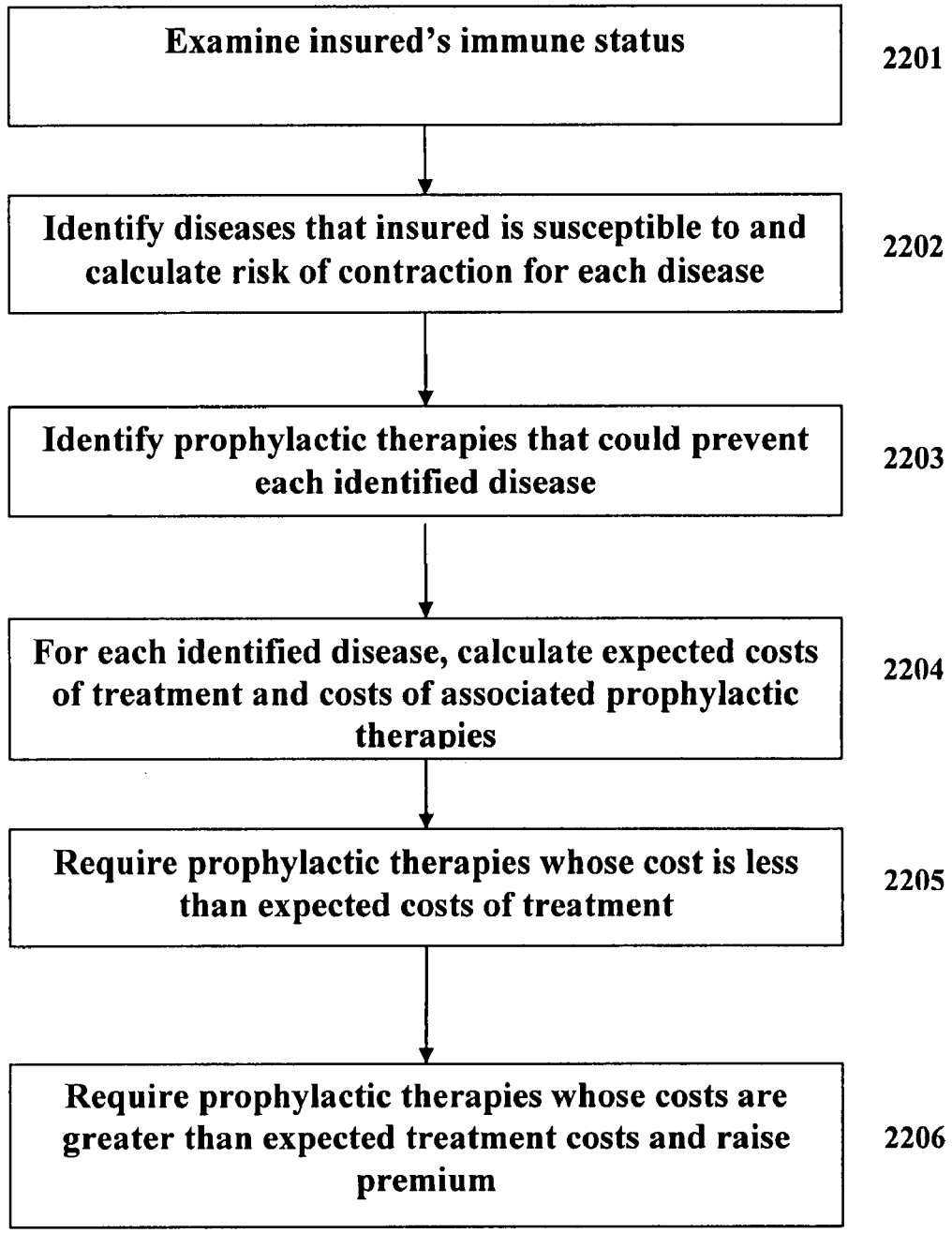
Figure 23:
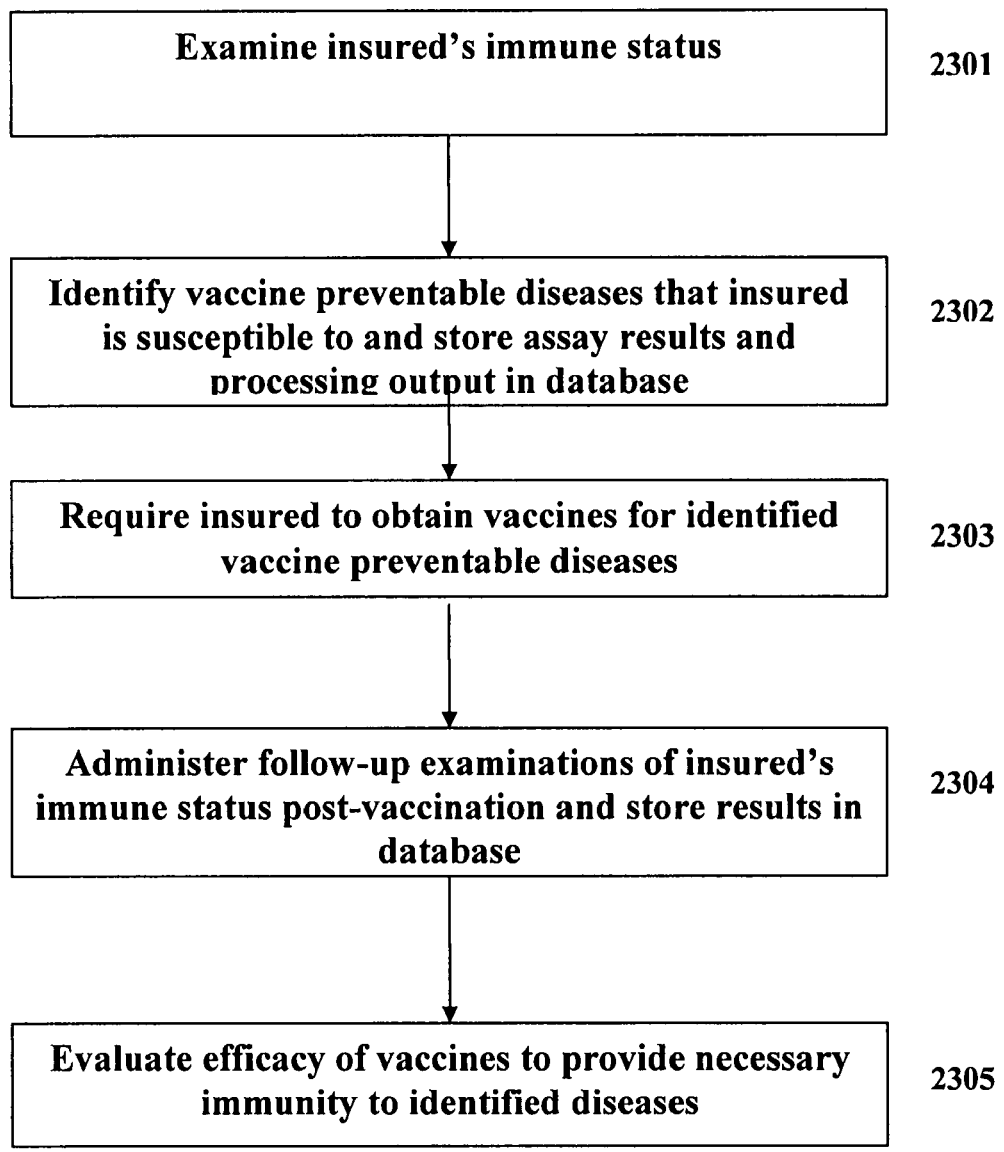
Figure 24:
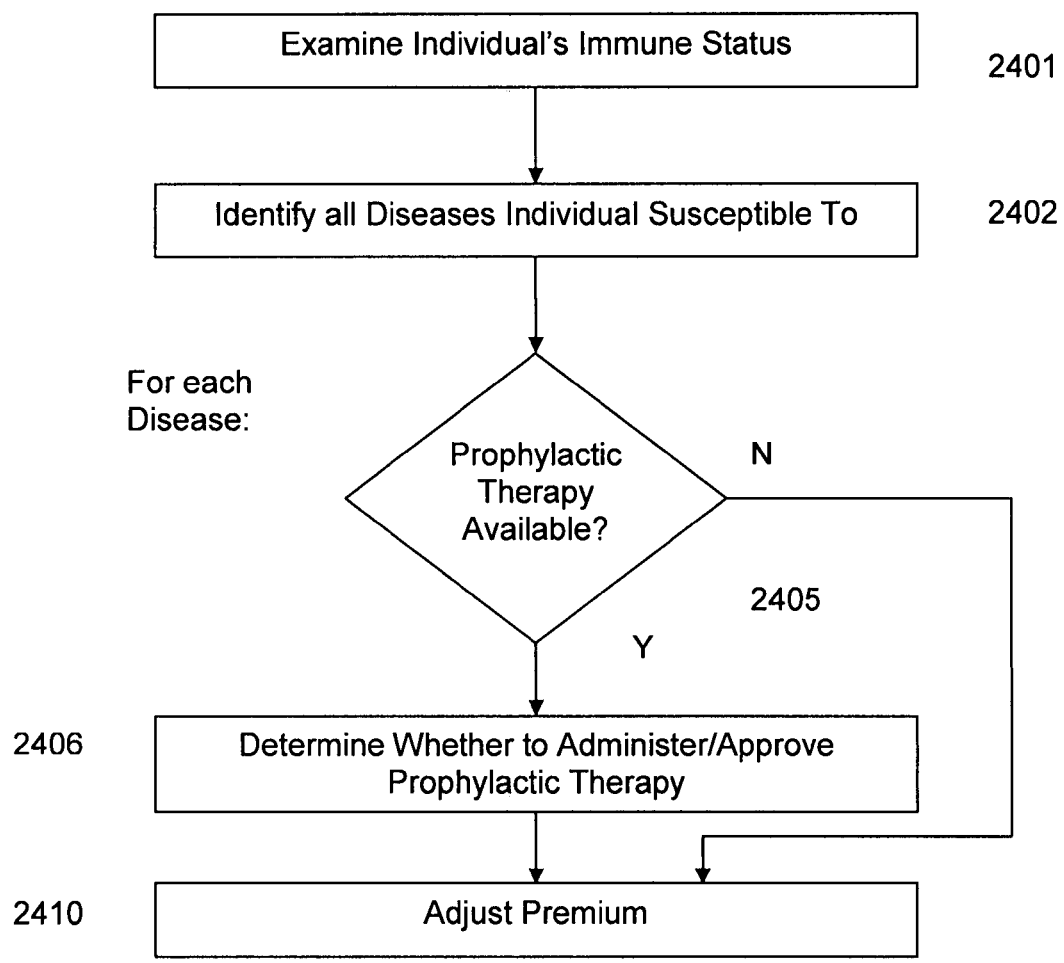
Figure 24A:
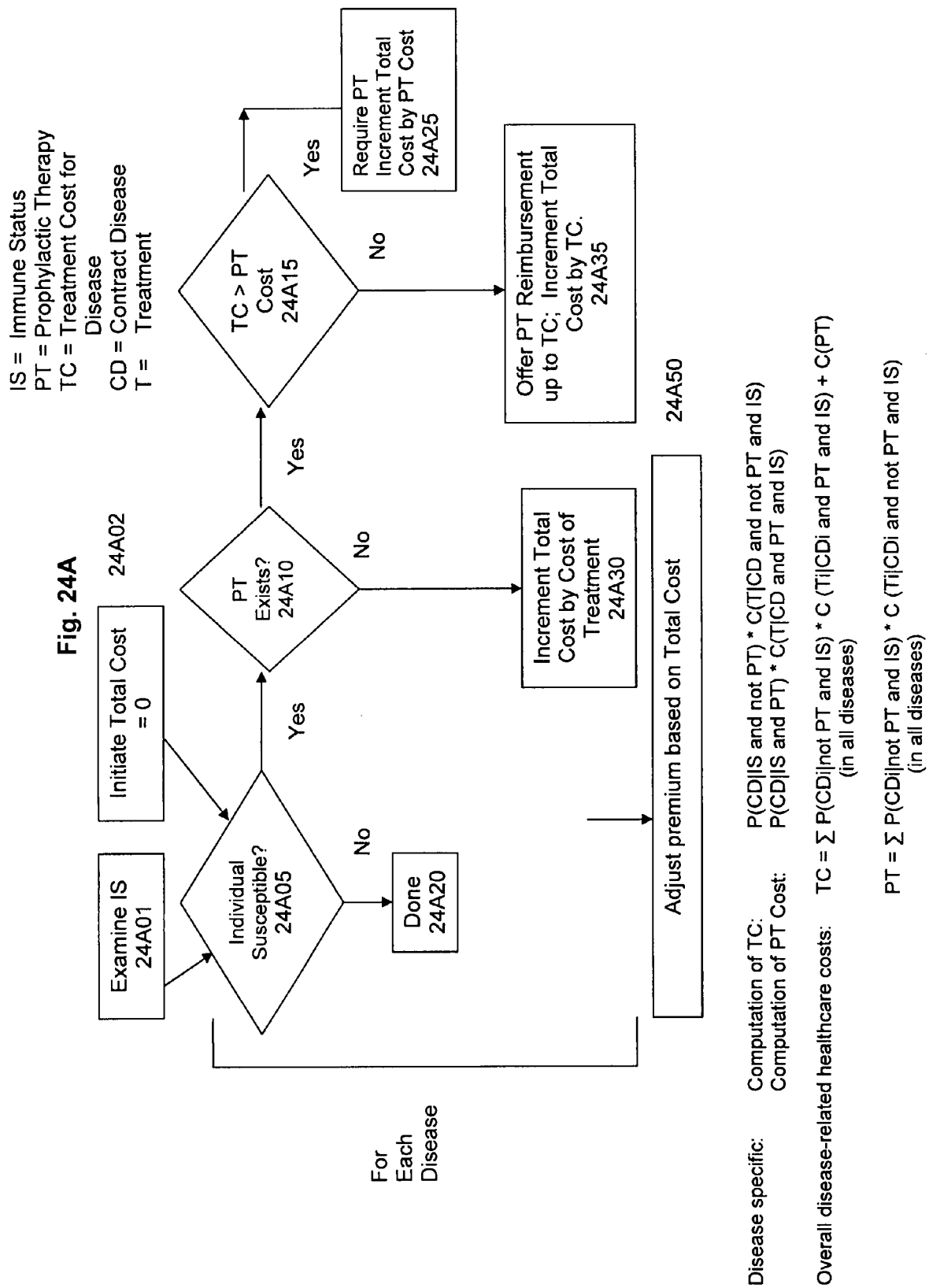
Figure 25:
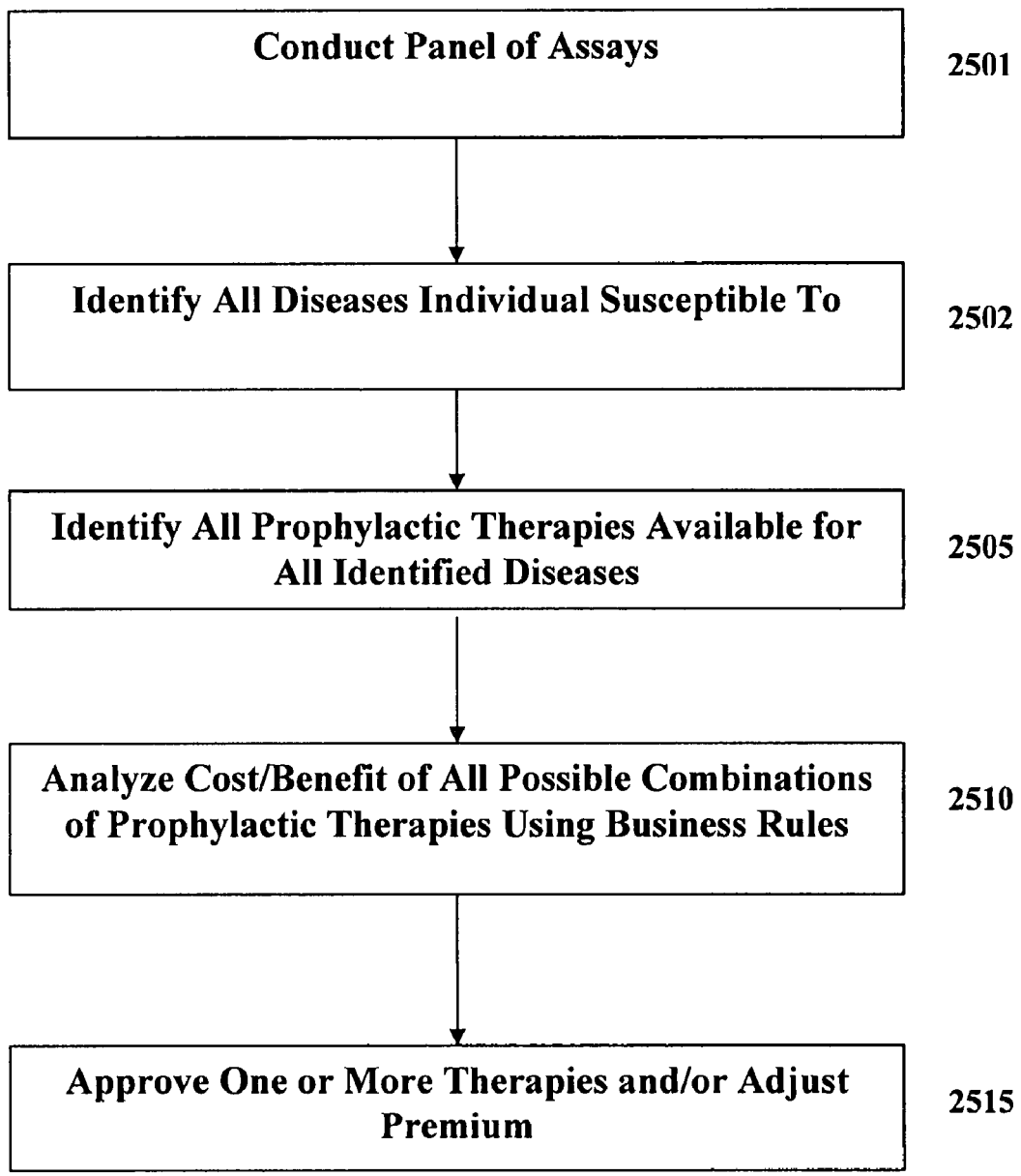
Figure 25A:
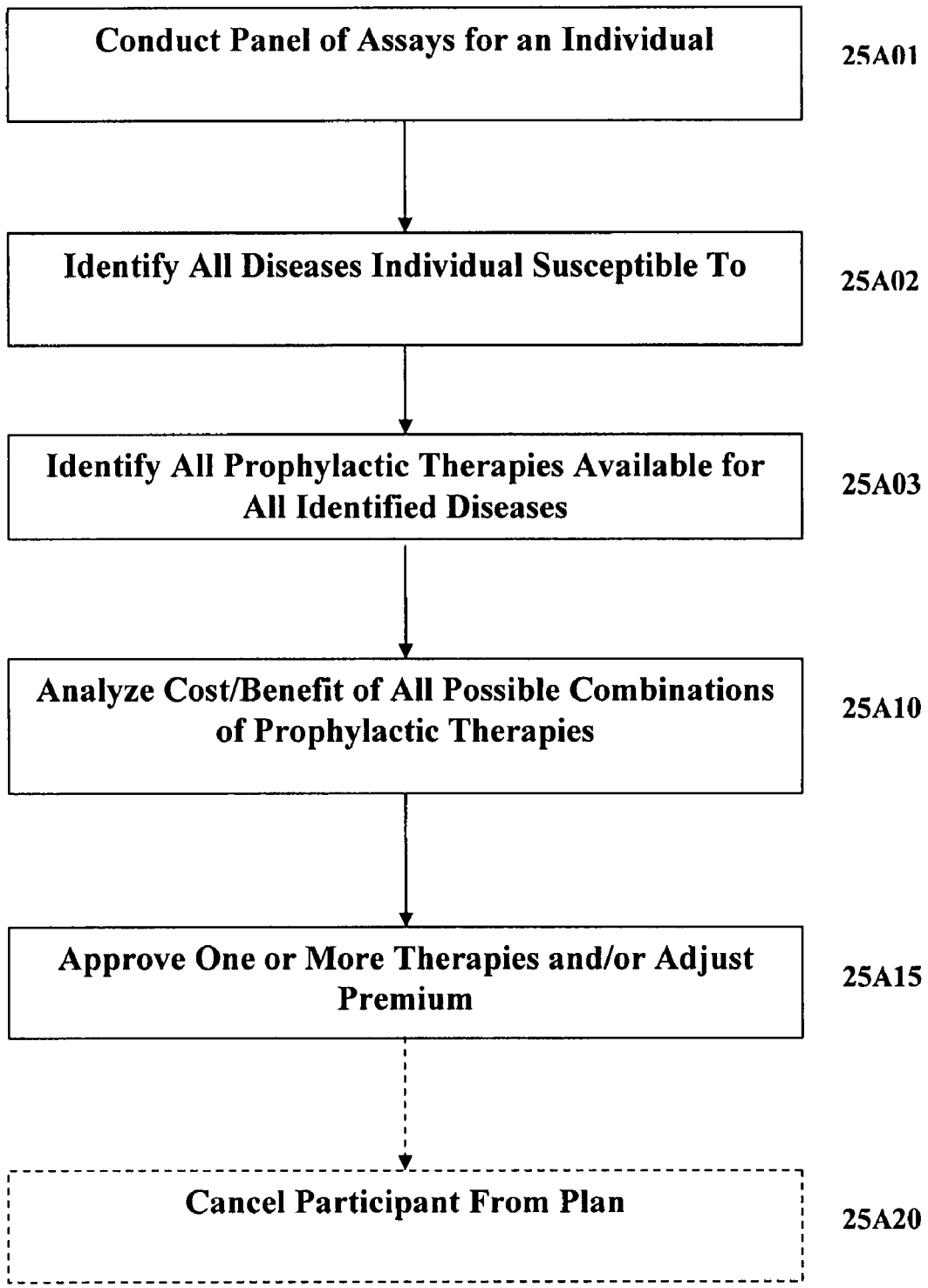
Figure 26:
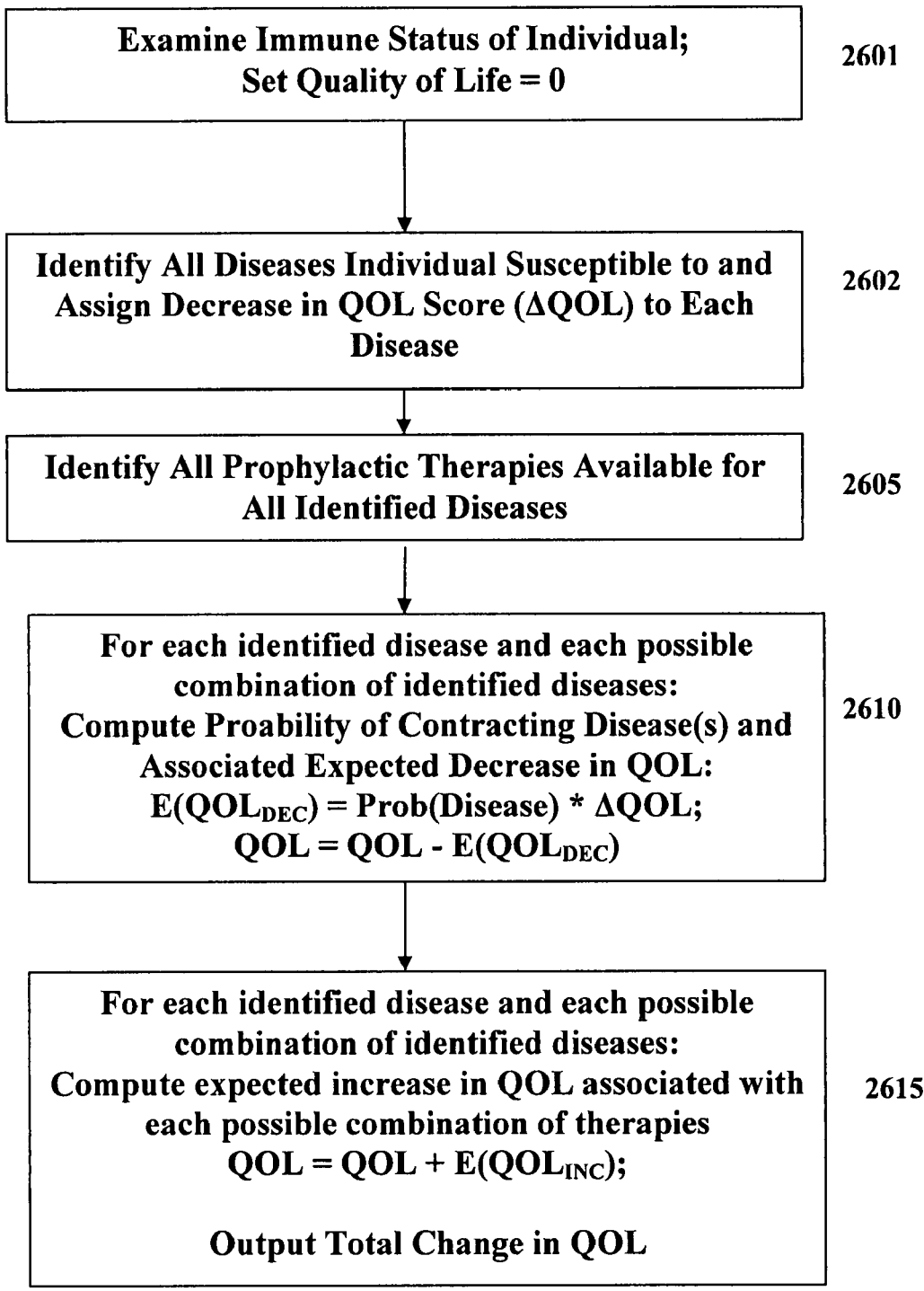
Figure 26A:
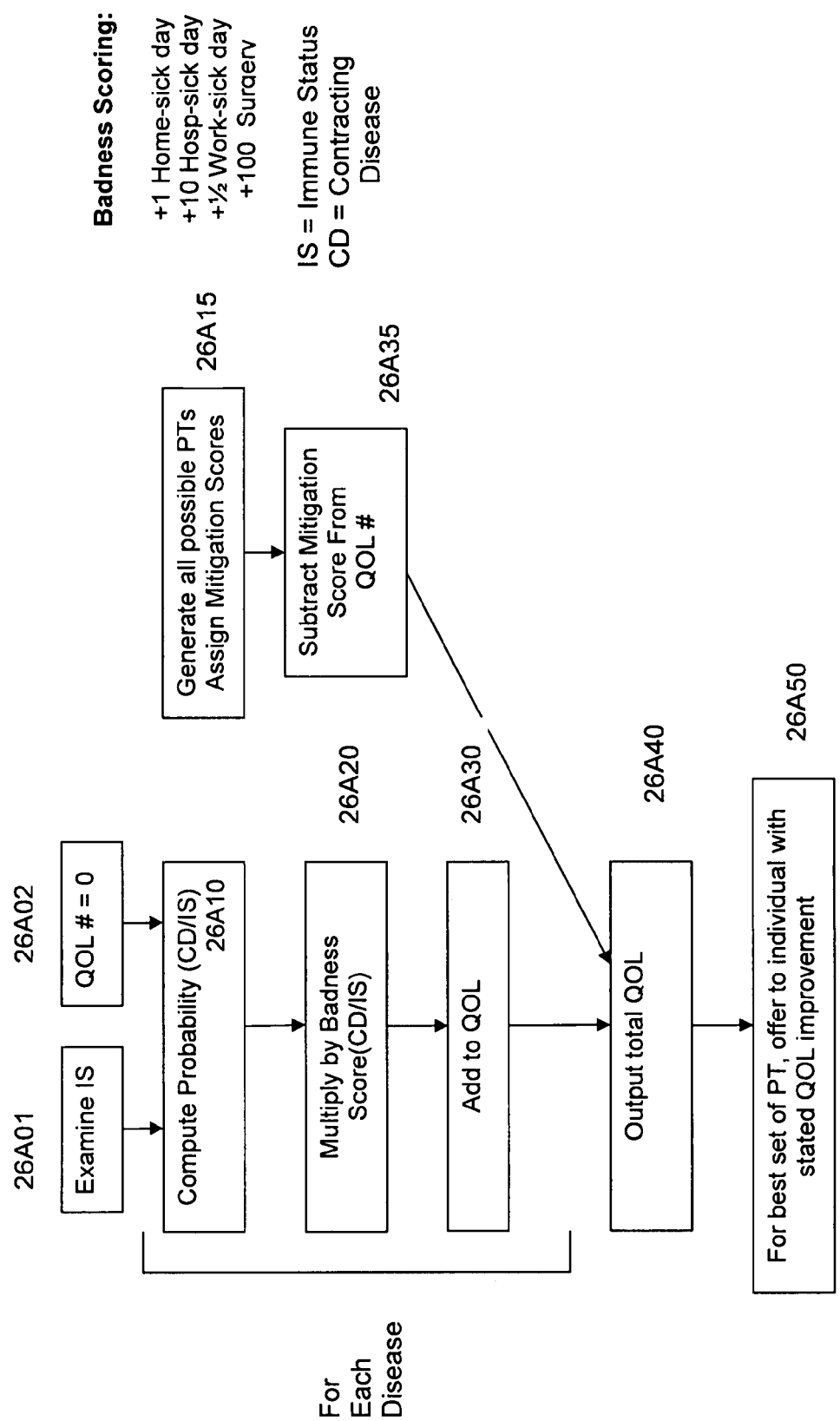
Figure 27:
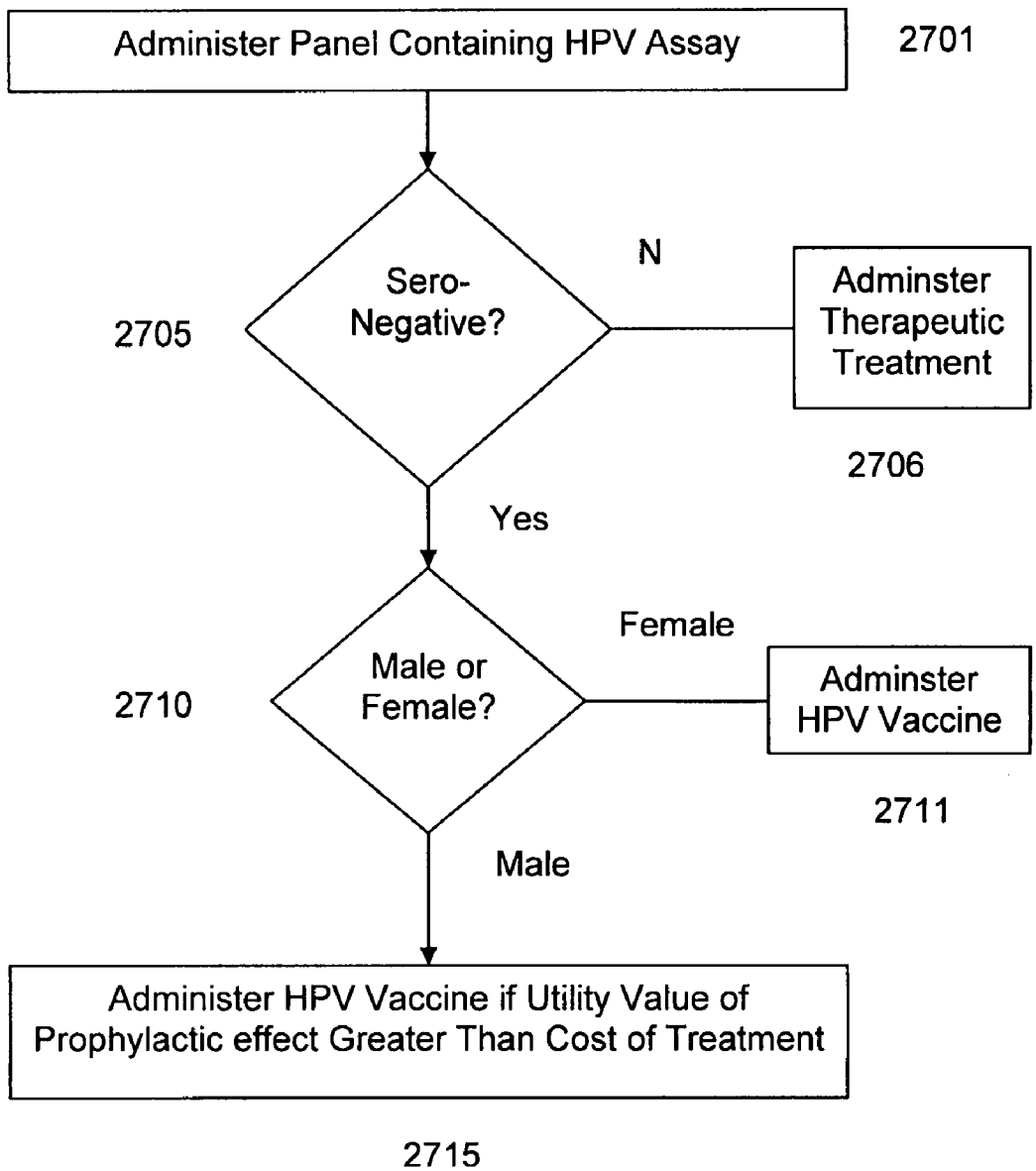
Figure 28:
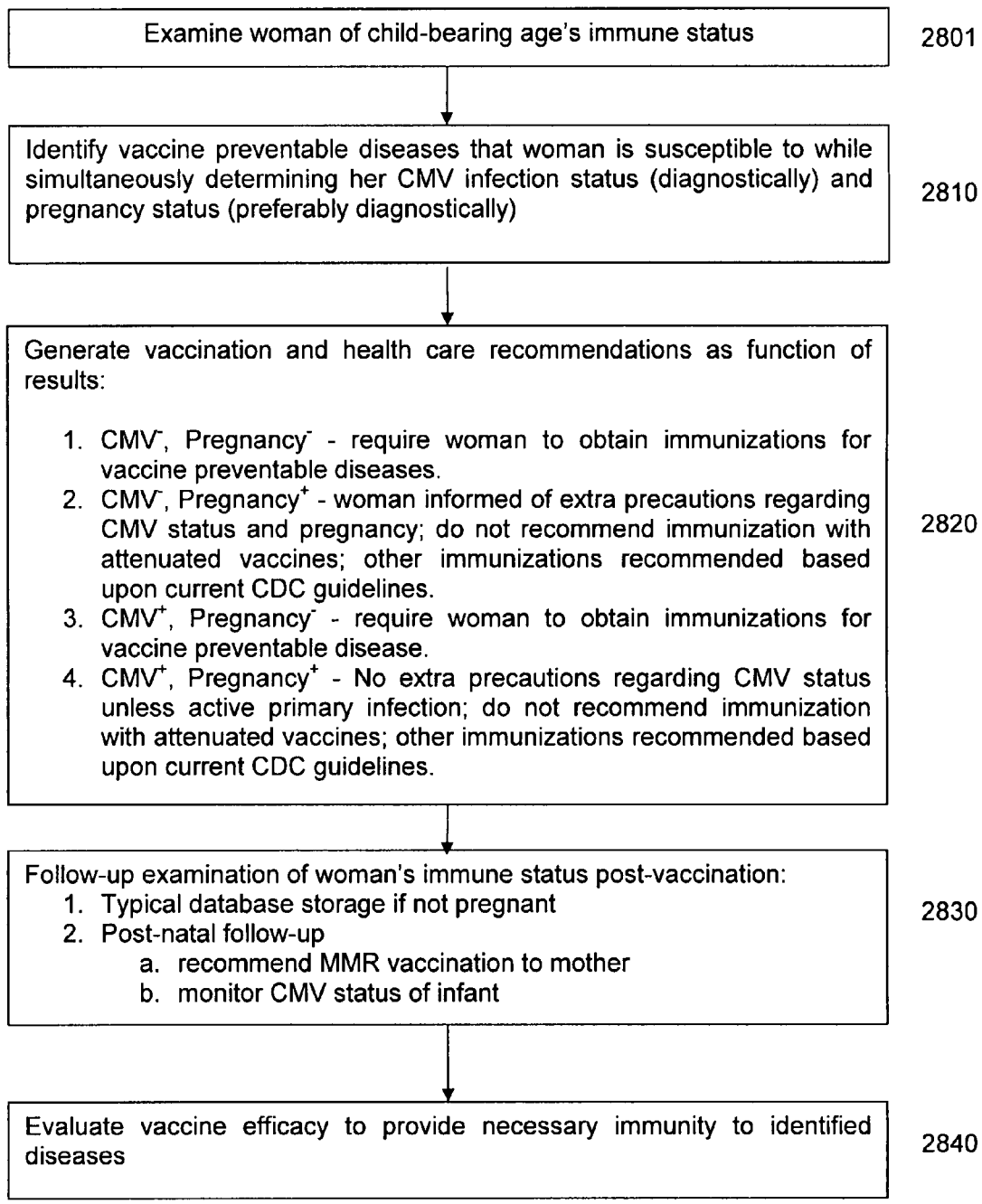
Figure 29:
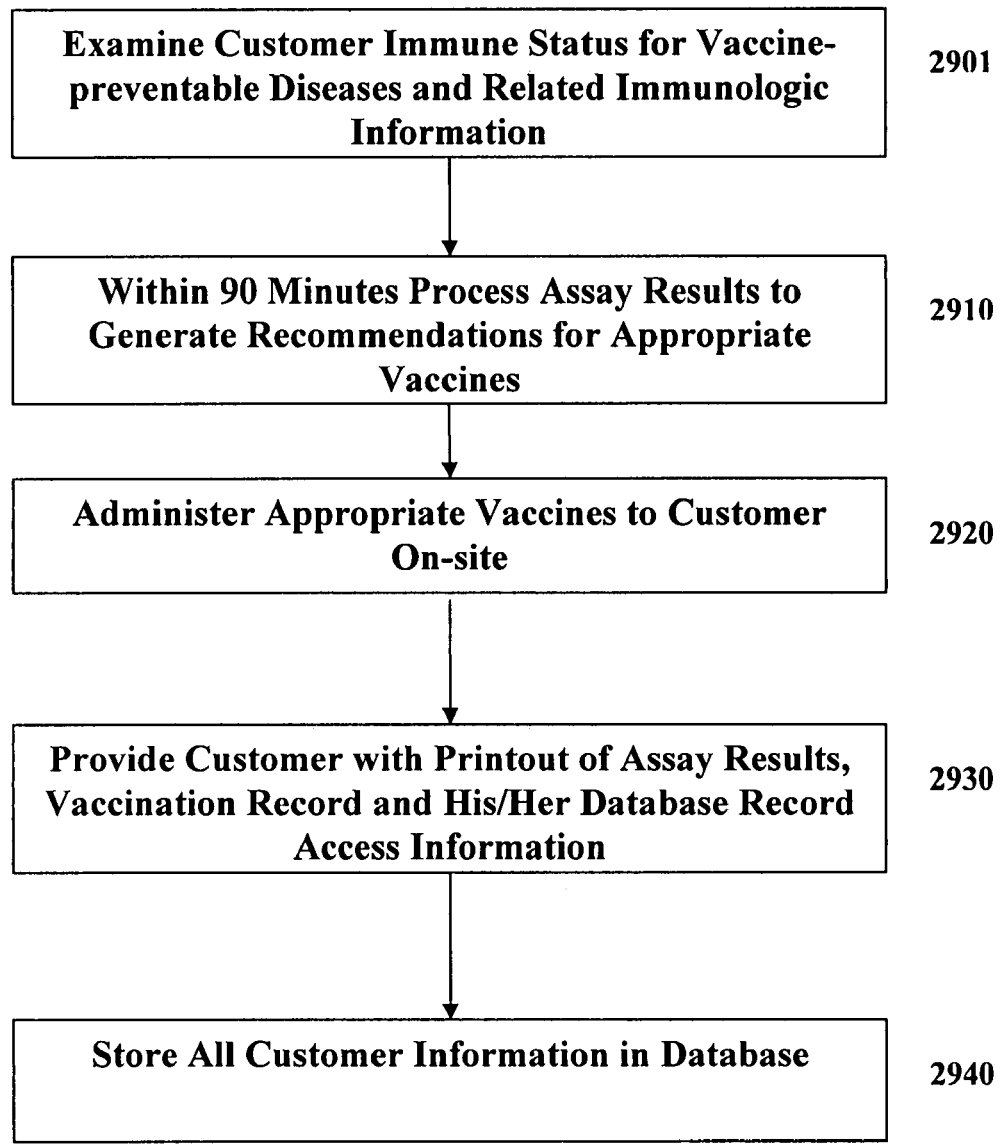
Figure 29A:
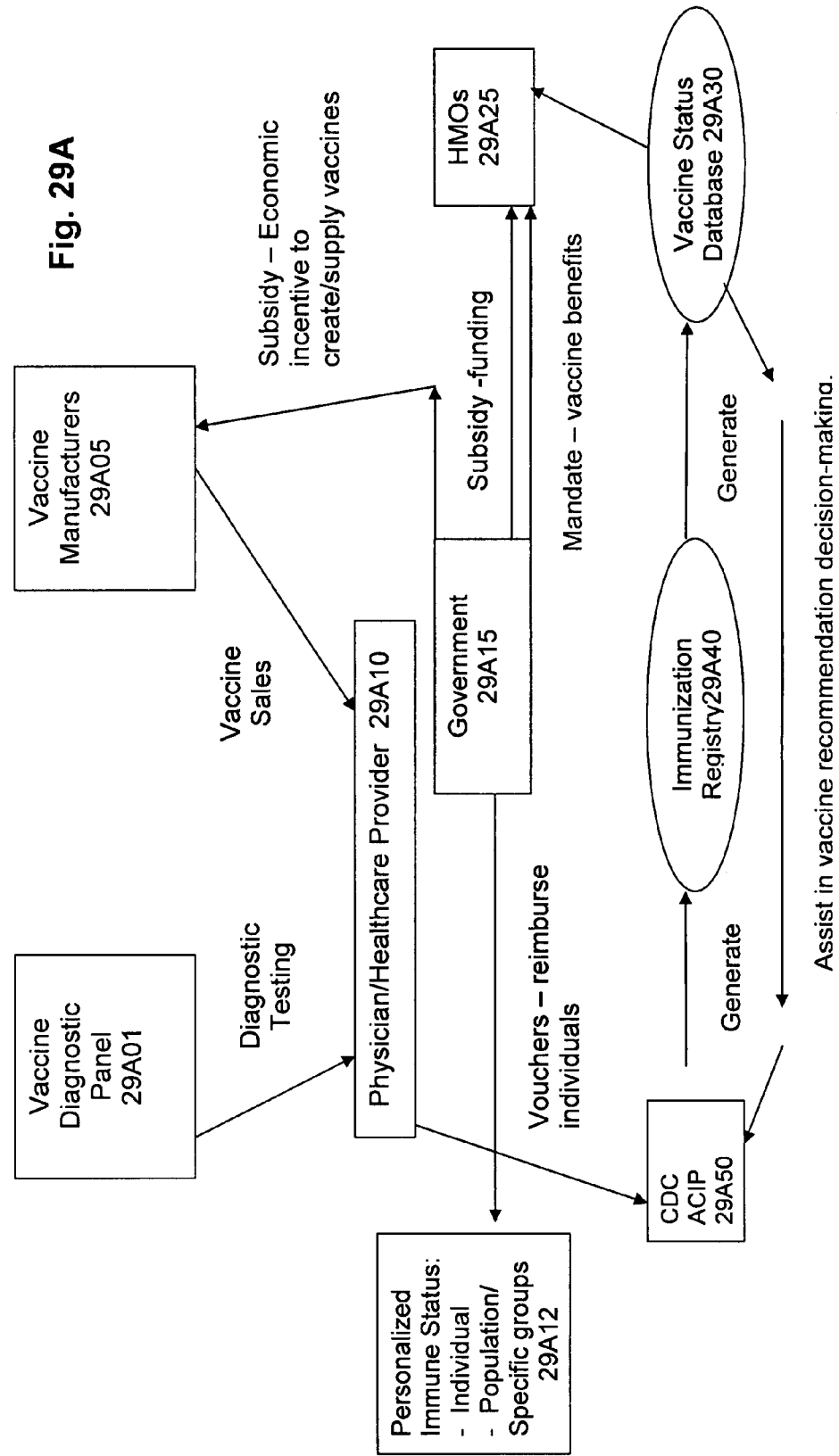
Figure 29B:
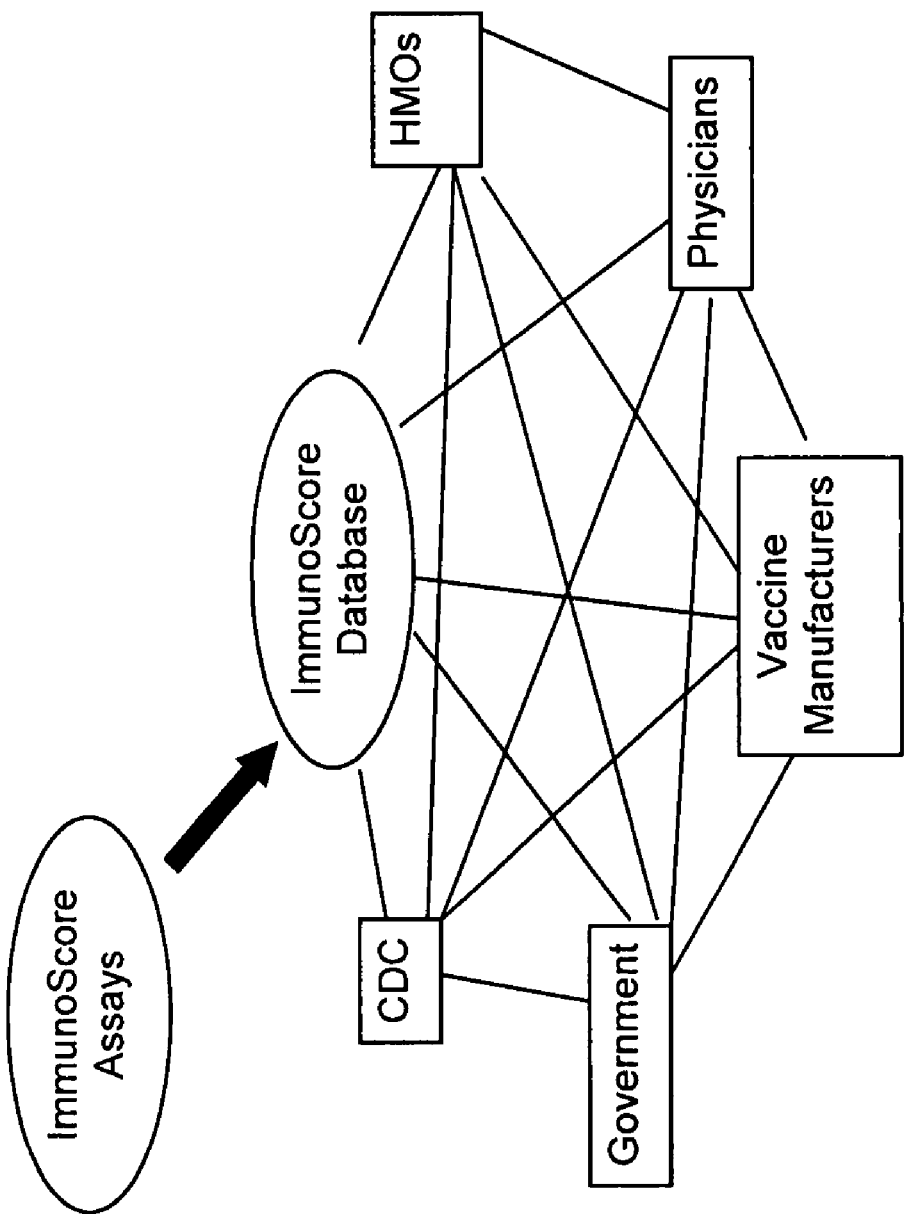
Figure 29C:
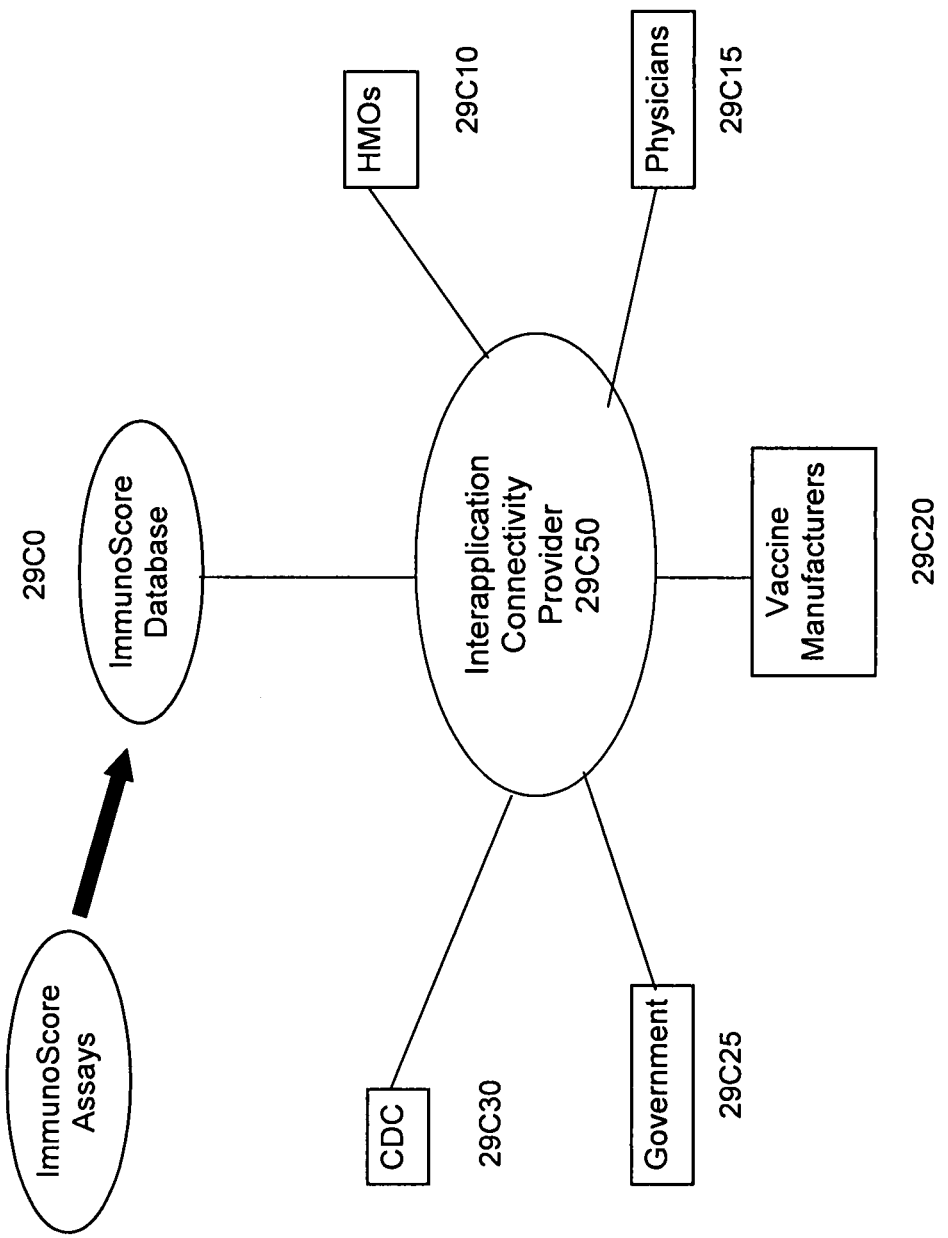
Figure 30:
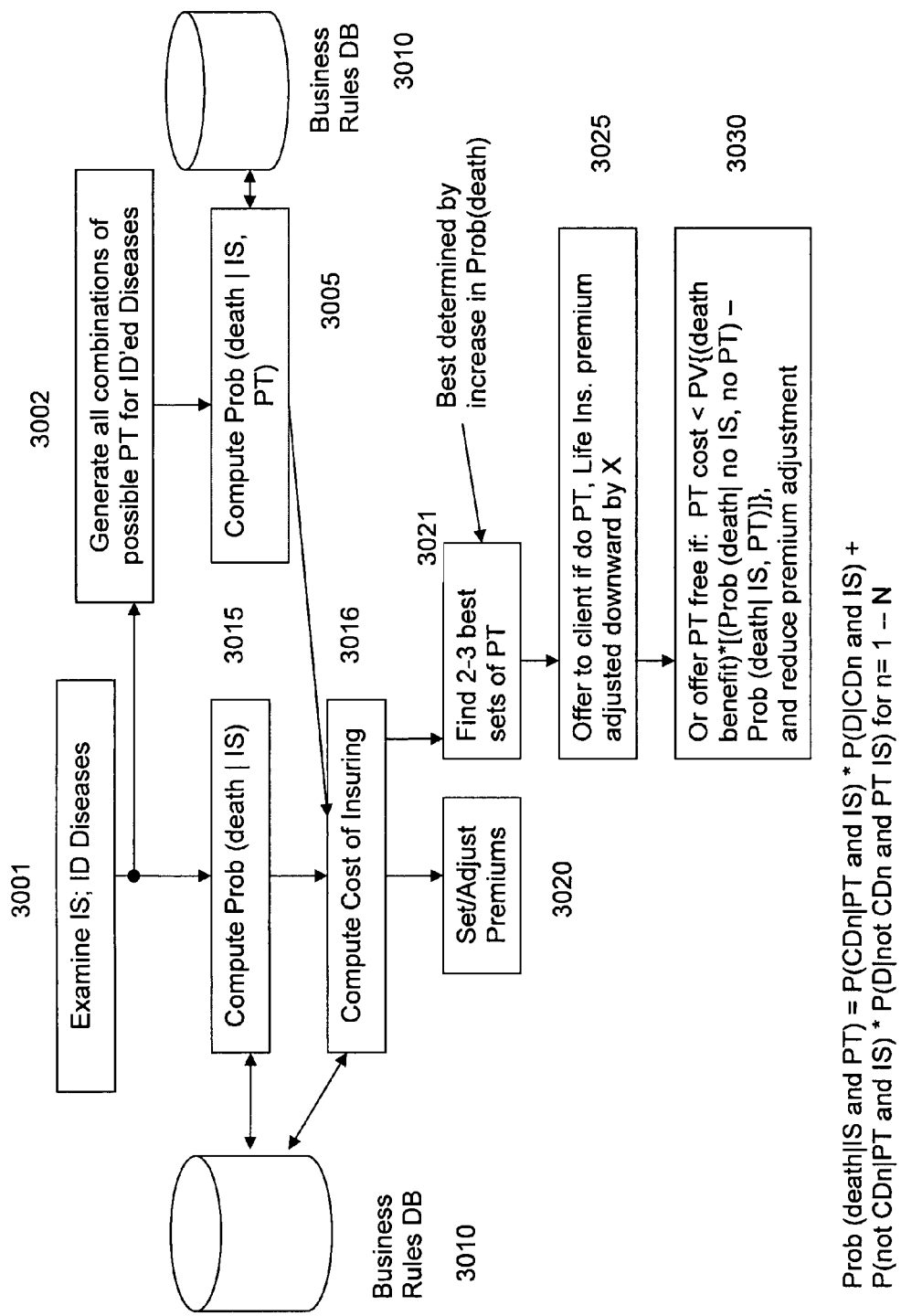
Figure 31:
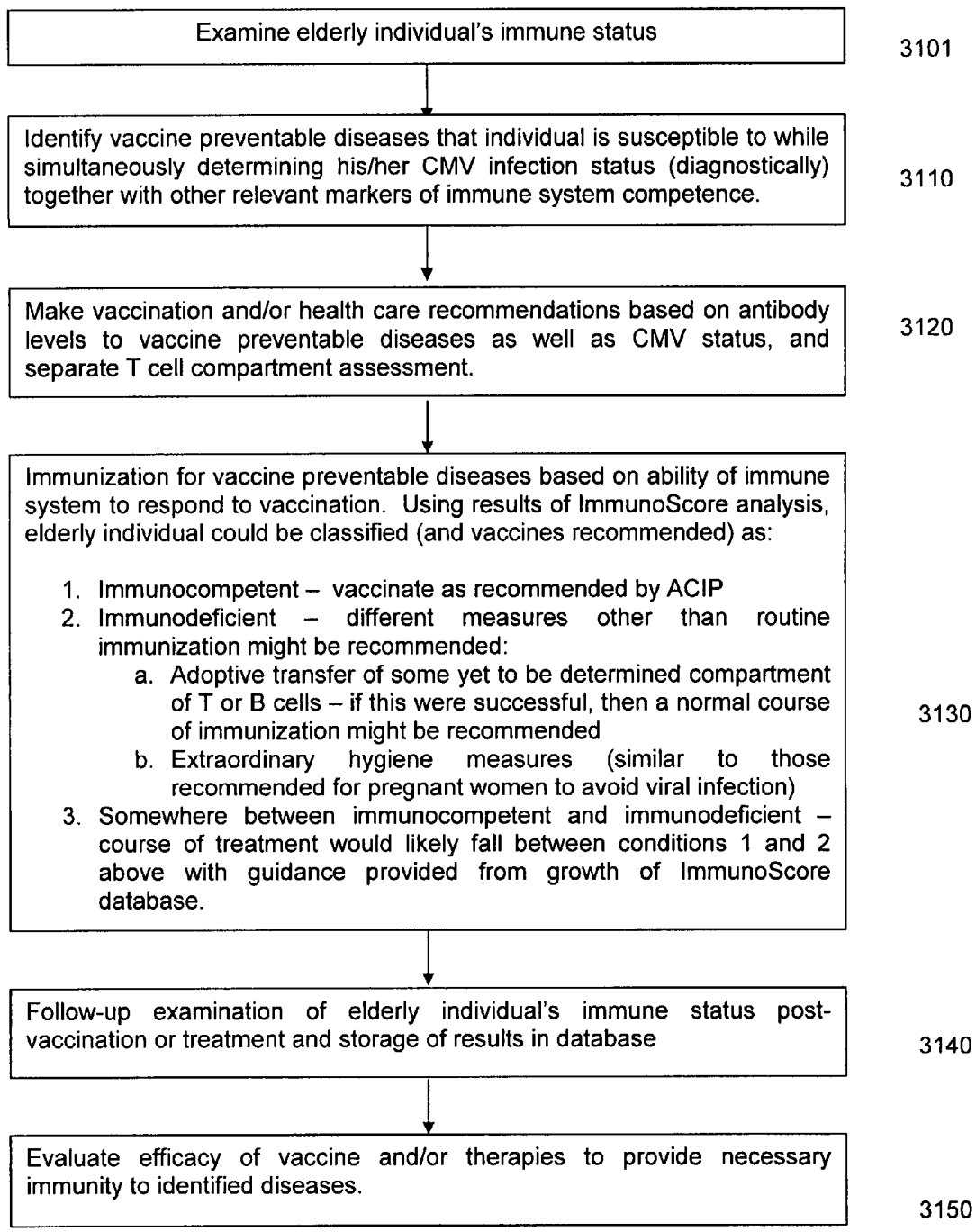
Figure 32:
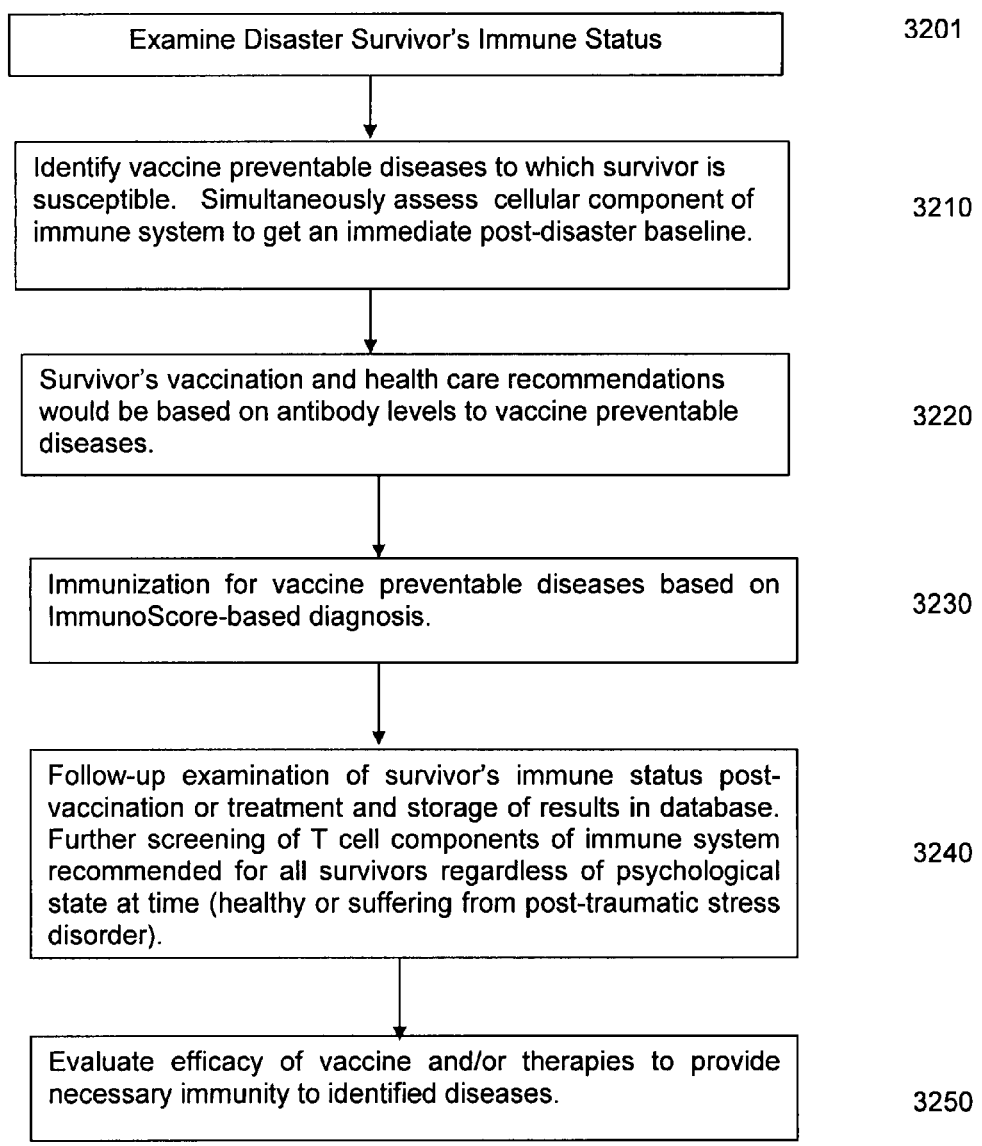
Figure 33:
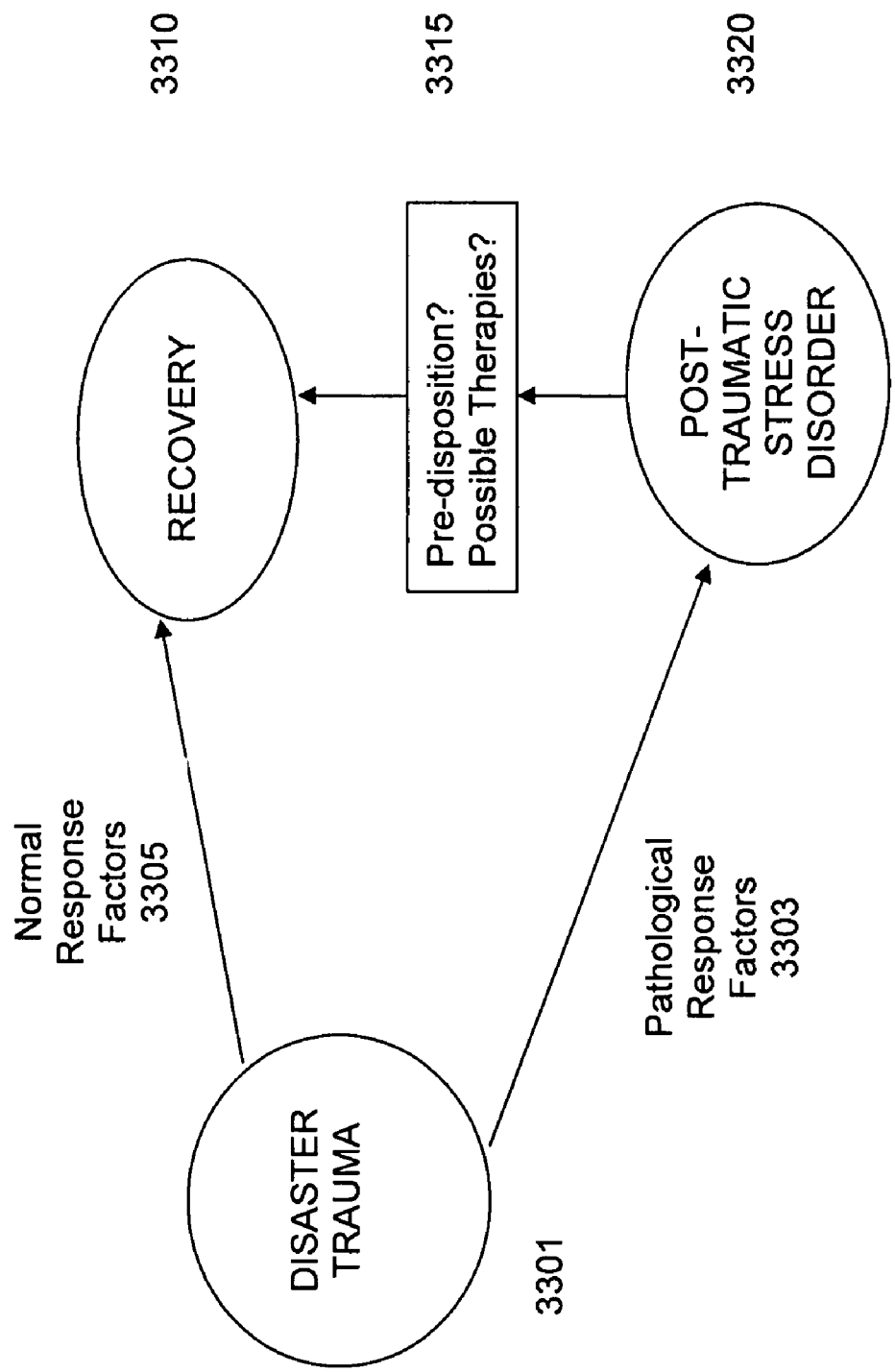
Figure 34:
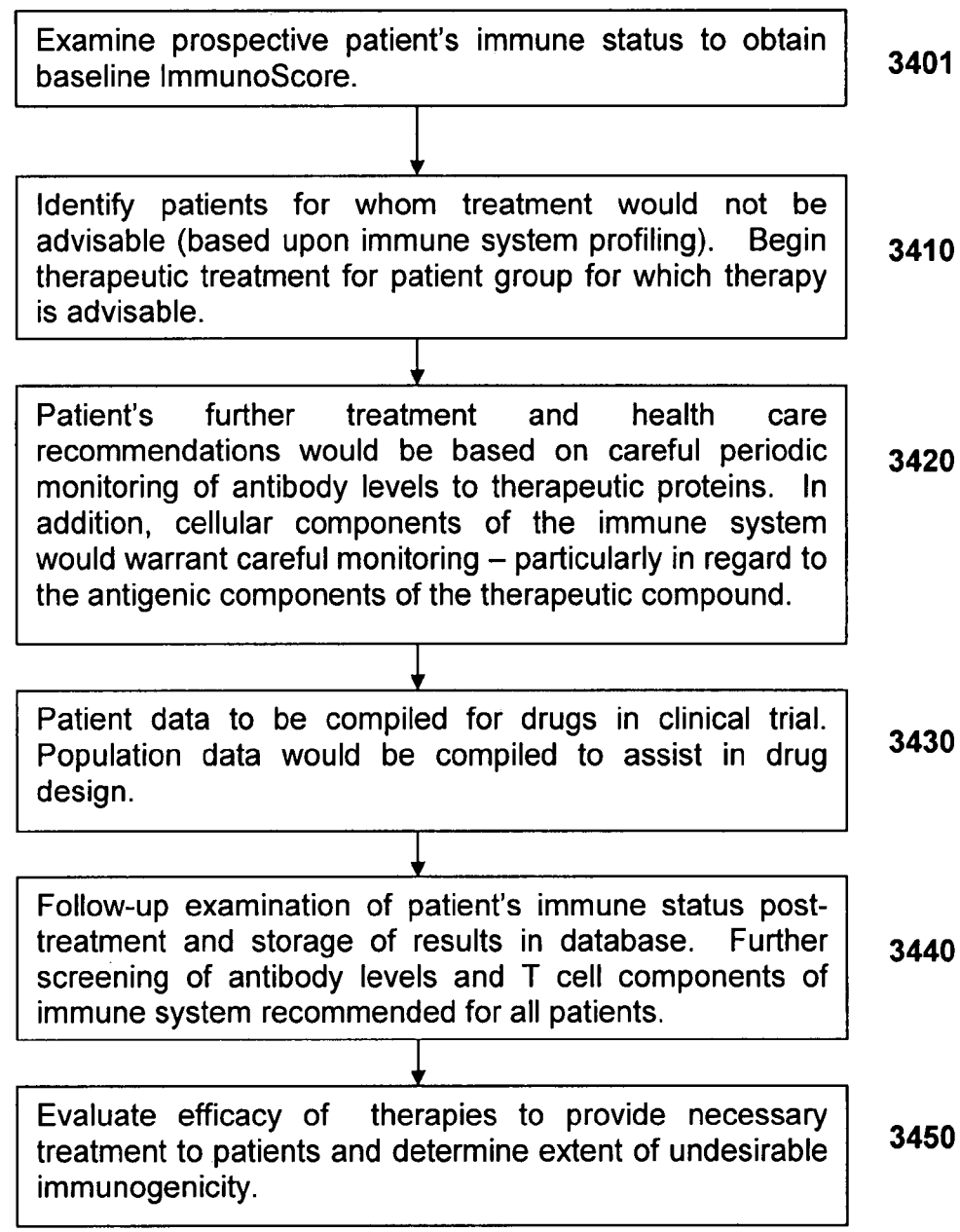
Figure 35:
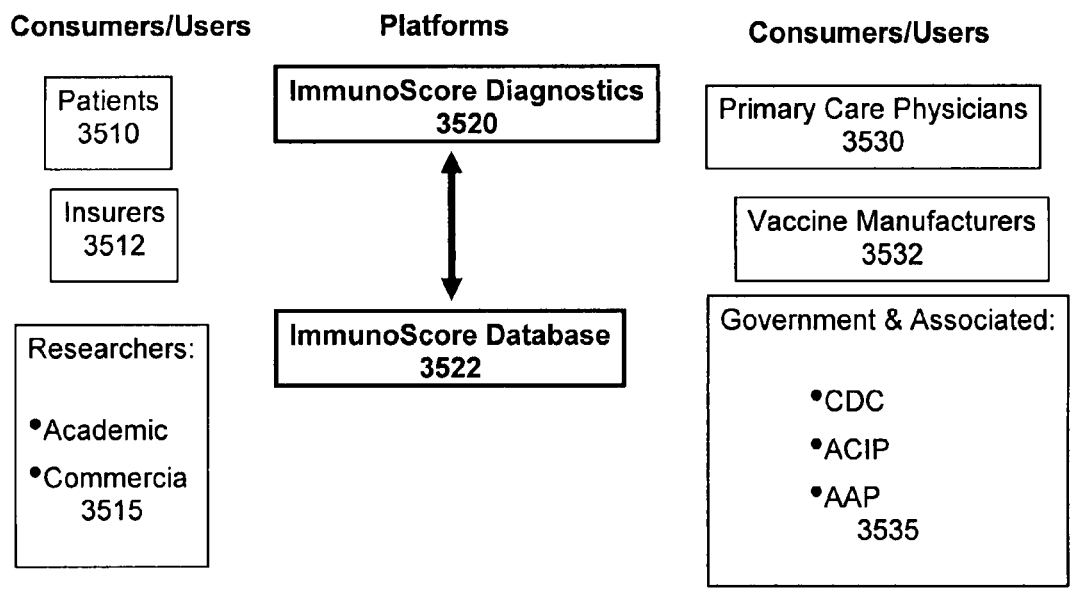
Figure 36:
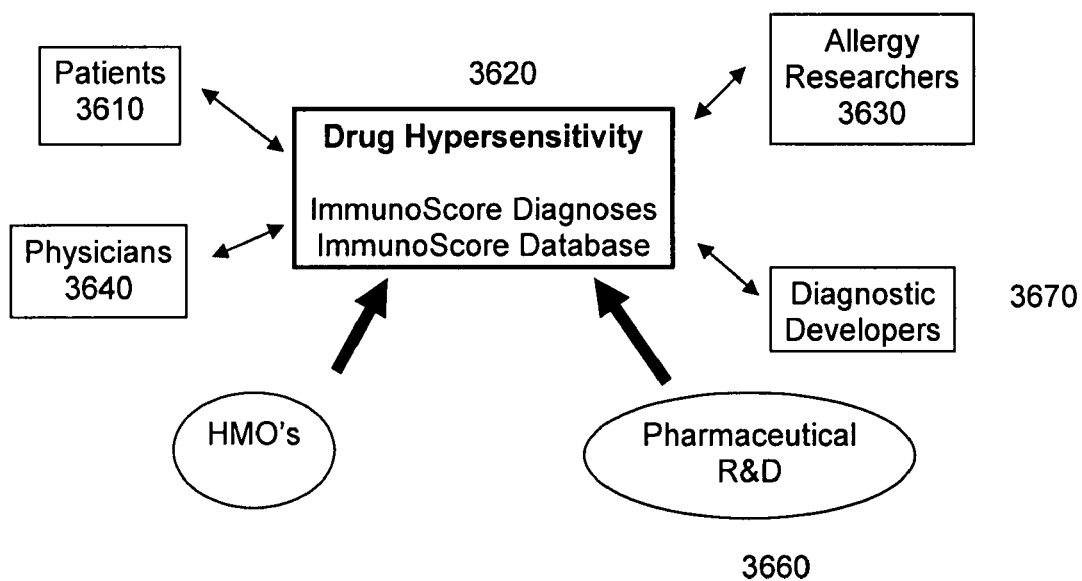

FIG. 22 is a process flow diagram for use in a healthcare management embodiment according to the present invention;

FIG. 23 is a subset of the process flow depicted in FIG. 22;

FIG. 24 is an alternative process flow chart for healthcare management according to the exemplary embodiment of the present invention;

FIG. 24A is a more detailed process flow chart similar to that of FIG. 22;

FIG. 25 is an alternative process flow chart for managing healthcare according the exemplary embodiment of the present invention;

FIG. 25A is the process flow chart of FIG. 25 with an additional optional element;

FIG. 26 is an alternative process flow chart for managing healthcare according to the exemplary embodiment of the present invention;

FIG. 26A is an alternative version of the process flow of FIG. 26 with greater detail;

FIG. 27 is a process flow chart for cervical cancer prevention according to the exemplary embodiment of the present invention;

FIG. 28 is a process flow chart for managing the care of women of childbearing age according to the exemplary embodiment of the present invention;

FIG. 29 is a process flow chart for an exemplary "Vaccine-O-Mat" application according to an exemplary embodiment of the present invention;

FIG. 29A is a system diagram of entities involved in the vaccine distribution application according to an exemplary embodiment of the present invention;

FIG. 29B illustrates the necessary connectivity for the vaccine distribution application illustrated in FIG. 29A;

FIG. 29C is the connectivity displayed in that FIG. 29B recast by use of an interapplication connectivity provider according to an exemplary embodiment of the present invention;

FIG. 30 is an exemplary flow chart for use in a life insurance optimization application according to an exemplary embodiment of the present invention;

FIG. 31 is an exemplary process flow chart for use in an immunosenescence management application according to an exemplary embodiment of the present invention;

FIG. 32 is an exemplary process flow chart for a disaster management application according to an exemplary embodiment of the present invention;

FIG. 33 is an alternative process flow chart for the psychological aspects of disaster response for a disaster response application according to an exemplary embodiment of the present invention;

FIG. 34 depicts exemplary process flow in an immunogenicity discovery application according to an exemplary embodiment of the present invention;

FIG. 35 illustrates components of an exemplary two-sided market application according to an exemplary embodiment of the present invention; and FIG. 36 illustrates components of an exemplary drug hypersensitivity two-sided market application according to an exemplary embodiment of the present invention.

TABLE OF CONTENTS

SECTION I EXEMPLARY ASSAY PANELS
    A. COLLEGE STUDENT DIAGNOSTIC PANELS
        1. Meningococcal Diagnostic Panel
        2. Sexually Transmitted Diseases Assay Panel
    B. Persistent Immunity Induced by Childhood Vaccines
    C. ADULT DIAGNOSTIC PANELS
    D. Measurement of Immunity Induced By Vaccines for Military Personnel
    E. ImmunoScore Measurement of Vaccine-Induced Immunity for Travelers
    F. ImmunoScore Measurement of Immunity in Health Care Workers
        1.1. Immunocompromised Health-Care Workers
        5. ImmunoScore Analyses and Bioterrorism
        6. ImmunoScore Analyses for Infection and Chronic Disease
        7. Th1-Th2 Paradigm
        2. 7.1 Th1-Th2 Based Diagnostic Panel
        3. Autoimmunity/Inflammatory Disease
        9. ImmunoScore Diagnostic Panel and Preventive Therapy for Autoimmune Disease
        10. 10. ImmunoScore Diagnostic Panel: Aging, Longevity, Cancer and Human Cytomegalovirus SECTION II EXEMPLARY IMMUNOSCORE SYSTEM DATABASES
    A. General Overview
    B. Exemplary Illustrative Database
        1. Overall Description
        2. Impact of Data Mining
        3. Diagnostic Module
            3.1. Overview
            3.2. Perceptron algorithms
            3.3. Alternate algorithmic approaches
                3.3.1. Additional input data
                3.3.2. Decision rule algorithms
        4. Data Mining Module
            4.1. Overview
            4.2. Sample Data
            4.3. Exemplary Use of the Patent Event Database
    C. Exemplary Canadian Immigrant Project Database Used To Illustrate Data Mining and Hypothesis Generation
    D. Data Mining—Analyses and Conclusions
        1. Linear regression analysis—correlation coefficients
        2. Geometric mean values
        3. Percent support between variables
        4. Possible Conclusions
        5. Expansion of database
        6. Distribution of geometric means according to age
        7. Focus on CMV and Tetanus
        8. Simulation: Sampling over time
    E. Pattern Detection and Hypothesis Generation
SECTION III USES OF IMMUNOSCORE INFORMATION IN VARIOUS COMMERCIAL, RESEARCH AND GOVERNMENTAL CONTEXTS
    A. Health Insurance Underwriting ad Management—Healthy Credits Exchange
    B. Health Care/Health Insurance Credit Exchance
    C. Veterans Health Care Management (Variant of Health Care)
    D. Socialized Medicine Management
    E. Supplemental Insurance (AFLAC Model)
    F. ImmunoScore and the Wellness Industry
    G. Women of Childbearing Age/Screening of Pregnant Women
    H. Vaccine-o-Mat/Vaccine Distribution Network
    I. Consumer Accessibility to Immunologic Information
    J. Immunoscore Connectivity Via Interapplication Translator/Data Integrator
    K. Immunologic Informatics Based Life Insurance Underwriting
    L. Diagnosing and Managing Immunosenescence in the Elderly
    M. Frozen Storage of Naive Immune Cells (IRP Considerations)
    N. Vaccine Use Outcome/Design
    O. Research Services
    P. Immigration Consulting
    Q. Disaster Survivors: Immunizations, Recovery, Prognosis and Treatment
    R. Monitor Adoptive Immunotherapy/Transplants
    S. Elective Surgery
    T. Services to Charitable Foundations Promoting Immunological Well Being
    U. Discovery of Unwanted Immunogenicity of Therapeutics
    V. Two-Sided Market Applications
    W. Drug Hypersensitivity
    X. Health Care Transparency and Competition
        1. Consistent high quality
        2. Lower cost—follows from high quality. Higher quality is often naturally less expensive. Providers improve quality by honing their organizational processes to become more efficient and effective—to avoid error and to do things right the first time
        3. Available to all—for ethical, political, systemic, and business reasons, health care must be available to everyone
        4. Single model—every provider in the system must compete to offer the best product at the best price
        5. Shaped by market forces—the consumer market has the sustained systemic power to bring consumers more for less
        6. Practical—the solution must arise from present realities
        7. Progressive—dramatic change can not occur all at once
        8. Self-reinforcing—as any part of the health care system moves toward a new reality, that movement must allow and encourage other parts to move forward as well
    Y. User Access Via Data Networks and On-line Advertising Applicant notes that the TOC is defective, especially as regards Section I. Applicant reserves the right to amend the Specification to correct the TOC via Preliminary Amendment.

DETAILED DESCRIPTION OF THE INVENTION

General Overview

In what follows, systems and methods of the present invention will be often referred to as the "ImmunoScore" system, method and/or database, as the case may be. "ImmunoScore" is a trademark and/or service mark currently envisioned by the assignee hereof to be utilized in connection with exemplary embodiments of the present invention.

The present invention is directed to the collection, processing, and use of immunologic information. Immunologic information is to be understood in a broad sense, including any information which may be useful as an indicator of any immunological function of a mammalian body. More specifically, the present invention includes acquiring information that is indicative of the immune status of an individual, processing that information, storing the raw information as well as the outputs from the processing stage, and of that information at various times and in various ways to recommend various actions such as prophylactic or further diagnostic interventions, or abstention from action, for individual or population. The present invention exploits a number of advances in technology as well as advances in how people think about medical treatment. In exemplary embodiments of the present invention, a number of immunological or immunological related (in a broad sense) assays can be administered to an individual. Using modern technology such as, for example, the M1M Analyzer marketed by BioVeris™ Corporation of Gaithersburg, Md., one can run a large number of assays, such as, for example 20, 40 or 60, and obtain results therefrom in a relatively short period of time. Moreover, these assay results can be stored in a memory, either locally or at one or more central servers or in associated databases, and can be operated upon by various algorithms or rules which can generate information as to that individual's immune status as well as recommendations for further augmenting that immune status or taking further action in response to the information acquired, from the assays and their processing. This information can be used in a variety of commercial, research, and healthcare contexts. Thus a variety of business methods or opportunities can be created or facilitated using the information obtained according to the methods of the present invention.

The present invention is described in three distinct sections. The first section describes the scientific background and motivation for creating various assay panels to be administered, singularly or in combination with other assay panels, to different individuals in different populations at different times in each individual's life cycle. This discussion culminates in suggested or exemplary assay super panels which can be administered in various contexts to various individuals.

A second section describes how information obtained from results of the administered assays can be stored, processed, and utilized. This discussion comprises, inter alia, a description of an exemplary database in which (i) results from numerous assays can be stored along with (ii) individual-specific information and (iii) the outputs of various algorithms which operate upon the assay results of that individual. This section also presents an exemplary database upon which immunologic data mining was performed according to the techniques of the present invention, and summarizes interesting and illustrative results form that exercise.

In a third and final section, a variety of business and commercial methods are described in which information from the assay panels as stored in the database and further processed can be used to increase business efficiencies, create new markets and opportunities, and/or provide useful tools for research and development.

Before describing each of these three areas in detail, a brief overview of a generalized method and system according to exemplary embodiments of the present invention is presented with reference to FIGS. 1, 2, 2A and 2B.

FIG. 1 depicts an exemplary process flow according to an exemplary embodiment of the present invention. Beginning at 101, an assay or panel of assays can be conducted on a biological sample, e.g., blood, urine, etc., which has been taken from an individual. Such individual can simple be an individual or he or she can be a member of a population or sub-population whose immunologic informatics are of use to some entity or enterprise. For example, the individual could be an insured of a health insurance company that is using the techniques of the present invention to efficiently manage the healthcare of its insureds so as to minimize costs. Or, alternatively, such an individual could be an immigrant whose vaccination history is unknown but whose immune status is of interest to his new country's immigration service. Such exemplary embodiments are described more fully below in Section III.

In FIG. 1, at 102 the results of the assay or assays conducted at 101 can be obtained, and at 103 there can be an optional step of analyzing the assay results locally. In exemplary embodiments of the present invention assays can be conducted and read in a variety of assay reading devices. There are many assays available using known techniques. Some of them are more sophisticated and some less sophisticated. In exemplary embodiments of the present invention, an assay reading device can, for example, obtain results at 102, store those results and analyze them locally, for example, in a processor communicably connected to the assay reading device. Alternatively, if only raw assay results are obtained from a less sophisticated technology, those results can, for example, be sent over a data network and stored in a database record. This is illustrated at 104. At 105, the results can be analyzed by accessing the particular record associated with the particular individual to whom the assay panel or panels were administered at a given time. Such analysis can involve a variety of algorithms ranging from a simplistic look at quantity of antibodies per defined unit of blood or other bodily fluid, or it can also, for example, include a complex analysis where a variety of assay results are input and combined in linear and non-linear ways to produce some metric of immunologic significance. Such algorithms are described more fully below in Section II. Finally, at 106, based on the results of the above described analysis, recommendations can be generated. Such recommendations can include, for example, that the individual obtain one or more vaccines, that the individual be administered prophylactic therapies to boost his or her immune system, or that the individual be administered gene therapy to correct the genetic defect which places him or her at risk of communicating a certain disease or condition, to name a few.

In general, in many exemplary embodiments according to the present invention process flow will be equivalent to or substantially similar to the process flow depicted in FIG. 1. In each of those exemplary embodiments, one or more panels of assays can be conducted with respect to one or more individuals. Results can be obtained, stored and analyzed, and based on such analysis, recommendations for action (or inaction, such as, for example, in cases of over-vaccination, as described above) can be recommended.

Figure 2:
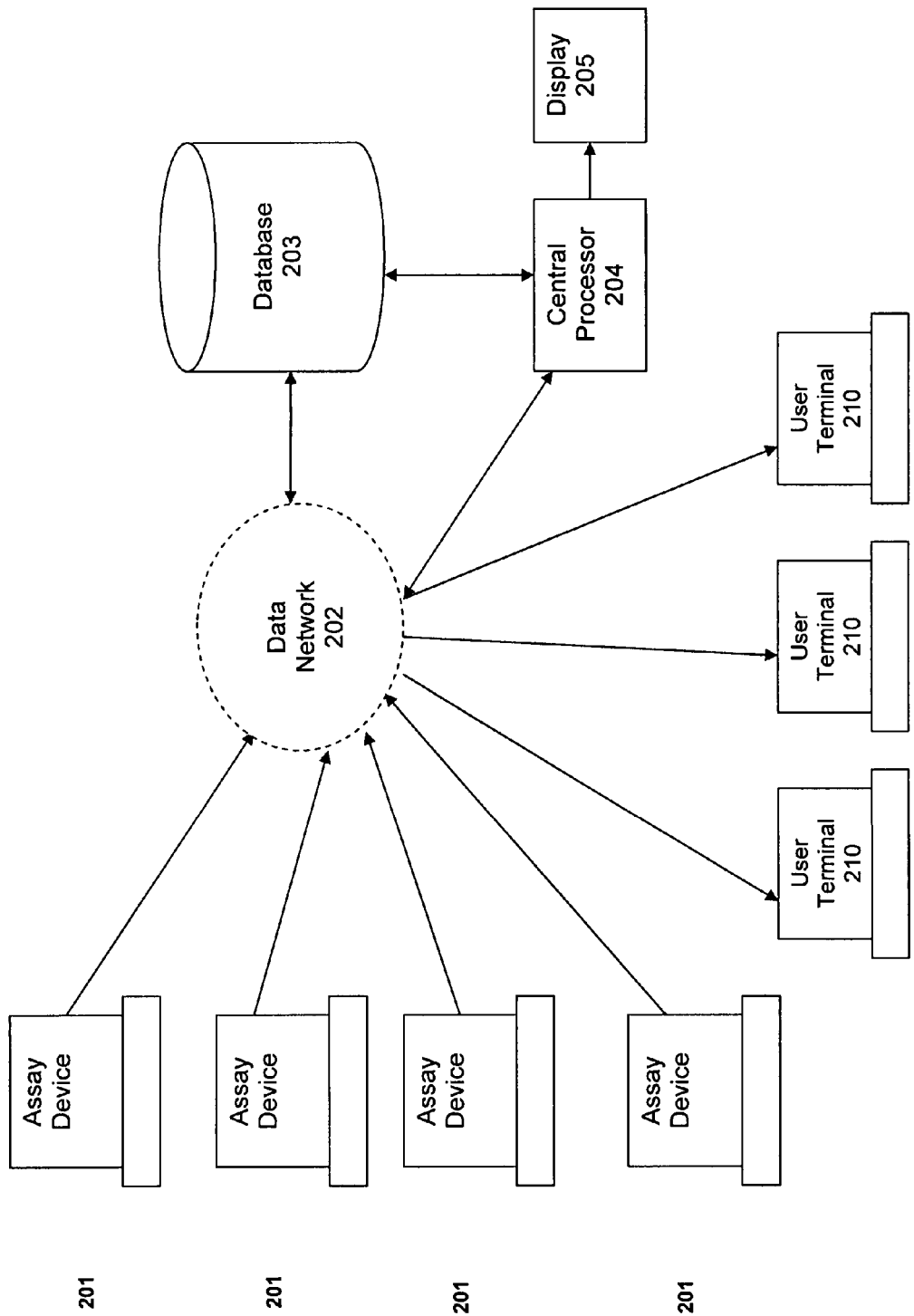
FIG. 2 depicts an exemplary system overview according to exemplary embodiments of the present invention.

FIG. 2 is an exemplary generalized system diagram which correlates to the generalized method depicted in FIG. 1. With reference to FIG. 2, there can be seen a number of assay devices 201. These assay devices include one or more assay panels which have been conducted with respect to an individual or individuals and for which results have been obtained. The results obtained from the assay devices can, as described in connection with the generalized method in FIG. 1, be locally analyzed at each assay device, provided that such assay device has a data processor and memory and the results can be stored locally at the assay device. Alternatively, the assay device results can, for example, be communicated over a data network 202 to a central processor 204 and stored in a central database 203. The central processor 204 can access the records which it has received and analyze them by implementing a number of analytic algorithms as described more fully below.

Central processor 204, based on its analysis, can generate recommendations based on decision trees and criteria embedded in the various analytic algorithms it implements. These recommendations can be displayed locally at the central processor at display 205 and can there be printed in a tangible medium for distribution to interested persons. Alternatively, the central processor 204 can, for example, send the results of its analysis over a data network to various users who can access the results at user terminals 210.

Figure 2A:
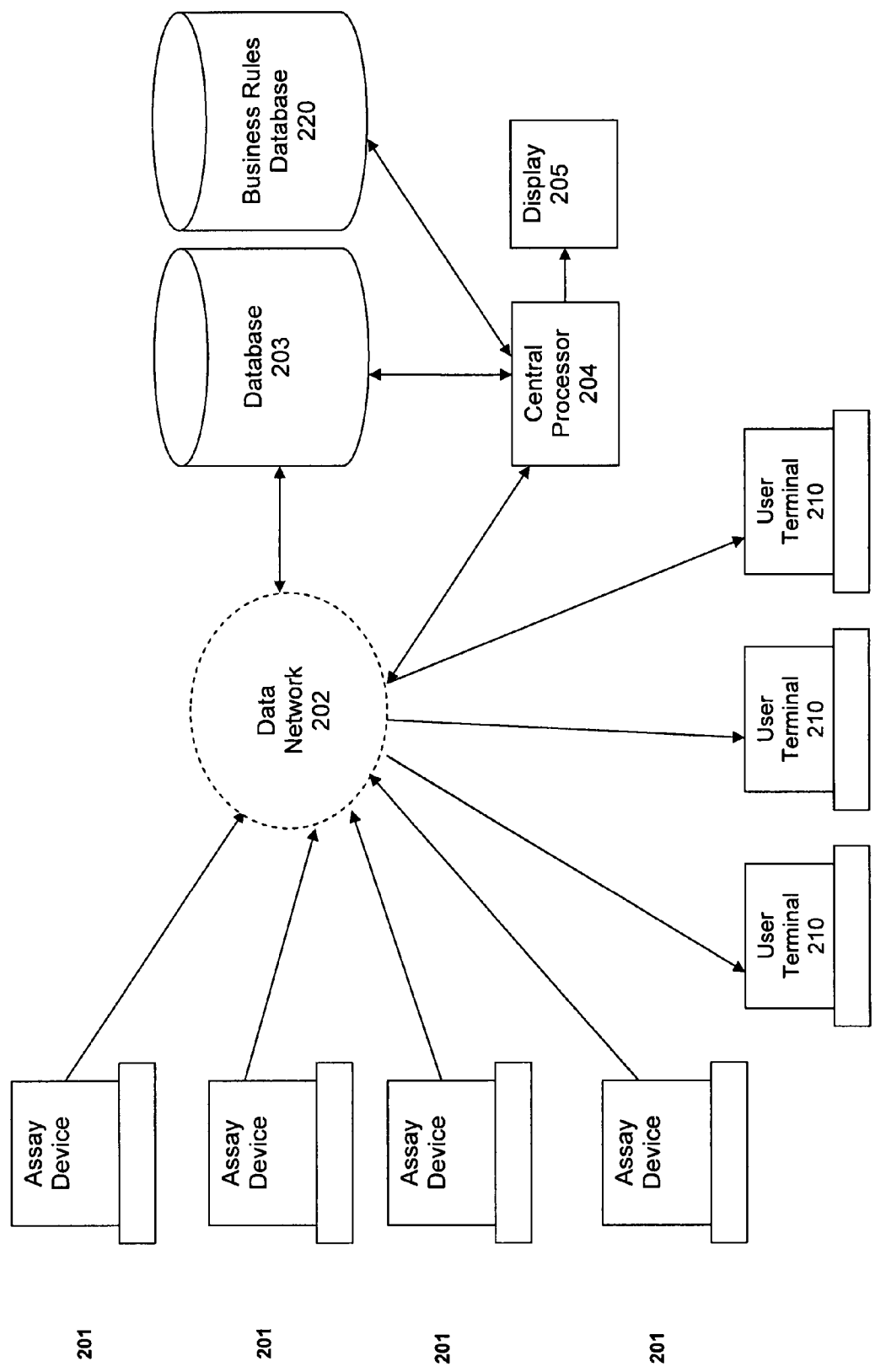
FIG. 2A depicts an alternate exemplary system overview according to exemplary embodiments of the present invention.

FIG. 2A presents an alternative generalized system diagram similar to FIG. 2. However, as can be seen in FIG. 2A, there is an additional database, the business rules database 220, communicably connected to central processor 204. In such an exemplary system the central processor can implement algorithms to operate on stored assay data which can, for example, also take as inputs various business rules in generating a decision regarding a recommendation. For example, as described more fully below in Section III, an exemplary embodiment of the present invention can be utilized to help a health insurance underwriter manage its population of insureds. There can, for example, be an annual or semi-annual requirement of all insureds to have assays for various immunological components conducted on their blood or other bodily fluids. After analysis of the results of such assays, an insurance company can determine whether a particular insured is susceptible to one or more given diseases or other ailments which would result in increased expenditures for medical treatment. The insurance company could then decide if it was not more economical to require the insured to undergo certain prophylactic treatments, such as, for example, vaccines or immune system boosting therapies, etc., where the cost of such prophylactic therapies is less than, as determined by some user determined factor, the expected exposure for medical care if the insured contracts one or more of the diseases or ailments to which he or she is susceptible.

In such context, there would need to be a number of business rules where such user defined quantities, threshold levels, cost functions or metrics, figures of merit, expected risks, etc., can be input and articulated or incorporated in a number of rules. Such rules can then be taken into account by the central processor in implementing algorithms which take as inputs data from business rules database 220 as well as a primary ImmunoScore database 203.

Figure 2B:
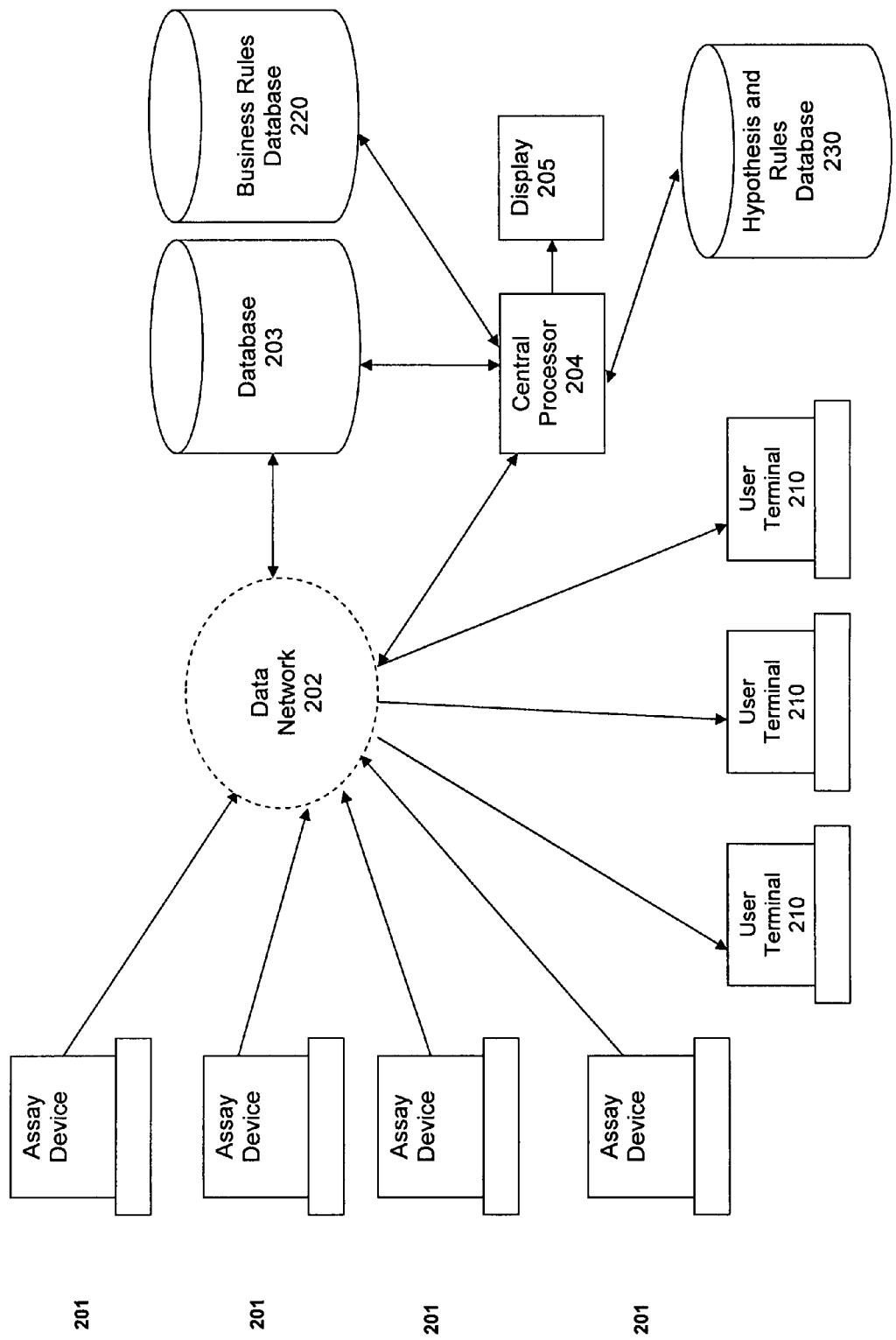
FIG. 2B depicts yet another alternate exemplary system overview according to exemplary embodiments of the present invention.

FIG. 2B presents an alternative generalized system diagram similar to FIGS. 2A and 2B. However, as can be seen in FIG. 2B, there is shown yet another additional database, a hypothesis and rules database 250, communicably connected to central processor 204. In such an exemplary system a central processor can, for example, implement data mining algorithms to operate on stored immunologic and background data to find a set of correlations. Such data mining algorithms can for example, be used to corroborate known or expected relationships, such as, for example, a correlation in antibody levels for measles, mumps and rubella in persons born in the United States after 1960, where the three vaccines were given simultaneously. In fact, an interesting follow-up would be to track if the rates of antibody levels for each of these three diseases change in the individual at a similar or a different rate, and if different, determine why.

Alternatively, for example, such data mining algorithms can be used to find counter-intuitive, or generally unknowns connections between variables or fields in the database.

In either case, once a set of correlations is obtained, intelligence in an exemplary system can be used to automatically generate a set of hypotheses to explain such correlations (or, if known, any follow-up data related thereto, as described above) and proceed to test the viability of each hypothesis using the data in the database. Or, alternatively, such intelligence can inform a user that additional data is needed to vet a hypothesis.

This process is explained more fully in Section II below.

Further, using such correlations, an exemplary system can, for example, also take as inputs various business rules in generating a decision regarding a recommendation. For example, as described more fully below in Section III, an exemplary embodiment of the present invention can be utilized to help a health insurance underwriter manage its population of insureds. There can, for example, be an annual or semi-annual requirement of all insureds to have assays for various immunological components conducted on their blood or other bodily fluids. After analysis of the results of such assays, an insurance company can determine whether a particular insured is susceptible to one or more given diseases or other ailments which would result in increased expenditures for medical treatment. The insurance company could then decide if it was not more economical to require the insured to undergo certain prophylactic treatments, such as, for example, vaccines or immune system boosting therapies, etc., where the cost of such prophylactic therapies is less than, as determined by some user determined factor, the expected exposure for medical care if the insured contracts one or more of the diseases or ailments to which he or she is susceptible.

In such context, there would need to be a number of business rules where such user defined quantities, threshold levels, cost functions or metrics, figures of merit, expected risks, etc., can be input and articulated or incorporated in a number of rules. Such rules can then be taken into account by the central processor in implementing algorithms which take as inputs data from business rules database 220 as well as a primary ImmunoScore database 203.

Given the generalized exemplary method of FIG. 1 and the generalized exemplary systems of FIGS. 2, 2A and 2B, what is next described are a number of exemplary assay panels which can be administered to an individual or members of a population according to exemplary embodiments of the present invention. The scientific background behind the various exemplary assay panel, as well as which segments of the general population such panels are best administered to, are also described.

Section I Exemplary Assay Panels

The present invention is, inter alia, concerned with assessing the "protective immune status" or "immunologic status" of an individual or population. A "protective immune status" is understood to be represented by an array of detectable components (phenotypic and/or genotypic) of an immune system (adaptive and/or innate) that comprise its protective capacity against harmful substances and/or cells (such as, for example, microorganisms or cancer). Such components can, for example, consist of genes as well as gene products. Genes can include, for example, those which encode immunologic receptors (such as, for example, toll-like receptors ("TLR"s) and chemoattractant receptors) as well as effector molecules (such as, for example, cytokines and chemokines) which may also, for example, exist as genetic polymorphisms capable of deleterious and/or beneficial effects. Gene products can include, for example, antibodies, complements, cytokines, chemokines, chemoattractant receptors, TLRs, lectins, and other immune-related ligands. Harmful substances can consist of, for example, chemicals and/or toxins originating from the environment, microorganisms, or one's self.

Once diagnostic information is acquired from an individual regarding his or her immune status, this information can be, for example, added to a system database. Such a database can contain, for example, not only the results of ImmunoScore diagnostic testing but a wide variety of demographic data and patient history information as well. Such a system database can, for example, be used to record adverse events occurring coincident with immunizations. Such information can be invaluable to, for example, the ACIP for making recommendations regarding immunization scheduling, as well as help discover unsuspected patterns and correlations relevant to immune status and immune response.

ImmunoScore diagnostic testing can be, for example, tailored to meet an individual's specific immunization status needs. In addition, each individual can, for example, receive their own personal ImmunoScore card that they could carry with them to health care office visits, and the database information can be easily transferable in the ever-increasingly likely event that they change physicians or other primary health care providers. Additionally, ImmunoScore data, analysis of such data and relevant database information can, for example, be stored as part of a person's totality of health information and medical records, in electronic formats such as, for example, entries in electronic health information databases, or computer chips embedded in, for example, "smart" cards or "smart driver's licenses."

For economy of description, most of the references cited herein are provided in full citation in Appendix A to the Immunologic Informatics Patent. Throughout the text citations are made to author and year of publication alone.

One component of ImmunoScore data can be, for example, the raw as well as processed results of diagnostic tests or assays relating to immune status, as described below. ImmunoScore diagnostic testing is envisioned to be done on a small assay device or testing instrument that can be located, for example, in a doctor's office. The testing can be done, for example, with a sample of an individual's whole blood, plasma, serum, saliva, milk, semen, tears, or urine. In the case of blood, for example, the sample can be obtained by a finger prick, heel stick, ear stick, other skin prick, capillary draw, venous draw, or an arterial draw. The instrument can, for example, take assay panels and the patient sample. Patient information can also be input. The resulting information can be, for example, displayed to a user, printed, stored in a removal medium, stored in the instrument, and/or transmitted (wired or wireless) to other devices such as via an intranet, a VPN or the Internet, for example.

Numerous systems and methods have been developed for the detection and quantitation of analytes of interest in biochemical and biological substances that can be used, for example, in such an instrument. Such methods and systems which are capable of measuring trace amounts of microorganisms, pharmaceuticals, hormones, viruses, antibodies, nucleic acids and other proteins can be of great value to researchers and clinicians.

A substantial body of art has been developed based upon well known binding reactions, such as, for example, antigen-antibody reactions, nucleic acid hybridization techniques, and protein-ligand systems. The high degree of specificity in many biochemical and biological binding systems has led to many assay methods and systems of value in research and diagnostics. Typically, the existence of an analyte of interest is indicated by the presence or absence of an observable "label" attached to one or more of the binding materials. Of particular interest are labels which can be made to luminesce through photochemical, chemical, and/or electrochemical means. "Photoluminescence" is the process whereby a material is induced to luminesce when it absorbs electromagnetic radiation. Fluorescence and phosphorescence are types of photoluminescence. "Chemiluminescent" processes entail the creation of luminescent species by chemical transfer of energy. "Electrochemiluminescence" entails creation of luminescent species electrochemically.

Electrochemiluminescent (ECL) assay techniques are an improvement over chemiluminescent techniques. They can, for example, provide a sensitive and precise measurement of the presence and concentration of an analyte of interest. In such techniques, the incubated sample is exposed to a voltammetric working electrode in order to trigger luminescence. In the proper chemical environment, such electrochemiluminescence is triggered by a voltage impressed on the working electrode at a particular time and in a particular manner. The light produced by the label is measured and indicates the presence or quantity of the analyte. For a fuller description of such ECL techniques, exemplary reference is made to U.S. Pat. Nos. 5,221,605; 5,705,402; 6,140,138; 6,325,973; and 6,451,225. The disclosures of the aforesaid patents are hereby incorporated herein by reference.

Amplification techniques for nucleic acids may be combined with the above assay techniques. For example, U.S. Pat. No. 6,048,687 discloses how NASBA can be combined with an ECL technique; and U.S. Pat. No. 6,174,709 discloses how PCR can be combined with an ECL technique. The disclosures of the aforesaid patents are also hereby incorporated herein by reference.

An assay instrument can, for example, be, or be similar to, the BioVeris Corporation M1R or M1M instruments with an added sample processing front end. Aspects of these instruments are disclosed in pending U.S. patent application Ser. Nos. 10/600,165 and 10/841,569, each under common assignment herewith. The disclosures of these patent applications are hereby incorporated herein by reference.

In exemplary embodiments of the present invention, an assay instrument can include, for example, amplification techniques such as PCR or NASBA. In exemplary embodiments of the present invention, the instrument can use fluorescence, chemiluminescence, or ECL assay techniques. In exemplary embodiments, multiple measurements can be done simultaneously; in other exemplary embodiments of the present invention, multiple measurements can be done sequentially. In exemplary embodiments of the present invention, an assay instrument can, for example, contain self-test and/or self-calibration components.

Figure 3:
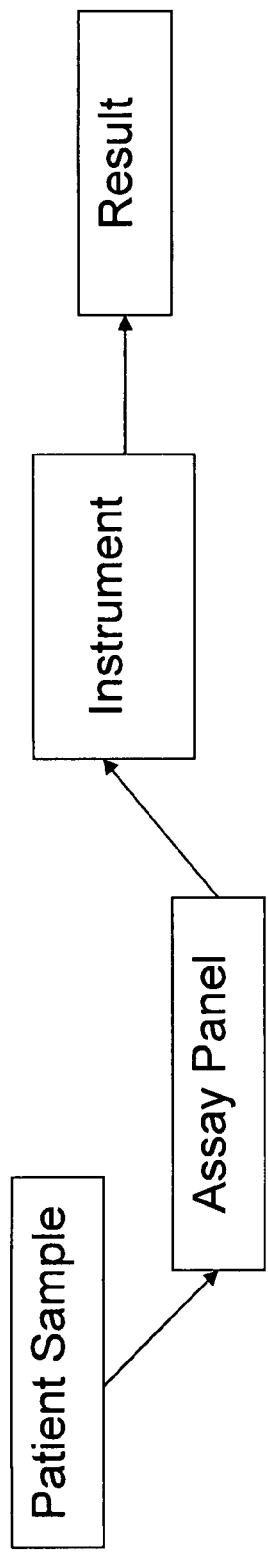
FIGS. 3 and 4 depict various exemplary configurations for assaying a patient sample according to an exemplary embodiment of the present invention.
Figure 4:
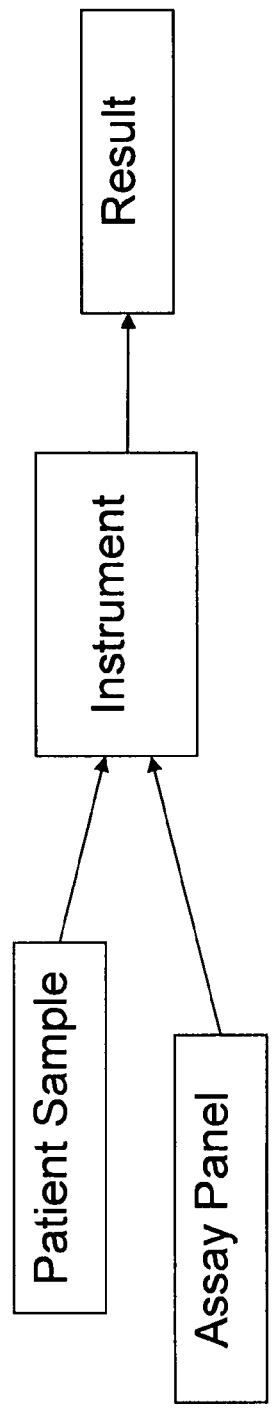

In exemplary embodiments of the present invention, a sample can be added to an assay panel, and the combination then inserted into the test instrument, as shown in FIG. 3. In alternate exemplary embodiments, the sample and assay panel can be separately inserted into the test instrument, as shown, for example, in FIG. 4.

As described below, entries to an exemplary master ImmunoScore database can be, for example, coded so as to protect patient confidentiality. A patient could, however, be able to learn from their physician in real time, for example, which vaccines he or she might need to ensure protection from vaccine-preventable illnesses. The physician can, for example, offer the vaccine, or other therapy, during the same visit, or shortly thereafter. Any possible adverse effects from any delivered vaccinations could be subsequently entered into an ImmunoScore database and that information could be shared with the ACIP or other agencies or bodies, as described more fully below.

The actual assays can be performed, for example, based upon the needs of the individual or individuals being examined. Age, occupation, travel plans, immigration status, military status, and previous health status can all be considered prior to initiation of ImmunoScore diagnostic analyses in exemplary embodiments. In exemplary embodiments of the present invention, the following exemplary broad categories can, for example, be utilized as focal points for test panels:

Entry to primary school.
College entry.
Age 19-49 years.
Age 50-64 years.
Age > 65 years.
Health-care professionals.
Military personnel:
    recruits and officer accessions;
    alert forces;
    individualized according to occupational or personal needs; and
    veterans.
Travelers.
Immigrants.

Individuals with identifiable health risks (not necessarily exclusively):
  a. Complement-deficient individuals (e.g. meningococcal disease susceptibility);
  b. Genetically identified (e.g. HLA haplotype, sepsis susceptibility) disease-susceptible individuals;
  c. Mannose-binding lectin-deficient individuals;
  d. Hepatitis B vaccine poor/non-responders; and
  e. Ethnic groups and others known to respond poorly to polysaccharide, conjugate, or other vaccines.

Although the health effects may be just as great, coverage levels for immunizations in adults are not as high as those achieved in children. Barriers to adult immunization can include, for example, not knowing that immunizations are needed, misconceptions about vaccines, and lack of recommendations from health care providers. Adding an ImmunoScore based diagnostic component to routine physical examinations in adults could easily point out where immunizations are needed, for example. Just as importantly, it could, for example, point out exactly which individuals would not need to be unnecessarily boosted if their serum antibody levels proved to be sufficient for any particular vaccine. The development and acceptance of an ImmunoScore vaccine diagnostic surveillance system can not only aid in increasing vaccine coverage, but can also, for example, add increased surveillance of the level of immune response and duration of protection thereof for a wide variety of recommended vaccines.

There are still great risks posed to the population by vaccine-preventable diseases. The risks posed by failure to immunize were vividly illustrated by the measles outbreak that began in 1989, which led to 43,000 cases and over 100 deaths, mainly among children in the United States. Despite better efforts at record-keeping for immunizations, for example, the development of the Adult and Adolescent Clinic Assessment Software Application (ACASA) to facilitate obtaining immunization data on adults and adolescents, adult compliance with vaccination protocols generally remains unsatisfactory. One way to demonstrate the need for vaccination in adults is to demonstrate a low antibody titer in an individual and present the need to boost the antibody titer using assigned correlates of protection from vaccine-preventable diseases. If an antibody titer to a specific agent is determined to not meet the recognized level of a correlate of protection by an exemplary ImmunoScore analysis, and that titer is easily boosted by vaccination, then that individual would likely be more easily convinced of the need for protective immunization. Not only would this diagnostic tool prove extremely beneficial to the individual, but data added to an ImmunoScore database can be collected regarding immune correlates of protection for very large populations. Demographic assessments can also be compiled from the database, leading to, for example, new discoveries regarding possible age-related or ethnic responses to immunizations and/or other immune status issues.

In exemplary embodiments of the present invention, targeted panels of immune status assays can be defined. Such exemplary targeted panels, can be organized, for example, into two broad groups, college students and adults.

For college students, three exemplary panels were defined: (a) a Meningococcal diagnostic panel, (b) a panel designed to measure the residual immunity induced by childhood vaccines, and (c) a panel directed to measuring immunity from common sexually transmitted diseases.

For the general adult population, exemplary panels were defined directed to the following groups or categories: (a) military personnel, (b) travelers, (c) adults-general immune status, (d) health care workers, (e) bioterrorism, (f) chronic disease, (g) Th-1-Th2 diagnostic panel, and (h) immigrants and internationally adopted children.

Using these basic panels of assays as building blocks, in exemplary embodiments of the present invention, aggregations of one or more panels, with variations thereto as may be desired, can be defined for various purposes. These can be referred to, for example, as ImmunoScore "superpanels." For example, a primary school panel can be defined, to be administered upon a child's entry into grammar school. Such a panel could include, for example, a persistent immunity to childhood vaccines assay panel. Similarly, a middle school student superpanel can be defined as well. Such a superpanel can include, for example, a persistent immunity to childhood vaccines panel and a sexually transmitted disease panel. Another exemplary superpanel could be defined for women of childbearing years. Such an exemplary superpanel can include, for example, a newly defined women of childbearing years panel, a persistent immunity induced by childhood vaccines panel, and a sexually transmitted disease panel.

College Student Diagnostic Panels

9. Meningococcal Diagnostic Panel

In exemplary embodiments of the present invention, the following tests can be included in a meningococcal diagnostic panel:

1. Antibody (Ig) to (4 tests):
   Group A Meningococcal Polysaccharide (GAMP)
   Group C Meningococcal Polysaccharide (GCMP)
   Group Y Meningococcal Polysaccharide (GYMP)
   Group W-135 Meningococcal Polysaccharide (GWMP)
2. Antibody (IgM) to Group B Meningococcal Polysaccharide (GBMP) (1 test)
3. Serum levels of complement components (7 tests):
   C5
   C6
   C7
   C8
   C9
   Properdin
   MBL
4. Measurement of genetic polymorphisms (5 tests):
   FcγRIIa receptor
   IL-1
   IL-1R
   IL-6
   IL-10

In exemplary embodiments of the present invention, results from an exemplary meningococcal diagnostic panel can be analyzed as follows:

Serum Ig levels for vaccine-preventable serogroups (A, C, Y, and W-135) of N. meningitidis can be assessed. An Ig level exceeding 2.0 µg/mL of all four serogroups would be presumptive of protection in an otherwise healthy individual. There would be no immediate recommendation for meningococcal vaccination in these individuals.

If deficiencies were to be revealed in any of an individual's complement components assayed, or if any unfavorable genetic polymorphisms were shown to exist, then an Ig level of $\geq$5.0 µg/mL for the vaccine-preventable serogroups could be desirable in these individuals. If these individuals had Ig levels exceeding 5.0 µg/mL for all four serogroups, no vaccination would be recommended. If, however, the level of antibody to any of the four serogroups were to be below 5.0 µg/mL, then a vaccination could be recommended.

Once individuals were shown to have complement deficiencies, or unfavorable genetic polymorphisms, they could be, for example, "flagged" for future monitoring. These are individuals at greatest risk for meningococcal infections, so serum antibody levels are very important in this group. Initially, they could be monitored every 3-5 years for serum Ig to the vaccine-preventable meningococcal serogroup capsular antigens.

As yet there is limited information available regarding the persistence of serum Ig to the N. meningitidis group polysaccharides. As the system database grows, more information regarding antibody persistence can become available and analysts can, for example, have a better idea as to when to recommend retesting and, perhaps, revaccination of individuals more susceptible to meningococcal disease.

It has previously been demonstrated that repeated vaccination with the capsular polysaccharide from Group C organisms promotes immune hyporesponsiveness (Richmond, et al. 2000, Jokhdar, et al. 2004). This is a red flag to overuse of the vaccination protocol. Currently, immunocompromised individuals are recommended for repeated immunizations every 3-5 years. In exemplary embodiments of the present invention, the ImmunoScore meningococcal diagnostic panel can prevent over-immunization with the polysaccharide formulation by first measuring immune status vis-à-vis menigococcal disease prior to simply vaccinating following a standard schedule. Immunization with Group C conjugate vaccine overcomes the hyporesponsiveness, but is not yet approved in the United States.

10. Sexually Transmitted Diseases Assay Panel

In exemplary embodiments of the present invention, the following tests can, for example, be used for ImmunoScore measurement of immunity to STDs:
Antibodies to *Chlamydia*—IgG, IgA, and IgM (3)
Antibodies to HSV—IgG to HSV-1 and HSV-2 (2)
DNA analyses of HPV types—particular emphasis on high-risk
Antibody to *N. gonorrhoeae* (1)
Antibody to *T. pallidum* (1)
T-cell related response to *T. pallidum*
Antibody to HIV
T-cell related response to HIV
Antibodies to GBS serotypes (at least 3)
Measurement of Th1/Th2 cytokines (many as current evolving definitions)
  Currently, there are no vaccines available for any of these STDs. Until this situation is ameliorated, the objective of an ImmunoScore STD diagnostic panel would thus be to recommend treatment. The ImmunoScore database can generate correlate of protection information for all diseases. As vaccines are developed, ImmunoScore diagnoses can be designed to examine antibody and other related immune responses to vaccine components.

11. Persistent Immunity Induced by Childhood Vaccines

In exemplary embodiments according to the present invention, the following tests for measurement of immunity to childhood vaccines can be included in an exemplary ImmunoScore panel directed to college students, or in other exemplary embodiments, to adults in general:
Antibody to HBs (1)
Antibody to diphtheria toxin (1)
Antibody to tetanus toxin (1)
Pertusis antibodies (4):
  Antibody to pertussis toxin (PT)
  Antibody to pertactin (PRN)
  Antibody to filamentous hemagglutinin (FHA)
  Antibody to fimbriae
Antibody to PRP (Hib)(1)
Antibodies to poliovirus serotypes P1, P2, and P3 (3)
Antibody to measles (1)
Antibody to mumps (1)
Antibody to rubella (1)
Antibody to varicella (1)
Antibody to pneumococcal serotypes (7)
  Given the above-described tests for persistent immunity induced by childhood vaccines, in exemplary embodiments of the present invention, the following exemplary analyses and recommendations can, for example, be made:

For Hepatitis B, post-vaccination titers of anti-HBs IgG of 10 mIU or greater correlate with the induction of T cell helper responses that mediate the memory of B cells (Plotkin, 2001). An antibody titer below 10 mIU would indicate need for vaccination—one booster dose if previously vaccinated, or a course of three doses if unvaccinated.

The current indication for partial protection from diphtheria disease is an anti-diphtheria toxin antibody concentration between 0.01 and 0.1 IU/mL. Protection is considered to be complete above 0.1 IU/mL (Plotkin, 2002). In exemplary embodiments ImmunoScore diagnostics can recommend a booster dose if antibody concentration were to fall below 0.1 IU/mL. The ImmunoScore database can shed further light in the future as to the true protective level of anti-diphtheria toxin antibody.

The current indication for partial protection from tetanus disease is an anti-tetanus toxin antibody concentration between 0.01 and 0.1 IU/mL. Protection is considered to be complete above 0.1 IU/mL (Plotkin, 2002). ImmunoScore diagnostics can recommend a booster dose if antibody concentration were to fall below 0.1 IU/mL. The ImmunoScore database can shed further light in the future as to the true protective level of anti-tetanus toxin antibody.

One of the most controversial areas within the subject of correlates of immunity is pertussis vaccine. Two separate trials conducted in Sweden indicate that pertussis toxin can protect on its own (Trollfors, et al. 1995). One trial suggests that the addition of filamentous hemagglutinin (FHA) is helpful, two trials suggest that pertactin augments the efficacy of PT and one trial suggests that agglutinogens add efficacy beyond those of PT, FHA, and pertactin (Plotkin, et al. 1997). The problem is that the vaccines do not resemble each other in quantity of antigens, and reliance can be placed only on demonstrated efficacy in the field. The role of ImmunoScore diagnostics for this population can, for example, best be served in data acquisition and correlation to incidence of disease. There is not yet an adult pertussis vaccine, but development proceeds along those lines. The ImmunoScore diagnostic application can be beneficial in exemplary embodiments to ACIP for vaccine recommendations. Testing four components for pertussis disease would lend weight to the accumulated data.

Individuals vaccinated with Hib conjugate vaccines are considered to be protected with an IgG level>0.15 μg/mL (Goldblatt, et al. 1999). Booster vaccination can be recommended if an individual's antibody titer fell below that level.

Individual that receive oral polio vaccine (OPV) are protected by both serum and secretory antibodies. Inactivated polio vaccine (IPV) recipients are dependent primarily on serum antibody for protection against infection and disease (Onorato, et al. 1991). Neutralizing antibody assays are currently used to assess protective Ig levels (titer≧1:8). The format of these assays would necessarily need to be updated to be included in the ImmunoScore analyses. Currently, the duration of protection from IPV vaccination is not known, and ImmunoScore database analyses could, for example, lend strength to the current knowledge levels.

Serum antibody levels>120 mIU are considered to be completely protective against measles infection (Plotkin, 2001). Vaccination can be considered for individuals whose antibody titers fall below this level.

Protection against mumps disease is currently assessed with neutralization assays. Like the polio vaccine, the assay format would need updating for ImmunoScore diagnosis.

Protection against rubella disease is currently assessed with neutralization assays. Like the polio and measles vaccine, the assay format would need updating for ImmunoScore diagnosis.

Protection against varicella disease is currently assessed with neutralization assays. The assay format would need updating for ImmunoScore diagnosis.

Little is known about the correlate of protection for pneumococcal anti-capsular polysaccharide antibodies. It is likely that the protective IgG range would fall between 0.15 and 1.0 µg/mL, except for serotype 14, against which more antibody is necessary (Plotkin, 2001). An ImmunoScore diagnostic recommendation can, for example, initially be for a boost if antibody levels fell below 1.0 µg/mL, and then the database analyses can be able to shape future recommendations.

Adult Diagnostic Panels

12. Measurement of Immunity Induced by Vaccines for Military Personnel

In exemplary embodiments of the present invention military personnel can be administered the following diagnostic panels:

1. College Student ImmunoScore Panels consisting of:
   Meningococcal Diagnostic Panel;
   Sexually Transmitted Disease Diagnostic Panel;
   Persistent Immunity Induced by Childhood Vaccine Diagnostic Panel; and
as described above; and in addition 2. Military personnel can have specific vaccination needs as outlined in Table 3 below depending on their assignments and type of deployment. Specific branches of the service may also have specific vaccination needs and permutations of the basic diagnostic panels. Thus, in exemplary embodiments, military personnel can be administered one or more of the following tests:

TABLE 3

Vaccine Diagnostic Panels Exclusive to the Military:

| Vaccine | Antibody Marker |
| --- | --- |
| Adenovirus 4 & 7 | Neutralizing antibody |
| Anthrax | PA |
| Cholera | LPS IgG |
| Plague | Fraction I Capsular Antigen |
| Smallpox | Neutralizing antibody |
| Lyme disease | OspA |

In addition to the analytes listed above as exclusive to the military, an ImmunoScore diagnostic panel can, for example, be extremely flexible at adding new diagnostic tests for vaccines under development.

Analysis of results/recommendations for use of ImmunoScore diagnostic panel data for analytes for specific military applications can, in exemplary embodiments of the present invention, include the following:

Adenovirus vaccine is not currently given to military recruits, but infection with adenovirus remains a concern. Development and use of adenovirus vaccines are likely in the future and an exemplary ImmunoScore diagnostic application can require an updated assay format over the currently accepted neutralizing antibody assay.

Currently, serological correlates of protection to inhalation anthrax are being developed in animal models. ImmunoScore diagnostics can, for example, measure level of serum IgG to protective antigen (PA) and the ImmunoScore database can, for example, thus build serologic correlates of protection in humans.

Immunity to cholera is currently not completely understood. However, ImmunoScore diagnostics can focus first on levels of anti-LPS IgG, and further attempt to build meaning into the database correlates of protection.

The need for a new vaccine for pneumonic plague is evident given the limited efficacy of the current cellular vaccines, which consist of either the killed virulent 195/P or live EV76 strains. While an efficient and safe live cellular vaccine has not been identified yet, there is an effort to develop alternative subunit vaccines based on various antigens, including the F1 and V antigens. ImmunoScore diagnostics can, for example, monitor serum antibody levels to current plague vaccine components and be able to adapt to any new vaccine configurations. ImmunoScore database can, for example, compile immune response data and be correlate the relevant antibody levels to levels of protection.

Immune memory after smallpox vaccination is a valuable benchmark for understanding the kinetics and longevity of B cell memory in the absence of re-exposure to antigen, since immunization of the U.S. population was stopped in 1972 and smallpox disease was declared eradicated worldwide in 1980. Immune memory to smallpox is a useful benchmark both for understanding the longevity and the stability of immune memory in the absence of re-stimulation. Circulating antibody persists for over 50 years. ImmunoScore diagnostics can, in exemplary embodiments of the present invention, measure antibody to smallpox. Correlates of protection can, for example, be generated from analyses of the ImmunoScore database.

The human protective response to vaccination against Lyme disease is purely a serum-mediated antibody response. Individuals are generally considered protected with antibody levels against OspA greater than 1100 IU. Subjects with less antibody titers less than 1100 would, in exemplary embodiments of the present invention, be recommended to have a booster vaccination.

13. ImmunoScore Measurement of Vaccine-Induced Immunity for Travelers

In exemplary embodiments of the present invention, an ImmunoScore traveler's assay panel can, for example, include the following:

Antibody to HAV (1)
Antibody to HBs (1)
Antibody to Japanese Encephalitis (1)
Antibody to rabies (1)
    other rabies related cytokine assays (as necessary)
Antibody to Typhoid fever (1)
Antibody to yellow fever (1)
Antibody to diphtheria toxin (1)
Antibody to tetanus toxin (1)
Pertusis antibodies (4):
    Antibody to pertussis toxin (PT)
    Antibody to pertactin (PRN)
    Antibody to filamentous hemagglutinin (FHA)
    Antibody to fimbriae
Antibodies to poliovirus serotypes P1, P2, and P3 (3)
Antibody to measles (1)
Antibody to mumps (1)
Antibody to rubella (1)

In exemplary embodiments of the present invention, recommendations for use of a ImmunoScore diagnostic panel for analytes specific to travelers can include all of the uses of the results of the Meningococcal Diagnostic Panel tests, as described above. Additionally, the following recommendations/conclusions can be implemented:

- The protective level of antibody to hepatitis A has been established to be approximately 10 mIU/mL if that concentration is maintained for a two month period, although some individuals may be protected at much lower concentrations (Conrad and Lemon, 1987). An individual that had less than 10 mIU/mL of antibody to hepatitis A can be recommended for vaccination.
- Current analyses of antibody levels to Japanese Encephalitis consist of neutralization assays. These assays would need to be refined for ImmunoScore diagnostic applications. In exemplary embodiments of the present invention, an ImmunoScore database can catalog antibody levels in anticipation of establishing future serologic correlates of protection.
- The most important immune response to rabies vaccines is antibody to the G envelope protein (Wicktor, et al. 1973), and passively administered antibody is part of standard treatment to neutralize cell-free virus before it attaches to the axon of a neuron (Plotkin, 2000). Because passive antibody alone is poorly effective unless supplemented by active vaccination, CD4+ and CD8+ cell responses are probably also important to protection, but whether these critical responses relate to cytotoxic T lymphocyte function, interferon synthesis or other cytokines is unknown (Hemachudha, et al. 1999). ImmunoScore diagnostic assays can include at the very least antibody levels to G envelope protein and can also measure relevant cytokines to assess serological correlates of protection.
- Protection against typhoid fever might be best achieved by a vaccine that stimulates IgG antibody to Vi capsular polysaccharide in serum, IgG antibody to O antigen in serum, and cell-mediated immune responses (Tackett, et al. 2004). ImmunoScore diagnostic analysis can thus, in exemplary embodiments of the present invention, focus on antibody to Vi capsular polysaccharide. ImmunoScore data analyses can create necessary correlates of protection against typhoid fever disease.
- Protection against yellow fever appears to correlate with antibody titers above 0.7 IU. ImmunoScore diagnostic analysis can recommend that an individual with antibody titer below 0.7 IU be boosted.

14. ImmunoScore Measurement of Immunity in Health Care Workers

Because of their contact with patients and/or infective material from patients, many health-care workers (e.g. physicians, nurses, emergency medical personnel, dental professionals and students, medical and nursing students, laboratory technicians, hospital volunteers, and administrative staff) are at risk for exposure to and possible transmission of vaccine-preventable diseases. Maintenance of immunity is therefore an essential part of prevention and infection control programs for health-care workers. Optimal use of immunizing agents safeguards the health of workers and protects patients from becoming infected through exposure to infected workers. Consistent immunization programs could substantially reduce both the number of susceptible health-care workers in hospitals and health departments and the attendant risks for transmission of vaccine-preventable diseases to other workers and patients. In exemplary embodiments of the present invention, the judicious application of ImmunoScore diagnostics to the needs of health-care workers can assure that these individuals will be appropriately immunized and protected from both becoming infected and spreading infection. The Centers for Disease Control (CDC) has recommended various immunizing agents for health-care workers.

Any medical facility or health department that provides direct patient care is encouraged to formulate a comprehensive immunization policy for all health-care workers. The American Hospital Association has endorsed the concept of immunization programs for both hospital personnel and patients (AHA, 1992). The use of ImmunoScore diagnostic capability coupled with rigorous immunization programs can assist in the decline of nosocomial infections.

There are diseases for which the CDC strongly recommends vaccination for health-care workers. These include Hepatitis B, influenza, measles, mumps, rubella, varicella-zoster, and tuberculosis. There are other diseases that vaccination may be indicated for; these include Hepatitis A, meningococcal disease, Typhoid, and smallpox. Finally, for some health-care workers, there may be a recommendation for tetanus, diphtheria, pertussis, and pneumococcal disease.

Hepatitis B virus (HBV) infection is the major infectious health hazard for health-care personnel. Data indicate that 5-10% of HBV-infected workers become chronically infected. Individuals with chronic HBV infection are at risk for chronic liver disease and are potentially infectious throughout their lifetimes. The risk of acquiring HBV infection from occupational exposures is dependent on the frequency of percutaneous and permucosal exposures to blood or body fluids containing blood. Depending on the tasks he or she performs, any health-care or public safety worker may be at high risk for HBV exposure. Workers performing tasks involving exposure to blood or blood-containing body fluids should be vaccinated. For public safety workers whose exposure to blood is infrequent, timely post-exposure prophylaxis may be considered, rather than routine pre-exposure vaccination.

Pre-vaccination serologic screening for prior infection is not currently indicated for persons being vaccinated because of occupational risk. Post-vaccination testing for antibody to hepatitis B surface antigen response is indicated for health-care workers who have blood or patient contact and are at ongoing risk for injuries with sharp instruments or needlesticks. Knowledge of antibody response aids in determining appropriate post-exposure prophylaxis.

Vaccine-induced antibodies to HBV decline gradually over time, and <60% of persons who initially respond to vaccination will lose detectable antibodies over 12 years (Stevens, et al. 1992). Studies among adults have demonstrated that, despite declining serum levels of antibody, vaccine-induced immunity continues to prevent clinical disease or detectable viremic HBV infection (Hadler, et al. 1992). Therefore, booster doses are not considered necessary. Periodic serologic testing to monitor antibody concentrations after completion of the three-dose series is currently not recommended. An obvious advantage of the ImmunoScore diagnostic panel would be that periodic monitoring of immune status could be correlated with any outbreak of disease in health-care workers. The availability of an ImmunoScore database can be exceedingly beneficial to the health-care workers in the care settings. The possible need for booster doses can be assessed as additional data become available.

Asymptomatic HBV infections have been detected in vaccinated individuals by means of serologic testing for antibody to hepatitis B core antigen. However, these infections also provide lasting immunity and are not associated with HBV-related chronic liver disease.

During community influenza outbreaks, admitting patients infected with influenza to hospitals has led to nosocomial transmission of the disease (Balkovic, et al. 1980), including transmission from staff to patients. Transmission of influenza among medical staff causes absenteeism and considerable disruption of health care. In addition, influenza outbreaks have caused morbidity and mortality in nursing homes. Because there is a recommendation for an annual influenza vaccination for health-care workers, it is unlikely that there would be an ImmunoScore diagnostic application for flu. The only potential here would be to correlate vaccination and protection in a multitude of individuals working in the health-care field.

Nosocomial measles transmission has been documented in the offices of private physicians, in emergency rooms, and on hospital wards. Although only 3.5% of all cases of measles reported during 1985-1989 occurred in medical settings, the risk for measles infection in medical personnel is estimated to be thirteen fold that for the general population (Watkins, et al. 1987; Atkinson, et al. 1991). Of the 3,659 measles cases reported during 1992-1995, the setting of transmission was known for 2,735; 385 (13.9%) of these cases occurred in medical settings (CDC, 1997). Although birth before 1957 is considered acceptable evidence of measles immunity, serologic studies of hospital workers indicate that 5-9% of those born before 1957 are not immune to measles (Smith, et al. 1990). During 1985-1992, 27% of all measles cases among health-care workers occurred in individuals born before 1957 (CDC, 1997). Measles vaccination is contraindicated in pregnant and immunocompromised individuals, including HIV-infected persons who have evidence of severe immunosuppression. Measles is also contraindicated following recent administration of immune globulin.

In recent years, a substantial proportion of reported mumps has occurred among unvaccinated adolescents and young adults on college campuses and in the workplace (Cochi, et al. 1988; Kaplan, et al. 1988). Outbreaks of mumps in highly vaccinated populations have been attributed to primary vaccine failure. During recent years, the overall incidence of mumps has fluctuated only minimally, but an increasing proportion of cases have been reported in individuals aged $\geq 15$ years (CDC, 1995). The CDC states that programs to ensure that medical personnel are immune to mumps are prudent and are easily liked with measles and rubella control programs (CDC, 1997). Mumps vaccination is contraindicated in pregnant and immunocompromised individuals.

Nosocomial rubella outbreaks involving both health-care workers and patients have been reported (Greaves, et al. 1982). Although vaccination has decreased the overall risk for rubella transmission in all age groups in the United States by $\geq 95\%$, the potential for transmission in hospital and similar settings persists because 10-15% of young adults are still susceptible (Bart, et al. 1985). Although not as infectious as measles, rubella can be transmitted effectively by both males and females. Transmission can occur whenever many susceptible individuals congregate in one place. Aggressive rubella vaccination of susceptible men and women with trivalent MMR vaccine can eliminate rubella transmission. Persons born before 1957 are generally considered to be immune to rubella. However, findings of seroepidemiologic studies indicate that about 6% of health-care workers (including individuals born before 1957) do not have detectable rubella antibody (CDC, 1997). Rubella vaccination is contraindicated in pregnant and immunocompromised individuals.

For all the infectious disease above covered by the MMR vaccination, an ImmunoScore diagnostic panel would be a useful application for health-care workers. These vaccines are available as monovalent or trivalent combinations. Lack of protective levels of antibody to any one of the components could be ameliorated by vaccination. In addition, health-care workers would again provide a large population to add an exemplary ImmunoScore database.

Nosocomial transmission of varicella zoster virus (VZV) is well recognized. Sources for nosocomial exposure of patients and staff have included patients, hospital staff, and visitors who are infected with either varicella (chickenpox) or zoster (shingles). In hospitals, airborne transmission of VZV from persons who had varicella or zoster to susceptible persons who had no direct contact with the index case patient has occurred. Although all susceptible hospitalized adults are at risk: pregnant women, premature infants born to susceptible mothers, infants born at <28 weeks' gestation or who weigh<1,000 grams regardless of maternal immune status, and immunocompromised persons of all ages (including persons who are undergoing immunosuppressive therapy, have malignant disease, or are immunodeficient).

Strategies for managing clusters of VZV infections in hospitals include:
- isolating patients who have varicella and other susceptible patients who are exposed to VZV;
- controlling air flow;
- using rapid serologic testing to determine susceptibility;
- furloughing exposed susceptible personnel or screening these persons daily for skin lesions, fever, and systemic symptoms; and
- temporarily reassigning varicella-susceptible personnel to locations remote from patient-care areas.

A reliable history of chickenpox is a valid measure of VZV immunity. Serologic tests have been used to assess the accuracy of reported histories of chickenpox. Among adults, 97-99% of individuals with a positive history of varicella are seropositive. In addition, the majority of adults with negative or uncertain histories are seropositive (range 71-93%). Persons who do not have a history of varicella, or whose history is uncertain can be considered susceptible, and can be tested serologically by ImmunoScore diagnostic methodology to determine their immune status. In health-care institutions, serologic screening of personnel who have a negative or uncertain history of varicella is likely to be cost effective (CDC, 1996).

If susceptible health-care workers are exposed to varicella, they are potentially infective 10-21 days after exposure. They must be furloughed during this period, usually at substantial cost. Administration of varicella zoster immune globulin (VZIG) after exposure can be costly. VZIG does not necessarily prevent varicella, and may prolong the incubation period by a week or more, thus extending the time during which personnel should not work.

Varicella virus vaccine protects approximately 70-90% of recipients against infection and 95% of recipients against severe disease for at least 7-10 years after vaccination. Significant protection is long-lasting. Breakthrough infections have occurred among vaccinees after exposure to natural varicella virus. Estimates of vaccine efficacy and persistence in vaccinees are based on research conducted before widespread use of varicella vaccine began to influence the prevalence of natural VZV infection. Therefore, the extent to which boosting from exposure to natural virus increases the protection provided by vaccination remains unclear. Whether longer term immunity may wane as the circulation of natural VZV decreases also is unknown.

The CDC recommends that vaccination should be considered for unvaccinated health-care workers who lack documented immunity if they are exposed to varicella. However, because the effectiveness of post-exposure vaccination is unknown, individuals vaccinated after an exposure should be managed in the manner recommended for unvaccinated persons. Here, again, the ImmunoScore diagnostic assay for varicella would be a valuable assessment tool prior to initiation of vaccination of individuals uncertain of their immune status or disease history.

In the United States, Bacille Calmette-Guérin (BCG) vaccine has not been recommended for general uses because the population risk for infection with *Mycobacterium tuberculosis* (TB) is low and the protective efficacy of BCG vaccine uncertain. The immune response to BCG vaccine also interferes with the use of the tuberculin skin test to detect *M. tuberculosis* infection (CDC, 1996). TB prevention and control efforts are focused on interrupting transmission from patients who have active infectious TB, skin testing those at high risk for TB, and administering preventive therapy when appropriate. However, in certain situations, BCG vaccination may contribute to the prevention and control of TB when other strategies are inadequate.

The fundamental strategies for the prevention and control of TB include:
  Early detection and effective treatment of patients with active communicable TB.
  Preventative therapy for infected persons. Identifying and treating persons who are infected with *M. tuberculosis* can prevent the progression of latent infection to active infectious disease.
  Prevention of institutional transmission. The transmission of TB is a recognized risk in health-care settings and is of particular concern in settings where HIV infected individuals work, volunteer, visit, or receive care. Effective TB infection-control programs should be implemented in health-care facilities and other institutional settings (e.g. shelters for homeless persons and correctional facilities).

In a few geographic areas of the United States, increased risks for TB transmission in health-care facilities (compared with risks observed in health-care facilities in other parts of the United States) occur together with an elevated prevalence among TB patients of *M. tuberculosis* strains that are resistant to both isoniazid and rifampin. Even in such situations, comprehensive application of infection control practices should be the primary strategy used to protect health-care workers from infection with *M. tuberculosis*. BCG vaccination of health-care workers should not be used as a primary TB control strategy because:
  the protective efficacy of the vaccine in health-care workers is uncertain;
  even if BCG vaccination is effective for a particular health-care worker, other persons in the health-care facility (e.g. patients, visitors and other health-care workers) are not protected against possible exposure to and infection with drug-resistant strains of *M. tuberculosis*; and
  BCG vaccination may complicate preventive therapy because of difficulties in distinguishing tuberculin skin test responses caused by infection with *M. tuberculosis* from those caused by the immune response to vaccination.

Hepatitis C virus (HCV) is the etiologic agent in most cases of parenterally transmitted non-A, non-B hepatitis in the United States. CDC estimates that the annual number of newly acquired HCV infections has ranged from 180,000 in 1984 to 28,000 in 1995. Of these, and estimated 2-4% occurred among health-care personnel who were occupationally exposed to bleed. At least 85% of individuals who contract HCV infection become chronically infected, and chronic hepatitis develops in an average of 70% of all HCV-infected individuals (Shakil, et al. 1995).

Serologic enzyme immunoassays licensed for the detection of antibody to HVD have evolved since their introduction in 1990 and a third version is now available which detects anti-HCV in >95% of patients with HCV infection. These assays do not detect anti-HCV in all infected individuals and do not distinguish among acute, chronic, or resolved infection. In 80-90% of HCV-infected individuals, seroconversion occurs an average of 10-12 weeks after exposure to HCV. These screening assays also yield a high proportion (up to 50%) of falsely positive tests when they are used in populations with a low prevalence of HCV infection (CDC, 1991).

Based on seroepidemiological surveys, the core and the non-structural 3 (NS3) proteins of hepatitis C virus are thought to be two of the most immunogenic proteins of HCV (Chiba, et al. 1991). A majority of HCV-infected immunocompetent individuals develop HCV core antibodies (Chen, et al. 1995). However, there seems to be low or no HCV antibodies early in acute infection (Chen, et al. 1995). The major IgG subclasses of antibodies to HCV core are IgG1 and IgG3 (Sällberg, et al. 1992).

In the absence of effective prophylaxis, individuals who have been exposed to HCV may benefit from knowing their infection status so they can seek evaluation for chronic liver disease and treatment. IG or antiviral agents are not recommended for post-exposure prophylaxis of hepatitis C. No vaccine against hepatitis C is available. Health-care institutions should consider implementing policies and procedures to monitor health-care workers for HCV infection after percutaneous or permucosal exposures to blood. The CDC recommends, at minimum, that such policies should include:
  For the source, baseline serologic testing for anti-HCV;
  For the person exposed to an anti-HCV positive source, baseline and follow-up (e.g. six months) serologic testing for anti-HCV and alanine aminotransferase activity;
  Confirmation by supplemental anti-HCV testing of all anti-HCV results reported as repeatedly reactive by EIA;
  Education of health-care workers about the risk for and prevention of occupational transmission of all blood borne pathogens, including hepatitis C, using up-to-date and accurate information (CDC, 1997).

There are other diseases for which immunizations of health-care workers are or may be indicated. Diseases are included in this category for one of the following reasons:
  Nosocomial transmission occurs, but health-care workers are not at increased risk as a result of occupational exposure (e.g. hepatitis A),
  Occupational risk may be high, but protection via active or passive immunization is not available (i.e. pertussis), or
  Vaccines are available but are not routinely recommended for all health-care workers or are recommended only in certain situations (i.e. vaccinia and meningococcal vaccines).

Occupational exposure generally does not increase health-care worker's risk for hepatitis A virus (HAV) infection. When proper infection control practices are followed, nosocomial HAV transmission is rare. Outbreaks caused by transmission of HAV to neonatal intensive care unit staff by infants infected through transfused blood have occasionally been observed (Rosenblum, et al. 1991). Transmission of HAV from adult patients to health-care workers is usually associated with fecal incontinence in the patients. However, most patients hospitalized with hepatitis A are admitted after onset of jaundice, when they are beyond the point of peak infectivity (Goodman, 1985). Serologic surveys among many types of health-care workers have not identified an elevated prevalence of HAV infection compared with other occupational populations.

Two specific prophylactic measures are available for protection against hepatitis A—administration of immune globulin (IG) and hepatitis A vaccine. When administered within two weeks after an exposure, IG is >85% effective in preventing hepatitis. There are two inactivated hepatitis A vaccines currently available in the United States. The duration of clinical protection has not yet been established. An ImmunoScore database built from surveillance of health-care workers can thus be instrumental in the determination of the duration of clinical protection of each of these vaccines.

Nosocomial transmission of *Neisseria meningitidis* is uncommon. In rare instances, direct contact with respiratory secretions of infected persons (e.g. during mouth to mouth resuscitation) has resulted in transmission from patients with meningococcemia or meningococcal meningitis to health-care workers. Although meningococcal respiratory infections are rare, health-care workers may be at increased risk for meningococcal infection if exposed to *N. meningitidis*-infected patients with active productive coughs. Health-care workers can decrease the risk for infection by adhering to precautions to prevent exposure to respiratory droplets.

Post-exposure prophylaxis is advised for individuals who have had intensive, unprotected contact with infected patients (e.g. intubating, resuscitating, or closely examining the oropharynx of patients). Antimicrobial prophylaxis can eradicate carriage of *N. Meningitidis* and prevent infections in individuals who have unprotected exposure to patients with meningococcal infections.

Although useful for controlling outbreaks of serogroup C meningococcal disease, administration of quadrivalent A, C, Y, W-135 meningococcal polysaccharide vaccines is of little benefit for post-exposure prophylaxis. The serogroups A and C vaccines, which have demonstrated estimated efficacies of 85-100% in older children and adults, are useful for control of epidemics. The decision to implement mass vaccination to prevent serogroup C meningococcal disease depends on whether the occurrence of more than one case of the disease represents an outbreak or an unusual clustering of endemic meningococcal disease. Surveillance for serogroup C disease and calculation of attack rates can be used to identify outbreaks and determine whether use of meningococcal vaccine is warranted. The meningococcal diagnostic panel of the ImmunoScore diagnostic application would be a useful tool to monitor health-care workers, and to also identify health-care workers at increased risk for meningococcal disease.

Pertussis is highly contagious. Secondary attack rates among susceptible household contacts exceed 80% (Mortimer, 1990). Transmission occurs by direct contact with respiratory secretions or large aerosol droplets from the respiratory tract of infected persons. The incubation period is generally 7-10 days. The period of communicability starts with the onset of the catarrhal stage and extends into the paroxysmal stage. Vaccinated adolescents and adults, whose immunity wanes 5-10 years after the last dose of vaccine (usually administered at age 4-6 years), are an important source of pertussis infection for susceptible infants. The disease can be transmitted from adult patients to close contacts, especially unvaccinated children. Such transmission may occur in households and hospitals.

Transmission of pertussis in hospital settings has been documented in several reports (Christie, et al. 1995; Kurt, et al. 1972; Valenti, et al. 1980). Transmission has occurred from a hospital visitor, from hospital staff to patients, and from patients to hospital staff. Although of limited size, documented outbreaks were costly and disruptive. In each outbreak, larger numbers of staff were evaluated for cough illness and required nasopharyngeal cultures, serologic tests, prophylactic antibiotics, and exclusion from work.

During outbreaks that occur in hospitals, the risk for contracting pertussis among patients or staff is often difficult to quantify because exposure is not well defined. Serologic studies conducted among hospital staff during two outbreaks indicate that exposure to pertussis is much more frequent than the attack rates of clinical disease indicate (Mortimer, 1990; Christie, et al. 1995; Kurt, et al. 1972; Valenti, et al. 1980). Seroprevalence of pertussis agglutinating antibodies correlated with the degree of patient contact and was highest among pediatric house staff (82%) and ward nurses (71%), and lowest among nurses with administrative responsibilities (35%) (Linnemann, et al. 1975).

Prevention of pertussis transmission in health-care settings involves diagnosis and early treatment of clinical cases, respiratory isolation of infectious patients who are hospitalized, exclusion from work of staff who are infectious, and post-exposure prophylaxis. Early diagnosis of pertussis, before secondary transmission occurs, is difficult because the disease is highly communicable during the catarrhal stage, when symptoms are still non-specific. Pertussis should be one of the differential diagnoses for any patient with an acute cough illness of >7 days duration without another apparent cause, particularly if characterized by paroxysms of coughing, post-tussive vomiting, whoop, or apnea (CDC, 1997). Health-care settings would be the ideal placement for ImmunoScore diagnostic assays for pertussis. Periodic measurement of the level of pertussis antibody in health-care workers could become part of routine screening to protect both the health-care worker and the patient populations.

One acellular pertussis vaccine is immunogenic in adults, but does not increase risk for adverse events when administered with tetanus and diphtheria (Td) toxoids, as compared with the administration of Td alone (Edwards, et al. 1993). If acellular pertussis vaccines are licensed for use in adults in the future, booster doses of adult formulations of acellular pertussis vaccines may be recommended to prevent the occurrence and spread of the disease in adults, including health-care workers. However, acellular pertussis vaccines combined with diphtheria and tetanus toxoids (DTaP) will need to be reformulated for use in adults, because all infant formulations contain more diphtheria toxoid than is recommended for individuals aged $\geq 7$ years. Recommendations regarding routine vaccination of adults will require additional studies (e.g. studies of the incidence, severity, and cost of pertussis among adults; studies of the efficacy and safety of adult formulations of DTaP; and studies of the effectiveness and cost-effectiveness of a strategy of adult vaccination, particularly for health-care workers). Even prior to such a recommendation by the ACIP, an ImmunoScore diagnostic assay for pertussis and the patient database can be a valuable tool for evaluating the need and the effectiveness of the vaccine application.

The incidence of typhoid fever declined steadily in the United States from 1900 to 1960 and has remained at a low level. During 1985-1994, the average number of cases reported annually was 441 (CDC, 1997). Nearly three quarters of patients infected with *Salmonella typhi* reported foreign travel during the 30 days before onset of symptoms. During this ten year period, several cases of laboratory acquired typhoid fever were reported among microbiology laboratory workers, only one of whom had been vaccinated. *S. typhi* and other enteric pathogens may be nosocomially transmitted via the hands of personnel who are infected. Generally, personal hygiene, particularly hand washing before and after all patient contacts, will minimize risk for transmitting enteric pathogens to patients. If health-care workers contract an acute diarrheal illness accompanied by fever, cramps, or bloody stools, they are likely to be excreting large numbers of infective organisms in their feces. Excluding these workers from care of patients until the illness has been evaluated and treated will prevent transmission. Workers in microbiology laboratories who frequently work with S. typhi should be vaccinated with any one of the three typhoid vaccines distributed in the United States. ImmunoScore diagnostics would be able to monitor the immune status of vaccinated individuals.

Smallpox is a highly contagious infection caused by the DNA virus variola, a member of the genus Orthopoxvirus. As recently as 1967, millions of smallpox cases per year were reported in Asia and Africa. Smallpox is spread most efficiently in droplets or aerosols from the oropharynx of infected individuals. Smallpox also can be spread by direct contact with infected lesions or with clothing or bed linens contaminated with the virus. After the incubation period of 7 to 17 days, the period of infectivity begins as an exanthema and rash characterized by maculae progressing to papules, vesicles, and pustules all in the same stage, developing first on the face and extremities. Patients remain contagious until the scabs have been shed. Most patients are sick enough during the prodromal period to be confined to bed by the time the rash develops. For this reason, household contacts, hospital workers, and other health-care professionals are the most likely individuals to develop secondary cases.

Case fatality rates of 30% or higher were observed during epidemics of smallpox. In the absence of pre-existing immunity, a favorable prognosis is less likely for infants, the elderly and pregnant women. Immunodeficiency, whether from immunosuppressive therapy or from human immunodeficiency virus (HIV) infection, is likely to have a negative impact on prognosis. Secondary bacterial infections of the skin, eyes and respiratory tract can develop and lead to septicemia and disseminated bacterial disease. Laryngeal lesions can lead to edema and airway obstruction. Encephalitis also may complicate smallpox.

After an extensive worldwide eradication program, the last non-laboratory case of smallpox occurred in 1977 in Somalia. In 1972, routine smallpox immunization was discontinued in the United States, and since 1983, vaccine production has been halted. Stockpiled vaccine has been used only for laboratory researchers working on orthopoxviruses. In recent years, there has been a concern that smallpox virus stocks may be in the hands of bioterrorists, and this concern has been heightened by the terrorist attack on the World Trade Center and the Pentagon on Sep. 11, 2001. Because most of the population is considered to be non-immune, there is debate as to whether smallpox immunization should be resumed.

Protection from infection was provided in the past by immunizing all children beginning at one year of age. An individual's concentration of neutralizing antibodies declines significantly over a 5 to 10 year period, and people who were immunized as infants or children before 1972 are unlikely to remain fully protected against disease, but protection against death afforded by antibodies and cell-mediated immunity may persist for 30 years (AAC, 2003).

There are current concerns regarding smallpox. Stocks of smallpox virus were retained in government run laboratories of the United States and former Soviet Union. There are reports that, before the dissolution of the Soviet Union, smallpox was being developed as a weapon of biological warfare (Henderson, et al. 1999). In addition, decreasing financial support for Russian government laboratories in recent years led to concern that the virus and the expertise to propagate a large amount of smallpox virus may have fallen into non-Russian hands. The rapidity with which smallpox could spread in the U.S. population has led to concern that this agent would present a particularly potent threat if it were to be used as an agent of bioterrorism (O'Toole, 1999; Meltzer, et al. 2001).

Immunization causes a local infection that is pruritic and uncomfortable. Fever, malaise, and regional lymphadenitis often occur about a week after immunization. The site of immunization develops a papule that matures into a pustule and then a scab that separates by about the third week after immunization. Re-immunization typically causes a milder lesion that develops more quickly. Occasionally, satellite or distant pustules develop when a vaccine recipient scratches the pustule and auto inoculates the virus at another site.

A major reason not to initiate universal immunization in the absence of actual cases of smallpox besides the limited availability of vaccine is the risk of serious complications of immunization. Severe complications of immunization include death, post-vaccinal encephalitis, progressive vaccinia, eczema vaccinatum, generalized rash, and accidental inoculation to the face, eye or other sites. Smallpox vaccine has been known for decades to produce significant adverse effects, especially with immunocompromised individuals. In patients with chronic skin conditions, smallpox vaccine can cause a severe, sometimes fatal dermatologic involvement termed eczema vaccinatum. The list of conditions that place patients at risk of eczema vaccinatum is long and includes most disorders that disrupt epidermal integrity. Atopic dermatitis is the most common disorder associated with severe eczema vaccinatum, and people with this disorder may be susceptible even if the skin disorder is in remission. Even unimmunized susceptible individuals can have such reactions if the virus spreads to them from those who have been immunized.

Smallpox vaccine is not recommended for people with eczema or other exfoliative skin disorders, for pregnant women, or for people with immunodeficiencies, whether primary or secondary. Atopic dermatitis, a genetically based immune abnormality, occurs within the first five years of life and affects 15% of the population.

Before its discontinuation, universal smallpox immunization was recommended in the United States for children 1 to 2 years of age. Re-immunization was recommended every 5 years and annually for people working in endemic areas. The current recommendation for those individuals at high risk because of occupational exposure is immunization every 3 years. People with multiple immunizations during childhood probably have longer-lasting immunity, but the degree of protection for those immunized before 1972 is unknown.

In the event of a known bioterrorist release of the smallpox virus, vaccine would be administered to exposed individuals. If vaccine is given within 3 to 4 days of exposure, immunity can develop before the disease occurs, and this would be expected to prevent or ameliorated the severity of the disease. Post-exposure immunization is recommended for persons who have had face-to-face, household contact with or have been in proximity to a person who has active smallpox skin lesions, persons who have been involved in the care of such an individual, and persons exposed in any way to laboratory specimens or bedding from an infected patient. Such a plan (referred to as a "ring vaccination" program) would allow the most effective use of available stocks of vaccine while exposing a minimal number of individuals to the risks of immunization.

Variola virus as an agent of bioterrorism has been discussed widely, but the difficulty of introducing the virus into the population and the limited effects of doing so have persuaded most public health authorities that the chances of a smallpox outbreak are very small. Because of the known adverse effects of smallpox immunization, the large number of immunocompromised people in the population, and the currently limited supplies of vaccine and IG, all stockpiled vaccine is considered an investigational agent and is available for use by public health authorities only.

The major proposed strategies for smallpox immunization in the face of a bioterrorism threat include mass immunization, voluntary immunization, and ring vaccination or "surveillance and containment." The proponents of mass immunization claim it to be the strategy that would most effectively prevent spread of disease. They also postulate that a bioterrorist would be unlikely to introduce variola into a well immunized population. Those who favor voluntary immunization feel that each individual should be allowed to weigh the pros and cons of immunization and act according to his or her own analysis (Bicknell, 2002). Unfortunately, much of the population is not familiar with the problems and complications of vaccinia immunization. The ring vaccination strategy is supported by the American Academy of Pediatrics (AAP), which considers this option to be the best approach at present (AAP, 2002).

The AAP supports the current CDC recommendation of the strategy known as ring vaccination, also referred to as surveillance and containment. Using this approach, if smallpox were introduced in an act of terrorism, infected patients would be isolated. Contacts of infected individuals as well as their contacts would then be identified and immunized by specially trained teams of health-care professionals. This strategy can control a localized outbreak with minimal exposure of vulnerable populations to the complications of immunization. The ring strategy is based on the knowledge that vaccination can prevent or ameliorate disease severity if given within 3 to 4 days of initial exposure and can decrease symptoms if given within the first week of exposure.

Immunizing and monitoring a ring of people around each infected individual and his or her contacts would help protect those at the greatest risk of contracting the disease and form a buffer of immune individuals to prevent the spread of disease. The AAP supports the opinion of the ACIP that it is desirable to have patients with smallpox cared for by persons who have been immunized. Thus, national, state-based, and local teams of health-care professionals who already have been immunized will be trained in all aspects of smallpox investigation and care and will be available to go immediately to the site of a suspected or proven smallpox case. With teams available in every state, approximately 10,000 to 20,000 carefully screened individuals will receive smallpox vaccination. For health-care workers, it will be necessary to monitor their immune status with regards to smallpox immunizations. This can be a function of the ImmunoScore diagnostic panel. Health-care professionals and military personnel can provide a sound basis for the accumulated database regarding the persistence of immunity to smallpox infection.

Health-care workers are not at greater risk for diphtheria, tetanus, and pneumococcal disease than the general population. ACIP recommends that all adults be protected against diphtheria and tetanus, and recommends pneumococcal vaccination of all persons aged $\geq 65$ years and of younger individuals who have certain medical conditions. Thus, in exemplary embodiments of the present invention, an ImmunoScore diagnostic evaluation can be used to assess an individual health-care worker's immune status with regards to these, or other, as may be appropriate, infectious diseases.

14.1. Immunocompromised Health-Care Workers

A physician must assess the degree to which an individual health-care worker is immunocompromised. Severe immunosuppression can be the result of congenital immunodeficiency; HIV infection; leukemia; lymphoma; generalized malignancy; or therapy with alkylating reagents, antimetabolites, radiation, or large amounts of corticosteroids. All persons affected by some of these conditions are severely immunocompromised, whereas for other conditions (e.g. HIV infection), disease progression or treatment stage determines the degree of immunocompromise. A determination that a health-care worker is severely immunocompromised ultimately must be made by his or her physician. Immunocompromised health-care workers and their physicians should consider the risk for exposure to a vaccine-preventable disease together with the risks and benefits of vaccination.

The exact amount of systemically absorbed corticosteroids and the duration of administration needed to suppress the immune system of an otherwise healthy individual are not well defined. Most experts agree that steroid therapy usually does not contraindicate administration of live virus vaccines such as MMR and its component vaccines when therapy is a) short term ($\leq 14$ days) low to moderate dose; b) low to moderate dose administered daily or on alternate days; c) long-term alternate day treatment with short-acting preparations; d) maintenance physiologic doses (replacement therapy); or e) administered topically (skin or eyes) by aerosol, or by intra-articular, bursal, or tendon injection. Although the immunosuppressive effects of steroid treatment vary, many clinicians consider a steroid dose that is equivalent to or greater than a prednisone dose of 20 mg per day sufficiently immunosuppressive to cause concern about the safety of administering live virus vaccines. Persons who have received systemic corticosteroids in excess of this dose daily or on alternate days for an interval for $\geq 14$ days should avoid vaccination with MMR and its component vaccines for at least one month after cessation of steroid therapy. Individuals who have received prolonged or extensive topical, aerosol, or other local corticosteroid therapy should not receive MMR or its component vaccines, and varicella vaccine for at least one month after one month after cessation of therapy. Persons who have a disease that, in itself, suppresses the immune response and who are also receiving either systemic or locally administered corticosteroids generally should not receive MMR, its component vaccines, or varicella vaccine. The use of ImmunoScore diagnostic analyses and database for immunocompromised health-care workers can be used for assessing these workers and in monitoring them following corticosteroid therapy for levels of immune response.

In general, symptomatic HIV-infected individuals have suboptimal immunologic responses to vaccines. The response to both live and killed antigens may decrease as the disease progresses (Vardinon, et al. 1990). Administration of higher doses of vaccine or more frequent boosters to HIV-infected persons may be considered. However, because neither the initial immune response to higher doses of vaccine nor the persistence of antibody in HIV-infected patients has been systematically evaluated, recommendations cannot be made at this time (CDC, 1997).

Limited studies of MMR immunization in both asymptomatic and symptomatic HIV-infected patients who did not have evidence of severe immunosuppression documented no serious or unusual adverse events after vaccination (Onorato, et al. 1992). HIV-infected persons are at increased risk for severe complications if infected with measles. Therefore, MMR vaccine is recommended for all asymptomatic HIV-infected health-care workers who do not have evidence of severe immunosuppression. Administration of MMR to HIV-infected health-care professionals who are asymptomatic but do not have evidence of severe immunosuppression because of a) a case of progressive measles pneumonia has been reported after administration of MMR vaccine to a person with AIDS and severe immunosuppression, b) the incidence of measles in the United States is currently very low, c) vaccination-related morbidity has been reported in severely immunocompromised persons who were not HIV-infected, and d) a diminished antibody response to measles vaccination occurs among severely immunocompromised HIV-infected individuals.

Recommendations of the CDC (1997)

Recommendations for administration of vaccines and other immunobiological agents to health-care professionals are organized in three broad disease categories:
- those for which active immunization is strongly recommended because of special risks for health-care workers (i.e. hepatitis B, influenza, measles, mumps, rubella, and varicella);
- those for which active and/or passive immunizations of health-care workers may be indicated in certain circumstances (i.e. tuberculosis, hepatitis A meningococcal disease, typhoid fever, and vaccinia) or in the future (i.e. pertussis); and
- those for which the immunization of all adults is recommended (i.e. tetanus, diphtheria, and pneumococcal disease).

Immunization is strongly recommended for hepatitis B, influenza, measles, mumps, rubella, and varicella. In exemplary embodiments of the present invention, an ImmunoScore diagnostic panel can be in place in health-care settings for the routine monitoring of health-care professionals. Such an ImmunoScore database can combine information obtained from immune status of health-care workers with that of other segments of the population. The panel can be a valuable tool for the health-care industry and hopefully reduce the burden of vaccine-preventable nosocomial illnesses. There are other diseases for which vaccination should be considered; those include tuberculosis (pretty much as a last resort), hepatitis A, pertussis, meningococcal disease, typhoid fever, and vaccinia. Other vaccine-preventable diseases for which protection should be maintained include tetanus, diphtheria, and pneumococcal disease. Levels of antibodies can be monitored periodically by ImmunoScore diagnostic immune status assays. In addition, the overall immune health could be measured initially using the meningococcal diagnostic panel. A typhoid fever antibody assay could also be developed for health-care professionals. In addition, a hepatitis C antibody assay can also need to be established. There is as yet no vaccine for hepatitis C, but an HCV infection presents a risk of nosocomial infections.

TABLE 7

Recommended Immunizing Agents for Health Care Workers

| Vaccine | Schedule |
| --- | --- |
| Hepatitis B | 3 doses |
| Influenza | Annual |
| Measles, Mumps, Rubella | 1 dose |
| Varicella | 2 doses |
| Tuberculosis (BCG) | 1 does (in high risk settings) |
| Hepatitis A | 2 doses |
| Meningococcal disease | 1 dose |

TABLE 7-continued

Recommended Immunizing Agents for Health Care Workers

| Vaccine | Schedule |
| --- | --- |
| Pertussis | 1 dose (needs reformulation) |
| Typhoid | 1 dose, boost 2 yrs. |
| Vaccinia | 1 dose, boost 10 yrs. |
| Tetanus, diphtheria (Td) | 1 dose, boost 10 yrs. |
| Pneumococcal polysaccharide | 1 dose, boost > 5 yrs. in high risk settings |

The only analyte specific for health care workers is tuberculosis. There is no easily measurable correlate of immunity to tuberculosis. Delayed type hypersensitivity, as measured by the tuberculin test, is not a measure of resistance, because both reactivation and superinfection may occur in tuberculin-positive subjects (Plotkin, 2001). Although current experimental vaccinology is investigating the potential of proteins and capsule of *Mycobacterium tuberculosis*, the majority opinion is still that antibodies are irrelevant to protection (McAdam, 1997). Thus, in exemplary embodiments of the present invention, ImmunoScore diagnostic analysis can include measurement of as yet undetermined cellular components important to controlling TB infection.

15. ImmunoScore Analyses and Bioterrorism

Before the anthrax attacks of 2001, the threat of bioterrorism was based primarily on the events surrounding the sarin nerve agent attacks in Japan in 1995 and the biological weapons production and stockpiling programs of the former Soviet Union and Iraq. Now that terrorists have used the United States Postal Service to disseminate anthrax spores contained in letters, the threat of lethal bioterrorism has become a reality (Darling, et al. 2002).

In June of 1999, the Centers for Disease Control and Prevention (CDC) and a multidisciplinary panel of experts formed a strategic workgroup to outline steps to strengthen the US public health infrastructure and health-care capacity to protect against bioterrorism (CDC, 2000). They stated that the public health infrastructure must be prepared to prevent illness and injury that would result from biological and chemical terrorism, especially a covert terrorist attack.

In the past, most planning for emergency response to terrorism has been concerned with overt attacks (e.g. bombings). Chemical terrorism acts are likely to be overt because the effects of chemical agents absorbed through inhalation or by adsorption through the skin or mucous membranes are usually immediate and obvious. Such attacks elicit immediate response from police, fire, and EMS personnel.

In contrast, attacks with biological agents are more likely to be covert. They present different challenges and require an additional dimension of emergency planning that involves the public health infrastructure. Covert dissemination of a biological agent in a public place will not have an immediate impact because of the delay between exposure and the onset of illness. Consequently, the first casualties of a covert attack probably will be identified by physicians or other primary health-care providers.

Potential biological and chemical agents are numerous, and the public health infrastructure must be equipped to quickly resolve crises that would arise from a biological or chemical attack. However, to best protect the public, the preparedness efforts must be focused on agents that might have the greatest impact on U.S. health and security, especially agents that are highly contagious or that can be engineered for widespread dissemination via small-particle aerosols. Early detection requires increased biological and chemical terrorism awareness among front-line health-care providers because they are in the best position to report suspicious illnesses and injuries. Also, early detection will require improved communication systems between those providers and public health officials. In addition, state and local health-care agencies must have enhanced capacity to investigate unusual events and unexplained illnesses, and diagnostic laboratories must be equipped to identify biological and chemical agents that are rarely seen in the United States. Fundamental to these efforts is comprehensive, integrated training designed to ensure core competency in public health preparedness and the highest levels of scientific expertise among local, state, and federal partners. ImmunoScore diagnostic analyses can be an integral part of preparation of events of bioterrorism.

The CDC has outlined the following steps for preparation for terrorist attacks using biological agents:
Enhance epidemiologic capacity to detect and respond to biological attacks.
Supply diagnostic reagents to state and local public health agencies.
Establish communication programs to ensure delivery of accurate information.
Enhance bioterrorism-related education and training for health-care professionals.
Prepare educational materials that will inform and reassure the public during and after a biological attack.
Stockpile appropriate vaccines and drugs.
Establish molecular surveillance for microbial strains, including unusual or drug-resistant strains.
Support the development of diagnostic tests.
Encourage research on antiviral drugs and vaccines.

The planning group assembled by the CDC categorized biological agents according to their perceived level of threat. The first of these are Category A agents. These high-priority agents include organisms that pose a risk to national security because they:
can be easily disseminated or transmitted person-to-person;
cause high mortality, with potential for major public health impact;
might cause public panic and social disruption; and
require special action for public health preparedness.
Category A agents include:
Variola major (smallpox)
*Bacillus anthracis* (anthrax)
*Yersinia pestis* (plague)
*Clostridium botulinum* toxin (botulism)
*Francisella tularensis* (tularaemia)
filoviruses:
  Ebola hemorrhagic fever
  Marburg hemorrhagic fever
arenaviruses:
  Lassa (Lassa fever)
  Junin (Argentine hemorrhagic fever) and related viruses It would be difficult to create a more "perfect" biological weapon than *Bacillus anthracis*, the causative agent of anthrax. Infection, usually by spores, is introduced through scratches or abrasions of the skin, inhalation, eating insufficiently cooked infected meat, or by the bites of flies. Anthrax spores may remain stable for decades or can be produced, weaponized, and delivered as a wet or dry aerosol cloud.

The bioterrorism related inhalational anthrax cases that occurred during the fall of 2001 presented in a predictable manner with a few exceptions. Nearly all patients initially developed fatigue and malaise followed by minimal or non-productive cough. They soon developed fever, chills, nausea, vomiting, and drenching sweats. This progressed to chest pain and dyspnea.

*Bacillus anthracis* is detectable by Gram stain of the blood, blood culture on routine media, and by ELISA, but often not until later in the course of the illness. Approximately 50% of the cases are accompanied by hemorrhagic meningitis, and therefore organisms may also be identified in cerebrospinal fluid (Bush, et al. 2001). Only vegetative encapsulated bacilli are present during infection. Spores are not found within the body unless the bacilli are exposed to ambient air. Toxin production parallels the appearance of bacilli in the blood, and tests are available to rapidly detect the toxin. With the appearance of symptoms, the white blood cell count becomes elevated and remains so until death. The primary cause of morbidity and mortality is believed to be the extreme toxin load generated by the organism.

More than 30,000 patients have been taking ciprofloxacin or doxycycline as post-exposure prophylaxis since the bioterrorism incidents of October 2001 (CDC, 2001). If confirmed that anthrax has been used as a biological weapon, antibiotics should be continued for at least 60 days in all exposed individuals, and patients should be closely followed after antibiotics are discontinued. Military doctrine also requires that service members begin active immunization with anthrax vaccine while taking post-exposure antibiotics. Anthrax vaccine is not currently available for use by the general public. In response to the bioterrorism events of 2001, however, CDC offered anthrax vaccine as part of an investigational new drug (IND) protocol. This was necessary because anthrax vaccine was never licensed for use as a post-exposure treatment (Michigan Dept. Public Health, 1978): The CDC had no recommendation as to whether patients should or should not receive the vaccine; this led to considerable confusion and consternation among the public. Consequently, few patients chose to receive the vaccine.

On discontinuation of antibiotics, patients should be closely observed. If clinical signs of anthrax develop, empiric therapy for anthrax is indicated, pending etiologic diagnosis. Optimally, patients should have medical care available from a fixed facility with intensive care capabilities and readily available access to infectious disease consultants. ImmunoScore diagnostic assays could become integral to diagnosis and treatment of anthrax patients. The database information would be valuable at helping to determine the serological correlate of protection for anthrax vaccine.

Smallpox is caused by the Variola virus. There are no non-human reservoirs for smallpox and no human carriers. The disease has survived throughout history through continual person-to-person transmission. Smallpox was probably responsible for more than 100 million deaths during the $20^{th}$ century alone.

Smallpox is perhaps the most feared of potential biological warfare agents. Researchers estimate that vaccinated individuals retain immunity for approximately 10 years, although in selected populations this may continue past 20 years (Henderson and Moss, 1999). Therefore, most of the population of the United States is probably susceptible to smallpox. Vaccines are in short supply; however, the Federal government has entered into contracts to rectify this. Finally, because few physicians are familiar with the clinical presentation of smallpox, recognizing an outbreak may be problematic.

The smallpox virion is readily transmitted from person to person by way of respiratory particles. Virions can also remain viable on fomites for up to one week. The virus initially replicates in respiratory tract epithelial cells then migrates to regional lymph nodes. From there, a massive asymptomatic viremia ensues three to four days later and may result in focal infections involving lymphoid tissues, skin, intestines, lungs, kidneys, or brain (Henderson, et al. 1999). Initial symptoms resemble an acute viral illness. Following an incubation period of approximately 12 days, a second viremia, lasting two to five days, results in high fevers, malaise, headache, backache, rigors, and vomiting. The patient may develop delirium. A rash typically develops within 48 hours, beginning in the mouth, and heralds the onset of viral shedding. The rash rapidly spreads to the hands and forearms followed by the legs and trunk. The rash becomes distinctive when the lesions become pustular. Viral shedding and secondary infection cases may occur from the onset of rash until scabs have separated (Henderson, et al. 1999). Death usually occurs late in the first week or during the second week of the illness and is caused by the toxemia induced by the overwhelming viremia.

During the vesicular stage, the rash may resemble chickenpox. There are two important distinctions, however. First, the rash of smallpox develops synchronously, in contrast to the asynchronous development observed with varicella. Second, the rash of smallpox is concentrated on the face and extremities, as opposed to on the trunk as occurs in chickenpox (Henderson, 1999)

Initial diagnosis will likely be clinical, based on the characteristic rash. Diseases with similar skin manifestations must be considered in the differential diagnosis, including cutaneous lues (syphilis), meningococcemia, acute leukemia, or drug toxicity. Laboratory confirmation is extremely important, as a single case of smallpox must be treated as an international public health emergency. Smallpox can be confirmed through clinical presentation and identification of the virion particles on electron microscopy of vesicular fluid, although this only confirms presence of an orthopox virus. Further classification of the orthopox virus requires cell culture or growth on chorioallantoic egg membrane. ImmunoScore diagnostic analysis can be used to identify levels of smallpox antibody in sera of individuals. In addition, ImmunoScore database analyses could be performed on larger numbers of individuals to track the longevity of serum antibody to smallpox.

*Yersinia pestis*, a gram-negative *bacillus*, has tormented mankind throughout history. The Byzantine Empire recorded a sixth century pandemic, and the Black Death killed millions of people throughout 14$^{th}$ century Europe. The most recent pandemic originated in China and spread worldwide at the turn of the 20$^{th}$ century.

Plague is a zoonosis with a rodent host and a flea vector. The vector is not essential, however, and direct host-to-host transmission can occur by way of an infectious aerosol. A bite from an infected flea causes an infection in the lymphatic system leading to the bubonic form of the disease. Inhalation of aerosolized *bacillus*, preferred for deliberate dissemination, results in a primary pulmonary infection, known as pneumonic plague. The disease is rapidly fatal in the absence of prompt antibiotic treatment and may result in secondary contagion spread.

Modern efforts to weaponize *Y. pestis* were begun by the Japanese during World War II, but dissemination attempts were met with limited success. Infected fleas were bred by the billions and then released over northern Chinese cities that had not previously recorded plague casualties. Epidemics subsequently occurred and plague has remained endemic in the region since (Williams and Wallace, 1989). The United States dismissed plague as a potential weapon because of its persistence in the environment and friendly casualties after an attack. The former Soviet Union's extensive biological warfare program, however, reportedly included, dry, antibiotic-resistant, environmentally stable forms of the plague organism that could be disseminated as an aerosol (Alibek, 1999).

Skin penetration or direct ingestion of fewer than ten *Y. pestis* organisms can induce an infection in humans. The clinical course will vary substantially with the route of exposure. If plague were used as a biological weapon, the most likely exposure would be via inhalation. Pneumonic plague presents without buboes and may progress rapidly if vegetative organisms with previously developed antiphagocytic capsules and *Yersinia* outer-membrane protein (Yop) antigens have been inhaled as an aerosol (Poland, 1989). Most patients develop a productive cough with blood-tinged sputum within 24 hours of the onset of symptoms. This is an important diagnostic clue that should lead one to consider bioterrorism if many previously well patients present with this sign (Cavanaugh, et al. 1982).

Serum antibody to Fraction I capsular antigen, as measured by the passive hemagglutination (PHA) test, is correlated with resistance to *Y. pestis* infection in experimental animals. A comparable correlation between PHA titer and immunity probably occurs in humans (CDC, 1982). Plague vaccine that was protective against bubonic plague is no longer available. At any rate, it did not protect against aerosol infection in test models (Ehrenkranz and Meyer, 1955). A vaccine for pneumonic plague is under development, but that is not a guarantee of success. ImmunoScore diagnostic analysis should be a willing partner for analyses of any vaccines under development for combating plague.

The causative agent of tularemia, *Francisella tularensis*, is a small aerobic, non-motile, gram-negative, cocco-bacillus. Tularemia is a zoonotic disease that humans may acquire after skin or mucous membrane contact with tissues or body fluids of infected animals, or from bites of infected ticks, deerflies, or mosquitoes. Less commonly, inhalation of contaminated dusts or ingestion of contaminated foods or water may produce clinical disease. Respiratory exposure by aerosol would typically cause typhoidal or pneumonic tularemia. *F. tularensis* remains viable for weeks in water, soil, carcasses, hides, and for years in frozen meat. Resistant for months to temperatures of freezing and below, it is easily killed by heat and disinfectants (Evans and Friedlander, 1997).

*Francisella tularensis* was weaponized by the United States in the 1950s and 1960s during the U.S. offensive biowarfare program. Other countries are suspected to have weaponized this agent. This organism could potentially be stabilized for weaponization by an adversary and produced in a wet or dried form for delivery against U.S. forces or as a weapon of terror.

Onset of disease is usually acute and occurs after an incubation period that ranges from 1 to 21 days. In humans, as few as 10 to 50 organisms may cause disease if inhaled or injected intradermally (McCrumb, et al. 1957). All ages are susceptible, and recovery is generally followed by permanent immunity.

Typhoidal tularemia occurs mainly after inhalation of infectious aerosols, but can also occur after intradermal or gastrointestinal challenge. *F. tularensis* would most likely be delivered as an aerosol if used as a weapon and would primarily cause typhoidal tularemia that manifests as fever, prostration, and weight loss. Pneumonia may be severe and fulminant. Respiratory symptoms and a cough (productive or non-productive) may also be present. Case fatality rates may be greater than the 1-3% seen with appropriately treated natural disease. Case fatality rates are approximately 35% in untreated naturally acquired typhoidal cases (Darling, et al.

2002). Similar to many bacterial and viral diseases, early symptoms of exposure to *F. tularensis* are fairly generic and nonspecific, making differential diagnosis difficult.

At present, a live vaccine strain (LVS) tularemia vaccine is under IND status in a protocol at the U.S. Army Medical Research Institute of Infectious Diseases (USAMRIID), and is available only for at-risk U.S. military personnel. It is administered by scarification. Despite the increased risk of a bioterror threat felt after September 11, further vaccine development for tularemia remains slow. The projected date of a new licensed vaccine in the United States is not until 2009 (Nierengarten and Lutwick, 2002). There is some confusion over which arm of the immune system should be targeted. New lots of LVS produced in the United States show immunogenicity in human volunteers, producing both brisk cell-mediated and humoral immune responses. ImmunoScore diagnostic analysis can be applied in this setting to monitor the response to vaccines in clinical trials and follow the duration of the immune response. In addition, cellular components of the immune system can also be tracked, for example, through compilation of information added to an ImmunoScore database.

The viral hemorrhagic fevers are caused by a diverse group of RNA viruses in four separate families: Arenaviridae, Bunyaviridae, Filoviridae, and Flaviviridae. All have lipid envelopes, limited geographic ranges, are highly infectious by way of the aerosol route (except Dengue), and are believed to have animal reservoirs with arthropod vectors. Terrorist groups have attempted to weaponize agents from this class (Carus, 2001). Each disease is characterized by its own unique characteristics, but all have a final common pathway of diffuse hemorrhage and bleeding diathesis.

Yellow fever and dengue (Flaviviridae) are probably the archetypical diseases of this group, but are not considered significant biological warfare threat agents. Hantavirus (Bunyaviridae) is enzootic in rodents. West Africa's Lassa fever and Argentine, Bolivian, Brazilian, and Venezuelan hemorrhagic fevers (Arenaviridae) are also enzootic in rodents within their respective areas. The most publicized viral hemorrhagic fevers are the Ebola and Marburg (Filoviridae) viruses. These viruses produce grotesquely lethal diseases. The reservoir and natural transmission of Ebola and Marburg are unknown but they are readily transmissible by infected blood and tissue. Aerosols may be formed naturally when infectious body fluids are expelled or in the case of hantavirus when rodent feces and urine are resuspended by movement in the area. Laboratory cultures can yield sufficient concentrations of organisms to provide a credible terrorist weapon if disseminated as an aerosol (Darling, et al. 2002).

In a bioterrorism scenario, aerosol dissemination would result in many patients who shared a common location approximately three to eight days before presentation. Specific disease identification currently requires ELISA detection of antiviral IgM antibodies or direct culture of the viral agent from blood or tissue samples. During the clinical course of each of the diseases, hepatocellular enzymes are often elevated. Appropriate precautions should be observed in collection, handling, and processing of diagnostic samples, which should be sent to a Level D laboratory that currently exist only at the CDC or USAMRIID. The only likely application of ImmunoScore for hemorrhagic fever viruses would be in analyses of vaccines in development and the possible placement with the CDC or USAMRIID for diagnoses.

*Clostridium botulinum* is a gram-positive, spore-forming anaerobic *bacillus* found in soil around the world. Botulism is the syndrome caused by botulinum toxin produced by this bacterium. Cases have historically been categorized according to transmission as food-borne illness (from ingestion of the toxin in home-canned goods, poorly heated vegetables, or meats), wound botulism (secondary to soil-contaminated wounds, drug abuse, and C-section deliveries), and infantile illness (from ingestion of spores) (Arnon, et al. 2001).

*Botulinum* toxin is one of the most toxic substances known (Middlebrook and Franz, 1998). Seven distinct types of toxin exist, identified by antigenicity and referred to as types A-G. *Botulinum* toxin could be used to sabotage food supplies, although a more likely scenario would involve dissemination as an aerosol. During the Gulf War, Iraq produced 20,000 L of botulinum toxin, 12,000 L of which were used in field testing and to fill warheads (Zilinskas, 1997). Despite the efforts to produce an effective botulinum toxin weapon, most authorities agree that it is unlikely this toxin could ever be effectively deployed as a weapon of mass destruction. Aerosol delivery over a battlefield or a defined geographic region populated by civilians would require a precisely orchestrated effort. Large quantities of toxin would have to be delivered to the area at the optimum time because botulinum toxin quickly degrades in the environment. Even municipal water reservoirs are most likely safe from contamination by terrorist actions because literally ton quantities would be necessary because of the effects of dilution.

In the emergency setting the diagnosis of botulism intoxication will be clinical. An influx of patients with descending muscle paralysis and bulbar findings may herald a bioterrorist event or a natural outbreak of food-borne botulism. No routine laboratory tests will aid in the diagnosis. The toxin may be detected by assays of serum or gastric contents.

Three different antitoxin preparations are available in the United States. Antitoxin may prevent progression or shorten the course of the illness. A pentavalent toxoid of *Clostridium botulinum* toxin types A, B, C, D, and E is available as an IND product for pre-exposure prophylaxis. The currently recommended primary series of 0, 2, and 12 weeks, followed by a 1-year booster, induces immunity in greater than 90% of vaccinees after one year (Darling, et al. 2002). In exemplary embodiments, ImmunoScore analyses can be useful in examining response to the prophylactic vaccine as well as in following the duration of protection.

The Category B agents are the second highest priority and they include those agents that:
  are moderately easy to disseminate;
  cause moderate morbidity and low mortality; and
  require specific enhancements of CDC's diagnostic capacity and enhanced disease surveillance
  Category B agents include:
  *Coxiella burnetti* (Q fever)
  *Brucella* species
  *Burkholderia mallei*
  alphaviruses
  ricin toxin from *Ricinus communis* (castor beans)
  epsilon toxin of *Clostridium perfringens*
  *Staphylococcus* enterotoxin B
  *Salmonella* species
  *Shigella dysenteriae*
  *Escherichia coli* O157:H7
  *Vibrio cholerae*
  *Cryptosporidium parvum*
  The Category C agents are the third highest priority and they include emerging pathogens that could be engineered for mass dissemination in the future because of:
  availability;
  ease of production and dissemination; and
  potential for high morbidity and mortality and major health impact.

Category C agents include:
Nipah virus
hantaviruses
tickborne hemorrhagic fever viruses
tickborne encephalitis viruses
yellow fever
multidrug-resistant tuberculosis Preparedness for Category C agents requires ongoing research to improve disease detection, diagnosis, treatment, and prevention. Knowing in advance which newly emergent pathogens might be employed by terrorists is not possible; therefore linking bioterrorism preparedness efforts with ongoing disease surveillance and outbreak response activities is imperative. Although once considered unlikely, bioterrorism is now a reality in the United States since the anthrax cases began appearing in the fall of 2001. Intelligence sources indicate there are many countries and terrorist organizations that either possess biological weapons or are attempting to procure them. In the future it is likely that we will experience additional acts of bioterrorism. The CDC category A agents represent the greatest challenge because they have the potential to cause grave harm to the medical and public health systems of a given population. Thus, it is imperative that plans be developed now to deal with the consequences of an intentional release of any one or more of these pathogens (Darling, et al. 2002).

In exemplary embodiments of the present invention, an ImmunoScore diagnostic platform can be constructed so as to be able to grow with the needs of bioterror agent analyses. As new agents arise, diagnostic testing can available to test for immune responses to such agents as well as any vaccines that have been or will be developed.

16. Immunoscore Analyses for Infection and Chronic Disease

Chronic diseases take a huge toll. In the United States, more than 70% of all deaths are due to one or more chronic diseases, and more than 90 million people suffer daily. Even diseases not typically associated with pathogens may have underlying infectious causes. Of the eight million new cases of cancer in the world each year, one million are attributable to a known infectious agent.

The infectious origins of some chronic diseases have been known for decades. These include tuberculosis, syphilis, leprosy, and a number of parasitic diseases. Only more recently has it been realized that coronary artery disease, diabetes mellitus, cancer, and neurological disorders can have an infectious etiology, either as a cause or a co-factor.

Koch's postulates for distinguishing a pathogenic from an adventitious microbe were formulated in 1884. Koch stated for an organism to be pathogenic, it needed to fulfill the following criteria:
the organism is regularly found in the lesions of the disease
the organism can be isolated in pure culture on artificial media
inoculation of this culture produces a similar disease in experimental animals
the organism can be recovered from the lesions of these newly infected animals Koch's postulates are indeed relevant for acute infections, but there is a problem using them when considering chronic or long-term symptoms. With chronic illness, the requirements to culture microorganisms and demonstrate infectivity may have become obsolete. Microbes do not use one single strategy to disable their hosts for the long term. Several of the long-term strategies include:
induction of autoimmunity (Group A *Streptococcus* and heart valve disease)
persistent or repeated infection (HIV)
Non-obvious connection to chronic disease (*Helicobacter pylori* and gastric ulcers)

*Helicobacter pylori* is a gram-negative bacterium that causes a lifelong infection in over half of the world's human population. Without specific antimicrobial treatment, all infected individuals exhibit chronic gastric inflammation, and a small percentage will develop peptic ulcers and gastric adenocarcinoma or mucosa associated lymphoid tissue lymphoma. In response to infection, the host launches a vigorous immune response, including the mucosal infiltration of neutrophils, lymphocytes, and macrophages. This immune response is insufficient for clearance of the bacterium, suggesting the *H. pylori* is capable of evading host immune responses.

Infection with *H. pylori* induces apoptosis in macrophages, disrupts phagosome maturation, and disrupts cytokine signaling. Induction of macrophage apoptosis may represent a mechanism by which *H. pylori* usurps the host immune response to establish a chronic infection in humans.

Cardiovascular disease for all causes accounts for 29% of all deaths worldwide (behind only infectious and parasitic diseases). Deaths from cardiovascular disease are often premature, and millions of non-fatal events result in disability. Atherosclerosis, a major component of cardiovascular disease, has been considered a public health problem of industrialized countries.

Many individuals with atherosclerosis lack identifiable traditional risk factors (smoking, diet and exercise, hypercholesterolemia, hypertension, diabetes, and genetic factors). Atherogenic processes resemble many aspects of chronic inflammation, a response that may be promoted by microorganisms. Both *Chlamydia pneumoniae* and cytomegalovirus (CMV) are widely distributed, can infect blood vessel walls, and exhibit persistence, latency, and recurrence of infection.

There are several lines of evidence associating *C. pneumoniae* infection with atherosclerosis. These lines of evidence include:
seroepidemiologic studies
direct detection of bacterial components in atherosclerotic lesions
isolation of viable organisms from coronary and carotid atheromatous tissue
in vitro and animal experiments Cross-sectional and prospective studies have correlated seroprevalence with myocardial infarction, chronic coronary heart disease, or stroke.

More than 38 studies have reported a positive association between antibodies to *C. pneumoniae* and atherosclerotic disease. However, more than 50% of adults have been infected with *C. pneumoniae* at least once. The strongest evidence associating *C. pneumoniae* and atherosclerotic cardiovascular disease has been detection of bacterial components in atherosclerotic lesions. Historic findings do not, however, establish a causal role for *C. pneumoniae* in atherogenesis.

Studies have linked cytomegalovirus to three arterial diseases—primary atherosclerosis, post-angioplasty restenosis, and post-transplantation arteriosclerosis. Seroepidemiology has relied on single measures of viral IgG antibodies which only indicate previous exposure. Like *C. pneumoniae*, the worldwide ubiquity of lifelong, latent CMV infections could mask or falsely highlight causality.

Other microbes may be associated with cardiovascular disease. Several reports have suggested a relationship between chronic oral infections (e.g. periodontitis) and cardiovascular disease. These oral pathogens include *Porphyromonas gingivalis, Bacteroides forsythus, Campylobacter rectus, Fuso-*

*bacterium nucleatum, Treponema* spp., *Prevotella* spp., and *Streptococcus sanguis*. Raised *H. pylori* and Herpes Simplex Virus (HSV) antibody levels have also been associated with cardiovascular disease. Mycobacterial disease shares interesting connections to heart disease. Not only is tuberculosis the only microorganism to depend on cholesterol for its pathogenesis, but CDC maps for cardiovascular disease bear a striking similarity to those of State and regional tuberculosis cases. Present day markers suggested as indicators for heart disease susceptibility such as C-reactive protein (CRP), interleukin-6, and homocysteine are all similarly elevated in tuberculosis.

Group A streptococci are important human pathogens which cause a variety of pyrogenic infections that can be mild (e.g. pharyngitis, impetigo) to extremely severe (cellulites, necrotizing fasciitis, septicemia, pneumonia and streptococcal toxic shock syndrome). Molecular mimicry between streptococcal and heart components has been proposed as the triggering factor leading to autoimmunity in rheumatic heart disease.

Medically significant complications of Herpes Simplex Virus (HSV) are rare, but constitute a significant burden, given the high rates of HSV seropositivity in the population. HSV ocular infection is the leading cause of infectious corneal blindness in the United States. HSV-1 shedding is associated with reduced hospital survival in patients receiving assisted ventilation in intensive care units. Following productive infection by HSV at the site of inoculation, the virus spreads to and enters sensory neurons, where it establishes a latent infection. Latent infection forms a reservoir of virus for recurrent infection, disease, and transmission to other individuals. HSV-1 is usually associated with primary infections of the orofacial area and latent infections of the trigeminal ganglion. HSV-2 is usually associated with genital infections and latent infection in sacral ganglia.

Human papillomavirus (HPV) is one of the most common causes of sexually transmitted disease in both men and women world wide. HPV is associated with a variety of clinical conditions that range from innocuous lesions to cancer. Most HPV infections are benign—plantar and palmar warts, common warts, and flat warts. Strains that target the face make skin cancer more likely. Other strains that grow primarily in the lining of the mouth produce small elevated nodules that can develop into fatal squamous cell cancers. Cervical cancer is the third most common cancer in women in the United States. The magnitude of the association between HPV and cervical squamous cell carcinoma is higher than that for the association between smoking and lung cancer. HPV has been implicated in 99.7% of cervical squamous cell cancer cases world wide.

*Pseudomonas aeruginosa* is classified as an opportunistic pathogen, primarily infecting individuals who are immunocompromised, such as patients with cancer or AIDS. Cystic fibrosis (CF) almost always leads to chronic airway infection with *P. aeruginosa*. Despite advances in antibiotic therapy, after chronic infection, rapid deterioration in lung function occurs, increasing morbidity and mortality. Chronic *P. aeruginosa* airway infections remain the primary cause of morbidity and mortality in the CF population. Young children with CF may be infected as early as 6 months of age and *P. aeruginosa* becomes chronic in the first decade of life with pulmonary exacerbations increasing in frequency. A pulmonary infection with *P. aeruginosa* is characterized by a strong recruitment of neutrophils and significant inflammation in the lung parenchyma, which results in extensive damage to the lung tissue through the action of neutrophil enzymes and oxidants.

Tuberculosis has been declared a global emergency. Pulmonary TB is the second leading cause of mortality from infectious disease world wide, with 8 million new cases and 2 million deaths due to TB each year. There is an urgent need for rapid, cost-effective, and accurate methods for the diagnosis of TB. A serologic test is attractive because it would be relatively rapid and would not require sputum expectoration. Challenges for the development of effective serologic tests include:

the need to discriminate active disease from latent infection
to avoid cross-reactivity with *M. bovis* BCG or mycobacteria other than *M. tuberculosis*
to perform consistently with genetically and immunologically diverse populations Lyme disease is a troubling chronic infection. Infection of humans by *Borrelia burgodorferi* results in a spectrum of clinical illnesses. Earliest symptoms may include a typical or atypical rash, followed by flu-like illness. As the disease progresses, other neurologic and musculoskeletal symptoms and signs may develop. The pathophysiology of the chronic symptoms is not well understood, with hypotheses ranging from persisting infection to autoimmunity to a combination of the two. The diagnosis of chronic Lyme disease has been made difficult because of several factors. The multi-symptom complex consisting of fatigue, musculoskeletal pains and neurocognitive dysfunction cannot be distinguished from disorders that have been termed fibromyalgia, chronic fatigue and Gulf War syndrome. Laboratory testing has not been reliable, including cultures, antibody studies (ELISA, Western blot) and PCR-DNA tests.

Malaria, which had been eliminated or effectively suppressed in many parts of the world, is undergoing a resurgence. Malaria is estimated to cause up to 400 million clinical cases and 2 million deaths each year. Many of the clinical manifestations of malaria (including acute febrile illness, anemia, cerebral malaria, and hypoglycemia) are mediated in part by overproduction of pro-inflammatory cytokines such as tumor necrosis factor (TNF-$\alpha$), interleukin-1 (IL-1) and gamma interferon (IFN-$\gamma$).

Hepatitis C virus (HCV) is a small RNA virus that chronically infects 170-350 million people world wide. Of those acutely infected, only 15% recover, while the remaining 85% succumb to chronic hepatitis. Up to 20% of the individuals with chronic hepatitis C progress to cirrhosis and these patients are at greater risk of developing hepatocellular carcinoma. Extensive studies have been carried out in the past decade in order to find immunodominant HCV peptides and there are many peptides capable of inducing cellular immune responses. None of these, however, has proven to be clinically effective in preventing HCV disease. Although interferon and other agents are effective for eliminating HCV in certain patients, they are too expensive for the majority of HCV patients in most countries. There is an urgent need to determine immunodominant peptides useful for the development of effective and low-priced vaccines. In addition, there is also a need to develop a simple and low-priced diagnostic tool for HCV since the currently available kit is also expensive for the majority of people not living in developed countries.

Epstein-Barr Virus (EBV) is a B-lymphotropic human herpesvirus, and like other herpesviruses, establishes a lifelong presence in the host. The virus infects the vast majority of the world's adult population and is well known for its association with a broad spectrum of benign and malignant diseases including:

infectious mononucleosis
Burkitt's lymphoma
nasopharyngeal carcinoma
B-cell lymphoma in immunocompromised individuals.

Respiratory tract infections caused by viruses, *Chlamydia*, and *Mycoplasma* have been implicated in the pathogenesis of asthma. Viruses have been demonstrated to be associated with asthma epidemiologically in at least two ways. During infancy, certain viruses have been implicated as potentially being responsible for the inception of the asthmatic phenotype. In patients with established asthma, viral upper respiratory tract infections play a significant role in producing acute exacerbations of airway obstruction that may result in frequent outpatient visits or hospitalizations. Recent attention has focused on *Chlamydia* and *Mycoplasma* as potential contributors to both exacerbations and the severity of chronic asthma in terms of loss of lung function or medication requirements.

Various microorganisms are implicated in the initiation and/or progression of chronic illnesses. There are other effects of carriage of these microorganisms on the immune system (e.g. cytokines, cellular responses, effector molecules). Monitoring of antibody responses and plasma cytokine levels merit serious consideration for ImmunoScore diagnostic analyses in exemplary embodiments of the present invention.

17. Th1-Th2 Paradigm

Lymphocytes are the effector cells of acquired (or adaptive) immunity, originating as bone marrow stem cells that undergo hematopoiesis. A portion of these lymphocytes migrate to the thymus to undergo further differentiation and maturation to become T cells, which can be divided into subsets based on physical markers or surface receptors (e.g., CD4, CD8, and either $\alpha\beta$ or $\gamma\delta$ T cell receptor), representing a generally irreversible genetic commitment (for review, see Kidd P, 2003; Pier G B et al., 2004). Other subsets have been defined by functional properties that may be environmentally altered; e.g., expression of different cytokines, which are chemicals used for cell-to-cell communication. It was originally determined in mice that there are two T helper cell subsets, Th1 and Th2, based on two distinct cytokine profiles that resulted in the overall regulation of an immune response (Mosmann T R et al., 1986; Mosmann T R, Coffman R L, 1989). For example, FIG. 4I (from Harber M et al., 2000) shows some of the complex interactions between the polarized Th1 and Th2 responses.

It is clear from this Th1-Th2 paradigm that the cytokines secreted by the Th cells will feedback and reinforce the particular clonal phenotype from which they originated (e.g., IL-4 for Th1 vs. IFN-$\gamma$ for Th2), as well as suppress the alternate phenotype, resulting in crossregulation. The same Th1-Th2 paradigm from mice has been applied to humans (Romagnani S, 1991; Del Prete G F et al., 1991) to also explain the immunologic aspect of disease (Lucey D R et al., 1996; Romagnani S et al., 1997; Romagnani S, 1997). FIG. 4J (from Harber M et al., 2000) shows the complex balance between Th1 and Th2 cells as dictated by the Th1-Th2 paradigm regarding disease.

The Th1 cell (with its associated cytokines: INF-$\gamma$, TNF-$\alpha$, IL-2, IL-12) is biased towards the cell-mediated side of immunity, effective against intracellular parasites, and its downregulation of Th2 can provide relief from allergic reactions due to IgE; but detrimental effects may result in autoimmunity and graft rejection. On the other hand, the Th2 cell (with its associated cytokines: IL-4, IL-5, Il-6, IL-10, IL-13) favors humoral (antibody) immunity, providing an effective correlate of protection for most vaccines, and its downregulation of Th1 can result in some benefit of tolerance to prevent cellular autoimmune reactions; but certain harmful characteristics related to IgE-based allergies and autoimmunity may result.

The simplicity of the mouse system, however, has not translated well to humans. The clear Th1-Th2 polarization in mice with discrete cytokine profiles has given way to a more flexible continuum of responses in humans, where the functionality of Th cells may be more variable and not necessarily locked into a single type for subsequent generations (Kelso A, Groves P, 1997; Kelso A et al., 1999; Doyle A G et al., 1999; Fitzpatrick D R at al., 1999). This flexibility in human Th subsets and complexity of Th cell interactions have led some researchers to question the Th1-Th2 paradigm and the difficulty to generalize for all situations (Kelso A, 1995; Kunzendorf U et al., 1998; Biaze M E et al., 2003; Sheikh A, Strachan D P, 2004; Chaouat G et al., 2004). Nonetheless, the Th1-Th2 paradigm has provided valuable insight into the nature and treatment/prevention of infectious diseases and immunologic disorders (e.g., allergies and autoimmunity).

FIG. 4K (from Harber M et al., 2000) shows a more comprehensive picture of immune regulation with additional cell types. From this figure, one can see additional T regulator cells which contribute to the paradigm by providing suppressor functions (e.g., NKT, CD45RB$^{lo}$, CD4$^+$CD25$^+$), including some that are antigen-specific (e.g., Th3, Tr1), thereby preventing autoimmune diseases. In addition, others have identified a nonpolarized effector T cell, T$_{FH}$ (follicular helper T cell), that specifically provides help for the antibody-producing B lymphocytes (Mackay C R, 2000; Schaerli P et al., 2001; Chtanova T et al., 2004). Cytokine secretion and regulatory functions are not restricted to just lymphocytes or lymphoid cells, but these activities are also provided by and impact myeloid cells (also originating from stem cells through hematopoiesis), including neutrophils, eosinophils, basophils, mast cells, dendritic cells, monocytes, and macrophages.

FIG. 4L (left and right) (from Kidd P, 2003) show more of these interactions (left panel) as well as differentiation among different cell types (right panel), including antibody-producing B cells, antigen presenting cells (APC), and natural killer cells (NK).

Studies have shown that macrophage activation may occur in two different states (classical vs. alternative) that operate in parallel to the Th1-Th2 paradigm, resulting in pro- vs. anti-inflammatory responses (Birk R W et al., 2001), as well as regulation of endocytosis/antigen uptake through decreased vs. increased mannose receptor expression (Montaner L J et al., 1999). During the effector phase of an immune response, T cells and other effector cells find their way into specific tissue where needed and interact with each other in spatial and temporal patterns by way of secreted chemokines (chemotactic cytokines) and chemokine receptors expressed on their surfaces. T cells interact with eosinophils, mast cells, and basophils during allergic reactions, or with macrophages and neutrophils for delayed-type hypersensitivity reactions (Sallusto F et al., 2000).

Specific disease states have been identified that are associated with, and possibly result from, an imbalance of the immune regulatory process already described. The predominance of a particular phenotype (Th1 vs. Th2), or polarization towards one extreme, may determine the presentation and/or severity of disease (for reviews, see Lucey D R et al., 1996; Harber M et al., 2000; Kidd P, 2003). Atopy (familial allergy) in humans was shown to be characterized by a Th2 profile in whole blood cell culture, where high levels of IL-4 and low levels of IFN-$\gamma$ were observed for CD4$^+$ T cells, but the Th2 deviation in atopic asthma showed high levels of IFN-γ for CD8+ T cells (Magnan A O et al., 2000). IL-4 was used therapeutically to ameliorate the clinical disease in mice that were experimentally given an autoimmune disease, allergic encephalomyelitis, switching the Th1 cells to Th2 cells (Racke M K et al., 1994). It is now clear that the application of exogenous cytokines can be used to push the Th status in either direction, enabling the development of potential therapeutic applications (Lucey D R et al., 1996; Harber M et al., 2000; Kidd P, 2003; Sun Q L, Ran W, 2004).

Th1-Th2 Based Diagnostic Panel

In order to diagnose or predict an immunologic disease and/or provide therapy or prophylaxis, the Th polarization status must be determined; this should also be applied to measure susceptibility to infectious and neoplastic diseases. Th status is measurable in terms of cytokine profiles (House R V, 1999; Harber M et al., 2000; House R V, 2001), chemokine/chemoattractant receptors (Sallusto et al., 1998; Syrbe U et al., 1999; Sallusto et al., 2000; Kaplan A P, 2001; Cosmi L et al., 2001), specific effector cell products (Venge P et al, 1999; Venge P, 2004), or gene expression profiles (Rogge L, 2002). Table 8 below shows how the cytokines and chemokine/chemoattractant receptors can, for example, be aligned within the Th1-Th2 paradigm for an exemplary diagnostic panel according to an exemplary embodiment of the present invention.

TABLE 8

| Th1 | | Th2 | |
|---|---|---|---|
| Cytokines | Receptors | Cytokines | Receptors |
| INF-γ | CCR5 | IL-4 | CCR3 |
| TNF-α | CXCR3 | IL-5 | CCR4 |
| IL-2 | CCR1 | IL-6 | CCR8 |
| IL-12 | | IL-10 | CRTh2 |
| | | IL-13 | |

There are 4 major ways to measure cytokine profiles (House R V, 2001): bioassays, immunoassays, molecular biological techniques, and flow cytometry. Bioassays require living material to induce proliferation, maintain viability, stimulate migration, induce a secondary function, or inhibit a function. Immunoassays are commonly the enzyme-linked immunosorbent assay (ELISA) or the radioimmunoassay (RIA); the ELISA is most often used, being a colorimetric antibody-based assay. Molecular biological methods usually employ the polymerase chain reaction (PCR), or reverse transcriptase PCR (RT-PCR) to measure the mRNA representing a particular cytokine. Flow cytometry is used to detect and quantify cells that are stained with fluorescent anti-cytokine antibodies.

In addition, combinations of these assays can used for improved results concerning a particular application (House R V, 2001); e.g., RT-PCR ELISA, where the RT-PCR amplifies the message and the ELISA detects the result; in situ hybridization, where genetic material is detected with labeled antibodies; ELISPOT assay, where cytokines are detected from single cells by ELISA and molecular methodology; and cytokine immunotrapping assay, a capture ELISA where cytokine antibodies are used to capture cytokines expressed from isolated cells for analysis. Over 60 chemokine receptors have been identified (Pier G B et al., 2004), but only a few are preferentially expressed by specific Th clones (Sallusto et al., 2000) as indicated in a previous table. These receptors may appear as cell surface-bound and in soluble forms. Bioassays and immunoassays can measure soluble receptors, but flow cytometry and in situ hybridization would be more appropriate for surface-bound receptors (House R V, 2001).

Effector cells, such as eosinophils, release different cytotoxic products upon activation during allergic inflammation (Venge P, 2004). Some products include eosinophil cationic protein (ECP), eosinophil peroxidase (EPO), and eosinophil protein X/eosinophil-derived neurotoxin (EPX/EDN). ECP and EPO are most cell-specific for eosinophils, while EPX/EDN is also produced by neutrophils. Table 10 following (from Venge P, 2004) shows examples of secretory products that can used as markers for other inflammatory cells:

Effector cells, such as eosinophils, release different cytotoxic products upon activation during allergic inflammation (Venge P, 2004). Some products include eosinophil cationic protein (ECP), eosinophil peroxidase (EPO), and eosinophil protein X/eosinophil-derived neurotoxin (EPX/EDN). ECP and EPO are most cell-specific for eosinophils, while EPX/EDN is also produced by neutrophils. Table 10 following (from Venge P, 2004) shows examples of secretory products that can used as markers for other inflammatory cells:

TABLE 10

Inflamatory cells and some of their secretory products that may be used as markers of their activity and turnover Eosinophils
  Eosinophil cationic protein (ECP)*
  Eosinophil peroxidase (EPO)*
  Eosinophil protein X/eosinophil derived neurotoxin (EPX/EDN)
Mast cells
  Tryptase*
Neutrophils
  Bastase
  Human neutrophil lipocalin (HNL)*
  Lactoferrin
  Myeloperoxidase (MPO)
Manacytes/macrophages
  Lysozyme
  Interleukin (IL)-6
T-lymphocytes
  SIL2r
Endothelial cells
  E-selectin*

Unique and cell-specific markers are marked with asterisk.

ECP may be measured in serum, plasma, sputum, or saliva as an indicator of eosinophil granulocyte activity and turnover in the allergic or asthmatic patient (Venge P et al., 1999; Bjork A et al., 2000; Venge P, 2004). EPX/EDN may be measured in urine as another noninvasive way of monitoring eosinophil-related allergic inflammation (Venge P, 2004). Elevated urine levels of EPX/EDN have been shown in atopic dermatitis (Breuer K et al., 2001) and have also been predictive of asthma development in children (Oymar K, 2001).

As an alternative to measuring cytokines, receptors, and other immunologic products, the gene expression of these substances can also be evaluated, deriving gene expression profiles to correlate with the Th1-Th2 paradigm (Rogge L, 2002). Oligonucleotide microarrays have been used to assess human gene expression with a transcript level display capacity of 6000 human genes. From purified and stimulated Th1 and Th2 cells, 215 genes were found to be differentially expressed at a 95% confidence level (Rogge L, 2002). These results were also confirmed by RT-PCR for 28 out of 29 genes.

Infectious and Neoplastic Diseases

In the event of a microbial or cancerous attack, the type of immune response will usually dictate the outcome. It is generally considered that a Th1 cell-mediated response would be desirable against viruses, intracellular bacteria, fungi, parasites, and cancer, while a Th2 humoral response might work better for most mucosal and extracellular bacterial infections; however, this is really an over-simplification for a complex area fraught with conflicting scenarios (for review, see Lucey D R, 1996). For example, humoral antibody responses are often established as measurements of potency or correlates of protection for vaccines, even against viruses, such as poliovirus (Fox J P, 1984; Salk J, 1984; Sutter R W et al., 1995), and intracellular bacteria, such as *Salmonella typhi* (Klugman K P et al., 1996; Tacket C O et al., 2004). It is clear that 2 distinct mechanisms of protection (humoral vs. cell-mediated) can occur against the same disease (Kaul D, Ogra P L, 1998; Tacket C O et al., 2004). Due to the complexity of pathogenesis, with different stages of infection and transmission, it is likely that a balance of Th1 and Th2 is required to enable either part to play a role as needed. Nonetheless, it appears that a simple Th1-Th2 paradigm does apply to certain organisms, such as *Mycobacterium tuberculosis*, during a natural infection (Kidd P, 2003). Epidemiological studies have shown that Th1-mediated (IFN-γ, IL-12) protection is essential for protection against tuberculosis, and Th2 predominance leads to severe disease that is often fatal (Newport M J et al., 1996; Lienhardt C et al., 2002). It is probable that people who are predisposed to only one side of the Th1-Th2 paradigm would be at a disadvantage in terms of options available in response to disease. For a detailed review of infectious and neoplastic diseases in relation to Th1 and Th2 profiles, see Lucey D R et al., 1996.

Th1-Th2 and Immunologic Diseases (Allergy/Atopy and Autoimmunity/Inflammatory Disease)

Early Innate Modulation of Th1 or Th2 Cells

The nature of the immune response is first influenced by the specific signals that are involved in the early recruitment of immune components to the site of inflammation (Cookson, 2004). As different pattern-recognition receptors can signal through different pathways, different pathogens or antigens can induce different immune responses (Palaniyar, et al. 2002). Second, the nature of the local immune response might also be strongly influenced by tissue-specific facors, and it has been suggested that the epithelial cells, in general, tend to initiate Th2 rather then Th1-type responses (Matzinger, 2002). In addition, there is evidence that dendritic cells from airways encourage Th2-cell development by default (Stumbles, et al. 1998), and that the induction of Th2 or Th1 type responses by dendritic cells depends on the stimulus with which they are activated (Mazzoni and Segal, 2004).

The perception that specific early signals induced by different infections (or damage by different proteins or other entities) might modify the nature of the subsequent immune response has implications for the Th1-Th2 paradigm of atopic disease. One important issue is the timing of establishment of the Th2-cell bias: on the one hand, Th1- or Th2-cell responses to allergens might be fixed at the time of first exposure in early childhood, and the bias might be subsequently manipulated by bacterial and other adjuvants. On the other hand, Th1- or Th2-cell responses might develop as a consequence of activation of particular patter-recognition receptors by particular pattern-associated molecular patterns (PAMPs) that are present in allergens (Cookson, 2004).

Allergy/Atopy

Allergy or atopy (familial allergy) usually involves Th2 predominance, particularly related to IgE antibodies which attach to basophils and mast cells and cause the release of mediators such as histamine, leukotrienes, and prostaglandins (Kidd P, 2003). Injection of purified allergens (e.g., grass pollen) has been used successfully for immunotherapy towards allergies (Bousquet et al., 1991) by reducing Th2 (IL-4) cytokines (Secrist H et al., 1993) and increasing Th1 (IL-12) cytokines (Hamid Q A et al., 1997). The scientific evidence generally supports the idea that allergies correlate with detectable Th2-dominant conditions that can be treated with Th2-directed immunotherapy.

Any model of the immunology of asthma and atopic dermatitis (eczema) has to take into account the observation that both diseases have increased in prevalence during the past century. Asthma prevalence has been linked to increasing hygiene standards and the progressive westernization of lifestyles in many countries, and a protective effect against asthma of microbial exposure in early childhood has been suggested by the "hygiene hypothesis" (Strachan, 1989). This hypothesis argues that early childhood exposure to infections inhibit the tendency to develop allergic disease. As a consequence, children with westernized lifestyles, protected as they are from the infectious burdens of early life that are common in the developing world, suffer an increased risk of developing allergic disease. There is now strong evidence indicating that microbial exposure is important for protection against asthma, although the nature of the microbial protective effect is still unknown (Cookson, 2004).

Several theories have been put forward to explain the association between asthma and hygiene. The theory of immune deviation suggests that atopic asthma is initiated shortly after birth, when the naive immune system is first confronted with potentially allergenic airborne antigens (Holt, et al. 1999). It is suggested that the initial phase of allergen exposure results in \compartmentalization of immunological memory into either Th1 or Th2 cell phenotypes in non-atopic and atopic individuals, respectively. Microbial exposure in infancy encourages a milieu in which initial allergen exposures produce benign Th1 cell responses. In the absence of such exposure, Th2 cell responses predominate, and can be followed by chronic Th2 cell driven inflammation in the airways (Holt, et al. 1999). This raises the possibility that manipulation of the immune system in early life could result in persistent Th1 or Th2 type responses. If this is the case, vaccination to induce Th1 cell responses might be effective against asthma and other allergic disorders (Holt, 1994). As an alternative to the immune deviation theory, it has been proposed that lack of normal microbial exposure leads to reduced activity of regulatory T cells rather than Th2 cell deviation (Romagnani, 2004).

Asthma is an inflammatory condition, both atopic and nonatopic, that is generally Th2 (IL-4) dominant (Larche M, 2003). Asthma has now reached epidemic proportions, with more than 10% of children being affected in many westernized societies (Cookson, 2004). Allergen injections have been used effectively as immunotherapy in IgE-mediated disease (Abramson M J et al., 1995).

Studies of candidate genes have identified genes that might be involved in asthma susceptibility, many of which exert their effects in the mucosa. For example, IL-13 polymorphism influences mucus production as well as serum IgE levels through a receptor encoded by the polymorphic IL-4R (Ober, et al. 2000). FCERIB variants modify the activity of FcεRI on mast cells, possibly by modulating the level of expression of the receptor on the cell surface (Donnadieu, et al. 2003). A receptor expressed by T cells for the key mast cell signalling factor prostanoid DP has also been reported to be associated with asthma (Oguma, et al. 2004). These findings indicate that the role of mast cells in epithelial inflammation might also be a potential target in asthma therapy.

Other asthma susceptibility genes include the pattern-recognition receptors of the innate immune system, which are expressed by dendritic cells and other cells, and recognize specific microbial components and activate innate immune responses (Cookson, 2004). Polymorphism in CD14, Toll-like receptor 2 (TLR2), nucleotide-binding oligomerization domain 2 (NOD2, or alternatively CARD15), and T-cell immunoglobulin domain and mucin domain 1 have all been shown to influence asthma susceptibility (Baldini, et al. 1999; Eder, et al. 2004; Kabesch, et al. 2003; McIntire, et al. 2003), indicating that these genes might be important in providing the link between microbial exposure and reduced susceptibility to asthma (Cookson, 2004). TLR10, which responds to an unknown ligand, has recently been associated with asthma (Lazarus, et al. 2004). However, none of these studies has tested for IgE responses to particular allergens, so systemic studies of pattern-recognition receptor activation in asthma are now needed (Cookson, 2004).

Other recognized effects are from tumor-necrosis factor (Moffatt and Cookson, 1997), which encodes a potent pro-inflammatory cytokine that is released by many cells, including airway epithelial cells and transforming growth factor-β (Pulleyn, et al. 2001), which is an important local regulator of epithelial inflammation.

Atopic dermatitis (eczema) can involve a mixture of Th1 and Th2 states, depending on the type or stage of disease. The acute disease is usually Th2 (IL-4), while the chronic disease may show more Th1 (IL-12) cytokines (Singh V K et al., 1999). Further studies indicate that the initial phase of disease is Th2, while Th1 may appear later (Bohm I, Bauer R, 1997). For more detailed reviews and applications concerning Allergy/Atopy, see: Lucey D R et al., 1996; Kidd P, 2003.

Although the current emphasis in understanding asthma and atopic dermatitis is now moving from involvement of distant adaptive immune responses to local responses at epithelial-cell surfaces, it is probable that a full understanding of these diseases will also depend on studies that include commensal bacteria.

Current understanding of the hygiene hypothesis rests on the suggestion that microbial stimulation during early life is essential for the normal development of the immune system and to achieve the correct cytokine balance (Rook and Standford, 1998). However, the evidence described earlier indicated that damage to the epithelium is probably the initiating event in atopic disease, and the Th1- or Th2-cell bias of subsequent inflammation might be secondary to the nature of the damage (Cookson, 2004).

Alternative mechanisms for bacterial products to modify the risk of atopic diseases include the enhancement of an effective airway barrier by the induction of mucus production through IL-13 stimulation (Kuperman, et al. 2002), or the induction of sufficient polyclonal IgA or IgE to provide non-specific protection against allergens. Additionally, a protective role by microorganisms might follow the acquisition of distinct commensal or symbiotic organisms. Once an individual's commensal microflora is established in the first year of life, it remains relatively stable (Hooper and Gordon, 2001). Substantial differences have been observed in the intestinal microflora between neighboring countries with a different prevalence of atopic disease (Sepp, et al. 1997), and between atopic and non-atopic children living in each of these countries (Bjorksten, et al. 1999). As commensal and symbiotic organisms actively manipulate host immunity and the activity of other bacteria, it should be considered that interactions among commensal bacteria, pathogens and the host might contribute to the increase and prevalence of asthma and atopic dermatitis (Cookson, 2004).

18. Autoimmunity/Inflammatory Disease

Rheumatoid arthritis (RA) is an autoimmune disease with apparent Th cell involvement. Activated T-helper cells are found in the inflammatory filtrates, and T cell-directed therapies have provided some clinical benefit (Schulze-Koops H, Kalden J R, 2001). It appears to be Th1-driven (IFN-γ), but there may be a Th2 (IL-4, IL-10) component at the early stages of disease (Gerli R et al., 2002). It is interesting to note that pregnancy, which seems to have a Th2 bias, appears to ameliorate the progression of RA, providing indirect evidence of the role of Th1 in RA (Da Silva J A, Spector T D, 1992). Schulze-Koops and Kalden suggest that several of the current anti-RA drugs work by altering Th1/Th2 balance. But evidence for this is indirect and comes mostly from non-clinical settings. Schulze-Koops and Kalden concede that it may be overly simplistic to remold the RA data to make it fit the Th1/Th2 hypothesis. They admit it is possible Th1 is subject to simple guilt-by-association with RA, rather than being a major mechanism driving the disease (Schulze-Koops and Kalden, 2001). ImmunoScore analyses would further the understanding of the relationship between RA and the Th1/Th2 paradigm.

Multiple sclerosis (MS) is an autoimmune disease that appears to be Th1-driven (IL-12, IFN-γ), with some conflicting data (Kidd P, 2003); this may be a complication of the role of regulatory T cells (Tr) secreting cytokines (IL-10) to normally downregulate the Th1 cells (Bettelli E et al., 1998). Defining the factors that initiate and perpetuate the ongoing pathogenesis, as well as designing treatment strategies for this disease, have been complicated by absence of an identifiable causative agent, diversity of co-existing CNS lesion stages (ie, acute, chronic active, chronic inactive, remyelinating, gliotic plaque), an unpredictable relapsing-remitting clinical course early in the disease, lack of a direct correlation of clinical symptoms to the occurrence of new white matter lesions, and the absence of a naturally occurring animal form of the disease (Jordan, et al. 1999). One group tried T cell receptor peptide therapy on MS patients. Of the less than 200 patients studied, 50-90 percent supposedly showed immunological response to vaccination and as much as 35 percent had some degree of favorable clinical response (Vandenbark, et al. 2001).

Type 1 diabetes is an autoimmune disease that may be Th1 dominant. Data available thus far in human diseases favor a prevalent Th1 lymphokine profile in target organs of patients with organ-specific autoimmunity. Adjuvant therapy with BCG injections seems to benefit patients and nonobese diabetic mice by raising Th2 (IL-4) cytokine levels (Singh V K et al., 1999). However, administration of Th2 cells to nonobese diabetic mice can worsen the disease, if the recipient mice are immunocompromised (Pakala, et al. 1997).

In summary, for three major autoimmune diseases—RA, MS, and type 1 diabetes—a Th1 dominance has not been well enough established to rationalize balancing intervention. On both pragmatic and theoretical grounds there is real possibility of making the patient sicker through efforts to intervene with Th@ cells or Th2 cytokines (Kidd, 2003). The ImmunoScore diagnostic panel would be invaluable in assessing the relationship of Th1/Th2 cytokine levels in relationship to these disease conditions.

Miscarriage might be the result of an autoimmune response to the fetus during pregnancy, where the normally Th2 (IL-3, IL-4, IL-10) dominance during pregnancy has shifted to a Th1 state (IL-2, IFN-γ, TNF-α), allowing the maternal cell-mediated response to be directed towards the paternal antigens of the fetus (Chaouat G et al., 2004). While the simplicity of the Th1-Th2 paradigm applied to pregnancy is being questioned, particularly in terms of potential therapy and the inability to generalize across all individuals, there may still be a Th2 bias for normal pregnancies (Chaouat G et al., 2004).

Systemic lupus erythematosus is a chronic, recurrent, potentially fatal multisystem inflammatory disorder that typically shows anti-nuclear and other autoantibodies, with elevated Th1 (IL-2, IFN-γ) and Th2 (IL-4) cytokines (Kidd P, 2003). Patients with arthritis have higher Th1 cytokine levels, while those with CNS involvement have higher Th2 cytokine levels (Chang D M et al., 2002).

It is possible that the association of genetic polymorphism (Chang D M et al., 2002), along with disease stage and presentation, all work together to affect the Th1-Th2 pattern. Complete complement components C4A and C4B deficiencies have been identified and studied clinically (Yang, et al. 2004a). All but one of the complete C4-deficient subjects experienced symptoms related to immune complex clearance disorders such as SLE, a lupus-like disease, or glomerulonephritis (Yu, et al. 2003). The human C4 locus is remarkably complex. Among different individuals in a population, two to seven (possibly eight) C4 genes may be present in a diploid genome, leading to a 3- to 5-fold variation in plasma C4 protein concentrations and the presence of multiple allotypes (Yang, et al. 2003). Considering the roles of C4A and C4B in immunoclearance, memory, and effector functions of the humoral immune response, it is not unexpected that a deficiency of C4A or C4B is frequently associated with infectious and/or autoimmune diseases (Yang, et al. 2004b). An elucidation of the molecular basis of complete C4A and C4B deficiencies may help in designing a comprehensive screening strategy to determine the prevalence of C4A and C4B mutations in autoimmune, infectious, and kidney diseases (Yang, et al. 2004b).

In humans, outside of major histocompatibility complex (MHC) class II, genetic polymorphisms or defects in genes involved in antigen uptake and/or process and in immune complex clearance such as complement, FCGR2A and FCGR3A have been identified to contribute to SLE susceptibility (Wakeland, et al. 2001). Recently, programmed cell death gene 1 (PDCD1) which regulates B cell activation has been identified as an autoimmunity candidate gene in the mouse (Nishimura, et al. 1999), and a single-nucleotide polymorphism (SNP) in a putative RUNX1 binding site in the promoter of human PDCD1 gene has been implicated as a risk allele for SLE (Prokunina, et al. 2002).

Fibrotic disease, involving tissue fibrosis (scarring), is the result of a Th1-Th2 imbalance during wound healing in response to chronic inflammation, and is responsible for an estimated 45% of U.S. deaths (Wynn T A, 2004). In this case, the wound healing Th2 (IL-4, IL-5, IL-13) response, opposing the initial Th1 (IFN-γ, IL-12) regenerative inflammatory response, is continuous and leads to excessive tissue remodeling (permanent scar tissue). While the Th2 wound healing is necessary for long-term survival from an injury, persistent healing, in response to a chronic Th1 stimulus, might end in fibrotic tissue causing major organ failure and death (Wynn T A, 2004). For more detailed reviews and applications concerning Autoimmunity/Inflammatory Disease, see: Lucey D R et al., 1996; Kidd P, 2003.

8. Immunoscore Analyses for Immigrants and Internationally Adopted Children

The current U.S. Immigration and Naturalization law has vaccination requirements for the following vaccine-preventable diseases:
Measles
Mumps
Rubella
Polio
Tetanus
Diphtheria
Pertussis
*Haemophilus influenzae* type B (Hib)
Hepatitis B
Varicella
Pneumococcal disease
Influenza Vaccination of Internationally Adopted Children The ability of a clinician to determine that an individual is protected from vaccine-preventable disease on the basis of their country of origin and their personal medical records alone is limited. Currently, only written documentation should be accepted as evidence of prior vaccination. Although vaccines with inadequate potency have been produced in other countries, the majority of vaccines used worldwide are produced with adequate control standards and are potent. Data are inconclusive regarding the extent to which an internationally adopted child's immunization record reflects the level of the child's protection from vaccine-preventable diseases. For example, a record might indicate administration of Measles, Mumps, and Rubella (MMR) vaccine when only single antigen measles vaccine was administered. A study of children adopted from China, Russia, and Eastern Europe determined that only 39% of children with documentation of >3 doses of DTP had protective levels of diphtheria and tetanus antitoxin (Hostetter, et al. 1998). Rather than rely on records and memories that may be less than satisfactory, the ImmunoPrint diagnostic assay system would be a highly practical tool to test the specific antibody levels of individuals entering the country or children being adopted from other lands.

The CDC states that doses of measles-containing vaccine administered prior to the first birthday should not be counted as part of the series (CDC, 2002). They also state that serological testing for IgG antibody to MMR vaccine viruses can be considered if the individual lacks the appropriate paperwork. A child whose record indicates receipt of measles or measles-rubella vaccine at age ≧1 year and who has protective antibody levels against measles and rubella should receive a single dose of MMR as age appropriate to ensure protection against mumps.

Regarding poliovirus vaccine, the CDC suggests that the "simplest approach" is to revaccinate immigrants with IPV according to the U.S. schedule (CDC, 2002). They also state that children appropriately vaccinated with three doses of oral polio vaccine (OPV) in economically developing countries might have suboptimal seroconversion. Currently, serologic testing for neutralizing antibody to poliovirus types 1, 2, and 3 can be obtained commercially and at certain state health department laboratories. Incorporation of poliovirus assays into ImmunoPrint diagnostics would enable immigration authorities to screen individuals for seroconversion to poliovirus types 1, 2, and 3. Recommended immunization boosters could then be followed through with in timely fashion.

Vaccination providers can re-vaccinate a child with DTaP vaccine without regard to recorded doses; however, one concern regarding this approach is that data indicate increased rates of local adverse reactions after the fourth and fifth doses of DTP or DTaP. If a re-vaccination approach is adopted and a severe local reaction occurs, serologic testing for specific IgG antibody to tetanus and diphtheria toxins can be measured by ImmunoPrint analyses before administering additional doses. Protective concentration indicates that further doses are unnecessary and subsequent vaccination should occur as age-appropriate. There is, as yet, no serologic correlate of protection for pertussis. The lack of a serologic correlate of protection is one area where application of the ImmunoPrint database would be of great value.

Because the number of vaccinations needed for protection from *Haemophilus influenzae* type B (Hib) disease decreases with age and adverse events are rare, age-appropriate vaccinations for immigrants should be provided (CDC, 2002). Hib vaccination is not routinely recommended for children over 5 years of age.

The ACIP recommends serologic testing for hepatitis B surface antigen (HBsAg) for international adoptees (CDC, 2002). Children determined to be HBsAg positive should be monitored for the development of liver disease. Household members of HBsAg-positive children should be vaccinated. The current recommendation from the ACIP states that a child whose records indicate receipt of $\geq 3$ doses of vaccine can be considered protected and additional doses of vaccine are not needed if $\geq 1$ doses were administered at $\geq 6$ months of age. Those who have received <3 doses should complete the series at the recommended intervals (CDC, 2002). This rather complicated recommendation depending on accurate record-keeping could be replaced with ImmunoPrint diagnostic testing. A positive anti-HBsAg IgG antibody would be indicative of protection in these individuals.

Varicella vaccine is not administered in the majority of countries. The ACIP recommends that a child who lacks a reliable medical history regarding prior varicella disease should be vaccinated as age-appropriate (CDC, 1996). A well-timed ImmunoScore diagnostic assay can, in exemplary embodiments of the present invention, remove speculation from the vaccination protocol. Pneumococcal conjugate and pneumococcal polysaccharide vaccines are not administered in the majority of countries. The CDC recommends that vaccines should be administered as age-appropriate or as indicated by the presence of underlying medical conditions (CDC, 2002). ImmunoPrint diagnostic analysis could be used to point out the need for vaccination in immigrating individuals.

Each country may have needs for assessing the immune status of immigrants that may not necessarily coincide with the U.S. requirements as previously outlined. In addition, there may be other needs inside or outside the U.S., dictated by a particular investigation at a particular site. For example, Greenaway et al. (2004) have embarked on a mission to assess the immune status of immigrants in the Montreal area of Canada, with initial emphasis on 5 different infectious agents: hepatitis A, measles, mumps, rubella, and varicella (Greenaway C A, Boivin J F, Dongier P, Miller M A, Schwartzman K. Susceptibility to vaccine-preventable diseases in newly arrived immigrants. Abstract G-538, pp 254-5, In 44$^{th}$ ICAAC Abstracts 2004 [Interscience Conference on Antimicrobial Agents and Chemotherapy, Washington, D.C., Oct. 30-Nov. 2, 2004]: American Society for Microbiology, Washington, D.C.). Subsequent studies may expand to include tetanus and diphtheria, as well as other agents listed for routine immunizations of Canadians, which are essentially identical to those listed for the U.S. Note that hepatitis A, in the above study, does not represent an infectious agent designated for routine immunization in Canada or the U.S., but it is listed for selective immunization where people have been identified to be at greater risk of disease. Likewise, diagnostic panels may be expanded where appropriate to represent additional infectious agents that are listed for selected immunization.

In exemplary embodiments of the present invention diagnostic subpanels can be developed to accommodate the needs for different researchers where there is an interest to follow up on particular infectious agents in a region where there may be new or ongoing outbreaks of disease. The influx of immigrants that are unprotected against vaccine preventable diseases (VPD) has already been shown to contribute the increased incidence of disease. For example, varicella and rubella vaccines are not routinely administered in many countries, and this has therefore resulted in an over representation of immigrants in outbreaks of varicella and rubella in areas where these vaccines already exist. Studies have shown that in Canada, for example, immigrants are more likely to be susceptible to varicella, rubella, and mumps than North Americans. In addition, they have stated, "Adult immigrants may benefit from targeted vaccination programs but given the geographic variation in susceptibility to VPD, this must be taken into consideration when developing these programs." For this scenario, ImmunoScore diagnostic panels can prove invaluable to identify the target according to the individually assessed immune status.

Tuberculosis (TB) is another disease that may be of considerable importance to monitor, not necessarily for immune status, but for active infection, particularly in immigrant populations. It is estimated that one third of the global population is infected with TB. Due to improved laboratory services during the 1990s, there has been a resumption of an overall decline in U.S. cases of TB. Nonetheless, the CDC states, "TB continues to pose substantial social, public health, and economic costs." (Centers for Disease Control and Prevention. National plan for reliable tuberculosis laboratory services using a systems approach: recommendations from CDC and the Association of Public Health Laboratories Task Force on Tuberculosis Laboratory Services. MMWR 2005; 54-[No. RR-6]:1-12). This 2005 CDC report indicates that the U.S. spends nearly $1 billion annually on TB-related costs, with 9-14 million people having latent TB infections and 15,000 new cases reported in 2003. The CDC also states, "to eliminate TB in the United States, further improvements are needed in laboratory services to support TB treatment, prevention, and control." As a result, "TB control is now entering a new phase in the United States, a transition from low incidence to elimination." (Centers for Disease Control and Prevention. Progressing toward tuberculosis elimination in low-incidence areas of the United States: recommendations of the Advisory Council for the Elimination of Tuberculosis. MMWR 2002; 51[No. RR-5]:1-16). An ImmunoScore diagnostic panel containing TB, for example, could be utilized in this regard in the U.S.

The BCG vaccine, currently licensed for TB, is not recommended for routine use in the U.S. because of questionable efficacy; however, there are other countries that routinely use this vaccine. The United Kingdom, in 2005, announced that, after 50 years, it is dropping its school TB vaccination program for young teenagers, in favor of targeting infants in ethnic populations that are at greater risk (Celia Hall, Medical Editor, Telegraph Group Limited, Jul. 7, 2005). For example, they have indicated that the case rate in whites is 3.6 per 100,000, while the rate in Africans is 279.8 per 100,000, and the rate in Indian, Pakistani, and Bangladeshi people is 126.7. New immigrants from countries with high TB incidence would also be targeted for vaccinations. It is possible that a diagnostic panel which includes TB would prove useful for screening these populations.

As demonstrated in the UK, there is a greater incidence of TB in immigrants from certain regions of the world. It would be therefore useful to add a TB diagnostic to immigrant panels previously described. For example, a TB diagnostic could be included in the subpanel proposed for Canada, or used as a separate diagnostic, as a follow-up to the Greenaway et al. study. It is possible to use specific antibody detection to distinguish active TB infections from non-active or non-TB (Tong M et al. 2005. J Immunol Methods. 301:154-63). In this case, specific TB antigens, particularly those of a carbohydrate nature, may be selected for inclusion in the proposed diagnostic panels to identify people with active TB infections in need of treatment.

10. Immunoscore Diagnostic Panel and Preventive Therapy for Autoimmune Disease

Antibodies directed against self antigens and tissues are known as autoantibodies. These autoantibodies can be expressed years or decades before the autoimmunity causes clinical disease. The clinical disease arises when the autoantibodies cause so much damage that the afflicted individuals begin to show symptoms. For example, antibodies attacking self nuclear antigens cause glomeruloneprhtis and vasculitis as symptoms of systemic lupus erythematosus; and antibodies to myelin basic protein and myeling oligodendrocyte glycoprotein eventually cause brain invasion by $CD4^+$ T cells in multiple sclerosis. ImmunoScore technology may one day allow physicians to screen a healthy person's blood for autoantibodies years prior to causing disease, and thereby, enable a physician to recommend a course of treatment to delay, or even perhaps prevent, the manifestation of clinical disease.

There has already been much time and money invested in researching and developing the necessary tools to screen an individual's genetic makeup to see if a patient might be at risk for autoimmune disease. Most chronic diseases, however, arise from a complex interplay between environmental influences and multiple genes that each make a small contribution to the course of the disease. Many factors apparently play an as yet completely undefined role in the expression of Guillain-Barre syndrome. Elements that have been proposed to be of importance in the course of this disease include mannose-binding lectin polymorphisms; expression of apolipoprotein E (apo-E) isoform; levels of cytokines IFN-γ, IL-6, and TNF-α; levels of serum proteins including apo A-IV, haptoglobin, transthyretin, and fibrinogen; antibodies to GD1a/Gd1B complex, LM-1, and GM1; HLA haplotype; and even exposure to vaccine antigens. Detection of susceptible genes would not necessarily reveal when (or even if) an individual would be stricken with an autoimmune disease. Detection of specific antibodies with the ImmunoScore Autoimmune Disease detection panel would signal that a disease-causing process was already underway.

FIG. 5B depicts exemplary process flow in which one or more exemplary ImmunoScore autoimmune panels can be used. With reference thereto, at 5B10 healthy patients can, for example, be screened at regular intervals for antibodies or other markers known to be indicative of autoimmune disease (as described below) at, for example, their physician's office. Women and patients with a family history of autoimmune disease can, for example, be scheduled for more regular ImmunoScore Autoimmune Disease diagnostic screenings. The patient's HLA type can also, for example, be a useful input to the appropriate diagnostic determination. At 5B20, by implementing regular screenings, an individual patient's rise and fall of relevant antibody populations could be followed and stored in an ImmunoScore Database (sometimes referred to herein as an "ImmunoScoreKeeper"). If it happened, such as at 5B30, that a patient's antibody levels were not a cause for concern, that patient's data could be maintained in the database and referred to by researchers as well as that patient's physician(s) at subsequent visits. In addition, this information might be of use to insurance providers and health maintenance organizations for statistical analyses. At 5B35, if the patient has increased antibody levels, but no sign of clinical disease, a therapeutic course of action involving treatment with appropriate pharmaceuticals, or perhaps other suggested therapies including dietary modifications or similar recommendations can be implemented. In addition, the patient can be regularly screened for any change in the antibody or marker levels, as shown at 5B40. Such an early indication of autoimmune disease might be helpful to the insurance industry and the treatment prior to chronic disease would be more cost-effective to both the patient and the insurance provider. Therapies considered experimental can, for example, be monitored by researchers with regular ImmunoScore Autoimmune Disease diagnostic measurements during the course of the experimental treatment(s). Efficacy of drugs or behavior modifications could thereby be monitored before the disease outbreaks became full blown. The presence of predictive antibodies would not mean that a patient would get definitely sick, but would give a percentage risk of autoimmune disease developing over some years or months. Currently, there is a paucity of effective treatments for autoimmune disease conditions, but this should not stand in the way of ImmunoScore Diagnostic screening, which can, for example, accelerate the development of such treatments.

Thus, in exemplary embodiments of the present invention, by gathering data over a large patient population over a large interval of time, and processing the data and making available the data and any analyses thereof, as shown at 5B45, useful information can be provided to Insurers/HMOs 5B50, researchers 5B55 and Clinicians 5B57.

Cell therapy, pioneered for the treatment of malignancies in the form of bone marrow transplantation, has subsequently been tested and successfully employed in autoimmune diseases. Autologous hemopoietic stem cell transplantation (HSCT) has become a curative option for conditions with very poor prognosis such as severe forms of scleroderma, multiple sclerosis and lupus, in which targeted therapies have little or no effect (Dazzi, et al. 2007). Regulatory T cells, found abnormal in several autoimmune diseases, have been proposed as central to achieve long-term remissions. Mesenchymal stem cells of bone marrow origin have more recently been shown not only to be able to differentiate into multiple tissues, but also to exert a potent antiproliferative effect that results in the inhibition of immune responses an prolonged survival of hematopoietic stem cells. At the current time, all of these potential resources clearly need to be investigated at the preclinical level but support a great deal of enthusiasm for cell therapy of autoimmune diseases (Dazzi, et al. 2007).

Autoimmune Disease

Autoimmune diseases arise from an overactive immune response of the body against substances and tissues normally present in the body. The many diseases called autoimmune are either systemic (involving many body organs) or organ specific. The immune system may initiate an attack on self because the normal controlling mechanisms of the immune system are impaired, because a host response to an extrinsic immunogen, such as a virus, fails to distinguish between normal tissue and the object of the attack (cross-reactivity), or because immunogenic tissues, normally hidden from the immune system, are made visible to the immune system (loss of tolerance). Any or all of these mechanisms may occur in human autoimmune disease (Lockshin, 2001). Differences among authors among their definitions of autoimmunity cause published lists of autoimmune diseases to differ.

Women tend to be affected more often by autoimmune disorders—nearly 79% of autoimmune disease patients in the U.S. are women, most frequently during the childbearing years. Table I lists the striking female-to-male ratios in some autoimmune diseases (http://www.aarda.org). The reasons for the sex bias in autoimmune diseases are unclear but may include such factors as sex-related differences in immune responsiveness, response to infection, sex steroid effects and sex-linked genetic factors (Whitacre, et al. 1999). In human autoimmune illness, the term "female predominance" refers to sex differences of incidence, not severity. Severity differences are slight or nonexistent (Weyand, et al. 1998).

Many, but not all, autoimmune diseases primarily affect women. In humans, severity of illness does not differ between men and women. Men and women respond similarly to infection and vaccination, which suggests that the intrinsic differences in immune response between the sexes do not account for differences in disease frequency. In autoimmune-like illnesses caused by recognized environmental agents, sex discrepancy is usually explained by differences in exposure. Endogenous hormones are not a likely explanation for sex discrepancy; hormones could have an effect if the effect is a threshold rather than quantitative. X and Y chromosomal differences have not been studied in depth. Other possibilities to explain sex discrepancy include chronobiologic difference and various other biologies, such and pregnancy and menstruation, in which men differ from women (Lockshin, 2006).

If infections (as yet unidentified) or toxins induce autoimmune disease, exposure differences remain as plausible explanations for the sex differences. Gonadal hormones, if they play a role, likely do so through a threshold or permissive mechanism rather than through quantitative immunomodulation. Differences related to X inactivation, imprinting, X or Y chromosome genetic modulators, and intrauterine influences remain as alternate explanations for sex differences of incidence. The epidemiology of the sex-discrepant autoimmune diseases (afflicting preferentially young females) suggests that an explanation for sex discrepancy lies in differential exposure, vulnerable periods, or thresholds (Lockshin, 2001).

For T-cell mediated autoimmune diseases, the presence of serum antibodies can predate the onset of disease, and be predictive of the development of clinical symptoms.

Autoimmune Diseases

Acute disseminated encephalomyelitis (ADEM)—Acute disseminated encephalomyelitis (ADEM) is a monophasic autoimmune demyelinating disease of the central nervous system that typically follows a febrile infection or a vaccination. Children are predominantly affected. A plethora of viral and bacterial pathogens and a number of vaccinations have been associated with ADEM. Experimental animal studies indicate that both primary and secondary autoimmune responses contribute to central nervous system inflammation and subsequent demyelination. The clinical diagnosis of ADEM is strongly suggested by a close temporal relationship between an infectious incident or an immunization and the onset of leukoencephalopathic neurological symptoms (Menge, et al. 2005).

Addison's disease—about 7 in 10 cases are due to an autoimmune disease. In auto-immune Addison's disease, antibodies are made which attach to cells in the adrenal cortex. These destroy the cells which make cortisol and aldosterone. Patients with autoimmune Addison's disease (AAD) are prone to develop other autoimmune manifestations. An increased prevalence of celiac disease (CD) has recently been demonstrated in Northern European patients with AAD. In patients with AAD there is a high prevalence of both CD and IgA deficiency. Consequently, it is important to screen for CD with tissue transglutaminase autoantibodies of the IgA class and for IgA levels (Betterle, et al. 2006).

Ankylosing spondylitis—is a chronic, progressive autoimmune disease characterized by arthritis, inflammation, and eventual immobility of a number of joints. The disease usually involves the spine and surrounding spinal structures and usually begins between the ages of fifteen and thirty-five years and affects young white males three times as frequently as females. Some patients of this debilitating disease have antibodies to the bacterium *Klebsiella*. This micro-organism apparently has some antigenicity which causes the body to make antibodies which in turn attack the lower spine and cause ankylosing spondylitis.

Antiphospholipid antibody syndrome (APS)—affects blood-clotting process—causes blood clots to form in veins and/or arteries. There are three primary classes of antibodies associated with the antiphospholipid antibody syndrome: 1) anticardiolipin antibodies, 2) the lupus anticoagulant and 3) antibodies directed against specific molecules including a molecule known as beta-2-glycoprotein 1. (University of Illinois-Urbana/Champaign. Carle Cancer Center. Hematology Resource Page http://www-admin.med.uiuc.edu/hematology/PtAPS.htm).

Aplastic anemia—may be caused by autoimmune attack on the bone marrow, slowing or shutting down production of new blood cells. Some acquired aplastic anemia (AA) results from immune-mediated destruction of hematopoietic stem cells. Cytokine gene polymorphisms are implicated in controlling cytokine production and increasing the susceptibility to some autoimmune diseases (Gidvani, et al. 2007).

Autoimmune hepatitis—caused by attack on the liver by body's immune system. The disease is usually quite serious and, if not treated, gets worse over time. It's usually chronic, meaning it can last for years, and can lead to cirrhosis (scarring and hardening) of the liver and eventually liver failure. Autoimmune hepatitis is classified as either type I or II. Type I is the most common form in North America. It occurs at any age and is more common among women than men. About half of those with type I have other autoimmune disorders, such as type 1 diabetes, proliferative glomerulonephritis, thyroiditis, Graves' disease, Sjögren's syndrome, autoimmune anemia, and ulcerative colitis. Type II autoimmune hepatitis is less common, typically affecting girls ages 2 to 14, although adults can have it too (National Institute of Diabetes and Digestive and Kidney Diseases, NIH. http://digestive.niddk.nih.gov/ddiseases/pubs/autoimmunehep/index.htm).

Coeliac disease—characterized by chronic inflammation of the proximal portion of the small intestine. When people with celiac disease eat foods or use products containing gluten, their immune system responds by damaging the small intestine. The villi lining the small intestine are damaged or destroyed (National Institute of Diabetes and Digestive and Kidney Diseases, NIH. http://digestive.niddk.nih.gov/ddiseases/pubs/celiac/).

Crohn's disease—form of inflammatory bowel disease characterized by chronic inflammation of the intestinal tract—major symptoms include abdominal pain and diarrhea. The new treatment is an antibody designed to disable interleukin-12 (IL-12), an immune system protein involved in inflammation. People with Crohn's produce excess IL-12. Previous studies conducted by the NIAID linked IL-12 to the cascade of immune system events that leads to the debilitating symptoms of Crohn's disease (NIH News http://digestive.niddk.nih.gov/ddiseases/pubs/crohns/index.htm).

Diabetes mellitus—characterized by a deficiency or absence of insulin production (Type I)—often the consequence of autoimmune attack on the insulin-producing beta cells in the islets of Langerhans of the pancreas. LADA (latent Autoimmune Diabetes of Adulthood) or type 1.5 diabetes—a slowly progressive form of type 1 diabetes mellitus. Patients are often diagnosed as type II diabetes, but have positive pancreatic islet antibodies, especially to glutamic acid decarboxylase (GAD). They do not immediately require insulin for treatment, are often not overweight, and have little or no resistance to insulin (Johns Hopkins Autoimmune Disease Research Center. http://autoimmune.pathology.jhmi.edu/diseases.cfm?systemID=3&DiseaseID=23).

Goodpasture's syndrome—characterized by rapid destruction of the kidneys and hemorrhaging of the lungs through autoimmune reaction against an antigen found in both organs. Because the early symptoms are characteristically vague, and because of the tendency of the disease to undergo very rapid progression, it is common for the true diagnosis to be reached at a relatively late stage. Tests for anti-glomerular basement membrane antibodies (GBM) antibodies in the blood can be very useful. They should always combined with tests for antibodies to neutrophil cytoplasmic antigens (ANCA), as the two types of autoantibody can occur together. Kidney biopsy is almost always necessary. It is often the quickest way to secure a diagnosis, and even if the diagnosis looks certain, it may give valuable information about the likely effect of treatment (Yang, et al. 2007).

Grave's disease—most common form of hyperthyroidism—caused by anti-thyroid antibodies that have the effect of stimulating the thyroid into overproduction of thyroid hormone. Grave's disease is an autoimmune disorder in which antibodies to the thyrotropin receptor result in constitutive activation of the receptor and increased levels of thyroid hormone. Th1 and Th2-like cytokines are also involved in the pathogenesis of Graves' disease (Molnar, 2007).

Guillain-Barré syndrome (GBS)—an acquired immune-mediated inflammatory disorder of the peripheral nervous system—also called acute inflammatory demyelinating polyneuropathy, acute idiopathic polyradiculoneuritis, acute idopathic polyneuritis, and Landry's ascending paralysis. When Guillain-Barré is preceded by a viral or bacterial infection, it is possible that the virus has changed the nature of cells in the nervous system so that the immune system treats them as foreign cells. It is also possible that the virus makes the immune system itself less discriminating about what cells it recognizes as its own, allowing some of the immune cells, such as certain kinds of lymphocytes and macrophages, to attack the myelin. Sensitized T lymphocytes cooperate with B lymphocytes to produce antibodies against components of the myelin sheath and may contribute to destruction of the myelin. Scientists are investigating these and other possibilities to find why the immune system goes awry in Guillain-Barré syndrome and other autoimmune diseases. The cause and course of Guillain-Barré syndrome is an active area of neurological investigation, incorporating the cooperative efforts of neurological scientists, immunologists, and virologists (National Institute of Neurological Disorders and Stroke. http://www.ninds.nih.gov/disorders/gbs/gbs.htm).

Hashimoto's disease—common form of hypothyroidism—characterized by initial inflammation of the thyroid, and later dysfunction and goiter—there are several characteristic antibodies (e.g., anti-thyroglobulin). The quest continues for the identification of susceptibility genes for autoimmune thyroiditis. In addition to the classical major histocompatibility complex class II genes and cytotoxic T cell antigen-4, new studies have appeared on CD40 the protein tyrosine phosphatase-22. Too much iodine increases the incidence of Hashimoto's thyroiditis, perhaps by augmenting the antigenicity of thyroglobulin. T regulatory cells, Toll-like receptors and presentation of lipid antigens by CD1 molecules are new areas of basic immunological investigation that have been applied to autoimmune thyroiditis (Caturegli, et al. 2007).

Idiopathic thrombocytopenic purpura—an autoimmune disease where the body produces anti-platelet antibodies resulting in a low platelet count. Immune thrombocytopenic purpura is classified as primary or as secondary to an underlying disorder and as acute (of six months or less in duration) or chronic. In one study thirty-seven patients with idiopathic thrombocytopenic purpura (ITP) were treated with a standard *Helicobacter pylori* eradication regimen irrespective of *H. pylori* infection. Their results indicate that platelet recovery results from the disappearance of *H. pylori* itself, and is mediated, in part, through suppression of anti-platelet autoantibody production (Asahi, et al. 2006).

Multiple sclerosis (MS)—disorder of the central nervous system characterized by decreased nerve function due to myelin loss and secondary axonal damage. Analysis of antibodies against myelin oligodendrocyte glycoprotein (MOG) and myelin basic protein (MBP) in patients with a clinically isolated syndrome is a rapid, inexpensive, and precise method for the prediction of early conversion to clinically definite multiple sclerosis (Berger, et al. 2003).

Myasthenia gravis—a disorder of neuromuscular transmission leading to fluctuating weakness and fatigue—weakness is caused by antibodies that block acetylcholine receptors, that is anti-acetylcholine-receptor (anti-AChR) antibody at the neuromuscular junction. Immunosuppressive treatment has been shown to be effective in MG patients (Tsinzerling, et al. 2007).

Opsoclonus myoclonus syndrome (OMS)—a neurological disorder—result of autoimmune attack on the nervous system—symptoms include opsoclonus, myoclonus, ataxia, intention tremor dysphasia, dysarthria, mutism, hypotonia, lethargy, irritability, or malaise. Despite circumstantial evidence that opsoclonus-myoclonus (OM) is often immune mediated, no specific autoantigen has been identified. A group found frequent and heterogeneous immunity to neuronal autoantigens without a single specific antibody marker of OM (Bataller, et al. 2003).

Optic neuritis—inflammation of the optic nerve that may cause a complete or partial loss of vision. Patients with optic neuritis had more anti-myelin basic protein and anti-proteolipid protein antibodies than did control subjects (Sellebjerg, et al. 1995). Since high concentrations of GQ1b gangliosides are known to be present in the human optic nerve and anti-GQ1b antibodies can cross the blood-brain barrier, the optic disc oedema in [a]

patient could represent an anti-GQ1b IgM complement mediated inflammatory demyelination (Chan, 2003).

Ord's thyroiditis—similar to Hashimoto's disease, except the thyroid is reduced in size.

Pemphigus—an autoimmune disorder that causes blistering and raw sores on skin and mucous membranes. Patients with pemphigus develop antibodies that bind to the keratinocyte cell surface, the site of primary pathology (Payne, et al. 2005).

Pernicious anemia—autoimmune disorder characterized by anemia due to maladsorption of vitamin B12. Today, the best tests for diagnosing pernicious anemia are the vitamin B12 level, folic acid level, methylmalonic (MMA) level, and antibody tests for antibodies to intrinsic factor and parietal cells. Levels of MMA are elevated in both serum and urine before levels of vitamin B12 become abnormally decreased or symptoms of deficiency appear. The blood test for MMA is considered superior to the urine measurement (Greenwood and Sentry, 2007).

Primary biliary cirrhosis—an organ-specific autoimmune disease that predominantly affects women and is characterized by chronic, progressive destruction of small intrahepatic bile ducts with portal inflammation and ultimately fibrosis, leading to liver failure in the absence of treatment. The serologic hallmark of PBC is the presence of auto-antibodies to mitochondria, especially to the E2 component of the pyruvate dehydrogenase complex (PDC). Current theories on the pathogenesis of PBC favor the hypothesis that the disease develops as a result of an inappropriate immune response following stimulation by an environmental or infectious agent. The pathogenetic mechanism is believed to be caused by a defect in immunologic tolerance, resulting in the activation and expansion of self-antigen specific T and B lymphocyte clones and the production of circulating autoantibodies in addition to a myriad of cytokines and other inflammatory mediators. This leads to ductulopenia and persistent cholestasis, by developing end-stage hepaticcell failure (Reshetnyak, 2006).

Rheumatoid arthritis—a heterogeneous autoimmune disorder wherein the immune system attacks the bone joints. In asymptomatic patients and in patients with undifferentiated arthritis, the presence of anti-cyclic citrullinated peptide (CCP) antibodies is a predictor of progression to RA (Van Gaalen, et al. 2000). Other antibody reactivities include those against heat-shock proteins (Hsp65, Hsp90, DnaJ, and BiP), heterogeneous nuclear RNPs A2/B1 and D, annexin V, calpastatin, type II collagen, glucose-6-phosphate isomerase (GPI), elongation factor, and human cartilage gp39 (Van Boekel, et al. 2002).

Reiter's syndrome—autoimmune attack on various body systems in response to a bacterial infection and the body's confusion over the HLA-B27 marker. Other polymorphic determinants of MHC class I antigens might play a critical role in the pathogenesis of Reiter's syndrome (Shimamoto, et al. 2000).

Sjögren's syndrome—autoimmune disorder in which immune cells attack and destroy the exocrine glands that produce tears and saliva. Antibody self-reactivities include anti-fodrine and anti-salivary duct antibodies, rheumatoid factor, especially of the IgA isotype, and anti-nuclear antibodies, most notably anti-Ro/SSA and anti-La/SSB antibodies (Youinou, et al. 2005).

Systemic lupus erythematosus—a chronic autoimmune disease wherein the immune system becomes hyperactive and attacks normal tissue—this results in inflammation an brings about symptoms. About 90% of people who have lupus are young women in their late teens to 30s, but children (mostly girls) and older men and women can also be affected. The number and variety of antibodies that can appear in lupus are greater than those in any other disorder. These antibodies, which are the underlying physiologic problem in lupus, along with other unknown factors, determine which symptoms develop. However, the levels of these antibodies may not always be proportional to the person's symptoms. Laboratory tests can help doctors confirm the diagnosis. A blood test can detect antinuclear antibodies, which are present in almost all people who have lupus (http://www.merck.com/mmhe/sec05/ch068/ch068b.html).

Temporal arteritis—also known as giant cell arteritis—inflammation of blood vessels—most commonly the large and medium arteries of the head. Anticardiolipin antibody levels predict flares and relapses in patients with giant-cell (temporal) arteritis (Kerleau, et al. 1994).

Warm autoimmune hemolytic anemia—characterized by IgM attack against red blood cells. In the warm antibody type, the autoantibodies attach to and destroy red blood cells at temperatures equal to or in excess of normal body temperature. One study showed that the peak incidence of AIHA was in the first 4 years of life. No sex predominance was noted. Warm AIHA was the most common type of acquired immune hemolytic anemia; it comprised 64 of the 100 patients, whereas 26 patients showed a cold AIHA (Vaglio, et al. 2007).

Wegener's granulomatosis—form of vasculitis that affects the lungs, kidneys and other organs. It is a type of vasculitic syndromes that all feature the presence for an abnormal type of circulating antibody termed ANCAs (antineutrophil cytoplasmic antibodies) and affect small and medium-sized blood vessels (Aries, et al. 2007).

Diseases Suspected to be Linked to Autoimmunity

Alopecia universalis—suspected autoimmune disease in which the body's white blood cells attack hair and result in total baldness. Its association with other autoimmune disorders renders an autoimmune pathogenesis very likely, the targeted antigen being private to the hair follicle (Seifert, et al. *Blood.* 2005).

Behcçet's disease—multi-system condition where the immune system produces inflammation in bodily tissues, primarily causing vasculitis. Behcet's is one of the few forms of vasculitis in which there is a known genetic predisposition. The presence of the gene HLA-B51 is a risk factor for this disease. However, it must be emphasized that presence of the gene in and of itself is not enough to cause Behcet's: many people possess the gene, but relatively few develop Behcet's (http://vasculitis.med.jhu.edu/typesof/behcets.html).

Chagas disease—believed in the chronic phase to be result from homology of a *Trypanosoma cruzi* antigen to body tissue—resulting in a delayed autoimmune reaction leading to Chagasic cardiopathy (cardiomegaly), volvulus or constipation, and ultimately, death. Chagas disease afflicts about 30% of the 20 million people infected with T cruzi in South America (Marin-Neto, et al. 2007).

Chronic fatigue syndrome—a disorder whose primary symptom is usually intense fatigue—likely has multiple causes—some maintain that autoimmune damage to the brain stem is the principal mechanism in a significant subset of cases. Chronic fatigue syndrome is a disorder characterised by prolonged fatigue and debility and is mostly associated with post-infection sequelae although ongoing infection is unproven. Immunological aberration is likely and this may prove to be associated with an expanding group of vasoactive neuropeptides in the context of molecular mimicry and inappropriate immunological memory. Vasoactive neuropeptides including vasoactive intestinal peptide (VIP) and pituitary adenylate activating polypeptide (PACAP) belong to the secretin/glucagon superfamily and act as hormones, neurotransmitters, immune modulators and neurotrophes. They are readily catalysed to smaller peptide fragments by antibody hydrolysis. They and their binding sites are immunogenic and are known to be associated with a range of autoimmune conditions. Vasoactive neuropeptides are widely distributed in the body particularly in the central, autonomic and peripheral nervous systems and have been identified in the gut, adrenal gland, reproductive organs, vasculature, blood cells and other tissues. All documented symptoms of CFS are explained by vasoactive neuropeptide compromise, namely fatigue and nervous system dysfunction through impaired acetylcholine activity, myalgia through nitric oxide and endogenous opioid dysfunction, chemical sensitivity through peroxynitrite and adenosine dysfunction, and immunological disturbance through changes in immune modulation. Perverse immunological memory established against these substances or their receptors may be the reason for the protracted nature of this condition (Staines, 2004).

Dysautonomia—malfunction of the autonomic nervous system—including such disorders as postural orthostatic tachycardia syndrome. Post-viral autoimmune damage appears to be a frequent cause. Acute autonomic neuropathy can affect parasympathetic, sympathetic, and enteric nerves or neurons and is associated with antibodies to ganglionic nicotinic acetylcholine receptors. These antibodies appear to be causative based on a rabbit immunization model and serum transfer studies from patients and animals (Etienne and Weimer, 2006).

Endometriosis—common medical condition wherein the tissue lining the uterus is found outside the uterus, typically affecting other organs in the pelvis—can lead to serious health problems, primarily pain and infertility. Endometriosis and polycystic ovary syndrome (PCOS) are associated with higher values of anti-FSH-immunoglobulin (Ig)A, anti-V14D-IgA, and endometriosis with anti-V14D-IgG. These data suggest that anti-FSH-IgA could be a marker of ovarian disorders that cause infertility (Haller, et al. 2005).

Hidradenitis suppurativa—rare skin disease in which apocrine sweat glands become severely inflamed. A reduction in the percentage of NK cells over time and a lower monocyte response to triggering by bacterial components is observed in patients with hidradenitis suppurativa. Further research is needed to clarify if these changes are connected to an autoimmune mechanism in the pathogenesis of hidradenitis suppurativa (Giamarellos-Bourboulis, et al. 2007).

Interstitial cystitis—a urinary bladder disease characterized by any of the following symptoms—pelvic pain, urinary frequency, urgency, pain with sexual intercourse, and pain with urination. Interstitial cystitis (IC) has been deemed by some authors as a local manifestation of a systemic disease, particularly one of the autoimmune disorders (Porru, et al. 2005).

Lyme disease—caused by *Borrelia burgdorferi*—characterized by intermittent bouts of arthritis with severe joint pain and swelling. Some patients may develop chronic neurological complaints months to years after infection including shooting pains, numbness or tingling of hands or feet, and problems with concentration and short term memory. Although the causative agent of Lyme disease is definitively known to be the tick-borne spirochete, *Borrelia burgdorferi*, the etiology of chronic joint inflammation that ensues in a subset of patients remains less well understood. Persistence of arthritis after apparent eradication of the spirochete suggests an autoimmune reaction downstream of the original bacterial infection. Research has identified cytokeratin 10, present in synovial microvascular endothelium, as a target ligand and a putative autoantigen in chronic, antibiotic treatment-resistant Lyme arthritis. Furthermore, there is cross-reactivity between cytokeratin 10 and a prominent *B. burgdorferi* Ag, outer surface protein A. Release of the self protein in the context of inflammation-induced tissue injury and the resulting in situ response to it could set in motion a feed-forward loop, which amplifies the inflammatory process, thereby rendering it chronic and self-perpetuating, even in the absence of the inciting pathogen (Ghosh, et al. 2006).

Neuromyotonia—spontaneous muscular activity resulting from repetitive motor unit action potentials of peripheral origin. It develops as a result of both acquired and hereditary diseases. The acquired form is more frequent and is usually caused by antibodies against neuromuscular junction. About 40% of patients with acquired neuromyotonia will have detectable voltage-gated potassium-channel antibodies. Clinical, electrophysiological and immunological measurements are important in defining the phenotype of neuromyotonia, and other, milder forms of peripheral nerve hyperexcitability (Maddison, 2006).

Psoriasis—a skin disorder in which rapidly-multiplying skin cells produce itchy, scaly inflamed patches on the skin. Psoriasis is a common chronic inflammatory skin disease, the study of which might also be of considerable value to the understanding of other inflammatory and autoimmune-type diseases, such as rheumatoid arthritis, inflammatory bowel disease, multiple sclerosis and diabetes mellitus. There is clear evidence that T cells and dendritic cells have a central role in psoriasis (Boyman, et al. 2007).

Sarcoidosis—disease wherein granulomas can form anywhere in the body, but particularly in the lungs. Various autoimmune diseases have been reported to occur in patients with sarcoidosis (Takahashi, et al. 2006). In one study The prevalence of *Chlamydophila pneumoniae*-specific antibodies in bronchoalveolar lavage fluids was significantly higher in sarcoidosis patients for IgG and IgA (IgG: 74.4%; IgA: 46.2%) compared to controls (IgG: 14.7%; IgA: 14.7%) (Gaede, et al. 2002).

Schizophrenia—mental disease characterized by impairments in the perception or expression of reality and by significant social or occupational dysfunction. Initial investigations of the possible interaction between schizophrenia and the immune system began in the early 1900s and have proceeded in a rather halting fashion because of the methodological challenges faced by investigators. However, a confluence of recent data suggests that activation of the inflammatory response system, the cellular immune system, and the humoral immune system may be present in some patients with schizophrenia. Some of the most compelling data support the hypothesis that minor levels of immune activation may be associated with acute psychotic exacerbations. However, a second body of evidence suggests that some individuals with schizophrenia may have chronic, evolving autoimmune processes (Rapaport and Delrahim, 2001).

Scleroderma—chronic disease characterized by excessive deposits of collagen. Progressive systemic scleroderma can be fatal—the local type of the disease is not serious. Autoantibodies to centromeric proteins are commonly found in sera of limited scleroderma and other rheumatic disease patients. Utilizing samples from 263 anti-centromere immunofluorescence positive patients, 93.5% were found to have anti-CENP-A reactivity and 95.4% had anti-CENP-B reactivity by ELISA. Very few patient samples exclusively targeted CENP-A (2.7%) or CENP-B (4.2%) (Akbarali, et al. 2006).

Ulcerative colitis—an inflammatory disease of the bowel that usually affects the distal end of the large intestine and rectum. Complement activation observed in relation to epithelium-bound IgG1 in ulcerative colitis indicates that the surface epithelium is subjected to immunological attack by an autoimmune reaction. These luminal deposits regularly contain terminal cytotoxic complement, and often also C3b as a sign of persistent activation. Comparison of identical twins, discordant with regard to ulcerative colitis, suggests that the markedly skewed local IgG1 response seen in this IBD entity may be genetically determined (Brandtzaeg, et al. 2006). One study shows that in these models, IL-23 is essential for manifestation of chronic intestinal inflammation (Yen, et al. 2006).

Vitiligo—spontaneous loss of pigment from areas of skin—anti-melanocyte antibodies have been detected in some cases of vitiligo. Mannose binding lectin (MBL) is a calcium dependent lectin that causes predisposition to infections and autoimmune diseases. One study aimed to examine the presence of any association between MBL2 gene variants and vitiligo. Results suggested that codon 54 polymorphism in the MBL2 gene may play a role in susceptibility to vitiligo (Onay, et al. 2007).

TABLE 1

Female:Male Ratios in Autoimmune Disease

| | |
|---|---|
| Hashimoto's disease/hypothyroiditis | 50:1 |
| Systemic lupus erythematosis | 9:1 |
| Sjogren's syndrome | 9:1 |
| Antiphospholipid syndrome | 9:1 |
| Primary biliary cirrhosis | 9:1 |
| Mixed connective tissue disease | 8:1 |
| Chronic active hepatitis | 8:1 |
| Grave's disease/hyperthyroiditis | 7:1 |
| Rheumatoid arthritis | 4:1 |
| Scleroderma | 3:1 |
| Myasthenia gravis | 2:1 |
| Multiple sclerosis | 2:1 |
| Chronic idiopathic thrombocytopenic purpura | 2:1 |

Exemplary Immunoscore Assays for Autoimmunity Panel

Panels to examine levels/exposure in individuals:
Antibodies
Cytokines
Autoimmunity susceptibility genes
Environmental factors leading to autoimmunity (obtained by polling/surveillance)

In exemplary embodiments of the present invention, ImmunoScore assays for autoimmunity can include dozens of screening tests run on individual patients from "cradle to grave." Ideally, individuals would first be screened at the time of entry to the public school system to obtain baseline measurements. Those individuals with ImmunoScores of concern or familial history of autoimmune disease can be screened more frequently than other individuals as they aged. At the time of college entry/high school graduation, it would be more imperative to screen everyone for an adult baseline ImmunoScore for autoimmune disease predictability. The timing of the screening can, for example, thereby precede development of most autoimmune diseases in susceptible patients.

An exemplary autoimmune baseline screening panel follows. This screening can be performed on the young adult population. Females, particularly with a family history of autoimmune disease should be screened more regularly than males. Pregnant females could routinely be screened during pregnancy to monitor any possible onset of autoimmune symptoms. Males could again be screened at the 50 year old checkup as a means of gathering another appropriate timepoint to their personal ImmunoScore record.

In exemplary embodiments of the present invention, some or all of the following assays can be included in an ImmunoScore Autoimmune Screening/Diagnostic Panel:

1. Antibody Assays
   anti-myelin oligodendrocyte glycoprotein (MOG) antibody
   anti-measles virus antibodies
   anti-21-hydroxylase antibody
   anti-adrenal cortex antibody
   anti-*Klebsiella* antibodies
   anti-cardiolipin antibody
   anti-lupus anticoagulant antibody
   anti-beta-2-glycoprotein antibody
   anti-hematopoietic precursor cell antibodies
   anti-soluble liver antigen antibody
   anti-RO/SSA antibody
   anti-endomysial antibody (AEA)
   anti-tissue transglutaminase (anti-tTG)
   anti-*Saccharomyces cerevisiae* antibody (ASCA)
   anti-neutrophil antibody (pANCA)
   anti-porin protein C of *E. coli* antibody (anti-OmpC)
   anti-glutamic acid decarboxylase antibody (GADA) particularly anti-65 kDa isoform
   anti-protein tyrosine phosphatase-like molecule antibody (IA-2A)
   anti-glomerular basement membrane (GBM) antibody
   anti-neutrophil cytoplasmic antigens (ANCA)
   anti-GD1a/GD1b complex antibody
   anti-LM1 antibody
   anti-GM1 antibody
   anti-thyroglobulin antibody
   anti-nuclear antibodies (ANA)
     lupus anticoagulant (LA) antibody
     anti-phospholipid (aPL)
     anti-SS/A antibody
     anti-SS/B antibody
     anti-Sm antibody
     anti-RNP antibody
     anti-Jo1 antibody
     anti-Sc1-70 antibody
     anti-dsDNA antibody anti-Centromere B antibody
anti-Histone antibody
anti-alphaIIbbeta 3 IgM
anti-acetylcholine receptor (anti-AChR) antibody
anti-muscle-specific tyrosine kinase (MuSK) antibody
anti-neuroleukin antibody
anti-gliadin antibody
anti-CV 2 antibody
anti-GQ1b IgG
anti-GQ1b IgM
anti-thyroid peroxidase antibody
keratinocyte cell-surface antibodies
   anti-BP 180 (bullous pemphigoid antigen 2)
   anti-BP 230 (bullous pemphigoid antigen 1)
anti-intrinsic factor antibody
anti-parietal cell antibodies
anti-mitochondrial antibodies
   in particular, anti-E2 component of pyruvate dehydrogenase complex (PDC) antibody
anti-cyclic citrullinated peptide (CCP) antibody
anti-heat shock protein (HSP) 65 antibody
anti-HSP 90 antibody
anti-DnaJ antibody
anti-BiP antibody
anti-heterogeneous nuclear RNP A2/B1 antibody
anti-heterogeneous nuclear RNP D antibody
anti-annexin V antibody
anti-calpastatin antibody
anti-type II collagen antibody
anti-glucose-6-phosphate (GPI) antibody
anti-elongation factor
anti-human cartilage gp39 antibody
anti-*Chlamydia* antibodies
anti-La/SSB antibody
anti-fodrine antibody
anti-salivary duct antibodies
anti-Red Blood Cell (RBC) IgM
anti-neutrophil cytoplasmic antibodies
anti-thyroid microsomal antibody (ATMA)
anti-smooth muscle antibody (SMA)
anti-mitochondrial antibody (AMA)
anti-extractable nuclear antigens (ENA) antibody
anti-actin antibody (AAA)
anti-hair follicle antibodies
  anti-anagen matrix antibody
  anti-cuticle antibody
  anti-cortex keratinocytes antibody
  anti-melanocyte nuclear antigen
anti-human dermal microvascular endothelial cells (HDMEC) antibodies
  anti-81 kDa HDMEC antigen, in particular
anti-*Trypanosoma cruzi* antibodies
anti-oleic acid IgM
anti-palmitic acid IgM
anti-myristic acid IgM
anti-azelaic acid IgM
anti-malondialdehyde IgM
anti-aceylcholine IgM
anti-S-farnesyl-L-cysteine IgM
anti-ganglionic nicotinic acetylcholine receptor antibody
anti-follicle-stimulating hormone (FSH) IgA
anti-V14D IgA
anti-V14D IgG
anti-cytoskeleton-associated protein 4/p63 (CKA4/p63)-specific antibody
anti-cytokeratin 10 antibody
anti-Voltage-Gated Potassium Channels (VGKCs) antibodies
anti-*Chlamydia pneumoniae* antibodies
anti-human cytomegalovirus (CMV) antibodies
anti-*Toxoplasma gondii* antibodies
anti-CENP-A antibody
anti-CENP-B antibody 2. Cytokine Assays Interleukin-1α (IL-1α)
IL-1β
IL-2
IL-4
IL-5
IL-6
IL-7
IL-8
IL-10
IL-12
IL-13
IL-15
IL-18
Interferon α (IFN-α)
IFN-γ
TNF-α
G-CSF
MCP-1
MIP-1α
MIP-1β
MIP-3α
MIP-3β
EGF
VEGF
TNFRII
EGFR 3. Toll-like Receptor (TLR) genetic variants

TLR 2
TLR 3
TLR 4
TLR 7
TLR 8
TLR 9

4. HLA Haplotype screening

HLA A24
HLA B8
HLA B18
HLA B27
HLA B51
HLA B60
HLA B62
HLA DR2
HLA DR3
HLA DR4
HLA DR5
HLA DR7

5. Protein isoforms/genetic polymorphisms/serum protein levels

Apolipoprotein E isoforms
  apo E2
  apo E3
  apo E4
Serum Apolipoprotein A-IV level
Mannose-binding lectin (MBL) polymorphism
Serum Haptoglobin level
Serum Transthyretin level
Serum Fibrinogen level
Serum Vitamin B12 level
Serum Folic acid level

19. 10. Immunoscore Diagnostic Panel: Aging, Longevity, Cancer and Human Cytomegalovirus Old age is accompanied by an increased incidence of infection and poorer responses to vaccination. A progressive decline in the integrity of the immune system is one of the physiologic changes during mammalian aging. Perhaps the most profound clinical impact of age on the immune system concerns the response of the elderly to vaccination (Pawelec, 2005). An immune risk phenotype (IRP) was described wherein individuals possessed high CD8 and low CD4 numbers and poor proliferative response (Wikby, et al. 2005). Characteristics of the IRP are listed in Table I (Vasto, et al. 2007). The IRP consists of a cluster of these parameters, not each parameter individually. Which are the most important and which additional factors are involved remains to be determined.

Lifelong and chronic antigenic load may represent the major driving force for immunosenescence, which impacts on human lifespan by reducing the number of virgin antigen-non experienced T cells, and results in their replacement by expanded clones of antigen-experienced effector and memory T cells which display a late differentiation phenotype. Gradually, the T cell population shifts to a lower ratio of naïve cells to memory cells, the thymus releases fewer naïve T cells with age and those T cells remaining, especially the $CD8^+$ subset, also show increased oligoclonality with age. Presumably, the repertoire of cells available to respond to antigenic challenge from previously encountered pathogens shrinks. In addition, older organisms often are overrun by memory cells that carry a single type of T cell receptor, i.e. the clonal expansion referred to above. Therefore, the memory cells from old individuals might recognize a limited set of antigens despite being plentiful in number, and in addition, are likely to show various degrees of dysfunctionality. Many of the clonal expansions filling the individual's immune system seem to result from previous infections by persistent viruses, especially CMV (Ouyang, et al. 2003b), but also, to a lesser extent EBV (Ouyang, et al. 2003a) and possibly other herpes viruses (Vasto, et al. 2007). A high number of $CD8^+$ cells are found to be specific for a single CMV epitope (Pawelec, et al. 2005; Pawelec, et al. 2004). In humans, the accumulation of CMV-specific T cells has been observed to reduce T cell immunity toward EBV infection (Khan, et al. 2004) and influenza vaccination (Trzonkowski, et al. 2003). Functional analyses performed with T cells from nonagenarians demonstrated that they were characterized by decreased functional capacity when compared with similar cells isolated from middle aged individuals (Hadrup, et al. 2006). This suggests that increased numbers of CMV-specific T cells could be the result of a compensatory mechanism enabling control of CMV despite lower functional capacity (Hadrup, et al. 2006). The biology of CMV infection in humans can be conceptualized as an evolutionary "negotiated" balance between viral mechanisms of pathogenesis, persistence, and immune evasion and the host cellular immune response (Sylwester, et al. 2005).

One of the immunodominant viral antigens recognized by CMV-specific $CD8^+$ T cells is derived from the 65-kDa phosphoprotein (pp 65). Samples from octogenarian and nonagenarian populations revealed that a large number of $CD8^+$ $CD28^-$ cells were specific for the pp65 antigen. These findings imply a co-dominant role of CMV as a cause for a compromised immunity in old age (Vasto, et al. 2007). A second immunodominant antigen is the IE-1 antigen. Epitope specificity and immunodominance of CD8 T cells against IE-1 and pp 65 are comparable in acute infection and long-term memory often with marked focusing of responses that are probably established very early on. However, the kinetics of CD8 T cell responses for these antigens expressed at opposite ends of the replicative cycle of the virus reflect the different modes of antigen presentation, which probably depend on levels of viral activity occurring over the lifetime of the host (Khan, et al. 2007). Other studies have suggested an extraordinary complexity of CMV-specific T cell responses to chronic infection (Sylwester, et al. 2005). This complexity complicates efforts to understand the basis of the CMV immune balance and, in clinical practice, to determine the thresholds that define the boundary between controlled vs. progressive CMV infection in immunocompromised subjects and between normal and excessive CMV-specific immunity in the elderly (Sylwester, et al. 2005).

There are a suggested sequence of stages for IRP individuals that begin with the acquisition of CMV infection in earlier life, followed by generation of $CD8^+CD28^-$ cells to control persistent CMV infection, and eventually the development of an IRP. Recently, a group of rare individuals was discovered who moved out of the IRP category by a process of immune suppression, including increases in IL-6 and IL-10 and decreases in the number of $CD3^+CD8^+CD28^-$ cells (Wikby, et al. 2006).

There are two theories regarding the evolution of senescence—mutation accumulation and antagonistic pleiotropy. The mutation accumulation theory of senescence postulates that there are numerous loci subject to mutation to deleterious alleles, whose effects on survival or other components of fitness are restricted to narrow bands of ages (Rose, 1991). The equilibrium frequencies of such deleterious alleles will be higher the later in life in which they act (Charlesworth, 1994). The alternative path involves antagonistic pleiotropy, according to which genes that increase early performance are likely to become established in a population even if they have adverse effects on later performance (Williams, 1957; Rose, 1991). Antagonistic pleiotropy was originally defined as meaning opposite effects of the same allele at different ages (Williams, 1957). Antagonistic pleiotropy in evolutionary theory usually refers to opposite effects of a genotype on fecundity and survival. The existence of trade-offs between these two components of Darwinian fitness was proposed to explain the evolution of senescence and the maintenance, via the creation of the heterozygous advantage, of polymorphism at loci involved in the determination of both traits (Kirkwood and Rose, 1991). In a later model, antagonistic pleiotropy involved, instead, relative survival values of a genotype at different ages (Toupance, et al. 1998). The two theories are not mutually exclusive, and modeling exercises have examined the validity of each (Charlesworth and Hughes, 1996).

An example of antagonistic pleiotropy would be the high expression of testosterone in a male gorilla, which could lead to increased aggression and strength that would allow the male to become dominant and mate more frequently, but may eventually lead to a shortened lifespan due to increased atherosclerosis. Recent studies at the molecular level have suggested that cellular senescence may be antagonistically pleiotropic because it prevents tumorigenesis, but also contributes to organismic aging (Troen, 2003).

In one study, it was suggested that cellular senescence was antagonistically pleiotropic, protecting from cancer early in life, but promoting carcinogenesis in aged organisms (Krtolica, et al. 2001). Another study (Hughes, et al. 2002) found the AP (antagonistic pleiotropy) model is consistent with the existence of a few genes with individually large effects on late-life fitness, whereas the MA (mutation accumulation) process should lead to the maintenance of may deleterious alleles at intermediate frequencies within populations and these alleles can have individually small effects on late-life performance and health. Current methods of identifying aging genes (such as mutation studies and quantitative trait locus-mapping experiments) are most effective in finding alleles of large effect, and even well designed studies will probably miss genes with small effects. Novel approaches are needed to find such genes.

Cancer rates also increase sharply with age in both sexes, and the majority of cases of cancer occur in patients over the age of 65. Tumor progression is a complex process that depends on interactions between tumor cells and host cells. The inflammatory aspect of the host response is of particular interest because it includes the release of pro-inflammatory cytokines, some of which may promote tumor growth and hence influence survival. Some kinds of solid tumors are likely affected by regulatory cytokine genotypes. In particular, pro-inflammatory genotypes characterized by a low IL-10 or a high IL-6 producer seem to be associated with a worse clinical outcome (Caruso, et al. 2004). On the other hand, recent evidence has linked IL-10 and IL-6 cytokine polymorphisms to longevity. In fact, individuals who are genetically predisposed to produce high levels of IL-6 have a reduced capacity to reach the extreme limits of human life, whereas the high IL-10 producer genotype is increased among centenarians (Caruso, et al. 2004). The opposite effect of IL-6 and IL-10 in cancer and longevity is intriguing. Inflammatory genotypes may be both friends and enemies. The immune system has evolved to control pathogens, therefore pro-inflammatory responses are likely to be evolutionarily programmed to resist fatal infections, and a high IL-6 or a low IL-10 production is associated with increased resistance to pathogens. However, decreased level of IL-6 or increased level of IL-10 might better control inflammatory responses and cancer development. These conditions might result in an increased chance of long life survival in an environment with reduced pathogen loads (Caruso, et al. 2004).

Most tumor suppressor genes can be classified as either caretakers or gatekeepers (Kinzler and Voglestein, 1997). Caretaker tumor suppressor genes prevent cancer by protecting the genome from mutations. They generally act by preventing DNA damage or optimizing DNA repair. In addition to preventing cancer, genes that help maintain genomic integrity also prevent or retard the development of other aging phenotypes and age-related pathologies (Hasty, et al. 2003). Gatekeeper tumor suppressors, by contrast, prevent cancer by acting on intact cells—specifically, mitotic cells that are at risk for neoplastic transformation. Gatekeepers can virtually eliminate potential cancer cells by inducing programmed cell death (apoptosis). Alternatively, they can prevent potential cancer cells from proliferating by inducing permanent withdrawal from the cell cycle (cellular senescence). Although little is known about how cells choose between apoptotic and senescence responses, there is little doubt that both responses are crucial for suppressing cancer (Campisi, 2001; Green and Evan, 2002).

Increasing evidence suggests that the rise in cancer with age results from a synergy between the accumulation of mutations and age-related, pro-oncogenic changes in the tissue milieu. Most age related cancers derive from epithelial cells. Epithelial tissues are supported by a stroma, which is composed of extracellular matrix and several cell types. One age-related change that occurs in epithelial tissues is the accumulation of senescent cells. Cellular senescence is a potent tumor suppressive mechanism that irreversibly arrests proliferation in response to damage or stimuli that put cells at risk for neoplastic transformation. Senescent cells secrete factors that can disrupt tissue architecture and stimulate neighboring cells to proliferate. The suggestion has been made that senescent cells can create a tissue environment that synergizes with oncogenic mutations to promote the progression of age-related cancers (Krtolica and Campisi, 2003). The recent evidence indicates that cellular senescence may be an example of evolutionary antagonistic pleiotropy.

A major difference between microbial pathogens and tumors as potential vaccine targets is that cancer cells are derived from the host, and most of their macromolecules are normal self-antigens present in normal cells. To take advantage of the immune system's specificity, antigens must be found that clearly mark the cancer cells as different from host cells. An area generating much interest is the possibility of overcoming mechanisms that downregulate or attenuate the immune response, as is depicted in FIG. 5D (Berzofsky, et al. 2004b). With reference thereto, FIG. 5D illustrates negative regulation of tumor immunosurveillance and antitumor immune responses. FIG. 5D(A) depicts $CD4^+CD25^+$ T regulatory cells, induced by peptide presented by class II MHC molecules in the presence of IL-2, may inhibit induction of effector $CD4^+$ or $CD8^+$ T cells by a contact-dependent mechanism, possibly involving cell surface and/or secreted TGF-$\beta$, and FIG. 5D(B) illustrates how $CD4^+$ NKT cells may be induced by tumor glycolipid presented by CD1d to secrete IL-13, which stimulates $Gr-1^+CD11b^+$ myeloid cells to produce TGF-0, which inhibits induction of $CD8^+$ CTLs mediating tumor immunosurveillance. TGF-$\beta$ may also inhibit CD4+ T cells (not shown). Blockade of other mechanisms can improve immunosurveillance and the response to vaccines. Other suppressor or negative regulatory cells have been described in other contexts, but not as well study in the context of cancer (Berzofsky, et al.). Such mechanisms may have evolved to reduce inflammation and immunopathology or to prevent autoimmunity. Tumors have co-opted these mechanisms to evade immunosurveillance.

Thus, it has been postulated that the excess of dysfunctional CD8 T cells is indirectly immunosuppressive by filling the "immunologic space" and shrinking the T-cell repertoire for new antigens, as well as directly suppressive via cytokine secretion. It is associated with the IRP predicting two and four year mortality in longitudinal studies of very old people. It is hypothesized that deletion of such accumulations of dysfunctional cells would be beneficial to the individual. It may be possible to distinguish functional CMV-specific cells (which are essential to maintain immunosurveillance) from dysfunctional ones by their expression of certain surface molecules. This, coupled with methods directed at reinvigorating the thymus (such as, for example, the use of interleukin 7), and targeting CMV by pharmacologic and immunotherapeutic interventions might result in the immunorejuvenation sufficient to take elderly individuals out of the risk category and thereby extend healthy longevity (Pawelec, et al. 2006). Animal models suggest that IL-7 improves immune reconstitution through increasing thymic output and, perhaps more importantly, through antigen-independent homeostatic driven proliferation in the periphery (Sasson, et al. 2006). A study in old Rhesus macaques showed that treatment of the elderly with IL-7 may provide an effective therapy to improve the immune system (Aspinall, et al. 2007).

In rural Gambians, the season of birth strongly predicts adult mortality. Those born during the harvest season have longer life spans than do those born during the hungry season, and the deaths associated with infectious diseases suggest permanent early-life influences on immunity (Ngom, et al. 2004). One group studied thymic size and output in Gambian infants born in either the hungry or the harvest season by measuring signal-joint T cell receptor-rearrangement circles (sjTRECs) at birth and at 8 weeks of age. They found that by 8 weeks of age, those born in the hungry season had significantly lower sjTREC counts (indicating poor immune function) than did those born in the harvest season. These results correlated directly with lower ELISA measurements of IL-7 in mothers' breast milk (Ngom, et al. 2004). This research group speculated that these data show a plausible pathway linking external season insults to mothers with thymic development in their infants, which suggests possible implications for long-term programming of immunity.

ImmunoScore Measurements and Applications. Thus, there is a balance between viral mechanisms of pathogenesis, persistence, and immune evasion and the host cellular immune response. The immunologic basis of this balance has not been completely characterized. The nature and threshold of CMV-specific T cell responses required for long-term CMV containment yet remain to be defined. This information would facilitate identification of highly susceptible individuals and provide a specific target for immunotherapeutic approaches designed to establish, maintain, or restore immunologic protection (Sylwester, et al. 2005). There seem to be clinical consequences to an overly robust CMV-specific T cell response. An obvious prerequisite for a better understanding of what constitutes insufficient or excessive CMV-specific T cell immunity is the ability to evaluate the overall CMV-specific T cell response in infected individuals. Future longitudinal studies would benefit from combining data on viral reactivation and primary infection with immunological monitoring (Hadrup, et al. 2006). The ImmunoScore diagnostic and database systems would provide just such an opportunity for data collection and monitoring longitudinal data collection.

Although CMV seropositivity appears to be one of the driving forces for induction of CD8 T cell clonality, this is not currently detectable in the middle-age population (Hadrup, et al. 2006). The influence of CMV on clonality only becomes relevant at a detectable level in the elderly. Superior detection capabilities available through the ImmunoScore technology might lead to earlier detection of possible immune depletion as individuals pass through middle age.

ImmunoScore technology by its nature of compiling individual patient data would offer the opportunity for longitudinal design of research studies. The longitudinal design is a superior alternative to the cross-sectional method for conducting ageing research, but it has seldom been used due to extensive costs as studies are currently conducted. The ImmunoScore system would naturally build a longitudinal component into patient care at no increased initial cost. The database would yield important insights into ageing and all its implications at a lower cost and dramatically improve healthcare.

Questions have been raised concerning CMV infection and its relationship to the IRP (Vasto, et al. 2007). Uncertainties that require clarification are: Is there an immunogenetic component influencing the IRP phenotype that might explain the different degree of CMV clonal expansion vs. non-IRP phenotype? May this difference depend on social and/or environmental factors? Might the genetic or environmental component affect the degree of clonal expansion of CMV in IRP individuals? What can be the main cause of death in IRP? Can IRP selection be predictive in young as well as in old individuals? Is it possible to revert/prevent accumulation of CMV-specific cells?

These are all questions that can, in exemplary embodiments of the present invention, be addressed by the application of ImmunoScore diagnostic and database technologies.

Immunogenetic components can, for example, be monitored using unique technology designed to investigate single nucleotide polymorphisms (SNPs) rapidly and those data could be stored in the ImmunoScore central database. Additionally, social and environmental factors can be part of the ImmunoScore demographic data collected at routine patient visits to their physicians. The accumulation of these data on the ImmunoScore database would yield potential relationships regarding environmental and social factors to the IRP.

Careful monitoring of the ImmunoScore database would shed more light onto environmental and/or genetic factors contributing to the clonal expansion of CMV T cells in IRP individuals and the non-IRP individuals.

As the ImmunoScore data collection system is envisaged as a cradle-to-grave system of healthcare, the cause of death in IRP individuals can be collected and collated. Preliminary indications are that IRP selection is likely to be predictive in the young as well as in the very elderly. The ImmunoScore cradle-to-grave philosophy of patient data tracking can be invaluable in assessing these issues. Additionally, prevention/reversion of the accumulation of CMV-specific T cells would seem an issue of paramount importance. Preliminary studies in animal models regarding judicious use of IL-7 have been promising. ImmunoScore can, for example, track treatments and even shed light on when such treatments should commence in the life of the afflicted individuals.

CMV Vaccine and Vaccines Against Chronic Viral Infections and Cancer. In a recent review of priorities for vaccine development, CMV was ranked in the highest of five tiers by the Institute of Medicine in the United States as a potentially cost-saving vaccine target (Stratton, et al. 2000). In general, CMV is acquired earlier in life in developing countries and among the lower socioeconomic strata of the developed countries (Stagno and Cloud, 1990). Recently, the seroepidemiology of CMV was examined in Australia (Seale, et al. 2006). The pattern of age-specific seroprevalence of CMV antibody, as provided in FIG. 5C, closely matched the pattern found from analysis of the exemplary CIP database described in Section II, below. Indeed, a review of CMV seroprevalence studies conducted around the world revealed that residents of developing countries have higher rates of CMV seropositivity than those of developed countries (Enright and Prober, 2004). The potential benefits of a CMV vaccine would include reduced transmission to pregnant women and less CMV disease due to primary infection or reactivation in organ transplant recipients and the immunosuppressed (Griffiths, et al. 2000).

It is possible that the development of a vaccine that is effective against viruses that cause chronic infection may require consideration of a paradigm different than those previously used for organisms causing acute infection (Berzofsky et al. 2004). In most cases of chronic viral infection, the immune response to the natural infection is not sufficient to eradicate that infection. The challenge for the $21^{st}$ century is to apply the latest fundamental knowledge in molecular biology, virology, and immunology to developing vaccines that are more effective at eliciting immunity than the natural infections and consequently, effective against chronic viral and other infectious diseases in addition to cancer, which do not fit the classic paradigm. ImmunoScore diagnostic and database tracking would be invaluable in analyzing the efficacy of a CMV vaccine, as well as vaccines developed against HIV, hepatitis C virus (HCV), human papilloma virus (HPV) and Epstein-Barr virus (EBV), among others.

As prophylaxis against acute infectious diseases, vaccines have been among the most cost-effective agents, saving many millions of lives. However, for treatment of chronic infections and cancer, vaccines have yet to achieve widespread success. Increased understanding of the immune system has raised new hope of harnessing the exquisite specificity of the immune system to attack cancer (Berzofsky, et al. 2004b). In exemplary embodiments of the present invention exemplary ImmunoScore diagnostic panels and database systems can add considerably to this knowledge base and can, for example, assist in intelligent vaccine design and monitoring of the efficacy of the vaccines as they are developed.

TABLE I

Characteristics of the Immune Risk Phenotype (IRP)

CD4:CD8 ratio <1
Poor T cell proliferative responses to mitogens
Increased $CD8^+CD28^-$ and $CD8^+CD57^+$ cells
Low B cell count
CMV seropositivity
Clonal expansion of CD8 cells carrying receptors for CMV
High proportion of dysfunctional cells amongst the CMV-specific CD8 cells C. Exemplary Immunoscore Superpanels
1. Middle School Student ImmunoPrint Super Diagnostic Panel In exemplary embodiments of the present invention, a middle school superpanel can, for example, comprise the following exemplary panels:
1.1 Persistent Immunity Induced by Childhood Vaccines
    This panel is described above in section A3.
1.2 Sexually Transmitted Disease (STD) Diagnostic Panel
    For children entering middle school (grades six through eight) a baseline determination for antibody levels to STDs is advisable. Recommended tests for ImmunoPrint measurement of immunity to STDs:
    Antibodies to *Chlamydia*—IgG, IgA, and IgM (3)
    Antibodies to HSV—IgG to HSV-1 and HSV-2 (2)
    DNA analyses of HPV types—particular emphasis on high-risk
    Antibody to *N. gonorrhoeae* (1)
    Antibody to *T. pallidum* (1)
    T-cell related response to *T. pallidum*
    Antibody to HIV
    T-cell related response to HIV
    Antibodies to GBS serotypes (at least 3)
    Measurement of Th1/Th2 cytokines (many as current evolving definitions)
    Antibodies to organisms that cause Urinary Tract Infection (UTIs)
        *Escherichia coli*
        *Staphylococcus saprophyticus*
        *Proteus mirabilis*
        *Klebsiella pneumoniae*
        *Enterococcus* species
        *Pseudomonas aeruginosa*
    Currently, there are no vaccines available for any of these STDs, with the exception of the Merck HPV vaccine. Until this situation is ameliorated as to a particular vaccine preventable disease, an ImmunoScore STD diagnostic panel would thus be to recommend treatments, track immunological response or provide other analyses, and not be used to recommend a vaccine or track the persistence of immunity conferred by it. Thus, in exemplary embodiments of the present invention an exemplary ImmunoScore database can, for example, generate correlates of protection information for all disease-causing organisms. As vaccines are developed, ImmunoScore diagnoses could, for example, be designed to examine antibody and other related immune responses to vaccine components.

*Chlamydia trachomatis* infection is the most commonly reported sexually transmitted disease in the United States, with the highest rates among adolescent females and young women. Because up to 70% of chlamydial infections in women are asymptomatic, routine screening and treatment of infected persons is essential to prevent pelvic inflammatory disease, infertility, ectopic pregnancy, and perinatal infections. The third U.S. Preventive Services Task Force (USPSTF) recommends that primary care physicians routinely screen all women whether or not they are pregnant if they:
    Are sexually active and aged 25 or younger.
    Have more than one sexual partner, regardless of age.
    Have had an STD in the past, regardless of age.
    Do not use condoms consistently and correctly, regardless of age.
According to studies reviewed by the third USPSTF:
    The cost of screening women who are not pregnant and who are at risk for chlamydial infection may be less than the cost of treating *Chlamydia* and its complications.
    Screening patients at greatest risk is more cost effective than screening all patients.
    DNA or RNA amplification tests are more sensitive than culture.
A low cost diagnostic test for *Chlamydia* infection or immune response to a *Chlamydia* vaccine would be a welcome addition to immune status determination by ImmunoPrint diagnostic testing.
    Herpes simplex virus type 2 (HSV-2) is the primary cause of genital herpes, a common sexually transmitted disease with at least 40 to 60 million infected individuals in the U.S. Medically serious complications of HSV are rare but constitute a significant burden, given the high rates of HSV seropositivity in the population. Many prophylactic and therapeutic vaccination approaches have been explored for the prevention or treatment of HSV infection. Infection induces both humoral and T-cell immunity. Vaccine candidates for HSV-2 infection include subunit vaccines, killed and live attenuated virus vaccines, and viral DNA vaccines.
    Human papillomaviruses (HPV) are small double-stranded DNA viruses that are responsible for pathological conditions ranging from benign skin warts to invasive cervical carcinomas. Cervical cancer is the second leading cause of cancer death among women worldwide, and more than 99% of cervical cancers contain HPV, particularly the high-risk HRP type 16 (HPV-16). Two HPV oncoproteins, E6 and E7, are consistently expressed in HPV-associated cancer cells and are responsible for their malignant transformation. These oncogenic proteins represent ideal target antigens for developing vaccines and immunotherapeutic strategies against HPV-associated neoplasms. More than 10,000 American women a year are diagnosed with cancer or precancerous cells caused by HPV, and 3,700 of them will die. Eighty times that number will die worldwide. An effective vaccine could prevent nearly all of those deaths. The CDC is currently considering an HPV vaccine for all children aged 12 years. A positive recommendation by the ACIP could start states thinking of requiring the vaccine for entry into middle school.
*Neisseria gonorrhoeae*, the causative agent or gonorrhea, is one of the most common sexually transmitted pathogens worldwide. Although a robust inflammatory response ensues during symptomatic infection, no apparent protective immunity is developed following infection, as shown in a male human challenge study and by the high incidence of recidivism among patients attending sexually transmitted disease clinics. The search for a vaccine against gonorrhea has been largely disappointing. In human vaccine trials, partially lysed gonococci, purified pilin, and purified porin were shown to be immunogenic, but all failed to elicit protection upon subsequent natural exposure. The lack of protective immunity is likely due, in part, to the capacity of many gonococcal surface antigens to undergo high-frequency phase and antigenic variation.

Individuals infected with *Treponema pallidum* subsp. *pallidum* develop specific immune responses that are able to clear millions of treponemes from sites of primary and secondary syphilis. Despite the fact that humans develop robust immune responses against *T. pallidum*, they can be infected multiple times. The response is a T-cell mediated delayed-type hypersensitivity response in which T cells infiltrate syphilitic lesions and activate macrophages to phagocytose antibody-opsonized treponemes. How treponemes from heterologous isolates can evade the recall response of a previously infected individual is unknown. Data from animal studies suggest that both antibodies and T cells play a role in protection but neither alone prevents infection. It is possible that antigenic diversity of *T. pallidum* accounts for the lack of heterologous protection. The *T. pallidum* repeat protein K (TprK) is a strong candidate for a treponemal factor involved in immune evasion. Epitope mapping studies revealed that, during experimental infection, T cells are directed to the conserved regions of TprK, while the antibodies are directed to the variable regions.

A safe, effective prophylactic human immunodeficiency virus (HIV) vaccine is urgently needed to curb the current AIDS epidemic. There are currently 40 million individuals in the world infected with HIV, and nearly 16,000 new infections occur worldwide each day. Effective HIV-1 vaccines must be capable of protecting immunized individuals from infection with a broad array of diverse viral variants. Attempts to develop a safe and effective AIDS vaccine have been slowed, in part, by the difficulty in clearly defining specific immune responses that can prevent infection and limit disease progression. This is in part due to the poor immunogenicity of the envelope glycoprotein, the tremendous variability of the virus, its ability to evade and impair the host's immune system, and its ability to persist by integrating into the host's immune system, and its ability to persist by integrating into the host's genome of a number of different cell types. It is generally believed that an effective HIV-1 vaccine must be capable of inducing neutralizing antibodies as well as strong cell-mediated immune responses in outbred populations.

Group B Streptococci (GBS) emerged dramatically in the 1970s as the leading cause of neonatal infection and as an important cause of maternal uterine infection. The burden from GBS disease in elderly persons has also increased. In 1996, the first national consensus guidelines were released. Since then, there has been a 70% reduction in early-onset neonatal GBS infection. In 2002, new national guidelines were released recommending:
  solely a screen-based prevention strategy
  a new algorithm for patients with penicillin allergy
  more specific practices in certain clinical scenarios
Yet clinical issues remain, including implementation of new diagnostic techniques, management of preterm rupture of membranes, use of alternative antibiotic approaches, improvement of compliance, prevention of low birth weight infants, emergence of resistant organisms, and vaccine development.

Urinary tract infections (UTIs) are a leading cause of morbidity and mortality and health care expenditures in persons of all ages. Sexually active young women are disproportionately affected, but several other populations, including elderly persons and those undergoing genitourinary instrumentation and catheterization, are also at risk. UTIs are the leading cause of gram-negative bacteremia (Orenstein and Wong, 1999).

Lymphocytes are the effector cells of acquired immunity. There are two T helper subsets, Th1 and Th2, based on two distinct cytokine profiles that resulted in the overall regulation of the immune response. The Th1 cell (with its associated cytokines: INF-$\gamma$, TNF-$\alpha$, IL-2, IL-12) is biased towards the cell-mediated side of immunity, effective against intracellular parasites, and its down regulation of Th2 can provide relief from allergic reactions due to IgE; but detrimental effects may result in autoimmunity and graft rejection. On the other hand, the Th2 cell (with its associated cytokines IL-4, IL-5, IL-6, IL-10, IL-13) favors humoral immunity, providing an effective correlate of protection for most vaccines, and its down regulation of Th1 can result in some benefit of tolerance to prevent cellular autoimmune reactions; but certain harmful characteristics related to IgE-based allergies and autoimmunity may result. In order to diagnose or predict an immunologic disease and/or provide therapy or prophylaxis, the Th polarization status must be determined; this should also be applied to measure susceptibility to infectious and neoplastic diseases. Th status is measurable in terms of cytokine profiles, chemokine/chemoattractant receptors, specific effector cell products, or gene expression profiles. An exemplary diagnostic panel is described in the table below:

| Th1 | | Th2 | |
| --- | --- | --- | --- |
| Cytokines | Receptors | Cytokines | Receptors |
| INF-$\gamma$ | CCR5 | IL-4 | CCR3 |
| TNF-$\alpha$ | CXCR3 | IL-5 | CCR4 |
| IL-2 | CCR1 | IL-6 | CCR8 |
| IL-12 | | IL-10 | CRTh2 |
| | | IL-13 | |

2. Exemplary Immunoscore Diagnostic Panels for Women of Child-Bearing Years

Adult immunization rates have fallen short of national goals partly because of misconceptions about the safety and benefits of current vaccines. The danger of misconceptions is magnified during pregnancy when concerned physicians are hesitant to administer vaccines and patients are reluctant to receive them. Routine vaccines that are generally safe to administer during pregnancy include diphtheria, tetanus, influenza, and hepatitis B. Other vaccines, such as meningococcal and rabies, may be considered. Vaccines that are contraindicated, because of the theoretical risk of fetal transmission, include measles, mumps and rubella; varicella; and BCG. A number of other vaccines have not yet been adequately studied; therefore, theoretic risks of vaccination must be weighed against the risks of disease to mother and fetus.

The administration of vaccines during pregnancy poses a number of concerns to physicians and patients about the risk of transmitting a virus to a developing fetus. This risk is primarily theoretical. No evidence exists of risk from vaccinating pregnant women with inactivated virus or bacterial vaccines or toxoids (CDC, 2002). Physicians should consider vaccinating pregnant women on the basis of the risks of vaccination versus the benefits of protection in each particular situation, regardless of whether live or inactivated vaccines are used (Sur, et al. 2003). Generally, live-virus vaccines are contraindicated for pregnant women because of the theoretical risk of transmission of vaccine virus to the fetus. The following table summarizes recommendations for vaccines commonly administered and their indication for use during pregnancy.

TABLE 11

Immunizations During Pregnancy

| Considered safe if otherwise indicated | Contraindicated during pregnancy or safety not established | Special recommendations pertain |
|---|---|---|
| Tetanus and diphtheria toxoids (Td) | BCG* | Anthrax |
| Hepatitis B | Measles* | Hepatitis A |
| Influenza | Mumps* | Japanese encephalitis |
| Meningococcal | Rubella* | Pneumococcal |
| Rabies | Varicella* | Polio (IPV) |
|  |  | Typhoid |
|  |  | Vaccinia* |
|  |  | Yellow fever* |

*= Live, attenuated vaccine

Women in their second and third trimesters of pregnancy have an increased risk of influenza-related complications including pneumonia and a four-fold risk of hospitalization (Neuzil, et al. 1998). The CDC has recommended that women who will be in the second or third trimester during influenza season and all pregnant women with additional high-risk medical conditions should receive vaccination in the fall. Despite publication of these guidelines, rates of vaccination among high-risk patients remain low (Silverman and Greif, 2001; Schrag, et al. 2003). Many possible explanations exist for this discrepancy, including vaccine unavailability, logistical concerns, poor reimbursement, fear of side effects, and lack of adequate patient or physician education (Wallis, et al. 2004).

A number of maternal conditions were perceived as potential contraindications to influenza vaccination during pregnancy. The most common of these were the first trimester, history of preterm labor, history of intrauterine fetal demise, and pregnancy induced hypertension; none of these are listed by the CDC as contraindications (Wallis, et al. 2004). According to this group, another potentially significant obstacle to influenza vaccination during pregnancy was physician reimbursement. Several responders remarked that reimbursement from insurance companies played a part in whether they stocked the vaccine in their offices and whether it was administered to pregnant patients. Although they acknowledged the indications for the vaccine, some obstetricians stated that insurance plans have refused reimbursement for vaccination because they were not the patient's primary care provider for this "preventive" service. Although patients may still be instructed to obtain vaccination elsewhere, this additional obstacle to recommended obstetrical care may result in lower immunization rates. These authors concluded by stating that further research is needed to determine effective methods of increasing vaccination rates in this high-risk population.

Cytomegalovirus (CMV) is found universally throughout all geographic locations and socioeconomic groups, and infects between 50-80% of adults in the United States by 40 years of age. CMV is also the virus most frequently transmitted to a developing child before birth. The incidence of primary CMV infection in pregnant women in the U.S. varies from 1-3%. Healthy pregnant women are not at special risk for disease from CMV infection. When infected with CMV, most women have no symptoms and very few have a disease resembling mononucleosis. It is their unborn babies that may be at risk for congenital CMV disease. CMV remains the most important cause of congenital viral infection in the U.S. For infants who are infected by their mothers before birth, two potential problems exist:
1. Generalized infection may occur in the infant, and symptoms may range from moderate enlargement of the liver and spleen (with jaundice) to fatal illness. With supportive treatment most infants with CMV disease usually survive. However, from 80-90% will have complications within the first few years of life that may include hearing loss, vision impairment, and varying degrees of mental retardation.
2. Another 5-10% of infants who are infected but without symptoms at birth will subsequently have varying degrees of hearing and mental or coordination problems.

However, these risks appear to be almost exclusively associated with women who previously have not been infected with CMV and who are having their first infection during pregnancy. There appears to be little risk of CMV-related complications for women who have been infected at least six months prior to conception. The current recommendations from the CDC for pregnant women with regard to CMV infection are:
1. Throughout the pregnancy, practice good personal hygiene, especially hand washing with soap and water, after contact with diapers or oral secretions (particularly with a child who is in day care).
2. Women who develop a mononucleosis-like illness during pregnancy should be evaluated for CMV infection and counseled about the possible risks to the unborn child.
3. Laboratory testing for antibody to CMV can be performed to determine if a woman already had a CMV infection.
4. Recovery of CMV from the cervix or urine of women at or before the time of delivery does not warrant a cesarean section.
5. The demonstrated benefits of breast-feeding outweigh the minimal risk of acquiring CMV infection from the breast-feeding mother.
6. There is no need to either screen for CMV or exclude CMV-excreting children from schools or institutions because the virus is frequently found in many healthy children and adults.

Recently, it was found that hyperimmune globulin therapy in pregnant women was associated with a significantly lower risk of congenital CMV disease (Nigro, et al. 2005). This group concluded that treatment of pregnant women with CMV-specific hyperimmune globulin is sage, and their findings suggested that it may be effective in the treatment and prevention of congenital CMV infection.

Specific ImmunoScore diagnostic panel recommendations must take into account the woman of child-bearing years status with regard to pregnancy. Ideally, an ImmunoScore screening of a young women prior to child-bearing years would give an appropriate "baseline" reading of that individual. In this instance, for example, a positive serologic test for CMV would be an indication that CMV-like illness during pregnancy would not be a cause of concern regarding transmission to that mother's infant during a pregnancy later in that woman's life.

Clearly, women of child-bearing years that are not pregnant, or not planning to get pregnant in the six months following ImmunoScore screening would have different recommendations than pregnant women. An ideal location and time for ImmunoScore diagnostic screening women of child-bearing years would be during their annual recommended visit to the OB/GYN. An early baseline could be achieved for each patient and the Specialist could make use of the specific recommendations without confusion as to which immunizations would be appropriate. It is very important to assure immunity to the components of the measles-mumps-rubella vaccine prior to pregnancy and the ImmunoScore service would enable that assurance.

Accordingly, in exemplary embodiments of the present invention a Women of Child-Bearing Years ImmunoScore superpanel can be defined as follows.

2.1 Recommended Tests for Immunoscore Measurement of Immunity:

Antibody to Cytomegalovirus (1)
  History of CMV infection needs to be captured to complete ImmunoScore database and add relevance to pregnancy.
Pregnancy test (1)

A pregnancy test is critical to making the correct decisions regarding administration of vaccines to women of this age group. There are, of course, other considerations here, but the status of the woman in question regarding pregnancy must be resolved in order to make accurate therapeutic decisions. In addition to CMV antibody, the physician(s) of women of child bearing years need to be aware of the recommendations of the CDC regarding immunizing pregnant women and the risks of immunization vs. the risks of foregoing immunizations. In addition, physicians should be aware that following appropriate immunization protocols and assuring a competent immune status is extremely important for women of child-bearing years.

2.2 Persistent Immunity Induced by Childhood Vaccines Diagnostic Panel
  Described above.
2.3 Sexually Transmitted Disease (STD) Diagnostic Panel
  Described above.

Section II Exemplary Immunoscore System Databases
General Overview

In exemplary embodiments of the present invention the results of immunologic and other assays of an individual together with additional medical, lifestyle, environmental and other demographic information can be collected at the same time as, or derived from, the collected data, and can, for example, be stored in a system database. Such a database can, for example, serve as an electronic record of immune status and other data over a period of time, both for individuals as well as for populations or sub-populations, as described below. Additionally, for example, such a database can be augmented with information regarding diagnoses received, treatments administered, pharmaceuticals prescribed, costs of medical services performed, insurance re-imbursements, metrics as to the efficacy of treatments and/or pharmaceuticals administered, as well other relevant information to facilitate evaluation of the efficacy and efficiency of medical services rendered, as described more fully below.

Thus, for example, for each run of an exemplary ImmunoScore assay within an exemplary system, various categories of data can be collected. Data can, for example, be stored in an electronic database using standard techniques as are known in the art. An example of data which can be stored and the manner in which it can be stored is next described. It is understood that this example is not intended to preclude the storage of additional collected or derived data as may prove useful for the purposes of trending, data mining, evaluation or diagnostic improvement, as described below, or as may be needed in or useful to any of the exemplary applications described in Section III below.

For each assay an exemplary system can record a unique assay ID, which can incorporate, for example, among other information, an identifier for the assay instrument. This ID can be unique over the universe of instruments, ensuring that when data is aggregated into a central system no two assay result records will have the same identifier. A possible implementation of this functionality is given, for example, by Microsoft's use of the GUID (Globally Unique Identifier), a 16 byte identifier generated by a computer and guaranteed to be unique across all computers.

Each record can include the time and date that the assay was performed, stored to a time resolution of, for example, one second. As is known, there are a variety of standard means of storing time and date information in a database. One simple means is, for example, to record the number of seconds from an arbitrary start time, such as, for example, Jan. 1, 1900 at midnight.

Each record can, for example, also include an indication of the location where the sample was processed. This can include, for example, an identifier of the instrument used, as well as real-world location information, such as, for example, the name and address of the facility where the instrument has been installed.

The aforementioned exemplary fields comprise identification information which is important to maintain for all samples. In addition, information about the sample and patient can be stored in the database as well. Patient information can, for example, be stored in a form which is separate from the bulk of the data, and referenced by a data link. Patient information, which can include, for example, name, social security number, birth date or other information (such as is described below in detail), can be maintained with emphasis on security standards are known in the art.

The storage of identifiable individual patient information in a separate virtual location from the remaining data can help to maintain such a high level of security.

In exemplary embodiments of the present invention, a system can, for each assay result, also store an identifier indicating exactly which assay was performed on the sample. This can indicate not only the analyte to be determined, but also information regarding the production of the reagents used in the assay. This information can be used to distinguish between, and compensate for, for example, lot-to-lot variations in assay manufacture. It can also allow for converting different assays for the same analyte into a normalized value, so that trends across geography as well as time can be obtained.

The measurement of an immune response to a particular disease or other analyte can involve the collection of a large quantity of low level data generated by an instrument. For an ECL instrument, for example, an instrument can measure the light emitted from the electrochemiluminescence over some time period as well as other information such as voltages and currents used to induce the electrochemiluminescence and the temperature near the electrodes through which the electrical energy is delivered to drive the electrochemiluminescent reaction. From this "raw data" and possibly instrument calibration information, a single number, for example, can be computed to represent an ECL signal for that measurement. Additional information can be computed from the raw data and instrument calibration information that indicates the quality of the ECL signal, for example, whether the instrument was operating in an appropriate environmental condition, whether sample was present, or whether the instrument was operating as expected. The raw data and such derived data can, for example, be stored in an exemplary ImmunoScore system database. In general the size of the storage required for this raw data can vary depending upon the resolution at which the data is captured. It is possible that a finer-grained resolution, resulting in a larger data storage requirement, will yield more useful analysis for some assays rather than others. Storage of both the raw data and the derived values can be done, for example, using industry-standard methods for the persistence of floating point numbers. For example, four (4) bytes of storage, yielding approximately six (6) significant digits, can be used for each stored value.

The quantity of greatest interest in an assay is the concentration of the analyte under evaluation. This concentration can be determined by converting a computed ECL signal to a concentration. This conversion can be done, for example, by backfitting the ECL signal through a calibration curve that relates ECL signal to analyte concentration. In general, such a calibration curve can vary from assay to assay, and can change over time for a given assay as that assay is refined.

Calibration curves enable both interpolation and extrapolation of ECL signal measurements for samples with known analyte concentrations for ECL signal measurements of samples of unknown amounts of analyte. The form of the mathematical functions used in a curve fit can, for example, make assumptions regarding the continuity and/or smoothness of the underlying relation such as through interpolating the measurements with functions such as piecewise constant, piecewise linear, cubic spline, or for example, by throughfitting all the data with linear, quadratic, cubic, or quartic polynomials. For overconstrained systems, parameters can be computed by minimizing an error function such as, for example, least squares (e.g., Press et al. 1992) or total least squares (e.g., Van Huffel et al. 1991). The form of the mathematical function may make assumptions about the assay mechanism, such as a one site saturation, two site saturation, one site saturation with nonspecific binding, two site saturations with nonspecific binding, a sigmoidal dose response curve with or without a variable slope, one-site competition, two-site competition, or a four-parameter logistic. Generation of a calibration curve entails selecting the form of the mathematical function and then fitting the parameters of the function with measurements. The measurements can, for example, be done on the test instrument or can be done in whole or in part elsewhere (e.g., at the place the assay is manufactured). The measurements can either perfectly constrain or over-constrain the mathematical function. As noted, for overconstrained systems, model parameters can be computed by minimizing an error function such as least squares.

In exemplary embodiments of the present invention, for each analyte the form of the mathematical function or model (stored, for example, as an index into a table of known models), the computed model parameters, as well as the data used to compute the model parameters, can be associated with each measurement of the analyte. To reduce the amount of redundant information stored in the database, the association for each measurement can be a link to the calibration data rather than the calibration data itself. Instruments can be re-calibrated at any time, such as, for example, on a weekly basis or with every measurement. The quality of the calibration can also be assessed, for example, through the running of controls or by computing the residual error from an overconstrained curve fit.

Thus, a calculated concentration can be stored by the system. This can be, in exemplary embodiments of the present invention, the primary input to analysis recommendation algorithms employed by the remainder of the system. It is noted that not all assays will result in a quantitative concentration. For example, some assays, due to the shape of their calibration curve, may yield two different concentrations for the same measured signal. Such assays are said to "hook." In such cases the most an exemplary system can store is an indicator that the measured concentration is above a certain level, the lower of the two returned calculated values. Other assays, for various reasons, may return only qualitative results rather than true quantitative results. In all cases, a system database can be capable of storing and retrieving the result. For this reason, in exemplary embodiments of the present invention, the result of an assay can be stored not as a simple floating point number, but as a complex object which can take into account the various scenarios described above. Such an object can have, for example, several fields of its own.

A compressed version of the database can, in exemplary embodiments of the present invention, consist of only the initial ID information, patient ID information, test ID information, and the calculated concentration of analyte. This is a minimal set of data which can prove productive for data mining and trending analysis, as detailed below. The additional data described herein can, for example, be used to enhance the value of this analysis.

Algorithms encoded or implemented or implemented in an exemplary system can be used, for example, to determine a recommendation for action. This recommendation can be based upon a calculated concentration of, for example, antibody response. Other information can also be considered, including, for example, the results of other assays upon the same sample within a given assay panel.

Regardless of the means of determining the recommended action, as described above, a final recommendation can be stored in the database. A system database can, for example, also store the "reasoning" behind the recommendation, allowing a human to later query the database to determine why a given course of action was recommended. Given that the number of recommended courses of action can be broad, these actions can be categorized and encoded. For example, a recommendation to administer a particular vaccination may be encoded with one byte to indicate "give vaccination" and two additional bytes to indicate the particular vaccination that is warranted. A field for comments can also be included, to allow the capture of the system's reasoning—in this case, an explanation of how algorithms and rules were applied to determine the stated conclusion.

A system database according to an exemplary embodiment of the present invention can be implemented, for example, as a shared resource spread over multiple computer platforms. For purposes of trending and analysis, it may be necessary to accumulate the data from a large number of systems into a central repository as depicted in FIG. 2, or, for example, in the case of having only decentralized information, by using a mechanism or process to locate and query the distributed sources. The individual databases can therefore require the capability to link up with a defined central database and upload their contents. This can occur on a periodic basis, or as may be triggered by a user of the system. Additionally, there can be multiple central servers, so that a given enterprise may choose to aggregate their data at any level. Unique IDs associated with sample and panel records can serve to allow for the combination of data from disparate sources without data "collision."

The linkage between local databases and a central database can be implemented, for example, across a local area network (LAN), a private data network, a VPN, an intranet or across the Internet. It is also possible to link databases on a periodic basis using physical media, such as CD-ROMs. Similarly, various users such as, for example, health care providers, individuals, insurance executives, consumers of research services, health care management personnel, etc., can access an exemplary system via a web based interface across a local area network (LAN), a private data network, a VPN, an intranet or across the Internet.

Once data has been accumulated into a central repository, a separate system can be used to perform data mining and data trending analysis upon the stored data. There are many valuable sorts of analyses which can be performed on the accumulated data in an exemplary system according to the present invention.

Given that each data record can, for example, be identified with a particular individual or patient and a particular time and date, it becomes possible to perform trending analysis of a patient's (or a population's) ImmunoScore profile over time. In many cases an individual's absolute measured value of an analyte is not as important as the trending of that value over a time. Some individuals may have naturally low or naturally high values which are not best measured against a statistical mean for their demographic population, but rather against that individual's own measured history.

As described above, each patient can, for example, also be placed within certain demographic categories. It can be useful to compare a patient's measured ImmunoScore profile against the corresponding profile for the demographic groups to which he or she belongs. Deviation from the measured means for a demographic slice of the population can prove more meaningful than can a comparison to a total threshold. Thus, in exemplary embodiments of the present invention, collected data can be used to continually modify the demographic profile averages known to the system, taking care to not pollute the system with outlying data points. For example, it may prove useful to produce separate ImmunoScore demographic profiles for patients who are known to have experienced vaccinations versus those for whom there is no known immunization record. Alternatively, as is described below in Section III, such an immunization record can be inferred and reconstructed, as in the provision of ImmunoScore services to national immigration services or authorities or bodies dealing with such concerns.

Trending information in a demographic profile, for example, can also be useful. For example, tracking an indication of a typical person (e.g., mean, median, or mode), or an indication of the spread amongst people (e.g., standard deviation, interquartile range, or range) over time can enable an exemplary system to assess the relationship between immune status indicia and external factors, such as, for example, seasonal effects. Eating habits, sleeping habits, time aboard ship, etc. can be found to affect immune status in groups where these external factors are partially controllable (such as, for example, in military personnel). Comparing immune status indicators of differing demographic profiles can have important epidemiological significance.

Finally, it is expected that the collection of ImmunoScore data from a large number of individuals and/or populations can eventually lead to the improvement of diagnostic tests, thus forming a feedback loop. These improved diagnostic tests can then, for example, be deployed to field instruments, resulting in more accurate measurements and diagnoses. Such exemplary embodiments having feedback loops can be implemented, for example, with respect to particular populations or demographic groups, such as, for example, the military, college students, immigrants or any other group or combination thereof as described above.

Exemplary Illustrative Database
1. Overall Description

To illustrate the systems and methods of the present invention, a database system was constructed to serve as a testbed for the exercise of the business models described below. Such an exemplary database system was used to demonstrate the tools and techniques that might be used in a full scale system according to the present invention. Accordingly, a large data set was constructed using statistical techniques. The data was produced according to match existing knowledge about the distribution of immune response values among the general population.

The exemplary database system has two primary components. These two components represent the algorithmically interesting sections that can be, for example, present in a full-scale operational system according to an embodiment of the present invention. Such a full system could, for example, contain other modules as well, along the lines of industry standard large scale database systems. Such an exemplary system is depicted in FIG. 5 and is next generally described.

Figure 5:
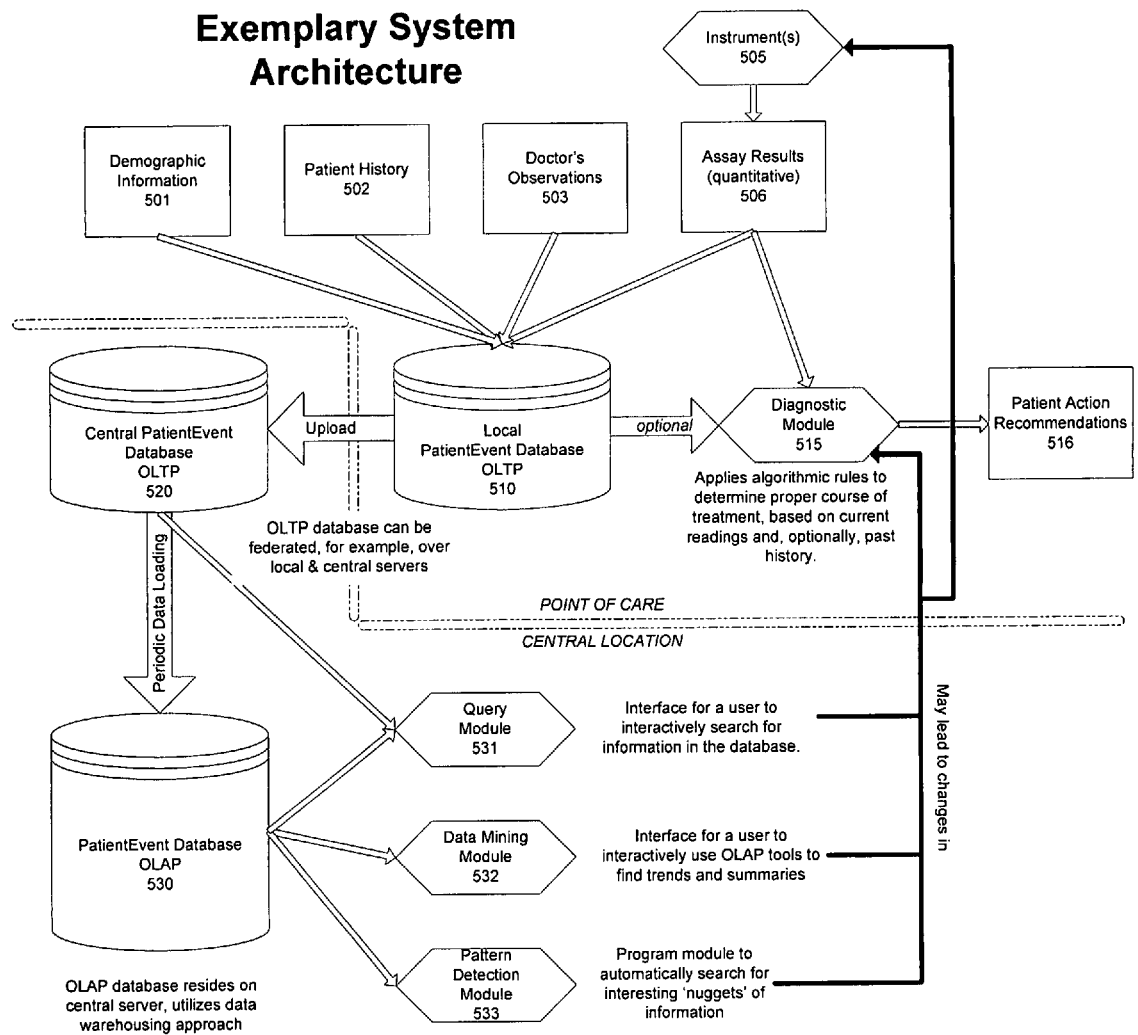
FIG. 5 depicts a detailed system diagram according to an exemplary embodiment of the present invention.

With reference to FIG. 5, an exemplary system architecture can be constructed. The exemplary system architecture can be, for example, divided into two sub-systems, one relatively local to "point of care" or locations where the individuals or patients whose immune status is to be analyzed are located. The other subsystem can be in a central location where complex data mining and analysis can occur. Thus, with reference to FIG. 5, an upper portion of the figure contains components which can be located at the point of care and a lower portion of the figure contains components which can be, for example, located at a system central location. The point of care is divided from the central location in the figure by a double dotted and dashed line for ease of identification.

With reference to the point of care sub-system, there can be one or more Instruments 505 which are devices which can read immunologic assays. Instruments 505 yield Assay Results 506. Assay Results 506, along with Doctor's Observations 503, Patient History 502 and Demographic Information 501 regarding the individual or patient can all be stored in Local PatientEvent Database 510. Database 510 can be, for example, an online transaction processing database. Because the point of care sub-system is generally directed to generating a recommendation in a relatively short time, there are two pathways to Diagnostic Module 515. Diagnostic Module 515 applies algorithmic rules to the assay results to determine a proper course of treatment or action based on current readings and optionally on past history. Thus, there is a flow of information from Assay Results 506 to Diagnostic Module 515. Alternatively, Diagnostic Module 515 can implement algorithms having other inputs besides the current Assay Results 506, such as, for example, Demographic Information 501, Patient History 502, and Doctor's Observations 503 (understood to include any observations by any health care provider, or the like, in a general sense) which can be stored in Local PatientEvent Database 510. Thus, in FIG. 5, there is an arrow labeled "optional" running from Local PatientEvent Database 510 to Diagnostic Module 515. Regardless of which source of information Diagnostic Module 515 draws upon, it can, for example, output the patient action recommendation 516 as indicated.

Returning to the central location sub-system of FIG. 5, a connection exists between Local PatientEvent Database 510 and a Central PatientEvent Database 520. This connects the two sub-systems. It is contemplated that at regular intervals data from Local PatientEvent Database 510 can be uploaded to Central PatientEvent Database 520. Moreover, although the central location sub-system could be mirrored in a number of distributed central location subsystems, the point of care sub-system is contemplated to take data from numerous instruments and in fact have numerous local patient event databases in those locales. In short, the point of care sub-system is found wherever potential customers or patients are found. It is noted that there can be a myriad of such locations, given the various and sundry applications and business models that exemplary embodiments of the present invention contemplate. Examples of such applications are described more fully in Section III, below. Therefore, there could be a great number of local patient event databases all of which feed into Central PatientEvent Database 520. None of these additional point of care sub-systems are shown in FIG. 5, for reasons of ease of illustration.

Returning again to Central PatientEvent Database 520, it is noted that this database can, for example, also be an online transaction processing database or OLTP. It is contemplated that this database can, for example, periodically load data to an online analytic processing database, or OLAP in the form of PatientEvent Database 530. PatientEvent Database 530 can be, for example, adapted to provide inputs to complicated algorithms dealing with data mining and pattern detection, as next described.

PatientEvent Database 530 can, for example, reside on a central server and utilize a data warehouse approach. There can be a variety of connections to PatientEvent Database 530 such as, for example, a Query Module 531, a Data Mining Module 532 and a Pattern Detection Module 533. Query Module 531 can be, for example, an interface by which a user can interactively search for information in database 530. Query Module 531 can also access Central PatientEvent Database 520 implement a variety of operations on the data there as well. Data Mining Module 532 can be an interface by which a user can interactively use OLAP tools to finds trends and summaries in the stored data. Finally, Pattern Detection Module 533 can be a program module which can be used to automatically search for patterns or other "hidden" correlations between various data points in a database. It is contemplated that in exemplary embodiments of the present invention Pattern Detection Module 533 can regularly sort through all of the stored data looking for patterns using various algorithms. Some of such algorithms can, for example, articulate some hunch or a correlative assumption provided by a panel of immunological experts for which they do not have hard data. Pattern Detection Module 533 is thus an important feature in exemplary embodiments of the present invention. Additional exemplary databases which Patter Detection Module 533 can utilize are described below in connection with FIG. 5A.

The exemplary system depicted in FIG. 5 will next be described in greater detail. A first module of interest is termed Diagnostic Module 515. The function of this software module is to input a set of assay results 506 obtained through measurements by instruments 505, and to make one or more recommendations 516 based upon the analysis of assay results 506. Diagnostic Module 515 can be designed in such a way that additional assay panels can be slotted into an existing system as they are developed. Some exemplary algorithms used to make recommendations as a function of assay results are described in more detail below, including descriptions both of algorithms used in the exemplary database as well as additional algorithms that could be implemented in various exemplary embodiments of the present invention.

Diagnostic Module 515 can rest upon a Local Database 510 containing Assay Results 506 obtained from Instruments 505. These results are pertinent to an individual patient. Local Database 510 can also, for example, contain background medical history 502 for that patient, demographic information 501 pertinent to the patient, and a summary of other medical observations 503 made by medical professionals or persons fulfilling a similar function. Local Database 510 can also, for example, contain statistical information obtained from a larger central database, as described below.

A second exemplary module of interest is Data Mining Module 532. Whereas Diagnostic Module 515 is intended for the analysis of a particular individual's data at a particular point in time, Data Mining module 532 can, for example, look at a broader range of data collected from many individuals over a range, or interval, of time. Through analysis of this collected data a system can, for example, be used to support various business methods and other applications by deducing trends and patterns within an immunological landscape. A particular result could be fed back into the Diagnostic Module's algorithms, improving their effectiveness by providing additional specificity with regard to an individual's background, possibly in terms of background or demographic information such as, for example, gender, racial background, geographic origin, lifestyle, economic circumstances social circumstances, or age.

As can be seen from FIG. 5, while the Diagnostic Module's functionalities are primarily local in nature and patient-specific, the Data Mining Module's functionalities are primarily central, and system-wide. As noted, this structure is reflected in the division of FIG. 5 into two zones, the "Point of Care" zone, shown at the top of the figure, and the "Central Location" zone, shown at the bottom of the figure.

Data Mining Module 532 depends upon the existence of a large central database containing records from a wide variety of individuals over a long span of time. Thus, the local databases described above can, for example, exist in a federated state with the central database, uploading their information on a regular basis, where this information can, for example, be integrated into the full system.

2. Impact of Data Mining

Patterns can be detected within the data in an exemplary database which are related to demographic and other non-immunologic information such as, for example, gender, age, ethnicity, geographic origin, employment, etc. These patterns may not be obvious until large numbers of individuals are assessed, using a computer that can be by nature much more efficient, unbiased, and precise in pattern recognition.

From such patterns, new correlates can, for example, can be established, and old correlates can be changed. For example, in immunization related applications, it may be proposed, based on previous data, that a serum antibody concentration of 2 micrograms per ml should be used to represent a threshold of protection against meningococcal disease, so that anyone with less antibody would be recommended for immunization. Subsequent and continued analysis, however, may show that this threshold value should be reduced or raised for given individuals, depending on, for example, age or ethnic background, or some other undefined parameter. In turn, an ethnicity evaluation could lead to the discovery of a specific biological or genetic marker. For example, the functional activity of *Haemophilus influenzae* type b (Hib) antibodies may vary with different individuals, where the same antibody concentration may not possess the same level of bacteriocidal activity due to differences in antibody avidity. For example, regarding age, Hib polysaccharides were shown to be poorly immunogenic in children less than 2 years of age (Granoff D M, 1985, J Pediatr 107:330-36). Similarly, regarding ethnicity it has been shown from previous studies that Eskimos and Apaches are more susceptible to Hib meningitis because they possess a less effective antibody repertoire to the Hib polysaccharide capsule, based on the presence or absence of certain variable region genes used in the production of the polysaccharide-specific antibodies.

Additionally, variations in host factors can lead to significant differences in the immune response to vaccines, which can also be discerned by data mining. For example, late-stage complement deficiency may have no impact on antibody production, but would certainly reduce the effectiveness of those antibodies in killing bacteria, thereby lowering their activity. In such case, the antibody threshold for protection may need to be raised in order to achieve the same level of protection in this subpopulation.

As previously described for Hib, the capacity for protective antibody production is the direct result of variable region gene haplotypes. In this case, ethnic differences were first observed as a gross marker, but the presence of specific genes was later determined to be responsible. In a similar but different manner, HLA haplotypes have also been correlated with the susceptibility to certain infections, as well as the unresponsiveness to certain vaccines. For example, certain HLA antigens appear to be correlated with chronic hepatitis B virus (HBV) infections and HBV vaccine nonresponsiveness. In such cases, in exemplary embodiments, of the present invention, subpopulations can be identified, initially by ethnicity, then later by genetics, to evolve a more specific and appropriate diagnostic outcome.

Another example of the influence of ethnicity on responsiveness to treatment is the case of NitroMed's BiDil™, which was approved by the U.S. FDA in 2005 for the treatment of heart failure in African Americans. BiDil™ is an orally administered, nitric oxide-enhancing drug that was shown to have clearly different effects on blacks versus whites in clinical trials, where the "differences may be related to environmental, social, lifestyle, or genetic factors or to interactions among all of these." (see http://www.fda.gov/fdac/features/2005/505_BiDil.html). In exemplary embodiments of the present invention, data mining can, for example, be used to observe and identify these kinds of effects and correlations, and then be later used to determine the specific underlying mechanisms.

Data mining can also be used, for example, to change or reverse previously held dogma(s) concerning long-term protection from vaccination. For example, immunity resulting from the smallpox vaccine, used extensively during the previous century, was originally thought to last for less than a decade. Recent analyses however, have shown that "more than 90% of volunteers vaccinated 25-75 years ago still maintain substantial humoral or cellular immunity (or both) against vaccinia, the virus used to vaccinate against smallpox." (Hammarlund E et al., 2003, Nature Medicine 9:1131-37). The same study further showed that "Antiviral antibody responses remained stable between 1-75 years after vaccination, whereas antiviral T-cell responses declined slowly, with a half-life of 8-15 years." While it is not clear what level and combination of responses is required for protection, the authors concluded that "the morbidity and mortality associated with an intentional smallpox outbreak would be substantially reduced because of pre-existing immunity in a large number of previously vaccinated individuals." This is exactly the type of information that could be obtained through data mining over time on large populations, as contemplated in exemplary embodiments of the present invention.

As noted above, an exemplary system similar to that depicted in FIG. 5 was built using standard software development tools and packages. The algorithms were encoded using the XML data description language. The engine for executing the algorithms was built using the Java programming language. An Oracle database was used for data storage and data mining querying. Excel spreadsheets were used for data construction and analysis. Details of the construction are given below.

3. Diagnostic Module 3.1. Overview

Diagnostic Module 515 forms the heart of an exemplary ImmunoScore decision system. At a basic level, the diagnostic module exists to provide relevant information and/or to suggest courses of recommended action (for various purposes, depending upon the application; see Section III below) based upon an individual's immune status, as measured by instrumentation or obtained from elsewhere, in combination with other supporting data. There are many different ways that such a determination could be made. Next described are some exemplary algorithms that were used in the example system as well as other exemplary decision support algorithms which could be implemented using the same techniques.

One essential function of a diagnostic module can be, for example, to assist a medical or other professional in making decisions regarding which actions to take with a specific individual, making use of data regarding that person's immune status. As noted, in exemplary embodiments of the present invention, an individual's immune status can be determined by conducting a panel of assays, each of which assays can produce an element of data. For purposes of the example database, information presumed to be obtainable through such assays is summarized in FIG. 6. It should be noted that in practice some of this information may not yet be obtainable, although it is expected that assays could be developed along the lines of existing tests in order to complete this spectrum.

In addition to immune status information obtained from assays, a diagnostic module can make use of other information specific to the patient being examined. This information falls into two principal categories: demographic information, such as, for example, age and gender, and patient medical history. Most demographic information can be simply expressed in a database. Patient medical history is more problematic, although there are many existing healthcare database systems which do this adequately. The difficulty with patient medical history, however, is in devising algorithms which can make use of this qualitative data. It is expected that particular care can be taken to use algorithmic techniques which have proven adept in dealing with inconsistent or unreliable data, such as, for example, neural networks, described in greater detail below. This is due to the inherent unreliability of self-reported medical history data, along with the historic problems found in the transfer of medical records. If a system with built-in reliability checks is implemented, then it can be possible to rely more strongly upon historical data.

Thus, the exemplary system described below can store both demographic and past medical history information for individual patients, but does not make use of these factors in performing diagnostic assessments or recommendations of courses of action. However, the algorithms implemented can easily be extended into these realms once more information becomes available.

The output of Diagnostic Module 515 can be, for example, a series of recommendations. A recommendation is simply defined as any discernible bit of data which might be of interest to a medical professional, health care or life insurer, medical services analyst, researcher or other user of the present invention in determining a given course of action. In the case of a patient's immune status, a common recommendation could be, for example, to recommend a particular vaccination, to conclude whether the individual is in an overall sense healthy, to conclude that certain potential hypotheses need further data to be fully explored, to tag the individual as being potentially immunosenescent, or to grant a health insurance credit or debit relative to a health insurance policy or HMO membership fee. Or, for example, a recommendation not to vaccinate, to reduce the over-vaccination of the populace. A summary of some exemplary types recommendations that can be offered by an exemplary Diagnostic Module are provided in FIG. 7.

In exemplary embodiments of the present invention a Diagnostic Module can be capable of producing a set of recommendations for each analysis. For example, it might recommend that both vaccine V be administered and that the individual be retested in three weeks to monitor his or her response to such vaccine. For each recommendation, an exemplary Diagnostic Module can, for example, also provide a confidence level, which is a measure of the system's support for any given conclusion. A user can take this confidence level into account when deciding upon a course of action. A course of action with a low confidence level but a high financial cost, for example, could be delayed until additional data could be gathered to more strongly support the course of action.

In exemplary embodiments of the present invention a Diagnostic Module can, for example, be constructed in a manner to allow the deployment of many different algorithms within its basic shell. For the exemplary system, an algorithmic approach based upon perceptrons was used. This approach is detailed below. Additionally described are alternative algorithmic approaches, each of which has different strengths and weaknesses. It is noted that some of these approaches are realistically infeasible until such time as large-scale data collection of immune status informatics becomes available.

3.2. Perceptron Algorithms

A perceptron is a simple neural network, a computer science representation based upon an analogy with the operation of human neurons. Perceptrons were invented by Frank Rosenblatt in 1957, and have been used in artificial intelligence research since that time. A perceptron is simplistic, but adequate for the computation of algorithmic diagnostic results within the exemplary system of the invention. More importantly, there is a clear progression between perceptrons and more sophisticated artificial intelligence techniques, which may be of use in more complex embodiments of the invention.

An example of a perceptron is given in FIGS. 8 and 8A. These networks encode the decision making process for the running of a Meningococcal Diagnostic Panel, as described above. There are seventeen inputs to the algorithm, one for each of the measurements that can be taken in an exemplary meningococcal assay panel. Five inputs are for the meningococcal serogroups, seven for the complement components, and five for the genetic poymorphisms. There are two output recommendations from this panel R1 810 (or in FIG. 8A, R2 810) and R3 840. R1/R2 is a recommendation to vaccinate an individual with a meningococcal vaccine. R3 840 is a recommendation to monitor the individual on a stricter interval schedule than normal, because the individual may be more susceptible to this condition than the average individual in the populace. FIGS. 8 and 8A depict the same perceptron, with different values for the various nodes upon firing.

With reference to FIG. 8, serum IgG levels for vaccine-preventable serogroups (A, C, W-135, and Y) of *Neisseria Meningitis* can be assessed. As seen in the fifth input to R1, the panel also has a built-in facility to measure and consider serogroup B, but there is no currently available vaccine or clearly known threshold of protection for this serogroup, so it was left blank. A serum IgG level exceeding 2.0 ug/mL for all four serogroups would be presumptive of protection in an otherwise healthy individual, i.e., an individual (i) found not deficient in serum levels of measured complement components, and (ii) having no deleterious genetic polymorphisms as indicated in the CC Test 820 and Genetic Polymorphism Test 830. There would be no immediate recommendation for meningococcal vaccination for these individuals.

The following is a description of rule execution flow for the exemplary perceptron of FIGS. 8 and 8A.

R1—Recommend Vaccination. With reference to FIG. 8, If the CC Test 820 and the Genetic Poly Test 830 show the person is normal, both of them will fire, giving a minimal total of 2.0 at R3. Then no contribution at R1 from R3, and if any of the serogroups is deficient, R1 will be at least=1.0 and R1 will fire. If the CC Test 820 or the Genetic Poly Test 830 show that the person is not normal, R3 840 will fire, giving a base total of −4.0. Nothing will be contributed from the R3 conclusion as even if the inputs to R1 810 from the four serogroup assays are all 1.0 (all deficient), this added to −4.0=0, which is <1.0, and R1 needs to be >=1.0 to fire. Thus FIG. 8 only operates as to normal individuals vis-à-vis the CC and Genetic Poly tests.

R3—Recommend Flagging. If the total at R3 840 is less than 2.0, the individual is not normal, R3 fires and the recommendation will be to flag this individual for monitoring.

FIG. 8A is similar to FIG. 8, except that it applies a different recommend vaccination rule, R2 at 810, for a different immunological context. The perceptron is modified as to values, but the nodes are identical.

R2—Recommend Vaccination. With reference to FIG. 8A, if deficiencies were to be revealed in any of an individual's complement components, or if any unfavorable genetic polymorphisms were shown to exist, then it is likely that a serum IgG level of >5.0 ug/mL (not the >2.0 UG level as in the rule of FIG. 8) for the vaccine-preventable serogroups would be desirable in these individuals. If these individuals had IgG levels exceeding 5.0 ug/mL for all four serogroups, no vaccination would be recommended. If the level of antibody to any of the four serogroups were to be below 5.0 ug/mL, then a vaccination would be recommended. If the CC Test or the Genetic Poly Test show the person is not normal, one of them will fire, giving a minimal total of 10 at R2. Then, all that is required is for one of the serogroups to be deficient (i.e., <5.0 ug/ml) in order for the recommendation at R2 to evaluate to true.

R3—Recommend Flagging. If the CC Test and the Genetic Poly Test show the person is normal, both of them will fire, giving a minimal total of 2.0. If the total is less than 2.0, R3 fires, they are not normal and the recommendation will be to flag this individual for monitoring.

Because al perceptrons operate on the data in parallel, an abnormal individual can, for example, be captured in the perceptron of FIG. 8A and can thus receive no vaccination recommendation from the perceptron of FIG. 8.

A perceptron operates through software by simulating the "firing" of nodes based upon numerical conditions being met. As each node fires, it can contribute to the firing of other nodes, in some cases positively and in some cases in an inhibitory fashion. The network as a whole has completed execution when the rightmost nodes, representing diagnostic recommendations, have either fired or have come to rest.

The perceptrons in the exemplary system were encoded manually based upon existing knowledge of diagnostic recommendations in use today. Each perceptron can be represented either graphically, as in FIG. 8, or textually, as in FIG. 9. FIG. 9 is thus a textual representation of the perceptron network using a language called XML, or eXtensible Markup Language. In the exemplary these XML files can be deployed to the diagnostic module as discrete packets. An exemplary Diagnostic Module connected to an instrument, or bank of instruments, could, for example, be configured with only those perceptron algorithms required for that site.

In addition, updated versions of these algorithms could be deployed as the algorithms are improved over time in a continuous process of system learning or iteration. Thus, in exemplary embodiments of the present invention, knowledge gained through use of the data mining module, detailed below, can be fed back into the individual diagnostic modules, thus improving the accuracy of the entire system. For example, it may be deduced through data mining of an exemplary database that the level of antibody activity which is a strong indication of the need for vaccination is lower in men than in women. A new perceptron algorithm could then be deployed, for example, including the gender of the patient as a new input node, with a link to the vaccination recommendation node.

More subtly, a perceptron can include within it a series of weights which can, for example, correspond to the importance of each bit of evidence to the recommendation procedure. Over time these weights can be continually adjusted and redeployed to reflect increased understanding of the role of each of the immunological factors being measured.

3.3. Alternate Algorithmic Approaches

There are a number of alternate algorithmic approaches which can be used within a Diagnostic Module. Each has varying strengths and weaknesses. An exemplary system can, for example, include a combination of these approaches in order to come up with the most complete recommendation for a course of action.

The process of evaluating algorithmic approaches involves a consideration of the goals which are to be met. A Diagnostic Module can, for example, be configured to optimize for any one of a number of different criteria. Possible goals can include, for example, optimizing the welfare of the patient, minimizing costs for the patient related to the disease in question, minimizing overall patient healthcare costs, and minimizing life insurance costs. The decision algorithm used in the diagnostic module can thus vary depending on how these goals are prioritized.

A key difference between a system according to the present invention and existing systems is the use of an individual's immune status information and associated data as inputs to the decision procedure. This allows the system to provide more tailored and individualized recommendations instead of relying upon aggregate statistical measures. A second key difference is the introduction of historical patient immune status and other data. It is possible, for example, that a given individual's antibody level is below some computed norm, but is in fact high in relation to that individual's past results. This might conventionally be, for example, a contraindication for vaccination, a recommendation which would not be made if the individual's immune status were only to be compared to the population standards.

Using the exemplary symbology laid out in FIG. 10, various diagnostic goals as shown in FIG. 11 can be summarized.

3.3.1. Additional Input Data

This section describes additional data which could be incorporated into a diagnostic module in exemplary embodiments of the present invention.

As noted above, historical immune status information can be a useful addition. Basing a recommendation solely upon an individual's status at the current point in time is an adequate approach, but it risks making incorrect recommendations for those patients who do not fall within the average range of the population at large. A simple extension to the system would be to move away from absolute measures of, for example, antibody level and antibody activity level, and to substitute instead relative measures based upon the percent change in these values since the last historical measurement, or in comparison to the individual's historical averages. The same decision procedures could be applied, but retooled so that a decision rule such as "the level is greater than 30" becomes "the level is greater than 15% above the patient's baseline". In order for this to occur, an exemplary system can either maintain a central record of the patient's immune status over time, or provide means to allow the portable storage and transfer of this historical record, perhaps under the patient's control. Various forms of "smartcard" or electronic storage technologies as are known could be used for this purpose.

A second type of additional input data relates to demographic information. Current decision procedures do little to distinguish treatment recommendations based upon an individual's age, gender or racial background, although it is known that these factors have a considerable effect on the interpretation of immune status information. Thus, an exemplary system could make use of such demographic information, customizing the diagnostic algorithms to take into account observed patterns. Additional research would be required to deduce these patterns in the population as a whole in order to make reasonable modifications to the decision procedures.

3.3.2. Decision Rule Algorithms

A clear successor to the perceptron approach could be to extend the system to full neural networks. The distinction between perceptrons and more complex neural networks is the incorporation into the latter of feedback links from later nodes to earlier nodes in the network. This not only increases the complexity of the algorithms which can be implemented, but allows for algorithms which improve over time through a learning mechanism. Neural networks are a well-established domain of artificial research. The primary impediment to neural networks is that they are difficult to construct by hand. A typical neural network is instead evolved through the use of training algorithms. These training algorithms require as input a set of training data. In an exemplary embodiment of the present invention, the training data could consist of immune status data from a large population of people coupled with data about the eventual onset of diseases in that population. Were such a database to exist, neural networks could be constructed which could predict the onset of disease based upon features in an individual's immune status information. An advantage to using neural networks is that they could be a simple drop-in replacement to the current Diagnostic Module in terms of inputs and outputs.

4. Data Mining Module

4.1. Overview

The Data Mining Module is the large-scale component of exemplary systems according to the present invention. As noted above, while the Diagnostic Module focuses upon obtaining results specific to a particular individual, the Data Mining Module can be, for example, designed to examine trends in large data sets assembled for many individuals and with many readings per individual. This capability is necessary to support business models in which information is deduced about immune status patterns, as well as to improve the functionality of the Diagnostic Module over time.

As noted, an exemplary system was constructed using an Oracle database server. The schema for the database system is given in FIGS. 12 through 14. The schema used is termed a 'star schema', which is a database layout optimized for online analytical processing. This is a standard concept in data mining. More information about the data storage is given below.

4.2. Sample Data

The sample database was intended to represent actual immune status information which could be collected from a large population over a large span of time. The test measurements contained within the database are randomly generated within the constraints detailed below.

The exemplary database contains three distinct sorts of information.

The first block of information is individual immune status information. As an example, the individual is assumed to be a patient in some healthcare context. The schema for the patient information table is given in FIG. 12. To summarize, the database contains information on the patient's birthdate, gender, racial background and geographic location. All of this information can potentially be used for data mining efforts related to immune status. The database also contains other information strictly for identification purposes, such as name and ID.

In the exemplary database, patient information was randomly generated. Gender was split evenly, and geographic placement was divided among four test cities. Racial backgrounds were assigned to match latest U.S. census figures available.

The second block of information is patient visit information. A schema for the patient visit information table is given in FIG. 13. To summarize, this information covers data that could, for example, be collected by a physician at the time of a patient's visit. There can be multiple visit information records for each patient. The majority of this information covers various symptoms present in the patient at the time of the visit. This information can be used within the Diagnostic Module, above, as part of an algorithm which takes into account diagnostic information other than the immune status assay results. This information can also be used in data mining to discover correlations between physical symptoms, immune status indicator levels, and subsequent onset of disease. The visit information section of the database is also used to store recommendations from the Diagnostic Module.

In the exemplary database, symptomatic information was assigned randomly. The example Diagnostic Module did not make use of symptomatic information.

The third block of information is the actual results of immune status assays. In the exemplary database there are 48 distinct simulated measured quantities, although this can be expanded, for example, to any reasonable number in a straightforward manner. The schema for this data block is given in FIG. 14.

In the exemplary database, assay test results are generated with care. The distribution of antibody levels are randomly generated based upon a log-normal distribution with an average of 50 micrograms per milliliter, as is consistent with measured antibody levels in practice. These values are used as initial baseline levels for the patients in the database. New values are then entered to simulate readings taken at set time intervals in the exemplary patients' lives, as indicated in FIG. 15. At each age, the antibody levels were perturbed using a small normal distribution, to simulate variation in the population over time. Results are biased to match the observed behavior of antibody activity in populations as they age, as shown in FIG. 16. All data in FIG. 16 is from simulated vaccinated patients.

Half of the sample population was treated as if they had received a standard vaccination schedule at age 5; the other half was left untreated. Antibody levels were adjusted to suit, as shown in FIG. 17. In addition, a subset of patients were given artificially lowered complement levels and antibody activity levels with no change to the measured antibody levels, simulating the effect of complement-deficient patients on the data mining procedure. This is shown in FIGS. 18 and 19.

The intent behind this production of sample data was to produce a population with interesting characteristics that could be highlighted in the data mining module. Although the exact features used may not be strictly representative of the population as a whole, they represent the type of correlation that a system such as this could detect within real patient data. It could easily be imagined, for example, that individuals of a particular racial background might naturally have elevated levels of a particular antibody. The system being described could be used to deduce that fact, which may have implications for the immunological care that such individuals would receive.

It is noted that all assay results, such as antibody levels, such as, for example, "Gcmp AVG" in FIG. 16, may be measured and quantified as units (U) per volume (e.g., ml), where U may be defined as some arbitrary unit of a particular assay for the purpose of relative comparisons. In addition, U may be replaced by a more precise measurement of mass, such as micrograms, where possible and appropriate. Antibody activity, such as, for example, "Gcmp AVG" in FIG. 16, refers to the functional activity of an antibody, which may consist of, but not necessarily be restricted to, bactericidal or bacterial killing properties. In these specific examples, assay results from individuals may be processed for statistical purposes in the evaluation of a population, as in FIG. 16, where individuals may be averaged (AVG) by appropriate statistical formulas. Where statistical processing assumes a normal distribution, geometric means may be used to average the results from different individuals, thereby requiring a log transformation of data sets, since it is generally found that only the log values of immune responses will follow a normal distribution.

4.3. Exemplary Use of the Patent Event Database

In exemplary embodiments of the present invention, a database used for data mining can, for example, be accessed in three different modes, as indicated in FIG. 5.

A first mode can be, for example, an interactive query mode. A user can interactively search for results in the database. Typically queries might include the retrieval of a single individual's immune status over time, or the comparison of two such individuals, as shown in FIG. 19. Queries can be submitted, for example, using either a graphical query tool or through the use of Structured Query Language (SQL), a computer language for the querying of databases. An exemplary SQL query is shown in FIG. 19A. Both of these methods of access are well-known in the industry. With reference to FIG. 5, a user can use the query mode via Query Module 531.

A second exemplary mode is the use of Online Analytical Processing tools, or OLAP tools, to find patterns within the database. A simple example of this is the production of aggregate statistics for subpopulations within the whole. In FIG. 19B, for example, a query for correlation coefficients to GCMP levels is restricted to female patients. A similar query might look at only patients from a distinct geographical area or racial background. Correlation statistics can also be generated, to test hypotheses about possible causal links among measured antibodies, between antibody measurements and physical symptoms, or correlations between any of these and demographic information. The utility of such a tool depends directly on the quantity and quality of data that is input into the system. For the exemplary system, trends that were deliberately introduced into the sample data can be "discovered", but other correlations are simply a function of random noise. In a real system, a variety of interesting patterns can be deduced. For the exemplary database, standard OLAP tools were used. With reference to FIG. 5, a user can use the data mining mode via Data Mining Module 532.

A third exemplary mode that is anticipated is the construction of a pattern detection module. This can, for example, comprise software programmed to sift through the accumulated immune status and other data and search for patterns that might not be evident to a human observer. It is generally true that there are statistically significant patterns in the underlying data which are too subtle or too complex for simple detection schemes. Such an automated detection system can, for example, rely upon one or more of the artificial intelligence pattern recognition techniques as described above and in the standard literature. In exemplary embodiments of the present invention both neural networks and genetic algorithms can, for example, be used to perform this task. With reference to FIG. 5, a user can use the pattern detection mode via Pattern Detection Module 533.

Figure 5A:
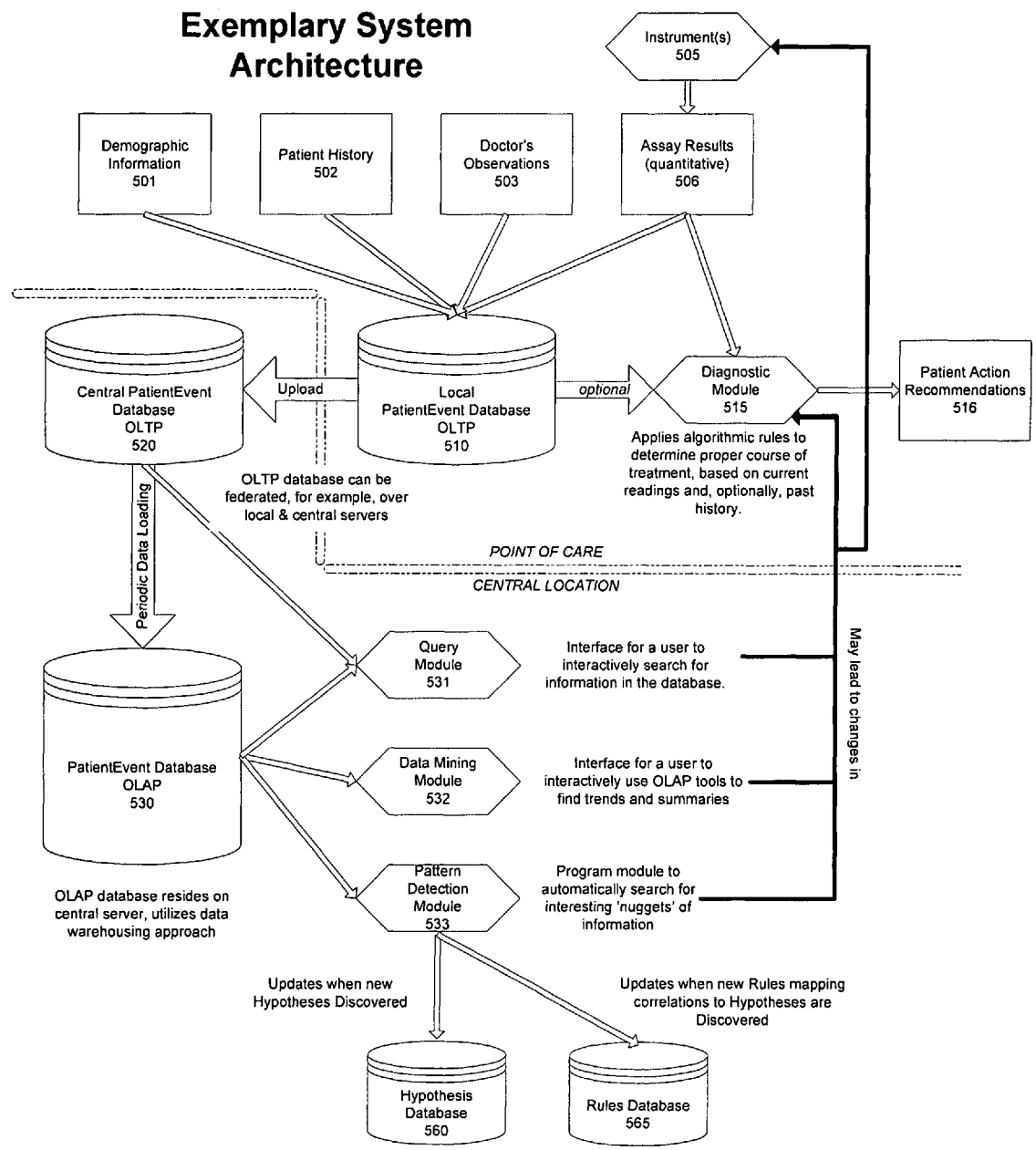
FIG. 5A depicts a detailed system diagram according to an alternate exemplary embodiment of the present invention.
Figure 5C:
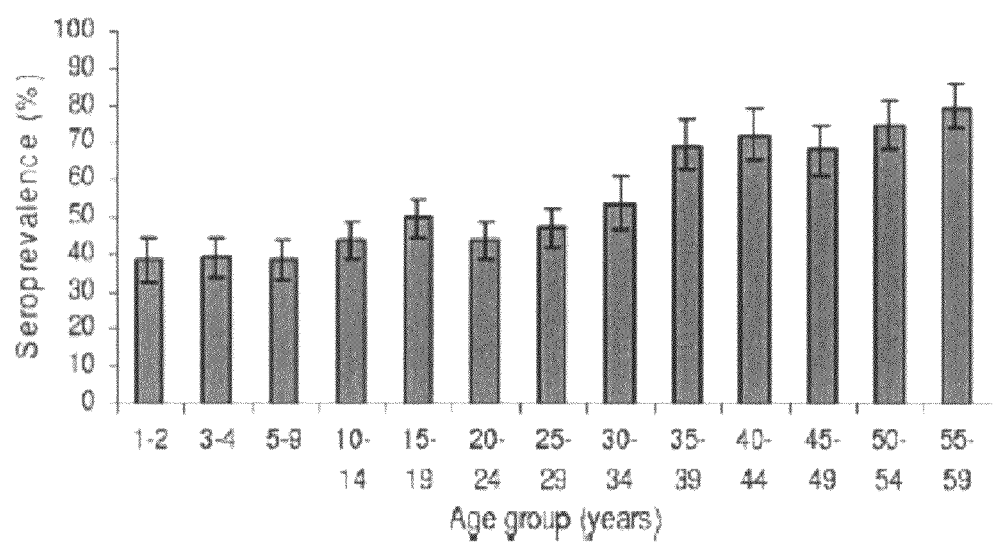
FIG. 5C is an exemplary bar graph depicting CMV prevalance by age group in Australia.

FIG. 5A illustrates an alternative exemplary system architecture to that of FIG. 5. FIG. 5A has a few additions, namely, Hypothesis Database 560 and Rules Database 565. Each of these databases can be used, for example, when pattern detection module 533 discovers a correlation between database variables. When that occurs, a list of such correlations can, for example, be reported to a human expert or group of experts for review. Or, for example, an intelligent system can attempt to recognize the characteristics of such a correlation and associate possible hypotheses to explain it. These can be generated, for example, from a Hypothesis Database 560, and the rules by which a given correlation can, for example, be mapped to one or more hypotheses can be stored, for example, in a Rules Database 565. In such exemplary embodiments, once a set of hypotheses is generated, an exemplary system itself can go back and mine the data to either rule out, corroborate, or confirm that there is insufficient data to either confirm or rule out, each hypothesis in the set. In the latter case the system can recommend that further information be collected, such as, for example, via additional assay panels known to the system, lab tests, additional patient history items, etc. This process is described in greater detail below.

Exemplary Canadian Immigrant Project Database Used to Illustrate Data Mining and Hypothesis Generation Appendix A contains selections (i.e. an initial set of records) from an exemplary database which was used to illustrate various data mining functionalities according to exemplary embodiments of the present invention. The database was created from data obtained in interviews with and by performing tests on blood obtained from a number of newly arrived immigrants to Canada under the auspices of Dr. Chris Greenaway (Assistant Professor in the Department of Medicine, McGill University, and a staff physician in the Departments of Microbiology and Internal Medicine, Sir Mortimer B. Davis Jewish General Hospital, Montréal, Quebec). As can be seen from the initial pages of the database, there are entries for assay results for each of measles, mumps, varicella, rubella, hepatitis A, tetanus, diphtheria, cytomegalovirus, hepatitis B, hepatitis C, as well as other factors such as age, gender, region/country of origin, socioeconomic status, etc. In the descriptions that follow, this database will sometimes be referred to as the CIP database (for Canadian Immigration Project). The entire CIP database has approximately 1500 records. Originally the database did not contain assay results for tetanus, diphtheria, cytomegalovirus, hepatitis B, hepatitis C, which were added later.

The database now contains, specifically, the following data:
Immunological Tests:
Hepatitis A
Measles (two different manufacturers for diagnostic testing)
Mumps
Rubella
Varicella
Tetanus
Diphtheria
Cytomegalovirus
Hepatitis B
Hepatitis C
Historical/Demographic Data:
Region of Origin, being one of:
Sub-Saharan Africa
Latin America and South America
Caribbean
Europe
Eastern Europe
South Asia
Southeast Asia
North Africa/Middle East
Demographic information:
Date recruited
Gender
Age (all participants were adults $\geq 18$ years of age)
Whether the interview was taken through an interpreter
Country of origin, being one of:
India
Bangladesh
Sri Lanka
Pakistan
Morocco
Vietnam
Congo
Other
Date moved to Canada
Citizenship status, being one of
Refugee claimant
Refugee
Immigrant
Other
Pregnancy
History of vaccine-preventable diseases
Participant had written vaccination record?
Participant's residence in home country had indoor toilet/no indoor toilet
If indoor toilet,
Flush?
Other?

Participant's residence in home country had outdoor toilet/no outdoor toilet
If outdoor toilet,
Outhouse?
Covered pit latrine?
Other?
Participant's residence in home country water supply
Tap inside?
Tap outside?
Closed well?
Public stand pipe?
Bottle?
Pump?
River?
Pump earth system?
Tap inside and closed well?
Other?
University education?
Participant's residence in home country degree of crowding (number of individuals/room)?
Participant's residence in home country had electricity/no electricity?

The CIP database could be augmented to facilitate a broader scope of data mining. In such embodiments results of the following assays could be added: Tuberculosis, Avian (H5N1) flu, Pandemic flu (not necessarily H5N1), Chronic infectious diseases other than CMV EBV, Herpes/Type?, Zoster outbreak/varicella antibody level following outbreak?, HPV, HIV HTLV I, *Helicobacter pylori*, Lyme disease, Tularemia, Parasite infections, Malaria, Strongyloides, Hantavirus, Leishmaniasis, Toxoplasmosis (particularly among pregnant women), Antibody levels to other infectious diseases currently on vaccination schedules: Hib, Pneumococcal (conjugate vs. PS vaccines); Meningococcal (conjugate vs. PS vaccines); Poliovirus; Traveler's vaccines; Japanese encephalitis; Cholera; Yellow fever; Military-specific vaccines: Anthrax, Smallpox, Plague, Rabies; Other infectious agents not currently vaccinated for, including: *Staphylococcus aureus, Moraxella catarrhalis*.

In exemplary embodiments of the present invention, the following non-immunologic data can, for example, also be obtained and stored in an individual's exemplary Immunoscore database record:
Environmental considerations
Zip/Postal code
Rural/Urban home environment
Working environment
many interactions with many people
few interactions with few people
Interactions with types of people at home/work:
adults
children/age of children
interactions with local travelers
interactions with global travelers
Commute to work
public transport/drive?
duration?
crowded/stressful?
Power source
proximity to power lines
type of fuel
proximity to power plant
Water
source
well
city
nature of treatment
Nutrition
Diet
high/low fat
meat/vegetable intake
Common food infections
*Salmonella*
Cholera
Hepatitis A
Typhoid
Alcohol consumption/volume
Vitamin supplements
Fitness
Regular exercise/sedentary
Cardiac/blood pressure assessment
History of smoking
Second hand smoking
School(s) attended
Day school/boarding school
Crowding at school?
Work environment
high/low/intermediate stress
job satisfaction
occupation
work described as physical/mental/combination?
safety considerations at work?
infectious organisms present
nosocomial infections a concern?
chemical agents?
Air quality
home
work
Animal exposure
pets
work
farm
lab
leisure
wooded environment?
horseback riding?
Family/personal history:
Chronic disease/nature?
Cancer/type?
Heart disease
Diabetes
Known immunodeficiency
Asthma
Kidney disease
Liver disease
Lung disease
Allergies/type?
Mental illness
Back problems
Joint pain/injury?
Chronic fatigue
Osteoporosis
Arthritis
Epilepsy
Education level
highest grade achieved
Education type
public/private?
education environment
crowding?
stress
quality of school (measured objectively, of course)
Military service?

Nature of deployment
Service branch?
Rank

It is understood that an exemplary database according to the present invention can contain records for various individuals from different countries and locales, being managed under various health care systems, and that various types of assays can be used to obtain assay results. Thus, in exemplary embodiments of the present invention, the data stored in the database can, for example, be normalized to some database wide standard defined for each data field used in the database, or, for example, can be stored in its original form and any algorithm that seeks to access data first performs normalizing of the various records which are input to that algorithm. It is for the purposes of such normalizing that information regarding assay manufacturer, type, and curve that maps an OD or other assay raw result to IUs of an antibody or other measured biochemical needs, in general, to be stored in the database.

Next described are the results of data mining and hypothesis generation studies performed on the exemplary CIP database. These examples illustrate methods and techniques that can be used in exemplary embodiments of the present invention.

Data Mining—Analyses and Conclusions

In exemplary embodiments of the present invention, immunologic information stored in an exemplary database (such as, for example, the CIP database, described above) can, for example, be analyzed in various ways and related to other variables in the database. Three useful examples of such analysis can, for example, include: (1) linear regression analysis on two variables to determine whether a positive or a negative correlation exists; (2) comparison of geometric mean immune values (obtained, for example, as antibody concentration, optical density, etc.) for both genders by geographical regions; and (3) percentage of positive or negative support within a population for one variable with respect to another. Examples of such analyses are described below using data from the CIP database.

5. Linear Regression Analysis—Correlation Coefficients

In exemplary embodiments of the present invention, tables of correlation coefficients (r) can, for example, be generated when comparing one particular immunologic variable (such as, for example, varicella antibody optical density) against other disease-related immune measurements, either for both genders together or separately. For example, FIG. 20 presents the correlation coefficients between Varicella OD and various other variables in the CIP database. FIG. 20 presents three tables. The top table is the correlation of Varicella OD with each of nine other variables from the CIP database for all persons in the CIP database. The second and third tables present this information segregating males and females. For example, in FIG. 20, r values have been highlighted by shading when they are either >0.05 or <−0.05, as a means of readily identifying patterns of relatedness (where |r|≧0.05 is considered as "related").

With reference to FIG. 20, Varicella optical density is obviously highly positively correlated with Varicella titration dilution, inasmuch as one is calculated from the other, but other relationships also appear, although somewhat less pronounced. If the genders are separated, then the relationships appear even more strongly, as expected, since scatter is thus reduced. From the tables presented in FIG. 20, Measles and Mumps immunity (Dade assay) appear to be slightly correlated with Varicella immunity.

The r values in the tables can also, for example, be graphed in such a way so as to better visualize any condition patterns, as is shown, for example, in FIG. 20A. Again, the Measles and Mumps relationship to Varicella stands out above the others (not considering the Varicella titration dilution data, which is obviously correlated to Varicella OD).

6. Geometric Mean Values

In exemplary embodiments of the present invention, immune data can, for example, be statistically analyzed for the purpose of characterizing populations of different geographical regions, as well as for comparing results across genders. Such mean values can thus be graphically compared by gender and region to visualize population dynamics. For example, the geometric means of Rubella antibody concentrations for different regions can be graphically analyzed by gender, as shown in FIG. 20B. With reference thereto, a trend can be seen where males have higher antibody levels than females across all populations in the database. It is also apparent that persons from Southeast Asia show a lower antibody level relative to the other regions in this study. To help facilitate this assessment, dotted lines were drawn on FIG. 20B to indicate the mean of the means (geometric) from all of the populations (excluding Southeast Asia) separately for males and females. The arrows above the bars for the Southeast Asia data show the difference between the mean values for Southeast Asia compared with such mean of the means for all other regions. It would thus appear that Southeast Asia has a lower immune profile for Rubella. This can, for example, be explained as the effect of (i) no specific Rubella vaccine program; and (ii) a possibly a lower exposure rate compared with the rest of the world, making Southeast Asians more susceptible to this disease when traveling to other geographic regions.

This finding highlights one of the many potential uses of the present invention. As described below in Section III, exemplary embodiments of the present invention can be directed to health insurance underwriting. Here, for example, knowledge of the fact that Southeast Asians tend to be vulnerable to Rubella would indicate that such persons, as a condition of maintaining insured status under a health plan or HMO, could be required to obtain Rubella vaccination.

In a similar manner, the geometric means of Hep A units in the CIP database (which are inversely proportional to antibody concentrations and derived from immunoassays), were plotted in FIG. 20C for different geographical regions, again separately for each gender. In this case, it appears that there is no significant difference between males and females across all populations except one, Eastern Europe. Also, once again, Southeast Asia appears to be different from the other regions, where the Hep A antibodies are lower, as shown by higher assay units which, as noted, are inversely related to antibody concentration. In addition, persons from Eastern Europe are also seen as being generally lower in antibodies, and the Eastern European females (dotted bars) are seen as having particularly lower antibodies than the males. Again, in FIG. 20C a dotted line has been drawn to represent the mean of the means (geometric) from all of the populations, excluding Southeast Asia and East Europe, but combining males and females. Another dotted line has been drawn to represent the mean of the means from the excluded populations, except for the Eastern European females, which are noticeably higher in units (and thus lower in antibodies). The arrows in FIG. 20C highlight the differences between (i) the overall population mean of means and the mean for Southeast Asians and Eastern European males; and (ii) the overall population mean of means and the unit levels for Eastern European females. Overall, there appears to be less Hep A reactivity for Southeast Asia and Eastern Europe when compared with other regions; this is especially so among East European females. This may, for example, indicate no vaccination and possibly less exposure, with greater disease susceptibility. Thus, from a health insurance/health management perspective, an adult female from Eastern Europe should have a Hep A vaccination.

7. Percent Support Between Variables

In exemplary embodiments of the present invention, the percentage of a population that demonstrates a positive or negative relationship for one variable with respect to another variable can, for example, be determined and graphically analyzed. For example, using data from the CIP database, Rubella antibody levels were measured in females from China, and the results were grouped according to immune status: immune support (protective high antibody level), low level support (equivocal antibody level), or susceptible support (non-immune antibody level). The percentage of each of these groups that supports an association with another immune variable, either positively or negatively, for various different diseases was then plotted in FIG. 20D. It is apparent that there is no significant difference in support for Rubella with Hep A (non-reactive or reactive) or with Varicella (positive); once again, in FIG. 20D dotted lines have been drawn to help visualize that the Rubella immune levels show no clear trend from immune to lower immunity to susceptible in these specific cases of other diseases. However, as regards Mumps, there is a clear trend for Rubella immune support when compared with Mumps. The arrow shows that there is a greater percentage of Rubella immune support for positive mumps, i.e., immune response for Rubella is correlated with that for Mumps.

The immune support of Mumps for other immune variables can, for example, also be used to compare different geographical regions, as is shown, for example, in FIG. 20E. In FIG. 20E, only the positive and negative Mumps support groups are plotted (leaving out the equivocal "low level support" group) for each of Eastern Europe and Sub Saharan Africa with respect to Hep A=non-reactive, measles=positive, and Rubella=immune. Dotted lines have been drawn to illustrate that there is no difference in Mumps immune support for Hep A=non-reactive in both regions, but the arrows show that there is a difference for Measles=positive in Eastern Europe only, and a difference for Rubella=immune in both regions. Thus, a higher percentage of Mumps immunity is seen with Measles immunity in East Europe, and with Rubella immunity in both East Europe and Sub Saharan Africa.

In exemplary embodiments of the present invention, immune support can also be related to other variables that do not measure immune status, such as, for example, education. An example of such a correlation analysis is shown in FIG. 20F. In this example, the positive and negative Mumps support groups are plotted for Southeast Asia and East Europe with respect to university attendance. From these results it appears that for Southeast Asia, a higher percentage of negative Mumps immune support occurs when there is less university attendance, and in the expected reciprocal way, a higher percentage of positive Mumps immune support occurs with university attendance. For Eastern Europe, however, there is no relationship seen between Mumps immune support and university attendance.

8. Possible Conclusions

The data mining examples described above demonstrate the usefulness, in exemplary embodiments of the present invention, of an analysis of relationships among different variables, both immunologic and otherwise in an unbiased mathematical manner. Regression analysis can, for example, be performed to just look for correlations at random, but the relationships may be weak and difficult to see. Additionally, for example, population means can be used to detect broad population differences or similarities. Also, percentage support analysis between different variables can, for example, allow for a greater focus on specific relationships between different immune status results and other factors that may affect them.

The examples described above point towards interesting correlations, some of which can be explained based on known immunization practices, and others which may, for example, indicate previously unforeseen relationships involving exposure to disease. For example, in countries where MMR (Measles, Mumps, Rubella) vaccines are administered, one might expect to see a clear correlation of immunity for all three diseases; but this would usually occur only in developed countries such as the U.S., Canada, and parts of Europe. Also, in some cases, there may only be single immunizations for Measles. The immigrant populations used in the examples discussed above, however, were most likely not immunized for the diseases under analysis, and thus most of the observed immunity would be due to environmental exposure to the infectious agents of disease, or possibly some other agents or substances that cross-react with these disease agents.

Due to socioeconomic conditions in these regions, it is possible that exposure to one disease might also indicate exposure to others, particularly in crowded areas, or areas where diseases are known to be endemic. It is therefore not surprising to see positive correlations between Mumps and Measles or Rubella, as seen in the China and Eastern Europe data. In certain circumstances, however, the disease exposure may be so prevalent (>90% of population) that there would be no way to establish correlations to other factors since everyone has it; this might be the case, for example, for Mumps support with Measles in Sub Saharan Africa as shown in FIG. 20E.

Increased immunity for Mumps in Southeast Asia for those who attend a university could be the result of these more fortunate people being allowed greater access to vaccines, or, for example, it could be due to greater disease exposure in crowded dormitories. No difference in Mumps for university attendance in Eastern Europe might mean that there is greater disease incidence, or, for example, that there is greater university attendance, since both positive and negative support percentages are high. No difference in Rubella support for Hep A reactivity or positive Varicella in China may be, for example, the result of higher disease prevalence and exposure overall. A trend towards higher Rubella antibodies in males for all regions might indicate an unforeseen gender preference that could warrant further epidemiological studies in relation genetic polymorphism if this is not the result of broad cultural practices regarding vaccinations or disease exposure. The significantly lower Hep A antibody levels (higher assay units) only for females in Eastern Europe may, for example, might indicate a cultural phenomenon for further study.

These examples merely scratch the surface of what can be explored in terms of epidemiology, immunity, socioeconomics, and genetic polymorphism in exemplary embodiments of the present invention. Such exemplary analyses, can be used, for example, to design more focused studies on specific areas of interest or, for example, to test specific relationships that are only hinted at in the beginning. It is also useful to remember that the data in these examples only represent immigrants entering Canada; it may therefore be important, in exemplary embodiments of the present invention, to collect more samples and expand the database to other population segments, and/or to follow the same persons through time taking samples of each participant annually for an extended period of time.

As can be seen from the above description, in exemplary embodiments of the present invention, once a list of correlations has been obtained by analysis of a given set of records in an exemplary database, either humans or intelligent systems are needed to postulate explanatory hypothesis, which can then be verified, or at least can be attempted to be verified, excluded or determined as inconclusive.

9. Expansion of Database

The database was expanded, since the previous items analyzed and discussed in sections 1 through 4 above, to include additional immunologic values that cover the following infectious diseases or infectious agents: Cytomegalovirus (CMV), Tetanus, Diphtheria, Hepatitis A, and Hepatitis B. CMV was of particular interest because of the prevailing scientific literature supporting its role in the development of immunosenescence during natural human aging. Tetanus and Diphtheria also appeared to be good candidate markers for following the immune status regarding vaccines that are commonly received in childhood and often as adults (particularly Tetanus). The possibility was anticipated that we might see an inverse correlation between CMV and other immune markers such as Tetanus. In fact such correlations have been observed, which will be demonstrated in the following sections (6 and 7).

As in section 1, tables of correlation coefficients have been constructed to include the new data. FIG. 20G1 represents the correlation of CMV with the other immune factors. To be more selective, we raised the highlighting (color) threshold to + or −0.1. At this level, South Asia was the only region that showed no overall correlation for CMV, and males generally showed more correlations than females in other parts of the world. Looking at the graphic representation in FIG. 20G2, FIG. 20G3, and FIG. 20G4, there appears to be more negative correlations overall in SE Asia for Diphtheria and Hep B, and more positive correlation in Eastern Europe for Tetanus. These tables and graphs, however, do not take into account differences that may relate to aging, which is the subject of the following sections.

10. Distribution of Geometric Means According to Age

Next the effects of age were looked at globally as to effect on the geometric mean immune values in order to observe any gross patterns, particularly regarding CMV, Tetanus, and Diphtheria, which are respectively represented in FIGS. 20G5, 20G6, and 20G7. As a result, an inverse correlation between CMV and Tetanus antibody levels was discovered. FIG. 20G5 shows that CMV gradually increases with age, while Tetanus sharply declines in FIG. 20G6, and Diphtheria showed no clear change in FIG. 20G7. This correlation can, for example, be an indication of an immunosuppressive effect of CMV infection on the immune status regarding Tetanus (hypothesis associated with correlation). Since Tetanus and Diphtheria vaccines are usually given in combination, this would imply a specific interaction for Tetanus.

While it may be normal for immunity to wane with age, the decline for Tetanus appeared to be more evident than what was observed for others. Based on the step-like rise observed for CMV, where the ages in years can be grouped in 3 categories (18-35, 36-55, 56-80), the age range was split into three groups for analysis of any trend in geometric means for those groups. With this approach, all showed mostly a rise in immunity with age (as seen in FIGS. 20G8, 20G10, 20G11, 20G12, 20G13, 20G14, 20G15, 20G16, 20G17, and 20G18), except for Hep B (FIG. 20G19 and FIG. 20G20), which may also be inversely correlated with CMV. Tetanus, of course, again showed a decline, as depicted in FIG. 20G9. It is noted that FIG. 20G17 does show a rise for Hep A, even though the means are declining in the graph, because the low assay values actually translate into high immune values. Also, FIG. 20G18 shows mostly a flat response for Rubella, with a possible convergence of the genders as they age.

11. Focus on CMV and Tetanus

Based on the above described correlations, it became clear that CMV and Tetanus needed closer scrutiny. As described above in section 2, the geometric mean immune values for males and females by geographic region were next looked at. Comparing CMV in FIG. 20G21 with Tetanus in FIG. 20G22, it is apparent that the pattern of bar heights from each graph is generally opposite in configuration; i.e., up in one becomes down in the other, and vice versa—another demonstration of the inverse correlation on a global scale. For example, Latin America and East Europe have the highest Tetanus levels, and the lowest CMV levels. In addition, the males are higher for Tetanus and lower for CMV when compared with the females. In contrast, the patterns for Diphtheria in FIG. 20G23 and Hep C in FIG. 20G24 more closely resemble CMV (except for Eastern Europe).

The females in Sub Saharan Africa appeared to have notably higher Tetanus responses than the males, so it was decided to focus more on regions in Africa (North versus Sub Saharan), along with their age groups. In this case, the age range was split into two categories (18-35 and 36-80) in order to maintain higher numbers of people per group (which declines rapidly in the older age range). Comparing CMV in FIG. 20G25 with Tetanus in FIG. 20G26, the females of Sub Saharan Africa showed dramatically higher Tetanus levels, regardless of age, along with high CMV levels, but the Tetanus level dropped for North Africa as they became older, while CMV increased. One might suspect that vaccine intervention could cause this effect for Tetanus, which is what we believe occurred in Sub Saharan Africa. For example, it is known that WHO has supported campaigns against neonatal Tetanus in Sub Saharan Africa by immunizing women. FIG. 20G27 also shows an increase in Diphtheria levels as the population aged, which might be expected if they were vaccinated with Tetanus and Diphtheria in combination.

As in section 3, the percent support between immune variables was investigated. First, examining the Tetanus and Diphtheria reactive support for gender, FIG. 20G28 shows that Tetanus has greater support in females than males of Sub Saharan Africa, but Diphtheria shows no difference in FIG. 20G29, all as expected. For CMV reactive support, the confidence level was not high enough from the database to determine the values for Sub Saharan Africa. FIGS. 20G30 and 20G31, however, do show greater CMV reactive support respectively for Tetanus in South Asia and Diphtheria in South and SE Asia. FIGS. 20G32 and 20G33 show, in several regions, that Tetanus and Diphtheria respectively provide higher support for each other in females than males. Finally, university attendance may have less reactive support from CMV (FIG. 20G34), but more reactive support from Tetanus (FIG. 20G35) and Diphtheria (FIG. 20G36). It should be noted that one needs to consult tables of total numbers and percentages (FIG. 20G37) for the occurrence of these reactive thresholds in the different populations, as discussed above in section 4, in order to be sure that high support is not just a result of high occurrence in a population.

12. Simulation: Sampling Over Time

One should be able to measure immune variables for individuals over time, where the visits to the clinic or office may occur after lengthy time intervals, allowing for trend analyses that might aid in predicting the status of individuals over many years. This was simulated by trending the data for populations over different age ranges. For example, using 10 year intervals, it was estimated that the CMV levels would increase by 50 OD units, Tetanus would decrease by 0.05 OD unit, and Varicella would increase by 0.1 OD unit. The global population was then split into two age groups, 18-35 and 36-76. All the individuals would have their OD units incremented by their respective amounts every 10 years, with the population moving in time from one age group to the next. This would lead to the young group disappearing as the individuals aged, while the older individuals would be removed on the other end (past age 76) as they would be expected to naturally die off. The data were simulated in this way to account for a total of four visits, where the first visit represents the original data from the database.

FIG. 20G38 shows the CMV response moving from the young group to the older group, increasing with time for each visit. FIG. 20G39 shows the Tetanus response decreasing over time for each visit. FIG. 20G40 shows the Varicella response increasing with each visit. Finally, Hep A was looked at as an example of a response that might change upon leaving the original environment as an immigrant. In this case, one might predict that the immigrant population from the developing world, arriving in a developed country (Canada), would no longer be exposed to Hep A, thereby leading to a reduction in Hep A in the older age group, which is really a lack of increase in Hep A as the younger individuals age. For this study, remember that the high Hep A values represent low antibody levels; so, higher bars would represent the maintenance of low Hep A, which is exactly what is shown in FIG. 20G41, where nothing was added (or subtracted) to the values as they aged.

Pattern Detection and Hypothesis Generation

FIG. 21A illustrates an exemplary process flow for pattern detection according to exemplary embodiments of the present invention. With reference thereto, at 21A01 patient information attributes can be collected and then grouped together into separate logical groupings. The following table illustrates such an exemplary grouping.

| Logical group | Attributes Example |
| --- | --- |
| Patient Information | Patient's information that never changes e.g. Gender, Birth Date |
| Current medical information | Visit date, female patient is pregnant or not at the time of visit, patient is taking medication or not etc. |
| Geography | Patient's country of origin, region of origin |
| Immune Status | Optical density of various diseases like HepA, Rubella etc and also the immune interpretation i.e. Positive, negative or susceptible for a disease. |
| Environmental conditions | Patients education level, Type of toilet, water supply, average people in house hold, number of rooms in house hold, type of water supply etc. |
| Patients medical history | Has patient been hospitalized before? If the patient had diseases like measles, mumps etc and at what age, patient has vaccine record. |
| Miscellaneous | Information that does not fall into any of the above |

Next, at 21A05, the logical groups can be prioritized in an order in which they are to be correlated. For example, one could choose the highest priority logical groups that you want to find correlations between (e.g. Immune Status v. Geography of the patient). This can be done, for example, at 21A15, for all the logical groups. At 21A20, correlations can be sought. This can be done, for example, as follows:

1. obtain the percentage of people in the same geographical regions that are immune, not immune or susceptible to diseases.
2. try to find a region where the patient population has variation in immunity status towards a disease. The reason for this is that if 89% of the people are Immune to Mumps in, say, N. America, this means that there is not enough data for people who are not immune to Mumps for evaluation. Whereas in South East Asia 67% are immune to Rubella, therefore there is a large percentage of the population (33%) that are either susceptible to Rubella or not immune. Thus when there is difference in immune status in population in the same region the remaining data can be explored to attempt to determine the cause.
3. Try to evaluate the above results by next logical group (i.e. patient information—does the immunity status of a region differ by gender?). Obtain the percentage of population by region and gender that are immune, not immune or susceptible to the disease. If there is a major variation in the percentage of male-female population for same region that are immune or not immune, then there is a discrepancy and the other data can then be explored to attempt to determine a cause.
4. Use a data mining tool to find the correlations of the next logical group (i.e., for example environmental conditions on the patients within the same region and gender and same immune status).
5. Obtain the geometric means of the optical density of the various diseases by geography and gender. This can determine if there is a difference in the antibody level between genders living in the same geographical regions. After seeking correlations at 21A20, if a correlation is found at 21A25, it can be reported at 21A27. The process can continue until all groups have been searched, and process flow ends, at 21A50.

In exemplary embodiments of the present invention, Oracle Data Miner can be used, for example, as a tool for finding patterns in a database.

Using this tool, for example, there are different ways of finding correlations in the data.

Association Rules

Oracle data miner uses Apriori Algorithm to find these association rules.

Apriori Algorithm Details

Oracle Data Miner calculates the following two properties of association rules:

Support: Support of an associating pattern is the percentage of task-relevant data transactions for which the data is true.

If A=>B Support (A=>B)=Number of tuples containing both A and B Total number of tuples Confidence: Confidence is defined as the measure of certainty or trustworthiness associated with each discovered pattern.

If A=>B Confidence (A=>B)=Number of tuples containing both A and B Number of tuples containing A Associations can be calculated in 3 steps:

1. Find all combinations of items, called frequent itemsets, whose support is greater than minimum support.
2. Decide the minimum support and minimum confidence required for choosing the rules. As the data set under consideration was small we kept the minimum support=0.1 and minimum confidence as 0.1 so that we do not miss any data that might have any inverse co relation or strong co relation.
3. Use the frequent itemsets to generate the desired rules. Rules that satisfy both minimum support threshold and minimum confidence threshold are called strong rules. Reading the confidence and support get the rules that are correlated.

For example, association rules generated for Chinese females who are immune to rubella.

Some exemplary rules that can be generated can be, for example:

| Rules | Confidence | Support |
|---|---|---|
| If Hep A Non-Reactive then Rubella Immune | 1.00000 | 0.25532 |
| If Hep A Reactive then Rubella Immune | 1.00000 | 0.74468 |
| If Measles = Negative then Rubella Immune | 1.00000 | 0.17021 |
| If Measles = Positive then Rubella Immune | 1.00000 | 0.80851 |
| If Varicella = Positive then Rubella Immune | 1.00000 | 0.97872 |

Conclusions can be derived, for example, from the rules generated by data miner. Thus, Rule 1 means that 25% of the Chinese females who are immune to Rubella are Hep A non reactive. The trustworthiness of this statement is 100%.

Regression:

Regression creates predictive models. The difference between regression and classification is that regression deals with numerical/continuous target attributes, whereas classification deals with discrete/categorical target attributes. In other words, if the target attribute contains continuous (floating-point) values, a regression technique is required. If the target attribute contains categorical (string or discrete integer) values, a classification technique is called for.

The most common form of regression is linear regression, in which a line that best fits the data is calculated, that is, the line that minimizes the average distance of all the points from the line.

This line becomes a predictive model when the value of the dependent variable is not known; its value is predicted by the point on the line that corresponds to the values of the independent variables for that record. Oracle Data Mining provides both linear and non-linear regression models.

Algorithm options: Support Vector Machines (SVM)

Support Vector Machine (SVM) is a classification and regression prediction tool that uses machine learning theory to maximize predictive accuracy while automatically avoiding over fit of the data.

Geometric Mean:

$$GM_y = \sqrt[n]{y_1 y_2 y_3 \ldots y_n}$$

The geometric mean of a set of positive data is defined as the $n^{th}$ root of the product of all the members of the set, where n is the number of members.

Another way to calculate the geometric mean, which may aid in statistical analyses, is to define it as the antilog of the mean of the log values for a set of numbers.

Exemplary Data Mining Algorithm

Using the CIP database, the following exemplary algorithm was performed:

1. The logical groups were prioritized so that the immune status (immune assay results) could be shown according to geography, followed by Gender. This is shown in all examples of the data mining (regression analysis, geometric means, and percent support). All other logical groups could be examined later for possible relationships that might help explain the observed correlations.
2. Regression analyses were performed between all immune variables at each geographic location, and by gender. Varying cut-offs could be set to detect patterns of correlations from tabulated correlation coefficients. For example, r values were highlighted in the table where they were >0.05 or <−0.05, is described above in connection with FIG. 20. This resulted a possible association of Varicella with Measles and Mumps. These r values were also graphed to facilitate any visualization, as demonstrated.
3. Geometric means of immune assay results were calculated for all geographic regions, and by gender. Graphic analyses were performed, as demonstrated, to detect differences or similarities between regions, as well as gender. For example, there appeared to be a gender difference globally for Rubella immunity in favor of males, and a lower immunity overall in Southeast Asia. Hep A showed this gender difference only for East Europe, with lower overall reactivity in both Southeast Asia and East Europe.
4. Setting the confidence at 100% for different immune subsets of a disease, different geographical regions were examined for the percent support of the association with other variables. For example, in each immune subset of Rubella (immune, low level, susceptible) for Chinese females, the percent support was determined for each of the other disease immune variables. The graph (FIG. 20D) shows that there is a greater association of Rubella immune support for positive Mumps, when compared with Rubella low level or susceptible support. In another graph (FIG. 20E), positive and negative Mumps support was associated with other diseases in different geographical locations. In this case, there was a greater percent positive Mumps support for Measles and Rubella in both East Europe and Sub Saharan Africa.
5. To enhance the chances of seeing meaningful associations, regions where there was a lower incidence of immune status result (e.g., <80%) were looked at, so that associations were not just based on the fact that everyone has a particular status. For example, if 95% of a population has a particular status, then that status could likely be associated with anything; however, as noted above, since there is 67% immunity for Rubella in Southeast Asia, then there was enough non-immunity to allow some possibility of detecting meaningful associations.
6. Other logical groups were then now be examined for other possible associations and explanations of previous associations. For example, an association was graphically demonstrated between positive Mumps support and university attendance in Southeast Asia (FIG. 20F).

FIG. 21B depicts the exemplary pattern detection process flow of FIG. 21A with additional expert system functionalities. Thus, at 21B60, for each correlation, the hypothesis database can be searched for possible explanations of the given correlation. In general, this can be done, for example, by using a Rules Database and Hypothesis as shown in FIG. 5A (and FIG. 2B) to map correlations to hypotheses according to defined rules. Once a set of hypotheses is generated, for example, at 21B65 each hypothesis can be tested, to the extent possible, authomatically, using data in the system database. Finally, at 21B67, a report can be generated which lists the generated hypothesis and states, based on system data, if that hypothesis is corroborated, ruled out, or inconclusive, as next described.

Thus, in exemplary embodiments of the present invention, a Hypothesis Database (and associated Rules Database) can function as a repository for expert knowledge. When correlations are discovered by the system, these databases can be consulted to provide possible explanations as to why certain correlations may exist. A Rules Database can, for example, map—as a function of its conditions on attributes, such as, for example, the database variables involved in the correlation—correlations to hypothesis already stored in a Hypothesis Database. For example, a possible sequence may occur as follows:

1. Database Searched.
2. Correlation found between Rubella and Varicella where Antibody levels are directly proportional.
3. Consult Hypotheses Database for possible explanations.
4. Possible explanations:
   a. Cross Reactivity (when exposed to one disease, build up resistance to the other)
   b. Multiple disease vaccinations; and
   c. Patient living in an area where risk of exposure is great.
5. System can automatically seek to verify whether each hypothesis generated by the system, using the Rules Database and Hypothesis Database, as above, is valid.

For example, the database records for the individuals involved in the correlation can be checked for (i) vaccinations for either or both of Rubella and Varicella, and for (ii) living and/or socioeconomic conditions conducive to exposure.

Next, the hypothesis and the support/nonsupport/non-conclusiveness of each hypothesis can be reported to humans, as shown in 21B67 of FIG. 21B.

6. After receiving a report, each correlation can be analyzed by a human to determine if a new hypothesis should be added and fed back into the Hypotheses Database; or if an existing hypothesis is operative in the given context.

An example of this process can be illustrated with reference to FIG. 20B, which presents levels of Rubella antibody concentration across various regions using data form the CIP database. First, the data was grouped by gender and region to determine if any trends were discovered.

As noted above, it was discovered that the females in Southeast Asia had especially low levels of Rubella antibodies. Upon further, lower level, geographic analysis it was found that the individuals from China were the ones with low levels.

Possible hypotheses for this occurrence are, for example:
1. The females tested were never vaccinated for Rubella.
2. The females tested were not exposed to Rubella via the general populace.

As above, data already in the system can be used to examine the validity of each of these hypotheses.

In this way future correlations can, for example, be analyzed by the system itself to suggest possible reasons as to why trends or patterns have emerged.

Exemplary Automatic Pattern Detection Module

FIG. 21C depicts exemplary process flow for an exemplary automated pattern detection module according to an exemplary embodiment of the present invention. With general reference thereto, the following exemplary process can be implemented in exemplary embodiments of the present invention for such a module:

1. Prepare data for data mining. Most data mining algorithms require data to be suitably transformed in order to produce good results. Some common data transformations are: binning, normalization, missing value imputation, and outlier removal. In exemplary embodiments of the present invention, techniques used for transforming the data can be, for example, selected based on attribute data type, attribute value range, attribute cardinality, and percentage of missing values for an attribute or a record. (21C01, 21C03, 21C05)

2. Group the attributes of the data into different logical groups like patient current immune status, patient history, environmental conditions they lived in, geography, etc. (21C07)

3. As this is a data centric data mining system for diseases, a focal point is to get the disease immune status relativity. The attribute importance of each attribute can be found to rank them in an ascending order to determine which attributes effect patient's immune status to a particular disease. Attribute Importance ranks the predictive attributes by eliminating redundant, irrelevant, or uninformative attributes and identifying those predictor attributes that may have the most influence in making predictions. (21C07)

Example For rubella interpretation attribute the following was found
   Attribute Importance Order

| RUBELLA_ANTIBODY_LEVEL | 1 |
   | MEASLES_OPD_ZEUS | 2 |
   | ELECTRICITY | 3 |
   | PT_GENDER | 4 |

4. For each disease immune status (21C15) find a correlation with all possible combinations of identified set of attributes found in Step 3. (21C1B), (21C20)

For example, a correlation between Rubella interpretation and Rubella antibody level and gender was found.

5. For each correlation a threshold can be with the help of a (human) domain expert (21C30)

6. Compare the correlation found by the data miner with the thresholds set. Verify the combination of attributes resulting correlation with the disease immunity status with acceptable threshold with the hypotheses database. If such relation already exists remove this combination from further investigation.

7. If the correlation can not be explained by existing hypotheses, analyze this attribute combination further for each attribute's contribution to the correlation of the whole set of attributes with disease immune status.

8. Derive association rules for the correlated attribute set found from Step 7.

9. Check rules with the discovered set of rules for its existence.

10. Analyze the Rules for determining the patterns in the data set using line or curve fitting.

11. Report discovered pattern and verify with existing hypotheses database.

For the exemplary analyses of the CIP database described above, where data was received in the form of an Excel spreadsheet, and data mining was accomplished using Oracle software, the following process was utilized. Similar processes can be implemented in exemplary embodiments of the present invention.

Data Mining Steps
Data Preparation:
1. The data is received in .xls format.
2. The data then needs to be scrutinized for each column and modified.

Example: some columns have data like ">250". That needs to be changed to some number greater than 250 (Scientist discretion) since the data needs to be imported into the database as a number and ">250" is not a number.

3. All the data is checked for valid values in the xls sheet before importing into the database.
4. Save the data.xls file as data.csv file (Comma separated file).
5. Create the table using the data received using the script createtable.sql.
6. Now import the data from the .xls sheet into the new table using the Immunoscore_Mar2007.ctl file.

Association Rules:
Association Rules provide the ability to show relationships that exist in the data.
To find the association rules between the attributes of the data use the Oracle Data Miner (ODM).
E.g. Get association rules for everyone that has a Measles Interpretation which is positive
1. Create a view of records that have the attribute value "measles interpretation" as "positive".
2. Next go to Oracle Data Miner.
3. Click on Models>Association Rules>Build.
4. Name your Model and Click Next to continue.
5. Specify the location of the data used to build the model.
   Schema: Select the schema containing the input table.
   Input table: Select the table or view to use.
   Records per Case: Select Single Record per case. (As each patient record is 1 record in your view).
   Click Next to continue.
6. ODM supports Apriori Algorithm to build Association Rules. You can change the defaults.
   Minimum Support: A real number between 0-1. Ask the scientist for details.
   Minimum Confidence: A real number between 0-1. Ask the scientist for details.
   Limit Number of Attributes in Each Rule: Number between 2-100.
   After specifying the values Click Next to continue.
7. Select data preparation if any is required. Click Next to continue.
8. Choose the attribute to include in your model. Click Next to continue
9. Click Finish to queue your mining activity.
10. Once the mining activity is executed without error, get the rules based on Rule Length Ascending, Support Descending and Confidence Descending.
11. Export the rules to an .xls sheets.

Regression:
Regression Models provide the ability to predict numerical attributes about data entities.
Steps:
1. Create an Oracle View from the main table with all the numerical fields that you want in your regression model.
2. Click on ODM.
3. Click Model>Regression>Build
4. Name your Model. Click Next to continue.
5. Specify the location of the data used to build the model.
   Schema: Select the schema containing the input table.
   Input table: Select the table or view to use.
   Records per Case: Select Single Record per case. (As each patient record is 1 record in your view).
   Click Next to continue.
6. ODM uses the Support Vector Machine algorithm for regression. Change the values of the defaults by asking the scientists. Currently defaults given by ODM are used.
7. Click Next to Continue.
8. Select Automatic Preparation option for your Model. Click Next to continue.
9. Select the attribute you want to predict. Click Next to continue.
10. Select all the attributes that must be in your model. Click Next to continue.
11. Click Finish to queue the mining task on the server.
12. Once the task is done export the results to an .xls sheet.

Section III Uses of Immunoscore Information in Various Commercial, Research and Governmental Contexts In exemplary embodiments of the present invention, ImmunoScore information (including, for example, results of assay panels, individual history and records of health care visits and treatments administered or undergone) processed in an exemplary system and stored in an exemplary database can be used in a variety of commercial, research and governmental applications. These uses can range from optimizing the health care costs of a medical insurance underwriter to facilitating immunogenicity studies for a pharmaceutical manufacturer, or, for example, to tracking the incoming and subsequent immune status of immigrants. In what follows, descriptions of several exemplary business methods which leverage or exploit the use of ImmunoScore informatics are presented.

A. Health Insurance Underwriting and Management

In exemplary embodiments of the present invention, systems and methods according to the present invention can be used, for example, to optimize the business of health insurers as well as healthcare providers, who are essentially self insurers. In general, a health insurance underwriter or a health insurance provider has a population of individuals, generally called insureds or plan members, whose medical care costs are reimbursed or paid for directly by the healthcare insurer or the healthcare plan. In such contexts, it is useful to monitor the health of the population of insureds or plan members, especially those who are older and in those years, generally, for example, starting at age 60, when individuals begin to encounter greater health and medical problems.

In exemplary embodiments of the present invention, each plan member or insured, or, for example, each plan member or insured above a certain age, can be assayed, and the results can be used to determine whether any prophylactic therapy should be administered to these individuals. Sometimes the decision is as simple as identifying vaccine preventable diseases for which the individual does not have sufficient levels of antibodies. In that case, the prophylactic therapy would be the administration of the vaccine in question. More complicated decisions could include identification of diseases, or of biochemical markers therefor, that an insured or plan member is susceptible to that do not have a direct and economical prophylactic therapy. In that case, there can be, for example, a more complex algorithm which decides, given (i) assay results and (ii) the relative costs of assuming the risk that the insured will contract the disease versus the costs of prophylactic therapies to prevent the disease or diseases implicated what to do. Such algorithms could, for example, be implemented in a system such as is depicted in FIG. 2A, where, for example, in addition to database 203 where the results of assays conducted on individuals are stored, there can also be a business rules database 220 which can also supply inputs to a central processor 204 which implements such analysis and algorithms. The inputs to such algorithms can then be, for example, not just assay results, medical history and demographic information, but also a set of business rules allowing a decision to be made or facilitated, taking into account the relative costs and benefits of administering prophylactic therapies. Such benefits to be considered, can, for example, be those inuring to the individual as well as those inuring to the members of the health care plan as a whole, or, those which seek to maximize profits or efficiencies. In exemplary embodiments of the present invention such a healthcare insurance optimization method could be implemented as is illustrated in process flow diagrams FIGS. 22 and 23.

As can be envisioned from the CIP database, it appears that the level of anti-Rubella antibody is uniformly lower in those individuals from SE Asia. Rubella is a generally a mild, self-resolving infection except in pregnant females, in which instance there are undue complications to the newborn, known as Chronic Rubella Syndrome (CRS). In an immigrant population such as the one documented in the CIP database, if women of child-bearing age from SE Asia were demonstrated to be susceptible to Rubella infection, health care authorities, as well as those underwriting insurance policies would be well made aware of such information. Not only are those women more at risk during pregnancy, but this particular immigrant population would be more likely to infect native Canadians of child-bearing age (assuming that their own antibody levels had waned). The general health of the population, therefore, would be well-served making sure that these individuals were appropriately vaccinated to avoid Rubella infection and possible complications to child-bearing women. These data reveal that Canadian authorities (and by extension, those in the United States) could, for example, be well served and fiscally responsible in the long run by testing and immunizing the immigrant population against Rubella and other vaccine-preventable diseases.

FIG. 22 depicts an exemplary process flow for a health care management application. With reference thereto, at 2201 an insured's immune status can be examined, for example by conducting one or more assays or panels of assays such as, for example, those that are described above. At 2202, for example, the results of those assays can be used to identify diseases that the insured is susceptible to, and moreover, the risk of contraction of each disease for that individual can be calculated. At 2203, prophylactic therapies that could prevent each identified disease can be identified, and at 2204, for each identified disease a decision can be made by calculating the expected costs of treatment (such as, for example, by taking the known costs of treatment multiplied by the probability of contraction) and the costs of associated prophylactic therapies. Finally, at 2205, prophylactic therapies that cost less than the expected costs of treatment can be required for the insured as a condition of maintaining his or her insurance coverage or membership in the health plan, and at 2206, for those prophylactic therapies whose costs are greater than expected treatment costs, they can also be required and the insured's premium increased.

FIG. 23 depicts a particular subset of the process flow illustrated in FIG. 22 where the prophylactic therapies are simple and the ailments identified are vaccine preventable diseases. Beginning at 2301, an insured or plan member's immune status is examined by conducting one or more assays or panels of assays such as those described above. At 2302, vaccine preventable diseases that the insured is susceptible to are identified based on an analysis of the results of the immune status from 2301. At 2303, the insured can be, for example, required to obtain vaccines for the identified vaccine preventable diseases. At 2304, follow-up examinations of the insured's immune status post-vaccination can be made, again by conducting one or more assays or panels of assays, and these results can also be stored in the database. At 2305, the follow-up examination results can be used to evaluate the efficacy of any administered vaccines to provide the necessary immunity to the identified diseases for this individual. When extended to an entire population, such as, for example, the insureds of a health insurance company or the members of a health plan, this can, for example, provide a means of evaluating the efficacy of vaccines in an aging population. This can also be very useful in the context of measuring and dealing with immunosenescense, as described below.

Next described are a number of process flow charts which illustrate exemplary process flow according to various embodiments of the present invention applied to healthcare management applications. FIG. 24 is an alternative process flow to that depicted in FIG. 22, is concerned with adjusting an insurance premium or an HMO participation fee for an individual based upon identification of potential diseases that an individual is susceptible to using ImmunoScore diagnostics.

The context of FIG. 24 could arise, for example, in the context of an insurance company or HMO requiring an annual ImmunoScore diagnostic panel as a condition of maintaining insurance coverage or participation under a healthcare plan. Such annual requirement would be akin to the annual information questionnaires that automobile insurance companies require of all of their insureds wherein an insured must state if he has had any serious health problems, if he has been involved in any accidents, or if other out of the ordinary events have occurred. With reference to FIG. 24 at 2401, the individual's immune status can be examined and at 2402, based upon the results of such examination, all diseases that the individual is susceptible to can be identified. 2405 is a decision tree which is applied to each disease identified at 2402. Thus, at 2405, for each disease a decision is made as to whether a prophylactic therapy is available. If no, flow terminates at 2410 where the insured's premium is adjusted upwards, to account for the additional risk the insurance company is taking in continuing to cover this individual. If, at 2405 there is a prophylactic therapy available then the flow moves to 2406 where it is determined whether to administer or approve the prophylactic therapy. Based upon this decision, the premium can also be adjusted.

FIG. 24A is a more detailed version of the analyses described in connection with FIGS. 22 and 24. With reference to FIG. 24A, at 24A01 the immune status of an individual can be examined, and at 24A02 the initial total cost can be set to zero. 24A02 through 24A35 are then applied in a loop which cycles over all of the diseases tested for in the examination at 24A01. Such identified diseases can be, for example, those indicated by analyzing the results of assays conducted and other data associated with the individual or various populations to which he/she belongs, as described above. For each potential disease, at 24A05 it can be determined whether the individual is susceptible or not based upon the assay results. If no, process flow can terminate as to that disease at 24A20 and no incrementation of cost occurs. If yes, flow moves to 24A10 where it is determined whether a prophylactic therapy exists. If a prophylactic therapy does not exist, at 24A30 the total cost is incremented by the cost of treatment. If it does exist, at 24A05 it can be determined whether the treatment cost from the disease is greater than the cost of the prophylactic therapy. If no, then at 24A35 the prophylactic therapy can be offered to be reimbursed up to the treatment cost and the total cost can be incremented by the treatment cost. If yes, then at 24A25 the individual is required to take the prophylactic therapy and the total cost can be incremented by the prophylactic therapy's cost. After looping through all of the potentially relevant diseases, at 24A50 the premium can be adjusted based upon the total cost. The computation of total cost and prophylactic therapy cost at both the disease specific level and the over all levels can be given by the following rules:

Disease Specific:

| | |
|---|---|
| Computation of TC: | P(CD\|IS and not PT) * C(T\|CD and not PT and IS) |
| Computation of PT Cost: | P(CD\|IS and PT) * C(T\|CD and PT and IS) |

Overall Disease-Related Healthcare Costs:

$$TC = \Sigma P(CDi | \text{not } PT \text{ and } IS) * C(Ti | CDi \text{ and } PT \text{ and } IS) + C(PT) \text{ (in all diseases)}$$

$$PT = \Sigma P(CDi | \text{not } PT \text{ and } IS) * C(Ti | CDi \text{ and not } PT \text{ and } IS)$$

The various exemplary implementations of healthcare management described above have considered each disease individually. FIG. 25 addresses a more complicated situation where all of the potential diseases are identified and all prophylactic therapies available for all of the identified diseases are also identified in all possible combinations of diseases and prophylactic therapies are analyzed using a cost benefit approach. Thus, with reference to FIG. 25, at 2501 a panel of assays can be conducted. At 2502, based upon the results of such assays all diseases the individuals are susceptible to are identified. At 2505 all prophylactic therapies which are available for each of the identified diseases can also be identified, and at 2510 a cost benefit analysis of all possible combinations of prophylactic therapies and diseases can be, for example, undertaken using business rules. This functionality represents a much more complex level of analysis in order to implement as it is necessary to first define all possible combinations of diseases and prophylactic therapies. For example, if the individual is susceptible to five diseases and a prophylactic therapy exists for each of them but these prophylactic therapies vary widely in cost, it can be, for example, useful to a healthcare manager or a healthcare insurance underwriter to know whether it may be more economical to only administer some of the identified prophylactic therapies and run the risk of the individual contracting the diseases for which prophylactic therapies are not administered. For each of the possible combinations a cost in terms of cost of administering the prophylactic therapy and expected cost of treatment without the therapy is assessed and at 2515 one or more therapies can be approved and/or the insured's premium or the individual's insurance premium adjusted.

It is understood that in the description of the various possible algorithms which can be used in an ImmunoScore analysis for healthcare management that the term individual, insured, and healthcare plan participant are functionally equivalent. While some algorithms are expressed in terms of health insurance context that can easily the same analysis represented by them can be applied to HMO management or management of other healthcare plans. As will be described below, the same techniques can be applied where the entire population is covered under a healthcare plan, such as, for example, in a socialized medicine jurisdiction. Alternatively, the same techniques can be applied where a large population of some mutual affinity is covered by a single healthcare plan such as, for example, United States Veterans whose healthcare is provided by the U.S. Veteran's Administration. Thus, it is understood that any particular algorithm or method described in one context also applies to any other.

FIG. 25A is identical to FIG. 25 except that it offers an additional option. At 25A20, if in fact the minimum cost, which is simply the total cost of the least costly permutation at 25A10, is, for example, too great for underwriting limits or healthcare management criteria at 25A20, the participant can, for example, be canceled from the plan.

FIG. 26 depicts an exemplary process flow for use in healthcare management applications. FIG. 26 is not concerned with dollar costs but rather cost in terms of quality of life. Such an analysis would be useful where dollar cost is less important than quality of life, such as, for example, in exemplary embodiments where a supplemental insurance company insures a minimum quality of life and undertakes to provide for whatever healthcare cost are necessary to maintain that quality of life. Additionally, a socialized medicine jurisdiction, for example, could have a minimum quality of life which it seeks to provide to each citizen as a basic human right which that jurisdiction sees as all its citizens as having. With reference to FIG. 26, at 2601, an immune status of an individual can be examined and the quality of life can be set to zero. For the purposes of FIG. 26, a higher quality of life score translates to a higher quality of life. At 2602 all diseases to which the individual is susceptible are identified and a decrease in QOL score can, for example, be assigned to each disease. The scoring data (i.e., a map of identified health scenarios to some QOL metric) can, for example, be stored in a business rules database such as is depicted in FIG. 2A. Such a decrease in quality of life score can be, for example, a measure of unexpected pain and suffering, a measure of how many sick days are generally associated with it, or, for example, whether the sick days are at home, taken at the hospital, or taken while still at work, and finally whether surgery is involved. At 2605, all prophylactic therapies which are available for all of the identified diseases at 2602 can also be identified. At 2610 for each identified disease and each possible combination of identified diseases (assuming that the individual could contract more than one disease, either simultaneously or in succession) the probability of contracting the disease can be computed and from that probability an associated expected decrease in quality of life can be, for example, computed. As provided in FIG. 26, an exemplary formula which can be used in this context:

$$E(QOL_{DEC}) = \text{Prob(Disease)} * \Delta QOL;$$

$$QOL = QOL - E(QOL_{DEC})$$

At 2615 an increase in quality of life can be assessed for each identified disease or combination of identified diseases for which either prophylactic therapies or therapeutic therapies exist. Thus, in exemplary embodiments of the present invention, the quality of life score can be incremented by looping through each disease and adding the expected increase in quality of life associated with either (i) providing a prophylactic therapy or (ii) a therapeutic measure to mitigate the loss and quality of life due to contracting the disease. For example, not every disease for which there is a prophylactic therapy can be totally obviated. Some diseases to which individuals are susceptible can be mitigated but not prevented by prophylactic therapies. For example, when people feel they onset of a cold they often take echinacea. Echinacea tends to lower the amount of time one is symptomatic but rarely totally prevents contracting the cold. Alternatively, if a prophylactic therapy completely obviates the individual from contracting the disease then the $E(QOL_{inc})$ should exactly equal the $E(QOL_{dec})$. If the prophylactic therapy happens, for example, to bestow other benefits besides preventing the disease, then the expected increase in the QOL associated with undergoing the prophylactic therapy would exceed the $E(QOL_{dec})$. Similar computations would apply to various possibilities. At the end of process flow in FIG. 26 a net quality of life figure can thus be computed.

FIG. 26A is a more detailed process flow for the example illustrated in FIG. 26. At 26A01 immune status can be examined and at 26A02 the quality of life can be set to zero. At 26A10 the probability of contracting a disease given the immune status obtained in at 26A01 can, for example, be computed. At 26A20 the probability of contracting the disease given the immune status can be multiplied by a "badness" score. At 26A30 this product can be added to the quality of life score. 26A10 through 26A35 can then be repeated for each disease for which susceptibility could be examined, given the assays administered at 26A01. In this exemplary process flow a better quality of life is associated with a lower number which is the opposite convention of that adopted in the process flow of FIG. 26. It is for this reason that a "badness" score is assigned to each disease and a expected "badness" is added to the quality of life at 26A30. Additionally, at 26A15, all possible physical therapies for the identified disease (it is noted that 26A15 and 26A35 are within the for-each-disease loop as well) can be generated and mitigation scores can be assigned for each physical therapy or combination thereof. At 26A35, the mitigation score can be, for example, subtracted from the quality of life score and once flow is looped from 26A10 through 26A35 for each disease, at 26A40 a total quality of life score can, for example, be output. Using this total quality of life score, at 26A50 the best set of prophylactic therapies in terms of higher quality of life can be offered to the individual with the stated quality of life improvement.

It is noted that in the schema of FIG. 26A a badness score is associated with each contracted identified disease. An exemplary badness scoring system is presented in the upper right of FIG. 26A and comprises, for example, +1 for a home sick day, +10 for a hospital sick day, +½ for a work sick day, and +100 for a surgery. Accordingly, the quality of life score would dramatically decrease if the individual was found to susceptible to a number of diseases each of which required surgery if contracted.

FIG. 27 is a final healthcare management exemplary process flow chart. FIG. 27 addresses the newly discovered HPV vaccine which is 100% effective in preventing cervical cancer in women. The question is who should receive the vaccine and when should they be tested. From the point of view of society as a whole, perhaps everybody who has not contracted HPV should be vaccinated to prevent them from ever contracting it and thus prevent the females amongst them, and females in contact with the males amongst them, from ever contracting cervical cancer. Of course, this has a greater cost than simply vaccinating women prior to their exposure to HPV. Therefore, the decision as to who receives the HPV vaccine will often depend upon who is managing the healthcare of the population in question. This will be described in connection with the final decision at 2715.

With reference to FIG. 27, beginning at 2701, an assay panel containing an HPV assay can, for example, be conducted relative to one or more individuals. At 2705 it can be determined whether that individual is seronegative or seropositive to the HPV virus. If seronegative, the individual has not yet contracted HPV and flow moves to 2710, where the decision as to the individual's gender is made. If the individual is not seronegative, he is seropositive to HPV, then flow can terminate at 2706 and any therapeutic treatments that are available can be administered. Continuing at 2710, if the individual is a female flow terminates at 2711 and the HPV vaccine is always administered. Whether the healthcare manager is an insurance company, an HMO, a socialized medicine jurisdiction or a large scale healthcare management entity such as the Veteran's Administration, any female whose healthcare is being managed should be vaccinated to prevent any healthcare expenditure in treatment expenditure for cervical cancer. However, what about males? The only utility derived from vaccinating males is that females in sexual contact with them will not contract HPV. If those females are managed by a different healthcare entity there is little utility in protecting "our" men. If those females are protected in the same healthcare management entity, then there is utility in protecting them. Alternatively, even if the females are not provided healthcare or healthcare insurance under a given plan, a government regulating that plan may see a social benefit in wiping out cervical cancer, or at least those cervical cancers attenuated to HPV, which are the vast majority of them. Accordingly, given all of these concerns, at 2715, the HPV vaccine can be administered if the utility value of the prophylactic effect is greater than the cost of treatment, which is simply the cost of the vaccine. The utility value will, as noted above, be a complicated function of number of factors, most prominent of which being who is responsible (financially, politically or morally) for the healthcare of the females that this male may come in contact with.

B. Health Care/Health Insurance Credit Exchange

The applications that have been described thus far relating to healthcare management all assume that in the cost benefit analysis, additional costs can be passed to an insured, or, for example, if too high, the insured or member of a health plan (such as an HMO) can be canceled. While this may maximize profits for the health plan or the health insurance company in the short run, it can result in the dissatisfied insureds and eventually loss of a certain percentage of the insured base of individuals. Loss of customers is never a good thing, even if under certain analyses they are unprofitable customers. One way of solving this problem is instead of passing costs through to consumers, i.e., to insureds or health plan members, is to set up a means by which they can procure credits in years when they are predominately healthy and use those credits when not costs but—debits—are assessed against them as per the exemplary analyses are described above in connection with FIGS. 22 through 27. Thus, in exemplary embodiments of the present invention, a health care provider, a health care insurance company, or other financial intermediary in conjunction with the health insurance provider or health care provider, such as an HMO, can set up a health insurance credit exchange. Such an exchange can operate in a similar fashion as do those government programs which have rules against excessive energy use or excessive pollution derived from an entity's activities. An entity which is a polluter, or an "excessive" user of energy or a natural resource such as water, for example, can purchase credits from other individuals or entities who have a low energy use, low water use or are low polluters. In this fashion, those individuals or entities who exceed a certain threshold of some desirable metric, such as, for example, low energy use, low water use, or other "green" factors, can purchase, negotiate, trade or otherwise procure credits from those who are below such threshold so as to avoid fines or negative consequences from violating the environmental or natural resource use standards.

Thus, in the health care context there are always some individuals who are more sick than others. Individuals do not know whether they will be in the underwriting bin of more sickly than average or less sickly than average. Insurance companies try to spread the risk of the more sickly amongst a larger population which obviously includes those who are less sickly, and charge an essentially average health insurance premium to everyone. However, as underwriting becomes more granular, using exemplary embodiments of the present invention, it can be predicted, even decades in advance whether a particular individual is more or less likely to contract a disease, such as for example, autoimmune diseases as described above. For example, as described above in Section I, certain autoimmune diseases have markers which are harbingers of their eventual symtomology 7-10 years in advance. Thus, using exemplary embodiments of the present invention, health care plans, health care administrators and health care insurers will be able to divide the population into many more bins of insureds and associate with each of them a more accurate health insurance premium cost. This can cause those in the more risky bins to have a much greater insurance cost. One way of ameliorating this is to encourage people to join health care plans early in their lives when they are healthy and before even the onset of eventual disease emerges, such as via a marker or predictor in an Immunoscore assay result marker context. In so doing, people who are healthy can receive credits which they can bank within the system or buy, sell or trade. If regular Immunoscore audits of individuals reveal that someone is moving from a less risky bin into a more risky bin, and a cost would be added to their health insurance premium (i.e., a debit), instead of paying an extra premium they can procure a credit through a health care credit exchange either from their own account which they banked in earlier years or from other healthy peoples' accounts which are presently available for exchange.

Thus, in exemplary embodiments of the present invention, an insurance company could, by setting up and maintaining such a healthcare credit exchange, retain more customers as well as encourage customers to join its ranks of insureds early on in their lives so as to be able to bank for the future and/or sell credits for being healthy. By acting as intermediary, an exemplary system can make a market for such health care credits, and not have to wait for a particular debit holder to find a particular credit holder willing to exchange. Acting in some ways as a securities market maker, an Immunoscore based third party can buy credits and sell debits.

Thus, in exemplary embodiments of the present invention, insureds can thus be induced to pay higher premiums when they are younger and more healthy which would therefore give them extra protection against being assessed debits later on should they become sick. This results in a net flow of capital to the health insurers, or the HMOs, because they can charge higher premiums than the "true" or correct "premium" with the full consent of the insured in exchange for allowing and facilitating participation in the health care credits exchange. On the other hand, they can also retain more customers because people who are subject to debits as a result of more granular analyses of their overall health via Immunoscore diagnostics can simply use credits they have accumulated earlier in their lives or procure credits from other insureds which would ultimately be cheaper for them than having to find substandard coverage. Additionally, the insurance company is not faced with canceling bad insureds and then having to spend client development money to procure new "good" insureds, rather, it can more or less retain its insured base as well as generate additional profits from the maintenance of the healthcare credit exchange.

Further, if a healthcare management entity sets up a health care credit exchange it can, in exemplary embodiments of the present invention, require immunoscore diagnostics, such as set forth in Section 1 above, at various significant life points in each insureds lifetime. This can have the effect of positive feedback in the amount of data that an immunoscore database has available and thus, an improvement and greater accuracy and predictive value of the algorithms of the immunoscore analysis can provide to the insurer. Over the course of the time an insurer will tend to make more money and have more accurate predictive models than its competitors who do not use such an Immunoscore system.

Finally, ImmunoScore databases lend themselves to storing health care credit and debit information as part of an individual's record, making it nearly seamless to create algorithms to track such credits/debits and manage the exchange. After all, ImmunoScore is the tool being used to generate the very granularity that assigns the credits/debits and makes the entire business possible.

C. Veterans Health Care Management (Variant of Health Care)

A special instance of health care management relates to veteran's care. In the United States, the Veterans Health Administration (VHA) provides a broad spectrum of medical, surgical, and rehabilitative care to its customers. Individuals that qualify for veterans healthcare services include, for example, returning Active Duty, National Guard and Reserve service members of Operation Enduring Freedom (OEF) and Operation Iraqi Freedom (OIF). The vision statement of the VHA states that it needs to be a comprehensive, integrated healthcare system that provides excellence in health care value, excellence in service as defined by its customers, and excellence in education and research, and needs to be an organization characterized by exceptional accountability and by being an employer of choice.

In exemplary embodiments of the present invention, veterans, with their special requirements based on service, can be well served by ImmunoScore diagnostics and data management. As previously described in Section I, soldiers have very specific vaccination requirements based on their deployment and area of expertise. ImmunoScore diagnostic panels can be tailored to the needs and context of the individual soldier based upon his or her previous exposure to immunization and also to different infectious agents depending on the relevant theater of deployment. In addition to immune response to infectious agents, veterans are likely candidates for measurement of immune system perturbations induced by, for example, Post Traumatic Stress Disorder (PTSD), exposure to unique chemical agents (e.g., Agent Orange), Gulf War Syndrome, and recovery from injuries sustained in service.

As described above in connection with the CIP database, linear regression analysis of a patient database could yield valuable information pertinent to appropriate treatment of veterans after their years of service. Those analyses displayed possible correlations between, for example, measles and mumps immunity and immunity to varicella infection, for example. Any possible associations between service locale and adverse agents could be documented and analyzed by an exemplary ImmunoScore data mining process in similar fashion.

The VA Research and Development program (The Office of Research and Development) aspires to lead the Veterans Health Administration in providing unequaled health care value to veterans. The ImmunoScore technology can help contain healthcare costs for veterans by monitoring and analyzing immunologic information.

D. Socialized Medicine Management

A socialized medicine jurisdiction is essentially a health care provider or insurer for an entire population. Thus, the health care management applications of ImmunoScore described above can also be implemented in a socialized medicine jurisdiction. Countries with socialized medicine, such as the UK, New Zealand, and particularly Canada, present opportunities to stress preventive medicine for the good of the populace (i.e., by maximizing QOL for a given health care budget) and the advantages of lower cost healthcare as represented by ImmunoScore managed healthcare. These governments could be provided with healthcare management services via an implementation of the ImmunoScore system.

The CIP database discussed in Section II above, has revealed the utility of an exemplary ImmunoScore database for a country with an immigrant population. There has been much concern regarding outbreaks of mumps in the United States and Europe. This disease has clearly been shown to spread from contact with travelers (CDC, 2006). The CIP database indicates a degree of relatedness between patients that had antibodies to both Rubella and Mumps. If this type of analysis were to be extended to geographic regions and associated with specific genders, a government that supported socialized medicine could, for example, be very much in favor of assuring that an immigrant population was properly immunized, for the protection of that immigrant population, as well as the native population.

E. Supplemental Insurance (AFLAC Model)

AFLAC is the leading provider of supplemental insurance, which provides help with expenses not covered by an individual's major medical plan. The company is the number one provider of guaranteed-renewable insurance in the United States and Japan. Its products provide protection to more than 40 million people and go beyond the traditional insurance by directly paying claimants with cash benefits.

With the cost of health care rising, the challenge for most employers is to satisfy the specialized needs of each employee without having to fund expensive new plans.

AFLAC provides products including, for example, the following: Accident Disability; Short Term; Disability; Cancer Benefit; Hospital Indemnity.

ImmunoScore diagnostic testing and database storage can provide information for use in just such supplemental insurance programs. ImmunoScore can, for example, provide an individual with immune status testing that could be monitored over time and offer the peace of mind that would come from knowing that that patient had a "healthy" immune system. In addition, an insurer would be better able to underwrite premiums for supplemental health insurance with a sounder understanding of the patient's health status.

Additionally, in exemplary embodiments of the present invention, a "immunological insurance plan" could be offered. Such a plan could provide all immunological monitoring and therapeutics to each insured for a fixed annual premium and guarantee a certain defined quality of life to each insured. Such a plan could utilize one or more of the health care management processes described above.

To be able to effectively underwrite such supplemental insurance, supplemental insurance firms need to be aware of relatedness between immune parameters as revealed by database analyses. For instance, the CIP database revealed tendencies for Hepatitis A antibody to be present in individuals from certain geographic regions. Supplemental insurance coverage could benefit from insuring that travelers to these regions were assured of their own immune system's ability to combat Hepatitis A infections in regions where the disease is endemic. Or, for example, the CIP database revealed a possible suspension of Tetanus immunity amongst individuals reactive to CMV. In exemplary embodiments of the present invention, a health insurer (whether supplemental or primary) would take special care to take such a factor into account.

F. Immunoscore and the Wellness Industry

In 1994, the U.S. Congress laid the groundwork for the Wellness Industry by passing the Dietary Supplement Health and Education Act (DSHEA). This Act set new standards for the manufacturing, testing and marketing of nutritional products. Products that meet strict government standards earn the title of nutraceuticals. Blurring the line between conventional foods and drugs, nutraceuticals are defined as foods or parts of food that confer health or medicinal value, including the prevention and treatment of disease.

The Food Policy Institute (http://www.foodpolicyinstitute.org) has defined drivers of nutraceutical industry growth. The nutraceutical market was once viewed as largely a counter-culture "back to nature" phenomenon, but is now buoyed by a number of solid fundamentals.

Changing consumer demographics. Americans are living longer and emphasizing the importance of quality of life in their later years. As the baby boomers approach ages where personal health becomes more paramount, the demand for mechanisms for conveying health will grow.

Increasing ethnic diversification. The mainstream U.S. nutraceuticals industry is a relatively new phenomenon. However, the use of foods, herbals, and other natural products to convey health and medicinal values has a long history of acceptance by many of the world's cultures.

Paradigm shift in personal health. Americans are taking more responsibility for their personal health, embracing the concept of health maintenance and wellness. Thus, the paradigm is shifting away from disease treatment and towards disease prevention.

Dissatisfaction with Western healthcare. Americans are becoming more reticent about accepting the side effects of synthetic drugs and remedies. Similarly, rising healthcare costs are encouraging Americans to explore alternatives to traditional orthodox medicine.

Increasing acceptance of alternative healthcare practices. There is a growing acceptance among Americans of alternative or complementary therapies and wellness modalities. Recent years have witnessed increased use, for example, of chiropractic care, vitamin therapy, aromatherapy, meditation and relaxation techniques, and acupuncture.

Increased understanding and awareness of diet-disease relationships. Many of the leading causes of premature death in the U.S. are diet-related. Examples include heart disease, diabetes, and many types of cancer. The USDA estimates that diet-related disease and death costs the U.S. in excess of $250 billion each year.

The Food Policy Institute goes on to state that the nutraceutical industry is facing challenges.

Few farmers are producing herbals and other botanical inputs (due to limited market knowledge, technical requirements and other obstacles).

Limited access to finance and capital constrains industry development and expansion.

Ambiguous regulatory framework for ensuring product standardization and efficacy.

Regulatory restrictions on marketing products via health claims impede retail efforts.

Raw material supply issues (consistency of quality and availability) for botanical manufacturers.

Limited endorsement by traditional healthcare practitioners.

Consumers can not differentiate between high and low quality products and are not sufficiently educated to make informed decisions about proper product use.

ImmunoScore diagnoses and database could provide the answers to these challenges. Individuals and populations could be studied with respect to the efficacy of a nutraceutical diet. ImmunoScore would either pave the way for more growth in curtain nutraceuticals, or perhaps point out the sale of "snake oil." Individual products, or product lines could be endorsed as valid by ImmunoScore measurements.

The Wellness Industry is expected to grow. The Wellness Industry includes the concept of "wellness insurance" to lower health care costs to individuals. This may provide yet another opportunity to leverage ImmunoScore testing and data storage into the insurance industry.

In addition, workplace wellness as a concept has been used extensively in recent years by management in business and industry, health professionals, fitness experts, and others. Well-designed and administered programs deliver positive outcomes for employers as well as employees. Because healthy employees cost less than employees suffering from illness, ImmunoScore can be a part of employee insurance offered by employers wanting the best and most affordable health care for their employees.

Analyses of the CIP database have shown the development of positive and negative relationships for one variable with respect to another variable (for example, Rubella antibody and Hepatitis A antibody levels as is illustrated in FIG. 20D, and for example, Mumps, antibody vis-a-vis Hep A, Measles and Rubells, as shown in FIG. 20E). This type of analysis could be extended to other variables regarding "wellness." For example, fitness measurements could be incorporated (body mass index, cardiac function, etc) into an overall immune fitness relationship.

Virtual Physicals™—Incorporate ImmunoScore Diagnostic and Database

The Virtual Physical™ is a comprehensive diagnostic screening procedure that uses state-of-the-art technology to take a global look at a patient's body and identify a variety of conditions at early stages where intervention can be most helpful. A Virtual Physical™ may also be viewed as an integral component of a holistic, behavioral medicine program, where the body, and one's diet, exercise, and lifestyle habits are viewed as a whole, determining where problems may exist and where changes might be required.

The Virtual Physical's™ early detection capability can uncover asymptomatic and often life-threatening diseases generally not detectable by physical exam or standard screening tests. This allows the management of disease in early stages, where medical therapy and treatment options are typically less costly, less invasive and more effective.

Virtual Physical's™ comprehensive scan of an individual's body is significantly more detailed than an X-ray. It covers: (a) the heart and arteries, identifying near microscopic amounts of plaque; (b) the lungs at the air cell level showing the earliest stages of smoke damage, emphysema, or lung cancer; (c) the spine, evaluating for osteoporosis, disc disease and other back problems; (d) internal organs for detection of tumors, stones and cysts of all sizes; (e) aneurysms in the abdominal and chest cavities; (f) thyroid and parathyroid disease; (g) joint disease; and (h) uterine, ovarian, and prostate disease.

In the interest of determining a patient's "totality of health," ImmunoScore screening could accompany a Virtual Physical™ to add an immune health component to the virtual screening. It is possible that insurance will cover a Virtual Physical™ in the future, and ImmunoScore testing and data storage could be incorporated into the patient's records that could be transferred to the patient's primary care physician or specialist.

G. Women of Childbearing Age/Screening of Pregnant Women

A superpanel for women of childbearing age was described above in Section I.

With light thereof, ImmunoScore diagnostic tests and database storage availability in the offices of obstetricians would greatly enable appropriate immunization of pregnant women as well as find correlates of prenatal interest. In addition to screening pregnant women for their immune status regarding vaccine preventable diseases, ImmunoScore diagnoses and data management could also be of value in determining the immune status of pregnant women regarding, for example, group B streptococcal infection, cytomegalovirus (CMV) infection, and other infectious diseases that may adversely effect the newborn, yet are treatable prenatally. Early onset GBS infection has been the leading cause of death attributable to infection in newborn infants for over three decades, with over 6,000 cases a year in the United States (Vallejo, et al. 1994). Antibiotics have been used to good effect to prevent newborn GBS infection. There is also promising preliminary data on an effective intervention to prevent CMV infection in newborns in pregnant women that has been published recently (Nigro, et al. 2005). All these treatments can be more advantageously administered using ImmunoScore technology.

FIG. 28. depicts and exemplary process flow for managing the immune status of women of child-bearing age. Beginning at 2801 the immune status of a women of child-bearing age is examined. At 2810 the vaccine preventable diseases that the woman is susceptible to are identified as well as the woman CMV infection status and pregnancy status. At 2820 these three variables are used to generate healthcare recommendations, as follows. If the woman has not been infected with CMV and is not pregnant she is advised to obtain immunizations for the identified vaccine preventable diseases. If she is an insured under a healthcare insurance plan, or her healthcare is provided by an HMV or socialized medicine entity she can be, for example, required to obtain these immunizations to save future treatment costs as well as to serve the utility of having a healthy population. If she has not been infected with CMV but is pregnant she can be informed of extra precautions regarding CMV status and pregnancy. Moreover, no immunization with attenuated vaccines is recommended or should be performed, however, other immunizations should be recommended based upon current CDC guidelines. If the woman is seropositive to CMV and not pregnant she can be advised or required, as the case may be, to obtain immunizations for the identified vaccine preventable disease. Finally, if she seropositive for CMV and pregnant no extra precautions should be taken regarding the CMV status unless there is an active primary infection. Moreover, no attenuated vaccine should be recommended or administered. However, other immunizations can be recommended or required based upon current CDC guidelines. At 2830 a follow-up examination of the women's immune status post-vaccination can be conducted, and if she is not pregnant the information can simply be stored in a system database. If she is pregnant a post-natal follow-up can be recommended or required, as the case may be, comprising MMR vaccination to the mother and monitoring of CMV status of the child. Finally, at 2840, based upon the post-vaccination follow-up at 2830 the efficacy of the administered vaccines can be evaluated as to whether they provide the necessary immunity to the identified vaccine preventable diseases identified at 2810.

The CIP clearly points out the need for antibody measurements in women of child-bearing years. The obvious antibody to be examined is that for Rubella, in which the women of SE Asia were shown to have levels below average. Other important antibodies in women of child bearing years are, of course, those to group B Streptococcal organisms and others that effect fetal development or those associated with neonatal illnesses. From an insurance and public health perspective, these are extremely important issues.

H. Vaccine-o-Mat/Vaccine Distribution Network

In exemplary embodiments of the present invention, ImmunoScore technologies can be used to facilitate the easy dispensing of vaccines to the public as well as giving the public access to their immunologic information. Therefore, in exemplary embodiments of the present invention a business analogous to the "Fotomat" photograph finishing stores, once located in malls and strip malls across America, can be created. For purposes of the present description, this exemplary embodiment of the present invention can be called "Vaccine-o-Mat". Vaccine-o-Mats can be located in small buildings in corners of malls and strip malls, as concessions in large chain stores such as Target or Wal-Mart, or in appropriate markets they can be located almost anywhere and one day be as ubiquitous as Starbucks Coffee centers. At a Vaccine-o-Mat a member of the public can have his immune status checked and can receive any vaccines that he may be deficient in. If an individual steps on a rusty nail and doesn't remember the last time he had a tetanus booster he can simply drive to the nearest Vaccine-o-Mat, have a panel of assays containing tetanus and any related compliments as conducted and determine then and there whether he needs a vaccine. What makes the Vaccine-o-Mat business possible is instruments which can process large numbers of assays in a relatively short period of time, as noted above. One of such instruments is the M1M analyzer currently marketed by BioVeris Corporation of Gaithersburg, Md., the assignee hereof.

FIG. 29 depicts an exemplary process flow for use at a Vaccine-o-Mat. At 2901, the customer's immune status is examined for vaccine preventable diseases and related immunologic information. It is further contemplated that a particular customer may want to have his bodily fluids assayed for a wide variety of immunologic tests and not have them restricted to vaccine preventable diseases. Therefore 2901 need not to be strictly directed towards vaccine preventable diseases. At 2910, within 90 minutes the assay results can be processed to generate recommendations for appropriate vaccines. This functionality depends upon, as noted above, instruments which can process a large number of assays in a relatively short amount of time. This concept allows for partnering with large chain stores or malls where customers could make their first stop at the Vaccine-o-Mat have their blood tested. They could then continue shopping and then return at the end of their shopping excursion to receive any necessary vaccines and report regarding their immune status. At 2920 appropriate vaccines can be administered to the customer on site, and at 2930 the customer can be provided with a printout of the assay results the updated vaccination record and his or her database record from the ImmunoScore database along with instructions on how to access that information in the future. Finally, at 2940 all of the additionally required customer information resulting from that particular visit is stored in the database for future reference.

One of the benefits of the ImmunoScore technology is the ability to link diagnostic testing of the immune system with rapid delivery of medication at the point of care (ideally, during the course of an office visit). Thus, in exemplary embodiments of the present invention a vaccine distribution network can be set up, for example, to link vaccine manufacturers to physicians offices—or other authorized vaccine dispensing personnel—equipped with diagnostic facilities. Vaccine distribution can also, for example, become part of the ImmunoScore database tracking specific manufacturer's lot numbers to points of sale. This can be important in getting timely information incorporated into the Vaccine Adverse Event Reporting System (VAERS).

FIG. 29A depicts exemplary envisioned interactions between various parties according to an exemplary embodiment of the present invention directed towards vaccine distribution. Information gathered to an exemplary ImmunoScore database can, for example, be shared with the various agencies responsible for dictating vaccination decisions. Unsuspected or unknown relationships regarding immune health or function can be, for example, "fished" or "mined" from a system database using appropriate queries and analysis. In addition, in exemplary embodiments of the present invention, suspected adverse events from vaccination could be addressed and acknowledged or dismissed, based upon information gleaned from the system database.

With reference to FIG. 29A, various entities and institutions which can, for example, be involved in vaccine distribution or vaccine distribution network are depicted. They include any vaccine manufacturers 29A05 who through vaccine sales provide vaccines to physicians or healthcare providers 29A10. The physicians or healthcare providers 29A10 also receive diagnostic testing kits and research services, such as, for example, ImmunoScore vaccine diagnostic panels 29A01. The government 29A15 has a variety of roles in a vaccine distribution network, including subsidizing or providing economic incentives to create or build a supply of vaccines by a transfer of funds to, or via tax incentives to, vaccine manufacturers 29A05. The government can further subsidize or fund HMOs 29A25 and in this context the Veteran's Administration, described above can be considered one of them. Additionally, the government 29A15 can mandate vaccine benefits to certain segments of the population and those can be provided by HMO 29A25 or equivalent. Finally, the government 29A15 can itself access personalized immune status data as to individuals or populations or sub-populations 29A12 for a variety of research or health management purposes. The CDC and ACIP 29A50 can receive input from Physicians/Healthcare Providers 29A10 as well as from a vaccine status database 29A30. Vaccine status database 29A30 can be generated from an Immunization Registry 29A40 set up by the CDC, ACIP or other similar institutions or bodies to maintain immunization records for the population so as to better know who should be vaccinated. FIGS. 29B and 29C, described below illustrate improving connectivity between entities and organizations who could access and utilize ImmunoScore information in this context, allowing the benefits of ImmunoScore to be ubiquitously available.

I. Consumer Accessibility to Immunologic Information

Americans are playing a risky game of sexual roulette, according to a new poll that found only 39 percent of respondents always ask a new lover if they are infected with HIV. The poll, taken by Zogby for MSNBC.com also found that 73 percent of respondents were involved in a monogamous relationship, 66 percent of those surveyed had had unprotected sex while under the influence of alcohol. While 39 percent of respondents said they always asked whether a new partner is infected with HIV or other sexually transmitted diseases, 31 percent said they never discuss the touchy issue with a new partner. Moreover, the survey found that 15 percent of Americans had paid for sex, 35 percent of respondents said they had been with between one and five sexual partners, and 19 percent said they had had more than 25 partners.

In exemplary embodiments of the present invention this "risky business" can be ameliorated. Accordingly, at the Vaccine-o-Mat described above, individuals can have their immune status tested by conducting, for example, an STD assay panel, as described in Section I above, which can then be shown to potential sexual partners to fully disclose the immunologic risks that may be involved in any proposed liason. For example, a couple can stop at a Vaccine-o-Mat near a romantic restaurant of their choice. They can have the assays conducted and go off to dine. If things are going well, by the time their coffee has arrived they can obtain each other's immune status and be off—either alone or together—depending upon the ImmunoScore results.

Alternatively, for example, someone worried by past promiscuities can routinely procure his or her immune status at the local Vaccine-o-Mat in 90 minutes, and put any worries to rest, or at least know what they are facing.

J. Immunoscore Connectivity Via Interapplication Translator/Data Integrator

In many exemplary embodiments according to the present invention, the power of an ImmunoScore diagnosis and database lies in the interaction of the database with many different organizations, as shown in FIG. 29B. Use of a web services interconnector to provide this connectivity is illustrated in FIG. 29C, next described. The CDC, the government (or governments, for that matter), health maintenance organizations, vaccine manufacturers, and physicians would all be able to interact with the database and each other to make the best possible decisions regarding the health and welfare of the citizenry.

With reference to FIGS. 29B and 29C, a number of entities and organizations who could access and utilize ImmunoScore information are shown. FIG. 29B shows a complicated information exchange structure wherein each entity involved has to set up a separate communications line or pathway to each of the other entities in the network. This can easily be remedied, as shown in FIG. 29C, by utilization of an Interapplication Connectivity Provider 29C50 which can interconnect the various individual and sometimes proprietary computer systems, computer networks, databases, and applications of each of the individual entities participating in the vaccine distribution/creation network so that they can talk to each other. This technology is often referred to as interapplication connectivity or interapplication translation. One example of such a interapplication connectivity provider is the IBM, in particular the IBM Web Services Centers Of Excellence. Additionally, Enterprise Computing service companies, such as, for example, EDS also provide products which link different and disparate computing platforms so that they can exchange data and information in an efficient manner.

The CIP database has only scratched the surface of what can be captured and shared by a large ImmunoScore database, but important information can be gleaned from this database, such as it is, of use to government sources, patients, physicians, and insurers. Demographic information regarding crowding and sanitary facilities have been shown to correlate to degrees of protection to vaccine-preventable diseases in the populations examined. If the database were to also include information regarding the movement of patients (for instance), much useful information could be shared among these concerned groups.

K. Immunologic Informatics Based Life Insurance Underwriting

In the exemplary embodiments of the present invention ImmunoScore data can be used to optimize the underwriting of life insurance. Additionally, assuming that regulatory restrictions are not preclusive, ImmunoScore data can be used by companies which provide both life and health insurance to the same clientele. The use of ImmunoScore technology for these purposes is depicted in the exemplary process flow chart of FIG. 30.

With reference to FIG. 30, at 3001 an individual's immune status can be examined and any diseases to which he or she is susceptible identified. At 3015, by accessing Business Rules Database 3010, the probability of death of the individual given the immune status identified at 3001 can be computed. At 3016 the cost of insuring that individual, based on the probability of death of years to death calculated in at 3015 can be computed and premiums can be set at 3020. It is noted that the term "death" appearing in FIG. 30 is a shorthand for "years remaining until death."

Additionally, at 3002 all combinations of possible prophylactic therapies can be generated given the immune status obtained at 3001. From these combinations, at 3005, the probability of time (generally in years) to death given the immune status and the various combinations of prophylactic therapies can be computed. Such computation, at 3005, exchanges data with Business Rule Database 3010. For convenience, two Business Rules Databases 3010 are depicted n FIG. 30; in exemplary embodiments of the present invention there could be one or many Business Rules Databases each devoted to a specific informational domain. In the depicted exemplary embodiment of FIG. 30 they could most likely be combined inasmuch as they are providing information which allows a system to compute the probable time to death given an immune status. However, the Business Rules Database on the right side of the figure may require more complex information to also factor in the available set of possible preventive therapies for each identified disease.

At 3016, the outputs of 3015 and 3005 are input to allow the exemplary system to compute the cost of insuring the given individual. At 3021 the system can select the two or three best sets of prophylactic therapies from the information generated at 3002, and at 3025 it can offer these prophylactic therapies to the client with a proviso that the life insurance premium set at 3020 in absence of factoring in prophylactic therapies could be lower by (x) if the client chooses to undertake the prophylactic therapies. Alternatively, at 3030 it may be in an insurance company's interest to pay for the prophylactic therapies, i.e., offering them to the insured for free, if the cost of the prophylactic therapies is less than the present value of the expected savings to the life insurance companies by the insured having the prophylactic therapies perform. This can be expressed, for example, as:

$$PT\text{ cost} < PV\{(\text{death benefit})*[(\text{Prob}(\text{death}|\text{no } IS, \text{no } PT) - \text{Prob}(\text{death}|IS, PT)]\}$$

Thus, if at 3030 such an offer is made, any premium adjustment at 3020 can be diminished or completely reduced. The function of 3030 is to increase the profits to the life insurance company by not only identifying the premium at which it would charge the insured but also, based on the immune status data obtained during the underwriting process (or during an annual audit process), to identify prophylactic treatments that could be offered to increase the time to death for the same individual thus allowing the insurance company to continue to earn the return on the cumulative premiums prior to having to pay the death benefit to the survivors.

It is also noted that at 3021 where the 2-3 best sets of prophylactic therapies are found the term best is really a function of how much the probable time to death is increased. Finally, the availability of probable time to death given a certain immune status and certain prophylactic therapy can be computed using the following equation as noted in FIG. 30:

$$\text{Prob}(\text{death}|IS \text{ and } PT) = P(CD|PT \text{ and } IS)*P(D|CD \text{ and } IS) + P(\text{not } CD|PT \text{ and } IS)*P(D|\text{not } CD \text{ and } PT\text{ }IS)$$

When offering prophylactic therapies to an insured, unique opportunities arise for insurance companies providing both life and health. A healthier insured lives longer and uses less health care, resulting in twofold savings for an insurer.

Because such a life insurance company also approves health care expenditures, there is no red tape or customer effort spent on securing approval for any offered or recommended prophylactic therapies. Thus, in such contexts, the real world optimizations can actually converge on the theoretical optimizations calculated by an ImmunoScore analysis as depicted in FIG. 30. This can, in exemplary embodiments, increase QOL for insureds and profits for the insurers, as well as hopefully.

Patient commonalities, as revealed by analyses of the CIP database, could be visualized. For example, if a population immigrating from Eastern Europe were shown, in general, to have lower protection against a specific disease or diseases, that information could, for example, be of interest to health/life insurance companies.

L. Diagnosing and Managing Immunosenescence in the Elderly

Human aging is associated with progressive decline in immune functions and increased frequency of infections. Morbidity and mortality due to infectious disease is greater in the elderly than in the young, at least partly because of age-associated decreased immune competence, which renders individuals more susceptible to pathogens (Pawelec, et al. 2005). A decline in immune function is a hallmark of aging that affects the ability to resist influenza and respond to vaccination. An accumulation of dysfunctional T cells may be detrimental under conditions of chronic antigenic stress (chronic infection, cancer, autoimmunity). The most important changes occur in T-cell immunity, and are manifested particularly as altered clonal expansion of cells of limited antigen specificity (Fulop, et al. 2005). This is most marked in the $CD8^+$ T cell subset, which displays a decrease in both responsiveness and normal function. Normally, $CD8^+$ T cells appear to be strongly associated with cytolytic activity, either by direct killing of antigen-bearing target cells by granule-mediated exocytosis or Fas-mediated cytotoxic mechanisms. In addition, it is suggested that antigen-activated $CD8^+$ T lymphocytes can eliminate or control viral infection by secretion of antiviral cytokines, such as gamma interferon (IFN-$\gamma$) and tumor necrosis factor alpha (TNF-$\alpha$). IFN-$\gamma$ production by $CD8^+$ T cells can have both local and systemic consequences, whereas cytotoxins such as perforin are cytolytic for the cells that come in direct contact with the cytolytic T lymphocytes (CTL).

The output of the T cell pool is governed by output from the thymus and not by replication (Aspinall and Andrew, 2000). As thymic T cell production diminishes with age, a decline in contribution made by thymic emigrants to the naive T cell pool occurs (Mackall, et al. 1995). Diminution in the size of the naive T cell pool is a common finding with aging, and is a consequence of reduced thymic output (Kurashima, et al. 1995). Thymic atrophy is thought to result from a failure of the thymic microenvironment to support thymopoiesis in old age and recent evidence suggests that a decline in interleukin-7 (IL-7) expression may limit thymocyte development by restricting combinations of survival, proliferation and rearrangement of the beta chain of the T cell receptor (Andrew and Aspinall, 2002). Therapeutic intervention with IL-7 and derivatives has been shown to reverse thymic atrophy in old animals and also lead to improved immune function compared with age and sex matched control animals (Aspinall, 2005).

The $CD8^+$ T cell repertoire becomes less diverse in old age due to reduced thymic output and the accumulation of clonally expanded memory $CD8^+$ T cells as a consequence of prolonged antigenic stimulation. Clonally expanded T cells are usually CD8+ and show an increased incidence with age, so far it seems that clonal expansion is not due to malignancy but may follow antigen stimulation (Aspinall, 2005). It has been suggested that repeated or persistent infections with viruses such as influenza, cytomegalovirus (CMV), and Epstein-Barr virus (EBV) may drive responses that result in large T cell clones. Longitudinal studies suggest that a set of immune parameters including high percentages of peripheral CD8+ $CD28^-$ $CD57^+$T cells, low CD4+ and B cell counts, and poor T cell proliferative responses to mitogens is associated with decreased remaining longevity in the free-living very elderly (>85 years) (Ouyang, et al. 2003). CMV seropositivity is closely associated with increases in the size of the $CD57^+$ $CD8^+$ T cell pool, which is thought to represent a highly differentiated population of late memory cells. Furthermore, CMV seropositivity is associated with increases in $CD8^+$ count in old age and has been documented to have negative influences on immune parameters in the very elderly. A group concluded that the "obsession" of a large fraction of the entire $CD8^+$ T cell subset with one single viral epitope may contribute to the increased incidence of infectious disease in the elderly by shrinking the T cell repertoire for responses to other antigens (Ouyang, et al. 2003). Like CMV, EBV manages to persist for the lifetime of the infected host. During chronic asymptomatic infection in healthy individuals, EBV resides in memory T cells (Babcock, et al. 1998). Expansion of peripheral CD8+ CD28– T cells in response to chronic EBV infection has been linked to rheumatoid arthritis (Klatt, et al. 2005). The clinical consequences of these changes are as yet not well defined, except for their extremely important negative impact on defense against infections. Considering the public health consequences of decreased immune competence in old age, strategies for immune response modulation are desirable to decrease the health burden for the elderly and improve their quality of life. (Fulop, et al. 2005).

Features of successful aging have been associated with well-preserved immune function while poor survival is predicted by high CTL counts, low numbers of B cells and poor responses by T cells to polyclonal stimulation. The phenomenon of replicative sensescence has been associated with these changes and relates to a finite number of doublings (25-30 cycles) after which cell cycle arrest occurs. In CTLs, this growth arrest is associated with increased production of several pro-inflammatory cytokines, resistance to apoptosis and loss of the co-stimulatory molecule, CD28, required for optimal stimulation of CTLs. In older adults, greater than 50% of CTLs fail to express CD28 and these cells are resistant to apoptosis.

The loss of CD28 expression due to replicative senescence has been associated with a number of the adverse effects of aging on immune function. Although the frequency of influenza virus-specific CTLs does not appreciably change with age, the decline in CTL activity against influenza may be due to a loss of antigen-specific proliferation and/or diminished lytic activity. Normal loss of CD28 expression during CTL activation and the potential for these cells to undergo activation-induced cell death, may be confused with the loss of CD28 with replicative senescence and resistance of CTLs to apoptosis.

Furthermore, the role of cytokines (such as IL-2, IL-7, and IL-15) in preventing activation-induced cell death and age-related changes in the production of these cytokines create a complex array of interactions that may confound the interpretation of in vitro experiments. Understanding the complexity will provide an opportunity to optimize the CTL response to vaccination by manipulating CTLs that retain their replicative capacity in response to appropriate antigenic stimuli.

Currently, influenza vaccination of elderly individuals is recommended worldwide. A recent study looked retrospectively at influenza vaccine efficacy in individuals aged 65 years or older (Jefferson, et al. 2005). They found that in homes for elderly individuals, that vaccines were not significantly effective against influenza, influenza-like illness, or pneumonia. More encouragingly, vaccine performance was improved for admissions to the hospital for influenza or pneumonia, respiratory diseases, and cardiac disease (Jefferson, et al. 2005). This group concluded that the usefulness of influenza and pneumococcal vaccines was modest. On the same day the Jefferson report was published online, the American Medical Directors Association released a special announcement regarding the Jefferson study and influenza vaccine recommendations for the elderly (http://www.amda.com/newsroom/092205_vaccines.htm). While not disagreeing with the tenets of the study, they continued to recommend for vaccination of the elderly because influenza vaccination is effective at preventing severe illness, secondary complications, and deaths. They also reiterated that the CDC recommends influenza vaccination for people age 65 years and over and for all persons in long-term care facilities (http://www.amda.com/newsroom/092205_vaccines.htm). Both groups concluded that better influenza vaccines that offer more protection in older persons are desirable and a high priority of influenza researchers.

The threat of pandemic influenza has increased with the direct transmission of highly pathogenic avian H5N1 viruses to humans. Continued reliance in killed virus or subunit vaccines will leave adults at significantly higher risk of illness, disability and death in the event of an influenza pandemic. Research that increases our understanding of how immunosenescence affects the cell-mediated response to influenza and vaccine responsiveness is critical to the development of effective pandemic influenza vaccines for older people. In the absence of influenza vaccines that target these defects, an influenza pandemic will have a significant impact on older people and quickly overwhelm the health care system.

The CDC has recently (Aug. 8, 2005) stated that the effectiveness of inactivated influenza vaccine depends primarily on the age and the immunocompetence of the vaccine recipient and the degree of similarity between the viruses in the vaccine and those in circulation. When the vaccine and circulating viruses are antigenically similar, influenza vaccine prevents influenza illness among approximately 70-90% of healthy adults aged <65 years. Children aged ≧6 months can develop protective levels of anti-influenza antibody against specific influenza virus strains after vaccination, although the antibody response among children at high risk for influenza-related complications might be lower than among healthy children. In addition, no efficacy was demonstrated among children who had received only one dose of influenza vaccine, illustrating the importance of administering two doses of vaccine to previously unvaccinated children aged <9 years. Older persons and persons with certain chronic diseases might develop lower post-vaccination antibody titers than healthy young adults and thus remain susceptible to influenza infection and influenza-related upper respiratory tract illness (http://www.cdc.jzov/flu/professionals/vaccination/efficacy.htm). While current vaccines are cost-saving, new influenza vaccines will likely be needed to avoid the crisis anticipated in health care related to the general aging of the population.

Another component to the aging immune system is the relationship between innate immunity and inflammation. During evolution the human was set to live 40 or 50 years; today, however, the immune system must remain active for a much longer time. This very long activity leads to a chronic inflammation that slowly but inexorably damages one or several organs. This is a typical phenomenon linked to aging and it is considered the major risk factor for age-related chronic diseases. Alzheimer's disease, atherosclerosis, diabetes, sarcopenia, and cancer to name several, all have an important inflammatory component, though disease progression seems also dependent on the genetic background of individuals (Licastro, et al. 2005). Inflammatory genotypes are an important and necessary part of the normal host response to pathogens in early life, but the overproduction of inflammatory molecules might also cause immune-related inflammatory diseases and eventual death later (Licastro, et al. 2005).

Most age-related diseases have complex etiology and pathogenic mechanisms. The clinical diagnosis and therapy of these diseases requires a multidisciplinary approach with progressively increased costs. A body of experimental and clinical evidence suggest that the immune system is implicated, with a variable degree of importance, in almost all age-related or associated diseases. Both innate and the clonotypic immune system are usually involved in the pathogenesis of these chronic diseases (Caruso, et al. 2004; Pawelec, et al. 2002). Several functional markers of the immune system may be used either as markers of successful aging or conversely as markers of unsuccessful aging. A combination of high $CD8^+$ and low $CD4^+$ and poor T cell proliferation has been associated with higher mortality in very old subjects (Caruso, et al. 2004). Old men carrying an anti-inflammatory IL-10 high-producer genotype or a pro-inflammatory IL-2 low-producer genotype show the lowest values of CD8+ cells (Caruso, et al. 2004). This study, however, did not do a functional assessment of T cells.

In a mouse model looking at T cell subset patterns, researchers found that a composite combination of subset values was a significant predictor of longevity among genetically heterogeneous mice, with a strength of association higher in older mice than among the young (Miller and Chrisp, 2002). Developing useful biomarkers of aging has proven to be remarkable difficult, in part because many age-sensitive variables tested as candidate biomarkers are sensitive to genetic and nongenetic influences other than aging. Any individual assay, for example a test of a specific T cell subset in a single blood sample, is likely to have a good deal of uncertainty, but the combination of results from related tests may increase the signal-to-noise ratio and thus provide stronger predictive power than any single assay by itself (Miller and Chrisp, 2002). In humans, ImmunoScore testing would help build the models of T cell subset patterns. Possible courses of therapy would then be ideally tailored to meet the needs of the individual and not a "best guess, one size fits all" course of treatment.

Clearly, the population aged ≧65 years would be better served by ImmunoScore diagnostics rather than the current state of affairs. A blanket recommendation for an influenza or pneumococcal vaccination for the entire elderly population may not be in the best interest of an individual being immunized. ImmunoScore diagnostic tests could, for example, first reveal levels of protective antibody to vaccine-preventable diseases. Of particular interest would be antibody levels against influenza, pneumococcal infection, tetanus, diphtheria, pertussis, hepatitis, varicella, CMV, and EBV. Just as important as determination of antibody levels in elderly patient sera, ImmunoScore diagnostic tests could reveal the status of cellular components of the immune system. The proportion of naive/committed T and B cells would be crucial for further recommendations by the attending medical staff. As therapeutic interventions are developed for dealing with immunosenescence, the ImmunoScore diagnostic information regarding individuals and compiled database information will shed valuable light onto the effects of treatments on the immune system. As the population ages, strategies for immune response modulation are desirable to decrease the health burden for the elderly and improve their quality of life.

A preliminary immune risk phenotype (IRP) has been developed from longitudinal studies of the elderly (Wikby, et al. 2005). Immune system measurements consisted of determinations of T-cell subsets, plasma IL-6, IL-2 responsiveness to conconavalin A, and CMV and EBV serology. Regression analyses indicated that the IRP and cognitive impairment together predicted 58% of observed deaths. This type of analysis would be a valuable adjunct to assessing insurance premiums.

The following table captures exemplary desirable analytes to monitor in the population as individuals age. A database storing the results of such assays could ensure that a given individual's analyte levels could be tracked over time rather than merely captured as a snapshot.

TABLE 1

Alterations in the T-cell compartment with age

| Alteration | Analyte |
|---|---|
| ↑ | CD45RO+ cells |
| ↑ | CD95+ cells |
| ↓ | CD28 expression |
| ↑ | CD152 expression |
| ↑ | killer cell lectin-like receptor G1 |
| ↓ | apoptosis of CD8 cells |
| ↑ | apoptosis of CD4 cells |
| ↓ | IFN-γ production |
| ↓ | IL-2 production |
| ↓ | telomere lengths |
| ↓ | telomerase induction |
| ↑ | DNA damage |
| ↓ | DNA repair |
| ↓ | stress resistance and heat-shock protein expression |

Thus, in exemplary embodiments of the present invention an Immunosenescence superpanel can be defined, comprising the following panels:
Meningococcal Diagnostic Panel;
Persistent Immunity Induced by Childhood Vaccines; and
Immunosenescence Diagnostic Panel The first two panels are defined in Sections IA1 and IA3 of the Immunologic Information Patent, and an Immunosenesence panel can, for example, be defined as follows.

Human aging is associated with progressive decline in immune functions and increased frequency of infections. A decline in immune function is a hallmark of aging that affects the ability to resist influenza and respond to vaccination. The most important changes occur in T cell immunity. An accumulation of dysfunctional T cells may be detrimental under conditions of chronic antigenic stress (chronic infection, cancer, autoimmunity).

Exemplary Alterations in T-cell compartment to monitor:

| Typical Alteration | Analyte |
|---|---|
| Increased | CD45RO+ cells |
| Increased | CD95+ cells |
| Decreased | CD 28 expression |
| Increased | CD152 expression |
| Increased | Killer cell lectin-like receptor G1 |
| Decreased | Apoptosis of CD8+ cells |
| Increased | Apoptosis of CD4+ cells |
| Decreased | IFN-γ production |
| Decreased | IL-2 production |
| Decreased | Telomere lengths |
| Decreased | Telomerase induction |
| Increased | DNA damage |
| Decreased | DNA repair |
| Decreased | Stress resistance and heat-shock protein expression |

Other analytes of particular interest in an immunosenescence assay panel can, for example, include:
Antibody to CMV
Antibody to EBV
Antibody to influenza
Antibody to pneumococcal disease
Antibody to pertussis
Antibody to tetanus
Antibody to diphtheria
Plasma levels of IL-6
Th1/Th2 components as described below:

| Th1 | | Th2 | |
|---|---|---|---|
| Cytokines | Receptors | Cytokines | Receptors |
| INF-γ | CCR5 | IL-4 | CCR3 |
| TNF-α | CXCR3 | IL-5 | CCR4 |
| IL-2 | CCR1 | IL-6 | CCR8 |
| IL-12 | | IL-10 | CRTh2 |
| | | IL-13 | |

FIG. 31 depicts an exemplary process flow for managing immunosenescent individuals, either in a health care provider or a health care insurer context.

In exemplary embodiments of the present invention immunosenescence in an individual can be managed using the process exemplary flow depicted in FIG. 31. With reference thereto, at 3101. an elderly individual's immune status can be examined. This can be accomplished by conducting one or more assay panels as described above in Section I. At 3110, the vaccine preventable diseases that the elderly individual is susceptible to can be identified at the same time the individuals CMV infection status together with other relevant markers of an immune system competence can also be determined. At 3120 vaccine and/or other healthcare recommendations can be made based upon the immune status examined at 3101. Additionally, a separate T cell compartment can be assessed. 3130 the individual can be immunized for vaccine preventable disease based upon his or her immune system's ability to response to vaccination. Using the ImmunoScore data, the individual can be classified as either (1) immunocompetent (2) immuno-deficient or (3) somewhere in between immunocompetent or immuno deficient. At 3130 an immuno-competent individual can be vaccinated as recommended by current ACIP recommendations. An immuno-deficient individual would need to be managed using different measures than routine vaccination. Such measures could include, for example, adoptive transfer of a compartment of T ob B cells or extraordinary hygiene measures. The individuals who falls somewhere between immuno-competence and immuno-deficiency need some kind of hybrid health management between standard vaccination and immunoadjuvant therapies such as adoptive transfer of T or B cells and extraordinary hygiene measures. At 3140, the elderly individual's immune status can be followed-up post vaccination or post treatment and these results stored in the system database. At 3150 this information can be used to evaluate the efficacy of the vaccination or other therapies as to their abilities to provide the necessary immunity to the identified diseases.

M. Frozen Storage of Naive Immune Cells (IRP Considerations)

As previously described, the immune risk phenotype (IRP) is an emerging concept—predicting mortality based on CMV seropositivity (Pawelec, et al. 2005). This group maintained that the manner in which CMV and the host immune system interact is critical in determining the IRP and is hence predictive of mortality. The consequences of IRP is early expression of immunosenescence. Immunosenescence leads to: a) decreased T- and B-cell responses to foreign antigen; b) increased responses to self antigens; c) increased morbidity and mortality to infectious disease; and d) decreased response to vaccine antigens.

Greater elucidation of the IRP and its consequences is to be expected in the future. Genetic screening at a very early age could be predictive of immune health at a much more advanced age. The ImmunoScore diagnostic screen could be performed from a heel stick done at birth, and a child's baseline immune status could almost instantaneously be generated. Pre-natal screening tests could also be developed in the future as an immunodiagnostic tool.

Concerned parents may wish to store their child's cord blood as a source of hematopoietic progenitor cells that could be stored (at a cost to the parents or the insurer's) for that child for treatment of developing IRP symptoms much later in life. Umbilical cord blood (UCB) is currently used as a source of these hematopoietic progenitor cells as an alternative to the bone marrow or peripheral blood for treatment of several onco-hematological diseases (Adami, et al. 2005).

On Apr. 18, 2005 the Institute of Medicine (IOM) issued a report recommending that a new cord blood coordinating center—similar to the existing National Marrow Donor Program—be set up to ensure a standardized and interconnected national system to cost-effectively store and distribute these cells.

ImmunoScore diagnostics shows the need for storing cord blood.

Another application for ImmunoScore diagnostics is to link storage and analysis of naive cells of the immune system (innate or adaptive), as next described.

T cells currently used for adoptive immunotherapy trials are selected for their capacity to produce high levels of IFN-γ and for their ability to efficiently and specifically lyse relevant target cells (Dudley and Rosenburg, 2003; Yee, et al. 2002). However, it was found that $CD8^+$ T cells that acquire complete effector properties and exhibit increased anti-tumor activity in vitro are less effective at triggering tumor regressions and cures in vivo (Gattinoni, et al. 2005). While the progressive acquisition of terminal effector properties is characterized by pronounced in vitro tumor killing, in vivo T cell activation, proliferation, and survival are progressively impaired. These findings suggest that the current methodology for selecting T cells for transfer is inadequate (Gattinoni, et al. 2005). It is clear that new solutions are needed to generate more effective anti-tumor T cells for the development of experimental human adoptive transfer-based therapies.

The indication is that storage of naive T and B cells is important for individuals who will become immunocompromised later in life, whether those cells come from that individual or from another source. Naive cells would also not necessarily be isolated from cord blood, but could also be isolated from bone marrow or peripheral blood. In addition, screening methods can be used to characterize those immune cells regarding cell surface characteristics and cytokine expression. Here too, ImmunoScore can be used to a distinct advantage.

N. Vaccine Use Outcome/Design

Currently, what the public considers vaccines are designed as a prophylactic means to avoid illness caused by infectious disease. In practice, agents used to promote an immune response as a therapeutic course of action for cancer or immunotherapy have also been termed "vaccines." It is the intent of the ImmunoScore design to be able to monitor changes in an individual's immune system in relation to a prophylactic or therapeutic vaccine and enable the individual patient and his physician to make the best possible decisions regarding the patient's immune system health regarding prophylactic vaccination, therapeutic vaccination, or other therapeutic treatment in attempt to "shift" the immune system of that patient. In addition, the ImmunoScore database will compile important population data regarding demographics and population genetics.

O. Research Services

In exemplary embodiments of the present invention ImmunoScore technologies can be used to provide research services, such as, for example, for clinical trials in the following areas:

1. vaccines;
2. transplants;
3. adoptive immunotherapy;
4. population modeling; and
5. government applications.

P. Immigration Consulting

Testing the immigrant population for vaccine-preventable diseases is another embodiment of the invention. Governments are very interested in the immunization status of individuals and families immigrating into their countries. The invention can rapidly provide the results of assays to governmental authorities for all required immunizations. There would be no need to rely on paperwork—a diagnostic examination would yield more suitable data regarding immune status. The current vaccination requirements for immigration into the United States are for measles, mumps, rubella, polio, tetanus, diphtheria, pertussis, influenza, hepatitis B and any other vaccinations recommended by the Advisory Committee for Immunization Practices (ACIP). Current recommendations of the ACIP also include varicella, *Haemophilus influenzae* type B, and pneumococcal vaccines. The current law requires all individuals applying for status as a lawful permanent resident (either by applying for an immigrant visa abroad or for adjustment of status in the United States) to establish that they have been vaccinated. Nonimmigrant (temporary) visa applicants are not required to comply with the vaccination requirements as a condition of visa issuance, but must comply if they apply for adjustment of status at a later date (Immigration and Naturalization Services, 2001).

One or more exemplary ImmunoScore diagnostic panels could, for example, be provided to INS or other immigration authorities as a means to determine the immune status of immigrants. In practice, ImmunoScore diagnostic testing can be more cost-effective than a paper record trail and more likely to be reliable as an accurate assessment of immune status of individuals relocating to the United States.

Additionally, the Institute of Medicine (IOM) has concluded that the United States quarantine system is in need of a strategic overhaul. The IOM reports that the United States once had 55 federal quarantine stations, but the perception that microbial threats had been controlled led to dismantling of most of the system in the 1970s. However, nearly 40 new infectious diseases have been identified since 1973, and bioterrorism has become a serious concern. The 25 stations that will make up the expanded quarantine station system now receive more than 75 million international travelers a year, according to IOM reports. The stations screen travelers, refugees, immigrants, animals, and cargo for disease agents shortly before and during their arrival. However, the quarantine system relies on a much broader network that includes local public health agencies, hospitals, customs agents, agricultural inspectors, and others, the IOM said.

The IOM recommended the following:

The quarantine stations, the CDC, and the DGMQ (called the quarantine core) should lead the effort by developing a national strategic plan with uniform principles and outcomes. The quarantine core should shift its main focus from inspecting people and cargo at ports to leading the activities of the overall quarantine system. The strategic plan should help participating government agencies and other groups in the system to prioritize activities and focus resources on the greatest risks.

The quarantine core should work with partners in the quarantine network to define or redefine each group's roles, authority, and communication channels.

The quarantine system needs enhanced skills, more people, more training, more space, and better use of technology to fulfill its evolving role. An example of technology cited in the news release was targeted use of passenger locator cards that could be used on flights to and from countries with disease outbreaks. The cards would log passenger seat numbers and contact information in a scannable format. This could simplify tracking of passengers potentially exposed to disease, such as those who flew to the United States from Sierra Leone in 2004 with a man who later died of Lassa fever.

The quarantine core must review its methodology periodically to ensure stations are in the best places and appropriately staffed.

The quarantine core must have plans, capacity, resources, and "clear and sufficient legal authority" to respond quickly to surges in activity at one or more ports.

The core must define and fund a research agenda to measure the effectiveness of its procedures. The committee found that many routines at quarantine stations are based on experience and tradition and lack a scientific basis.

The core must use scientifically sound methods to measure the effectiveness and quality of its operations, including assessing performance of critical functions throughout the system. It must also address any shortfalls that come to light. (http://www.nap.edu/books/030909951X/html).

ImmunoScore technology could be useful at such immigration port of entry screening points. There is a need for global health that can not be understated. The cost of failure could be extremely high. There are people moving around the globe and among the states with clear health needs, and they are currently moving without the ability of government authorities to track them.

Additionally, ImmunoScore technologies can be used to discover links between immunological phenomena. For example, from the results of Greenway (discussed above in Section I regarding the immigrant panel) a possible link between TB infection and HepB prevalence in can be investigated by analyzing sera from an immigrant population for both active TB and HepB seropositivity. It is possible that more than one co-infection may be found in this manner. For example, in the following study, *A high prevalence of hepatitis B virus infection among tuberculosis patients with and without HIV in Rio de Janeiro, Brazil*, Blal C A et al Eur J Clin Microbiol Infect Dis. 2005 January; 24(1):41-3, such a correlation was in fact found.

The Blal study sought to investigate the prevalence and exposure factors associated with hepatitis B infection in tuberculosis patients with and without HIV type 1 co-infection, the presence of hepatitis B virus serological markers was investigated in a retrospective study. The seroprevalence of hepatitis B virus in patients with tuberculosis only was 14.6%, and in tuberculosis patients co-infected with HIV it increased to 35.8%. In patients with HIV and tuberculosis co-infection, homosexuality constituted the principal exposure factor, while in tuberculosis patients without HIV, a gradual increase in hepatitis B virus seroprevalence was noted along with increasing age. These results demonstrate that hepatitis B infection is highly prevalent in tuberculosis patients in Brazil and suggest that a vaccination program for the general population should be considered in order to prevent further hepatitis B infections.

Q. Disaster Survivors: Immunizations, Recovery, Prognosis and Treatment

In exemplary embodiments of the present invention, rapid response services to disaster survivors can be provided. FIG. 32 depicts an exemplary process flow for such an application.

At 3201 a disaster survivors immune status can be examined using one or more ImmunoScore assay panels as described above in Section I. At 3210 the vaccine preventable diseases to which the survivor is susceptible can be identified and simultaneously the cellular component of his or her immune system can be assessed to get an immediate post disaster baseline. At 3220 vaccination and healthcare recommendations can be generated based upon antibody levels to the identified to the assay vaccine preventable diseases. At 3230 immunization can be carried out and at 3240 follow-up examination of the survivor's immune status can be administered and the results stored in the system database. Further screening of T cell components of the immune system is recommended for all survivors regardless of their psychological state at the time in order to develop data regarding post-traumatic stress disorder. Finally, at 3250 the efficacy of the vaccine and/or therapies can be evaluated as to their ability to provide necessary immunity to the identified diseases.

There are many different possible responses of an individual to an event perceived as potentially life-threatening. It is difficult to predict long-term responses to trauma based on the acute response to a traumatic event. If physiological risk factors are important in understanding how psychopathology develops, then ImmunoScore measurements can provide invaluable research information and possibly identify treatments yet to be defined. This could pave the way to personalized medicine. FIG. 33 illustrates possible responses to trauma.

With reference thereto, at 3301 a Disaster Trauma occurs. There are two pathways leading from 3301, namely, Normal Response Factors 3305 and Pathological Response Factors 3303. A Normal Response Factors 3305 pathway from Disaster Trauma 3301 leads to Recovery at 3310. However, Pathological Response Factors 3303 lead an individual from Disaster Trauma 3301 to Post-Traumatic Stress Disorder 3320. It is the job of healthcare personnel to put the individual on a Pathway to Recovery 3310. In exemplary embodiments of the present invention ImmunoScore technologies can be used to determine possible therapies 3315, as well as to track immunological correlates of PTSD to verify diagnosis and evaluate therapeutic efficacies.

In the immediate aftermath of a traumatic event, most people experience a combination of the following symptoms: (a) difficulty sleeping, (b) difficulty concentrating, (c) irritability, (d) nightmares, (e) recurrent thoughts of the trauma, and (f) distress at the reminder of the traumatic event. The question in the determination of a pathological response is when does the continuation of these "normal" responses become pathological, and have serious effect on the health of the individual's immune system?

There are different possible outcomes of trauma exposure. There is an increased risk of: (a) Post-Traumatic Stress Disorder (PTSD), (b) major depression, (c) panic disorder, (d) generalized anxiety disorder, (e) substance abuse, and (f) other somatic symptoms or expressions of physical illness including hypertension, asthma, and chronic pain syndromes. The differential outcomes may rely on different physiological parameters.

Pre-existing cognitive factors may or may not be the cause, result, or correlate of pre-existing biological alterations, either or both setting the stage for an extreme response to the trauma. Clarifying the precise nature and biological correlates of symptoms that appear in the immediate aftermath of a trauma will assist in developing models for potential prophylactic interventions and early treatments. In this regard the ImmunoScore diagnostic panel could initially be used in a research application to track immune system markers and relate them to specific conditions. As a system database evolves, ImmunoScore panels can, for example, be used as a guide to therapeutic treatment.

Individuals currently at the greatest risk for developing PTSD following trauma are those individuals with (a) a family history of psychopathology, (b) a history of childhood abuse, (c) prior trauma exposure, and (d) the cognitive factors of lower IQ, female gender, an poor social support. There is increased concordance for PTSD in monozygotic twins compared with dizygotic twins lending support to the genetic pre-disposition argument of PTSD.

R. Monitor Adoptive Immunotherapy/Transplants

After adoptive transfer, several events must occur for T cells to cause the regression of established tumors. T cells must be activated in vivo through antigen-specific vaccination. They must then vigorously expand to levels capable of causing the destruction of significant tumor burdens. Finally, anti-tumor T cells must survive long enough to complete the eradication of all tumor cells (Overwijk, et al. 2003). It has been found in an animal model that the progressive differentiation of T cells to a terminal differentiated effector stage results in a series of phenotypic and functional changes that make them less "fit" to perform these functions (Gattinoni, et al. 2005).

In patients under consideration for adoptive immunotherapy and/or transplantation, history and analyses of exposure to CMV, EBV, West Nile Virus, and viral hepatitis in both the donor and recipient are crucial. ImmunoScore diagnoses of both the donor and recipient would examine the immune history of both individuals.

S. Elective Surgery

Many patients opt for elective surgery—plastic surgery, facial plastic surgery, dermatology, cosmetic dentistry, vision, urology, and infertility among others. Whenever undergoing surgery, there is a risk of nosocomial infection. Common organisms that cause nosocomial infections are *Apergillus, Candida, Staphylococcus aureus, Staphylococcus epidermidis, Pseudomonas aeruginosa*, and *Bordetella pertusis*. Prior to elective surgery, it would benefit the patient and the attending surgeon to know the level of antibody protection to these infectious agents. An ImmunoScore panel could be tailored to meet these diagnostic needs and immunizations could be provided to those agents with available vaccine. In addition, following surgery patients could be screened for c reactive protein (CRP), tumor necrosis factor-alpha (TNF-α), IL-6, and soluble IL-2 receptor (sIL-2R) as possible early indicators of inflammation leading to sepsis. It is important to screen for a panel of analytes indicating sepsis, as one analyte is often not enough to get a proper diagnosis.

T. Services to Charitable Foundations Promoting Immunological Well being

Currently, the lack of accurate, affordable, and accessible diagnostic tests significantly impedes global health efforts. The Global Alliance for Vaccines and Immunizations (GAVI) was created in 1999 to protect health and save children's lives throughout the widespread use of modern vaccines. GAVI is a partnership of governments, international organizations, major philanthropists, research institutions, and the private sector that work together to: (a) improve access to sustainable immunization services, (b) expand the safe use of all needed cost-effective vaccines, (c) accelerate research and development efforts for new vaccines needed in developing countries, (d) make immunization coverage a key indicator of development, (e) promote sustainability by adequate financing, and (f) reinforce global and national immunization goals including eradicating polio, eliminating maternal and neonatal tetanus, reducing measles, and increasing access to vitamin A.

Underlying all health care tools—including therapeutic products, vaccines, and other preventative tools—are "platform" technologies that define and facilitate their use. For example, immunochromatography is a technology platform that has enabled the development of affordable, easy-to-use dipstick format diagnostic tools. The ImmunoScore diagnostic panel, a platform technology, can be used to great advantage by GAVI to improve global health efforts GAVI issues requests for proposal (RFPs) to support research efforts to create diagnostic technology platforms and tolls that enable improved prevention, treatment, and surveillance in developing country settings. The foundation issues RFPs to support the systemic evaluation of sets of genes, proteins, and cellular pathways to determine their potential role in contributing to the development of new vaccines, diagnostics, and drugs for GAVI's priority diseases and conditions. One area of concern is population genetics and how to design drugs and vaccines to discourage the emergence of resistance and to discover how genetics affects the efficacy of drugs and other interventions. The ImmunoScore database would be an ideal tool for GAVI to use to evaluate genetic parameters and immune response to vaccines and drugs under consideration. A second area is applied immunology. Here systematic approaches, such as that provided by the ImmunoScore technology, are needed to measure the human immune response to guide vaccine design and define biological signs that identify early or latent infection.

U. Discovery of Unwanted Immunogenicity of Therapeutics

There is potential of the human immune system to identify biological therapeutic products as foreign and mount an immune response. There are three main areas of concern with the production of antibodies against biological therapeutics in humans:

Safety—assurance of safety involves the assessment of whether antibodies induced could have adverse clinical implications.

Efficacy—can be affected by the presence of antibodies binding to the product and reducing its potency.

Measurement of phamacokinetic/pharmacodynamic parameters—the presence of antibodies can alter these clinical parameters and also interfere in the assays used in their assessment (Koren, et al. 2002).

The immunogenicity of therapeutic proteins can be influenced by many factors, including the genetic background of the patient, the type of disease, the type of protein (human or nonhuman), the presence of conjugates or fragments, the route of administration, dose frequency, and duration of treatment (Schellekens, 2002). Manufacturing, handling, and storage can introduce contaminants, or alter the three dimensional structure of the protein via oxidation or aggregate formation. Various means have been suggested by which therapeutic proteins might be modified to reduce their immunogenicity, including PEGylation, site-specific mutagenesis, exon shuffling, and humanization of monoclonal antibodies (Schellekens, 2002). In the future, it may be possible to predict the immunogenicity of new therapeutic proteins more accurately, using specifically designed animal models, including nonhuman primates and transgenic mice.

ImmunoScore diagnoses and database storage could be instrumental in the development of analytical techniques to monitor both the drugs and the patient population. An individual's tendency to mount an immune challenge to a protein therapeutic could be revealed prior to initiation of the treatment based upon the patient's ImmunoScore profile. In addition, once therapeutic treatment began, ImmunoScore diagnoses and database management could track a patient's immune response to the drug. The drug manufacturers would be able to use the ImmunoScore technology to conduct clinical trials and also to select an appropriate population in which to test the drug. Based upon ImmunoScore population data, the drug could be designated for use based upon the genotype of the individual being treated.

FIG. 34 depicts an exemplary process flow for an ImmunoScore immunogenicity study in exemplary embodiments of the present invention. The exemplary study is directed to immunogenicity of therapeutic proteins.

With reference thereto, at 3401 a prospective patient's immune status can be examined to obtain a baseline ImmunoScore. At 3410 patients for whom treatment would not be advisable (based upon immune system profiling) can be identified, and therapeutic treatment for a patient group for which therapy is advisable can be initiated. At 3420 patients' further treatment and health care recommendations can be made, based on careful periodic monitoring of antibody levels to therapeutic proteins. In addition, cellular components of the immune system would warrant careful monitoring—particularly in regard to the antigenic components of the therapeutic compound. At 3430 patient data can be compiled for drugs in clinical trial. Population data can also be compiled to assist in drug design. At 3440, follow-up examinations of patients' immune status post-treatment can be implemented and the results stored in a system database. Further screening of antibody levels and T-cell components of immune system can be implemented for all patients. Finally, at 3450 the efficacy of therapies to provide necessary treatment to patients can be evaluated, and extent of undesirable immunogenicity can be determined.

V. Two-Sided Market Applications

A two-sided market is a market wherein there are two sets (at least) of customers that, in effect, need each other. Each type of customer values the market more if the other type of customer also buys the service. Businesses service such markets by acting as "matchmakers."

Examples of Two-Sided Markets:
  computer operating systems
    software developers write applications
    computer users run applications
  video game console manufacturers serve
    video game players
    video game designers
  payment card companies
    consumers
    merchants These businesses all produce platforms that make matches between two or more distinct groups of consumers.

The description of two-sided markets likely came about from payment card companies and legal ramifications of what may have been perceived as monopolistic business practices, but was actually the demonstration of two-sided marketing practices. A key aspect to the business model for most of these industries involves the optimal pricing structure: the division of revenues between the two sides of the market that gets both sides on board. The need for pricing structure as well as pricing level distinguishes industries based on a two-sided market from the industries ordinarily studied by economists. In two-sided markets, the product may not exist at all if the business does not get the pricing structure right. Currently, there is no appreciable market for adult vaccines, other than those for influenza and pneumococcus. ImmunoScore diagnostics can, for example, likely reveal lapses in protection for vaccine preventable diseases, such as pertussis, tetanus, diphtheria, mumps, measles, and others. Diagnostic testing can thus reveal a large marketing potential for vaccine manufacturers.

Both the ImmunoScore diagnostic application and the ImmunoScore database management modules can be considered as two-sided marketing opportunities, in that none of the participants (patients, insurers, researchers, primary care physicians, vaccine manufacturers, or government entities) may necessarily be willing to enter into a beneficial marketing alliance without direction provided by the ImmunoScore platforms, as illustrated in FIG. 35. ImmunoScore can act as a "matchmaker" for these different groups of consumers. An ImmunoScore diagnostic platform can, for example, serve to link patients, physicians, and vaccine manufacturers and help to illustrate the need for continuing vaccine coverage in adults and children at risk. As an ImmunoScore database module grows from an ImmunoScore diagnostic module, insurers, research groups (both academic and commercial), and groups responsible for vaccine decision-making (ACIP and AAP) and tracking (CDC and VAERS) can be able to take advantage of the data generated from assessing the immune status of patients.

Network effects. A network effect arises when the value that one user receives from a product increases with the number of other users of that product. It goes without saying that the value to governmental decision-making, insuring, and research interests can expand enormously with the increase in size of an ImmunoScore patient database. Health insurers can also be involved at ImmunoScore diagnostic platform level. Insurers that would be interested in providing insurance based upon an individual patient's ImmunoScore would benefit most from the ImmunoScore database platform. Most network effects arise because a product tends to be two sided. ImmunoScore, having more than two interactive sides, would demonstrate large network effects that should benefit society as a whole, with better health for the population at large and decreased costs for the insurers. Information garnered from an ImmunoScore Database can enable the performance of vaccine researchers and the vaccine decision-makers in the government tremendously.

Survey of Two-Sided Markets

Diverse industries:
credit cards
computer operating systems
video games
corporate bond trading
residential real estate Firms in these industries have adopted similar business models and pricing strategies for solving the problem they have in common—getting and keeping two sides of a market on board. The intermediary helps customers complete a transaction by providing a platform. The transaction occurs when both sides get together. Currently, there is a real need to get adult patients and vaccine manufacturers together for the betterment of public health. ImmunoScore diagnostics will be an effective facilitator of this interaction, with the medical insurance companies being a third beneficiary. The intermediaries succeed in the businesses by figuring out how a pricing structure that internalizes the externalities between the two sides. In the case of ImmunoScore Diagnostics, the health insurers should be willing to pay for the diagnostic testing as well as the cost of vaccination, as those costs would be less than those to treat debilitating diseases otherwise preventable by judicious use of vaccination.

A market is two-sided if at any point in time there are:

two distinct groups of customers—with ImmunoScore diagnostic and ImmunoScore database platforms, there would be patients, vaccine manufacturers, health insurers, vaccine researchers, and vaccine decision-making organizations that would benefit from the two-sided ImmunoScore platforms.

the value obtained by one kind of customer increases with the number of the other kind of customers—as the number of patients were added to the database, the database would increase in potential utility to researchers, vaccine decision-makers, insurers, and vaccine manufacturers. The more the database grows, the better it would be for the patient population as physicians would better be able to determine individual patients' immune status based on knowledge accumulated over the entire patient population.

the intermediary is necessary for internalizing the externalities created by one group for the other group—there is currently no real push for adults or older children to have diagnostic screening related to vaccine-preventable diseases. As ImmunoScore data accumulate, there should be an added impetus for adult and adolescent vaccination coverage.

Researchers have examined the pricing and production strategy of a firm in a two-sided market. Consider the case in which both sides of the market are buying a "transaction" and in which the seller incurs a marginal cost for consummating that transaction. The prices charged to the buyers and sellers are two prices. The buyer's demand depends only on the price faced by the buyer and the seller's demand depends only on the price faced by the seller. The demands can be thought of, roughly speaking, as the number of buyers and sellers using the system. The transactions that a seller engages in, and its benefits from those transactions, increase proportionally with the number of buyers on the system. The same holds for an individual buyer. Total demand equals the product of the two demands. Thus, if there were 500 sellers and 100 buyers, there would be 50,000 transactions. The assumption of a multiplicative demand between the two sides actually understates the importance of the indirect network effects. It ignores the fact that the value each side obtains from the other side increases with the number of customers on the other side. In the cases of ImmunoScore diagnostics and an ImmunoScore database, the benefit to all sides of the market could increase dramatically (presumably something more than a multiplicative effect) as the number of consumers grows. Feeding information to the database can only assist patients, physicians, vaccine decision-making bodies, vaccine manufacturers, and health insurers.

None of the conditions for determining the price level or the price structure in two-sided markets corresponds to marginal revenue equaling marginal costs on either side of the market. Such conditions have no meaning in two-sided markets because there is no way to allocate the increases in revenues from changes in prices to one side or the other. Changes in prices result in more "transactions" from which each side jointly benefits.

Business Models in Two-Sided Markets. Both sides need to be brought on board. For instance, there would be no demand by households for payment card is they could not be used anywhere, and no demand by retailers if no one had them to use. Investment and pricing strategies are key to getting both sides on board. Even with both sides on board, businesses have to carefully balance their two demands. They have to consider how changes on one side of the market will impact the other side of the market. The need to balance the needs of the various consumers will be of utmost importance to the careful development of ImmunoScore diagnostics and ImmunoScore database management as two-sided markets. Currently, patients, physicians, and vaccine manufacturers seem painfully unaware of the need for diagnostic testing and boosting for vaccine-preventable diseases.

Getting both sides on board. One way to get both sides on board is to obtain a critical mass of users on one side of the market by giving them the service for free or even paying them to take it. Another way to solve the chicken-and-egg problem is to invest in one side of the market to lower the costs to consumers on that side of participating in the market. Providing low prices or transfers to one side of the market helps the platform solve the chicken-and-egg problem by encouraging the benefited group's participation—which in turn, due to network effects, encourages the non-benefited group's participation. Another effect of providing benefits to one side is that this assistance can discourage use of competing two-sided firms. In the case of the ImmunoScore diagnostic and database platforms, initially the medical insurance industry would likely bear the burden of any associated costs, but the benefit to this industry in increased wellness of their clientele should offset any up-front costs. In addition, to those patients who are seen to have an unfavorable ImmunoScore the supplemental insurance industry should be available and able to come in and insure those individuals with special needs.

Pricing strategies and balancing interests. Firms in mature two-sided markets still have to devise and maintain an optimal pricing structure. In most observed two-sided markets, companies seem to settle on pricing structures that are heavily skewed towards one side of the market. Certain customers on one side of the market may be extremely valuable to customers on the other side of the market—"marquee buyers." In the case of the ImmunoScore diagnostic and database platforms, the "marquee buyers" could be seen as large HMOs that would in truth benefit from having a healthier patient population. The existence of marquee buyers tends to reduce the price to all buyers and increase it to its sellers. Acceptance of ImmunoScore platforms by large insurance organizations and government agencies would enable "bringing on board" smaller insurance agencies. A similar phenomenon occurs when certain customers are extremely loyal to the two-sided firm—perhaps because of long-term contracts or sunk-cost investments.

Multihoming. Most two-sided markets in the real world appear to have several competing two-sided firms and at least one side appears to multihome. Multihoming affects both the price level and the pricing structure. Not surprisingly the price level tends to be lower with multihoming. The possibility of multihoming may encourage firms to lower their prices on the side of the market in which multihoming could occur. By lowering their prices, firms discourage customers on that side from affiliating with other two-sided firms. The firm can then charge more to customers on the other side, for whom fewer substitutes are available.

Two-Sided Markets and Social Welfare. A relatively small number of firms tend to compete in two-sided markets. That is because these markets have network effects and usually incur substantial fixed costs for getting one or both sides on board. Larger firms have advantages over smaller firms because larger size delivers more value—a bigger network—to consumers. Firms in concentrated two-sided markets may have opportunities to earn supra-competitive profits—i.e. profits that exceed those necessary to attract capital to the industry after accounting for risk. Several factors affect the extent to which this can happen over time.

7. The extent to which firms are competing to become established in a two-sided market. This results in investment to court customers, to provide them with subsidies in the form of equipment, and to offer them low or negative prices. Vaccine manufacturers and physicians offices might initially need to be coaxed into the ImmunoScore diagnostic and database markets, but should see the benefits as the structure grows.

8. The extent to which there are first mover advantages in getting either side of the market on board then the competition to make these investments should reduce the opportunities to earn significant supra-competitive returns. Savvy Health Maintenance Organizations could be the first to realize the benefits to their coverage that ImmunoScore diagnostics and database platforms could provide, and as such may be eager to get into this opportunity at the ground level. The governmental organizations could also be made to see the benefits of diagnosing and cataloging lapses in vaccine-preventable disease conditions.

The consequences of having relatively few competitors in two-sided markets, and the existence of network effects, raise familiar issues concerning the efficacy of competitive markets and the possible roles for government intervention. The pricing and investment strategies that firms in two-sided markets use to get both sides on board and balance the interests of both sides raise novel questions. These pricing and other business strategies are needed to solve a fundamental economic problem arising from the interdependency of demand on both sides of the market. In some cases, the product could not even exist without efforts to subsidize one side of the market or the other. In the case of the ImmunoScore platforms, the patients would likely need to be subsidized by the participation of health insurers.

Researchers have compared the pricing structure adopted by firms in two-sided markets to the pricing structure that would maximize social welfare. Interestingly, they find that a monopoly firm, a firm with competition, and a benevolent social planner would adopt similar pricing structures. The precise relative prices would differ somewhat. They found that the pricing structure adopted by the market is not biased towards one side of the market or the other side of the market compared to the pricing structure that would be adopted by the benevolent social planner. ImmunoScore diagnostic and database platforms may be though of as a benevolent social plan. The welfare of the patients is paramount, and there would be additional benefits presented to vaccine manufacturers, research groups, and government organizations.

Two-sided markets are an increasingly important part of the global economy. Firms that provide platforms for multiple consumer groups are a critical part of many interrelated segments of the computer industry. In most industrialized countries a large fraction of payments takes place through firms and associations that provide platforms for merchants and customers to exchange money. The increased importance of the Internet for household-to-household, business-to-household, and business-to-business transactions and the emergence of e-pay systems on the Internet will increase the fraction of payments going through commercial payment platforms. ImmunoScore diagnostic and database platforms would help bring health care into the $21^{st}$ century. There is a tremendous need for portability in health care record-keeping, and the ImmunoScore database platform would be instrumental in the transfer of health care records from primary care physician to specialist.

Two-sided firms have to come up with the right price structure and the right investment strategy for balancing the demands of the customer groups they must get and keep on their platforms.

In many industries, platforms court two (or more) sides that use the platform to interact with each other. The platform may charge interaction-independent fixed fees. For example, American Express charges yearly fees to cardholders. In the case of video games, platforms charge game developers fees for development kits on top of royalties per copy sold, and they charge garners for the console. In the case of the ImmunoScore database platform, it might be appropriate to charge academic and commercial research groups for use of the information captured by the database modules.

Managers devote considerable time and resources to figure out which side should bear the pricing burden, and commonly end up making little money on one side (or even using this side as a loss-leader) and recouping their costs on the other side. Marketing managers for the ImmunoScore platforms will need to carefully balance many consumers' needs and the applications of fees.

Pricing Principles for Two-Sided Platforms. Departures from standard business strategies that result from the platform's internalization of the other side's welfare (the linkage between the two sides from the platform's viewpoint). This linkage is most apparent when the platform makes no or loses money on one side. A factor that is conducive to a high price on one side, to the extent that it raises the platform's margin on that side, tends also to call for a low price on the other side as attracting members on that other side becomes more profitable. In the case of the ImmunoScore platforms, it is imperative to bring patients on board, but their participation might be encouraged by the duel factors of their curiosity as to their personal ImmunoScore and also the participation of their insurer in the platform.

Platforms must perform a balancing act with respect to their price structure as well as other policy dimensions; quite generally, they encourage positive externalities and discourage negative ones and to do so usually constrain one side to the benefit of the other. While asymmetric information and the concomitant rent extraction concerns keep the platform's price structure neutral, it is nonetheless a source of suboptimal trade among end-users. The platform has an incentive to cap or alter through a subsidy the price charged to buyers so as to boost buyer's surplus and their willingness to join the platform. Then the platform behaves pretty much like a public utility commission that addresses a market power problem by setting a price cap or by subsidizing some services through a fund levied from other services.

The rationale for constraining the price charged by the seller to the buyer would vanish if the industry were organized according to the vertical view: were the platform not to deal directly with buyers, the platform would want to provide sellers with the maximal profit in their relationship with buyers and therefore would grant them maximal commercial freedom. It is only because the platform can extract surplus on the buyer side that it is willing to displease the seller side by constraining it.

End-users often care not only about the price (that they pay to the platform and to the other side), but also about the quality of the interaction. In health care, the quality of the physician-patient interaction assumes particular importance. An ImmunoScore Diagnostic platform will help nurture the doctor-patient relationship and focus on the patient's "wellness" rather than strictly on "treatment."

While price regulation is complex or inefficient, the platform may still make itself attractive to one side of the market by encouraging competition on the other side. Competition on the other side brings prices closer to marginal cost, and the volume of interactions closer to the efficient volume; it also protects against the hold up of one's specific investments. An ImmunoScore diagnostic platform could encourage competition among vaccine manufacturers on behalf of the patient population. The manufacturers should still realize greater sales, but their prices should remain competitive for the insurers and patient population. Accordingly, a two-sided platform benefits from allowing competition on a given side as it can at least partly recoup benefits on the other side.

Dynamics. To create a two-sided market, a "chicken or egg" problem has to be solved: to convince some buyers to adopt a certain intermediation platform, it is necessary to convince first some sellers, but to convince the sellers, there must be some buyers on the market. In most models, this problem is avoided by assuming the simultaneous arrival of agents on the two market sides, in a rational expectations equilibrium. However, there are circumstances in which one market side has to intervene before the other one. The most cited case is the one of videogame consoles which, to get customers, must appear on the market already equipped with a complete range of games and complementary applications. There appears to be a growing need for the determination of a patient's immune status. There is a current outbreak of mumps disease in the Midwest in individuals that have received two MMR immunizations. The incidence of pertussis continues to increase. Travel has now been related to the spread of Severe Acute Respiratory Syndrome (SARS), influenza, measles, tuberculosis, and mumps. The time is appropriate for the introduction of the measurement of the immune status of individual patients, and the tracking of information regarding each individual's immune status. ImmunoScore diagnostic and database platforms can tip the balance from a display of need to a mode of action going forward.

W. Drug Hypersensitivity
Incorporating Drug Hypersensitivity into a Two-Sided Business Model Adverse drug reactions are common. Identifying true drug allergy, however, can be challenging. Drug hypersensitivity is a clinical diagnosis based upon available data. Drug hypersensitivity is defined as an immune-mediated response to a drug agent in a sensitized patient. Identifiable risk factors for drug hypersensitivity reactions include age, female gender, concurrent illnesses, and previous hypersensitivity to related drugs. Monitoring drug hypersensitivity in patients and incorporating those data into an ImmunoScore database platform is another example of a two-sided market opportunity. As with the other examples of two-sided markets, the medical insurance organizations would likely initially cover most of the expenditures to bring the other market components into the market that would be beneficial to all participants. Other "sides" of the market would involve patients, physicians, researchers for both the pharmaceutical industry and allergy specialists.

The Gel and Coombs classification system describes the predominant immune mechanisms that lead to clinical symptoms of drug hypersensitivity (Table 1). This classification system includes IgE-mediated Type I reactions, cytotoxic Type II reactions, Type III reactions involving the formation of immune complexes, and the delayed, cell-mediated Type IV reactions. However, some drug hypersensitivity reactions are difficult to classify because of a lack of evidence supporting a predominant immunologic mechanism. These include certain cutaneous drug reactions and specific drug hypersensitivity syndromes.

Diagnostic testing for these reactions remains somewhat problematic. The current types of tests and therapeutic considerations are for each of the four types of hypersensitivity reactions are described in Table 2 below. Confirmation of suspected Type I hypersensitivity reactions require the detection of antigen-specific IgE. Currently, skin testing is a useful diagnostic procedure for reactivity to penicillin. With other drug agents, a negative skin test does not effectively rule out the presence of specific IgE. Further IgE test for other agents await development. The sensitivity of ECL technology as embodied in an exemplary ImmunoScore diagnostic platform can be a very effective tool to enable researchers to better study IgE populations specific for drug component antigens. Currently, the diagnosis of drug hypersensitivity is usually based upon clinical judgment because definitive, confirmatory drug-specific testing is often difficult.

Once the diagnosis has been established, appropriate documentation should be included in the medical record specifying the causative drug and the nature of the adverse effect. Immune-mediated drug hypersensitivity reactions typically pose a predictable, more serious health risk with re-exposure to the drug. In this application of the technology, an exemplary ImmunoScore database platform can, for example, capture all pertinent information related to any adverse drug reaction. This would not only be of benefit to the patient, but also as data was accrued, pharmaceutical companies would benefit from statistical information gathered from mining the database. Real drug hypersensitivity would also be separated from reactions that may not be hypersensitivity. Instead of relying on patient recall and a faulty data collection system, an exemplary ImmunoScore database can only include documented case histories. Patient medications can, for example, be tracked via an ImmunoScore database and real hypersensitivity can be officially documented.

The most important drug-related risk factors for drug hypersensitivity concern the chemical properties and molecular weight of a drug. Larger drugs with greater structural complexity are more likely to be immunogenic. Heterologous antisera, streptokinase and insulin are examples of complex antigens capable of eliciting hypersensitivity reactions. Another factor affecting the frequency of hypersensitivity drug reactions is the route of drug administration; topical, intramuscular, and intravenous administrations are more likely to cause hypersensitivity reactions. These effects are caused by the efficiency of antigen presentation in the skin, the adjuvant effects of repository drug preparations, and the high concentrations of circulating drug antigen rapidly achieved with intravenous therapy. Oral medications are less likely to result in drug hypersensitivity.

Most medications, because of their small molecular size, are unable to elicit an immune response independently. Drugs must first covalently bind to larger carrier molecules such as tissue or serum proteins to act as complete multivalent antigens. This process is called haptenation, and the drugs act as haptens. The elicited immune response may be humoral, with the production of specific antibodies, cellular, with the generation of specific T lymphocytes, or both. Frequently, the identity of the metabolites is unknown, making it impossible to develop accurate diagnostic tests for drug allergy (Solensky, 2006).

A thorough history is an essential component of the evaluation of patients with suspected drug allergies. The history helps guide the clinician in the choice of diagnostic tests and the decision whether it is safe to reintroduce the medication. Typically, years or decades have passed since reactions occurred, and, as a result, these records are usually unavailable at the time of consultation.

Patients labeled penicillin-allergic are more likely to be treated with more expensive and broad-spectrum antibiotics, a practice that leads to the development and spread of multiple drug-resistant bacteria and higher direct and indirect health care costs. Among patients with a reported history of penicillin allergy, 80-90% have no evidence of IgE antibodies to penicillin on skin testing and thus avoid penicillin unnecessarily. The discrepancy between claimed and real penicillin allergies probably results from several factors. The reaction may have been predictable or due to the underlying illness and hence may have been mislabeled as allergic from the onset. Another contributor to the discrepancy is the tendency of patients with type 1 penicillin allergy to lose penicillin-specific IgE antibodies over time. Insight into the immunochemistry of penicillin has allowed for the development of validated skin-test reagents to detect penicillin-specific IgE.

Together with penicillin, cephalosporins are the antibiotics most widely used for treating common infections, and like penicillin, can cause immediate reactions. Manifested clinically by urticaria, angio-edema, rhinitis, brochospasm, and anaphylactic shock, such reactions are generally IgE-mediated and are among the most dangerous. Although the incidence of severe immediate reactions to cephalosporins does not seem to be much different from that to penicillin, studies of cephalosporins as allergens are not nearly as numerous or thorough as those on penicillin, and very few have been dedicated to the still little known determinants responsible for allergic reactions.

Unpredictable adverse reactions to aspirin and NSAIDS fall into several major categories. Respiratory reactions occur in patients with underlying asthma, non-allergic rhinitis, and nasal polyposis. The preferred term for this disorder is aspirin-exacerbated respiratory disease (AERD). The reactions typically involve the entire respiratory tract, with symptoms of rhinitis, conjunctivitis, and bronchospasm. Patients who have AERD exhibit cross-reactivity with all non-steroidal anti-inflammatory drugs (NSAIDS), but they can tolerate cyclo-oxygenase 2 enzyme (COX-2) selective inhibitors. No in vitro tests to detect aspirin sensitivity exist, and oral challenge remains the gold standard diagnostic test for AERD.

True hypersensitivity reactions to local anesthetics are uncommon and usually consist of delayed contact dermatitis; anaphylaxis from local anesthetics occurs rarely if ever. Most adverse reactions are vasovagal, psychogenic, toxic, or predictable side effects of epinephrine that is often used in combination with local anesthetics. Large-scale studies have found that, following full evaluation, virtually all patients with a history of allergy to local anesthetics are able to tolerate these drugs. Unfortunately, patients who experience any adverse reaction to local anesthetics are frequently labeled allergic and told to avoid all "-caines" in the future. Because evaluation of these patients invariably finds them able to receive a local anesthetic, such evaluation prevents them from being subjected to the increased risk of general anesthesia or, alternatively, to pain from the absence of anesthesia. Evaluation of patients with a supposed allergy to local anesthetics is also important because it serves to alleviate dentists' or physicians' legal (malpractice-related) concerns regarding use of a drug to which the patient is listed as being allergic.

Allergic drug reactions compose a small percentage of adverse drug reactions, yet they are commonly encountered in clinical practice, and physicians are taught to routinely question patients about these reactions during history taking. Medical history taking is critical in the evaluation of antibiotic allergy and in distinguishing allergic reactions from other adverse reactions. This information is important, since overdiagnosis of allergic reactions can lead to unnecessary use of more costly antimicrobial agents and may promote the development of resistant microorganisms. Whenever possible, patients who are being evaluated for possible antibiotic allergy should be encouraged to provide all medical records related to previous adverse drug reactions.

Treatment. For drugs that are presumed to be mediated by IgE, drug desensitization my be performed if the implicated agent is required for treatment. Desensitization involves the administration of increasing amounts of the antibiotic slowly over a period of hours until a therapeutic dose is reached. The mechanism by which clinical tolerance is achieved is unclear, but it is thought to involve antigen-specific mast-cell desensitization. Since maintenance of a desensitized state requires the continuous presence of the drug, desensitization must be repeated if the antibiotic is required again later.

For reactions that are not considered to be mediated by IgE, management depends on the clinical manifestations of the previous reaction. For macropapular eruptions, the specialist may consider a graded drug challenge, which is equivalent to provocation testing. Initial starting doses are generally higher than those used for desensitization, and the interval between doses varies, ranging from hours to days or weeks. The decision whether to discontinue an antibiotic if a reaction occurs depends on the nature of the reaction; bullous lesions or those involving mucous membranes warrant withdrawal of the drug, whereas it may be reasonable to treat through milder reactions, such as maculopapular eruptions, with the use of antihistamines, corticosteroids, or both as needed.

Cephalosporin in patients with penicillin allergy. Penicillins and cephalosporins share a β-lactam ring structure, making cross-reactivity a concern. Whereas most patients who have a history of penicillin allergy will tolerate cephalosporins, indiscriminate administration cannot be recommended, especially for patients who have had life-threatening reactions. For patients with a history of penicillin allergy who require a cephalosporin, treatment depends on whether the previous reaction was mediated by IgE. If testing is positive and a cephalosporin is considered necessary, then desensitization should be performed with the use of the particular cephalosporin chosen for treatment.

Areas of Uncertainty. (Gruchalla and Pirmohamed, 2006) The mechanisms underlying antibiotic allergy have not been clearly elucidated. This understanding is needed to facilitate the development of better diagnostic tools and drugs then are less immunogenic. Better understanding is needed of factors mediating individual susceptibility to allergic reactions to antibiotics. Some patients have reported adverse reactions to many chemically unrelated antibiotics. The existence of the so-called multiple drug allergy syndrome is controversial, and accepted diagnostic tests are needed to document drug allergy in these patients.

For the HMOs and other insurers, drug hypersensitivity diagnoses and cataloging by ImmunoScore are a natural marriage. There are dual concerns in health care regarding the expense of exotic antibiotics and the development of antibiotic-resistant strains of organisms. Real patient information regarding drug hypersensitivity (as opposed to patient recall and limited health records) would certainly be welcomed by the medical and insurance professions.

TABLE 1

Gell and Coombs Classification of Drug Hypersensitivity Reactions (Riedl and Casillas, 2003)

| Immune reaction | Mechanism | Clinical manifestations | Timing of reactions |
| --- | --- | --- | --- |
| Type I (IgE mediated) | Drug-IgE complex binding to mast cells with release of histamine, inflammatory mediators | Urticaria, angioedema, bronchospasm, pruritus, vomiting, diarrhea, anaphylaxis | Minutes to hours after drug exposure |
| Type II (cytotoxic) | Specific IgG or IgM antibodies directed at drug-hapten coated cells | Hemolytic anemia, neutropenia, thrombocytopenia | Variable |
| Type III (immune complex) | Tissue deposition of drug-antibody complexes with complement activation and inflammation | Serum sickness, fever, rash, arthralgias, lymphoadenopathy, urticaria, glomerulonephritis, vasculitis | 1 to 3 weeks after drug exposure |
| Type IV (delayed, cell-mediated) | MHC presentation of drug molecules to T cells with cytokine and inflammatory mediator release | Allergic contact dermatitis, maculopapular drug rash | 2 to 7 days after cutaneous drug exposure |

Recommendations. Patients who report a history of antibiotic allergy require a careful assessment of the nature of the reaction to determine if the likelihood that it was immunologically mediated. For patients whose history suggests and IgE-mediated reaction to penicillin, skin testing is indicated. If the test results are negative, the β-lactam agent may be administered. If the test results are positive or testing cannot be done, the drug should be avoided or a desensitization procedure should be performed.

ImmunoScore and Drug Hypersensitivity. Exemplary ImmunoScore diagnostic and ImmunoScore database platforms can be seen as examples of two-sided markets in both the diagnoses of drug hypersensitivity as well as in the retention of an individual patient's drug hypersensitivity testing and records for future health care medication decisions as shown in FIG. 36. In such cases, it would be predicted that the health maintenance organizations and pharmaceutical manufacturers (seen at the base of the diagram, propping up the platform structure) would belong to the side(s) of the market most eager to subsidize the other partners. Patients, physicians, and allergy specialists are natural partners to exemplary ImmunoScore diagnostic and database platforms regarding drug hypersensitivity. Because the diagnoses of drug hypersensitivity reactions are in their infancy from a scientific standpoint, research groups developing diagnostic assays are also natural customers for the two ImmunoScore platforms.

Initial patient histories should include a recording of all prescription and non-prescription drugs taken within the last month, including dates of administration and dosage. This is a real example of the proposed utility of the ImmunoScore database platform, wherein patient medications could be tracked and also easily transferable from primary care physicians to specialists.

TABLE 2

Diagnostic Testing and Therapy for Drug Hypersensitivity (Solensky, 2005)

| Immune reaction | Laboratory tests | Therapeutic considerations |
| --- | --- | --- |
| Type I (IgE-mediated) | Skin testing Radioallergosorbent test (RAST) Serum trypase | Discontinue drug Consider epinephrine, antihistamines, systemic corticosteroids, bronchodilators Inpatient monitoring, if severe |
| Type II (cytotoxic) | Direct or indirect Coombs' test | Discontinue drug Consider systemic corticosteroids Transfusion in severe cases |
| Type III (immune complex) | Erythrocyte sedimentation rate (ESR) Complement studies Antinuclear antibody, antihistone antibody Tissue biopsy for immunofluorescence studies | Discontinue drug Consider NSAIDS, antihistamines, or systemic coricosteroids; or plasmapheresis, if severe |
| Type IV (delayed, cell-mediated) | Patch testing Lymphocyte proliferation assay | Discontinue drug Consider topical corticosteroids, antihistamines, or systemic corticosteroids, if severe |

X. Health Care Transparency and Competition

Currently, health care in the United States consumes $2 trillion per year. Out-of-pocket costs for those who have insurance have nearly tripled in the last six years, and 46 million Americans are uninsured. Unpaid and unpayable health care bills account for the majority of all personal bankruptcies in the country. Eight criteria for improving health care can be articulated as:
1. Consistent high quality
2. Lower cost—follows from high quality. Higher quality is often naturally less expensive. Providers improve quality by honing their organizational processes to become more efficient and effective—to avoid error and to do things right the first time.
3. Available to all—for ethical, political, systemic, and business reasons, health care must be available to everyone.
4. Single model—every provider in the system must compete to offer the best product at the best price.
5. Shaped by market forces—the consumer market has the sustained systemic power to bring consumers more for less.
6. Practical—the solution must arise from present realities.
7. Progressive—dramatic change can not occur all at once.
8. Self-reinforcing—as any part of the health care system moves toward a new reality, that movement must allow and encourage other parts to move forward as well.

Competition thus far has failed to work the same wonders in health care that it has in so many other industries. In *Redefining Health Care: Creating Value-Based Competition on Results*, Michael Porter and Elizabeth Teisberg argue that this is because competition has taken place at the wrong level and over the wrong goals. Further exacerbating the problem is the complete absence of feedback loops. Very little in health care has a real price or a real measurable result. Competition in health care has consisted of health plans' and providers' attempts to push cost and risk of themselves and onto each other or onto employers—and now, onto the consumers. Consumers are not looking to embrace an institution, but are looking for a solution for a particular problem. One can envision a world in which health care is organized mainly around products tailored to particular medical conditions. Such products can be delivered by medically integrated practice units made up of teams that work together on the same medical condition over long periods of time. In this particular vision, transparency drives quality. Health plans could steer patients toward the providers who offer the best results for the least money. Referring physicians could refuse to recommend any specialist or package with quality scores in the lower quintiles, for fear of being sued for malpractice themselves. When health care providers compete at the level of the medical condition, on real prices and real results, feedback loops can become extremely compelling. Offering the highest possible quality at the lowest possible price will no longer be voluntary, and health plans will also be forced to compete on the basis of real results and genuine customer service at the lowest price, rather than at their current modus operandi—which can include denying coverage and shifting cost and risk to employers, consumers, and providers.

New structures for public reporting of medical results are popping up on federal, state and regional levels. In many of these initiatives, process measures are starting to give way to results measures. In a number of regions, new tiered payment models use co-payments and other means to encourage patients to use the providers with the lowest cost and highest quality scores. Such models also reward more efficient systems, those that beat their risk-adjusted cost targets, with higher reimbursements, and punish those less efficient providers with lower reimbursements.

The pieces—transparency, integrated products, and true measurement—are coming into play in the health care marketplace. Once it becomes common for health care providers to post actual prices and actual results in standardized ways that produce comparable data, it is hard to see how consumers, insurance companies, and referring physicians would ever choose low quality at high prices.

In exemplary embodiments of the present invention, ImmunoScore diagnostics and database management can, for example,
  keep score not only of patient's immune data, but effectiveness of treatments/vaccine
  tie records of physician recommendations relating immune status to fiscal responsibility and patient well-being
  provide data for insurers
  provide data for providers
  provide data for consumers Major decisions about health care in the U.S. have traditionally been made by employers, who determine for their employees which benefits and forms of coverage are needed, what types of providers are included in the network, and which organizations administer the benefits. But this paternalistic approach effectively allowed the consumer to be a passive participant in his or her own health care. The consumer to this point has had no economic incentive to seek the best care at the fairest price, or to give up unhealthy habits. It has been written (Knott, et al. 2007) that new health care formats and competitors are gaining traction, with Minute-Clinics and RediClinics—low cost walk-in health care centers for common ailments at one end of the spectrum, and highly personalized "concierge care" at the other. In addition, companies that are not traditional health care players are leveraging their capabilities to create entirely new offerings that enable and encourage the move toward health care consumerism. Fidelity, for example, is developing products and tools that exploit the emerging health-wealth intersection, such as a calculator that helps predict out-of-pocket health care costs. Standardized data on cost, service, and outcomes has the power to establish a new basis of competition. Payers are also pushing for new payment mechanisms, such as pay-for-performance, that base reimbursement on outcomes or adherence to broadly accepted clinical guidelines, known as evidence based medicine.

To make competition and innovation among payers and suppliers possible, an exemplary system could include the following:
  consumers who live healthy lives and plan for their future health care needs
  a fundamentally restructured supply side that provides consumers all the information they need to make wise choices and is quick to respond to changing consumer demands
  new kinds of intermediaries to help align the supply and demand sides and help consumers navigate the complex system Much of what is needed on the demand side is in place today or likely to emerge in the near term. Consumer-directed health plan (CDHP) enrollees offer an early glimpse of subtle changes in a retail market. CDHP enrollees are more likely to be aware of price and quality differences in products and services and more likely to have seen information and shop around; they are more likely to ask for prices up front, more likely to negotiate prices, and more willing to trade convenience for lower prices. They are also more likely to plan ahead when making health care decisions and to invest dollars now to prevent problems later.

The overall design of the ImmunoScore technology is one in which preventative medicine takes the forefront in treatment options. Vaccine status is the most obvious application, and patients lacking protective antibody levels can be vaccinated. Other levels of immune preparedness would also be similarly assessed and preventative measures could be undertaken prior to clinical manifestations of autoimmune disease, cancer, or immunosenescence. Similarly, evaluations of physicians and health plans could be readily facilitated using the ImmunoScore database. ImmunoScore can be used to discover and define fundamental relationships, such as, for example, (i) optimal Th1/Th2 balances, or (ii) lack of any members for immunosenescense or autoimmune disease, that can serve as indicators of overall immune system harmony. Such relationships can, for example, be quantified as one or more "ImmunoScores." Patients with healthy ImmunoScores would point to their primary care physicians and their insurers as providers of admirable health care practices. Prevention being much more cost-effective than treatment would provide the best of all worlds to the patients, physicians and insurers. Physicians whose patients had consistently lower ImmunoScores would raise a cautionary flag and those doctors and practices could be scrutinized for provision of first rate health care (or something less). If the records were transparent, patients as consumers would use their dollars to pay for the best possible health care rather than pay for poor care at high cost. For example, in 2005, Aetna began testing tools that allow consumers to compare physicians on actual cost, so that they can gauge their out-of-pocket expenses. WellPoint has embarked on a pilot program at the suggestion of General Motors to provide complete comparative cost data for hospitals on "episodes of care." A number of employers are also finding success with wellness programs. Typical wellness programs feature free or low-cost health screenings and other sorts of preventive care.

It has been approved proposed that additional investments in health information technology and greater connectivity among providers will be needed to ease sharing of patient information and enable consumers to better manage their own health. ImmunoScore database management can, for example, serve as an excellent tool to address connectivity issues that patients, physicians, and insurers would have. Thus, ImmunoScore technology proposes to be a new intermediary in health care connectivity. Patients would have more control over their own health care decisions—spending as well as courses of treatment.

Public health and data collection. In public health, the current underlying assumption is that good data will lead to better decisions, which will result in enhanced population health. In practice, no necessary linear sequence exists from good data to better health (AbouZahr, et al. 2007). Various types of data are obtained at different levels of the health system, to be used by several actors for many reasons. Providers generate and use information in the context of patients' care; managers need data to enhance efficiency and effectiveness; planners rely on statistics for operational decisions; and policymakers use information for prioritization and resource allocation (AbouZahr, et al. 2007). There are different data sources currently used to formulate public policy—each with advantages and disadvantages:

Routinely reported service data. Routine and administrative reports are generated as a by-product of patient-provider interactions and health facility functioning. Health facilities are a primary source of data for notifiable diseases and are at the heart of a country's surveillance and response programs, although facility case reporting needs to be complemented by active case seeking strategies to generate a complete picture of epidemic risk. No matter how many data elements are routinely reported, information is inevitably biased by patterns of service use and non-use, and the extent or direction of bias is impossible to ascertain without recourse to other sources of data. Services delivered (number of immunizations, antenatal visits, outpatients seen, etc) do not necessarily equate to population need.

Population based data. Mistrust of service-based statistics has fuelled interest in household surveys that can generate unbiased data for populations as a whole rather than just the sections that use available health services. These household surveys have several disadvantages. They need large investments in human and financial resources and therefore are usually funded externally, resulting in bias towards the interests of donors or well-sponsored programs. They are also time-consuming and are undertaken only occasionally, and generate results spanning a period, rather than the immediate past. Samples are rarely of sufficient size to deliver nationally valid results. Growth in surveys to generate health related data has been fuelled by their ability to deliver statistics on child mortality, population coverage, and certain risk factors. In the past few years, scope for measurement of health status with household surveys has greatly expanded owing to cheap and reliable diagnostic tests that can be used in the research setting to generate population-based estimates of disease prevalence. But surveys are not as effective for measurement of adult mortality, which is a relatively rare event compared with child mortality.

ImmunoScore would relieve much of the concern regarding public health and data collection. As stated above, there has been concern regarding bias in the routinely reported service data. As ImmunoScore grows in size and popular usage, concerns about bias can be alleviated. Services delivered to any individual patient would be based solely upon the needs of that particular patient, and tailored to that individual patient's immunologic needs, with no regard for social stratum. Political justifications for mis-representation of data would be eliminated by the automatic and mechanical nature of the data acquisition.

The tremendous requirement for human and financial resources for collecting population based data would also be alleviated by ImmunoScore technology. Data can be collected at hundreds of remote locations and transferred back to an exemplary ImmunoScore central database. There would be no need for third party human resources—data collection would occur at the hospital, clinic, or physician's office and stored for future use.

ImmunoScore Tracking of Medical Services (ImmunoScoreKeeping)

As has been described, heath care processes are very complex, involving both clinical and administrative tasks, large volumes of data, and a large number of patients and personnel. Health care processes are also very dynamic. As new processes are initiated, changes in health care treatments, drugs, and protocols can invalidate current methodologies, requiring reparative actions. ImmunoScoreKeeping can, for example, capture all of such complicated dynamic components and provide accurate performance measurements ("ImmunoScoreCards") not only for individual patients, but also as a means of tracking relative efficiencies of other complex components of the health care system.

For example, upon a visit to a provider using an ImmunoScore system, the patient's data can be captured by an "ImmunoScoreKeeper." (an exemplary POC assay reader connected to a system database, as described above). Not only demographic and test data, but also treatments/drugs prescribed, physician's ID number, and insurer can be stored. Any additional testing or measurements (blood chemistry, X-rays, physical therapy, etc.) can be entered into the remote ImmunoScore data collection system at, for example, the physician's office. A critical requirement for efficient management of health care is the management of the quality of service. Appropriate control of quality of service leads to the creation of quality care services; these, in turn, can fulfill patient satisfaction.

Traditionally, health care services have been managed using limited forms of workflow. Some examples of these are clinical and administrative protocols. However, these protocols have remained limited in their usefulness in part because developers have rarely incorporated both clinical and administrative activities into one comprehensive care protocol. This lack of integration hinders the delivery of care, as the effectiveness of protocols is often dependent on many administrative tasks being properly executed at the correct time.

Thus, in exemplary embodiments of the present invention, ImmunoScoreKeeping can enable medical practices to provide better quality care at reduced costs. ImmunoScore can, for example, maintain keep ImmunoScoreCards on:

individual patients
physicians
groups of physicians/managed care organizations
insurers In addition, as vaccines, drugs, and therapies prescribed can all be monitored and tracked, an ImmunoScoreKeeper can also monitor the efficacy of the vaccines, drugs, and treatments prescribed. As these data are compiled, they can be shared and submitted to appropriate oversight organizations (FDA, CDC, ACIP, Physician's organizations, drug and vaccine manufacturers, etc.) to better enable these groups to make clear decisions and/or recommendations. Such organizations would be consumers of ImmunoScore data.

Thus, an ImmunoScoreKeeper can allow insurers to rate physicians and enable their customers (the patients) to make better informed decisions regarding their choice of physician. An ImmunoScoreKeeper can track effectiveness of treatments to patient outcomes. Prescription drug and vaccine efficacies can be monitored not only in population-based samplings, but longitudinally in individual patients with repeated ImmunoScore diagnostic testing protocols. Physicians can thus monitor the efficiency of the practice that they are associated with, and thereby make the best career choices to advance their careers in the most efficient practices. Hospitals could be measured for effectiveness in patient care against other hospitals and groups of physicians. Types of hospital settings could be evaluated prospectively. Causes of nosocomial infections might be tracked, for example, to certain types of hospital environments. Insurers can be measured against common metrics and be forced to compete for business via accurate ImmunoScoreKeeping.

In exemplary embodiments of the present invention, an ImmunoScoreKeeper can, for example, provide a means of integrated monitoring of individual patient treatment and also administration of both physicians and insurers practices. The ImmunoScoreKeeper can, for example, generate a numerical value for each component of the health care system upon which real competition among providers and insurers could be generated. This competition would thereby provide substantial increases in health care quality and decreases in health care costs.

Y. User Access Via Data Networks and On-Line Advertising

In exemplary embodiments of the present invention, users can, for example, access an ImmunoScore Database via computer data networks. Such networks can include, for example, VPN's or the Internet. In exemplary embodiments of the present invention, an ImmunoScore database can be accessed, updated and queried via one or more web page portals. With a substantial ImmunoScore subscriber base of clinicians, health care management professionals, individuals, health insurance managers and executives, and pharmaceutical company researchers and management personnel, a given ImmunoScore embodiment can serve as an indispensable portal for anyone involved in the health care, health insurance, life sciences and related industries. This creates an opportunity for targeted on-line advertising.

Online advertising is growing quickly. Recent research predicts that global spending on Internet ads will overtake radio in 2008. It has also been predicted that the rate of spending on Internet ads will grow six times faster than that for traditional media between 2006 and 2009, a trend already taking shape in the Middle East and Europe. Even companies that do not engage in e-commerce, such as, for example, Unilever, nonetheless want to create better user experiences for people online. They want to improve their brand presence.

Many other companies have started to use Web 2.0 technologies, such as, for example, blogging and video clips, to increase brand awareness. Last year (2006) in China, Pepsi invited people to write screenplays for company spokesmen and a famous pop singer. And when it launched its Qashqai car in the UK last month, Nissan offered a game website where people could try to shoot the car; it broadcast video clips of the car, which could be linked to blogs and social networking sites; and it ran banners over some Yahoo sites.

This summer, two companies, Joost and BabelGum, will start to broadcast entire TV programs free over the Internet. The content owners in effect have their own channels and advertising will pay the way. In effect, "people will watch Friends on a website. We may thus see the death of the TV station and the birth of the network station.

Given this state of affairs, in exemplary embodiments of the present invention an exemplary system according to the present invention can be used as an Internet portal for everyone associated with health care in the broadest system (thus encompassing any consumers or providers of any of the business models described above). In the same sense that individuals utilize online search engines, such as, for example, Google or answer.com, to research a topic, anyone remotely connected to health care, can, for example, access an exemplary ImmunoScore webportal. Whether the individual is simply an individual who has records in an ImmunoScore database, whether the individual is an executive of a health insurance company or an HMO, whether the individual in question is a physician or hospital administrator, or whether the individual is a researcher or someone who works in sales or the technical side of pharmaceutical developments, an exemplary ImmunoScore system and an associated ImmunoScore web interface can become a ubiquitous tool used each and every day by millions of people. Targeted online advertising can then be used to deliver business to business, or business to individual in the case of individual to consumers, advertising to a market which is already attuned to the benefits of technology which is applied to healthcare and understands the value of preventive medicine, individualized medicine, and a granular approach to health care provision and analysis and follow-up as to efficiency and efficacy of health care.

For example, individuals whose ImmunoScore record, after the appropriate analysis, has disclosed a potential likelihood of having an autoimmune disease can be provided literature, products, news of new drugs, experimental clinical trials, etc., for their review and potential participation and/or purchase. Similarly, health insurance companies offering a healthcare credit exchange program, as described above, can also advertise such programs and enhancements to such programs to a target audience of sophisticated health care consumers. An interested third party operator of an exemplary system according to the present invention could even, for example, offer to create and operate a health care exchange program to all health care insurance companies using ImmunoScore! All of these examples list just a few of the possibilities. Thus, the more data that a exemplary ImmunoScore database obtains and learns how to best process to extract all of the information latent therein, the greater impact Immunoscore technology can have and the greater draw an ImmunoScore based web portal can provide.

The present invention has been described in connection with exemplary embodiments and implementations, as examples only. It will be understood by those having ordinary skill in the pertinent art that modifications to any of the embodiments may be easily made without materially departing from the scope and spirit of the present invention which is defined by the appended claims. Such modifications can include, for example, using other appropriate assays or tests, other rules or analyses of the results thereof, as may be known in the art to assess the immune status of individuals or populations. Additionally, such modifications can include, for example, using various assay devices and techniques as may be known, using various available methods of storing and analyzing data (including various "data mining" techniques) as may be available, and defining various alternative demographic groups and various sets of ImmunoScore test panels to be administered thereto.

APPENDIX A

Exemplary CIP Database

1. List of CIP Database Variables/Fields and Additional Notes
2. First 99 Records From Exemplary CIP Database
1. List of CIP Database Variables/Fields

| | |
|---|---|
| v2_h | Date recruited |
| v4 | Sex (0 = male, 1 = female) |
| v5 | Date of birth |
| v6 | Age (in years) |
| v14a | Questionnaire taken through an interpreter (0 = No; 1 = Yes) |
| v14b | If Interpreter Language of Interview |
| v15a | Country of Origin (1 = India 2 = Bangledesh 3 = Sri Lanka 4 = Pakistan 5 = Morocco 6 = Vietnam 7 = Congo 8 = Other) |
| v15aO | Country of Origin (Each country is listed) |
| v15b | Region of Origin 1 = SSAfrica, 2 = SAsia, 3 = NAfrica, 4 = Latin Amer/Caribbean 5 = E.Europe, 6 = SEAsia |
| v17a | Date moved to Canada |
| months_ca | Number of Months in Canada |
| v18 | Citizenship Status 0 = Refugee Claimant, 1 = Refugee, 3 = Immigrant 4 = Other |
| v20_h | Have you ever lived in refugee camp? (0 = No; 1 = Yes) |
| v21 | Do you have any medical problems (0 = No; 1 = Yes; 2 = Unknown) |
| v22 | Have you ever been hospitalized? (0 = No; 1 = Yes; 2 = Unknown) |
| v23 | Do you take any medications? (0 = No; 1 = Yes; 2 = Unknown) |
| v24a | Are you Pregnant? (0 = No; 1 = Yes) |
| v24b_h | If Pregnant, number of months pregnant |
| v251a | History of Measles (0 = No; 1 = Yes; 2 = Unknown) |
| v251b_h | Age of Measles |
| v252a | History of Mumps (0 = No; 1 = Yes; 2 = Unknown) |
| v252b | Age of Mumps |
| v253a | History of Rubella (0 = No; 1 = Yes; 2 = Unknown) |
| v253b_h | Age of Rubella |
| v254a | History of Chickenpox (0 = No; 1 = Yes; 2 = Unknown) |
| v254b | Age of Chickenpox |

-continued

| | |
|---|---|
| v255a | History of Tetanus (0 = No; 1 = Yes; 2 = Unknown) |
| v255b_h | Age of Tetanus |
| v256a | History of Diphtheria (0 = No; 1 = Yes; 2 = Unknown) |
| v256b_h | Age of Diphtheria |
| v257a | History of Hepatitis (0 = No; 1 = Yes; 2 = Unknown) |
| OpDenTetanus | Optical Density for Tetanus |
| IUTetanus | International Units for Tetanus |
| OpDenDiph | Optical Density for Diphtheria |
| IUDiph | International Units for Diphtheria |
| CMVIg | CMV Optical Density |
| CMVIgINT | Interpretation of test (positive or negative) |
| HBcAb | Hepatitis B core Antibody Optical Density |
| HBcAbINT | Interpretation of HBcAb (positive or negative) |
| HBSAb | Hepatitis B Surface Antibody Optical Density |
| HBSAg | Hepatitis B Surface Antigen Optical Density |
| HBSAgINT | Interpretation of HBSAg (reactive or non-reactive) |
| HepBeAb | Hepatitis B e Antibody Ratio |
| HBeAbINT | Interpretation of HBeAb (reactive or non-reactive) |
| HepBeAg | Hepatitis B e Antigen Ratio |
| HBeAgINT | Interpretation of HBeAb (reactive or non-reactive) |
| HCV | Hepatitis C antibodies (EIA) Optical Density |
| HCVINT | Interpretation of HCV EIA result (positive, grayzone, negative) |
| HCVPCR | Hepatitis C PCR (positive or negative) |
| HCVLIA | Hepatitis C Line ImmunoAssay results (positive or negative) |

Notes Re: Interpretation of Tetanus, Diptheria, Hepatitis B, Hepatitis C and CMV Assay Results Hepatitis B assays. Anti-HBc (HBcAb) determinations to measure hepatitis B virus core antigen, can be used to monitor the progress of hepatitis B viral infection. Anti-HBc is found in serum shortly after the appearance of Hepatitis B surface antigen (HBsAg) in acute hepatitis B infections. It will persist after the disappearance of HBsAg and before the appearance of detectable antibody to HBsAg (anti-HBs). In the absence of information about any other hepatitis B virus (HBV) markers, it must be considered that any individual with detectable levels of anti-HBc may be actively infected with HBV, or that infection may have resolved, leaving the person immune. Anti-HBc may be the only serological marker of hepatitis B viral infection and potentially infectious blood. In the particular assay run for this diagnostic application, the presence or absence of anti-HBc in the sample is determined by comparing the rate of formation of fluorescent product to a cutoff rate determined from a previous index calibration. If the rate of formulation of fluorescent product in the test sample is less than or equal to the cutoff rate, the sample is considered "reactive" for anti-HBc (HBcAb). Samples not considered "reactive" are "negative" for HBcAb.

Assays for hepatitis B surface antigen (HBsAg) are used to screen blood and blood products for the presence of HBsAg to prevent transmission of HBV to recipients of these products. HBsAg assays are also routinely used to diagnose suspected HBV infection and to monitor the status of infected individuals; i.e., whether the patient's infection has resolved or the patient has become a chronic carrier of the virus. In addition, these assays are used to evaluate the efficacy of anti-viral drugs by monitoring the levels of HBsAg in patient sera or plasma. HBsAg assay interpretation (INT) is considered either "reactive" or "negative" for the presence of this antigen.

HBsAb assays are used to measure the amount of antibody to the hepatitis B surface antigen present in human serum or plasma. These particular assays are often used to monitor the success of hepatitis B vaccination. The presence of HBsAb has been shown to be important in the protection against HBV infection. Assays for HBsAb are also used to monitor the convalescence and recovery of hepatitis B infected individuals. The presence of anti-HBs after acute HBV infection and loss of HBsAg can be a useful indicator of disease resolution. Detection of HBsAb in an asymptomatic individual may indicate previous exposure to HBV. Samples with less than 10 m Internation Units (mIU)/mL are considered "non-reactive," while samples whose concentrations are ≧10 mIU/mL are considered "reactive."

HBe assays are used for quantitative measurement of hepatitis B e antigen in human serum or plasma. HBeAg is found in the early phase of HBV infection after the appearance of HBsAg. The presence of HBeAg correlates with increased numbers of infectious virus, the occurrence of core particles in the nucleus of the hepatocyte, and the presence of viral specific DNA polymerase in serum. During the HBeAg positive stage, hepatitis B patients are at increased risk of transmitting the virus to their contacts. Persistence of HBeAg in the hepatitis B carrier is often associated with chronic active hepatitis. Samples with a Sample Rate/Cutoff Rate (S/CO) values less than 1.0 are considered "non-reactive," samples with S/CO values≧1.0 are considered "reactive."

Hepatitis B e Ag (HBe) and its antibody (anti-HBe) are found only in association with HBV infection. HBeAg becomes undetectable after the peak of viral replication and onset of resolution of disease. A negative HBeAg result alone may indicate (1) early HBe antigenemia before the peak of viral replication or (2) early convalescence when HBeAg has declined below detectable levels. The presence of anti-HBe (HBeAb) serves to distinguish between these two periods. The appearance of anti-HBe indicates a reduced level of infectious virus due to a decrease in viral replication. Although resolution of the disease generally follows, a HBsAg carrier state may persist. Patient samples are considered "reactive" or "non-reactive" based on S/CO ratios as explained above for the HBe assay. There are limitations with this protocol as it currently exists. A non-reactive test does not exclude the possibility of exposure to HBV. Serum lipids are also known to interfere with this test as currently formatted.

Hepatitis C assay. The hepatitis C test is a qualitative assay for detection of antibody to the hepatitis C virus (HCV). The antibody test run for this panel has been designed to detect antibodies to putative structural and non-structural proteins of the HCV genome. The presence of anti-HCV indicates that an individual may have been infected with HCV, may harbor infectious HCV and/or may be capable of transmitting HCV infection. Specimens with S/CO values under 1.0 are considered "non-reactive," while those with S/CO values≧1.0 are "reactive."

Cytomegalovirus assay. Infections with cytomegalovirus (CMV) are common and are usually mild and asymptomatic. The assay used was a semi-quantitative method for the measurement of IgG antibodies to CMV in serum and plasma. The presence of at least 15 Antibody Units (AU)/mL is indicative ("positive") of past or current infection with CMV. Antibody levels less than 15 AU/mL are considered "negative."

Tetanus Toxoid assay. This assay is for the measurement of specific IgG antibodies specific for tetanus toxoid. These assays are typically used to measure a patient's response to immunization. The level of "protective" antibody has been cited in the literature as between 0.01 and 0.15 IU/mL. Due to the ranges quoted, it is recommended that each laboratory determine its own protective range.

Diphtheria Toxoid assay. This assay is for the measurement of specific IgG antibodies specific for diphtheria toxoid. These assays are typically used to measure a patient's response to immunization. The level of "protective" antibody has been cited in the literature as between 0.01 and 0.10 IU/mL. Due to the ranges quoted, it is recommended that each laboratory determine its own protective range.

2. First 99 Records From Exemplary CIP Database

| ID | v2_h | v4 | v5 | v6 | v14a | v14b | v15a | v15aO |
|---|---|---|---|---|---|---|---|---|
| 1 | 15630 | 1 | Feb. 2, 1957 | 44 | 1 | Punjabi | 4 | Pakistan |
| 2 | 15630 | 1 | May 7, 1970 | 31 | 0 | | 8 | Nigeria |
| 3 | 15995 | 0 | Feb. 18, 1938 | 64 | 0 | | 7 | Congo |
| 4 | 15631 | 0 | May 24, 1977 | 25 | 0 | | 8 | Uganda |
| 5 | 15631 | 0 | Mar. 15, 1962 | 41 | 0 | | 2 | Banglade |
| 6 | 15634 | 0 | Aug. 28, 1966 | 36 | 0 | | 1 | India |
| 7 | 15634 | 0 | Oct. 18, 1954 | 48 | 0 | | 1 | India |
| 8 | 15635 | 1 | Mar. 8, 1974 | 28 | 0 | | 8 | Tunisia |
| 9 | 15635 | 0 | Jul. 30, 1962 | 40 | 0 | | 7 | Congo |
| 10 | 15635 | 1 | May 29, 1972 | 30 | 0 | | 8 | Peru |
| 11 | 15638 | 1 | Sep. 9, 1970 | 32 | 0 | | 8 | Mexico |
| 12 | 15638 | 0 | Dec. 10, 1975 | 26 | 0 | | 3 | Sri Lank |
| 13 | 15638 | 1 | Nov. 30, 1975 | 26 | 1 | Urdu | 3 | Sri Lank |
| 14 | 15638 | 1 | Dec. 30, 1965 | 37 | 0 | | 8 | Ghana |
| 15 | 15641 | 0 | Jan. 1, 1942 | 60 | 0 | | 4 | Pakistan |
| 16 | 15641 | 1 | Jul. 20, 1951 | 51 | 1 | Punjabi | 4 | Pakistan |
| 17 | 15641 | 0 | Apr. 23, 1984 | 18 | 0 | | 8 | Mexico |
| 18 | 15641 | 1 | Jun. 9, 1958 | 44 | 0 | | 8 | Mexico |
| 19 | 15641 | 1 | May 31, 1962 | 40 | 0 | | 8 | Mexico |
| 20 | 15641 | 0 | Jul. 3, 1968 | 34 | 0 | | 8 | Nigeria |
| 21 | 15642 | 1 | Jun. 24, 1972 | 30 | 0 | | 2 | Banglade |
| 22 | 15643 | 0 | Jan. 1, 1975 | 27 | 0 | | 8 | Mauritan |
| 23 | 15644 | 1 | Feb. 9, 1972 | 31 | 1 | Russian | 8 | Russia |
| 24 | 15644 | 0 | Jun. 25, 1979 | 23 | 0 | | 8 | Cameroon |
| 25 | 15644 | 0 | May 16, 1976 | 26 | 0 | | 1 | India |
| 26 | 15645 | 0 | Mar. 5, 1950 | 52 | 0 | | 3 | Sri Lank |
| 27 | 15645 | 0 | Apr. 6, 1944 | 58 | 1 | Persian | 8 | Iran |
| 28 | 15648 | 1 | Jun. 12, 1964 | 38 | 0 | | 8 | Zimbabwe |
| 29 | 15648 | 0 | Dec. 12, 1959 | 42 | 1 | Punjabi | 1 | India |
| 30 | 15648 | 0 | Jan. 20, 1974 | 28 | 1 | Punjabi | 1 | India |
| 31 | 15648 | 1 | May 14, 1971 | 31 | 0 | | 8 | Mexico |

-continued

| | | | | | | | | | |
|---|---|---|---|---|---|---|---|---|---|
| 32 | 15649 | 0 | Jun. 18, 1950 | 52 | 1 | Punjabi | 1 | India | |
| 33 | 15649 | 1 | Apr. 21, 1972 | 30 | 0 | | 7 | Congo | |

| ID | v15b | v17a | months_ca | v18 | v20_h | v21 | v22 | v23 | v24a |
|---|---|---|---|---|---|---|---|---|---|
| 1 | 2 | May 8, 2002 | 5.3 | 0 | 0 | 1 | 1 | 0 | 0 |
| 2 | 1 | Apr. 18, 2001 | 18 | 0 | 0 | 1 | 0 | 1 | 1 |
| 3 | 1 | Jun. 18, 2002 | 16 | 0 | 0 | 0 | 0 | 0 | 0 |
| 4 | 1 | Aug. 29, 2002 | 1.6 | 0 | 0 | 0 | 0 | 0 | 0 |
| 5 | 2 | Nov. 23, 2001 | 10.8 | 1 | 0 | 0 | 0 | 0 | 0 |
| 6 | 2 | Aug. 5, 2002 | 2.5 | 0 | 0 | 0 | 0 | 0 | 0 |
| 7 | 2 | Aug. 6, 2002 | 2.5 | 0 | 0 | 0 | 0 | 0 | 0 |
| 8 | 3 | Dec. 31, 2000 | 21.7 | 4 | 0 | 0 | 1 | 0 | 1 |
| 9 | 1 | Aug. 21, 2002 | 2 | 0 | 0 | 0 | 0 | 0 | 0 |
| 10 | 4 | Jun. 7, 2001 | 16.5 | 1 | 0 | 1 | 0 | 1 | 0 |
| 11 | 4 | Jul. 11, 2002 | 3.5 | 0 | 0 | 0 | 0 | 1 | 0 |
| 12 | 2 | Oct. 18, 2002 | 0.2 | 0 | 0 | 0 | 1 | 0 | 0 |
| 13 | 2 | Oct. 18, 2002 | 0.2 | 0 | 0 | 0 | 0 | 0 | 0 |
| 14 | 1 | Jul. 13, 2002 | 3.4 | 0 | 0 | 0 | 0 | 0 | 0 |
| 15 | 2 | Jun. 28, 2001 | 16 | 0 | 0 | 1 | 0 | 1 | 0 |
| 16 | 2 | Apr. 9, 2002 | 6.6 | 0 | 0 | 1 | 1 | 1 | 0 |
| 17 | 4 | Sep. 4, 2002 | 1.8 | 0 | 0 | 0 | 0 | 0 | 0 |
| 18 | 4 | Sep. 4, 2002 | 1.8 | 0 | 0 | 0 | 1 | 0 | 0 |
| 19 | 4 | Sep. 4, 2002 | 1.8 | 0 | 0 | 0 | 0 | 0 | 0 |
| 20 | 1 | Aug. 14, 2002 | 2.5 | 0 | 0 | 0 | 0 | 0 | 0 |
| 21 | 2 | Jun. 30, 2002 | 4 | 0 | 0 | 1 | 1 | 0 | |
| 22 | 1 | Jul. 8, 2002 | 3.7 | 0 | 0 | 0 | 0 | 0 | 0 |
| 23 | 5 | Jun. 24, 2002 | 4.2 | 3 | 0 | 1 | 1 | | 1 |
| 24 | 1 | Jul. 10, 2001 | 15.7 | 0 | 0 | 0 | 1 | 0 | 0 |
| 25 | 2 | Aug. 6, 2002 | 2.8 | 0 | 0 | 0 | 0 | 0 | 0 |
| 26 | 2 | | | 0 | 0 | 1 | 0 | 1 | 0 |
| 27 | 3 | Aug. 24, 2002 | 2.3 | 0 | 0 | 0 | 0 | 1 | 0 |
| 28 | 1 | Aug. 1, 2001 | 15.1 | 0 | 0 | 0 | 0 | 1 | 0 |
| 29 | 2 | Jun. 30, 2002 | 4.2 | 0 | 0 | 0 | 0 | 0 | 0 |
| 30 | 2 | Sep. 21, 2001 | 13.4 | 0 | 0 | 0 | 1 | 1 | 0 |
| 31 | 4 | Jul. 10, 2002 | 3.8 | 0 | 0 | 0 | 0 | 0 | 0 |
| 32 | 2 | Nov. 22, 2001 | 11.4 | 0 | 0 | 1 | 1 | 1 | 0 |
| 33 | 1 | Apr. 18, 2002 | 6.6 | 0 | 0 | 0 | 0 | 0 | 0 |

| ID | v24b_h | v251a | v251b_h | v252a | v252b | v253a | v253b_h | v254a | v254b |
|---|---|---|---|---|---|---|---|---|---|
| 1 | 91 | 2 | 91 | 2 | | 2 | 91 | 0 | |
| 2 | 99 | 2 | 91 | 1 | 6 | 2 | 91 | 1 | 6 |
| 3 | 91 | 1 | 10 | 1 | 35 | 0 | 91 | 1 | 35 |
| 4 | 91 | 0 | 91 | 0 | | 2 | 91 | 1 | 24 |
| 5 | 91 | 2 | 91 | 0 | | 2 | 91 | 1 | 11 |
| 6 | 91 | 0 | 91 | 0 | | 2 | 91 | 0 | |
| 7 | 91 | 2 | 91 | 0 | | 2 | 91 | 0 | |
| 8 | 99 | 1 | 4.5 | 0 | | 2 | 91 | 1 | 19 |
| 9 | 91 | 2 | 91 | 0 | | 2 | 91 | 0 | |
| 10 | 91 | 0 | 91 | 0 | | 1 | 0.7 | 1 | 18 |
| 11 | 91 | 0 | 91 | 1 | 10 | 1 | 16 | 1 | 19 |
| 12 | 91 | 2 | 91 | 2 | | 2 | 91 | 1 | 22 |
| 13 | 91 | 0 | 91 | 1 | 12 | 0 | 91 | 1 | 19 |
| 14 | 91 | 2 | 91 | 2 | | 2 | 91 | 1 | 25 |
| 15 | 91 | 2 | 91 | 2 | | 2 | 91 | 2 | |
| 16 | 91 | 2 | 91 | 2 | | 2 | 91 | 2 | |
| 17 | 91 | 2 | 91 | 1 | 6 | 1 | 6 | 1 | 6 |
| 18 | 91 | 2 | 91 | 2 | | 2 | 91 | 2 | |
| 19 | 91 | 2 | 91 | 1 | 8 | 2 | 91 | 2 | |
| 20 | 91 | 2 | 91 | 0 | | 2 | 91 | 1 | 30 |
| 21 | 91 | 2 | 91 | 1 | 6 | 2 | 91 | 1 | 7 |
| 22 | 91 | 2 | 91 | 2 | | 2 | 91 | 2 | |
| 23 | 3 | 0 | 91 | 2 | | 2 | 91 | 2 | |
| 24 | 91 | 0 | 91 | 0 | | 2 | 91 | 0 | |
| 25 | 91 | 2 | 91 | 0 | | 2 | 91 | 1 | 17 |
| 26 | 91 | 2 | 91 | 1 | 10 | 2 | 91 | 2 | |
| 27 | 91 | 2 | 91 | 1 | 10 | 2 | 91 | 2 | |
| 28 | 91 | 1 | 6 | 1 | 7 | 2 | 91 | 1 | 35 |
| 29 | 91 | 2 | 91 | 2 | | 2 | 91 | 2 | |
| 30 | 91 | 2 | 91 | 2 | | 2 | 91 | 2 | |
| 31 | 91 | 0 | 91 | 0 | | 2 | 91 | 0 | |
| 32 | 91 | 2 | 91 | 2 | | 2 | 91 | 2 | |
| 33 | 91 | 0 | 91 | 0 | | 2 | 91 | 0 | |

| ID | v255a | v255b_h | v256a | v256b_h | v257a | v257b | v258a | v258b_h | v259a |
|---|---|---|---|---|---|---|---|---|---|
| 1 | 0 | 91 | 0 | 91 | 0 | | 0 | 91 | 0 |
| 2 | 0 | 99 | 0 | 91 | | | 2 | 91 | 0 |
| 3 | 0 | 91 | 0 | 91 | 0 | | 0 | 91 | 0 |

-continued

| | | | | | | | | | |
|---|---|---|---|---|---|---|---|---|---|
| 4 | 0 | 91 | 2 | 91 | 0 | | 0 | 91 | 0 |
| 5 | 0 | 91 | 2 | 91 | 0 | | 2 | 91 | 0 |
| 6 | 0 | 91 | 2 | 91 | 0 | | 2 | 91 | 0 |
| 7 | 0 | 91 | 2 | 91 | | | 2 | 91 | 0 |
| 8 | 0 | 91 | 2 | 91 | 0 | | 2 | 91 | 0 |
| 9 | 0 | 91 | 0 | 91 | | | 2 | 91 | 0 |
| 10 | 0 | 91 | 0 | 91 | 0 | | 2 | 91 | 0 |
| 11 | 0 | 91 | 0 | 91 | 0 | | 2 | 91 | 0 |
| 12 | 0 | 91 | 2 | 91 | 0 | | 2 | 91 | 0 |
| 13 | 0 | 91 | 0 | 91 | 1 | 24 | 2 | 91 | 0 |
| 14 | 2 | 91 | 2 | 91 | 0 | | 2 | 91 | 0 |
| 15 | 2 | 91 | 2 | 91 | 0 | | 2 | 91 | 0 |
| 16 | 2 | 91 | 2 | 91 | 0 | | 2 | 91 | 0 |
| 17 | 0 | 91 | 0 | 91 | 0 | | 2 | 91 | 0 |
| 18 | 2 | 91 | 2 | 91 | 0 | | 2 | 91 | 0 |
| 19 | 2 | 91 | 2 | 91 | 0 | | 2 | 91 | 0 |
| 20 | 0 | 91 | 0 | 91 | | | 2 | 91 | 0 |
| 21 | 2 | 91 | 2 | 91 | | | 2 | 91 | 0 |
| 22 | 2 | 91 | 2 | 91 | | | 2 | 91 | 0 |
| 23 | 0 | 91 | 0 | 91 | 0 | | 2 | 91 | 0 |
| 24 | 0 | 91 | 2 | 91 | 2 | | 2 | 91 | 0 |
| 25 | 2 | 91 | 2 | 91 | | | 2 | 91 | 0 |
| 26 | 2 | 91 | 2 | 91 | | | 2 | 91 | 0 |
| 27 | 2 | 91 | 2 | 91 | 0 | | 2 | 91 | 0 |
| 28 | 2 | 91 | 2 | 91 | | | 2 | 91 | 0 |
| 29 | 2 | 91 | 2 | 91 | 2 | | 2 | 91 | 0 |
| 30 | 2 | 91 | 2 | 91 | 0 | | 2 | 91 | 0 |
| 31 | 0 | 91 | 2 | 91 | 0 | | 2 | 91 | 0 |
| 32 | 2 | 91 | 2 | 91 | | | 2 | 91 | 0 |
| 33 | 0 | 91 | 2 | 91 | | | 2 | 91 | 0 |

| ID | v259b_h | v26 | v33a | v33b | v33c | v34a | v34a1 | v34c | v34c1 |
|---|---|---|---|---|---|---|---|---|---|
| 1 | 91 | 0 | 4 | 12 | 2 | 1 | 1 | 1 | 1 |
| 2 | 91 | 0 | 4 | 14 | 2 | 0 | | 0 | |
| 3 | 91 | 0 | 5 | 16 | 2 | 1 | 1 | 0 | |
| 4 | 91 | 0 | 4 | 14 | 2 | 0 | | 0 | |
| 5 | 91 | 0 | 4 | 12 | 1 | 1 | 1 | 0 | |
| 6 | 91 | 0 | 3 | 9 | 2 | 0 | | 1 | 3 |
| 7 | 91 | 0 | 3 | 10 | 2 | 1 | 1 | 1 | 3 |
| 8 | 91 | 0 | 5 | 16 | 2 | 1 | 1 | 0 | |
| 9 | 91 | 0 | 5 | 17 | 2 | 1 | 1 | 1 | 1 |
| 10 | 91 | 0 | 5 | 18 | 1 | 1 | 1 | 0 | |
| 11 | 91 | 0 | 5 | 16 | 2 | 1 | 1 | 0 | |
| 12 | 91 | 0 | 4 | 12.5 | 2 | 1 | 1 | 1 | 1 |
| 13 | 91 | 0 | 5 | 17 | 2 | 1 | 1 | 1 | 1 |
| 14 | 91 | 0 | 3 | 12 | 2 | 1 | 1 | 0 | |
| 15 | 91 | 0 | 4 | 15 | 2 | 1 | 1 | 0 | |
| 16 | 91 | 0 | 2 | 5 | 1 | 1 | 1 | 0 | |
| 17 | 91 | 0 | 3 | 14 | 1 | 1 | 1 | 0 | |
| 18 | 91 | 0 | 5 | 16 | 1 | 1 | 1 | 0 | |
| 19 | 91 | 0 | 5 | 20 | 2 | 1 | 1 | 0 | |
| 20 | 91 | 0 | 5 | 17 | 2 | 1 | 1 | 0 | |
| 21 | 91 | 0 | 3 | 10 | 1 | 1 | 1 | 0 | |
| 22 | 91 | 0 | 5 | 14 | 2 | 0 | | 1 | 1 |
| 23 | 91 | 0 | 5 | 15 | 2 | 1 | 1 | 0 | |
| 24 | 91 | 0 | 4 | 8 | 2 | 1 | 1 | 0 | |
| 25 | 91 | 0 | 3 | 12 | 2 | 1 | 1 | 1 | 3 |
| 26 | 91 | 0 | 4 | 17 | 2 | 1 | 1 | 0 | |
| 27 | 91 | 0 | 5 | 18 | 2 | 1 | 1 | 1 | 1 |
| 28 | 91 | 0 | 4 | 16 | 2 | 1 | 1 | 1 | 1 |
| 29 | 91 | 0 | 2 | 5 | 2 | 1 | 1 | 1 | 3 |
| 30 | 91 | 0 | 3 | 10 | 2 | 1 | 1 | 1 | 3 |
| 31 | 91 | 0 | 5 | 17 | 2 | 1 | 1 | 0 | |
| 32 | 91 | 0 | 1 | 0 | | 1 | 1 | 1 | 3 |
| 33 | 91 | 0 | 5 | 17 | 1 | 1 | 1 | 0 | |

| ID | v35 | v37a | v37b | UNIVERSITY | crowding | ELECTRICITY | HABIPN | HAVAB | MEINT |
|---|---|---|---|---|---|---|---|---|---|
| 1 | 4 | 8 | 6 | 0 | 1.3333333333 | 1 | Reactive | 0.070 | Positive |
| 2 | | | | 0 | | | Reactive | 0.079 | Positive |
| 3 | 1 | 5 | 10 | 1 | 0.5 | 1 | Reactive | 0.048 | Positive |
| 4 | | | | 0 | | | Reactive | 0.077 | Positive |
| 5 | 5 | 10 | 5 | 0 | 2 | 0 | Reactive | 0.057 | Positive |
| 6 | 5 | 6 | 6 | 0 | 1 | 0 | Reactive | 0.073 | Positive |
| 7 | 1 | 7 | 6 | 0 | 1.1666666667 | 0 | Reactive | 0.042 | Positive |
| 8 | 1 | 6 | 5 | 1 | 1.2 | 1 | Reactive | 0.062 | Positive |
| 9 | 5 | 7 | 6 | 1 | 1.1666666667 | 1 | Reactive | 0.067 | Positive |
| 10 | 1 | 6 | 8 | 1 | 0.75 | 1 | Nonreactive | 2.038 | Positive |
| 11 | 1 | 9 | 6 | 1 | 1.5 | 1 | Reactive | 0.064 | Positive |

-continued

| | | | | | | | | | |
|---|---|---|---|---|---|---|---|---|---|
| 12 | 1 | 9 | 6 | 0 | 1.5 | 1 | Reactive | 0.085 | Positive |
| 13 | 1 | 6 | 6 | 1 | 1 | 1 | Nonreactive | 2.032 | Positive |
| 14 | 1 | 3 | 1 | 0 | 3 | 1 | Reactive | 0.091 | Positive |
| 15 | 1 | 8 | 5 | 0 | 1.6 | 1 | Reactive | 0.084 | Positive |
| 16 | 1 | 10 | 8 | 0 | 1.25 | 1 | Reactive | 0.069 | Positive |
| 17 | 1 | 4 | 6 | 0 | 0.6666666667 | 1 | Nonreactive | 1.914 | Positive |
| 18 | 1 | 5 | 6 | 1 | 0.8333333333 | 1 | Reactive | 0.057 | Positive |
| 19 | 1 | 12 | 8 | 1 | 1.5 | 1 | Reactive | 0.074 | Positive |
| 20 | 1 | 10 | 10 | 1 | 1 | 0 | Reactive | 0.054 | Positive |
| 21 | 1 | 7 | 4 | 0 | 1.75 | 1 | Reactive | 0.066 | Positive |
| 22 | 1 | 5 | 4 | 1 | 1.25 | 0 | Reactive | 0.077 | Positive |
| 23 | 1 | 2 | 2 | 1 | 1 | 1 | Nonreactive | 1.997 | Positive |
| 24 | 1 | 10 | 15 | 0 | 0.6666666667 | 1 | Reactive | 0.074 | Positive |
| 25 | 5 | 10 | 5 | 0 | 2 | 0 | Reactive | 0.049 | Positive |
| 26 | 1 | 9 | 3 | 0 | 3 | 1 | Reactive | 0.057 | Positive |
| 27 | 1 | 6 | 5 | 1 | 1.2 | 0 | Reactive | 0.077 | Positive |
| 28 | 1 | 5 | 6 | 0 | 0.8333333333 | 1 | Reactive | 0.046 | Positive |
| 29 | 1 | 7 | 4 | 0 | 1.75 | 0 | Reactive | 0.067 | Positive |
| 30 | 1 | 5 | 3 | 0 | 1.6666666667 | 0 | Reactive | 0.055 | Positive |
| 31 | 1 | 7 | 4 | 1 | 1.75 | 1 | Reactive | 0.064 | Positive |
| 32 | 1 | 9 | 6 | 0 | 1.5 | 0 | Reactive | 0.084 | Positive |
| 33 | 1 | 15 | 7 | 1 | 2.1428571429 | 1 | Reactive | 0.066 | Positive |

| ID | meaod_1 | meati_1 | mezod_1 | meodr_1 | MPGI | mumod_1 | MUMTI | VZV | vzvod_1 |
|---|---|---|---|---|---|---|---|---|---|
| 1 | 1.314 | 4379.94 | | | Positive | 0.272 | 542.42 | Positive | 0.4 |
| 2 | 1.262 | 4070.99 | | | Positive | 1.356 | 6052.64 | Positive | 1.397 |
| 3 | 0.836 | 2000.37 | | | Positive | 0.589 | 1570.13 | Positive | 1.507 |
| 4 | 1.531 | 5811.27 | | | Positive | 1.281 | 5479.58 | Positive | 0.89 |
| 5 | 1.397 | 4899.95 | | | Equivocal | 0.16 | 286.11 | Positive | 1.131 |
| 6 | 0.753 | 1686.75 | | | Positive | 0.39 | 872.33 | Positive | 1.316 |
| 7 | 1.45 | 5249.65 | | | Positive | 0.381 | 844.99 | Positive | 0.747 |
| 8 | 1.383 | 4809.89 | | | Positive | 0.377 | 832.95 | Positive | 0.862 |
| 9 | 0.331 | 501.05 | | | Positive | 0.411 | 937.53 | Positive | 1.546 |
| 10 | 0.706 | 1521.36 | | | Negative | 0.083 | 0.00 | Positive | 1.314 |
| 11 | 0.609 | 1207.23 | | | Positive | 0.321 | 671.93 | Positive | 0.826 |
| 12 | 1.658 | 6759.78 | | | Positive | 0.924 | 3163.05 | Positive | 1.122 |
| 13 | 1.302 | 4307.5 | | | Positive | 0.254 | 497.50 | Positive | 1.148 |
| 14 | 1.226 | 3864.57 | | | Positive | 0.487 | 1190.03 | Positive | 0.89 |
| 15 | 0.768 | 1741.38 | | | Positive | 0.561 | 1461.04 | Positive | 0.948 |
| 16 | 1.077 | 3073.57 | | | Positive | 0.993 | 3559.35 | Positive | 1.131 |
| 17 | 0.378 | 600.89 | | | Positive | 0.532 | 1351.86 | Positive | 1.887 |
| 18 | 1.099 | 3184.06 | | | Positive | 0.499 | 1232.29 | Positive | 1.154 |
| 19 | 0.678 | 1426.95 | | | Positive | 0.308 | 636.53 | Positive | 0.481 |
| 20 | 0.919 | 2342.17 | | | Positive | 0.658 | 1854.49 | Positive | 1.04 |
| 21 | 1.341 | 4545.44 | | | Positive | 0.354 | 765.13 | Positive | 1.367 |
| 22 | 0.913 | 2316.5 | | | Positive | 0.283 | 570.57 | Positive | 0.817 |
| 23 | 1.264 | 4082.64 | | | Positive | 0.35 | 753.58 | Positive | 1.299 |
| 24 | 1.747 | 7475.43 | | | Positive | 0.558 | 1449.57 | Positive | 0.74 |
| 25 | 0.906 | 2286.74 | | | Equivocal | 0.19 | 349.36 | Positive | 0.925 |
| 26 | 0.669 | 1397.26 | | | Positive | 0.582 | 1542.52 | Positive | 0.572 |
| 27 | 1.891 | 8725.5 | | | Positive | 0.996 | 3577.13 | Positive | 1.415 |
| 28 | 1.959 | 9356.59 | | | Positive | 1.095 | 4189.64 | Positive | 1.578 |
| 29 | 1.117 | 3276.06 | | | Negative | 0.008 | 0.00 | Negative | 0.024 |
| 30 | 0.472 | 824.13 | | | Negative | 0.002 | 0.00 | Positive | 0.361 |
| 31 | 0.64 | 1303.69 | | | Equivocal | 0.134 | 234.50 | Positive | 0.377 |
| 32 | 0.584 | 1132.1 | | | Negative | 0.005 | 0.00 | Positive | 1.096 |
| 33 | 0.592 | 1155.89 | | | Positive | 0.258 | 507.36 | Positive | 0.815 |

| ID | vzvti | new_rubin2 | New_Rube | OpDenTetanus | IUTetanus | OpDenDiph | IUDiph | CMVIg | CMVIgINT |
|---|---|---|---|---|---|---|---|---|---|
| 1 | 192.88 | 0 | 31.3 | 1.208 | 1.712 | 0.731 | 0.587 | >250.00 | Reactive |
| 2 | 1361.08 | 0 | 91.8 | 0.103 | 0.039 | 0.12 | 0.042 | >250.00 | Reactive |
| 3 | 1564.73 | 0 | 228.4 | 0.922 | 1.078 | 0.211 | 0.103 | 72.20 | Reactive |
| 4 | 626.14 | 0 | 81 | 0.57 | 0.525 | 0.427 | 0.28 | 82.60 | Reactive |
| 5 | 935.66 | 0 | 79.2 | 1.212 | 1.722 | 0.982 | 0.887 | >250.00 | Reactive |
| 6 | 1221.73 | 0 | 88.2 | 0.216 | 0.135 | 0.298 | 0.17 | 166.50 | Reactive |
| 7 | 473.89 | 0 | 31.8 | 0.776 | 0.824 | 0.257 | 0.137 | >250.00 | Reactive |
| 8 | 594.55 | 0 | 90.6 | 1.121 | 1.496 | 0.35 | 0.213 | >250.00 | Reactive |
| 9 | 1641.02 | 0 | 323.5 | 0.115 | 0.048 | 0.336 | 0.201 | | |
| 10 | 1218.4 | 0 | 61.6 | 0.742 | 0.77 | 0.21 | 0.102 | 1.50 | Negative |
| 11 | 555.23 | 0 | 163.7 | 1.268 | 1.874 | 0.224 | 0.112 | >250.00 | Reactive |
| 12 | 922.85 | 0 | 269.3 | 1.346 | 2.105 | 0.7 | 0.553 | >250.00 | Reactive |
| 13 | 960.14 | 0 | 53 | | | | | 159.00 | Reactive |
| 14 | 626.14 | 0 | 22.1 | 0.116 | 0.049 | 0.335 | 0.2 | | |
| 15 | 694.41 | 0 | 49.8 | 0.256 | 0.172 | 0.426 | 0.279 | 237.20 | Reactive |
| 16 | 935.66 | 0 | 28.9 | 0.101 | 0.037 | 0.276 | 0.152 | >250.00 | Reactive |
| 17 | 2404.71 | 0 | 37.8 | 0.083 | 0.024 | 0.084 | 0.021 | 115.70 | Reactive |
| 18 | 968.86 | 0 | 84.1 | 2.959 | 1238.41 | 0.207 | 0.1 | >250.00 | Reactive |
| 19 | 247.86 | 0 | 30.9 | 1.083 | 1.409 | 0.169 | 0.073 | >250.00 | Reactive |

-continued

| | | | | | | | | | |
|---|---|---|---|---|---|---|---|---|---|
| 20 | 810.69 | 0 | 92.2 | 0.089 | 0.028 | 0.44 | 0.292 | 196.10 | Reactive |
| 21 | 1308.44 | 0 | 40.8 | 0.924 | 1.081 | 0.261 | 0.14 | 242.10 | Reactive |
| 22 | 545.62 | 0 | 57.7 | 0.225 | 0.143 | 0.491 | 0.339 | | |
| 23 | 1193.59 | 0 | 62.3 | 1.035 | 1.304 | 1.37 | 1.439 | 1.10 | Negative |
| 24 | 467.01 | 0 | 126.9 | 0.136 | 0.065 | 0.187 | 0.086 | | |
| 25 | 666.88 | 0 | 61.9 | 1.166 | 1.605 | 0.233 | 0.119 | >250.00 | Reactive |
| 26 | 317.17 | 0 | 35.9 | 1.305 | 1.981 | 0.229 | 0.116 | >250.00 | Reactive |
| 27 | 1393.26 | 0 | 36.2 | 0.143 | 0.071 | 0.181 | 0.082 | >250.00 | Reactive |
| 28 | 1705.25 | 0 | 500 | 2.135 | 7.108 | 1.538 | 1.714 | >250.00 | Reactive |
| 29 | 0 | 0 | 57.4 | 0.687 | 0.687 | 0.837 | 0.709 | >250.00 | Reactive |
| 30 | 168.6 | 0 | 40.9 | 0.775 | 0.822 | 0.218 | 0.108 | >250.00 | Reactive |
| 31 | 178.39 | 0 | 91.1 | 0.425 | 0.348 | 0.221 | 0.11 | >250.00 | Reactive |
| 32 | 886.4 | 0 | 134.7 | 1.64 | 3.239 | 0.725 | 0.58 | >250.00 | Reactive |
| 33 | 543.49 | 0 | 112.9 | 0.133 | 0.063 | 0.452 | 0.303 | >250.00 | Reactive |

| ID | HBcAb | HBcAbINT | HBSAb | HBSAg | HBSAgINT | HepBeAb | HBeAbINT | HepBeAg | HBeAgINT |
|---|---|---|---|---|---|---|---|---|---|
| 1 | 1.990 | Nonreactive | 0.0 | | | | | | |
| 2 | 1.750 | Nonreactive | 0.0 | | | | | | |
| 3 | 2.279 | Nonreactive | 0.0 | | | | | | |
| 4 | 1.907 | Nonreactive | 0.0 | | | | | | |
| 5 | 2.021 | Nonreactive | 0.0 | | | | | | |
| 6 | 0.913 | Reactive | >1000.0 | 0.83 | Nonreactive | | | | |
| 7 | 2.021 | Nonreactive | 1.8 | | | | | | |
| 8 | 1.489 | Nonreactive | 0.0 | | | | | | |
| 9 | | | | | | | | | |
| 10 | 1.684 | Nonreactive | 25.2 | | | | | | |
| 11 | 2.152 | Nonreactive | 0.0 | | | | | | |
| 12 | 2.091 | Nonreactive | 0.0 | | | | | | |
| 13 | 0.071 | Reactive | 6.8 | 0.73 | Nonreactive | | | | |
| 14 | | | | | | | | | |
| 15 | 2.102 | Nonreactive | 0.0 | | | | | | |
| 16 | 0.105 | Reactive | 15.7 | 0.67 | Nonreactive | | | | |
| 17 | 1.794 | Nonreactive | 0.0 | | | | | | |
| 18 | 1.802 | Nonreactive | 0.0 | | | | | | |
| 19 | 1.853 | Nonreactive | 0.0 | | | | | | |
| 20 | 2.154 | Nonreactive | 0.0 | | | | | | |
| 21 | 1.853 | Nonreactive | 0.0 | | | | | | |
| 22 | | | | | | | | | |
| 23 | 1.642 | Nonreactive | 0.0 | | | | | | |
| 24 | | | | | | | | | |
| 25 | 1.933 | Nonreactive | 0.0 | | | | | | |
| 26 | 2.120 | Nonreactive | 0.0 | | | | | | |
| 27 | 2.106 | Nonreactive | 0.0 | | | | | | |
| 28 | 2.057 | Nonreactive | 0.0 | | | | | | |
| 29 | 2.079 | Nonreactive | 0.0 | | | | | | |
| 30 | 2.018 | Nonreactive | 0.0 | | | | | | |
| 31 | 2.052 | Nonreactive | 0.0 | | | | | | |
| 32 | 2.069 | Nonreactive | 0.0 | | | | | | |
| 33 | 2.017 | Nonreactive | 0.0 | | | | | | |

| ID | HCV | HCVINT | HCVPCR | HCVLIA |
|---|---|---|---|---|
| 1 | 0.59 | Nonreactive | | |
| 2 | 0.22 | Nonreactive | | |
| 3 | 0.56 | Nonreactive | | |
| 4 | 0.25 | Nonreactive | | |
| 5 | 0.28 | Nonreactive | | |
| 6 | 0.36 | Nonreactive | | |
| 7 | 0.73 | Nonreactive | | |
| 8 | 0.25 | Nonreactive | | |
| 9 | | | | |
| 10 | 0.35 | Nonreactive | | |
| 11 | 0.51 | Nonreactive | | |
| 12 | 0.58 | Nonreactive | | |
| 13 | 0.43 | Nonreactive | | |
| 14 | | | | |
| 15 | 0.59 | Nonreactive | | |
| 16 | 0.38 | Nonreactive | | |
| 17 | 0.21 | Nonreactive | | |
| 18 | 0.18 | Nonreactive | | |
| 19 | 0.33 | Nonreactive | | |
| 20 | 0.27 | Nonreactive | | |
| 21 | 0.40 | Nonreactive | | |
| 22 | | | | |
| 23 | 0.29 | Nonreactive | | |
| 24 | | | | |
| 25 | 0.29 | Nonreactive | | |
| 26 | 0.33 | Nonreactive | | |
| 27 | 0.32 | Nonreactive | | |

-continued

|  | 28 | 0.36 | Nonreactive |
|---|---|---|---|
|  | 29 | 0.24 | Nonreactive |
|  | 30 | 0.20 | Nonreactive |
|  | 31 | 0.20 | Nonreactive |
|  | 32 | 0.26 | Nonreactive |
|  | 33 | 0.38 | Nonreactive |

| ID | v2_h | v4 | v5 | v6 | v14a | v14b | v15a | v15aO |
|---|---|---|---|---|---|---|---|---|
| 34 | 15649 | 0 | Oct. 27, 1971 | 31 | 0 |  | 8 | Nigeria |
| 35 | 15649 | 1 | Feb. 9, 1979 | 23 | 0 |  | 8 | Peru |
| 36 | 15650 | 1 | Apr. 5, 1971 | 31 | 1 | Spanish | 8 | Colombia |
| 37 | 15651 | 0 | Mar. 30, 1979 | 22 | 0 |  | 8 | Zimbabwe |
| 38 | 15652 | 0 | Jan. 1, 1978 | 24 | 0 |  | 8 | Guinea |
| 39 | 15652 | 0 | May 7, 1979 | 23 | 0 |  | 8 | Zimbabwe |
| 40 | 15652 | 1 | Jan. 1, 1980 | 22 | 0 |  | 2 | Banglade |
| 41 | 15652 | 0 | Jul. 6, 1962 | 40 | 0 |  | 1 | India |
| 42 | 15655 | 0 | Jan. 15, 1970 | 32 | 0 |  | 4 | Pakistan |
| 43 | 15655 | 0 | Oct. 3, 1979 | 23 | 0 |  | 8 | Malaysia |
| 44 | 15655 | 0 | Jun. 30, 1966 | 36 | 0 |  | 1 | India |
| 45 | 15656 | 0 | Oct. 2, 1935 | 67 | 1 | Punjabi | 1 | India |
| 46 | 15656 | 0 | May 25, 1973 | 29 | 1 | Punjabi | 1 | India |
| 47 | 15656 | 0 | Jun. 30, 1959 | 43 | 0 |  | 1 | India |
| 48 | 15656 | 1 | Mar. 7, 1978 | 24 | 0 |  | 4 | Pakistan |
| 49 | 15687 | 0 | Jan. 3, 1956 | 46 | 0 |  | 8 | Zimbabwe |
| 50 | 15657 | 0 | Nov. 5, 1977 | 25 | 0 |  | 8 | Malaysia |
| 51 | 15657 | 0 | Jan. 8, 1975 | 27 | 0 |  | 8 | Cameroon |
| 52 | 15657 | 0 | Mar. 10, 1966 | 36 | 0 |  | 8 | China |
| 53 | 15658 | 1 | Jul. 10, 1973 | 29 | 0 |  | 8 | Haiti |
| 54 | 15658 | 0 | Jan. 25, 1945 | 57 | 0 |  | 4 | Pakistan |
| 55 | 15658 | 0 | Jul. 14, 1963 | 39 | 0 |  | 8 | Venezuel |
| 56 | 15659 | 1 | Apr. 7, 1972 | 30 | 1 | Malay | 8 | Malaysia |
| 57 | 15659 | 1 | Oct. 31, 1968 | 34 | 0 |  | 8 | Iran |
| 58 | 15659 | 1 | Jan. 1, 1966 | 36 | 1 | Arabic | 5 | Morocco |
| 59 | 15662 | 0 | Apr. 13, 1967 | 35 | 0 |  | 8 | Mexico |
| 60 | 15663 | 1 | Apr. 11, 1959 | 43 | 0 |  | 8 | Ukraine |
| 61 | 15663 | 0 | Nov. 7, 1967 | 35 | 0 |  | 7 | Congo |
| 62 | 16029 | 0 | Apr. 13, 1956 | 46 | 1 | Punjabi | 1 | India |
| 63 | 15665 | 1 | Jun. 25, 1973 | 29 | 1 | Hindi | 1 | India |
| 64 | 15666 | 0 | Mar. 18, 1945 | 57 | 0 |  | 4 | Pakistan |
| 65 | 15666 | 1 | Mar. 17, 1954 | 48 | 1 | Urdu | 4 | Pakistan |
| 66 | 15666 | 0 | Feb. 14, 1964 | 38 | 1 | Punjabi | 1 | India |

| ID | v15b | v17a | months_ca | v18 | v20_h | v21 | v22 | v23 | v24a |
|---|---|---|---|---|---|---|---|---|---|
| 34 | 1 | May 10, 2002 | 5.9 | 0 | 0 | 0 | 1 | 0 | 0 |
| 35 | 4 | Dec. 28, 2001 | 10.3 | 1 | 0 | 1 | 1 | 1 | 0 |
| 36 | 4 | May 31, 2002 | 5.2 | 0 | 0 | 0 | 0 | 0 | 0 |
| 37 | 1 | Sep. 28, 2001 | 13.3 | 0 | 0 | 0 | 1 | 0 | 0 |
| 38 | 1 | Jun. 22, 2002 | 4.6 | 0 | 0 | 0 | 1 | 0 | 0 |
| 39 | 1 | Oct. 30, 2001 | 12.3 | 0 | 0 | 0 | 0 | 0 | 0 |
| 40 | 2 | Nov. 4, 2001 | 12.1 | 3 | 0 | 0 | 0 | 0 | 1 |
| 41 | 2 | Mar. 6, 2002 | 8.1 | 0 | 0 | 0 | 0 | 1 | 0 |
| 42 | 2 | Nov. 4, 2001 | 12.2 | 1 | 0 | 0 | 0 | 0 | 0 |
| 43 | 6 | Jun. 20, 2002 | 4.7 | 0 | 0 | 1 | 0 | 0 | 0 |
| 44 | 2 | Jan. 5, 2002 | 10.2 | 0 | 0 | 0 | 0 | 0 | 0 |
| 45 | 2 | Jul. 10, 2001 | 16.1 | 0 | 0 | 1 | 1 | 1 | 0 |
| 46 | 2 | May 20, 2002 | 5.8 | 0 | 0 | 0 | 1 | 1 | 0 |
| 47 | 2 | Aug. 26, 2002 | 2.6 | 0 | 0 | 1 | 0 | 1 | 0 |
| 48 | 2 | Dec. 25, 2001 | 10.6 | 0 | 0 | 1 | 0 | 1 | 0 |
| 49 | 1 | Nov. 11, 2001 | 13.1 | 0 | 0 | 1 | 0 | 1 | 0 |
| 50 | 6 | Mar. 26, 2002 | 7.6 | 0 | 0 | 0 | 0 | 0 | 0 |
| 51 | 1 | Jun. 10, 2001 | 17.1 | 0 | 0 | 0 | 0 | 0 | 0 |
| 52 | 6 | Nov. 15, 2000 | 23.9 | 3 | 0 | 0 | 1 | 0 | 0 |
| 53 | 4 | Oct. 15, 2002 | 1 | 3 | 0 | 0 | 1 | 0 | 0 |
| 54 | 2 | Sep. 9, 2002 | 2.2 | 0 | 0 | 0 | 0 | 0 | 0 |
| 55 | 4 | Jun. 7, 2002 | 5.3 | 0 | 0 | 0 | 0 | 1 | 0 |
| 56 | 6 | Sep. 18, 2002 | 1.9 | 0 | 0 | 0 | 0 | 0 | 0 |
| 57 | 3 | May 15, 2001 | 18 | 3 | 0 | 0 | 1 | 0 | 0 |
| 58 | 3 | Jun. 7, 2001 | 17.3 | 3 | 0 | 0 | 0 | 0 | 0 |
| 59 | 4 | Jun. 8, 2001 | 17.4 | 0 | 0 | 0 | 1 | 1 | 0 |
| 60 | 5 | May 31, 2001 | 17.7 | 3 | 0 | 0 | 0 | 0 | 0 |
| 61 | 1 | Sep. 25, 2002 | 1.8 | 0 | 0 | 0 | 0 | 0 | 0 |
| 62 | 2 | Dec. 8, 2001 | 23.4 | 0 | 0 | 0 | 0 | 1 | 0 |
| 63 | 2 | Apr. 16, 2002 | 7.2 | 0 | 0 | 1 | 0 | 1 | 0 |
| 64 | 2 | Apr. 1, 2002 | 7.7 | 0 | 0 | 1 | 1 | 1 | 0 |
| 65 | 2 | Apr. 1, 2002 | 7.7 | 0 | 0 | 1 | 1 | 1 | 0 |
| 66 | 2 | Jan. 21, 2002 | 10 | 0 | 0 | 0 | 0 | 1 | 0 |

-continued

| ID | v24b_h | v251a | v251b_h | v252a | v252b | v253a | v253b_h | v254a | v254b |
|---|---|---|---|---|---|---|---|---|---|
| 34 | 91 | 1 | 8 | 0 |  | 2 | 91 | 1 | 20 |
| 35 | 91 | 0 | 91 | 0 |  | 2 | 91 | 1 | 7 |
| 36 | 91 | 2 | 91 | 2 |  | 2 | 91 | 1 | 6 |
| 37 | 91 | 0 | 91 | 2 |  | 2 | 91 | 1 | 13 |
| 38 | 91 | 2 | 91 | 2 |  | 2 | 91 | 0 |  |
| 39 | 91 | 2 | 91 | 2 |  | 2 | 91 | 1 | 14 |
| 40 | 8 | 2 | 91 | 2 |  | 2 | 91 | 0 |  |
| 41 | 91 | 2 | 91 | 2 |  | 2 | 91 | 2 |  |
| 42 | 91 | 2 | 91 | 2 |  | 2 | 91 | 2 |  |
| 43 | 91 | 2 | 91 | 1 | 10 | 2 | 91 | 1 | 17 |
| 44 | 91 | 2 | 91 | 2 |  | 2 | 91 | 2 |  |
| 45 | 91 | 2 | 91 | 0 |  | 2 | 91 | 0 |  |
| 46 | 91 | 0 | 91 | 0 |  | 2 | 91 | 2 |  |
| 47 | 91 | 1 | 4 | 2 |  | 2 | 91 | 2 |  |
| 48 | 91 | 2 | 91 | 2 |  | 2 | 91 | 2 |  |
| 49 | 91 | 2 | 91 | 1 | 5 | 2 | 91 | 2 |  |
| 50 | 91 | 2 | 91 | 2 |  | 2 | 91 | 1 | 16 |
| 51 | 91 | 2 | 91 | 2 |  | 2 | 91 | 2 |  |
| 52 | 91 | 2 | 91 | 1 | 28 | 2 | 91 | 2 |  |
| 53 | 91 | 0 | 91 | 0 |  | 2 | 91 | 0 |  |
| 54 | 91 | 2 | 91 | 1 | 27 | 2 | 91 | 2 |  |
| 55 | 91 | 2 | 91 | 2 |  | 2 | 91 | 2 |  |
| 56 | 91 | 2 | 91 | 2 |  | 2 | 91 | 2 |  |
| 57 | 91 | 2 | 91 | 2 |  | 2 | 91 | 2 |  |
| 58 | 91 | 2 | 91 | 2 |  | 2 | 91 | 2 |  |
| 59 | 91 | 2 | 91 | 2 |  | 2 | 91 | 2 |  |
| 60 | 91 | 2 | 91 | 2 |  | 2 | 91 | 2 |  |
| 61 | 91 | 2 | 91 | 2 |  | 2 | 91 | 2 |  |
| 62 | 91 | 2 | 91 | 2 |  | 2 | 91 | 2 |  |
| 63 | 91 | 2 | 91 | 2 |  | 2 | 91 | 2 |  |
| 64 | 91 | 2 | 91 | 2 |  | 2 | 91 | 2 |  |
| 65 | 91 | 2 | 91 | 2 |  | 2 | 91 | 2 |  |
| 66 | 91 | 2 | 91 | 2 |  | 2 | 91 | 2 |  |

| ID | v255a | v255b_h | v256a | v256b_h | v257a | v257b | v258a | v258b_h | v259a |
|---|---|---|---|---|---|---|---|---|---|
| 34 | 0 | 91 | 2 | 91 |  |  | 0 | 91 | 0 |
| 35 | 0 | 91 | 2 | 91 | 1 | 5 | 2 | 91 | 0 |
| 36 | 2 | 91 | 2 | 91 | 0 |  | 2 | 91 | 0 |
| 37 | 2 | 91 | 2 | 91 | 0 |  | 0 | 91 | 0 |
| 38 | 2 | 91 | 2 | 91 |  |  | 2 | 91 | 0 |
| 39 | 2 | 91 | 2 | 91 |  |  | 2 | 91 | 0 |
| 40 | 2 | 91 | 2 | 91 |  |  | 2 | 91 | 0 |
| 41 | 2 | 91 | 2 | 91 |  |  | 2 | 91 | 0 |
| 42 | 2 | 91 | 2 | 91 |  |  | 2 | 91 | 0 |
| 43 | 2 | 91 | 2 | 91 | 0 |  | 2 | 91 | 0 |
| 44 | 2 | 91 | 2 | 91 |  |  | 2 | 91 | 0 |
| 45 | 2 | 91 | 2 | 91 |  |  | 2 | 91 | 0 |
| 46 | 2 | 91 | 2 | 91 | 0 |  | 2 | 91 | 0 |
| 47 | 2 | 91 | 2 | 91 |  |  | 2 | 91 | 0 |
| 48 | 2 | 91 | 2 | 91 | 0 |  | 2 | 91 | 0 |
| 49 | 2 | 91 | 2 | 91 | 0 |  | 2 | 91 | 0 |
| 50 | 2 | 91 | 2 | 91 |  |  | 2 | 91 | 0 |
| 51 | 2 | 91 | 2 | 91 | 0 |  | 2 | 91 | 0 |
| 52 | 2 | 91 | 2 | 91 |  |  | 2 | 91 | 0 |
| 53 | 2 | 91 | 2 | 91 | 0 |  | 2 | 91 | 0 |
| 54 | 2 | 91 | 2 | 91 |  |  | 2 | 91 | 0 |
| 55 | 2 | 91 | 2 | 91 | 0 |  | 2 | 91 | 0 |
| 56 | 2 | 91 | 2 | 91 | 2 |  | 2 | 91 | 0 |
| 57 | 2 | 91 | 2 | 91 | 2 |  | 2 | 91 | 0 |
| 58 | 2 | 91 | 2 | 91 | 2 |  | 2 | 91 | 0 |
| 59 | 2 | 91 | 2 | 91 | 2 |  | 2 | 91 | 0 |
| 60 | 2 | 91 | 2 | 91 | 2 |  | 2 | 91 | 0 |
| 61 | 2 | 91 | 2 | 91 | 2 |  | 2 | 91 | 0 |
| 62 | 2 | 91 | 2 | 91 | 2 |  | 2 | 91 | 0 |
| 63 | 2 | 91 | 2 | 91 | 2 |  | 2 | 91 | 0 |
| 64 | 2 | 91 | 2 | 91 | 2 |  | 2 | 91 | 0 |
| 65 | 2 | 91 | 2 | 91 | 2 |  | 2 | 91 | 0 |
| 66 | 2 | 91 | 2 | 91 | 2 |  | 2 | 91 | 0 |

| ID | v259b_h | v26 | v33a | v33b | v33c | v34a | v34a1 | v34c | v34c1 |
|---|---|---|---|---|---|---|---|---|---|
| 34 | 91 | 0 | 5 | 16 | 2 | 1 | 1 | 0 |  |
| 35 | 91 | 0 | 4 | 14 | 1 | 1 | 1 | 0 |  |
| 36 | 91 | 0 | 4 | 12 | 2 | 1 | 1 | 0 |  |
| 37 | 91 | 0 | 3 | 13 | 2 | 1 | 1 | 0 |  |
| 38 | 91 | 0 | 4 | 13 | 2 | 1 | 1 | 1 | 1 |
| 39 | 91 | 0 | 3 | 13 | 2 | 1 | 1 | 0 |  |

-continued

| | | | | | | | | | |
|---|---|---|---|---|---|---|---|---|---|
| 40 | 91 | 0 | 5 | 15 | 2 | 1 | 2 | 0 | |
| 41 | 91 | 0 | 5 | 14 | 2 | 1 | 1 | 0 | |
| 42 | 91 | 0 | 5 | 17 | 2 | 1 | 1 | 1 | 3 |
| 43 | 91 | 0 | 4 | 11 | 2 | 1 | 1 | 1 | 2 |
| 44 | 91 | 0 | 3 | 10 | 2 | 1 | 1 | 1 | 1 |
| 45 | 91 | 0 | 2 | 4 | 2 | 1 | 1 | 0 | |
| 46 | 91 | 0 | 3 | 12 | 2 | 1 | 1 | 1 | 3 |
| 47 | 91 | 0 | 3 | 10 | 2 | 1 | 1 | 0 | |
| 48 | 91 | 0 | 5 | 16 | 2 | 1 | 1 | 0 | |
| 49 | 91 | 0 | 5 | 17 | 2 | 1 | 1 | 1 | 2 |
| 50 | 91 | 0 | 4 | 14 | 1 | 1 | 1 | 0 | |
| 51 | 91 | 0 | 4 | 17 | 2 | 1 | 1 | 0 | |
| 52 | 91 | 0 | 5 | 18 | 2 | 1 | 1 | 0 | |
| 53 | 91 | 0 | 5 | 17 | 1 | 1 | 1 | 1 | 2 |
| 54 | 91 | 0 | 4 | 14 | 1 | 1 | 1 | 0 | |
| 55 | 91 | 0 | 4 | 13 | 2 | 1 | 1 | 0 | |
| 56 | 91 | 0 | 3 | 8 | 2 | 1 | 1 | 1 | |
| 57 | 91 | 0 | 5 | 19 | 2 | 1 | 1 | 0 | |
| 58 | 91 | 0 | 2 | 5 | 2 | 1 | 1 | 0 | |
| 59 | 91 | 0 | 3 | 10 | 2 | 1 | 1 | 0 | |
| 60 | 91 | 0 | 5 | 14 | 2 | 1 | 1 | 0 | |
| 61 | 91 | 0 | 5 | 14 | 2 | 1 | 1 | 0 | |
| 62 | 91 | 0 | 2 | 3 | 2 | 1 | 1 | 0 | |
| 63 | 91 | 0 | 5 | 15 | 2 | 1 | 1 | 0 | |
| 64 | 91 | 0 | 4 | 13 | 1 | 1 | 1 | 1 | 1 |
| 65 | 91 | 0 | 3 | 10 | 1 | 1 | 1 | 1 | 1 |
| 66 | 91 | 0 | 3 | 7 | 2 | 1 | 1 | 1 | 3 |

| ID | v35 | v37a | v37b | UNIVERSITY | crowding | ELECTRICITY | HABIPN | HAVAB | MEINT |
|---|---|---|---|---|---|---|---|---|---|
| 34 | 1 | 6 | 6 | 1 | 1 | 1 | Reactive | 0.057 | Positive |
| 35 | 1 | 6 | 7 | 0 | 0.8571428571 | 1 | Reactive | 0.059 | Positive |
| 36 | 1 | 5 | 4 | 0 | 1.25 | 1 | Reactive | 0.059 | Positive |
| 37 | 1 | 10 | 11 | 0 | 0.9090909091 | 1 | Reactive | 0.071 | Positive |
| 38 | 1 | 30 | 16 | 0 | 1.875 | 1 | Reactive | 0.071 | Positive |
| 39 | 1 | 6 | 5 | 0 | 1.2 | 1 | Reactive | 0.071 | Positive |
| 40 | 1 | 4 | 3 | 1 | 1.3333333333 | 0 | Reactive | 0.053 | Positive |
| 41 | 1 | 6 | 5 | 1 | 1.2 | 0 | Reactive | 0.075 | Positive |
| 42 | 5 | 9 | 9 | 1 | 1 | 1 | Reactive | 0.061 | Positive |
| 43 | 1 | 5 | 4 | 0 | 1.25 | 1 | Nonreactive | 2.036 | Positive |
| 44 | 5 | 4 | 6 | 0 | 0.6666666667 | 1 | Reactive | 0.080 | Positive |
| 45 | 1 | 6 | 8 | 0 | 0.75 | 0 | Reactive | 0.079 | Positive |
| 46 | 5 | 4 | 10 | 0 | 0.4 | 0 | Reactive | 0.072 | Positive |
| 47 | 1 | 6 | 4 | 0 | 1.5 | 0 | Reactive | 0.089 | Positive |
| 48 | 1 | 13 | 7 | 1 | 1.8571428571 | 0 | Reactive | 0.102 | Positive |
| 49 | 1 | 5 | 6 | 1 | 0.8333333333 | 1 | Reactive | 0.064 | Positive |
| 50 | 1 | 5 | 3 | 0 | 1.6666666667 | 1 | Nonreactive | 1.941 | Positive |
| 51 | 1 | 5 | 7 | 0 | 0.7142857143 | 1 | Reactive | 0.068 | Positive |
| 52 | 1 | 5 | 5 | 1 | 1 | 1 | Reactive | 0.061 | Positive |
| 53 | 4 | 3 | 2 | 1 | 1.5 | 0 | Reactive | 0.078 | Positive |
| 54 | 1 | | 3 | 0 | 1.6666666667 | 1 | Reactive | 0.076 | Positive |
| 55 | 1 | 8 | 3 | 0 | 2.6666666667 | 1 | Reactive | 0.058 | Positive |
| 56 | 1 | 6 | 3 | 0 | 2 | 1 | Nonreactive | 1.927 | Positive |
| 57 | 1 | 8 | 6 | 1 | 1.3333333333 | 1 | Reactive | 0.070 | Negative |
| 58 | 1 | 8 | 2 | 0 | 4 | 1 | Reactive | 0.076 | Positive |
| 59 | 1 | 7 | 6 | 0 | 1.1666666667 | 1 | Reactive | 0.087 | Positive |
| 60 | 1 | 6 | 3 | 1 | 2 | 1 | Nonreactive | 1.831 | Positive |
| 61 | 1 | 10 | 15 | 1 | 0.6666666667 | 0 | Reactive | 0.064 | Positive |
| 62 | 1 | 6 | 1 | 0 | 6 | 1 | Reactive | 0.077 | Positive |
| 63 | 1 | 4 | 5 | 1 | 0.8 | 1 | Reactive | 0.099 | Positive |
| 64 | 1 | 7 | 8 | 0 | 0.875 | 1 | Reactive | 0.072 | Positive |
| 65 | 1 | 10 | 5 | 0 | 2 | | Reactive | 0.069 | Positive |
| 66 | 1 | 8 | 3 | 0 | 2.6666666667 | 0 | Reactive | 0.088 | Positive |

| ID | meaod_1 | meati_1 | mezod_1 | meodr_1 | MPGI | mumod_1 | MUMTI | VZV | vzvod_1 |
|---|---|---|---|---|---|---|---|---|---|
| 34 | 0.699 | 1497.47 | | | Positive | 0.406 | 921.83 | Positive | 1.137 |
| 35 | 1.874 | 8571.86 | | | Positive | 0.665 | 1884.58 | Positive | 0.485 |
| 36 | 0.826 | 1961.11 | | | Positive | 0.552 | 1426.75 | Positive | 0.936 |
| 37 | 0.273 | 388.45 | | | Positive | 0.25 | 487.71 | Positive | 0.83 |
| 38 | 0.564 | 1073.69 | | | Positive | 0.437 | 1020.99 | Positive | 0.46 |
| 39 | 0.873 | 2149.21 | | | Positive | 0.269 | 534.83 | Positive | 0.829 |
| 40 | 0.753 | 1686.75 | | | Positive | 0.238 | 458.78 | Positive | 0.624 |
| 41 | 1.318 | 4404.23 | | | Negative | 0.046 | 0.00 | Positive | 1.323 |
| 42 | 1.13 | 3343.41 | | | Positive | 0.264 | 522.28 | Positive | 0.937 |
| 43 | 0.971 | 2571.02 | | | Positive | 0.321 | 671.93 | Positive | 0.93 |
| 44 | 0.998 | 2694.4 | | | Positive | 0.574 | 1511.24 | Positive | 1.393 |
| 45 | 1.006 | 2731.56 | | | Positive | 0.52 | 1307.80 | Positive | 1.124 |
| 46 | 0.62 | 1241.04 | | | Positive | 0.446 | 1050.58 | Positive | 1.263 |
| 47 | 1.12 | 2333.08 | | | Equivocal | 0.13 | 219.88 | Positive | 0.562 |

-continued

| | | | | | | | | | |
|---|---|---|---|---|---|---|---|---|---|
| 48 | 0.555 | 779.78 | | Equivocal | 0.111 | 185.63 | Negative | 0.051 | |
| 49 | 2.197 | 7909.7 | | Positive | 0.655 | 1763.97 | Positive | 1.67 | |
| 50 | 2.302 | 8666.67 | | Negative | 0.024 | 0.00 | Positive | 1.992 | |
| 51 | 0.332 | 386.22 | | Positive | 0.679 | 1862.79 | Positive | 1.066 | |
| 52 | 0.721 | 1150.64 | | Positive | 0.658 | 1776.18 | Positive | 1.568 | |
| 53 | 1.46 | 3692.85 | | Negative | 0.028 | 0.00 | Equivocal | 0.176 | |
| 54 | 1.599 | 4349.72 | | Positive | 0.569 | 1430.64 | Positive | 1.621 | |
| 55 | 1.551 | 4116.01 | | Positive | 0.302 | 597.99 | Positive | 1.692 | |
| 56 | 1.154 | 2453.89 | | Positive | 0.285 | 555.14 | Positive | 1.779 | |
| 57 | 0.01 | 0 | | Positive | 0.621 | 1628.32 | Positive | 0.669 | |
| 58 | 0.668 | 1024.81 | | Positive | 0.964 | 3235.52 | Positive | 0.764 | |
| 59 | 0.694 | 1085.65 | | Positive | 0.312 | 623.76 | Positive | 1.305 | |
| 60 | 0.619 | 914.7 | | Positive | 0.252 | 475.40 | Positive | 1.269 | |
| 61 | 2.303 | 8674.08 | | Positive | 0.438 | 984.35 | Positive | 1.445 | |
| 62 | 0.454 | 586.98 | | Positive | 0.372 | 787.16 | Positive | 1.16 | |
| 63 | 1.288 | 2962.35 | | Negative | 0.065 | 0.00 | Positive | 0.623 | |
| 64 | 0.756 | 1237.62 | | Positive | 0.664 | 1800.73 | Positive | 2.13 | |
| 65 | 1.151 | 2443.1 | | Positive | 0.556 | 1383.05 | Positive | 2.677 | |
| 66 | 0.872 | 1548.4 | | Negative | 0.028 | 0.00 | Positive | 0.853 | |

| ID | vzvti | new_rubin2 | New_Rube | OpDenTetanus | IUTetanus | OpDenDiph | IUDiph | CMVIg | CMVIgINT |
|---|---|---|---|---|---|---|---|---|---|
| 34 | 944.26 | 0 | 107.2 | 0.682 | 0.68 | 0.183 | 0.083 | >250.00 | Reactive |
| 35 | 250.74 | 0 | 40.4 | 0.193 | 0.114 | 0.216 | 0.107 | 56.20 | Reactive |
| 36 | 679.97 | 0 | 69.6 | 1.522 | 2.725 | 0.342 | 0.206 | | |
| 37 | 559.52 | 0 | 38.8 | 0.198 | 0.119 | 0.165 | 0.071 | >250.00 | Reactive |
| 38 | 233.01 | 0 | 110.5 | 0.214 | 0.133 | 0.506 | 0.354 | 199.80 | Reactive |
| 39 | 558.45 | 0 | 160 | 0.686 | 0.686 | 0.178 | 0.08 | >250.00 | Reactive |
| 40 | 360.45 | 0 | 83.6 | 0.324 | 0.24 | 0.17 | 0.074 | | |
| 41 | 1233.42 | 0 | 36.9 | 1.888 | 4.712 | 0.318 | 0.186 | >250.00 | Reactive |
| 42 | 681.16 | 0 | 113.2 | 0.356 | 0.273 | 3 | 5.41 | 80.70 | Reactive |
| 43 | 672.81 | 0 | 184.6 | 2.116 | 6.872 | 0.245 | 0.128 | >250.00 | Reactive |
| 44 | 1353.99 | 0 | 23.5 | 0.453 | 0.381 | 0.392 | 0.249 | >250.00 | Reactive |
| 45 | 925.69 | 0 | 91.2 | 0.109 | 0.044 | 0.228 | 0.115 | >250.00 | Reactive |
| 46 | 1135.27 | 0 | 479 | 0.711 | 0.723 | 0.312 | 0.181 | >250.00 | Reactive |
| 47 | 249.84 | 0 | 95.7 | 0.69 | 0.692 | 0.334 | 0.199 | 178.10 | Reactive |
| 48 | 0 | 0 | 29.8 | 0.115 | 0.048 | 0.202 | 0.096 | >250.00 | Reactive |
| 49 | 1434.05 | 0 | 87.2 | 1.491 | 2.604 | 0.115 | 0.039 | >250.00 | Reactive |
| 50 | 1996.49 | 1 | 0.4 | 1.045 | 1.325 | 0.325 | 0.192 | >250.00 | Reactive |
| 51 | 658.11 | 1 | 3.7 | 0.065 | 0.011 | 0.148 | 0.059 | 235.90 | Reactive |
| 52 | 1278.59 | 0 | 39.8 | 0.081 | 0.022 | 0.13 | 0.048 | 46.90 | Reactive |
| 53 | 61.44 | 0 | 30 | 1.952 | 5.216 | 0.288 | 0.162 | >250.00 | Reactive |
| 54 | 1358.05 | 0 | 18.9 | 1.624 | 3.164 | 0.438 | 0.29 | >250.00 | Reactive |
| 55 | 1468.97 | 0 | 215.2 | 1.409 | 2.31 | 0.209 | 0.102 | >250.00 | Reactive |
| 56 | 1611.99 | 0 | 74 | 1.957 | 5.258 | 0.232 | 0.118 | >250.00 | Reactive |
| 57 | 320.28 | 0 | 60.8 | 1.638 | 3.23 | 0.431 | 0.284 | >250.00 | Reactive |
| 58 | 389.9 | 0 | 226.7 | 1.383 | 2.223 | 0.404 | 0.26 | | |
| 59 | 924.68 | 0 | 67.4 | 1.999 | 5.63 | 0.144 | 0.057 | >250.00 | Reactive |
| 60 | 881.29 | 0 | 69.7 | 1.876 | 4.624 | 0.348 | 0.211 | >250.00 | Reactive |
| 61 | 1104.85 | 0 | 83.9 | 1.018 | 1.268 | 1.76 | 2.114 | >250.00 | Reactive |
| 62 | 756.98 | 0 | 183.6 | 0.161 | 0.086 | 0.212 | 0.104 | >250.00 | Reactive |
| 63 | 288.97 | 0 | 137.4 | 2.774 | 44.649 | 1.259 | 1.27 | >250.00 | Reactive |
| 64 | 2272.79 | 0 | 61.2 | 0.131 | 0.061 | 0.205 | 0.099 | >250.00 | Reactive |
| 65 | 3597.36 | 0 | 44.1 | 0.123 | 0.055 | 0.546 | 0.393 | >250.00 | Reactive |
| 66 | 461.38 | 0 | 114.1 | 0.62 | 0.592 | 0.345 | 0.208 | >250.00 | Reactive |

| ID | HBcAb | HBcAbINT | HBSAb | HBSAg | HBSAgINT | HepBeAb | HBeAbINT | HepBeAg | HBeAgINT |
|---|---|---|---|---|---|---|---|---|---|
| 34 | 1.976 | Nonreactive | 0.0 | | | | | | |
| 35 | 2.154 | Nonreactive | 0.0 | | | | | | |
| 36 | | | | | | | | | |
| 37 | 0.873 | Reactive | 226.4 | 0.79 | Nonreactive | | | | |
| 38 | 0.064 | Reactive | 0.0 | 375.49 | Reactive | 0.093 | Reactive | 0.400 | Nonreactive |
| 39 | 2.199 | Nonreactive | 0.0 | | | | | | |
| 40 | | | | | | | | | |
| 41 | 1.720 | Nonreactive | 0.0 | | | | | | |
| 42 | 0.093 | Reactive | 334.2 | 0.82 | Nonreactive | | | | |
| 43 | 2.039 | Nonreactive | 0.0 | | | | | | |
| 44 | 0.118 | Reactive | 1.1 | 1.07 | Nonreactive | | | | |
| 45 | 0.528 | Reactive | >1000.0 | 0.97 | Nonreactive | | | | |
| 46 | 1.726 | Nonreactive | 0.1 | | | | | | |
| 47 | 2.042 | Nonreactive | 358.5 | | | | | | |
| 48 | 2.106 | Nonreactive | 0.0 | | | | | | |
| 49 | 1.997 | Nonreactive | 0.0 | | | | | | |
| 50 | 1.896 | Nonreactive | 0.0 | | | | | | |
| 51 | 2.139 | Nonreactive | 0.0 | | | | | | |
| 52 | 2.016 | Nonreactive | >1000.0 | | | | | | |
| 53 | 2.096 | Nonreactive | 0.0 | | | | | | |
| 54 | 0.158 | Reactive | 38.4 | 0.83 | Nonreactive | | | | |
| 55 | 0.122 | Reactive | >1000.0 | 0.69 | Nonreactive | | | | |

-continued

| | | | | | | | | | |
|---|---|---|---|---|---|---|---|---|---|
| 56 | 2.020 | Nonreactive | 0.0 | | | | | | |
| 57 | 2.181 | Nonreactive | 2.0 | | | | | | |
| 58 | | | | | | | | | |
| 59 | 0.102 | Reactive | 0.0 | 418.85 | Reactive | 0.083 | Reactive | 0.310 | Nonreactive |
| 60 | 2.242 | Nonreactive | 0.0 | | | | | | |
| 61 | 0.087 | Reactive | 1.6 | 0.91 | Nonreactive | | | | |
| 62 | 1.800 | Nonreactive | 0.0 | | | | | | |
| 63 | 2.191 | Nonreactive | 0.0 | | | | | | |
| 64 | 2.173 | Nonreactive | 0.0 | | | | | | |
| 65 | 2.148 | Nonreactive | 0.0 | | | | | | |
| 66 | 2.069 | Nonreactive | 961.1 | | | | | | |

| ID | HCV | HCVINT | HCVPCR | HCVLIA |
|---|---|---|---|---|
| 34 | 1.66 | Reactive | Negative | Negative |
| 35 | 0.52 | Nonreactive | | |
| 36 | | | | |
| 37 | 0.21 | Nonreactive | | |
| 38 | 0.28 | Nonreactive | | |
| 39 | 0.28 | Nonreactive | | |
| 40 | | | | |
| 41 | 0.43 | Nonreactive | | |
| 42 | 0.39 | Nonreactive | | |
| 43 | 0.26 | Nonreactive | | |
| 44 | 0.46 | Nonreactive | | |
| 45 | 0.37 | Nonreactive | | |
| 46 | 0.39 | Nonreactive | | |
| 47 | 0.59 | Nonreactive | | |
| 48 | 0.37 | Nonreactive | | |
| 49 | 1.09 | Reactive | Negative | Negative |
| 50 | 0.78 | Nonreactive | | |
| 51 | 0.27 | Nonreactive | | |
| 52 | 0.41 | Nonreactive | | |
| 53 | 0.75 | Nonreactive | | |
| 54 | 0.40 | Nonreactive | | |
| 55 | 0.34 | Nonreactive | | |
| 56 | 0.57 | Nonreactive | | |
| 57 | 0.32 | Nonreactive | | |
| 58 | | | | |
| 59 | 0.36 | Nonreactive | | |
| 60 | 0.29 | Nonreactive | | |
| 61 | 0.51 | Nonreactive | | |
| 62 | 0.46 | Nonreactive | | |
| 63 | 0.75 | Nonreactive | | |
| 64 | 0.35 | Nonreactive | | |
| 65 | 0.29 | Nonreactive | | |
| 66 | 0.30 | Nonreactive | | |

| ID | v2_h | v4 | v5 | v6 | v14a | v14b | v15a | v15aO |
|---|---|---|---|---|---|---|---|---|
| 67 | 15666 | 0 | Aug. 10, 1955 | 47 | 0 | | 8 | Peru |
| 68 | 15669 | 0 | Oct. 21, 1968 | 34 | 0 | | 3 | Sri Lank |
| 69 | 15669 | 0 | Dec. 11, 1961 | 41 | 1 | Punjabi | 1 | India |
| 70 | 15669 | 0 | Jul. 20, 1964 | 38 | 0 | | 2 | Banglade |
| 71 | 15670 | 1 | Jan. 1, 1981 | 22 | 1 | Bengali | 2 | Banglade |
| 72 | 15670 | 1 | Nov. 22, 1968 | 34 | 0 | | 8 | Guinea |
| 73 | 15671 | 0 | Jan. 2, 1975 | 27 | 0 | | 1 | India |
| 74 | 15672 | 0 | Jun. 15, 1957 | 45 | 1 | | 4 | Pakistan |
| 75 | 15672 | 1 | Aug. 10, 1958 | 44 | 0 | | 1 | India |
| 76 | 15672 | 0 | Nov. 5, 1972 | 30 | 0 | | 7 | Congo |
| 77 | 15666 | 0 | Oct. 7, 1976 | 26 | 0 | | 1 | India |
| 78 | 15673 | 1 | Feb. 7, 1980 | 22 | 0 | | 8 | Gabon |
| 79 | 15676 | 1 | Nov. 12, 1982 | 21 | 0 | | 8 | Mexico |
| 80 | 15676 | 1 | Nov. 28, 1964 | 38 | 0 | | 7 | Congo |
| 81 | 15677 | 0 | Dec. 11, 1969 | 32 | 0 | | 8 | Guatemal |
| 82 | 15677 | 0 | Aug. 20, 1983 | 19 | 0 | | 8 | Kenya |
| 83 | 15678 | 1 | Sep. 21, 1978 | 24 | 0 | | 2 | Banglade |
| 84 | 15678 | 0 | Oct. 1, 1954 | 48 | 0 | | 4 | Pakistan |
| 85 | 15699 | 1 | Mar. 24, 1969 | 33 | 0 | | 8 | Romania |
| 86 | 15679 | 1 | Apr. 9, 1977 | 25 | 0 | | 3 | Sri Lank |
| 87 | 15679 | 1 | Feb. 9, 1969 | 33 | 0 | | 8 | Senegal |
| 88 | 15680 | 1 | Sep. 23, 1965 | 37 | 0 | | 8 | Nigeria |
| 89 | 15680 | 1 | Aug. 27, 1961 | 41 | 1 | Spanish | 8 | Mexico |
| 90 | 15683 | 1 | Nov. 9, 1972 | 30 | 0 | | 4 | Pakistan |
| 91 | 15684 | 0 | Oct. 10, 1974 | 28 | 0 | | 7 | Congo |
| 92 | 15686 | 0 | May 16, 1968 | 34 | 0 | | 8 | Togo |
| 93 | 15686 | 1 | Oct. 15, 1967 | 35 | 0 | | 8 | Nigeria |
| 94 | 15687 | 0 | Jun. 12, 1965 | 37 | 0 | | 4 | Pakistan |
| 95 | 15691 | 0 | May 25, 1956 | 46 | 0 | | 4 | Pakistan |
| 96 | 15691 | 0 | Jan. 2, 1955 | 47 | 1 | Punjabi | 1 | India |

-continued

| | | | | | | | | | |
|---|---|---|---|---|---|---|---|---|---|
| 97 | 15691 | 0 | Sep. 23, 1972 | 30 | 0 | | 8 | Seychell | |
| 98 | 15691 | 0 | Jun. 18, 1967 | 35 | 0 | | 1 | India | |
| 99 | 15692 | 1 | Oct. 7, 1981 | 21 | 0 | | 8 | Tunisia | |

| ID | v15b | v17a | months_ca | v18 | v20_h | v21 | v22 | v23 | v24a |
|---|---|---|---|---|---|---|---|---|---|
| 67 | 4 | Jun. 9, 2002 | 5.5 | 0 | 0 | 1 | 1 | 1 | 0 |
| 68 | 2 | Jan. 21, 2001 | 22.1 | 3 | 0 | 0 | 0 | 0 | 0 |
| 69 | 2 | Aug. 29, 2001 | 14.9 | 1 | 0 | 0 | 1 | 1 | 0 |
| 70 | 2 | Jul. 6, 2002 | 4.7 | 3 | 0 | 0 | 0 | 1 | 0 |
| 71 | 2 | Jul. 6, 2002 | 4.7 | 3 | 0 | 0 | 0 | 0 | 0 |
| 72 | 1 | Jul. 3, 2002 | 4.8 | 0 | 0 | 0 | 1 | 1 | 0 |
| 73 | 2 | Apr. 6, 2002 | 7.7 | 0 | 0 | 0 | 1 | 1 | 0 |
| 74 | 2 | Jun. 11, 2002 | 5.6 | 0 | 0 | 1 | 0 | 1 | 0 |
| 75 | 2 | Nov. 25, 2001 | 12.1 | 0 | 0 | 0 | 0 | 1 | 0 |
| 76 | 1 | Jul. 7, 2002 | 4.7 | 0 | 0 | 0 | 1 | 0 | 0 |
| 77 | 2 | Jan. 30, 2002 | 9.7 | 0 | 0 | 0 | 1 | 0 | 0 |
| 78 | 1 | Jan. 26, 2001 | 22.1 | 1 | 0 | 0 | 0 | 0 | 0 |
| 79 | 4 | Feb. 23, 2002 | 9.3 | 0 | 0 | 0 | 0 | 0 | 0 |
| 80 | 1 | Oct. 28, 2001 | 13.2 | 1 | 0 | 1 | 0 | 1 | 0 |
| 81 | 4 | Sep. 8, 2002 | 2.8 | 1 | 0 | 0 | 1 | 0 | 0 |
| 82 | 1 | Jul. 17, 2002 | 4.6 | 0 | 0 | 0 | 1 | 0 | 0 |
| 83 | 2 | Jul. 15, 2002 | 4.7 | 0 | 0 | 0 | 0 | 1 | 0 |
| 84 | 2 | Jun. 24, 2002 | 5.4 | 0 | 0 | 0 | 1 | 0 | 0 |
| 85 | 5 | Sep. 21, 2001 | 15.1 | 3 | 0 | 0 | 0 | 0 | 0 |
| 86 | 2 | May 31, 2001 | 18.2 | 0 | 0 | 1 | 0 | 0 | 0 |
| 87 | 1 | Sep. 26, 2002 | 2.3 | 0 | 0 | 0 | 0 | 0 | 1 |
| 88 | 1 | Jun. 11, 2002 | 5.9 | 0 | 0 | 1 | 1 | 1 | 0 |
| 89 | 4 | Aug. 1, 2002 | 4.2 | 0 | 0 | 0 | 1 | 0 | 0 |
| 90 | 2 | Oct. 2, 2002 | 2.2 | 0 | 0 | 1 | 1 | 1 | 0 |
| 91 | 1 | Sep. 5, 2002 | 3.2 | 0 | 0 | 0 | 0 | 0 | 0 |
| 92 | 1 | Jun. 16, 2002 | 5.9 | 0 | 0 | 0 | 0 | 0 | 0 |
| 93 | 1 | Aug. 28, 2002 | 3.5 | 0 | 0 | 1 | 0 | 1 | 0 |
| 94 | 2 | Mar. 29, 2002 | 8.5 | 0 | 0 | 0 | 1 | 0 | 0 |
| 95 | 2 | Dec. 21, 2001 | 11.9 | 0 | 0 | 1 | 0 | 1 | 0 |
| 96 | 2 | Nov. 23, 2001 | 12.8 | 0 | 0 | 0 | 0 | 0 | 0 |
| 97 | 1 | Jul. 24, 2002 | 4.8 | 0 | 0 | 1 | 1 | 1 | 0 |
| 98 | 2 | Sep. 10, 2001 | 15.2 | 0 | 0 | 0 | 0 | 0 | 0 |
| 99 | 3 | Dec. 27, 2001 | 11.7 | 0 | 0 | 0 | 0 | 0 | 0 |

| ID | v24b_h | v251a | v251b_h | v252a | v252b | v253a | v253b_h | v254a | v254b |
|---|---|---|---|---|---|---|---|---|---|
| 67 | 91 | 2 | 91 | 2 | | 2 | 91 | 2 | |
| 68 | 91 | 2 | 91 | 2 | | 2 | 91 | 2 | |
| 69 | 91 | 2 | 91 | 2 | | 2 | 91 | 2 | |
| 70 | 91 | 2 | 91 | 2 | | 2 | 91 | 0 | |
| 71 | 91 | 1 | 10 | 1 | 18 | 0 | 91 | 1 | 9 |
| 72 | 91 | 1 | 28 | 2 | | 2 | 91 | 2 | |
| 73 | 91 | 2 | 91 | 2 | | 2 | 91 | 2 | |
| 74 | 91 | 0 | 91 | 0 | | 2 | 91 | 0 | |
| 75 | 91 | 0 | 91 | 0 | | 0 | 91 | 1 | 7 |
| 76 | 91 | 1 | 4 | 1 | 6 | 2 | 91 | 1 | 10 |
| 77 | 91 | 2 | 91 | 0 | | 2 | 91 | 0 | |
| 78 | 91 | 0 | 91 | 0 | | 2 | 91 | 1 | 7 |
| 79 | 91 | 0 | 91 | 0 | | 2 | 91 | 1 | 18 |
| 80 | 91 | 2 | 91 | 2 | | 2 | 91 | 2 | |
| 81 | 91 | 0 | 91 | 1 | 5 | 0 | 91 | 1 | |
| 82 | 91 | 1 | 8 | 0 | | 2 | 91 | 0 | |
| 83 | 91 | 1 | 5 | 0 | | 0 | 91 | 1 | 12 |
| 84 | 91 | 0 | 91 | 0 | | 2 | 91 | 0 | |
| 85 | 91 | 1 | 5 | 1 | 6 | 2 | 91 | 1 | 7 |
| 86 | 91 | 0 | 91 | 0 | | 0 | 91 | 1 | 15 |
| 87 | 3 | 2 | 91 | 2 | | 2 | 91 | 2 | |
| 88 | 91 | 1 | 13 | 0 | | 0 | 91 | 1 | 18 |
| 89 | 91 | 0 | 91 | 0 | | 2 | 91 | 2 | |
| 90 | 91 | 2 | 91 | 0 | | 2 | 91 | 2 | |
| 91 | 91 | 2 | 91 | 0 | | 2 | 91 | 1 | 15 |
| 92 | 91 | 0 | 91 | 0 | | 0 | 91 | 0 | |
| 93 | 91 | 2 | 91 | 0 | | 2 | 91 | 1 | 12 |
| 94 | 91 | 0 | 91 | 0 | | 2 | 91 | 0 | |
| 95 | 91 | 0 | 91 | 0 | | 0 | 91 | 0 | |
| 96 | 91 | 0 | 91 | 1 | 10 | 2 | 91 | 0 | |
| 97 | 91 | 2 | 91 | 0 | | 2 | 91 | 1 | |
| 98 | 91 | 0 | 91 | 0 | | 2 | 91 | 2 | |
| 99 | 91 | 0 | 91 | 1 | 12 | 2 | 91 | 0 | |

| ID | v255a | v255b_h | v256a | v256b_h | v257a | v257b | v258a | v258b_h | v259a |
|---|---|---|---|---|---|---|---|---|---|
| 67 | 2 | 91 | 2 | 91 | 2 | | 2 | 91 | 0 |
| 68 | 2 | 91 | 2 | 91 | 2 | | 2 | 91 | 0 |

-continued

| | | | | | | | | | |
|---|---|---|---|---|---|---|---|---|---|
| 69 | 2 | 91 | 2 | 91 | 2 | | 2 | 91 | 0 |
| 70 | 2 | 91 | 2 | 91 | 2 | | 2 | 91 | 0 |
| 71 | 2 | 91 | 2 | 91 | 0 | | 0 | 91 | 0 |
| 72 | 0 | 91 | 2 | 91 | 0 | | 0 | 91 | 0 |
| 73 | 2 | 91 | 2 | 91 | 0 | | 2 | 91 | 0 |
| 74 | 0 | 91 | 2 | 91 | 0 | | 1 | 91 | 0 |
| 75 | 0 | 91 | 0 | 91 | 0 | | 2 | 91 | 0 |
| 76 | 2 | 91 | 2 | 91 | 0 | | 2 | 91 | 0 |
| 77 | 0 | 91 | 2 | 91 | 0 | | 2 | 91 | 0 |
| 78 | 2 | 91 | 2 | 91 | 0 | | 2 | 91 | 0 |
| 79 | 0 | 91 | 2 | 91 | 0 | | 2 | 91 | 0 |
| 80 | 2 | 91 | 2 | 91 | 0 | | 2 | 91 | 0 |
| 81 | 2 | 91 | 2 | 91 | 1 | 12 | 2 | 91 | 0 |
| 82 | 2 | 91 | 2 | 91 | 0 | | 2 | 91 | 0 |
| 83 | 0 | 91 | 2 | 91 | 0 | | 0 | 91 | 0 |
| 84 | 0 | 91 | 2 | 91 | 0 | | 0 | 91 | 0 |
| 85 | 0 | 91 | 0 | 91 | 0 | | 0 | 91 | 0 |
| 86 | 0 | 91 | 2 | 91 | 0 | | 0 | 91 | 0 |
| 87 | 2 | 91 | 2 | 91 | 0 | | 2 | 91 | 0 |
| 88 | 0 | 91 | 0 | 91 | 1 | 12 | 0 | 91 | 0 |
| 89 | 0 | 91 | 0 | 91 | 0 | | 2 | 91 | 0 |
| 90 | 0 | 91 | 2 | 91 | 0 | | 2 | 91 | 0 |
| 91 | 2 | 91 | 2 | 91 | 0 | | 2 | 91 | 0 |
| 92 | 0 | 91 | 0 | 91 | 0 | | 0 | 91 | 0 |
| 93 | 0 | 91 | 0 | 91 | 0 | | 0 | 91 | 0 |
| 94 | 0 | 91 | 2 | 91 | 0 | | 2 | 91 | 0 |
| 95 | 0 | 91 | 0 | 91 | 1 | 45 | 0 | 91 | 0 |
| 96 | 0 | 91 | 0 | 91 | 0 | | 0 | 91 | 0 |
| 97 | 0 | 91 | 0 | 91 | 0 | | 2 | 91 | 0 |
| 98 | 0 | 91 | 0 | 91 | 0 | | 2 | 91 | 0 |
| 99 | 0 | 91 | 0 | 91 | 0 | | 0 | 91 | 0 |

| ID | v259b_h | v26 | v33a | v33b | v33c | v34a | v34a1 | v34c | v34c1 |
|---|---|---|---|---|---|---|---|---|---|
| 67 | 91 | 0 | 4 | 15 | 1 | 1 | 1 | 0 | |
| 68 | 91 | 0 | 4 | 12 | 2 | 1 | 1 | 0 | |
| 69 | 91 | 0 | 1 | 0 | | 1 | 1 | 0 | |
| 70 | 91 | 1 | 5 | 17 | 2 | 1 | 1 | 0 | |
| 71 | 91 | 0 | 3 | 12 | 1 | 1 | 1 | 0 | |
| 72 | 91 | 0 | 5 | 17 | 2 | 1 | 1 | 0 | |
| 73 | 91 | 0 | 4 | 10 | 1 | 1 | 1 | 0 | |
| 74 | 91 | 0 | 2 | 6 | 2 | 1 | 1 | 1 | 3 |
| 75 | 91 | 0 | 4 | 15 | 1 | 1 | 1 | 1 | 3 |
| 76 | 91 | 0 | 5 | 17 | 1 | 1 | 1 | 0 | |
| 77 | 91 | 0 | 3 | 10 | 2 | 1 | 1 | 0 | |
| 78 | 91 | 0 | 4 | 14 | 2 | 1 | 1 | 1 | 2 |
| 79 | 91 | 0 | 4 | 11 | 2 | 1 | 1 | 0 | |
| 80 | 91 | 0 | 4 | 13 | 2 | 1 | 1 | 0 | |
| 81 | 91 | 0 | 5 | 19 | 1 | 1 | 1 | 0 | |
| 82 | 91 | 0 | 3 | 12 | 2 | 1 | 1 | 1 | 1 |
| 83 | 91 | 0 | 5 | 16 | 1 | 1 | 1 | 0 | |
| 84 | 91 | 0 | 4 | 13 | 2 | 1 | 1 | 1 | 3 |
| 85 | 91 | 1 | 4 | 13.5 | 2 | 1 | 1 | 0 | |
| 86 | 91 | 0 | 4 | 12 | 2 | 1 | 1 | 1 | 1 |
| 87 | 91 | 0 | 5 | 19 | 2 | 1 | 1 | 0 | |
| 88 | 91 | 0 | 4 | 13 | 1 | 1 | 1 | 0 | |
| 89 | 91 | 0 | 3 | 11 | 2 | 1 | 1 | 0 | |
| 90 | 91 | 0 | 5 | 16 | 2 | 1 | 1 | 0 | |
| 91 | 91 | 0 | 5 | 14 | 2 | 1 | 1 | 0 | |
| 92 | 91 | 0 | 4 | 13 | 2 | 1 | 1 | 0 | |
| 93 | 91 | 0 | 5 | 15 | 2 | 1 | 1 | 0 | |
| 94 | 91 | 0 | 4 | 14 | 2 | 1 | 1 | 0 | |
| 95 | 91 | 0 | 3 | 8 | 2 | 1 | 1 | 0 | |
| 96 | 91 | 0 | 3 | 7 | 2 | 1 | 1 | 1 | 3 |
| 97 | 91 | 0 | 4 | 12 | 2 | 1 | 1 | 1 | 1 |
| 98 | 91 | 0 | 3 | 9 | 2 | 1 | 1 | 0 | |
| 99 | 91 | 0 | 5 | 15 | 2 | 1 | 1 | 0 | |

| ID | v35 | v37a | v37b | UNIVERSITY | crowding | ELECTRICITY | HABIPN | HAVAB | MEINT |
|---|---|---|---|---|---|---|---|---|---|
| 67 | 1 | 15 | 15 | 0 | 1 | 1 | Reactive | 0.062 | Positive |
| 68 | 1 | 6 | 3 | 0 | 2 | 1 | Reactive | 0.067 | Positive |
| 69 | 5 | 5 | 5 | 0 | 1 | 0 | Reactive | 0.068 | Positive |
| 70 | 1 | 7 | 6 | 1 | 1.1666666667 | 0 | Reactive | 0.063 | Positive |
| 71 | 1 | 7 | 4 | 0 | 1.75 | 0 | Reactive | 0.066 | Positive |
| 72 | 1 | 15 | 9 | 1 | 1.8888888889 | 0 | Reactive | 0.071 | Positive |
| 73 | 1 | 6 | 7 | 0 | 0.8571428571 | 0 | Reactive | 0.074 | Positive |
| 74 | 1 | 8 | 8 | 0 | 1 | 0 | Reactive | 0.074 | Positive |
| 75 | 5 | 5 | 4 | 0 | 1.25 | 0 | Reactive | 0.066 | Positive |
| 76 | 1 | 9 | 7 | 1 | 1.2857142857 | 1 | Reactive | 0.051 | Positive |

-continued

| | | | | | | | | | |
|---|---|---|---|---|---|---|---|---|---|
| 77 | 5 | 4 | 6 | 0 | 0.6666666667 | 0 | Reactive | 0.079 | Positive |
| 78 | 1 | 7 | 5 | 0 | 1.4 | 1 | Reactive | 0.082 | Equivocal |
| 79 | 1 | 7 | 6 | 0 | 1.1666666667 | 1 | Reactive | 0.068 | Negative |
| 80 | 1 | 10 | 3 | 0 | 3.3333333333 | 0 | Reactive | 0.058 | Positive |
| 81 | 1 | 4 | 9 | 1 | 0.4444444444 | 1 | Reactive | 0.056 | Positive |
| 82 | 1 | 6 | 6 | 0 | 1 | 1 | Reactive | 0.069 | Positive |
| 83 | 1 | | | 1 | | 1 | Nonreactive | 1.807 | Positive |
| 84 | 1 | 7 | 3 | 0 | 2.3333333333 | 0 | Reactive | 0.060 | Positive |
| 85 | 1 | 6 | 6 | 0 | 1 | 1 | Reactive | 0.075 | Positive |
| 86 | 1 | 4 | 7 | 0 | 0.5714285714 | 1 | Reactive | 0.063 | Positive |
| 87 | 1 | 10 | 8 | 1 | 1.25 | 1 | Reactive | 0.079 | Positive |
| 88 | 1 | 13 | 10 | 0 | 1.3 | 0 | Reactive | 0.080 | Positive |
| 89 | 1 | 6 | 6 | 0 | 1 | 1 | Reactive | 0.101 | Positive |
| 90 | 1 | 8 | 8 | 1 | 1 | 1 | Reactive | 0.081 | Positive |
| 91 | 1 | 14 | 7 | 1 | 2 | 0 | Reactive | 0.082 | Positive |
| 92 | 1 | 6 | 12 | 0 | 0.5 | 0 | Reactive | 0.117 | Positive |
| 93 | 1 | 9 | 5 | 1 | 1.8 | 0 | Reactive | 0.095 | Positive |
| 94 | 1 | 6 | 7 | 0 | 0.8571428571 | 0 | Reactive | 0.074 | Positive |
| 95 | 1 | 7 | 4 | 0 | 1.75 | 1 | Reactive | 0.077 | Positive |
| 96 | 3 | 5 | 2 | 0 | 2.5 | 1 | Reactive | 0.077 | Positive |
| 97 | 1 | 7 | 6 | 0 | 1.1666666667 | 1 | Reactive | 0.062 | Positive |
| 98 | 1 | 7 | 6 | 0 | 1.1666666667 | 1 | Reactive | 0.082 | Positive |
| 99 | 1 | 7 | 6 | 1 | 1.1666666667 | 1 | Reactive | 0.088 | Positive |

| ID | meaod_1 | meati_1 | mezod_1 | meodr_1 | MPGI | mumod_1 | MUMTI | VZV | vzvod_1 |
|---|---|---|---|---|---|---|---|---|---|
| 67 | 1.342 | 3182.11 | | | Negative | 0.044 | 0.000 | Positive | 1.883 |
| 68 | 0.222 | 234.7 | | | Positive | 0.666 | 1808.94 | Positive | 0.586 |
| 69 | 1.995 | 6567.83 | | | Positive | 0.418 | 922.66 | Equivocal | 0.102 |
| 70 | 1.075 | 2178.17 | | | Positive | 0.212 | 384.81 | Positive | 0.952 |
| 71 | 1.717 | 4955.79 | | | Positive | 0.493 | 1162.78 | Positive | 2.338 |
| 72 | 1.992 | 6549.01 | | | Positive | 0.504 | 1200.01 | Positive | 1.057 |
| 73 | 0.829 | 1429.12 | | | Positive | 0.674 | 1841.99 | Positive | 1.122 |
| 74 | 0.629 | 936.69 | | | Equivocal | 0.172 | 300.87 | Positive | 0.69 |
| 75 | 2.059 | 6977 | | | Positive | 0.593 | 1520.41 | Positive | 1.949 |
| 76 | 0.953 | 1786.34 | | | Positive | 0.211 | 382.63 | Positive | 1.416 |
| 77 | 1.538 | 4053.96 | | | Positive | 0.35 | 725.49 | Positive | 1.629 |
| 78 | 0.135 | 134.27 | | | Positive | 0.431 | 962.57 | Positive | 2.07 |
| 79 | 0.048 | 0 | | | Positive | 0.437 | 981.23 | Positive | 0.945 |
| 80 | 0.653 | 990.47 | | | Positive | 0.412 | 904.48 | Positive | 1.484 |
| 81 | 0.867 | 1534.28 | | | Positive | 0.255 | | Positive | 2.023 |
| 82 | 2.368 | 9163.92 | | | Positive | 0.395 | 853.79 | Positive | 0.902 |
| 83 | 2.222 | 8086.18 | | | Equivocal | 0.151 | 259.46 | Positive | 2.306 |
| 84 | 1.128 | 2361.21 | | | Equivocal | 0.104 | 173.38 | Positive | 1.185 |
| 85 | 2.245 | 8250.6 | | | Positive | 0.548 | 1354.13 | Positive | 1.079 |
| 86 | 1.805 | 5437.62 | | | Positive | 0.647 | 1731.59 | Positive | 1.881 |
| 87 | 0.78 | 1299.06 | | | Equivocal | 0.136 | 231.00 | Positive | 0.71 |
| 88 | 1.725 | 4998.53 | | | Positive | 0.706 | 1977.02 | Positive | 1.622 |
| 89 | 1.019 | 1993.25 | | | Positive | 0.207 | 373.96 | Positive | 0.978 |
| 90 | 1.804 | 5432 | | | Positive | 0.261 | 496.70 | Equivocal | 0.122 |
| 91 | 0.691 | 1078.55 | | | Equivocal | 0.133 | 225.42 | Positive | 1.15 |
| 92 | 1.707 | 4902.67 | | | Positive | 0.316 | 634.19 | Positive | 1.774 |
| 93 | 1.83 | 7149.01 | | | Positive | 0.352 | 864.52 | Positive | 1.389 |
| 94 | 2.018 | 8647.88 | | | Positive | 0.325 | 775.95 | Positive | 0.912 |
| 95 | 1.568 | 5335.27 | | | Positive | 0.348 | 851.15 | Positive | 1.009 |
| 96 | 1.405 | 4359.43 | | | Positive | 0.245 | 536.51 | Positive | 1.291 |
| 97 | 0.999 | 2397.83 | | | Positive | 0.272 | 613.49 | Negative | 0.011 |
| 98 | 1.038 | 2558.72 | | | Positive | 1.321 | 6848.62 | Positive | 0.803 |
| 99 | 0.66 | 1227.65 | | | Positive | 0.59 | 1817.84 | Positive | 0.827 |

| ID | vzvti | new_rubin2 | New_Rube | OpDenTetanus | IUTetanus | OpDenDiph | IUDiph | CMVIg | CMVIgINT |
|---|---|---|---|---|---|---|---|---|---|
| 67 | 1793.52 | 0 | 212 | 0.085 | 0.025 | 0.176 | 0.078 | >250.00 | Reactive |
| 68 | 264.92 | 1 | 4.9 | 0.811 | 0.881 | 0.153 | 0.063 | 148.80 | Reactive |
| 69 | 36.17 | 0 | 26.3 | 0.321 | 0.236 | 0.29 | 0.163 | >250.00 | Reactive |
| 70 | 548.22 | 0 | 240 | 0.266 | 0.182 | 0.323 | 0.19 | 69.20 | Reactive |
| 71 | 2731.9 | 0 | 425.7 | 1.127 | 1.51 | 0.101 | 0.03 | >250.00 | Reactive |
| 72 | 649.04 | 0 | 62.6 | 1.382 | 2.22 | 1.472 | 1.603 | 79.10 | Reactive |
| 73 | 716.1 | 0 | 78.3 | 0.995 | 1.22 | 0.532 | 0.379 | 138.20 | Reactive |
| 74 | 335.08 | 0 | 158 | 0.14 | 0.069 | 0.316 | 0.184 | | |
| 75 | 1914.84 | 0 | 99.8 | 0.893 | 1.024 | 0.76 | 0.62 | >250.00 | Reactive |
| 76 | 1066.02 | 0 | 24.3 | 0.355 | 0.272 | 0.5 | 0.348 | 210.50 | Reactive |
| 77 | 1370.29 | 0 | 48.7 | 1.514 | 2.693 | 1.173 | 1.145 | 100.80 | Reactive |
| 78 | 2149.96 | 0 | 148.2 | 1.082 | 1.406 | 0.225 | 0.113 | >250.00 | Reactive |
| 79 | 541.82 | 0 | 55.4 | 0.221 | 0.14 | 0.253 | 0.134 | | |
| 80 | 1158.34 | 0 | 138.8 | 0.277 | 0.193 | 2.226 | 3.113 | | |
| 81 | 2056.65 | 0 | 11 | 0.768 | 0.811 | 0.761 | 0.621 | 1.30 | Negative |
| 82 | 503.38 | 0 | 151.4 | 0.515 | 0.455 | 0.142 | 0.055 | 37.10 | Reactive |
| 83 | 2657.83 | 0 | 97 | 0.131 | 0.067 | 0.676 | 0.49 | 207.70 | Reactive |
| 84 | 784.56 | 0 | 62.8 | 0.123 | 0.06 | 1.033 | 0.889 | >250.00 | Reactive |

-continued

| | | | | | | | | | |
|---|---|---|---|---|---|---|---|---|---|
| 85 | 671.34 | 0 | 37.5 | 0.417 | 0.358 | 0.373 | 0.217 | >250.00 | Reactive |
| 86 | 1789.92 | 1 | 4.9 | 1.567 | 3.179 | 0.291 | 0.153 | >250.00 | Reactive |
| 87 | 349.49 | 0 | 25.3 | 0.701 | 0.756 | 0.309 | 0.167 | 186.10 | Reactive |
| 88 | 1359.58 | 0 | 276.3 | 1.021 | 1.375 | 0.301 | 0.161 | >250.00 | Reactive |
| 89 | 572.33 | 0 | 51.7 | 1.304 | 2.15 | 0.225 | 0.106 | >250.00 | Reactive |
| 90 | 42.69 | 0 | 33.9 | | | | | | |
| 91 | 746.1 | 0 | 152.8 | 0.128 | 0.064 | 0.389 | 0.23 | 159.80 | Reactive |
| 92 | 1603.55 | 0 | 62.2 | 0.106 | 0.046 | 0.186 | 0.079 | >250.00 | Reactive |
| 93 | 1137.53 | 0 | 54.8 | 1.023 | 1.38 | 0.205 | 0.092 | | |
| 94 | 559.74 | 0 | 231.9 | 1.626 | 3.469 | 0.245 | 0.12 | >250.00 | Reactive |
| 95 | 659.21 | 0 | 208.2 | 1.772 | 4.315 | 0.704 | 0.519 | >250.00 | Reactive |
| 96 | 1000.06 | 0 | 34.2 | 0.091 | 0.035 | 0.611 | 0.427 | >250.00 | Reactive |
| 97 | 0 | 1 | 8 | 0.499 | 0.461 | 0.917 | 0.75 | 178.50 | Reactive |
| 98 | 458.22 | 0 | 97.4 | 2.673 | 27.51 | 0.539 | 0.359 | >250.00 | Reactive |
| 99 | 479.66 | 0 | 15.8 | 1.556 | 3.128 | 0.744 | 0.56 | >250.00 | Reactive |

| ID | HBcAb | HBcAbINT | HBSAb | HBSAg | HBSAgINT | HepBeAb | HBeAbINT | HepBeAg | HBeAgINT |
|---|---|---|---|---|---|---|---|---|---|
| 67 | 2.025 | Nonreactive | 0.0 | | | | | | |
| 68 | 2.187 | Nonreactive | 0.0 | | | | | | |
| 69 | 2.194 | Nonreactive | 195.2 | | | | | | |
| 70 | 2.117 | Nonreactive | 8.2 | | | | | | |
| 71 | 2.104 | Nonreactive | 0.0 | | | | | | |
| 72 | 0.158 | Reactive | 4.8 | 0.98 | Nonreactive | | | | |
| 73 | 2.149 | Nonreactive | 0.0 | | | | | | |
| 74 | | | | | | | | | |
| 75 | 1.990 | Nonreactive | 0.0 | | | | | | |
| 76 | 2.273 | Nonreactive | 0.0 | | | | | | |
| 77 | 2.270 | Nonreactive | 0.0 | | | | | | |
| 78 | 2.144 | Nonreactive | 0.0 | | | | | | |
| 79 | | | | | | | | | |
| 80 | | | | | | | | | |
| 81 | 2.001 | Nonreactive | 13.6 | | | | | | |
| 82 | 2.107 | Nonreactive | 0.0 | | | | | | |
| 83 | 1.932 | Nonreactive | 0.0 | | | | | | |
| 84 | 2.052 | Nonreactive | 308.8 | | | | | | |
| 85 | 2.093 | Nonreactive | 155.5 | | | | | | |
| 86 | 2.113 | Nonreactive | 0.0 | | | | | | |
| 87 | 0.573 | Reactive | 884.9 | 0.85 | Nonreactive | | | | |
| 88 | 2.162 | Nonreactive | 28.4 | | | | | | |
| 89 | 2.083 | Nonreactive | 0.0 | | | | | | |
| 90 | | | | | | | | | |
| 91 | 0.300 | Reactive | 86.6 | 0.72 | Nonreactive | | | | |
| 92 | 2.112 | Nonreactive | 0.0 | | | | | | |
| 93 | | | | | | | | | |
| 94 | 2.188 | Nonreactive | 0.0 | | | | | | |
| 95 | 2.128 | Nonreactive | 0.0 | | | | | | |
| 96 | 2.059 | Nonreactive | 0.0 | | | | | | |
| 97 | 1.848 | Nonreactive | 0.0 | | | | | | |
| 98 | 2.052 | Nonreactive | 0.0 | | | | | | |
| 99 | 2.103 | Nonreactive | 0.0 | | | | | | |

| ID | HCV | HCVINT | HCVPCR | HCVLIA |
|---|---|---|---|---|
| 67 | 0.31 | Nonreactive | | |
| 68 | 0.44 | Nonreactive | | |
| 69 | 0.24 | Nonreactive | | |
| 70 | 0.40 | Nonreactive | | |
| 71 | 0.25 | Nonreactive | | |
| 72 | 0.36 | Nonreactive | | |
| 73 | 0.21 | Nonreactive | | |
| 74 | | | | |
| 75 | 0.31 | Nonreactive | — | |
| 76 | 0.37 | Nonreactive | — | |
| 77 | 0.18 | Nonreactive | | |
| 78 | 0.26 | Nonreactive | | |
| 79 | | | | |
| 80 | 0.27 | Nonreactive | | |
| 81 | 0.45 | Nonreactive | | |
| 82 | 0.30 | Nonreactive | | |
| 83 | 0.20 | Nonreactive | | |
| 84 | 0.49 | Nonreactive | | |
| 85 | 0.20 | Nonreactive | | |
| 86 | 0.43 | Nonreactive | | |
| 87 | 0.36 | Nonreactive | | |
| 88 | 0.36 | Nonreactive | | |
| 89 | | | | |
| 90 | 0.34 | Nonreactive | | |
| 91 | 0.24 | Nonreactive | | |
| 92 | | | | |

| | | | |
|---|---|---|---|
| 93 | 0.26 | Nonreactive | |
| 94 | 129.18 | Reactive | Positive |
| 95 | 0.40 | Nonreactive | — |
| 96 | 0.33 | Nonreactive | — |
| 97 | 0.32 | Nonreactive | — |
| 98 | 0.33 | Nonreactive | — |
| 99 | | | |

What is claimed is:

1. A computerized method of assessing the immunological status of one or more individuals in a population, comprising:
 (a) establishing a database comprising a plurality of records of information, each representative of the immune status of an individual in the population, each of said records including
  (1) current information from one or more assays for the presence of a biochemical, including at least one antibody, and
  (2) individual-specific information comprising one or more of said—individual's medical history, said individual's doctors' observations and/or historical, demographic, lifestyle, and familial information relating to said individual;
 (b) processing the information in said database to find trends or patterns relating to the immune status of individuals in said population; and
 (c) using the said trends or patterns found in (b) as part of a health care related decision making process,
 wherein said processing the information in said database includes:
  automatically generating a list of statistical correlations between variables or fields in the database; and
  for each correlation in the list:
   automatically generating a set of hypotheses that may explain said statistical correlation;
   as to each hypothesis in the set, automatically refuting, supporting or stating that there is insufficient data to analyze said hypothesis by further processing of the database; and
   reporting the correlations, their associated hypotheses and the refutation, support, or determination of insufficient data to refute or support, to a user,
 and wherein said processing the information is performed using a data processor.

2. The method of claim 1, further comprising, as to each hypothesis that is determined to have insufficient data, requesting additional data to support or refute it.

3. The method of claim 2, as to each said hypothesis, further comprising obtaining the additional data and automatically refuting, supporting or stating that there is insufficient data to analyze said hypothesis by further processing of the database.

4. A computerized method of analyzing information related to the immune status of one or more individuals in a population, comprising:
 (a) establishing a database comprising a plurality of records of information each representative of the immune status of an individual in the population, each of said records including:
  (i) current information from one or more assays, including at least one antibody, to determine the immunity of said individual to one or more vaccine-preventable diseases; and
  (ii) patient-specific information comprising one or more of said patient's medical history, said patients doctors observations, and/or social, environmental, lifestyle and other demographic information relating to said patient; and
 (b) processing the information in said database to find statistical trends or patterns relating to the immune status of individuals in said patient population;
 wherein said processing the information in said database includes:
  automatically generating a list of statistical correlations between variables or fields in the database; and
  for each correlation in the list:
   automatically generating a set of hypotheses that may explain said correlation; and
   as to each hypothesis in the set, automatically analyzing the data to refute, support or stating that there is insufficient data to analyze said hypothesis by further processing of the database,
 and wherein said processing the information is performed using a data processor.

5. A computerized method for analyzing information related to the immune status of one or more individuals in a population, comprising:
 (a) establishing a database comprising a plurality of records of information each representative of the immune status of an individual in the population, to one or more vaccine-preventable diseases, each of said records including
  (1) current information from one or more assays, including at least one antibody, to determine the immunity of said individual to one or more vaccine-preventable diseases, and
  (2) patient-specific information comprising one or more of said patients medical history, said patients doctors observations and/or demographic information relating to said patient;
 (b) updating said records from time to time with current information as recited in (a)(1) and/or (a)(2);
 (c) processing the information in said database to find statistical trends or patterns relating to the immune status of individuals in said patient population;
 (d) modifying the said algorithms to reflect the patterns and trends found in step (c);
 (e) processing the information in an individual's record through said algorithms, and
 (f) processing the information in said database to find trends or patterns relating to the immune status of individuals in said patient population;
 wherein said processing the information in said database in steps (c) and (f) includes:
  generating a list of correlations between variables or fields in the database;
  for each correlation in the list:
   generating a set of hypotheses that may explain said correlation; and as to each hypothesis in the set, automatically analyzing the data to refute, support or stating that there is insufficient data to analyze said hypothesis by further processing of the database; and wherein said processing the information in steps (c), (e), and (f) is performed using a data processor.

6. A computerized method for generating recommendations for vaccinating one or more individuals in a patient population, comprising:
(a) establishing a database comprising a plurality of records of information each representative of the immune status of an individual in the population, to one or more vaccine-preventable diseases, each of said records including
(i) current information from one or more assays to determine the immunity of said individual to one or more vaccine-preventable diseases, and
(ii) patient-specific information comprising one or more of said patient's medical history, said patients doctors observations, and/or demographic information relating to said patient;
(b) updating said database from time to time with current information;
(c) providing one or more algorithms to determine whether or not to vaccinate said individuals based upon an assay result for antibodies for said one or more vaccine-preventable diseases and other defined factors;
(d) processing the information in said database to find statistical trends or patterns relating to the immune status of individuals in said patient population to said vaccine preventable disease;
(e) incorporating information comprising said patterns or trends into one or more of said algorithms;
(f) processing the information in an individual's record through one or more of said algorithms, and
(g) thereby generating a recommendation for vaccinating said individual;
wherein said processing the information in said database includes:
generating a list of correlations between variables or fields in the database;
for each correlation in the list:
generating a set of hypotheses that may explain said correlation; and
as to each hypothesis in the set, automatically analyzing the data to refute, support or stating that there is insufficient data to analyze said hypothesis by further processing of the database,
and wherein said processing the information is performed using a data processor.

7. A computerized method of optimizing the management of health care for an insured individual in a population, comprising:
examining the insured individual's immune status;
identifying diseases that the insured may be susceptible to;
calculating the risk of contraction for each disease;
identifying all prophylactic therapies that could prevent each identified disease;
calculating, for all possible combinations of said diseases and said prophylactic therapies, expected costs of treatment and costs of associated prophylactic therapies; and
requiring prophylactic therapies optimized for overall health care cost, wherein at least one of said examining immune status and identifying diseases that the individual may be susceptible to includes:
(a) establishing a database comprising a plurality of records of information each representative of the immune status of an individual in the population, to one or more vaccine-preventable diseases, each of said records including
(1) current information from one or more assays to determine the immunity of said individual to one or more vaccine-preventable diseases, and
(2) patient-specific information comprising one or more of said patients medical history, said patients doctors observations and/or demographic information relating to said patient;
(b) processing the information in said database to find statistical trends or patterns relating to the immune status of individuals in said patient population; and
(c) using the said trends or patterns found in (b) in deciding whether or not to vaccinate an individual;
wherein said processing the information in said database includes:
generating a list of correlations between variables or fields in the database;
for each correlation in the list:
generating a set of hypotheses that may explain said correlation; and
as to each hypothesis in the set, automatically refuting, supporting or stating that there is insufficient data to analyze said hypothesis by further processing of the database;
and wherein said examining, identifying, calculating and processing steps are performed using a data processor.

8. The method of claim 7, further comprising assessing, as a condition of continued insurance coverage for the insured, an additional premium charge if the overall cost places the insured into a higher risk bin.

9. The method of claim 8, wherein a debit that is exchangeable on a health care credit/debit exchange is issued in lieu of an additional premium.

10. A system, comprising:
at least one local assay device;
a central processor connected to an input/output device;
a system database;
a hypothesis database;
a rules database; and
a data network connecting the local assay devices and the central processor;
wherein in operation immunologic and other data, including the results of at least one antibody assay, relative to a plurality of individuals is obtained at the assay devices and sent to the system database for storage, wherein the central processor accesses said data and firstly processes said data to find statistical correlations between variables or fields in the database across many individuals, and secondly processes said correlations via rules stored in said rules database to generate a set of hypotheses from those stored in said hypothesis database, and thirdly processes said hypotheses and said data to confirm, exclude or state as inconclusive each of said hypotheses for one or more of said correlations,
and wherein said first, second and third processing are performed using a data processor.

* * * * *